United States Patent
Thurkauf et al.

(10) Patent No.: US 7,271,270 B2
(45) Date of Patent: Sep. 18, 2007

(54) HIGH AFFINITY SMALL MOLECULE C5A RECEPTOR MODULATORS

(75) Inventors: Andrew Thurkauf, Danbury, CT (US); Xiao-shu He, Branford, CT (US); He Zhao, Branford, CT (US)

(73) Assignee: Neurogen Corporation, Branford, CT (US)

( * ) Notice: Subject to any disclaimer, the term of this patent is extended or adjusted under 35 U.S.C. 154(b) by 413 days.

(21) Appl. No.: 10/853,731

(22) Filed: May 24, 2004

(65) Prior Publication Data

US 2007/0027158 A1 Feb. 1, 2007

Related U.S. Application Data

(62) Division of application No. 10/461,311, filed on Jun. 12, 2003, now Pat. No. 6,884,815, which is a division of application No. 09/672,071, filed on Sep. 28, 2000, now Pat. No. 6,723,743.

(60) Provisional application No. 60/156,390, filed on Sep. 28, 1999, provisional application No. 60/202,749, filed on May 8, 2000, provisional application No. 60/212,449, filed on Jun. 16, 2000, provisional application No. 60/221,787, filed on Jul. 31, 2000, provisional application No. 60/224,036, filed on Aug. 9, 2000.

(51) Int. Cl.
C07D 235/02 (2006.01)
C07D 233/00 (2006.01)

(52) U.S. Cl. .............................. 548/304.7; 548/311.1
(58) Field of Classification Search ............. 548/304.7, 548/311.1
See application file for complete search history.

(56) References Cited

U.S. PATENT DOCUMENTS

| | | | |
|---|---|---|---|
| 5,159,083 A | 10/1992 | Thurkauf et al. | |
| 5,428,164 A | 6/1995 | Thurkauf et al. | |
| 5,478,934 A | 12/1995 | Yuan et al. | |
| 5,633,376 A | 5/1997 | Thurkauf et al. | |
| 5,633,377 A | 5/1997 | Thurkauf et al. | |
| 5,646,280 A | 7/1997 | Thurkauf et al. | |
| 5,681,956 A | 10/1997 | Thurkauf et al. | |
| 6,723,743 B1 * | 4/2004 | Thurkauf et al. | 514/396 |
| 6,884,815 B1 * | 4/2005 | Thurkauf et al. | 514/397 |

FOREIGN PATENT DOCUMENTS

WO    WO 02/14265    2/2002

OTHER PUBLICATIONS

Database CA on STN, (Columbus, OH, USA), No. 128:3703, Thurkauf, et al. 'Preparation of 4-aryl substituted piperazinylmethylphenyl imidazoles as a new class of dopamine receptor subtype specific ligands', abstract, Oct. 28, 1997.
Database CA on STN, (Columbus, OH, USA), No. 123:55767, Thurkauf, et al. '2-Phenyl-4-(aminomethyl)imidazoles as potential antipsychotic agents. Synthesis and dopamine D2 receptor binding,' abstract, J. Med. Chem., vol. 38, No. 12, pp. 2251-2255, 1995.
Database CA on STN, (Columbus, OH, USA), No. 117: 2513500350, Thurkauf, etal., 'Preparation of (aminomethyl)phenylimidazoles as dopamine receptor ligands,' abstract, Jul. 23, 1992.
Database CA on STN, (Columbus, OH, USA), No. 105:191381, Shiga, et al., 'Silane derivatives,' abstract, Mar. 24, 1986.
Database CA on STN, (Columbus, OH, USA), No. 131:257737, He, et al., 'Enantioselective total synthesis of aspidophytine,' abstract, J. Am. Chem. Soc., vol. 121, No. 28, pp. 6771-6772, 1999.
Drug Report for "C5a antagonists", Merck & Co., from the Investigational Drugs database, search done Feb. 18, 2002, last update Apr. 17, 2001. Summary, 1 page.
de Laszlo et al., "A Nonpeptide Agonist Ligand of the Human C5A Receptor: Synthesis, Binding Affinity Optimization and Functional Characterization," Bioorganic & Medicinal Chemistry Letters vol. 7, No. 2 pp. 213-218 and pp. 907-912 (1997).
Shilcrat, et al, "A New Regioselective Synthesis of 1,2,5-Trisubstituted 1H-Imidazoles and its Application to the Development of Eprosartan", J. Org. Chem. 1997, 62, pp. 8449-8454.

* cited by examiner

Primary Examiner—D. Margaret Seaman
(74) Attorney, Agent, or Firm—Edwards Angell Palmer & Dodge LLP; Peter F. Corless; Dwight D. Kim

(57) ABSTRACT

This invention relates to low molecular weight, non-peptidic, non-peptidomimetic, organic molecules that act as modulators of mammalian complement C5a receptors, preferably ones that act as high affinity C5a receptor ligands and also to such ligands that act as antagonists or inverse agonists of complement C5a receptors. Preferred compounds of the invention possess some or all of the following properties in that they are: 1) multi-aryl in structure, 2) heteroaryl in structure, 3) a pharmaceutically acceptable oral dose can provide a detectable in vitro effect, 4) comprise fewer than four or preferably no amide bonds, and 5) capable of inhibiting leukocyte chemotaxis at nanomolar or sub-nanomolar concentrations.

This invention also relates to pharmaceutical compositions comprising such compounds and the use of such compounds in treating a variety of inflammatory and immune system disorders. Additionally, this invention relates to the use such compounds as probes for the localization of C5a receptors.

18 Claims, 1 Drawing Sheet

FIG. 1

SEQ ID NO:1 cccaggagaccccaccatgaactccttcaattataccacccctgattatgggcactatgatgacaaggat
accctggacctcaacacccctgtggataaaacttctaacacgctgcgtgttccagacatcctggccttgg
tcatctttgcagtcgtcttcctggtggagtgctgggcaatgccctggtggtctgggtgacggcattcga
ggccaagcggaccatcaatgccatctggttcctcaacttggcggtagccgacttcctctcctgcctggcg
ctgcccatcttgttcacgtccattgtacagcatcaccactggccctttggcggggccgcctgcagcatcc
tgccctccctcatcctgctcaacatgtacgccagcatcctgctcctggccaccatcagcgccgaccgctt
tctgctggtgtttaaacccatctggtgccagaacttccgaggggccggcttggcctggatcgcctgtgcc
gtggcttggggtttagccctgctgctgaccatacccctccttcctgtaccgggtggtccgggaggagtact
ttccaccaaaggtgttgtgtggcgtggactacagccacgacaaacggcgggagcgagccgtggccatcgt
ccggctggtcctgggcttcctgtggcctctactcacgctcacgatttgttacactttcatcctgctccgg
acgtggagccgcagggccacgcggtccaccaagacactcaaggtggtggtggcagtggtggccagttttct
ttatcttctggttgccctaccaggtgacggggataatgatgtccttcctggagccatcgtcacccacctt
cctgctgctgaataagctggactccctgtgtgtctcctttgcctacatcaactgctgcatcaacccatc
atctacgtggtggccggccagggcttccagggccgactgcggaaatccctccccagcctcctccggaacg
tgttgactgaagagtccgtggttagggagagcaagtcattcacgcgctccacagtggacactatggccca
gaagacccaggcagtgtaggcgacagcc

HIGH AFFINITY SMALL MOLECULE C5A RECEPTOR MODULATORS

This application is a divisional of U.S. Ser. No. 10/461,311 filed Jun. 12, 2003, now U.S. Pat. No. 6,884,815, which application was a divisional of U.S. Ser. No. 09/672,071 filed Sep. 28, 2000, now issued as U.S. Pat. No. 6,723,743, which application claims priority from the following five U.S. Provisional applications: 1) application No. 60/156,390, filed Sep. 28, 1999; 2) application No. 60/202,749, filed May 8, 2000; 3) application No. 60/212,449, filed Jun. 16, 2000; 4) application No. 60/221,787, filed Jul. 31, 2000; and 5) application No. 60/224,036, filed Aug. 9, 20000, all of which five applications which are incorporated herein by reference for their teachings with regard to C5a receptor ligands, including arylimidazoles, arylpyridyls, aryl-substituted cycloalkylimidazoles, arylpyrazoles, and benzimidazoles.

BACKGROUND

1. Field of the Invention

This invention relates to low molecular weight, non-peptidic, non-peptidomimetic, organic molecules that act as modulators of mammalian complement C5a receptors, preferably ones that act as high affinity C5a receptor ligands. The invention also relates to such ligands that act as antagonists (including inverse agonists) of complement C5a receptors, preferably human C5a receptors. This invention also relates to pharmaceutical compositions comprising such compounds. It further relates to the use of such compounds in treating a variety of inflammatory and immune system disorders. Additionally, this invention relates to the use such compounds as probes for the localization of C5a receptors.

2. Background of the Invention

C5a, a 74 amino acid peptide, is generated in the complement cascade by the cleavage of the complement protein C5 by the complement C5 convertase enzyme. C5a has both anaphylatoxic (e.g., bronchoconstricting and vascular spasmogenic) and chemotactic effects. Therefore, it is active in engendering both the vascular and cellular phases of inflammatory responses. Because it is a plasma protein and, therefore, generally almost instantly available at a site of an inciting stimulus, it is a key mediator in terms of initiating the complex series of events that results in augmentation and amplification of an initial inflammatory stimulus. The anaphylatoxic and chemotactic effects of the C5a peptide are believed to be mediated through its interation with the C5a receptor (CD88 antigen), a 52 kD membrane bound G-protein coupled receptor (GPCR). C5a is a potent chemoattractant for polymorphonuclear leukocytes, bringing neutrophils, basophils, eosinophils and monocytes to sites of inflammation and/or cellular injury. C5a is one of the most potent chemotactic agents known for a wide variety of inflammatory cell types. C5a also "primes" or prepares neutrophils for various antibacterial functions, e.g., phagocytosis. Additionally, C5a stimulates the release of inflammatory mediators (e.g., histamines, TNF-α, IL-1, IL-6, IL-8, prostaglandins, and leukotrienes) and the release of lysosomal enzymes and other cytotoxic components from granulocytes. Among its other actions, C5a also promotes the production of activated oxygen radicals and the contraction of smooth muscle.

Considerable experimental evidence implicates increased levels of C5a in a number of autoimmune diseases and inflammatory and related disorders.

Antagonists that block the binding of C5a to its receptor or other agents, including inverse agonists, which modulate signal transduction associated with C5a-receptor interactions, can inhibit the pathogenic events, including chemotaxis, associated with anaphylatoxin activity contributing to such inflammatory and autoimmune conditions. Despite many attempts, no one has previously been able to provide any small molecule (less than 700 Daltons MW, or amu) non-peptide, non-peptidomimetic, non-peptoid, C5a antagonist that is essentially free of agonist activity at the C5a receptor and that exhibits a binding affinity for the C5a receptor of less than 1 micromolar, and preferably less than 100 nanomolar.

3. Description of Related Art

Certain modified C5a peptides (i.e., modifications of C5a) have been identified as partial C5a antagonists and have been shown to block a number of C5a mediated actions including neutrophil chemotaxis, neutropenia and superoxide formation. Various C5a peptidomimetic compounds have also been reported as modulating C5a activity, including cyclic peptoids (a peptoid is a peptidomimetic compound comprising an oligomeric assemblage of naturally occurring amino acids that have been N-substituted). Typically these C5a modulatory compounds exhibit a molecular weight greater than 500 Daltons, and generally greater than 700 Daltons.

SUMMARY OF THE INVENTION

The present invention provides novel compounds that are small molecule C5a receptor antagonists that are non-peptide, non-peptidomimetic, and are preferably free of C5a receptor agonist activity, which compounds exhibit high affinity for the C5a receptor, i.e., an affinity constant for binding to the C5a receptor of less than 1 micromolar. Highly preferred compounds exhibit very high affinity for the C5a receptor, i.e., an affinity constant for binding to the C5a receptor of less than 100 nanomolar. Preferred compounds are C5a receptor antagonists (including inverse agonists). Preferred antagonists exhibit an antagonist $EC_{50}$ (which as used herein includes $IC_{50}$) of less than 1 micromolar, preferably less than 100 nanomolar, in an assay of C5a mediated chemotaxis. Preferred C5a receptors are mammalian, preferably primate receptors, including human C5a receptors, and may either be cloned, recombinantly expressed receptors or naturally expressed receptors. In certain preferred embodiments, compounds of the invention exhibit an affinity for human C5a receptors that is higher than for rodent C5a receptors, preferably at least five times higher, more preferably ten times higher.

The compounds of the present invention do not interact with dopamine receptors with even moderate affinity, i.e., they do not bind to dopamine receptors with $K_i$ values of less than 100 micromolar. Preferred compounds of the invention do not bind to any naturally occurring receptors other than C5a receptors with high affinity, and preferably they do not bind to any naturally occurring receptors other than C5a receptors with even moderate affinity.

In certain embodiments these compounds also possess one or more, and preferably two or more, three or more, four or more, or all of the following properties in that they are: 1) multi-aryl in structure (having a plurality of un-fused or fused aryl groups), 2) heteroaryl in structure, 3) orally available in vivo (such that a sub-lethal or preferably a pharmaceutically acceptable oral dose can provide a detectable in vivo effect such as a reduction of C5a-induced neutropenia), 4) comprised of fewer than four, preferably fewer than three, or fewer than two, or no amide bonds, and 5) capable of inhibiting leukocyte chemotaxis at nanomolar concentrations and preferably at sub-nanomolar concentrations.

In a highly preferred aspect, the invention provides non-peptidic, non-peptidomimetic, low molecular weight compounds that act as high affinity antagonists of the human C5a receptor. Specifically exemplified representative compounds include, but are not limited to optionally substituted arylimidazoles (i.e. imidazoles having one or more ring substituents of optionally substituted carbocyclic aryl or optionally substituted heteroaryl), optionally substituted arylpyridyls (i.e. pyridyls having one or more ring substituents of optionally substituted carbocyclic aryl or optionally substituted heteroaryl), optionally substituted aryl-substituted cycloalkylimidazoles (i.e. cycloalkylimidazoles having one or more ring substituents of optionally substituted carbocyclic aryl or optionally substituted heteroaryl), optionally substituted arylpyrazoles (i.e. pyrazoles having one or more ring substituents of optionally substituted carbocyclic aryl or optionally substituted heteroaryl), optionally substituted benzimidazoles, optionally substituted aryl-substituted tetrahydroisoquinolines (i.e. tetrahydroisoquinolines having one or more ring substituents of optionally substituted carbocyclic aryl or optionally substituted heteroaryl), and optionally substituted biaryl carboxamides (i.e. a carboxamide that has one or more optionally substituted bi-carboxylic aryl or heteroaryl substituents). Novel intermediates useful for synthesizing compounds of the invention are also provided.

Preferred compounds of the invention are compounds of Formula I, shown below, that bind specifically, and preferably with high affinity, to C5a receptors.

The invention also provides pharmaceutical compositions comprising compounds of the invention, including those of Formula I, including otppinally substituted arylimidazoles, optionally substituted arylpyridyls, optionally substituted aryl-substituted cycloalkylimidazoles, optionally substituted arylpyrazoles, optionally substituted benzimidazoles, optionally substituted aryl-substituted tetrahydroisoquinolines, and optionally substituted biaryl carboxamides. The C5a receptor antagonist compounds described herein are particularly useful in the treatment of C5a-mediated inflammation, e.g., inflammation associated with various inflammatory and immune system disorders. The invention further comprises a method of treating a patient in need of such anti-inflammatory treatment or immune treatment an effective amount of a compound of the invention, e.g. an amount of a compound of the invention sufficient to yield a plasma concentration of the compound (or its active metabolite, if a pro-drug) high enough to inhibit white blood cell (e.g., neutrophil) chemotaxis in vitro. Treatment of humans, domesticated companion animals (pets) or livestock animals suffering such conditions with an effective amount of a compound of the invention is contemplated by the invention. For treating non-human animals of any particular species, a compound exhibiting high affinity for the C5a receptor of that particular species is preferred.

In a separate aspect, the invention provides methods of using compounds of the invention as positive controls in assays for receptor activity and using appropriately labeled compounds of the invention as probes for the localization of receptors, particularly C5a receptors, e.g., in tissue sections (e.g., via autoradiography) or in vivo (e.g., via positron emission tomography, PET, or single positron emission computed tomography, SPECT, scanning and imaging).

The invention provides compounds and compositions that are useful as inhibitors of C5a-mediated chemotaxis (e.g., they may be used as standards in assays of such chemotaxis). The invention additionally comprises methods of inhibiting C5a-mediated cellular chemotaxis, preferably leukocyte (e.g., neutrophil) chemotaxis. These methods comprise contacting white blood cells, particularly primate white blood cells, especially human white blood cells, with one or more compounds of the invention. Preferably the concentration is sufficient to inhibit chemotaxis of white blood cells in an in vitro chemotaxis assay, so that the levels of chemotaxis observed in a control assay (e.g., one to which a compound of the invention has not been added) are significantly higher (significantly here measured as $p \leq 0.05$ using a conventional parametric statistical analysis method such as a student's T-test) than the levels observed in an assay to which a compound of the invention has been added.

Accordingly, a broad aspect of the invention is directed to non-peptidic organic (carbon-containing) molecules, having a molecular mass of less than 700 amu, that exhibit C5a antagonist activity or C5a inverse agonist activity with an $EC_{50}$ of less than 500 nM in an assay of C5a mediated leukocyte chemotaxis.

More particularly the invention includes compounds of Formula I,

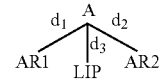

Formula I wherein:

AR1 and AR2 are independently carbocyclic aryl or heteroaryl;

LIP represents an alkyl, carbocyclic aryl, heteroaryl, or arylalkyl;

A is oxygen or nitrogen;

$d_1$ represents the distance between A and the geometric center of AR1 and is between 3 and 6 angstroms in at least one energetically accessible conformer of the compound;

$d_2$ represents the distance between A and the geometric center of AR2 and is between 5 and 10 angstroms in at least one energetically accessible conformer of the compound; and $d_3$ represents the distance between A and the nearest atom of LIP and is between 3 and 6 angstroms in at least one energetically accessible conformer of the compound. Preferred compounds of Formula I exhibit antagonist (including inverse agonist) activity at C5a Receptors, and essentially no or little agonist activity at this receptor. Preferably such compounds contain one or more heteroaryl rings.

Preferred compounds of the invention exhibit good activity in standard in vitro C5 receptor mediated chemotaxis assay, specifically the assay as specified in Example 12, which follows and is defined below. Alternative preferred assays include the calcium mobilization assay. Preferred compounds of the invention exhibit an $EC_{50}$ of about 500 nM or less in such a standard C5a mediated chemotaxis assay, more preferably an $EC_{50}$ of about 200 nM or less in such a standard C5a mediated chemotaxis assay, still more preferably an $EC_{50}$ of about 100, 50, 25 and 10 nM in such a standard C5a mediated chemotaxis assay, even more preferably an $EC_{50}$ of about 5 nM in such a standard C5a mediated chemotaxis assay.

The invention includes additional methods such as methods for localizing C5a receptors in tissue section samples, comprising cotacting a tissue sample with detectably labelled one or more compounds of the invention that are preferably detectably labeled, optionally washing the contacted tissue sample, and detecting the bound compound associated with the tissue sample. Suitable detectable labels include e.g. $^{125}$I, tritium, $^{32}$P, $^{99}$Tc or the like. A variety of detection methods could be employed include single emission photono computed tomography ("SPECT").

Other aspects of the invention are discussed infra

BRIEF DESCRIPTION OF THE DRAWINGS

FIG. 1 is the sequence of SEQ ID NO-1.

DETAILED DESCRIPTION OF THE INVENTION

Preferred compounds of the invention include carbon-containing molecules that comprise:
 i) having a molecular mass of less than 700 amu;
 ii) that is nonpeptidic;
 iii) that exhibits C5a antagonist activity or C5a inverse agonist activity with an $EC_{50}$ of less than 500 nM in an assay of C5a mediated leukocyte chemotaxis; and
 iv) exhibits less than 10% intrinsic agonist activity in an assay of leukocyte chemotaxis.

Among such compounds, particularly preferred are those that contain one or more heteroaryl and/or carbocyclic rings. For example, preferred are compounds of the following formula:

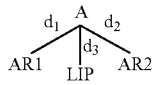

AR1 and AR2 are independently optionally substituted carbocyclic aryl or optionally substituted heteroaryl;
LIP represents an optionally substituted alkyl, optionally substituted carbocyclic aryl, optionally substituted heteroaryl, or optionally substituted arylalkyl;
A is oxygen or nitrogen;
$d_1$ represents the distance between A and the geometric center of AR1 and is between 3 and 6 angstroms in at least one energetically accessible conformer of the compound;
$d_2$ represents the distance between A and the geometric center of AR2 and is between 5 and 10 angstroms in at least one energetically accessible conformer of the compound; and
$d_3$ represents the distance between A and the nearest atom of LIP and is between 3 and 6 angstroms in at least one energetically accessible conformer of the compound.

Preferred compounds of the invention also include heterocycles of the following formula II:

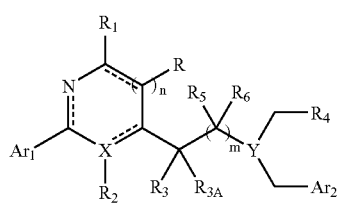

or a pharmaceutically acceptable salt thereof, wherein the compound exhibits an $EC_{50}$ of 1 uM or less in an assay of C5a mediated chemotaxis, wherein:

the ring system represented by

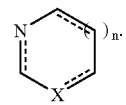

is a 5 to 7 membered heterocycle that may be either aromatic or partially unsaturated;

X is N, C, or $CR_7$, wherein $R_7$ is hydrogen, hydroxy, halogen, amino, cyano, nitro, optionally substituted haloalkyl, optionally substituted alkoxy, optionally substituted mono- or dialkylamino, optionally substituted alkyl, optionally substituted alkenyl, optionally substituted alkynyl or optionally substituted (cycloalkyl)alkyl;

Y is N or CH;

n is 0, 1, or 2;

m is 0, 1, or 2;

R and $R_1$ are independently chosen from hydrogen, hydroxy, halogen, amino, cyano, nitro, optionally substituted haloalkyl, optionally substituted alkoxy, optionally substituted mono- or dialkylamino, optionally substituted alkyl, optionally substituted alkenyl, optionally substituted alkynyl, optionally substituted cycloalkyl, optionally substituted (cycloalkyl)alkyl,
 optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms;

$R_2$, $R_3$, $R_{3A}$, $R_5$ and $R_6$ are independently selected from hydrogen, hydroxy, halogen, amino, cyano, nitro, optionally substituted haloalkyl, optionally substituted alkoxy, optionally substituted mono- or dialkylamino, optionally substituted alkyl, optionally substituted alkenyl, optionally substituted alkynyl, optionally substituted cycloalkyl, and optionally substituted (cycloalkyl)alkyl;

When n is 0, $R_1$ and $R_3$ may be joined to form a cycloalkyl or heterocycloalkyl ring, each of which may be optionally substituted;

When n is 1, R and $R_3$ may be joined to form a cycloalkyl or heterocycloalkyl ring, each of which may be optionally substituted;

$R_4$ is alkyl, alkenyl, alkynyl, cycloalkyl, (cycloalkyl)alkyl each of which may be optionally substituted; or $R_4$ is optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms; and $Ar_1$ and $Ar_2$ are independently optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms.

Preferred compounds of the above Formula II include those compounds wherein:

R and $R_1$ are independently selected from
 i) hydrogen, halogen, hydroxy, amino, alkoxy, mono- or dialkylamino, cyano, nitro, haloalkyl, and ii) alkyl, alkenyl, alkynyl, cycloalkyl, and (cycloalkyl) alkyl, each of which may be unsubstituted or substituted by one or more of halogen, nitro, cyano, trifluoromethyl, trifluoromethoxy, haloalkyl, hydroxy, acetoxy, alkoxy, amino, and mono- or dialkylamino, iii) phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, each of which may be optionally substituted or substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino;

$R_2$, $R_3$, $R_{3A}$, $R_5$, and $R_5$ are independently selected from
  i) hydrogen, halogen, hydroxy, amino, alkoxy, mono- or dialkylamino, cyano, nitro, haloalkyl, and
  ii) alkyl, alkenyl, alkynyl, cycloalkyl, and (cycloalkyl) alkyl, each of which may be unsubstituted or substituted by one or more of halogen, nitro, cyano, trifluoromethyl, trifluoromethoxy, haloalkyl, hydroxy, acetoxy, alkoxy, amino, and mono- or dialkylamino:

$R_7$ is hydrogen, hydroxy, halogen, amino, cyano, nitro, or haloalkyl, or $R_7$ is alkoxy, mono- or dialkylamino, alkyl, alkenyl, alkynyl or (cycloalkyl)alkyl, each of which may be unsubstituted or substituted by one or more of halogen, nitro, cyano, trifluoromethyl, trifluoromethoxy, haloalkyl, hydroxy, acetoxy, alkoxy, amino, and mono- or dialkylamino;

When n is 0, $R_3$ and $R_3$ may be joined to form a cycloalkyl or heterocycloalkyl ring, each of which may be unsubstituted or substituted with one or more substituents selected from halogen, nitro, cyano, trifluoromethyl, trifluoromethoxy, haloalkyl, hydroxy, acetoxy, alkyl, alkenyl, alkynyl, alkoxy, amino, mono- or dialkylamino;

When n is 1, R and $R_3$ may be joined to form a cycloalkyl or heterocycloalkyl ring, each of which may be unsubstituted or substituted with one or more substituents selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino;

$R_4$ is alkyl, alkenyl, alkynyl, cycloalkyl, (cycloalkyl)alkyl, each of which may be unsubstituted or substituted with
  one or more substituents selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino; or $R_4$ is phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, mono- or dialkylamino, carboxylic acid, esters of carboxylic acids, aminocarbonyl, mono or dialkylaminocarbonyl, N-alkylsulfonylaminocarbonyl, 1-azetidinyl, 1-pyrrolidinyl, and 1-piperidyl; or $R_4$ is a bicyclic oxygen-containing group of the formula:

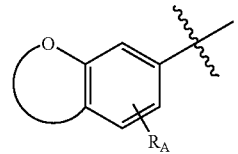

wherein $R_A$ represents 0 to 3 groups selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino; and $Ar_1$ and $Ar_2$ are independently chosen from
  i) phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, mono- or dialkylamino, carboxylic acid, esters of carboxylic acids, aminocarbonyl, mono or dialkylaminocarbonyl, N-alkylsulfonylaminocarbonyl, 1-azetidinyl, 1-pyrrolidinyl, and 1-piperidyl, and
  ii) bicyclic oxygen-containing groups of the formula:

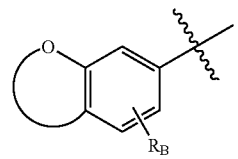

wherein $R_B$ represents 0 to 3 groups selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino.

Additional preferred compounds of the above formula II include those wherein

R and $R_1$ are independently selected from
  i) hydrogen, halogen, hydroxy, amino, $C_1$–$C_6$ alkoxy, mono- or di($C_1$–$C_6$)alkylamino, cyano, nitro, haloalkyl, and
  ii) $C_1$–$C_8$ alkyl, $C_2$–$C_6$ alkenyl, $C_2$–$C_6$ alkynyl, $C_3$–$C_8$ cycloalkyl, and ($C_3$–$C_8$)cycloalkyl) $C_1$–$C_3$ alkyl, each of which may be unsubstituted or substituted by one or more of halogen, nitro, cyano, trifluoromethyl, trifluoromethoxy, haloalkyl, hydroxy, acetoxy, alkoxy, amino, and mono- or di($C_1$–$C_6$)alkylamino,
  iii) phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, each of which may be optionally substituted or substituted with up to four groups independently selected from halogen, nitro, cyano, trifluoromethyl, trifluoromethoxy, haloalkyl, hydroxy, acetoxy, $C_1$–$C_8$ alkyl, $C_2$–$C_6$ alkenyl, $C_2$–$C_6$ alkynyl, $C_1$–$C_6$ alkoxy, amino, and mono- or di($C_1$–$C_6$)alkylamino;

When n is 0, $R_1$ and $R_3$ may be joined to form a $C_3$–$C_8$ cycloalkyl or $C_3$–$C_8$ heterocycloalkyl ring, each of which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino;

When n is 1, R and $R_3$ may be joined to form a $C_3$–$C_8$ cycloalkyl or $C_3$–$C_8$ heterocycloalkyl ring, each of which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino;

$R_2$, $R_3$, $R_{3A}$, $R_5$, and $R_6$ are independently selected from
i) hydrogen, halogen, hydroxy, amino, $C_1$–$C_6$ alkoxy, mono- or di($C_1$–$C_6$)alkylamino, cyano, nitro, haloalkyl, and
ii) $C_1$–$C_8$ alkyl, $C_2$–$C_6$ alkenyl, $C_2$–$C_6$ alkynyl, $C_3$–$C_8$ cycloalkyl, and ($C_3$–$C_8$ cycloalkyl) $C_1$–$C_3$ alkyl, each of which may be unsubstituted or substituted by one or more of halogen, nitro, cyano, trifluoromethyl, trifluoromethoxy, haloalkyl, hydroxy, acetoxy, $C_1$–$C_6$ alkoxy, amino, mono- or di($C_1$–$C_6$)alkylamino;

$R_7$ is hydrogen, hydroxy, halogen, amino, cyano, nitro, or haloalkyl, $R_7$ is alkoxy, mono- or di($C_1$–$C_6$)alkylamino, $C_1$–$C_6$ alkyl, $C_2$–$C_6$ alkenyl, $C_2$–$C_6$ alkynyl or ($C_3$–$C_8$ cycloalkyl) $C_1$–$C_3$ alkyl, each of which may be unsubstituted or substituted by one or more of halogen, nitro, cyano, trifluoromethyl, trifluoromethoxy, haloalkyl, hydroxy, acetoxy, $C_1$–$C_6$ alkoxy, amino, and mono- or di($C_1$–$C_6$)alkylamino;

$R_4$ is $C_1$–$C_8$ alkyl, $C_2$–$C_6$ alkenyl, $C_2$–$C_6$ alkynyl, $C_3$–$C_8$ cycloalkyl, ($C_3$–$C_8$ cycloalkyl) $C_1$–$C_3$ alkyl, each of which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino; or $R_4$ is phenyl, phenyl($C_1$–$C_4$)alkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, and 1-piperidyl; or $R_4$ is a bicyclic oxygen-containing group of the formula:

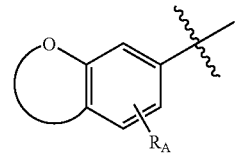

wherein $R_A$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino; and $Ar_1$ and $Ar_2$ are independently chosen from phenyl, phenyl($C_1$–$C_4$)alkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, carboxylic acid, esters of carboxylic acids, aminocarbonyl, mono or di($C_1$–$C_6$)alkylaminocarbonyl, N—($C_1$–$C_6$) alkylsulfonylaminocarbonyl, 1-azetidinyl, 1-pyrrolidinyl, and 1-piperidyl; and ii) bicyclic oxygen-containing groups of the formula:

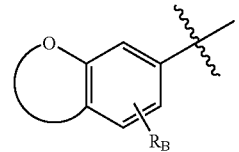

wherein $R_B$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino.

Still additional preferred compounds of the above formula II include those compounds of the following formula:

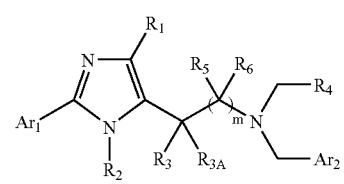

and additionally include those compounds of the following formula:

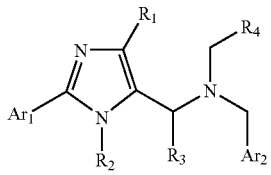

m is 0, 1, or 2;

$R_1$ is chosen from hydrogen, hydroxy, halogen, amino, cyano, nitro, haloalkyl, alkoxy, mono- or dialkylamino, optionally substituted alkyl, optionally substituted alkenyl, optionally substituted alkynyl, optionally substituted cycloalkyl, optionally substituted (cycloalkyl)alkyl, optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms;

$R_2$, $R_3$, $R_{3A}$, $R_5$, and $R_6$ are independently selected from hydrogen, hydroxy, halogen, amino, cyano, nitro, haloalkyl, alkoxy, mono- or dialkylamino, optionally substituted alkyl, optionally substituted alkenyl, optionally substituted alkynyl, optionally substituted cycloalkyl, and optionally substituted (cycloalkyl)alkyl;

$R_4$ is alkyl, alkenyl, alkynyl, cycloalkyl, (cycloalkyl)alkyl each of which may be optionally substituted; or $R_4$ is optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms; and $Ar_1$ and $Ar_2$ are independently optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms.

Additional preferred compounds of the above formula II include those compounds of the following formula:

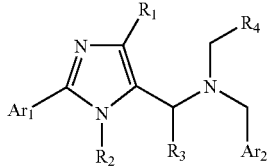

wherein:

$R_1$ is hydrogen, $C_1$–$C_7$ alkyl, halogen or phenyl optionally substituted with $C_1$–$C_6$ alkyl, $C_1$–$C_6$ alkoxy, halogen, hydroxy, amino, or mono- or di($C_1$–$C_6$)alkylamino;

$R_2$ is $C_1$–$C_8$ alkyl or $C_3$–$C_8$ cycloalkyl; and $R_3$ is hydrogen or $C_1$–$C_7$ alkyl.

Additional preferred compounds of the above formula II include those compounds of the following formula:

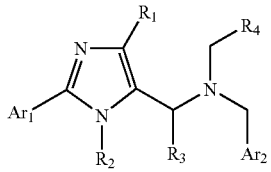

wherein:

$Ar_1$ is phenyl, phenylalkyl, thienyl, imidazolyl, pyridyl, pyrimidyl, benzodioxinyl, benzodioxolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino;

$Ar_2$ is defined as in Claim 2;

$R_1$ is hydrogen, $C_1$–$C_7$ alkyl, halogen or phenyl optionally substituted with $C_1$–$C_6$ alkyl, $C_1$–$C_6$ alkoxy, halogen, hydroxy, amino, or mono- or di($C_1$–$C_6$)alkylamino;

$R_2$ is $C_1$–$C_8$ alkyl or $C_3$–$C_8$ cycloalkyl; and $R_3$ is hydrogen or $C_1$–$C_7$ alkyl; and $R_4$ is $C_1$–$C_8$ alkyl, $C_3$–$C_8$ cycloalkyl, or ($C_3$–$C_8$ cycloalkyl)$C_1$–$C_3$ alkyl, each of which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino.

Additional preferred compounds of the above formula II include those compounds of the following formula:

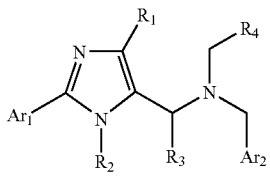

wherein:

$Ar_1$ is phenyl, phenylalkyl, thienyl, imidazolyl, pyridyl, pyrimidyl, benzodioxinyl, benzodioxolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino; $Ar_2$ is defined as in Claim 4;

$R_1$ is hydrogen, $C_1$–$C_7$ alkyl, halogen or phenyl optionally substituted with $C_1$–$C_6$ alkyl, $C_1$–$C_6$ alkoxy, halogen, hydroxy, amino, or mono- or di($C_1$–$C_6$)alkylamino;

$R_2$ is $C_1$–$C_8$ alkyl or $C_3$–$C_8$ cycloalkyl; and $R_3$ is hydrogen or $C_1$–$C_7$ alkyl; and $R_4$ is phenyl, phenyl($C_1$–$C_4$)alkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino; or $R_4$ is a bicyclic oxygen-containing group of the formula:

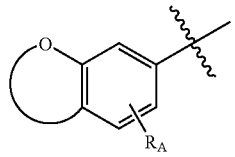

wherein $R_A$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino.

Additional preferred compounds of the above formula II include those compounds of the following formula:

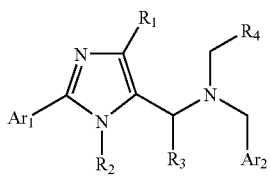

wherein:

$Ar_1$ is phenyl, phenylalkyl, thienyl, or pyridyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino;

$Ar_2$ is defined as in formula II;

$R_1$ is hydrogen, methyl, ethyl, or optionally substituted phenyl;

$R_2$ is $C_3$–$C_8$ alkyl or $C_3$–$C_8$ cycloalkyl; and $R_3$ is hydrogen or methyl; and $R_4$ is $C_1$–$C_8$ alkyl, $C_3$–$C_8$ cycloalkyl, or ($C_3$–$C_8$ cycloalkyl) $C_1$–$C_3$ alkyl, each of which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino.

Additional preferred compounds of the above formula II include those of the following formula:

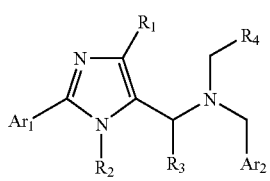

wherein:

$Ar_1$ is phenyl, phenylalkyl, thienyl, or pyridyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino;

$Ar_2$ is defined as in Claim 4;

$R_1$ is hydrogen, methyl, ethyl, or phenyl;

$R_2$ is $C_3$–$C_8$ alkyl or $C_3$–$C_8$ cycloalkyl; and $R_3$ is hydrogen or methyl; and $R_4$ is phenyl, phenyl($C_1$–$C_4$)alkyl, thienyl, pyridyl, pyrimidyl, pyrazinyl, naphthyl, indolyl, indanyl, benzo[b]thiophenyl, benzodioxinyl, benzodioxolyl, benz[d]isoxazolyl, quinolinyl, isoquinolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino; or $R_4$ is a bicyclic oxygen-containing group of the formula:

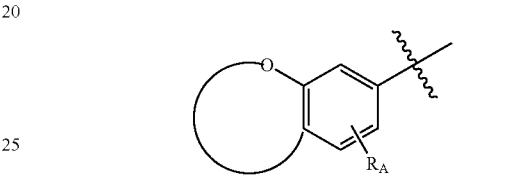

wherein $R_A$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino.

Still additional preferred compounds of the above formula Ii include of the following formula:

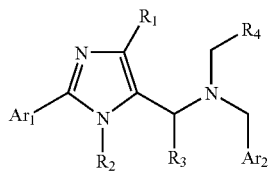

wherein:

$Ar_1$ is phenyl, phenylalkyl, thienyl, or pyridyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino;

$Ar_2$ is chosen from phenyl, phenyl($C_1$–$C_4$)alkyl, thienyl, pyridyl, pyrimidyl, pyrazinyl, naphthyl, indolyl, indanyl, benzo[b]thiophenyl, benzodioxanyl, benzodioxinyl, benzodioxolyl, benz[d]isoxazolyl, quinolinyl, isoquinolinyl, and quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, and 1-piperidyl; or Ar$_2$ is a bicyclic oxygen-containing groups of the formula:

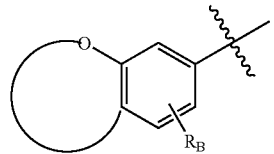

wherein R$_B$ represents 0 to 3 groups selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino;

R$_1$ is hydrogen, methyl, ethyl, or phenyl;

R$_2$ is C$_3$–C$_8$ alkyl or C$_3$–C$_8$ cycloalkyl; and

R$_3$ is hydrogen or methyl; and

R$_4$ is C$_1$–C$_8$ alkyl, C$_3$–C$_8$ cycloalkyl, or (C$_3$–C$_8$ cycloalkyl) C$_1$–C$_3$ alkyl, each of which may be unsubstituted or substituted with one or more substituents selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino.

Still further preferred compounds of the above formula II include those of the following formula:

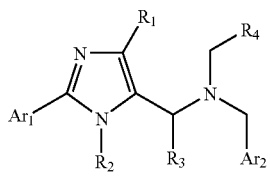

wherein:

Ar$_1$ is phenyl, phenyl(C$_1$–C$_4$)alkyl, thienyl, or pyridyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino;

Ar$_2$ is chosen from phenyl, phenyl(C$_1$–C$_4$)alkyl, thienyl, pyridyl, pyrimidyl, pyrazinyl, naphthyl, indolyl, indanyl, benzo[b]thiophenyl, benzodioxanyl, benzodioxinyl, benzodioxolyl, benz[d]isoxazolyl, quinolinyl, isoquinolinyl, and quinoxalinyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino, carboxylic acid, esters of carboxylic acids, aminocarbonyl, mono or di(C$_1$–C$_6$)alkylaminocarbonyl, N—(C$_1$–C$_6$)alkylsulfonylaminocarbonyl, 1-azetidinyl, 1-pyrrolidinyl, and 1-piperidyl; or Ar$_2$ is a bicyclic oxygen-containing groups of the formula:

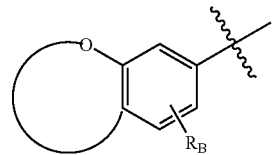

wherein R$_8$ represents 0 to 3 groups selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino;

R$_1$ is hydrogen, methyl, ethyl, or phenyl;

R$_2$ is C$_3$–C$_8$ alkyl or C$_3$–C$_8$ cycloalkyl; and

R$_3$ is hydrogen or methyl; and

R$_4$ is phenyl, phenyl(C$_1$–C$_4$)alkyl, thienyl, pyridyl, pyrimidyl, pyrazinyl, naphthyl, indolyl, indanyl, benzo[b]thiophenyl, benzodioxinyl, benzodioxolyl, benz[d]isoxazolyl, quinolinyl, isoquinolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino; or R$_4$ is a bicyclic oxygen-containing group of the formula:

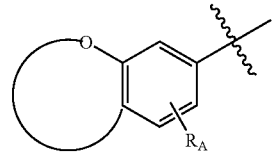

wherein R$_A$ represents 0 to 3 groups selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino.

Preferred compounds of the invention also include those of the following formula III:

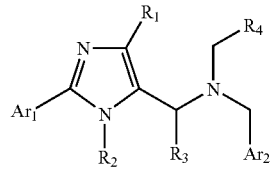

or a pharmaceutically acceptable salt thereof, wherein:

Ar$_1$ is phenyl, phenyl(C$_1$–C$_4$)alkyl, thienyl, or pyridyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino;

Ar$_2$ is a bicyclic oxygen-containing groups of the formula:

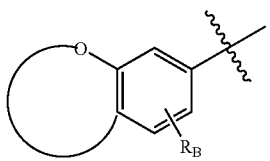

wherein R$_B$ represents 0 to 3 groups selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino;

R$_1$ is selected from
  i) hydrogen, halogen, hydroxy, amino, C$_1$–C$_6$ alkoxy, mono- or di(C$_1$–C$_6$)alkylamino, cyano, nitro, haloalkyl, and
  ii) C$_1$–C$_8$ alkyl, C$_2$–C$_6$ alkenyl, C$_2$–C$_6$ alkynyl, C$_3$–C$_8$ cycloalkyl, and (C$_3$–C$_8$)cycloalkyl) C$_1$–C$_3$ alkyl, each of which may be unsubstituted or substituted by one or more of halogen, nitro, cyano, trifluoromethyl, trifluoromethoxy, haloalkyl, hydroxy, acetoxy, alkoxy, amino, and mono- or di(C$_1$–C$_6$)alkylamino; or R$_1$ is selected from
  phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, each of which may be optionally substituted or substituted with up to four groups independently selected from halogen, nitro, cyano, trifluoromethyl, trifluoromethoxy, haloalkyl, hydroxy, acetoxy, C$_1$–C$_8$ alkyl, C$_2$–C$_6$ alkenyl, C$_2$–C$_6$ alkynyl, C$_1$–C$_6$ alkoxy, amino, and mono- or di(C$_1$–C$_6$)alkylamino;

R$_2$ and R$_3$ are independently selected from
  i) hydrogen, halogen, hydroxy, amino, C$_1$–C$_6$ alkoxy, mono- or di(C$_1$–C$_6$)alkylamino, cyano, nitro, haloalkyl, and
  ii) C$_1$–C$_8$ alkyl, C$_2$–C$_6$ alkenyl, C$_2$–C$_6$ alkynyl, C$_3$–C$_8$ cycloalkyl, and (C$_3$–C$_8$ cycloalkyl) C$_1$–C$_3$ alkyl, each of which may be unsubstituted or substituted by one or more of halogen, nitro, cyano, trifluoromethyl, trifluoromethoxy, haloalkyl, hydroxy, acetoxy, C$_1$–C$_6$ alkoxy, amino, mono- or di(C$_1$–C$_6$)alkylamino; and R$_4$ is C$_1$–C$_8$ alkyl, C$_2$–C$_6$ alkenyl, C$_2$–C$_6$ alkynyl, C$_3$–C$_8$ cycloalkyl, (C$_3$–C$_8$ cycloalkyl) C$_1$–C$_3$ alkyl, each of which may be unsubstituted or substituted with one or more substituents selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino; or R$_4$ is phenyl, phenyl(C$_1$–C$_4$)alkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino, carboxylic acid, esters of carboxylic acids, aminocarbonyl, mono or di(C$_1$–C$_6$)alkylaminocarbonyl, N—(C$_1$–C$_6$)alkylsulfonylaminocarbonyl, 1-azetidinyl, 1-pyrrolidinyl, and 1-piperidyl; or R$_4$ is a bicyclic oxygen-containing group of the formula:

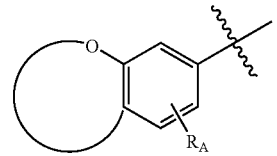

wherein R$_A$ represents 0 to 3 groups selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$, alkoxy, amino, and mono- or di(C$_1$–C$_6$)alkylamino.

Preferred compounds of the above formula III include those wherein:
R$_1$ is hydrogen, methyl, ethyl, or phenyl;
R$_2$ is C$_3$–C$_8$ alkyl or C$_3$–C$_8$ cycloalkyl;
R$_3$ is hydrogen or methyl; and
R$_4$ is C$_1$–C$_8$ alkyl, C$_2$–C$_6$ alkenyl, C$_2$–C$_6$ alkynyl, C$_3$–C$_8$ cycloalkyl, (C$_3$–C$_8$ cycloalkyl) C$_1$–C$_3$ alkyl, each of which may be unsubstituted or substituted with one or more substituents selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino.

Additional preferred compounds of formula III include those wherein:
R$_1$ is hydrogen, methyl, ethyl, or phenyl;
R$_2$ is C$_3$–C$_8$ alkyl or C$_3$–C$_8$ cycloalkyl;
R$_3$ is hydrogen or methyl; and
R$_4$ is C$_1$–C$_8$ alkyl, C$_2$–C$_6$ alkenyl, C$_2$–C$_6$ alkynyl, C$_3$–C$_8$ cycloalkyl, (C$_3$–C$_8$ cycloalkyl) C$_1$–C$_3$ alkyl, each of which may be unsubstituted or substituted with one or more substituents selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino.

Still additional preferred compounds of formula III above include those wherein:
R$_1$ is hydrogen, methyl, ethyl, or phenyl;
R$_2$ is C$_3$–C$_8$ alkyl or C$_3$–C$_8$cycloalkyl;
R$_3$ is hydrogen or methyl; and
phenyl, phenyl(C$_1$–C$_4$)alkyl, thienyl, pyridyl, pyrimidyl, pyrazinyl, naphthyl, indolyl, indanyl, benzo[b]thiophenyl, benzodioxinyl, benzodioxolyl, benz[d]isoxazolyl, quinolinyl, isoquinolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino.

Preferred compounds of formula III above also include those wherein:
R$_1$ is hydrogen, methyl, ethyl, or phenyl;
R$_2$ is C$_3$–C$_8$ alkyl or C$_3$–C$_8$ cycloalkyl;
R$_3$ is hydrogen or methyl; and $R_4$ is a bicyclic oxygen-containing group of the formula:

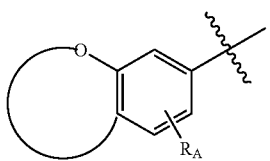

wherein $R_A$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino.

The invention also includes compounds of the following formula IV:

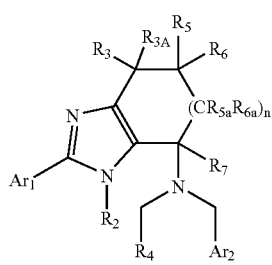

IV or a pharmaceutically acceptable salt thereof, wherein:
n is an integer from 0 to 3; and
$R_2$ is hydrogen or
  alkyl, alkenyl, alkynyl, cycloalkyl, (cycloalkyl)alkyl, or haloalkyl, each or which may be substituted or unsubstituted;
$R_4$ is hydrogen or
  alkyl, alkenyl, alkynyl, cycloalkyl, (cycloalkyl)alkyl, haloalkyl, each or which may be substituted or unsubstituted; or
$R_4$ is optionally substituted carbocyclic aryl, optionally substituted arylalkyl, or an optionally substituted heteroaromatic or heteroalicyclic group having from 1 to 3 rings, 3 to 8 members in each ring and from 1 to 3 hetero atoms,
$R_3$ and $R_{3A}$ are the same or different and represent hydrogen or alkyl; or
$R_3$ and $R_{3A}$, taken together with the carbon atom to which they are attached, form a cycloalkyl ring;
$R_5$ and $R_6$ are the same or different and represent hydrogen, halogen, hydroxy, alkyl, or alkoxy; or
$R_5$ and $R_6$, taken together with the carbon atom to which they are attached form a cycloalkyl ring;
$R_{5a}$ and $R_{6a}$ are the same or different, and are independently selected at each occurrence from hydrogen, halogen, hydroxy, alkyl, and alkoxy;
$R_7$ represents hydrogen or alkyl;
$Ar_1$ and $Ar_2$ are independently optionally substituted carbocyclic aryl, optionally substituted arylalkyl, or an optionally substituted heteroaryl or heteroalicyclic group having from 1 to 3 rings, 3 to 8 members in each ring and from 1 to 3 hetero atoms.

Also preferred are compounds of that formula IV above (such preferred compounds referred to as compounds of formula IV-A) wherein n, $R_3$, $R_{3A}$, $R_5$, $R_6$, $R_{5a}$, $R_{6a}$, and $R_7$ are as defined in that formula IV, and
$R_2$ is hydrogen or
  alkyl, alkenyl, alkynyl, cycloalkyl, (cycloalkyl)alkyl, or haloalkyl, each or which unsubstituted or substituted by one or more of halogen, nitro, cyano, trifluormethyl, trifluoromethoxy, haloalkyl, hydroxy, acetoxy, alkoxy, amino, and mono- or dialkylamino;
$R_4$ is hydrogen or
  alkyl, alkenyl, alkynyl, cycloalkyl, (cycloalkyl)alkyl, haloalkyl, each or which may be unsubstituted or substituted with one or more substituents selected from halogen, nitro, cyano, trifluoromethyl, trifluoromethoxy, haloalkyl, hydroxy, acetoxy, alkyl, alkenyl, alkynyl, alkoxy, amino and mono- or dialkylamino, $R_4$ is phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, mono- or dialkylamino, aminoalkoxy, carboxylic acid, esters of carboxylic acids, aminocarbonyl, mono or dialkylaminocarbonyl, N-alkylsulfonylaminocarbonyl, 1-azetidinyl, 1-pyrrolidinyl, 1-piperidyl and —$XR_B$, wherein X and $R_B$ are as defined below; or
$R_4$ is a bicyclic oxygen-containing group of the formula:

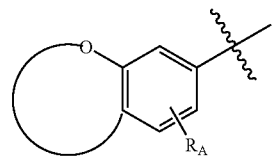

wherein $R_A$ represents 0 to 3 groups selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino;
$Ar_1$ and $Ar_2$ are independently chosen from
i) phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, mono- or dialkylamino, aminoalkoxy, carboxylic acid, esters of carboxylic acids, aminocarbonyl, mono or dialkylaminocarbonyl, N-alkylsulfonylaminocarbonyl, 1-azetidinyl, 1-pyrrolidinyl, 1-piperidyl and —$XR_B$, wherein X and $R_B$ are as defined below; and ii) bicyclic oxygen-containing groups of the formula:

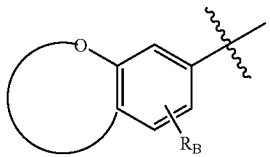

wherein $R_B$ represents 0 to 3 groups selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino;

X is independently selected at each occurrence from the group consisting of —$CH_2$—, —$CHR_C$—, —O—, —$S(O)_m$—, —NH—, —$NR_C$—, —C(=O)NH—, —C(=O)$NR_C$—, —$S(O)_m$NH—, —$S(O)_m NR_C$—, —NHC(=O)—, —$NR_C$C(=O)—, $NHS(O)_m$—, —C(=O)$NHS(O)_m$—, and —$NR_C S(O)_m$— (where m is 0, 1, or 2); and $R_B$ and $R_C$, which may be the same or different, are independently selected at each occurrence from the group consisting of:
hydrogen, straight, branched, or cyclic alkyl groups, which may contain one or more double or triple bonds, each of which may unsubstituted or substituted with one or more substituent(s) selected from:
oxo, hydroxy, —O(alkyl), —NH(alkyl), —N(alkyl)(alkyl), —NHC(O) (alkyl), —N(alkyl)C(O) (alkyl), —$NHS(O)_x$(alkyl), —$S(O)_x$(alkyl), —$S(O)_x$NH(alkyl), —$S(O)_x$N(alkyl)(alkyl), (where x is 0, 1, or 2).

Also preferred are compounds of formula IV above wherein (such preferred compounds referred to as compounds of formula IV-B)
n is defined as in formula IV above, and
$R_3$ and $R_{3A}$ are the same or different and represent hydrogen or $C_1$–$C_6$ alkyl; or
$R_3$ and $R_{3A}$, taken together with the carbon atom to which they are attached, form a $C_{3-8}$ cycloalkyl ring;
$R_5$ and $R_6$ are the same or different and represent hydrogen, halogen, hydroxy, $C_1$–$C_6$. alkyl, or $C_1$–$C_6$ alkoxy; or
$R_5$ and $R_6$, taken together with the carbon atom to which they are attached form a $C_{3-8}$ cycloalkyl ring;
$R_{5a}$ and $R_{6b}$ are the same or different, and are independently selected at each occurrence from hydrogen, halogen, hydroxy, $C_1$–$C_6$ alkyl, and $C_1$–$C_6$ alkoxy;
$R_2$ is hydrogen or
$C_1$–$C_8$ alkyl $C_{2-8}$ alkenyl, $C_{2-8}$ alkynyl, $C_{3-8}$ cycloalkyl, ($C_{3-8}$ cycloalkyl) $C_{1-3}$ alkyl, or $C_1$–$C_6$ haloalkyl each or which unsubstituted or substituted by one or more of halogen, nitro, cyano, trifluormethyl, trifluoromethoxy, $C_{1-3}$ haloalkyl, hydroxy, acetoxy, alkoxy, amino, and mono- or di($C_1$–$C_6$)alkylamino;
$R_4$ is hydrogen or
$C_{1-3}$ alkyl, $C_{2-8}$ alkenyl, $C_{2-8}$ alkynyl, $C_{3-8}$cycloalkyl, ($C_{3-8}$ cycloalkyl)$C_{1-4}$alkyl, haloalkyl, each or which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino and mono- or di($C_1$–$C_6$)alkylamino;
$R_4$ is phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, iscindolyl, benzofuranyl, isobenzofuranyl, benzo[b]thiophenyl, benzodioxanyl, benzodioxinyl, benzodioxolyl, benz[d]isoxazolyl quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$,alkylsulfonylaminocarbonyl, 1-azetidinyl, 1-pyrrolidinyl, 1-piperidyl, —$XR_B$, wherein X and $R_B$ are as defined below; or
$R_4$ is a bicyclic oxygen-containing group of the formula:

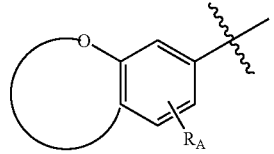

wherein $R_A$ represents 0 to 3 groups selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$)alkylamino;
$Ar_1$ and $Ar_2$ are independently chosen from
i) phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, and —$XR_B$, wherein X and $R_B$ are as defined below; and
ii) bicyclic oxygen-containing groups of the formula:

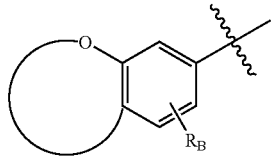

wherein $R_B$ represents 0 to 3 groups selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$)alkylamino;

X is independently selected at each occurrence from the group consisting of —$CH_2$—, —$CHR_C$—, —O—, —S(O)$_m$—, —NH—, —NR$_C$—, —C(=O)NH—, —C(=O)NR$_C$—, S(O)$_m$NH—, —S(O)$_m$NR$_C$—, —NHC(=O)—, —NR$_C$C(=O)—, —NHS(O)$_m$—, —C(=O)NHS(O)$_m$—, and —NR$_C$S(O)$_m$— (where m is 0, 1, or 2); and R$_B$ and R$_C$, which may be the same or different, are independently selected at each occurrence from the group consisting of:

hydrogen, straight, branched, or cyclic alkyl groups, which may contain one or more double or triple bonds, each of which may unsubstituted or substituted with one or more substituent(s) selected from:

oxo, hydroxy, —O(C$_1$–C$_6$ alkyl), —NH(C$_1$–C$_6$ alkyl), —N(C$_1$–C$_6$ alkyl)(C$_1$–C$_6$ alkyl), —NHC(O)(C$_1$–C$_6$ alkyl), —N(C$_1$–C$_6$ alkyl)C(O)(C$_{1-6}$ alkyl), —NHS(O)$_x$(C$_1$–C$_6$ alkyl), —S(O)$_x$(C$_1$–C$_6$ alkyl), —S(O)$_x$NH(C$_1$–C$_6$ alkyl), —S(O)$_x$N(C$_1$–C$_6$ alkyl)(C$_1$–C$_6$ alkyl), (where x is 0, 1, or 2).

Also preferred are compounds of formula IV above (such preferred referred to as compounds of formula IV-C) wherein n, R$_2$, R$_3$, R$_{3A}$, R$_5$, R$_6$, R$_{5a}$, R$_{6a}$, and R$_7$ are as defined in formula IV above, R$_4$ is hydrogen or C$_1$–C$_8$ alkyl, C$_2$–C$_8$ alkenyl, C$_2$–C$_8$ alkynyl, C$_3$–C$_8$cycloalkyl, (C$_3$–C$_8$cycloalkyl) C$_1$–C$_4$alkyl, haloalkyl, each or which may be unsubstituted or substituted with one or more substituents selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino and mono- or di(C$_1$–C$_6$)alkylamino, R$_4$ is phenyl, naphthyl, thienyl, pyridyl, pyrimidyl, dihydrobenzofuranyl, furanyl, benzodioxanyl, indolyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino, amino(C$_1$–C$_6$)alkoxy, carboxylic acid, esters of carboxylic acids, aminocarbonyl, mono or di(C$_1$–C$_6$)alkylaminocarbonyl, N—(C$_1$–C$_6$)alkylsulfonylaminocarbonyl, 1-azetidinyl, 1-pyrrolidinyl, 1-piperidyl, —XR$_B$, wherein X and R$_a$ are as defined below; or R$_4$ is a bicyclic oxygen-containing group of the formula:

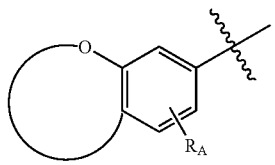

wherein R$_A$ represents 0 to 3 groups selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino;

Ar$_1$ is phenyl, thienyl, or pyridyl, pyrimidyl, dihydrobenzofuranyl, furanyl, benzodioxanyl, indolyl, each of which is unsubstituted or substituted with up to four substituents independently selected from:

halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino, amino(C$_1$–C$_6$)alkoxy, carboxylic acid, esters of carboxylic acids, aminocarbonyl, mono or di(C$_1$–C$_6$)alkylaminocarbonyl, N—(C$_1$–C$_6$)alkylsulfonylaminocarbonyl, 1-azetidinyl, 1-pyrrolidinyl, 1-piperidyl, and —XR$_B$, wherein X and R$_B$ are as defined below;

Ar$_2$ is phenyl, naphthyl, thienyl, pyridyl, pyrimidyl, dihydrobenzofuranyl, furanyl, benzodioxanyl, indolyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino, amino(C$_1$–C$_6$)alkoxy, carboxylic acid, esters of carboxylic acids, aminocarbonyl, mono or di(C$_1$–C$_6$)alkylaminocarbonyl, N—(C$_1$-occurrence from hydrogen and methyl.

Further preferred are compounds of the above formula IV-C wherein:

R$_3$ and R$_4$ are hydrogen;

R$_5$ and R$_6$ are the same or different and represent hydrogen or methyl; and

R$_{5a}$ and R$_{6a}$ are the same or different, and are independently selected at each occurrence from hydrogen and methyl.

Further preferred are compounds of the above formula IV-C wherein:

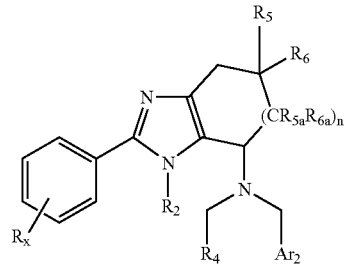

or a pharmaceutically acceptable salt thereof, wherein:

n is an integer from 0 to 3; and

R$_2$ is hydrogen or alkyl, alkenyl, alkynyl, cycloalkyl, (cycloalkyl)alkyl, or haloalkyl, each or which may be substituted or unsubstituted;

R$_4$ is hydrogen or

C$_1$–C$_8$ alkyl, C$_2$–C$_8$ alkenyl, C$_2$–C$_8$ alkynyl, C$_3$–C$_8$cycloalkyl, (C$_3$–C$_8$cycloalkyl) C$_1$–C$_4$alkyl, haloalkyl, each or which may be unsubstituted or substituted with one or more substituents selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino and mono- or di(C$_1$–C$_6$)alkylamino, R$_4$ is phenyl, naphthyl, thienyl, pyridyl, pyrimidyl, dihydrobenzofuranyl, furanyl, benzodioxanyl, indolyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino, amino(C$_1$–C$_6$)alkoxy, carboxylic acid, esters of carboxylic acids, aminocarbonyl, mono or di(C$_1$–C$_6$)alkylaminocarbonyl, N—(C$_1$–C$_6$)alkylsulfonylaminocarbonyl, 1-azetidinyl, 1-pyrrolidinyl, 1-piperidyl, —XR$_B$, wherein X and R$_B$ are as defined below; or $R_4$ is a bicyclic oxygen-containing group of the formula:

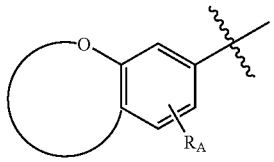

wherein $R_A$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino;

$Ar_2$ is phenyl, naphthyl, thienyl, pyridyl, pyrimidyl, dihydrobenzofuranyl, furanyl, benzodioxanyl, indolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, and —$XR_B$, wherein X and $R_B$ are as defined below; or $Ar_2$ is a bicyclic oxygen-containing group of the formula:

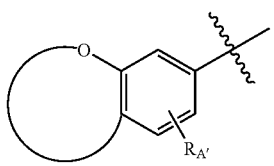

$C_6$)alkylsulfonylaminocarbonyl, 1-azetidinyl, 1-pyrrolidinyl, 1-piperidyl, and —$XR_B$, wherein X and $R_B$ are as defined below; or $Ar_2$ is a bicyclic oxygen-containing group of the formula:

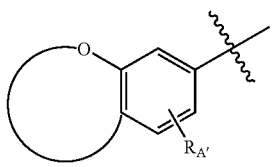

wherein $R_A{}'$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino;

X is independently selected at each occurrence from the group consisting of —$CH_2$—, —$CHR_C$—, —O—, —$S(O)_m$—, —NH—, —$NR_C$—, —C(=O)NH—, —C(=O)$NR_C$—, —$S(O)_m$NH—, —$S(O)_m NR_C$—, —NHC(=O)—, —$NR_C$C(=O)—, —$NHS(O)_m$—, —C(=O)$NHS(O)_m$—, and —$NR_C S(O)_m$— (where m is 0, 1, or 2); and $R_B$ and $R_C$, which may be the same or different, are independently selected at each occurrence from the group consisting of:

hydrogen, straight, branched, or cyclic alkyl groups, which may contain one or more double or triple bonds, each of which may unsubstituted or substituted with one or more substituent(s) selected from:

oxo, hydroxy, —O($C_1$–$C_6$ alkyl), —NH($C_1$–$C_6$ alkyl), —N($C_1$–$C_6$ alkyl)($C_1$–$C_6$ alkyl), —NHC(O)($C_1$–$C_6$ alkyl), —N($C_1$–$C_6$ alkyl)C(O)($C_1$–$C_6$ alkyl), —NHS(O)$_x$($C_1$–$C_6$ alkyl), —S(O)$_x$($C_1$–$C_6$ alkyl), —S(O)$_m$NH($C_1$–$C_6$ alkyl), —S(O)$_m$N($C_1$–$C_6$ alkyl)($C_1$–$C_6$ alkyl), (where x is 0, 1, or 2).

Further preferred are compounds of the above formula IV-C wherein:

$R_3$ and $R_4$ are the same or different and represent hydrogen or methyl;

$R_5$ and $R_6$ are the same or different and represent hydrogen or methyl; and $R_{5a}$ and $R_{6a}$ are the same or different, and are independently selected at each wherein $R_A{}'$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino;

X is independently selected at each occurrence from the group consisting of —$CH_2$—, —$CHR_C$—, —O—, —$S(O)_m$—, —NH—, —$NR_C$—, —C(=O)NH—, —C(=O)$NR_C$—, —$S(O)_m$NH—, $S(O)_m NR_C$—, —NHC(=O)—, —$NR_C$C(=O)—, —$NHS(O)_m$—, —C(=O)$NHS(O)_m$—, and —$NR_C S(O)_m$— (where m is 0, 1, or 2); and $R_B$ and $R_C$, which may be the same or different, are independently selected at each occurrence from the group consisting of:

hydrogen, straight, branched, or cyclic alkyl groups, which may contain one or more double or triple bonds, each of which may unsubstituted or substituted with one or more substituent(s) selected from:

oxo, hydroxy, —O($C_1$–$C_6$ alkyl), —NH($C_1$–$C_6$ alkyl), —N($C_1$–$C_6$ alkyl)($C_1$–$C_6$ alkyl), —NHC(O)($C_1$–$C_6$ alkyl), —N($C_1$–$C_6$ alkyl)C(O)($C_1$–$C_6$ alkyl), —NHS(O)$_x$($C_1$–$C_6$ alkyl), —S(O)$_x$($C_1$–$C_6$ alkyl), —S(O)$_m$NH($C_1$–$C_6$ alkyl), —S(O)$_m$N($C_1$–$C_6$ alkyl)($C_1$–$C_6$ alkyl), (where x is 0, 1, or 2).

$R_5$ and $R_6$ are the same or different and represent hydrogen or methyl;

$R_{5a}$ and $R_{6a}$ are the same or different, and are independently chosen at each occurrence from hydrogen and methyl; and $R_X$ represents up to four substituents independently chosen from hydrogen, halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, and amino($C_1$–$C_6$)alkoxy.

Further preferred are compounds of the above formula IV-C wherein:

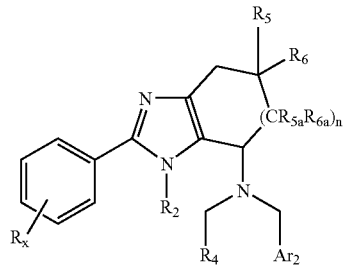

or a pharmaceutically acceptable salt thereof, wherein:
n is an integer from 0 to 3; and
$R_4$ is hydrogen or
  $C_1$–$C_8$ alkyl, $C_2$–$C_8$ alkenyl, $C_2$–$C_8$ alkynyl, $C_3$–$C_8$cycloalkyl, ($C_3$–$C_8$cycloalkyl) $C_1$–$C_4$alkyl, haloalkyl, each or which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino and mono- or di($C_1$–$C_6$)alkylamino,
$R_4$ is phenyl, naphthyl, thienyl, pyridyl, pyrimidyl, dihydrobenzofuranyl, furanyl, benzodioxanyl, indolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, —$XR_B$, wherein X and $R_B$ are as defined below; or
$R_4$ is a bicyclic oxygen-containing group of the formula:

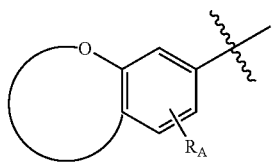

wherein $R_A$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino;
$Ar_2$ is phenyl, naphthyl, thienyl, pyridyl, pyrimidyl, dihydrobenzofuranyl, furanyl, benzodioxanyl, indolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, and —$XR_B$, wherein X and $R_B$ are as defined below; or $Ar_2$ is a bicyclic oxygen-containing group of the formula:

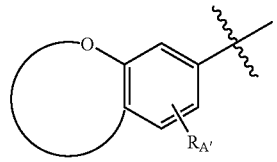

wherein $R_A'$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino;
X is independently selected at each occurrence from the group consisting of —$CH_2$—, —$CHR_C$—, —O—, —$S(O)_m$—, —NH—, —$NR_C$—, —C(=O)NH—, —C(=O)$NR_C$—, —$S(O)_m$NH—, —$S(O)_m NR_C$—, —NHC(=O)—, —$NR_C$C(=O)—, —$NHS(O)_m$—, —C(=O)$NHS(O)_m$—, and —$NR_C S(O)_m$— (where m is 0, 1, or 2); and
$R_B$ and $R_C$, which may be the same or different, are independently selected at each occurrence from the group consisting of:
  hydrogen, straight, branched, or cyclic alkyl groups, which may contain one or more double or triple bonds, each of which may unsubstituted or substituted with one or more substituent(s) selected from:
    oxo, hydroxy, —O($C_1$–$C_6$ alkyl), —NH($C_1$–$C_6$ alkyl), —N($C_1$–$C_6$ alkyl)($C_1$–$C_6$ alkyl), —NHC(O)($C_1$–$C_6$ alkyl), —N($C_1$–$C_6$ alkyl)C(O)($C_1$–$C_6$ alkyl), —NHS(O)$_x$($C_1$–$C_6$ alkyl), —S(O)$_x$($C_1$–$C_6$ alkyl), —S(O)$_x$NH($C_1$–$C_6$ alkyl), —$S(O)_m$N($C_1$–$C_6$ alkyl)($C_1$–$C_6$ alkyl), (where x is 0, 1, or 2).
$R_2$ is $C_3$–$C_8$ straight or branched chain alkyl, $C_2$–$C_8$ alkenyl, or $C_2$–$C_8$ alkynyl;
$R_5$ and $R_6$ are the same or different and represent hydrogen or methyl;
$R_{5a}$ and $R_{6a}$ are the same or different, and are independently chosen at each occurrence from hydrogen and methyl; and
$R_X$ represents up to four substituents independently chosen from hydrogen, halogen, nitro, cyano, trifluoromethyl, trifluoromethoxy, haloalkyl, hydroxy, acetoxy, $C_1$–$C_6$ alkyl, $C_2$–$C_8$ alkenyl, $C_2$–$C_8$ alkynyl, $C_1$–$C_6$ alkoxy, amino, mono- or di($C_1$–$C_6$)alkylamino, and amino($C_1$–$C_6$)alkoxy.

Further preferred are compounds of the above formula IV-C wherein:
  $Ar_2$, $R_X$, and n are as defined in formula IV-C, or a pharmaceutically acceptable salt thereof, wherein:
$R_2$ is $C_3$–$C_8$ straight or branched chain alkyl, $C_2$–$C_8$ alkenyl, or $C_2$–$C_8$ alkynyl; and
$R_4$ is $C_1$–$C_8$ straight or branched chain alkyl, $C_2$–$C_8$ alkenyl, or $C_2$–$C_8$ alkynyl.

Further preferred are compounds of the above formula IV-C, or a pharmaceutically acceptable salt thereof, wherein:
$R_2$ is $C_3$–$C_8$ straight or branched chain alkyl, $C_2$–$C_8$ alkenyl, or $C_2$–$C_8$ alkynyl;

$R_4$ is phenyl, which may be unsubstituted or substituted with:

$C_1$–$C_6$ alkyl, $C_2$–$C_6$ alkenyl, $C_2$–$C_6$ alkynyl, $C_3$–$C_8$ cycloalkyl, ($C_3$–$C_8$ cycloalkyl)$C_1$–$C_4$ alkyl, haloalkyl, $C_1$–$C_6$ alkoxy, halogen, hydroxy, amino, or mono- or di($C_1$–$C_6$)alkylamino; or $R_4$ is a bicyclic oxygen containing group of the formula:

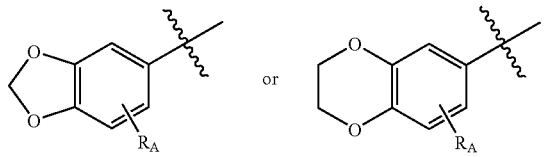

wherein $R_A$ is hydrogen, $C_1$–$C_6$ alkyl, $C_2$–$C_6$ alkenyl, $C_2$–$C_6$ alkynyl, $C_3$–$C_8$ cycloalkyl, ($C_3$–$C_8$cycloalkyl) $C_1$–$C_4$ alkyl, haloalkyl, alkoxy, halogen, hydroxy, amino, or mono- or di($C_1$–$C_6$)alkylamino;

$Ar_2$ is phenyl which is unsubstituted or optionally substituted or substituted with up to four groups independently selected from:

halogen, $C_1$–$C_7$ alkyl, $C_1$–$C_7$ alkoxy, cyano, amino, mono- or di($C_1$–$C_6$)alkylamino, carboxylic acid, esters of carboxylic acids, aminocarbonyl, mono or dialkylaminocarbonyl, N-alkylsulfonylaminocarbonyl, 1-azetidinyl, 1-pyrrolidinyl, 1-piperidyl, 1-morpholino, nitro, hydroxy, acetoxy, trifluoromethyl, and trifluoromethoxy or —$XR_B$, wherein X and $R_B$ are as defined for formula IV-C; or $Ar_2$ is a bicyclic oxygen-containing group of the formula:

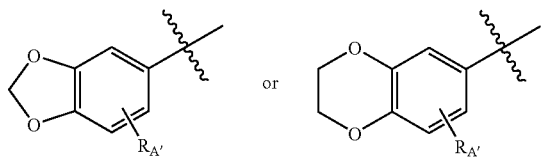

wherein $R_A$, $R_A'$, and n are as defined in formula IV-C.

Also preferred are compounds of formula IV-C as specified above, wherein:

n is an integer from 0 to 3;

$R_2$ is $C_3$–$C_8$ straight or branched chain alkyl, $C_2$–$C_8$ alkenyl, or $C_2$–$C_8$ alkynyl;

$R_4$ is $C_1$–$C_8$ straight or branched chain alkyl, $C_2$–$C_8$ alkenyl, or $C_2$–$C_8$ alkynyl;

$Ar_2$ is a bicyclic oxygen containing group of the formula:

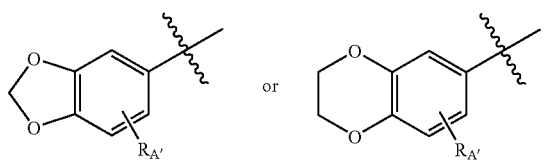

wherein $R_A'$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$) alkylamino.

Additional preferred compounds include those of the following formula V:

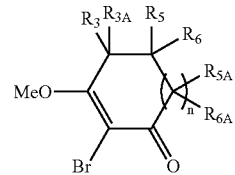

wherein:

n is an integer from 0 to 3;

$R_3$ and $R_{3A}$ are the same or different and represent hydrogen, halogen, hydroxy, alkyl, or alkoxy; or $R_3$ and $R_{3A}$, taken together with the carbon atom to which they are attached, form a cycloalkyl ring;

$R_5$ and $R_6$ are the same or different and represent hydrogen, halogen, hydroxy, alkyl, or alkoxy; or $R_5$ and $R_6$, taken together with the carbon atom to which they are attached form a cycloalkyl ring; and $R_{5A}$ and $R_{6A}$ are the same or different and represent hydrogen, halogen, hydroxy, alkyl, or alkoxy.

Preferred compounds of formula V include those compounds wherein:

$R_3$ and $R_{3A}$ are the same or different and represent hydrogen or $C_1$–$C_6$ alkyl; or $R_3$ and $R_{3A}$, taken together with the carbon atom to which they are attached, form a cycloalkyl ring of from three to six carbon atoms;

$R_5$ and $R_6$ are the same or different and represent hydrogen, halogen, hydroxy, $C_1$–$C_6$ alkyl, or $C_1$–$C_6$ alkoxy; or $R_5$ and $R_6$, taken together with the carbon atom to which they are attached form a cycloalkyl ring of from three to six carbon atoms; and $R_{5A}$ and $R_{6A}$ are the same or different and represent hydrogen, halogen, hydroxy, $C_1$–$C_6$ alkyl, or $C_1$–$C_6$ alkoxy.

Preferred compounds of formula V include those compounds wherein:

$R_3$ and $R_4$ are hydrogen; and $R_5$, $R_6$, $R_{5A}$, and $R_{6A}$ are the same or different and represent hydrogen or methyl.

The invention also includes compounds of the following formula VI:

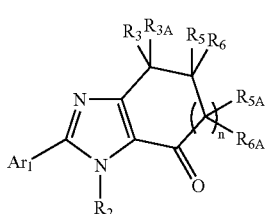

wherein:

n is an integer from 0 to 3;

$R_2$ is alkyl, alkenyl, alkynyl, cycloalkyl, (cycloalkyl)alkyl, or haloalkyl, each of which may be substituted or unsubstituted;

$R_3$ and $R_4$ are the same or different and represent hydrogen or alkyl; or $R_3$ and $R_{3a}$, taken together with the carbon atom to which they are attached, form a cycloalkyl ring;

$R_5$ and $R_6$ are the same or different and represent hydrogen, halogen, hydroxy, alkyl, or alkoxy; or $R_5$ and $R_6$, taken together with the carbon atom to which they are attached, form a cycloalkyl ring;

$R_{5A}$ and $R_{6A}$ are the same or different and represent hydrogen, halogen, hydroxy, alkyl, or alkoxy; and $Ar_1$ is unsubstituted or substituted carbocyclic aryl, unsubstituted or substituted arylalkyl, or a unsubstituted or substituted heteroaromatic or heteroalicyclic group having from 1 to 3 rings, 3 to 8 members in each ring and from 1 to 3 hetero atoms.

Preferred compounds of formula VI include those compounds wherein:

$R_2$ is $C_1$–$C_8$ straight or branched chain alkyl, $C_2$–$C_8$ alkenyl, $C_2$–$C_8$ alkynyl, $C_3$–$C_8$ cycloalkyl, $C_2$–$C_8$ (cycloalkyl) $C_1$–$C_4$ alkyl, or $C_1$–$C_8$ haloalkyl;

$R_3$ and $R_{3a}$ are the same or different and represent hydrogen or $C_1$–$C_6$ alkyl; or $R_3$ and $R_{3a}$, taken together with the carbon atom to which they are attached, form a cycloalkyl ring of from three to six carbon atoms; and $R_5$ and $R_6$ are the same or different and represent hydrogen, halogen, hydroxy, $C_1$–$C_6$ alkyl, or $C_1$–$C_6$ alkoxy; or $R_5$ and $R_6$, taken together with the carbon atom to which they are attached form a cycloalkyl ring of from three to six carbon atoms;

$R_{5A}$ and $R_{6A}$ are the same or different and represent hydrogen, halogen, hydroxy, $C_1$–$C_6$ alkyl, or $C_1$–$C_6$ alkoxy;

$Ar_1$ is phenyl, thienyl, or pyridyl, pyrimidyl, dihydrobenzofuranyl, furanyl, benzodioxanyl, indolyl, each of which is unsubstituted or substituted with up to four substituents independently selected from:

halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$) alkylsulfonylaminocarbonyl, 1-azetidinyl, 1-pyrrolidinyl, 1-piperidyl, and —$XR_B$, wherein X and $R_B$ are as defined below;

X is independently selected at each occurrence from the group consisting of —$CH_2$—, —$CHR_C$—, —O—, —$S(O)_m$—, —NH—, —$NR_C$—, —C(=O)NH—, —C(=O)$NR_C$—, —$S(O)_m$NH—, —$S(O)_m NR_C$—, —NHC(=O)—, —$NR_C$C(=O)—, —$NHS(O)_m$—, —C(=O)$NHS(O)_m$—, and —$NR_C S(O)_m$— (where m is 0, 1, or 2); and $R_B$ and $R_C$, which may be the same or different, are independently selected at each occurrence from the group consisting of:

hydrogen, straight, branched, or cyclic alkyl groups, which may contain one or more double or triple bonds, each of which may unsubstituted or substituted with one or more substituent(s) selected from:

oxo, hydroxy, —O($C_1$–$C_6$ alkyl), —NH($C_1$–$C_6$ alkyl), —N($C_1$–$C_6$ alkyl)($C_1$–$C_6$ alkyl), —NHC(O)($C_1$–$C_6$ alkyl), —N($C_1$–$C_6$ alkyl)C(O)($C_1$–$C_6$ alkyl), —NHS(O)$_x$($C_1$–$C_6$ alkyl), —S(O)$_x$($C_1$–$C_6$ alkyl), —S(O)$_x$NH($C_1$–$C_6$ alkyl), —S(O)$_x$N($C_1$–$C_6$ alkyl)($C_1$–$C_6$ alkyl), (where x is 0, 1, or 2).

Preferred compounds of the above formula VI include those of the following formula:

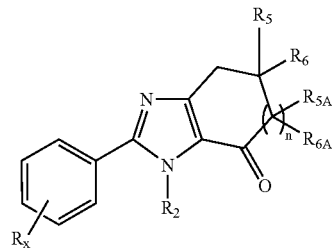

wherein:

n is 0, 1, or 2:

$R_2$ is $C_3$–$C_8$ straight or branched chain alkyl, $C_2$–$C_8$ alkenyl, or $C_2$–$C_8$ alkynyl;

$R_5$, $R_6$, $R_{5A}$, and $R_{6A}$ are the same or different and represent hydrogen or methyl; and $R_X$ represents up to four substituents independently chosen from hydrogen, halogen, nitro, cyano, trifluoromethyl, trifluoromethoxy, haloalkyl, hydroxy, acetoxy, $C_1$–$C_6$ alkyl, $C_2$–$C_8$ alkenyl, $C_2$–$C_8$ alkynyl, $C_1$–$C_6$ alkoxy, amino, mono- or di($C_1$–$C_6$)alkylamino, and amino ($C_1$–$C_6$)alkoxy.

The invention also includes compounds of the following formula VII:

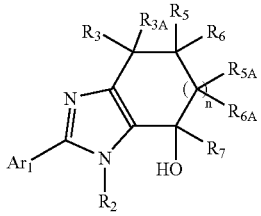

VIII wherein:

n is an integer from 0 to 3; and $R_2$ is alkyl, alkenyl, alkynyl, cycloalkyl, (cycloalkyl)alkyl, haloalkyl, each or which may be substituted or unsubstituted;

$R_3$ and $R_{3A}$ are the same or different and represent hydrogen or alkyl; or $R_3$ and $R_{3a}$, taken together with the carbon atom to which they are attached, form a cycloalkyl ring;

$R_5$ and $R_6$ are the same or different and represent hydrogen or alkyl; or $R_5$ and $R_6$, taken together with the carbon atom to which they are attached, form a cycloalkyl ring;

$R_{5a}$ and $R_{6a}$ are the same or different, and are independently selected at each occurrence from hydrogen, halogen, hydroxy, alkyl, and alkoxy;

$R_7$ represents hydrogen or alkyl; and $Ar_1$ is optionally substituted carbocyclic aryl, optionally substituted arylalkyl, or an optionally substituted heteroaryl or heteroalicyclic group having from 1 to 3 rings, 3 to 8 members in each ring and from 1 to 3 hetero atoms.

Preferred compounds of formula VII include those of the following formula:

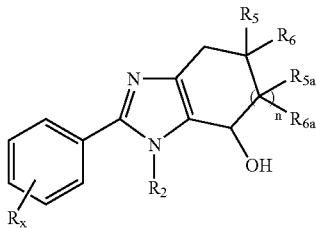

wherein:

n is an integer from 0 to 3;

$R_2$ is $C_3$–$C_8$ straight or branched chain alkyl, $C_2$–$C_8$ alkenyl, or $C_2$–$C_8$ alkynyl;

$R_5$, $R_6$, $R_{5A}$, and $R_{6A}$ are the same or different and represent hydrogen or methyl; and $R_X$ represents up to four substituents independently chosen from hydrogen, halogen, nitro, cyano, trifluoromethyl, trifluoromethoxy, haloalkyl, hydroxy, acetoxy, $C_1$–$C_6$ alkyl, $C_2$–$C_8$ alkenyl, $C_2$–$C_8$ alkynyl, $C_1$–$C_6$ alkoxy, amino, mono- or di($C_1$–$C_6$)alkylamino, and amino($C_1$–$C_6$)alkoxy.

The invention also includes methods of synthesis of compounds of the invention. In particular, the invention includes methods to synthesis compounds of the following formula VIII:

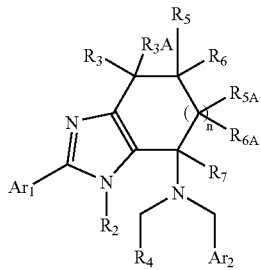

VIII wherein:

n is an integer from 0 to 3; and $R_2$ is hydrogen or alkyl, alkenyl, alkynyl, cycloalkyl, (cycloalkyl)alkyl, or haloalkyl, each or which may be substituted or unsubstituted;

$R_4$ is hydrogen or alkyl, alkenyl, alkynyl, cycloalkyl, (cycloalkyl)alkyl, haloalkyl, each or which may be substituted or unsubstituted; or $R_4$ is optionally substituted carbocyclic aryl, optionally substituted arylalkyl, or an optionally substituted heteroaromatic or heteroalicyclic group having from 1 to 3 rings, 3 to 8 members in each ring and from 1 to 3 hetero atoms, $R_3$ and $R_{3A}$ are the same or different and represent hydrogen or alkyl; or $R_3$ and $R_{3A}$, taken together with the carbon atom to which they are attached, form a cycloalkyl ring;

$R_5$ and $R_6$ are the same or different and represent hydrogen, halogen, hydroxy, alkyl, or alkoxy; or $R_5$ and $R_6$, taken together with the carbon atom to which they are attached form a cycloalkyl ring;

$R_{5a}$ and $R_{6a}$ are the same or different, and are independently selected at each occurrence from hydrogen, halogen, hydroxy, alkyl, and alkoxy;

$R_7$ represents hydrogen or alkyl;

$Ar_1$ and $Ar_2$ are independently optionally substituted carbocyclic aryl, optionally substituted arylalkyl, or an optionally substituted heteroaryl or heteroalicyclic group having from 1 to 3 rings, 3 to 8 members in each ring and from 1 to 3 hetero atoms. the process comprising:

reacting a compound of the formula:

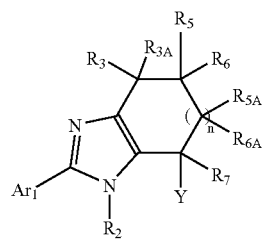

wherein Y is halogen or sulfonate ester, in a suitable solvent in the presence of a suitable base, with a secondary amine of the formula:

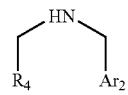

In that synthetic method, preferred are compounds (referred to as compounds of formula VIII-A) wherein n and Y are as defined above for formula VIII;

$R_3$ and $R_{3A}$ are the same or different and represent hydrogen or $C_1$–$C_6$ alkyl; or $R_3$ and $R_{3A}$, taken together with the carbon atom to which they are attached, form a $C_{3-8}$ cycloalkyl ring;

$R_5$ and $R_6$ are the same or different and represent hydrogen, halogen, hydroxy, $C_1$–$C_6$ alkyl, or $C_1$–$C_6$ alkoxy; or $R_5$ and $R_6$, taken together with the carbon atom to which they are attached form a $C_{3-8}$ cycloalkyl ring;

$R_{5a}$ and $R_{6a}$ are the same or different, and are independently selected at each occurrence from hydrogen, halogen, hydroxy, $C_1$–$C_6$ alkyl, and $C_1$–$C_6$ alkoxy;

$R_2$ is hydrogen or $C_{1-8}$ alkyl, $C_{2-8}$ alkenyl, $C_{2-8}$ alkynyl, $C_{3-8}$ cycloalkyl, ($C_{3-8}$ cycloalkyl) $C_{1-3}$ alkyl, or $C_1$–$C_6$ haloalkyl, each or which unsubstituted or substituted by one or more of halogen, nitro, cyano, trifluormethyl, trifluoromethoxy, $C_{1-3}$ haloalkyl, hydroxy, acetoxy, alkoxy, amino, and mono- or di($C_1$–$C_6$)alkylamino;

$R_4$ is hydrogen or $C_{1-8}$ alkyl, $C_{2-8}$ alkenyl, $C_{2-8}$ alkynyl, $C_{3-8}$cycloalkyl, ($C_{3-8}$ cycloalkyl)$C_{1-4}$alkyl, haloalkyl, each or which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino and mono- or di($C_1$–$C_6$)alkylamino, R$_4$ is phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_{2-6}$ alkenyl, C$_{2-6}$ alkynyl, C$_1$–C$_6$ alkoxy, amino, mono- or di(C$_1$–C$_6$)alkylamino, amino(C$_1$–C$_6$)alkoxy, carboxylic acid, esters of carboxylic acids, aminocarbonyl, mono or di(C$_1$–C$_6$)alkylaminocarbonyl, N—(C$_1$–C$_6$)alkylsulfonylaminocarbonyl, 1-azetidinyl, 1-pyrrolidinyl, 1-piperidyl, —XR$_B$, wherein X and R$_B$ are as defined below; or R$_4$ is a bicyclic oxygen-containing group of the formula:

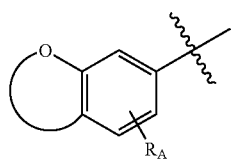

wherein R$_A$ represents 0 to 3 groups selected from halogen, nitro, cyano, trifluoromethyl, trifluoromethoxy, haloalkyl, hydroxy, acetoxy, C$_1$–C$_6$ alkyl, C$_{2-6}$ alkenyl, C$_{2-6}$ alkynyl, C$_1$–C$_6$ alkoxy, amino, and mono- or di(C$_1$–C$_6$)alkylamino;

Ar$_1$ and Ar$_2$ are independently chosen from i) phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_{2-6}$ alkenyl, C$_{2-6}$ alkynyl, C:—C$_6$ alkoxy, amino, mono- or di(C$_1$–C$_6$)alkylamino, amino (C$_1$–C$_6$)alkoxy, carboxylic acid, esters of carboxylic acids, aminocarbonyl, mono or di(C$_1$–C$_6$)alkylaminocarbonyl, N—(C$_1$–C$_6$)alkylsulfonylaminocarbonyl, 1-azetidinyl, 1-pyrrolidinyl, 1-piperidyl, and —XR$_B$, wherein X and R$_B$ are as defined below; and ii) bicyclic oxygen-containing groups of the formula:

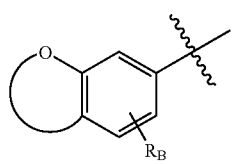

wherein R$_B$ represents 0 to 3 groups selected from halogen, nitro, cyano, trifluoromethyl, trifluoromethoxy, haloalkyl, hydroxy, acetoxy, C$_1$–C$_6$ alkyl, C$_{2-6}$ alkenyl, C$_{2-6}$ alkynyl, C$_1$–C$_6$ alkoxy, amino, and mono- or di(C$_1$–C$_6$)alkylamino:

X is independently selected at each occurrence from the group consisting of —CH$_2$—, —CHR$_C$—, —O—, —S(O)$_m$—, —NH—, —NR$_C$—, —C(=O)NH—, —C(=O)NR$_C$—, S(O)$_m$NH—, S(O)$_m$NR$_C$—, —NHC(=O)—, —NR$_C$C(=O)—, —NHS(O)$_m$—, —C(=O)NHS(O)$_m$—, and —NR$_C$S(O)$_m$— (where m is 0, 1, or 2); and R$_B$ and R$_C$, which may be the same or different, are independently selected at each occurrence from the group consisting of:

hydrogen, straight, branched, or cyclic alkyl groups, which may contain one or more double or triple bonds, each of which may unsubstituted or substituted with one or more substituent(s) selected from:

oxo, hydroxy, —O(C$_1$–C$_6$ alkyl), —NH(C$_1$–C$_6$ alkyl), —N(C$_1$–C$_6$ alkyl)(C$_1$–C$_6$ alkyl), —NHC(O)(C$_1$–C$_6$ alkyl), —N(C$_1$–C$_6$ alkyl)C(O)(C$_{1-6}$ alkyl), —NHS(O)$_x$(C$_1$–C$_6$ alkyl), —S(O)$_x$(C$_1$–C$_6$ alkyl), —S(O)$_x$NH(C$_1$–C$_6$ alkyl), —S(O)$_x$N(C$_1$–C$_6$ alkyl)(C$_1$–C$_6$ alkyl), (where x is 0, 1, or 2).

The invention also includes compounds of the above formula VIII and VIII-A, and pharmaceutically acceptable salts of such compounds.

The invention also provides compounds of the following formula IX:

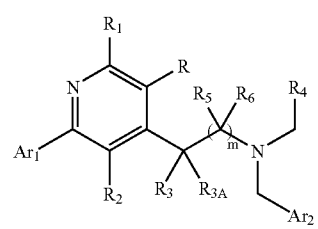

or a pharmaceutically acceptable salt thereof, wherein:

m is 0, 1, or 2;

R is hydrogen, hydroxy, halogen, amino, cyano, nitro, haloalkyl, alkoxy, mono- or dialkylamino, optionally substituted alkyl, optionally substituted alkenyl, optionally substituted alkynyl, optionally substituted cycloalkyl, optionally substituted (cycloalkyl)alkyl; or R is optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms;

R$_1$, R$_2$, R$_3$, R$_{3A}$, R$_5$, and R$_6$ are independently selected from hydrogen, hydroxy, halogen, amino, cyano, nitro, haloalkyl, alkoxy, mono- or dialkylamino, optionally substituted alkyl, optionally substituted alkenyl, optionally substituted alkynyl, optionally substituted cycloalkyl, and optionally substituted (cycloalkyl)alkyl;

R$_4$ is alkyl, alkenyl, alkynyl, cycloalkyl, (cycloalkyl)alkyl each of which may be optionally substituted; or R$_4$ is optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms; and Ar$_1$ and Ar$_2$ are independently optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms.

Preferred compounds of formula IX include those of the following formula IX-A:

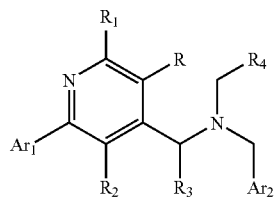

wherein Ar₁, Ar₂, R, R₁, R₂, R₃, and R₄ are for formula IX above.

Preferred compounds of formula IX-A above include those wherein:

R is selected from
  i) hydrogen, halogen, hydroxy, amino, alkoxy, mono- or dialkylamino, cyano, nitro, haloalkyl, and
  ii) alkyl, alkenyl, alkynyl, cycloalkyl, and (cycloalkyl)alkyl, each of which may be unsubstituted or substituted by one or more of halogen, nitro, cyano, trifluoromethyl, trifluoromethoxy, haloalkyl, hydroxy, acetoxy, alkoxy, amino, and mono- or dialkylamino; or R is selected from
phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, each of which may be optionally substituted or substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino; and R₁, R₂, and R₃ are independently selected from
  i) hydrogen, halogen, hydroxy, amino, alkoxy, mono- or dialkylamino, cyano, nitro, haloalkyl, and
  ii) alkyl, alkenyl, alkynyl, cycloalkyl, and (cycloalkyl)alkyl, each of which may be unsubstituted or substituted by one or more of halogen, nitro, cyano, trifluoromethyl, trifluoromethoxy, haloalkyl, hydroxy, acetoxy, alkoxy, amino, and mono- or dialkylamino;

R₄ is hydrogen or
alkyl, alkenyl, alkynyl, cycloalkyl, (cycloalkyl)alkyl, haloalkyl, each or which may be unsubstituted or substituted with one or more substituents selected from halogen, nitro, cyano, trifluoromethyl, trifluoromethoxy, haloalkyl, hydroxy, acetoxy, alkyl, alkenyl, alkynyl, alkoxy, amino and mono- or dialkylamino, R₄ is phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, mono- or dialkylamino, aminoalkoxy, carboxylic acid, esters of carboxylic acids, aminocarbonyl, mono or dialkylaminocarbonyl, N-alkylsulfonylaminocarbonyl, 1-azetidinyl, 1-pyrrolidinyl, 1-piperidyl, —XR_B, wherein X and R_B are as defined below; or R₄ is a bicyclic oxygen-containing group of the formula:

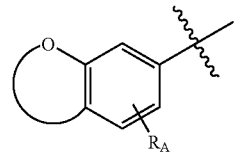

wherein R_A represents 0 to 3 groups selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino;

Ar₁ and Ar₂ are independently chosen from
i) phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, mono- or dialkylamino, aminoalkoxy, carboxylic acid, esters of carboxylic acids, aminocarbonyl, mono or dialkylaminocarbonyl, N-alkylsulfonylaminocarbonyl, 1-azetidinyl, 1-pyrrolidinyl, 1-piperidyl, and —XR_B, wherein X and R_B are as defined below; and ii) bicyclic oxygen-containing groups of the formula:

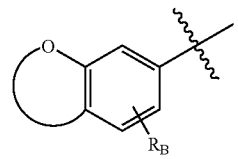

wherein R_B represents 0 to 3 groups selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino;

X is independently selected at each occurrence from the group consisting of —CH₂—, —CHR_C—, —O—, —S(O)_m—, —NH—, —NR_C—, —C(=O)NH—, —C(=O)NR_C—, —S(O)_mNH—, S(O)_mNR_C—, —NHC(=O)—, —NR_CC(=O)—, —NHS(O)_m—, —C(=O)NHS(O)_m—, and —NR_CS(O)_m— (where m is 0, 1, or 2); and R_B and R_C, which may be the same or different, are independently selected at each occurrence from the group consisting of:
  hydrogen, straight, branched, or cyclic alkyl groups, which may contain one or more double or triple bonds, each of which may unsubstituted or substituted with one or more substituent(s) selected from:
    oxo, hydroxy, —O(alkyl), —NH(alkyl), —N(alkyl)(alkyl), —NHC(O)(alkyl), —N(alkyl)C(O)(alkyl), —NHS(O)$_x$(C$_1$–C$_6$ alkyl), —S(O)$_x$(alkyl), —S(O)$_x$NH(alkyl), —S(O)$_x$N(alkyl)(alkyl), (where x is 0, 1, or 2).

Additional preferred compounds of formula IX-A include those wherein: R$_1$, R$_2$, and R$_3$ are independently selected from i) hydrogen, halogen, hydroxy, amino, C$_1$–C$_6$ alkoxy, mono- or di(C$_1$–C$_6$)alkylamino, cyano, nitro, haloalkyl, and ii) C$_1$–C$_8$ alkyl, C$_2$–C$_6$ alkenyl, C$_2$–C$_6$ alkynyl, C$_3$–C$_8$ cycloalkyl, and (C$_3$–C$_8$ cycloalkyl) C$_1$–C$_3$ alkyl, each of which may be unsubstituted or substituted by one or more of halogen, nitro, cyano, trifluoromethyl, trifluoromethoxy, haloalkyl, hydroxy, acetoxy, C$_1$–C$_6$ alkoxy, amino, mono- or di(C$_1$–C$_6$)alkylamino;

R is selected from i) hydrogen, halogen, hydroxy, amino, C$_1$–C$_6$ alkoxy, mono- or di(C$_1$–C$_6$)alkylamino, cyano, nitro, haloalkyl, and ii) C$_1$–C$_8$ alkyl, C$_2$–C$_6$ alkenyl, C$_2$–C$_6$ alkynyl, C$_3$–C$_8$ cycloalkyl, and (C$_3$–C$_8$)cycloalkyl) C$_1$–C$_3$ alkyl, each of which may be unsubstituted or substituted by one or more of halogen, nitro, cyano, trifluoromethyl, trifluoromethoxy, haloalkyl, hydroxy, acetoxy, alkoxy, amino, and mono- or di(C$_1$–C$_6$)alkylamino; or R is selected from phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, each of which may be optionally substituted or substituted with up to four groups independently selected from halogen, nitro, cyano, trifluoromethyl, trifluoromethoxy, haloalkyl, hydroxy, acetoxy, C$_1$–C$_8$ alkyl, C$_2$–C$_6$ alkenyl, C$_2$–C$_6$ alkynyl, C$_1$–C$_6$ alkoxy, amino, and mono- or di(C$_1$–C$_6$)alkylamino;

R$_4$ is hydrogen or

C$_{1-8}$ alkyl, C$_{2-8}$ alkenyl, C$_{2-8}$ alkynyl, C$_{3-8}$cycloalkyl, (C$_{3-8}$ cycloalkyl)C$_{1-4}$alkyl, haloalkyl, each or which may be unsubstituted or substituted with one or more substituents selected from halogen, nitro, cyano, trifluoromethyl, trifluoromethoxy, haloalkyl, hydroxy, acetoxy, C$_1$–C$_6$ alkyl, C$_{2-6}$ alkenyl, C$_{2-6}$ alkynyl, C$_1$–C$_6$ alkoxy, amino and mono- or di(C$_1$–C$_6$)alkylamino, R$_4$ is phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_{2-6}$ alkenyl, C$_{2-6}$ alkynyl, C$_1$–C$_6$ alkoxy, amino, mono- or di(C$_1$–C$_6$)alkylamino, amino(C$_1$–C$_6$)alkoxy, carboxylic acid, esters of carboxylic acids, aminocarbonyl, mono or di(C$_1$–C$_6$)alkylaminocarbonyl, N—(C$_1$–C$_6$)alkylsulfonylaminocarbonyl, 1-azetidinyl, 1-pyrrolidinyl, 1-piperidyl, —XR$_B$, wherein X and R$_B$ are as defined below; or R$_4$ is a bicyclic oxygen-containing group of the formula:

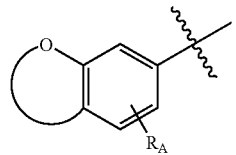

wherein R$_A$ represents 0 to 3 groups selected from halogen, nitro, cyano, trifluoromethyl, trifluoromethoxy, haloalkyl, hydroxy, acetoxy, C$_1$–C$_6$ alkyl, C$_{2-6}$ alkenyl, C$_{2-6}$ alkynyl, C$_1$–C$_6$ alkoxy, amino, and mono- or di(C$_1$–C$_6$)alkylamino; and Ar$_1$ and Ar$_2$ are independently chosen from i) phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_{2-6}$ alkenyl, C$_{2-6}$ alkynyl, C$_1$–C$_6$ alkoxy, amino, mono- or di(C$_1$–C$_6$)alkylamino, amino (C$_1$–C$_6$)alkoxy, carboxylic acid, esters of carboxylic acids, aminocarbonyl, mono or di(C$_1$–C$_6$)alkylaminocarbonyl, N—(C$_1$–C$_6$)alkylsulfonylaminocarbonyl, 1-azetidinyl, 1-pyrrolidinyl, 1-piperidyl, and —XR$_B$, wherein X and R$_B$ are as defined below; and ii) bicyclic oxygen-containing groups of the formula:

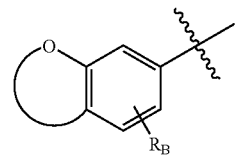

wherein R$_B$ represents 0 to 3 groups selected from halogen, nitro, cyano, trifluoromethyl, trifluoromethoxy, haloalkyl, hydroxy, acetoxy, C$_1$–C$_6$ alkyl, C$_{2-6}$ alkenyl, C$_{2-6}$ alkynyl, C$_1$–C$_6$ alkoxy, amino, and mono- or di(C$_1$–C$_6$)alkylamino;

X is independently selected at each occurrence from the group consisting of —CH$_2$—, —CHR$_C$—, —O—, —S(O)$_m$—, —NH—, —NR$_C$—, —C(=O)NH—, —C(=O)NR$_C$—, —S(O)$_m$NH—, —S(O)$_m$NR$_C$—, —NHC(=O)—, —NR$_C$C(=O)—, —NHS(O)$_m$—, —C(=O)NHS(O)$_m$—, and —NR$_C$S(O)$_m$— (where m is 0, 1, or 2); and R$_B$ and R$_C$, which may be the same or different, are independently selected at each occurrence from the group consisting of:

hydrogen, straight, branched, or cyclic alkyl groups, which may contain one or more double or triple bonds, each of which may unsubstituted or substituted with one or more substituent(s) selected from:

oxo, hydroxy, —O(C$_1$–C$_6$ alkyl), —NH(C$_1$–C$_6$ alkyl), —N(C$_1$–C$_6$ alkyl)(C$_1$–C$_6$ alkyl), —NHC(O)(C$_1$–C$_6$ alkyl), —N(C$_1$–C$_6$ alkyl)C(O)(C$_{1-6}$ alkyl), —NHS (O)$_x$(C$_1$–C$_6$ alkyl), —S(O)$_x$(C$_1$–C$_6$ alkyl), —S(O)$_x$NH(C$_1$–C$_6$ alkyl), —S(O)$_x$N(C$_1$–C$_6$ alkyl)(C$_1$–C$_6$ alkyl), (where x is 0, 1, or 2).

Additional preferred compounds of formula IX-A above include those wherein:

R is hydrogen, halogen, C$_1$–C$_8$ alkyl, C$_2$–C$_8$ alkenyl, C$_2$–C$_8$ alkynyl, C$_1$–C$_8$ cycloalkyl, (C$_3$–C$_8$cycloalkyl)C$_1$–C$_3$ alkyl, C$_1$–C$_8$ alkoxy, or C$_1$–C$_8$ haloalkyl, or R is a phenyl which may be substituted by up to five substituents independently chosen from C$_1$–C$_8$ alkyl, C$_2$–C$_8$ alkenyl, C$_2$–C$_8$ alkynyl, C$_1$–C$_8$ alkoxy, halogen, cyano, carboxylic acid, hydroxy, acetoxy, nitro, amino, mono or di(C$_1$–C$_6$)alkylamino, aminocarbonyl, sulfonamido, mono or di(C$_1$–C$_6$)alkylsulfonamido, 3,4-methylenedioxy, 3,4-(1,2-ethylene)dioxy, trifluoromethyl or trifluoromethoxy;

R$_1$ is hydrogen, C$_1$–C$_8$ alkyl, C$_2$–C$_8$alkenyl, C$_2$–C$_8$ alkynyl, C$_3$–C$_8$ cycloalkyl (C$_3$–C$_8$cycloalkyl)C$_1$–C$_3$ alkyl or C$_1$–C$_8$ haloalkyl;

R$_2$ is C$_1$–C$_8$ alkyl, C$_2$–C$_8$ alkenyl, C$_2$–C$_8$ alkynyl, C$_1$–C$_8$ cycloalkyl or (C$_3$–C$_8$cycloalkyl)C$_1$–C$_3$ alkyl or C$_1$–C$_8$ haloalkyl;

R$_3$ is hydrogen, C$_1$–C$_8$ alkyl, C$_2$–C$_8$ alkenyl, or C$_2$–C$_8$ alkynyl;

R$_4$ is C$_1$–C$_8$ alkyl, C$_3$–C$_8$ cycloalkyl, or (C$_3$–C$_8$ cycloalkyl) C$_1$–C$_3$ alkyl, each of which may be unsubstituted or substituted with one or more substituents selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino; or R$_4$ is phenyl, phenyl(C$_1$–C$_4$)alkyl, thienyl, pyridyl, pyrimidyl, pyrazinyl, naphthyl, indolyl, indanyl, benzo[b]thiophenyl, benzodioxinyl, benzodioxolyl, benz[d]isoxazolyl, quinolinyl, isoquinolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino; or R$_4$ is a bicyclic oxygen-containing group of the formula:

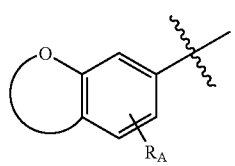

wherein R$_A$ represents 0 to 3 groups selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino; and Ar$_1$ and Ar$_2$ are independently chosen from phenyl, phenyl (C$_1$–C$_4$)alkyl, thienyl, pyridyl, pyrimidyl, pyrazinyl, naphthyl, indolyl, indanyl, benzo[b]thiophenyl, benzodioxanyl, benzodioxinyl, benzodioxolyl, benz[d]isoxazolyl, quinolinyl, isoquinolinyl, and quinoxalinyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino, carboxylic acid, esters of carboxylic acids, aminocarbonyl, mono or di(C$_1$–C$_6$)alkylaminocarbonyl, N—(C$_1$–C$_6$)alkylsulfonylaminocarbonyl, 1-azetidinyl, 1-pyrrolidinyl, and 1-piperidyl, and bicyclic oxygen-containing groups of the formula:

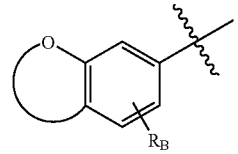

wherein R$_B$ represents 0 to 3 groups selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino.

Still additional preferred compounds of formula IX-A include those compounds wherein:

R is hydrogen, halogen, C$_1$–C$_8$ alkyl, C$_2$–C$_8$ alkenyl, C$_2$–C$_8$ alkynyl, C$_1$–C$_8$ cycloalkyl, (C$_3$–C$_8$cycloalkyl)C$_1$–C$_3$ alkyl, C$_1$–C$_8$ alkoxy, or C$_1$–C$_8$ haloalkyl, or R is a phenyl which may be substituted by up to five substituents independently chosen from C$_1$–C$_8$ alkyl, C$_2$–C$_8$ alkenyl, C$_2$–C$_8$ alkynyl, C$_1$–C$_8$ alkoxy, halogen, cyano, carboxylic acid, hydroxy, acetoxy, nitro, amino, mono or di(C$_1$–C$_6$)alkylamino, aminocarbonyl, sulfonamido, mono or di(C$_1$–C$_6$)alkylsulfonamido, 3,4-methylenedioxy, 3,4-(1,2-ethylene)dioxy, trifluoromethyl or trifluoromethoxy;

R$_1$ is hydrogen, C$_1$–C$_8$ alkyl, C$_2$–C$_8$ alkenyl, C$_2$–C$_8$ alkynyl, C$_3$–C$_8$ cycloalkyl (C$_3$–C$_8$cycloalkyl)C$_1$–C$_3$ alkyl or C$_1$–C$_8$ haloalkyl;

R$_2$ is C$_1$–C$_8$ alkyl, C$_2$–C$_8$ alkenyl, C$_2$–C$_8$ alkynyl, C$_1$–C$_8$ cycloalkyl or (C$_3$–C$_8$ cycloalkyl)C$_1$–C$_3$ alkyl or C$_1$–C$_8$ haloalkyl;

R$_3$ is hydrogen, C$_1$–C$_8$ alkyl, C$_2$–C$_8$ alkenyl, or C$_2$–C$_8$ alkynyl;

R$_4$ is C$_1$–C$_8$ alkyl, C$_3$–C$_8$ cycloalkyl, or (C$_3$–C$_8$ cycloalkyl) C$_1$–C$_3$ alkyl, each of which may be unsubstituted or substituted with one or more substituents selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, and mono- or di(C$_1$–C$_6$)alkylamino; or R$_4$ is phenyl, phenyl(C$_1$–C$_4$)alkyl, thienyl, pyridyl, pyrimidyl, pyrazinyl, naphthyl, indolyl, indanyl, benzo[b]thiophenyl, benzodioxinyl, benzodioxolyl, benz[d]isoxazolyl, quinolinyl, isoquinolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, C$_1$–C$_6$ alkyl, C$_2$–C$_6$ alkenyl, C$_2$–C$_6$ alkynyl, C$_1$–C$_6$ alkoxy, amino, mono- or di(C$_1$–C$_6$)alkylamino; or $R_4$ is a bicyclic oxygen-containing group of the formula:

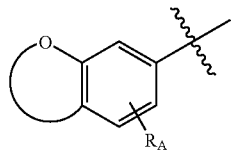

wherein $R_A$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino;

$Ar_1$ is phenyl, thienyl, or pyridyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$ alkylamino; and $Ar_2$ is phenyl, phenyl($C_1$–$C_4$)alkyl, thienyl, pyridyl, pyrimidyl, pyrazinyl, naphthyl, indolyl, indanyl, benzo[b]thiophenyl, benzodioxanyl, benzodioxinyl, benzodioxolyl, benz[d]isoxazolyl, quinolinyl, isoquinolinyl, and quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, and 1-piperidyl, or $Ar_2$ is a bicyclic oxygen-containing group of the formula:

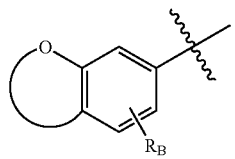

wherein $R_B$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino.

Still further preferred compounds of formula IX above include those wherein

R is hydrogen, halogen, methyl, ethyl, methoxy, ethoxy, trifluoromethyl, or phenyl;

$R_1$ is hydrogen, methyl or ethyl;

$R_2$ is $C_3$–$C_6$ alkyl;

$R_3$ is hydrogen, methyl or ethyl;

$R_4$ is $C_1$–$C_8$ alkyl, $C_3$–$C_8$ cycloalkyl, or ($C_3$–$C_8$ cycloalkyl) $C_1$–$C_3$ alkyl, each of which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino; or $R_4$ is phenyl, phenyl($C_1$–$C_4$)alkyl, thienyl, pyridyl, pyrimidyl, pyrazinyl, naphthyl, indolyl, indanyl, benzo[b]thiophenyl, benzodioxinyl, benzodioxolyl, benz[d]isoxazolyl, quinolinyl, isoquinolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino; or $R_4$ is a bicyclic oxygen-containing group of the formula:

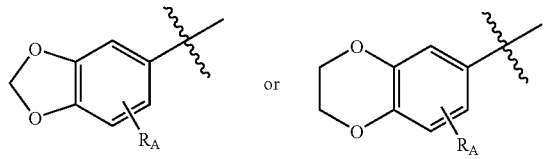

wherein $R_A$ represents 0 to 3 groups selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino;

$Ar_1$ is phenyl, thienyl, or pyridyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino; and $Ar_2$ is phenyl, phenyl($C_1$–$C_4$)alkyl, thienyl, pyridyl, pyrimidyl, pyrazinyl, naphthyl, indolyl, indanyl, benzo[b]thiophenyl, benzodioxanyl, benzodioxinyl, benzodioxolyl, benz[d]isoxazolyl, quinolinyl, isoquinolinyl, and quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_{2\text{-}6}$ alkynyl, $C_1$–$C_6$ alkoxy, amino, mono- or di($C_1$–$C_6$)alkylamino;

$Ar_2$ is a bicyclic oxygen-containing group of the formula:

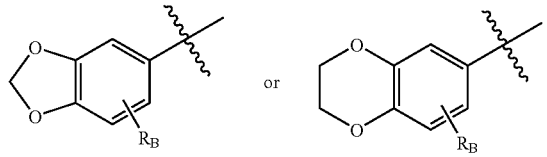

wherein $R_B$ represents 0 to 3 groups selected from halogen, nitro, cyano, trifluoromethyl, trifluoromethoxy, haloalkyl, hydroxy, acetoxy, $C_1$–$C_6$ alkyl, $C_2$ alkenyl, $C_2$–$C_6$ alkynyl, $C_1$–$C_6$ alkoxy, amino, and mono- or di($C_1$–$C_6$) alkylamino.

The invention also include compounds of the following formula X:

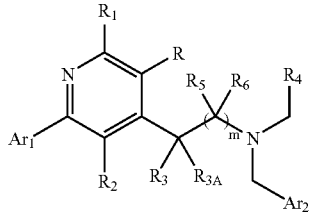

wherein:
m is 0, 1, or 2;
R is hydrogen, hydroxy, halogen, amino, cyano, nitro, haloalkyl, alkoxy, mono- or dialkylamino, optionally substituted alkyl, optionally substituted alkenyl, optionally substituted alkynyl, optionally substituted cycloalkyl, optionally substituted (cycloakyl)alkyl; or
R is optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms;
$R_1$, $R_2$, $R_3$, $R_{3A}$, $R_5$, and $R_6$ are independently selected from hydrogen, hydrogen, halogen, amino, cyano, nitro, haloalkyl, alkoxy, mono- or dialkylamino, optionally substituted alkyl, optionally substituted alkenyl, optionally substituted alkynyl, optionally substituted cycloalkyl and optionally substituted (cycloalkyl)alkyl;
$R_4$ is alkyl, alkenyl, alkynyl, cycloalkyl, (cycloalkyl)alkyl each of which may be optionally substituted; or
$R_4$ is optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms; and $Ar_1$ and $Ar_2$ are independently optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms.

Preferred compounds of formula X include those of the following formula X-A:

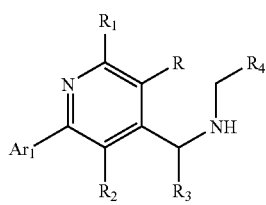

wherein $Ar_1$, R, $R_1$, $R_2$, $R_3$, $R_4$ are as defined for formula X above.

Additional preferred compounds of formula X include those wherein:
$R_1$, $R_2$, and $R_3$ are independently selected from
  i) hydrogen, halogen, hydroxy, amino, $C_1$–$C_6$ alkoxy, mono- or di($C_1$–$C_6$)alkylamino, cyano, nitro, haloalkyl, and
  ii) $C_1$–$C_8$ alkyl, $C_2$–$C_6$ alkenyl, $C_2$–$C_6$ alkynyl, $C_3$–$C_8$ cycloalkyl, and ($C_3$–$C_8$ cycloalkyl) $C_1$–$C_3$ alkyl, each of which may be unsubstituted or substituted by one or more of halogen, nitro, cyano, trifluoromethyl, trifluoromethoxy, haloalkyl, hydroxy, acetoxy, $C_1$–$C_6$ alkoxy, amino, mono- or di($C_1$–$C_6$)alkylamino;
R is selected from
  i) hydrogen, halogen, hydroxy, amino, $C_1$–$C_6$ alkoxy, mono- or di($C_1$–$C_6$)alkylamino, cyano, nitro, haloalkyl, and
  ii) $C_1$–$C_8$ alkyl, $C_2$–$C_6$ alkenyl, $C_2$–$C_6$ alkynyl, $C_3$–$C_8$ cycloalkyl, and ($C_3$–$C_8$)cycloalkyl) $C_1$–$C_3$ alkyl, each of which may be unsubstituted or substituted by one or more of halogen, nitro, cyano, trifluoromethyl, trifluoromethoxy, haloalkyl, hydroxy, acetoxy, alkoxy, amino, and mono- or di($C_1$–$C_6$)alkylamino; or
R is selected from
  phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, each of which may be optionally substituted or substituted with up to four groups independently selected from halogen, nitro, cyano, trifluoromethyl, trifluoromethoxy, haloalkyl, hydroxy, acetoxy, $C_1$–$C_8$ alkyl, $C_2$–$C_6$ alkenyl, $C_2$–$C_6$ alkynyl, $C_1$–$C_6$ alkoxy, amino, and mono- or di($C_1$–$C_6$)alkylamino;
$R_4$ is hydrogen or
  $C_{1-8}$ alkyl, $C_{2-8}$ alkenyl, $C_{2-8}$ alkynyl, $C_{3-8}$cycloalkyl, ($C_{3-8}$ cycloalkyl)$C_{1-4}$alkyl, haloalkyl, each or which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino and mono- or di($C_1$–$C_6$)alkylamino,
$R_4$ is phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, —$XR_5$, wherein X and $R_B$ are as defined below; or
$R_4$ is a bicyclic oxygen-containing group of the formula:

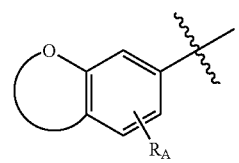

wherein $R_A$ represents 0 to 3 groups selected from halogen, nitro, cyano, trifluoromethyl, trifluoromethoxy, haloalkyl, hydroxy, acetoxy, $C_1-C_6$ alkyl, $C_{2-6}$ alkenyl, $C_{2-6}$ alkynyl, $C_1-C_6$ alkoxy, amino, and mono- or di($C_1-C_6$)alkylamino; and $Ar_1$ and $Ar_2$ are independently chosen from i) phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, $C_1-C_6$ alkyl, $C_{2-6}$ alkenyl, $C_{2-6}$ alkynyl, $C_1-C_6$ alkoxy, amino, mono- or di($C_1-C_6$)alkylamino, amino($C_1-C_6$)alkoxy, carboxylic acid, esters of carboxylic acids, aminocarbonyl, mono or di($C_1-C_6$)alkylaminocarbonyl, N—($C_1-C_6$)alkylsulfonylaminocarbonyl, 1-azetidinyl, 1-pyrrolidinyl, 1-piperidyl, and —$XR_B$, wherein X and $R_B$ are as defined below; and ii) bicyclic oxygen-containing groups of the formula:

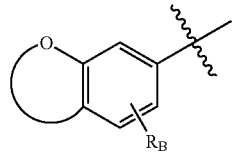

wherein $R_B$ represents 0 to 3 groups selected from halogen, nitro, cyano, trifluoromethyl, trifluoromethoxy, haloalkyl, hydroxy, acetoxy, $C_1-C_6$ alkyl, $C_{2-6}$ alkenyl, $C_{2-6}$ alkynyl, $C_1-C_6$ alkoxy, amino, and mono- or di($C_1-C_6$)alkylamino;

X is independently selected at each occurrence from the group consisting of —$CH_2$—, —$CHR_C$—, —O—, —$S(O)_m$—, —NH—, —$NR_C$—, —C(=O)NH—, —C(=O)$NR_C$—, —$S(O)_mNH$—, $S(O)_mNR_C$—, —NHC(=O)—, —$NR_CC(=O)$—, —$NHS(O)_m$—, —C(=O)$NHS(O)_m$—, and —$NR_CS(O)_m$— (where m is 0, 1, or 2); and $R_B$ and $R_C$, which may be the same or different, are independently selected at each occurrence from the group consisting of:

hydrogen, straight, branched, or cyclic alkyl groups, which may contain one or more double or triple bonds, each of which may unsubstituted or substituted with one or more substituent(s) selected from:

oxo, hydroxy, —O($C_1-C_6$ alkyl), —NH($C_1-C_6$ alkyl), —N($C_1-C_6$ alkyl)($C_1-C_6$ alkyl), —NHC(O)($C_1-C_6$ alkyl), —N($C_1-C_6$ alkyl)C(O)($C_{1-6}$ alkyl), —NHS(O)$_x$($C_1-C_6$ alkyl), —S(O)$_x$($C_1-C_6$ alkyl), —S(O)$_x$NH($C_1-C_6$ alkyl), —S(O)$_x$N($C_1-C_6$ alkyl)($C_1-C_6$ alkyl), (where x is 0, 1, or 2).

Additional preferred compounds of formula X above include those wherein:

R is hydrogen, halogen, methyl, ethyl, methoxy, ethoxy, trifluoromethyl, or phenyl;

$R_1$ is hydrogen, methyl or ethyl;

$R_2$ is $C_3-C_6$ alkyl;

$R_3$ is hydrogen, methyl or ethyl;

$R_4$ is $C_1-C_8$ alkyl, $C_3-C_8$ cycloalkyl, or ($C_3-C_8$ cycloalkyl)$C_1-C_3$ alkyl, each of which may be unsubstituted or substituted with one or more substituents selected from halogen, nitro, cyano, trifluoromethyl, trifluoromethoxy, haloalkyl, hydroxy, acetoxy, $C_1-C_6$ alkyl, $C_2-C_6$ alkenyl, $C_2-C_6$ alkynyl, $C_1-C_6$ alkoxy, amino, and mono- or di($C_1-C_6$)alkylamino; or $R_4$ is phenyl, phenyl($C_1-C_4$)alkyl, thienyl, pyridyl, pyrimidyl, pyrazinyl, naphthyl, indolyl, indanyl, benzo[b]thiophenyl, benzodioxinyl, benzodioxolyl, benz[d]isoxazolyl, quinolinyl, isoquinolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, $C_1-C_6$ alkyl, $C_2-C_6$ alkenyl, $C_2-C_6$ alkynyl, $C_1-C_6$ alkoxy, amino, mono- or di($C_1-C_6$)alkylamino; or $R_4$ is a bicyclic oxygen-containing group of the formula:

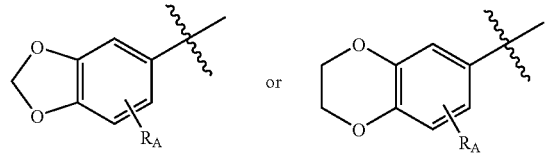

wherein $R_A$ represents 0 to 3 groups selected from halogen, nitro, cyano, trifluoromethyl, trifluoromethoxy, haloalkyl, hydroxy, acetoxy, $C_1-C_6$ alkyl, $C_2-C_6$ alkenyl, $C_2-C_6$ alkynyl, $C_1-C_6$ alkoxy, amino, and mono- or di($C_1-C_6$)alkylamino; and $Ar_1$ is phenyl, thienyl, or pyridyl, each of which may be optionally substituted or substituted with up to four groups independently selected from halogen, nitro, cyano, trifluoromethyl, trifluoromethoxy, haloalkyl, hydroxy, acetoxy, $C_1-C_6$ alkyl, $C_2-C_6$ alkenyl, $C_2-C_6$ alkynyl, $C_1-C_6$ alkoxy, amino, mono- or di($C_1-C_6$)alkylamino.

The invention also includes compounds of the following formula XI:

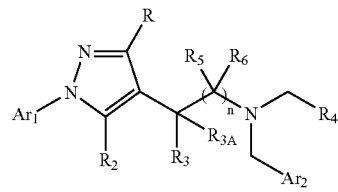

or pharmaceutically acceptable salt thereof, wherein:

n is 0, 1, or 2;

R is chosen from hydrogen, hydroxy, halogen, amino, cyano, nitro, haloalkyl, alkoxy, mono- or dialkylamino, optionally substituted alkyl, optionally substituted alkenyl, optionally substituted alkynyl, optionally substituted cycloalkyl, optionally substituted (cycloalkyl)alkyl, optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms;

$R_2$, $R_3$, $R_{3A}$, $R_5$, and $R_6$ are independently selected from hydrogen, hydroxy, halogen, amino, cyano, nitro, haloalkyl, alkoxy, mono- or dialkylamino, optionally substituted alkyl, optionally substituted alkenyl, optionally substituted alkynyl, optionally substituted cycloalkyl, and optionally substituted (cycloalkyl)alkyl;

R and $R_3$ may be joined to form an optionally substituted saturated carbocylic ring of from 5 to 8 members or an optionally substituted heterocyclic ring of from 5 to 8 members;

$R_4$ is alkyl, alkenyl, alkynyl, cycloalkyl, (cycloalkyl)alkyl each of which may be optionally substituted; or $R_4$ is optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms; and $Ar_1$ and $Ar_2$ are independently optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms.

The invention further includes compounds of the following formula XII:

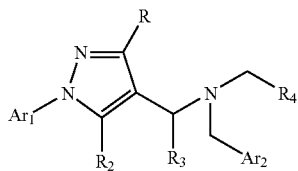

XII or a pharmaceutically acceptable salt thereof, wherein:

R is chosen from hydrogen, hydroxy, halogen, amino, cyano, nitro, haloalkyl, alkoxy, mono- or dialkylamino, optionally substituted alkyl, optionally substituted alkenyl, optionally substituted alkynyl, optionally substituted cycloalkyl, optionally substituted (cycloalkyl)alkyl, optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms;

$R_2$ and $R_3$ are independently selected from hydrogen, hydroxy, halogen, amino, cyano, nitro, haloalkyl, alkoxy, mono- or dialkylamino, optionally substituted alkyl, optionally substituted alkenyl, optionally substituted alkynyl, optionally substituted cycloalkyl, and optionally substituted (cycloalkyl)alkyl;

R and $R_3$ may be joined to form an optionally substituted carbocylic ring of from 5 to 8 members or an optionally substituted heterocyclic ring of from 5 to 8 members;

$R_4$ is alkyl, alkenyl, alkynyl, cycloalkyl, (cycloalkyl)alkyl each of which may be optionally substituted; or $R_4$ is optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms; and $Ar_1$ and $Ar_2$ are independently optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms.

Preferred compounds of formula XII above include wherein R and $R_3$ are not joined.

Also preferred are compounds of formula XII wherein:

R is selected from
   i) hydrogen, halogen, hydroxy, amino, alkoxy, mono- or dialkylamino, cyano, nitro, haloalkyl, and
   ii) alkyl, alkenyl, alkynyl, cycloalkyl, and (cycloalkyl)alkyl, each of which may be unsubstituted or substituted by one or more of halogen, nitro, cyano, trifluoromethyl, trifluoromethoxy, haloalkyl, hydroxy, acetoxy, alkoxy, amino, and mono- or dialkylamino,
   iii) phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, each of which may be substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino;

$R_2$ and $R_3$ are independently selected from
   i) hydrogen, halogen, hydroxy, amino, alkoxy, mono- or dialkylamino, cyano, nitro, haloalkyl, and
   ii) alkyl, alkenyl, alkynyl, cycloalkyl, and (cycloalkyl)alkyl, each of which may be unsubstituted or substituted by one or more of halogen, nitro, cyano, trifluoromethyl, trifluoromethoxy, haloalkyl, hydroxy, acetoxy, alkoxy, amino, and mono- or dialkylamino;

$R_4$ is hydrogen or
   alkyl, alkenyl, alkynyl, cycloalkyl, (cycloalkyl)alkyl, haloalkyl, each or which may be unsubstituted or substituted with one or more substituents selected from halogen, nitro, cyano, trifluoromethyl, trifluoromethoxy, haloalkyl, hydroxy, acetoxy, alkyl, alkenyl, alkynyl, alkoxy, amino and mono- or dialkylamino, $R_4$ is phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, mono- or dialkylamino, aminoalkoxy, carboxylic acid, esters of carboxylic acids, aminocarbonyl, mono or dialkylaminocarbonyl, N-alkylsulfonylaminocarbonyl, 1-azetidinyl, 1-pyrrolidinyl, 1-piperidyl and —$XR_B$, wherein X and $R_B$ are as defined below; or $R_4$ is a bicyclic oxygen-containing group of the formula:

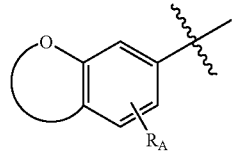

wherein $R_A$ represents 0 to 3 groups selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino;

$Ar_1$ and $Ar_2$ are independently chosen from
i) phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, mono- or dialkylamino, aminoalkoxy, carboxylic acid, esters of carboxylic acids, aminocarbonyl, mono or dialkylaminocarbonyl, N-alkylsulfonylaminocarbonyl, 1-azetidinyl, 1-pyrrolidinyl, 1-piperidyl and —$XR_B$, wherein X and $R_B$ are as defined below; and ii) bicyclic oxygen-containing groups of the formula:

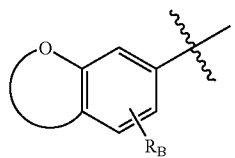

wherein $R_B$ represents 0 to 3 groups selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino;

X is independently selected at each occurrence from the group consisting of —$CH_2$—, —$CHR_C$—, —O—, —$S(O)_m$—, —NH—, —$NR_C$—, —$C(=O)NH$—, —$C(=O)NR_C$—, $S(O)_mNH$—, $S(O)_mNR_C$—, —NHC(=O)—, —$NR_CC(=O)$—, —$NHS(O)_m$—, $C(=O)NHS(O)_m$—, and —$NR_CS(O)_m$— (where m is 0, 1, or 2); and $R_B$ and $R_C$, which may be the same or different, are independently selected at each occurrence from the group consisting of:

hydrogen, straight, branched, or cyclic alkyl groups, which may contain one or more double or triple bonds, each of which may unsubstituted or substituted with one or more substituent(s) selected from:

oxo, hydroxy, —O(alkyl), —NH(alkyl), —N(alkyl)(alkyl), —NHC(O)(alkyl), —N(alkyl)C(O)(alkyl), —$NHS(O)_x$(alkyl), —$S(O)_x$(alkyl), —$S(O)_x$NH(alkyl), —$S(O)_x$N(alkyl)(alkyl), (where x is 0, 1, or 2).

Additional preferred compounds of formula XII include those wherein:

R is selected from
 i) hydrogen, halogen, hydroxy, amino, $C_1$–$C_6$ alkoxy, mono- or di($C_1$–$C_6$)alkylamino, cyano, nitro, haloalkyl, and
 ii) $C_1$–$C_8$ alkyl, $C_2$–$C_6$ alkenyl, $C_2$–$C_6$ alkynyl, $C_3$–$C_8$ cycloalkyl, and ($C_3$–$C_8$)cycloalkyl) $C_1$–$C_3$ alkyl, each of which may be unsubstituted or substituted by one or more of halogen, nitro, cyano, trifluoromethyl, trifluoromethoxy, haloalkyl, hydroxy, acetoxy, alkoxy, amino, and mono- or di($C_1$–$C_6$)alkylamino,
 iii) phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, each of which may be optionally substituted or substituted with up to four groups independently selected from halogen, nitro, cyano, trifluoromethyl, trifluoromethoxy, haloalkyl, hydroxy, acetoxy, $C_1$–$C_8$ alkyl, $C_2$–$C_6$ alkenyl, $C_2$–$C_6$ alkynyl, $C_1$–$C_6$ alkoxy, amino, and mono- or di($C_1$–$C_6$)alkylamino;

$R_2$ and $R_3$ are independently selected from
 i) hydrogen, halogen, hydroxy, amino, $C_1$–$C_6$ alkoxy, mono- or di($C_1$–$C_6$)alkylamino, cyano, nitro, haloalkyl, and
 ii) $C_1$–$C_8$ alkyl, $C_2$–$C_6$ alkenyl, $C_2$–$C_6$ alkynyl, $C_3$–$C_8$ cycloalkyl, and ($C_3$–$C_8$ cycloalkyl) $C_1$–$C_3$ alkyl, each of which may be unsubstituted or substituted by one or more of halogen, nitro, cyano, trifluoromethyl, trifluoromethoxy, haloalkyl, hydroxy, acetoxy, $C_1$–$C_6$ alkoxy, amino, mono- or di($C_1$–$C_6$)alkylamino;

$R_4$ is hydrogen or
 $C_{1-8}$ alkyl, $C_{2-8}$ alkenyl, $C_{2-8}$ alkynyl, $C_{3-8}$cycloalkyl, ($C_{3-8}$ cycloalkyl)$C_{1-4}$alkyl, haloalkyl, each or which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino and mono- or di($C_1$–$C_6$)alkylamino, $R_4$ is phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, —$XR_B$, wherein X and $R_B$ are as defined below; or $R_4$ is a bicyclic oxygen-containing group of the formula:

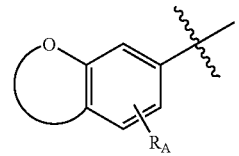

wherein $R_A$ represents 0 to 3 groups selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$)alkylamino;

$Ar_1$ and $Ar_2$ are independently chosen from
i) phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, and —$XR_B$, wherein X and $R_B$ are as defined below; and ii) bicyclic oxygen-containing groups of the formula:

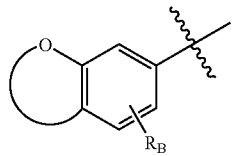

wherein $R_B$ represents 0 to 3 groups selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$)alkylamino;

X is independently selected at each occurrence from the group consisting of —$CH_2$—, —$CHR_C$—, —O—, —$S(O)_m$—, —NH—, —$NR_C$—, —C(=O)NH—, —C(=O)$NR_C$—, —$S(O)_m$NH—, —$S(O)_m NR_C$—, —NHC(=O)—, —$NR_C$C(=O)—, —$NHS(O)_m$—, —C(=O)$NHS(O)_m$—, and —$NR_C S(O)_m$— (where m is 0, 1, or 2); and $R_B$ and $R_C$, which may be the same or different, are independently selected at each occurrence from the group consisting of:

hydrogen, straight, branched, or cyclic alkyl groups, which may contain one or more double or triple bonds, each of which may unsubstituted or substituted with one or more substituent(s) selected from:

oxo, hydroxy, —O($C_1$–$C_6$ alkyl), —NH($C_1$–$C_6$ alkyl), —N($C_1$–$C_6$ alkyl)($C_1$–$C_6$ alkyl), —NHC(O)($C_1$–$C_6$ alkyl), —N($C_1$–$C_6$ alkyl)C(O)($C_{1-6}$ alkyl), —NHS(O)$_x$($C_1$–$C_6$ alkyl), —S(O)$_x$($C_1$–$C_6$ alkyl), —S(O)$_x$NH($C_1$–$C_6$ alkyl), —S(O)$_x$N($C_1$–$C_6$ alkyl)($C_1$–$C_6$ alkyl), (where x is 0, 1, or 2).

Also preferred are compounds of formula XII wherein:

R is hydrogen, halogen, hydroxy, $C_1$–$C_6$ alkoxy, haloalkyl, $C_1$–$C_8$ alkyl, $C_2$–$C_6$ alkenyl, $C_2$–$C_6$ alkynyl, $C_3$–$C_8$ cycloalkyl, and ($C_3$–$C_8$ cycloalkyl) $C_1$–$C_3$ alkyl, or R is phenyl substituted with up to five groups independently selected from halogen, nitro, cyano, trifluoromethyl, trifluoromethoxy, haloalkyl, hydroxy, acetoxy, $C_1$–$C_8$ alkyl, $C_2$–$C_6$ alkenyl, $C_2$–$C_6$ alkynyl, $C_1$–$C_6$ alkoxy, amino, and mono- or di($C_1$–$C_6$)alkylamino, aminocarbonyl, sufonamido, mono or di($C_1$–$C_6$)alkylsulfonamido, 3,4-methylenedioxy, and 3,4-(1,2-ethylene)dioxy;

$R_2$ is selected from $C_1$–$C_8$ alkyl, $C_2$–$C_6$ alkenyl, $C_2$–$C_6$ alkynyl, $C_3$–$C_8$ cycloalkyl, ($C_3$–$C_8$ cycloalkyl) $C_1$–$C_3$ alkyl and haloalkyl;

$R_3$ is hydrogen $C_1$–$C_8$ alkyl, $C_2$–$C_4$ alkenyl, $C_2$–$C_6$ alkynyl;

$R_4$ is $C_{1-8}$ alkyl, $C_{2-8}$ alkenyl, $C_{2-8}$ alkynyl, $C_{3-8}$cycloalkyl, ($C_{3-8}$ cycloalkyl)$C_{1-4}$alkyl, haloalkyl, each or which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino and mono- or di($C_1$–$C_6$)alkylamino, $R_4$ is phenyl, phenyl($C_1$–$C_4$)alkyl, thienyl, pyridyl, pyrimidyl, pyrazinyl, chromanyl, dihydrobenzofuranyl, naphthyl, indolyl, indanyl, benzo[b]thiophenyl, benzodioxanyl, benzodioxinyl, benzodioxolyl, benz[d]isoxazolyl, each of which may be substituted with up to five groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, $R_4$ is a bicyclic oxygen-containing group of the formula:

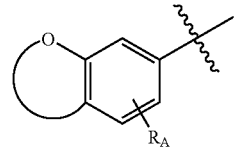

wherein $R_A$ represents 0 to 3 groups selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$)alkylamino;

$Ar_1$ and $Ar_2$ are independently chosen from i) phenyl, phenyl($C_1$–$C_4$)alkyl, thienyl, pyridyl, pyrimidyl, pyrazinyl, chromanyl, dihydrobenzofuranyl, naphthyl, indolyl, indanyl, benzo[b]thiophenyl, benzodioxanyl, benzodioxinyl, benzodioxolyl, and benz[d]isoxazolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$) alkylamino, amino($C_1$–$C_6$)alkoxy, carboxylic acid, esters of carboxylic acids, aminocarbonyl, mono or di($C_1$–$C_6$) alkylaminocarbonyl, N—($C_1$–$C_6$)alkylsulfonylaminocarbonyl, 1-azetidinyl, 1-pyrrolidinyl, 1-piperidyl; or ii) bicyclic oxygen-containing groups of the formula:

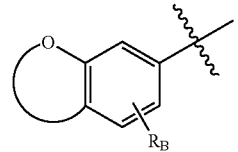

wherein $R_B$ represents 0 to 3 groups selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$) alkylamino.

Also preferred are compounds of formula XII wherein:

R, $R_2$, $R_3$, $R_4$, and $Ar_2$ are as defined in formula XII;

$Ar_1$ is phenyl with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, and amino($C_1$–$C_6$)alkoxy.

Also preferred are compounds of formula XII wherein:

R, $R_2$, and $R_3$ are as defined in formula XII;

$Ar_1$ is phenyl with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, and amino($C_1$–$C_6$)alkoxy;

$R_4$ is $C_3$–$C_8$ alkyl, $C_2$–$C_8$ alkenyl, $C_2$–$C_8$ alkynyl, $C_3$–$C_8$cycloalkyl, ($C_{3-8}$ cycloalkyl)$C_1$–$C_4$alkyl, $C_1$–$C_8$ haloalkyl, each or which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino and mono- or di($C_1$–$C_6$)alkylamino, $R_4$ is phenyl, phenyl($C_1$–$C_4$)alkyl, thienyl, pyridyl, pyrimidyl, pyrazinyl, chromanyl, dihydrobenzofuranyl, naphthyl, indolyl, indanyl, benzo[b]thiophenyl, benzodioxanyl, benzodioxinyl, benzodioxolyl, benz[d]isoxazolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$) alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl;

$Ar_2$ is phenyl, phenyl($C_1$–$C_4$)alkyl, thienyl, pyridyl, pyrimidyl, pyrazinyl, chromanyl, dihydrobenzofuranyl, naphthyl, indolyl, indanyl, benzo[b]thiophenyl, benzodioxanyl, benzodioxinyl, benzodioxolyl, or benz[d]isoxazolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl; or $Ar_2$ is bicyclic oxygen-containing groups of the formula:

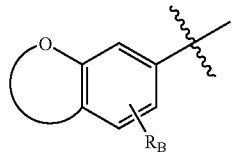

wherein $R_B$ represents 0 to 3 groups selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$) alkylamino.

Also preferred are compounds of formula XII wherein:

R is hydrogen, $C_1$–$C_8$ alkyl, $C_2$–$C_6$ alkenyl, $C_2$–$C_6$ alkynyl, $C_3$–$C_8$ cycloalkyl, or ($C_3$–$C_8$)cycloalkyl) $C_1$–$C_3$ alkyl, or R is phenyl substituted with up to five groups independently selected from halogen, nitro, cyano, trifluoromethyl, trifluoromethoxy, haloalkyl, hydroxy, acetoxy, $C_1$–$C_8$ alkyl, $C_2$–$C_6$ alkenyl, $C_2$–$C_6$ alkynyl, $C_1$–$C_6$ alkoxy, amino, and mono- or di($C_1$–$C_6$)alkylamino, aminocarbonyl, sufonamido, mono or di($C_1$–$C_6$)alkylsulfonamido, 3,4-methylenedioxy, and 3,4-(1,2-ethylene)dioxy;

$R_2$ is $C_3$–$C_6$ alkyl;

$R_3$ is hydrogen, methyl, or ethyl;

$R_4$ is $C_3$–$C_8$ alkyl, $C_2$–$C_8$ alkenyl, $C_2$–$C_8$ alkynyl, $C_3$–$C_8$cycloalkyl, ($C_{3-8}$ cycloalkyl)$C_1$–$C_4$alkyl, $C_1$–$C_8$ haloalkyl, each or which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino and mono- or di($C_1$–$C_6$)alkylamino, $R_4$ is phenyl, phenyl($C_1$–$C_4$)alkyl, thienyl, pyridyl, pyrimidyl, pyrazinyl, chromanyl, dihydrobenzofuranyl, naphthyl, indolyl, indanyl, benzo[b]thiophenyl, benzodioxanyl, benzodioxinyl, benzodioxolyl, benz[d]isoxazolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$) alkylamino, amino($C_1$–$C_6$)alkoxy, carboxylic acid, esters of carboxylic acids, aminocarbonyl, mono or di($C_1$–$C_6$) alkylaminocarbonyl, N—($C_1$–$C_6$)alkylsulfonylaminocarbonyl, 1-azetidinyl, 1-pyrrolidinyl, 1-piperidyl;

$Ar_1$ is phenyl with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, and amino($C_1$–$C_6$)alkoxy;

$Ar_2$ is phenyl, phenyl($C_1$–$C_4$)alkyl, thienyl, pyridyl, pyrimidyl, pyrazinyl, chromanyl, dihydrobenzofuranyl, naphthyl, indolyl, indanyl, benzo[b]thiophenyl, benzodioxanyl, benzodioxinyl, benzodioxolyl, or benz[d]isoxazolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$) alkylamino, amino($C_1$–$C_6$)alkoxy, carboxylic acid, esters of carboxylic acids, aminocarbonyl, mono or di($C_1$–$C_6$) alkylaminocarbonyl, N—($C_1$–$C_6$)alkylsulfonylaminocarbonyl, 1-azetidinyl, 1-pyrrolidinyl, 1-piperidyl; or $Ar_2$ is bicyclic oxygen-containing groups of the formula:

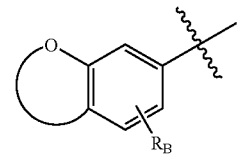

wherein $R_B$ represents 0 to 3 groups selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$) alkylamino.

Also preferred are compounds of formula XII wherein:

R is hydrogen, $C_1$–$C_8$ alkyl, $C_2$–$C_6$ alkenyl, $C_2$–$C_6$ alkynyl, $C_3$–$C_8$ cycloalkyl, or ($C_3$–$C_8$)cycloalkyl) $C_1$–$C_3$ alkyl, or phenyl;

$R_2$ is $C_3$–$C_6$ alkyl;

$R_3$ is hydrogen, methyl, or ethyl;

$R_4$ is $C_3$–$C_8$ alkyl, $C_2$–$C_8$ alkenyl, $C_2$–$C_8$ alkynyl, $C_3$–$C_8$cycloalkyl, ($C_{3-8}$ cycloalkyl)$C_1$–$C_4$alkyl, $C_1$–$C_8$ haloalkyl, each or which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino and mono- or di($C_1$–$C_6$)alkylamino;

$Ar_1$ is phenyl with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, and amino($C_1$–$C_6$)alkoxy; and $Ar_2$ is phenyl, phenyl($C_1$–$C_4$)alkyl, thienyl, pyridyl, pyrimidyl, pyrazinyl, chromanyl, dihydrobenzofuranyl, naphthyl, indolyl, indanyl, benzo[b]thiophenyl, benzodioxanyl, benzodioxinyl, benzodioxolyl, or benz[d]isoxazolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl; or $Ar_2$ is bicyclic oxygen-containing groups of the formula:

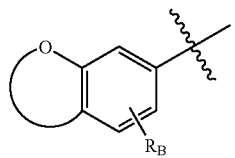

wherein $R_B$ represents 0 to 3 groups selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$) alkylamino.

Also preferred are compounds of formula XII wherein:

R is hydrogen, $C_1$–$C_8$ alkyl, $C_2$–$C_6$ alkenyl, $C_2$–$C_6$ alkynyl, $C_3$–$C_8$ cycloalkyl, or ($C_3$–$C_8$)cycloalkyl) $C_1$–$C_3$ alkyl, or phenyl;

$R_2$ is $C_3$–$C_6$ alkyl;

$R_3$ is hydrogen, methyl, or ethyl;

$R_4$ is phenyl, phenyl($C_1$–$C_4$)alkyl, thienyl, pyridyl, pyrimidyl, pyrazinyl, chromanyl, dihydrobenzofuranyl, naphthyl, indolyl, indanyl, benzo[b]thiophenyl, benzodioxanyl, benzodioxinyl, benzodioxolyl, benz[d]isoxazolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl;

$Ar_1$ is phenyl with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, and amino($C_1$–$C_6$)alkoxy;

$Ar_2$ is phenyl, phenyl($C_1$–$C_4$)alkyl, thienyl, pyridyl, pyrimidyl, pyrazinyl, chromanyl, dihydrobenzofuranyl, naphthyl, indolyl, indanyl, benzo[b]thiophenyl, benzodioxanyl, benzodioxinyl, benzodioxolyl, or benz[d]isoxazolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl; or $Ar_2$ is bicyclic oxygen-containing groups of the formula:

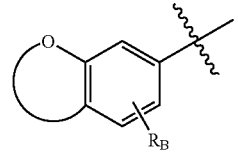

wherein $R_B$ represents 0 to 3 groups selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$) alkylamino.

The invention also includes compounds of the following formula XIII:

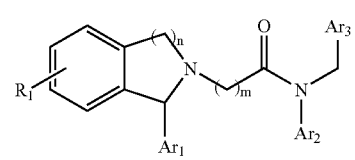

XIII or a pharmaceutically acceptable salt thereof, wherein:

n is 1, 2, or 3

represents a carbon chain that may be substituted with hydrogen, halogen, cyano, nitro amino, mono or dialkyl amino, alkenyl, alkynyl, alkoxy, trifluoromethyl, trifluoromethoxy, straight or branched chain alkyl, or cycloalkyl, and n is 1, 2, or 3;

$Ar_1$, $Ar_2$, and $Ar_3$ are independently optionally substituted carbocyclic aryl, optionally substituted arylalkyl, optionally substituted heteroaryl or heteroalicyclic group having from 1 to 3 rings, 3 to 8 members in each ring and from 1 to 3 heteroatoms; and $R_1$ represents up to 4 groups independently chosen from hydrogen, halogen, hydroxy, amino, alkoxy, acetoxy, mono- or dialkylamino, cyano, nitro, haloalkyl, alkyl, alkenyl, alkynyl, cycloalkyl, (cycloalkyl)alkyl, hydroxy carbonyl (COOH), aminocarbonyl (CONH$_2$), mono or dialkylaminocarbonyl, sulfonamido, and mono or dialkylsulfonamido.

Also preferred are compounds of formula XIII wherein n, m, and $R_1$ are defined as for formula XIII above;

$Ar_1$ and $Ar_3$ are independently chosen from phenyl, pyridyl, and pyrimidinyl each of which is optionally substituted or substituted with up to 4 groups independently chosen from hydrogen, halogen, hydroxy, amino, $C_1$–$C_6$ alkoxy, acetoxy, mono- or di($C_1$–$C_6$)alkylamino, cyano, nitro, $C_1$–$C_6$ haloalkyl, $C_1$–$C_6$ alkyl, $C_2$–$C_6$ alkenyl, $C_2$–$C_6$ alkynyl, $C_3$–$C_8$ cycloalkyl, ($C_3$–$C_8$cycloalkyl) $C_1$–$C_3$ alkyl, hydroxy carbonyl (COOH), aminocarbonyl (CONH$_2$), mono or di($C_1$–$C_6$)alkylaminocarbonyl, sulfonamido, 3,4-methylenedioxy, ethylenedioxy, and mono or di($C_1$–$C_6$)alkylsulfonamido; and Ar₂ represents suberanyl, indanyl, tetrhydronaphtyl, or indolyl, each of which is optionally substituted or substituted with up to 4 groups independently chosen from hydrogen, halogen, hydroxy, amino, $C_1$–$C_6$ alkoxy, acetoxy, mono- or di($C_1$–$C_6$alkylamino, cyano, nitro, $C_1$–$C_6$ haloalkyl, $C_1$–$C_6$ alkyl, $C_2$–$C_6$ alkenyl, $C_2$–$C_6$ alkynyl, $C_3$–$C_8$ cycloalkyl, ($C_3$–$C_8$cycloalkyl) $C_1$–$C_3$ alkyl, hydroxy carbonyl (COOH), aminocarbonyl (CONH₂), mono or di($C_1$–$C_6$)alkylaminocarbonyl, sulfonamido, 3,4-methylenedioxy, ethylenedioxy, and mono or di($C_1$–$C_6$)alkylsulfonamido.

Also preferred are compounds of formula XIII above wherein:

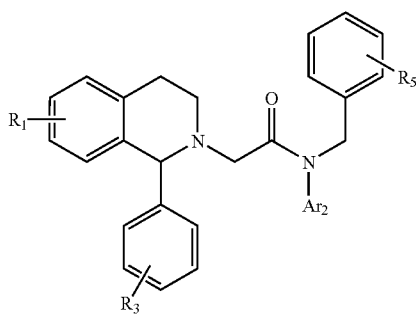

$R_1$, $R_3$, and $R_5$ each represent up to 4 groups independently chosen from hydrogen, halogen, hydroxy, amino, $C_1$–$C_6$ alkoxy, acetoxy, mono- or di($C_1$–$C_6$)alkylamino, cyano, nitro, $C_1$–$C_6$ haloalkyl, $C_1$–$C_6$ alkyl, $C_2$–$C_6$ alkenyl, $C_2$–$C_6$ alkynyl, $C_3$–$C_8$ cycloalkyl, ($C_3$–$C_8$cycloalkyl) $C_1$–$C_3$ alkyl, hydroxy carbonyl (COOH), aminocarbonyl (CONH₂), mono or di($C_1$–$C_6$)alkylaminocarbonyl, sulfonamido, and mono or di($C_1$–$C_6$)alkylsulfonamido; and represents suberanyl, indanyl, tetrhydronaphtyl, or indolyl, each of which is optionally optionally substituted or substituted with up to 4 groups independently chosen from hydrogen, halogen, hydroxy, amino, $C_1$–$C_6$ alkoxy, acetoxy, mono- or di($C_1$–$C_6$)alkylamino, cyano, nitro, $C_1$–$C_6$ haloalkyl, $C_1$–$C_6$ alkyl, $C_2$–$C_6$ alkenyl, $C_2$–$C_6$ alkynyl, $C_3$–$C_8$ cycloalkyl, ($C_3$–$C_8$ cycloalkyl) $C_1$–$C_3$ alkyl, hydroxy carbonyl (COOH), aminocarbonyl (CONH₂), mono or di($C_1$–$C_6$)alkylaminocarbonyl, sulfonamido, 3,4-methylenedioxy, ethylenedioxy, and mono or di($C_1$–$C_6$)alkylsulfonamido.

The invention also includes compounds of the following formula XIV:

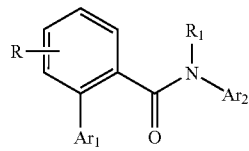

or a pharmaceutically acceptable salt, thereof, wherein:

R represents up to 4 groups independently chosen from hydrogen, halogen, hydroxy, amino, alkoxy, acetoxy, mono- or dialkylamino, cyano, nitro, haloalkyl, alkyl, alkenyl, alkynyl, cycloalkyl, (cycloalkyl)alkyl, hydroxy carbonyl (COOH), aminocarbonyl (CONH₂), mono or di($C_1$–$C_6$)alkylaminocarbonyl, sulfonamido, 3,4-methylenedioxy, ethylenedioxy, and mono or dialkylsulfonamido;

$R_1$ is alkyl, alkenyl, alkynyl, cycloalkyl, (cycloalkyl)alkyl each of which may be optionally substituted; or $R_1$ is optionally substituted carbocyclic aryl, optionally substituted arylalkyl, optionally substituted heteroaryl, optionally substituted heteroarylalkyl, optionally substituted heteroarylalkyl, or an optionally substituted heteroalicyclic or heteroalicyclicalkyl group having from 1 to 3 rings, 3 to 8 members in each ring and from 1 to 3 heteroatoms; and $Ar_1$ and $Ar_2$ are independently optionally substituted carbocyclic aryl, optionally substituted arylalkyl, optionally substituted heteroaryl, optionally substituted heteroarylalkyl, or an optionally substituted heteroalicyclic or heteroalicyclicalkyl group having from 1 to 3 rings, 3 to 8 members in each ring and from 1 to 3 heteroatoms.

Preferred compounds of formula XIV include those (referred to herein as compounds of formula XIV-A) wherein R represents up to 4 groups independently chosen from hydrogen, halogen, hydroxy, amino, $C_1$–$C_6$ alkoxy, acetoxy, mono- or di($C_1$–$C_6$)alkylamino, cyano, nitro, $C_1$–$C_6$ haloalkyl, $C_1$–$C_6$ alkyl, $C_2$–$C_6$ alkenyl, $C_2$–$C_6$ alkynyl, $C_3$–$C_8$ cycloalkyl, ($C_3$–$C_8$ cycloalkyl) $C_1$–$C_3$ alkyl, hydroxy carbonyl (COOH), aminocarbonyl (CONH₂), mono or di($C_1$–$C_6$)alkylaminocarbonyl, sulfonamido, 3,4-methylenedioxy, ethylenedioxy, and mono or di($C_1$–$C_6$)alkylsulfonamido;

$R_1$ is $C_{1-8}$ alkyl, $C_{2-8}$ alkenyl, $C_{2-8}$ alkynyl, $C_{3-8}$cycloalkyl, ($C_{3-8}$ cycloalkyl)$C_{1-4}$alkyl, each or which may be unsubstituted or substituted with one or more substituents selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino and mono- or di($C_1$–$C_6$)alkylamino, or $R_1$ is phenyl, phenylalkyl, chromanyl, chromanylalkyl, imidazolyl, imidazolylalkyl, pyridyl, pyridylalkyl, pyrimidyl, pyrimdylalkyl, pyrazinyl, pyrazinylalkyl, indolyl, indolylalkyl, indanyl, indanylalkyl, benzodioxolylalkyl, or benzodioxolyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, and 1-piperidyl;

$Ar_1$ is chosen from phenyl, pyrrolyl, imidazolyl, pyrazolyl, triazolyl, thiophenyl, and pyridyl, each of which may be optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino ($C_1$–$C_6$)alkoxy, carboxylic acid, esters of carboxylic acids, aminocarbonyl, mono or di($C_1$–$C_6$)alkylaminocarbonyl, and N—($C_1$–$C_6$)alkylsulfonylaminocarbonyl; and $Ar_2$ is chosen from phenyl, phenylalkyl, chromanyl, chromanylalkyl, pyrrolyl, pyrrolylalkyl, furanyl, furanylalkyl, thienyl, thienylalkyl, pyridyl, pyridylalkyl, pyrimidyl, pyrimidylalkyl, pyrazinyl, pyrazinylalkyl, benzimidazolyl, benzimidazolylalkyl, imidazopyrdinyl, imidazopyrdinylalkyl, naphthyl, napthylalkyl, indolyl, indolylalkyl, indanyl, indanylalkyl, benzofuranyl, benzofuranylalkyl, benzodioxinyl, benzodioxinylalkyl, benzodioxolyl, benzodioxolylalkyl, quinolinyl, quinolinylalkyl, isoquinolinyl, isoquinolinylalkyl, each of which may be optionally substituted or substituted with up to four groups independently selected from:

halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, mono- or di($C_1$–$C_6$)alkylamino($C_1$–$C_6$)alkyl, amino($C_1$–$C_6$)alkoxy, $C_1$–$C_6$ alkoxy$C_1$–$C_6$ alkyl, $C_1$–$C_6$ alkoxy$C_1$–$C_6$ alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, benzyl (which may be unsubstituted or substituted with one or more substituents independently chosen from halogen, $C_1$–$C_6$alkyl, and $C_1$–$C_6$alkoxy), —$C_1$–$C_6$ alkyl NR$_2$R$_3$ or —$C_1$–$C_6$alkoxy NR$_2$R$_3$ wherein the point of attachment to Ar$_2$ is at the $C_1$–$C_6$ alkyl or $C_1$–$C_6$ alkoxy, and R$_2$ and R$_3$ are hydrogen, or straight or branched chain alkyl and are optionally substituted with halogen, hydroxy, or $C_1$–$C_6$ alkoxy and R$_2$ and R$_3$ may be taken together with the nitrogen to which they are attached to form a heterocycloalkyl group.

Preferred compounds of formula XIV-A include those wherein:

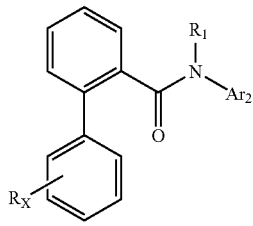

wherein:

Ar$_2$ is as defined in Claim in formula XIV-A;

R$_X$ represents up to 4 groups independently chosen from hydrogen, halogen, hydroxy, amino, $C_1$–$C_6$ alkoxy, acetoxy, mono- or di($C_1$–$C_6$)alkylamino, cyano, nitro, $C_1$–$C_6$ haloalkyl, $C_1$–$C_6$ alkyl, $C_2$–$C_6$ alkenyl, and $C_2$–$C_6$ alkynyl; and R$_1$ is $C_1$–$C_6$alkyl, $C_3$–$C_8$cycloalkyl, ($C_3$–$C_8$ cycloalkyl)$C_1$–$C_4$alkyl, phenyl, phenyl, $C_1$–$C_6$alkyl, chromanyl, chromanyl$C_1$–$C_6$alkyl, imidazolyl, imidazolyl$C_1$–$C_6$alkyl, pyridyl, pyridyl$C_1$–$C_6$alkyl, pyrimidyl, pyrimidyl$C_1$–$C_6$alkyl, pyrazinyl, pyrazinyl$C_1$–$C_6$alkyl, indolyl, indolyl$C_1$–$C_6$alkyl, indanyl, indanyl$C_1$–$C_6$alkyl, benzodioxolyl, or benzodioxolyl$C_1$–$C_6$alkyl each or which may be unsubstituted or substituted with up to 4 substituents selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino and mono- or di($C_1$–$C_6$)alkylamino.

Additional preferred compounds of formula XIV-A includes those of the following formula:

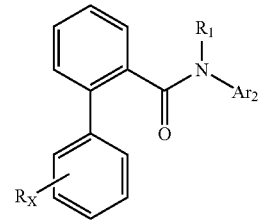

wherein:

R$_X$ represents up to 4 groups independently chosen from hydrogen, halogen, hydroxy, amino, $C_1$–$C_6$ alkoxy substituted with 0–2 R$_2$, acetoxy, mono- or di($C_1$–$C_6$)alkylamino, cyano, nitro, $C_1$–$C_6$ haloalkyl, $C_1$–$C_6$ alkyl, $C_2$–$C_6$ alkenyl, and $C_2$–$C_6$ alkynyl;

R$_1$ is phenyl, phenyl$C_1$–$C_6$ alkyl, $C_3$–$C_8$ cycloalkyl, $C_3$–$C_8$ cycloalky($C_1$–$C_4$ alkyl), naphthyl, napthyl$C_1$–$C_6$alkyl, indanyl, indanyl$C_1$–$C_6$ alkyl, benzodioxolanyl, or benzodioxolanyl$C_1$–$C_6$ alkyl, each of which may be substituted by up to 4 groups chosen from halogen, hydroxy, amino, $C_1$–$C_6$ alkoxy, acetoxy, mono- or di($C_1$–$C_6$)alkylamino, cyano, nitro, $C_1$–$C_6$ haloalkyl, $C_1$–$C_6$ alkyl; and Ar$_2$ represents phenyl, benzyl, indanyl, indanyl-CH$_2$—, benzodioxolanyl, or benzodioxolanyl-CH$_2$—; each of which is substituted by up to 4 groups independently chosen from hydrogen, halogen, hydroxy, amino, $C_1$–$C_6$ alkoxy, acetoxy, mono- or di($C_1$–$C_6$)alkylamino, cyano, nitro, $C_1$–$C_6$ haloalkyl, $C_1$–$C_6$ alkyl, $C_2$–$C_6$ alkenyl, and $C_2$–$C_6$ alkynyl.

Additional preferred compounds of formula XIV includes those wherein:

Ar$_2$ is as defined for formula XIV;

R represents up to 4 groups independently chosen from hydrogen, halogen, amino, $C_1$–$C_6$ alkoxy, $C_1$–$C_6$ alkyl, trifluoromethyl, and trifluoromethoxy;

R$_1$ is phenyl, benzyl, $C_3$–$C_8$ cycloalkyl, $C_3$–$C_8$ cycloalkyl ($C_1$–$C_4$ alkyl), naphthyl, naphthyl-CH$_2$—, indanyl, indandyl-CH$_2$—, benzodioxolanyl-CH$_2$—, or benzodioxolanyl, each of which may be substituted by up to 4 groups chosen from halogen, hydroxy, amino, $C_1$–$C_6$ alkoxy, acetoxy, mono- or di($C_1$–$C_6$)alkylamino, cyano, nitro, $C_1$–$C_6$ haloalkyl, $C_1$–$C_6$ alkyl; and Ar$_1$ is chosen from pyrrolyl, imidazolyl, pyrazolyl, triazolyl, thiophenyl, each of which may be optionally substituted or substituted with up to four groups independently selected from halogen, trifluoromethyl, trifluoromethoxy, $C_1$–$C_6$ alkoxy, $C_1$–$C_6$ alkyl, and amino.

Also preferred are compounds of the formula XIV above wherein:

R represents up to 4 groups independently chosen from hydrogen, halogen, amino, $C_1$–$C_6$ alkoxy, $C_1$–$C_6$ alkyl, trifluoromethyl, and trifluoromethoxy;

R$_1$ is benzyl which is unsubstituted or substituted by up to 4 groups chosen from halogen, hydroxy, amino, $C_1$–$C_6$ alkoxy, acetoxy, mono- or di($C_1$–$C_6$)alkylamino, cyano, nitro, $C_1$–$C_6$ haloalkyl, $C_1$–$C_6$ alkyl;

Ar$_1$ is chosen from pyrrolyl, imidazolyl, pyrazolyl, triazolyl, thiophenyl, each of which may be optionally substituted or substituted with up to four groups independently selected from halogen, trifluoromethyl, trifluoromethoxy, $C_1$–$C_6$ alkoxy, $C_1$–$C_6$ alkyl, and amino; and Ar₂ is chosen from phenyl, benzyl, indolyl, indolyl-CH₂—, indanyl, indanyl-CH₂—, chromanyl, chromanyl-CH₂—, benzofuranyl, benzofuranyl-CH₂—, benzodioxinyl, benzodioxinyl-CH₂—, benzodioxolyl-CH₂—, and benzodioxolyl, each of which may be optionally substituted or substituted with up to four groups independently selected from:
halogen, nitro, cyano, trifluoromethyl, trifluoromethoxy, haloalkyl, hydroxy, acetoxy, C₁–C₆ alkyl, C₂₋₆ alkenyl, C₂₋₆ alkynyl, C₁–C₆ alkoxy, amino, and mono- or di(C₁–C₆)alkylamino.

Preferred compounds of formula XIV also include those of the following formula IV-B:

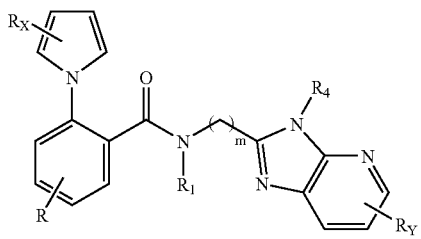

wherein:
m is 0, 1, 2, or 3, and

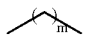

represents a carbon chain which is optionally substituted with methyl, ethyl, methoxy, ethoxy, hydoxy, halogen, or amino;
R represents up to 4 groups independently chosen from hydrogen, halogen, hydroxy, amino, C₁–C₆alkyl, C₂–C₆ alkenyl, C₁–C₆ alkynyl, C₁–C₆ alkoxy, acetoxy, mono- or di(C₁–C₆)alkylamino;
R_X and R_Y each represent up to 4 groups independently chosen from hydrogen, halogen, hydroxy, amino, C₁–C₆ alkoxy, acetoxy, mono- or di(C₁–C₆)alkylamino, cyano, nitro, C₁–C₆ haloalkyl, C₁–C₆ alkyl, C₂–C₆ alkenyl, and C₂–C₆ alkynyl; and
R₁ and R₄ are independently selected from C₁–C₆alkyl, C₃–C₈cycloalkyl, (C₃–C₈ cycloalkyl)C₁–C₄alkyl, phenyl, phenylC₁–C₆alkyl, pyridyl, and pyridylC₁–C₆alkyl, each or which may be unsubstituted or substituted with up to 4 substituents selected from halogen, nitro, cyano, trifluoromethyl, trifluoromethoxy, haloalkyl, hydroxy, acetoxy, C₁–C₆ alkyl, C₂₋₆ alkenyl, C₂₋₆ alkynyl, C₁–C₆ alkoxy, amino and mono- or di(C₁–C₆)alkylamino.

The invention also provides compounds of the following formula XV:

or a pharmaceutically acceptable salt thereof, wherein;
m is 0, 1, 2, or 3, and

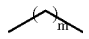

represents a carbon chain which is optionally substituted with methyl, ethyl, methoxy, ethoxy, hydoxy, halogen, or amino;
n is 0, 1, 2, or 3, and

represents a carbon chain which is optionally substituted with methyl, ethyl, methoxy, ethoxy, hydoxy, halogen, or amino;
R represents up to 4 groups independently chosen from hydrogen, halogen, hydroxy, amino, alkoxy, acetoxy, mono- or dialkylamino, cyano, nitro, haloalkyl, alkyl, alkenyl, alkynyl, cycloalkyl, and (cycloalkyl)alkyl;
R₂ is
  i) hydrogen, halogen, hydroxy, amino, alkoxy, mono- or dialkylamino, cyano, nitro, haloalkyl, and
  ii) alkyl, alkenyl, alkynyl, cycloalkyl, and (cycloalkyl)alkyl, each of which may be unsubstituted or substituted by one or more of halogen, nitro, cyano, trifluoromethyl, trifluoromethoxy, haloalkyl, hydroxy, acetoxy, alkoxy, amino, mono- or dialkylamino; and
Ar₁ and Ar₂ are independently optionally substituted carbocyclic aryl, optionally substituted arylalkyl, optionally substituted heteroaryl, optionally substituted heteroarylalkyl, optionally substituted heteroarylalkyl, or an optionally substituted heteroalicyclic or heteroalicyclicalkyl group having from 1 to 3 rings, 3 to 8 members in each ring and from 1 to 3 heteroatoms.

Preferred compounds of formula XV include those of the following formula:
m is 1 and

represents a carbon chain which is unsubstituted;
n is 1 and

represents a carbon chain which is unsubstituted;
R represents up to 4 groups independently chosen from hydrogen, halogen, hydroxy, amino, C₁–C₆ alkoxy, acetoxy, mono- or di(C₁–C₆)alkylamino, cyano, nitro, $C_1$–$C_6$ haloalkyl, $C_1$–$C_6$ alkyl, $C_2$–$C_6$ alkenyl, $C_2$–$C_6$ alkynyl, $C_2$–$C_6$ cycloalkyl, and ($C_3$–$C_8$ cycloalkyl) $C_1$–$C_4$ alkyl;

$R_2$ is $C_3$–$C_8$ alkyl or $C_3$–$C_8$ cycloalkyl;

$Ar_1$ and $Ar_2$ are independently chosen from phenyl, phenyl ($C_1$–$C_4$)alkyl, pyrrolyl, furanyl, thienyl, pyrazolyl, imidazolyl, thiazolyl, pyridyl, pyrimidyl, and pyrazinyl, each of which may be unsubstituted or optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino.

Compounds of the invention may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

Some compounds of the invention may exist as tautomers. Unless otherwise specified any description or claim of one tautomeric form is intended to encompass the other tautomer.

Specifically preferred compounds include those shown in the FIGS. 1 through 6. In those figures, the substituent X depicts the moiety linkage to the base compound whose structure is shown at the top of each Figure.

Additional preferred compounds of the invention include the following (compounds structures are shown directly above the compound chemical name in many instances):

1-(1-butyl)-2-phenyl-5-(N,N-di[3,4-methylenedioxyphenyl methyl])aminomethylimidazole;

1-(1-butyl)-2-phenyl-5-(1-[N-{3,4-methylenedioxyphenyl-methyl}-N-phenylmethyl]amino)ethylimidazole;

1-Butyl-2-phenyl-4-bromo-5-(N-phenylmethyl-N-[1-butyl])aminomethylimidazole;

1-(1-Butyl)-2-phenyl-4-methyl-5-(N-[3,4-methylenedioxyphenyl-methyl]-N-phenylmethyl)aminomethylimidazole;

1-(1-Butyl)-2-(4-fluorophenyl)-5-(N-[1,4-benzodioxan-6-yl]methyl-N-phenylmethyl) aminomethylimidazole;

1-(1-Butyl)-2-(4-fluorophenyl)-5-(N-[3,4-methylenedioxyphenylmethyl]-N-phenylmethyl) aminomethylimidazole;

1-(1-Butyl)-2-(4-fluorophenyl)-5-(N-[1,4-benzodioxan-6-yl]methyl-N-phenylmethyl) aminomethylimidazole;

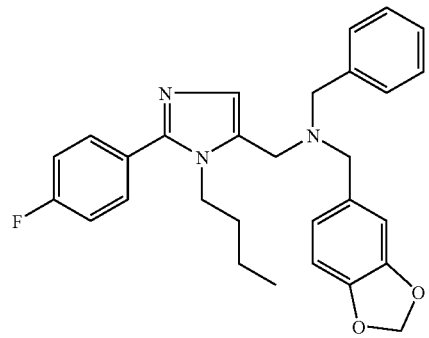

1-(1-Butyl)-2-(4-fluorophenyl)-5-(N-[3,4-methylenedioxyphenylmethyl]-N-phenylmethyl) aminomethylimidazole;

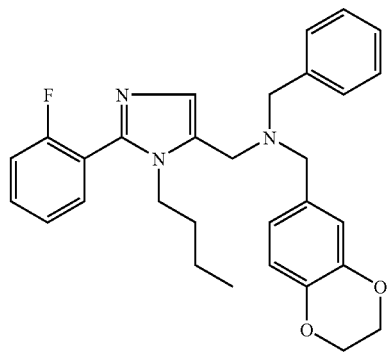

1-(1-Butyl)-2-(2-fluorophenyl)-5-(N-[1,4-benzodioxan-6-ylmethyl]-N-phenylmethyl)amino-methylimidazole;

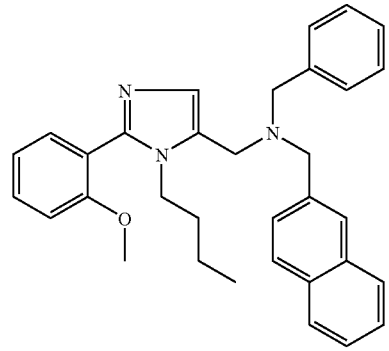

1-(1-Butyl)-2-(2-methoxyphenyl)-5-(N-[naphtha-2-ylmethyl]-N-phenylmethyl)amino-methylimidazole;

1-(1-Butyl)-2-(2-methoxyphenyl)-5-(N-[4-dimethylaminophenylmethyl]-N-phenylmethyl) aminomethylimidazole;

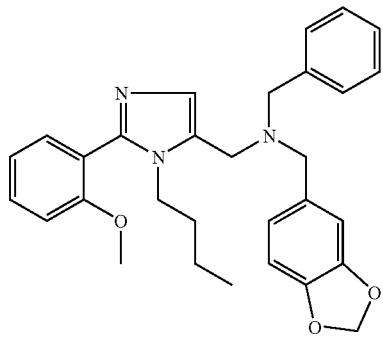

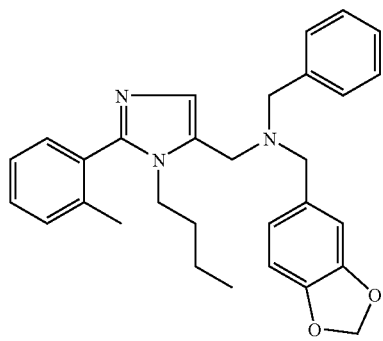

1-(1-Butyl)-2-(2-methoxyphenyl)-5-(N-[3,4-methylenedioxyphenylmethyl]-N-phenylmethyl) aminomethylimidazole;

1-(1-Butyl)-2-(2-methylphenyl)-5-(N-[3,4-methylenedioxyphenylmethyl]-N-phenylmethyl) aminomethylimidazole;

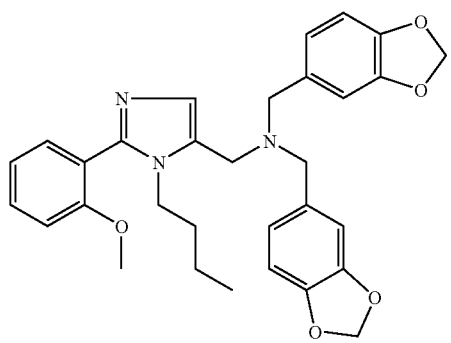

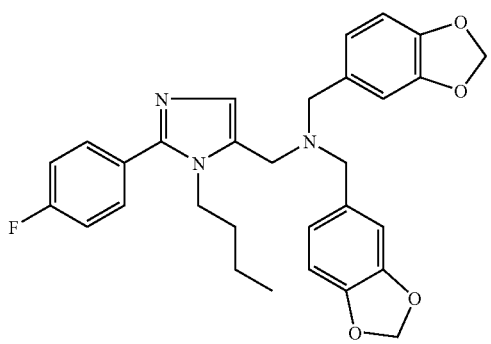

1-(1-Butyl)-2-(2-methoxyphenyl)-5-(N,N-di[3,4-methylenedioxyphenylmethyl]) aminomethylimidazole;

1-(1-Butyl)-2-(4-fluorophenyl)-5-(N,N-di[3,4-methylenedioxyphenylmethyl])amino-methylimidazole;

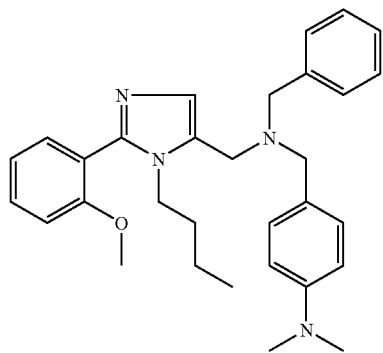

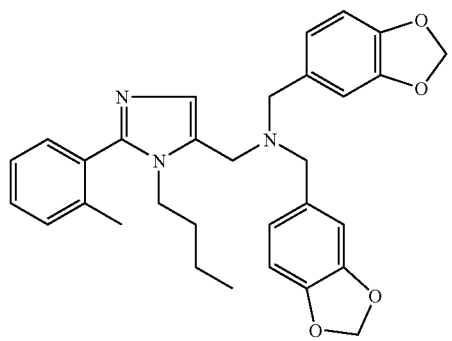

1-(1-Butyl)-2-(2-methylphenyl)-5-(N,N-di[3,4-methylene-dioxyphenylmethyl])amino-methylimidazole;

1-(1-Butyl)-2-(3-fluorophenyl)-5-(N,N-di[3,4-methylene-dioxyphenylmethyl])amino-methylimidazole;

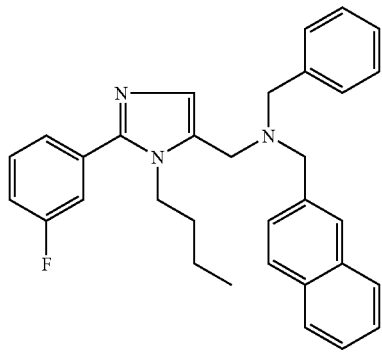

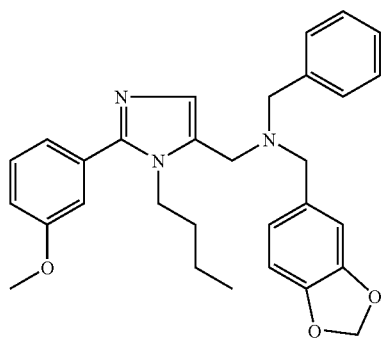

1-(1-Butyl)-2-(3-fluorophenyl)-5-(N-[naphth-2-ylmethyl]-N-phenylmethyl)amino methylimidazole;

1-(1-Butyl)-2-(3-methoxyphenyl)-5-(N-[3,4-methylene-dioxyphenylmethyl]-N-phenylmethyl)-aminomethylimidazole;

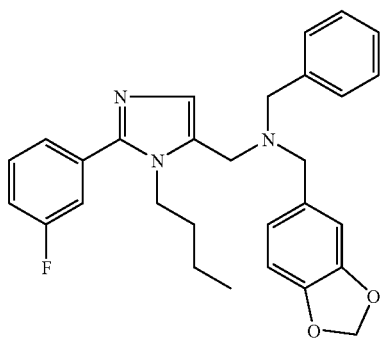

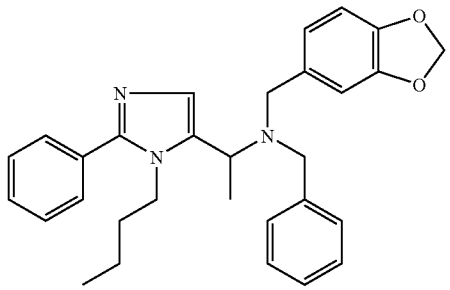

1-(1-Butyl)-2-(3-fluorophenyl)-5-(N-[3,4-methylenediox-yphenylmethyl]-N-phenylmethyl) aminomethylimidazole;

1-(1-Butyl)-2-phenyl-5-{1-(N-[3,4-methylenedioxyphenyl-methyl]-N-phenylmethyl)amino}ethylimidazole;

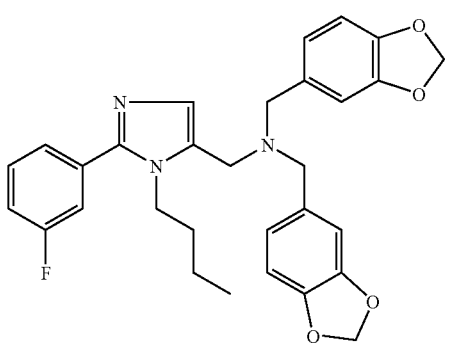

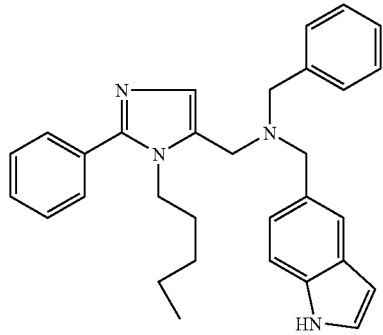

71

1-(1-Pentyl)-2-phenyl-5-(N-[indol-5-ylmethyl]-N-phenylmethyl) aminomethylimidazole;

72

4-({Benzyl-[1'-(3-butyl-2,5-diphenyl-3H-imidazol-4-yl)-ethyl]-amino}-methyl)-benzamide

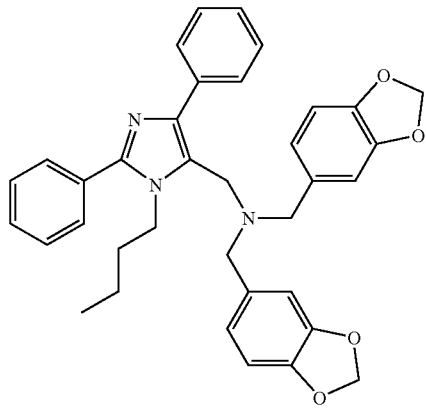

Bis-benzo[1,3]dioxol-5-ylmethyl-(3-butyl-2,5-diphenyl-3H-imidazol-4ylmethyl)-amine

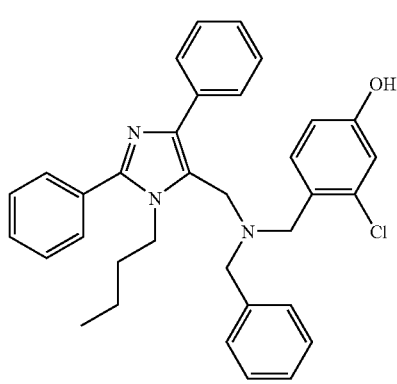

4-{[Benzyl-(3-butyl-2,5-diphenyl-3H-imidazol-4-ylmethyl)-amino]-methyl}-3-chloro-phenol

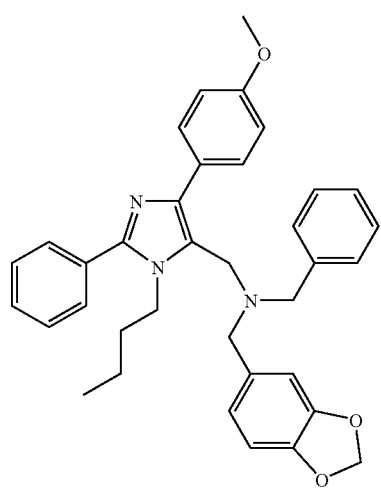

Benzo[1,3]dioxol-5-ylmethyl-benzyl-[3-butyl-5-(4-methoxy-phenyl)-2-phenyl-3H-imidazol-4-ylmethyl]-amine

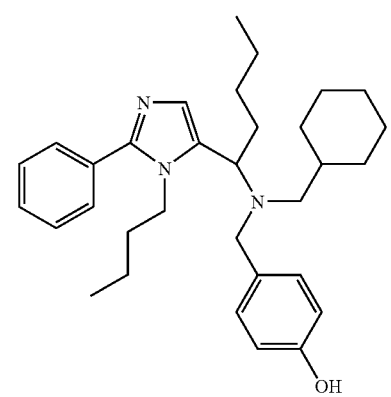

4-({[1-(3-Butyl-2-phenyl-3H-imidazol-4-yl)-pentyl]-cyclohexylmethyl-amino}-methyl)-phenol

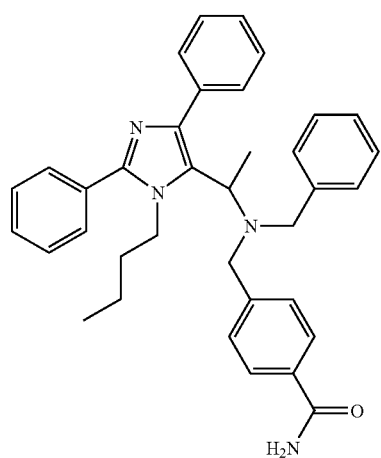

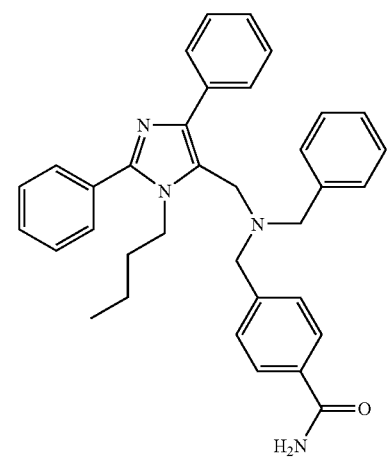

73

4-{[Benzyl-(3-butyl-2,5-diphenyl-3H-imidazol-4-ylmethyl)-amino]-methyl}-benzamide

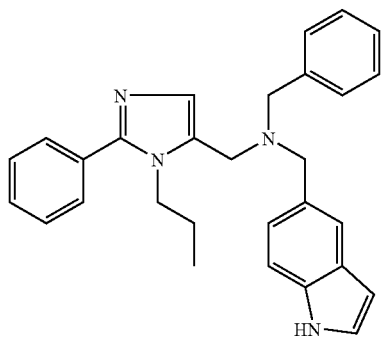

1-(1-Propyl)-2-phenyl-5-(N-[indol-5-ylmethyl]-N-phenylmethyl) aminomethylimidazole;

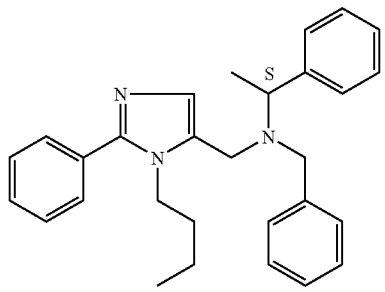

1-(1-Butyl)-2-phenyl-5-(N-[1-(S)-phenylethyl]-N-phenylmethyl)aminomethylimidazole;

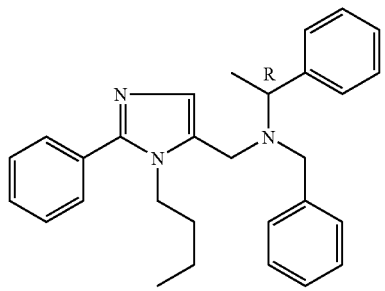

1-(1-Butyl)-2-phenyl-5-(N-[1-(R)-phenylethyl]-N-phenylmethyl)aminomethylimidazole;

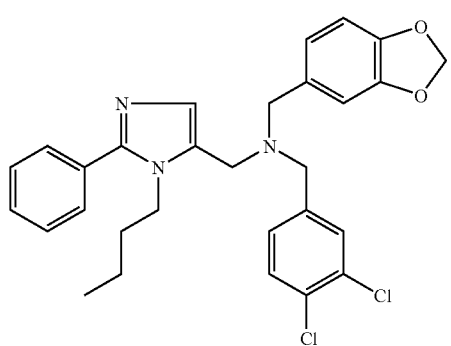

74

1-(1-Butyl)-2-phenyl-5-(N-[3,4-methylenedioxyphenylmethyl]-N-[3,4-dichlorophenyl]methyl)aminomethylimidazole;

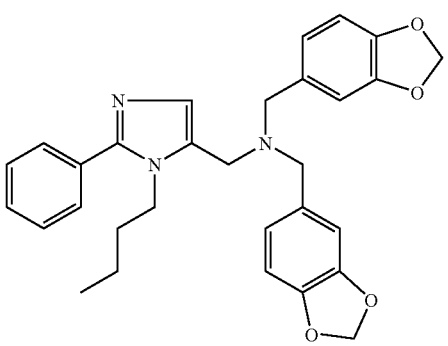

1-(1-Butyl)-2-phenyl-5-(N,N-di[3,4-methylenedioxyphenylmethyl]) aminomethylimidazole;

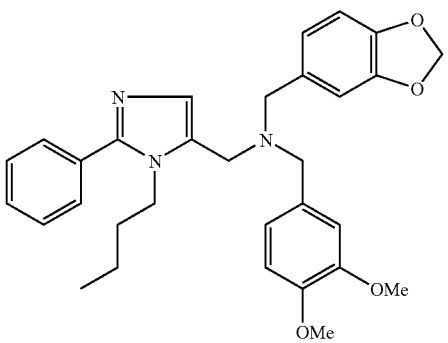

1-(1-Butyl)-2-phenyl-5-(N-[3,4-methylenedioxyphenylmethyl]-N-[3,4-methoxyphenylmethyl])-aminomethylimidazole;

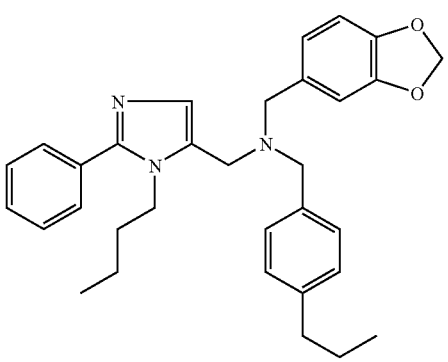

1-(1-Butyl)-2-phenyl-5-(N-[3,4-methylenedioxyphenylm-ethyl]-N-[4-{1-propyl}phenylmethyl]) aminomethylimi-dazole;

1-(1-Butyl)-2-phenyl-5-(N-[3,4-methylenedioxyphenylm-ethyl]-N-[4-{1-propyloxy}phenylmethyl)aminometh-ylimidazole;

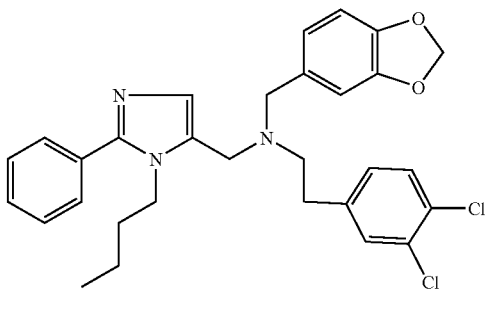

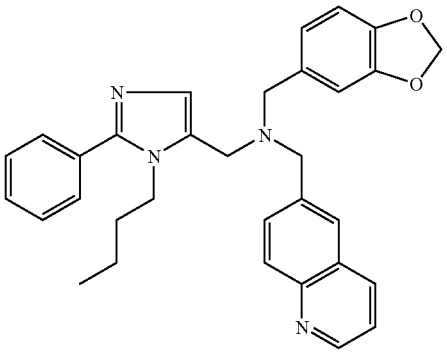

1-(1-Butyl)-2-phenyl-5-(N-[3,4-methylenedioxyphenylm-ethyl]-N-[3,4-dichlorophenylethyl]) aminomethylimida-zole;

1-(1-Butyl)-2-phenyl-5-(N-[3,4-methylenedioxyphenylm-ethyl]-N-[quinol-6-ylmethyl])-aminomethylimidazole;

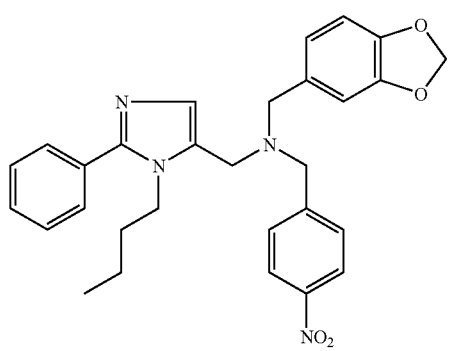

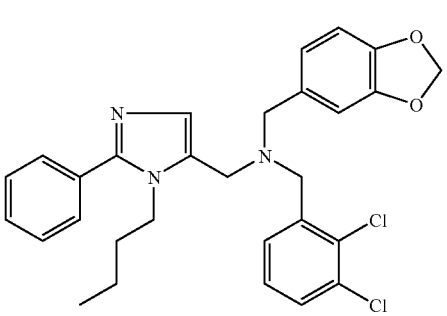

1-(1-Butyl)-2-phenyl-5-(N-[3,4-methylenedioxyphenyl]me-thyl-N-[4-nitrophenylmethyl]) aminomethylimidazole;

1-(1-Butyl)-2-phenyl-5-(N-[3,4-methylenedioxyphenylm-ethyl]-N-[2,3-dichlorophenylmethyl])-aminomethylimi-dazole;

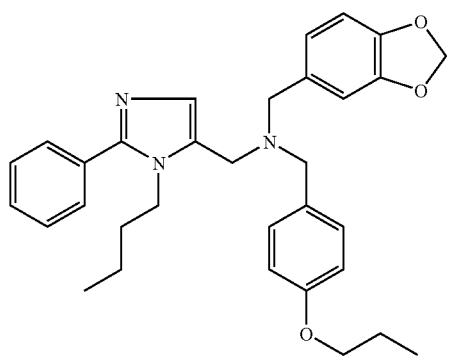

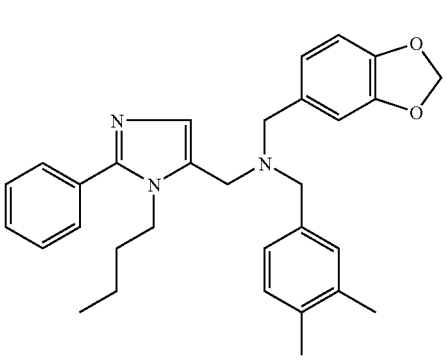

77

1-(1-Butyl)-2-phenyl-5-(N-[3,4-methylenedioxyphenylmethyl]-N-[3,4-dimethylphenylmethyl])-aminomethylimidazole;

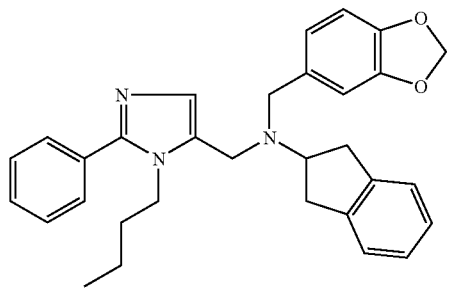

1-(1-Butyl)-2-phenyl-5-(N-[3,4-methylenedioxyphenyl]methyl-N-[indan-2-yl])-aminomethylimidazole;

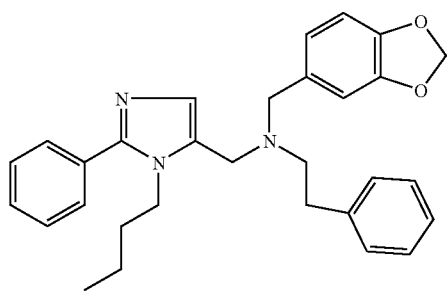

1-(1-Butyl)-2-phenyl-5-(N-[3,4-methylenedioxyphenylmethyl]-N-[2-phenylethyl])amino-methylimidazole;

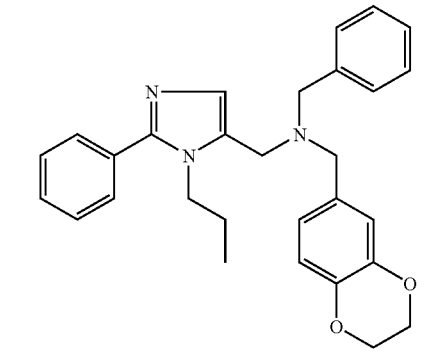

1-(1-Propyl)-2-phenyl-5-(N-[1,4-benzodioxan-6-ylmethyl]-N-phenylmethyl)aminomethyl-imidazole;

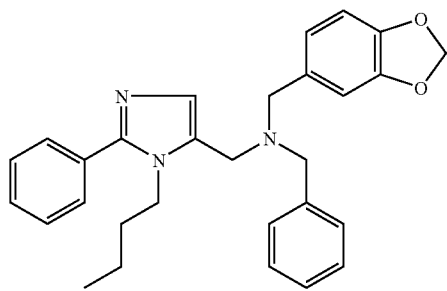

78

1-(1-Butyl)-2-phenyl-5-(N-[3,4-methylenedioxyphenylmethyl]-N-phenylmethyl)aminomethyl-imidazole;

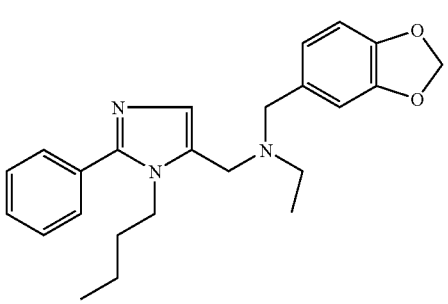

1-(1-Butyl)-2-phenyl-5-(N-[3,4-methylenedioxyphenylmethyl]-N-ethyl)aminomethylimidazole;

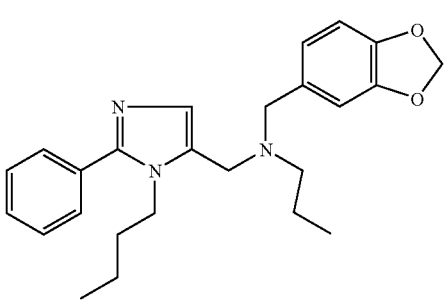

1-(1-Butyl)-2-phenyl-5-(N-[3,4-methylenedioxyphenylmethyl]-N-[1-propyl])aminomethyl-imidazole;

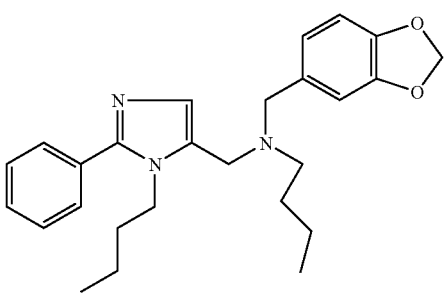

1-(1-Butyl)-2-phenyl-5-(N-[3,4-methylenedioxyphenylmethyl-N-[1-butyl])aminomethyl-imidazole;

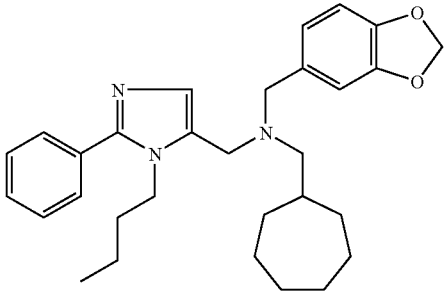

1-(1-Butyl)-2-phenyl-5-(N-[3,4-methylenedioxyphenylm-
ethyl]-N-cycloheptylmethyl)amino-methylimidazole;

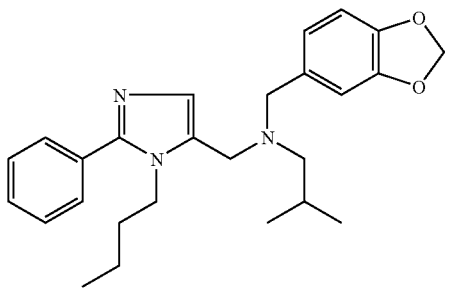

1-(1-Butyl)-2-phenyl-5-(N-[3,4-methylenedioxyphenylm-
ethyl]-N-isobutyl)aminomethyl-imidazole;

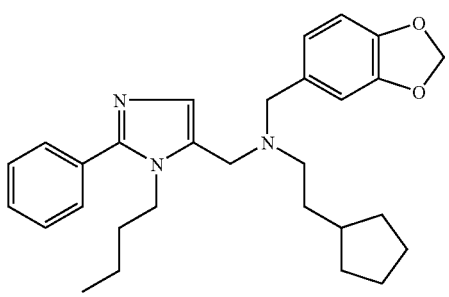

1-(1-Butyl)-2-phenyl-5-(N-[3,4-methylenedioxyphenylm-
ethyl]-N-[2-cyclopentylethyl])amino-methylimidazole;

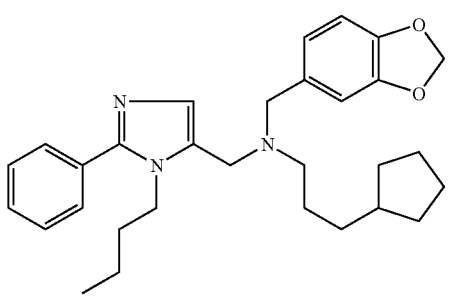

1-(1-Butyl)-2-phenyl-5-(N-[3,4-methylenedioxyphenylm-
ethyl]-N-[3-cyclopentylpropyl])amino-methylimidazole;

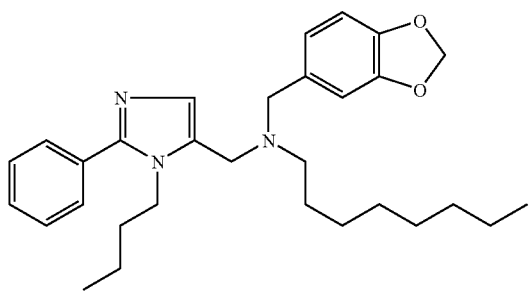

1-(1-Butyl)-2-phenyl-5-(N-[3,4-methylenedioxyphenylm-
ethyl]-N-[1 1-n-octyl])aminomethyl-imidazole;

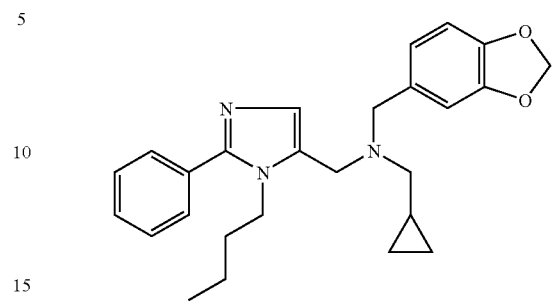

1-(1-Butyl)-2-phenyl-5-(N-[3,4-methylenedioxyphenylm-
ethyl]-N-cyclopropylmethyl)amino-methylimidazole;

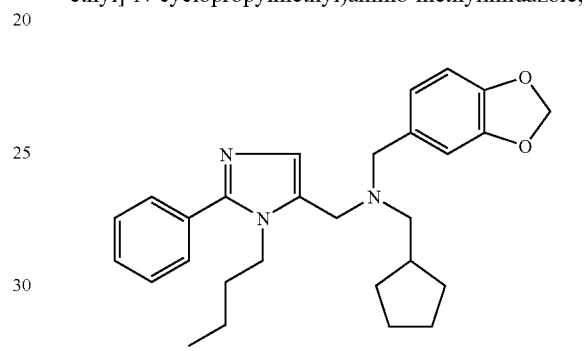

1-(1-Butyl)-2-phenyl-5-(N-[3,4-methylenedioxyphenylm-
ethyl]-N-cyclopentylmethyl)amino-methylimidazole;

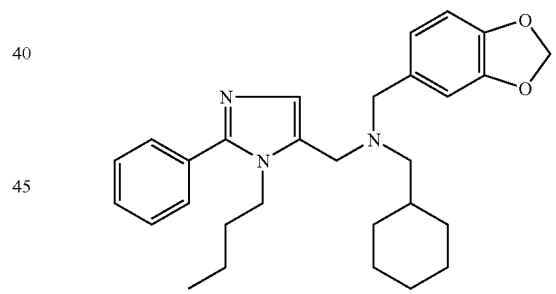

1-(1-Butyl)-2-phenyl-5-(N-[3,4-methylenedioxyphenylm-
ethyl]-N-cyclohexylmethyl)amino-methylimidazole;

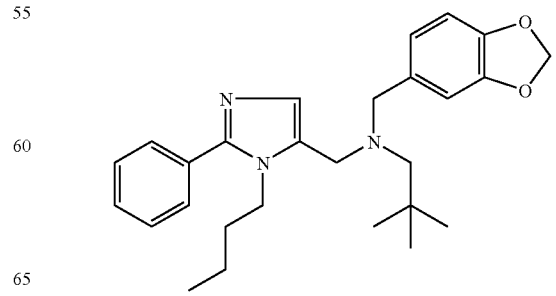

81

1-(1-Butyl)-2-phenyl-5-(N-[3,4-methylenedioxyphenylmethyl]-N-[t-amyl])aminomethylimidazole;

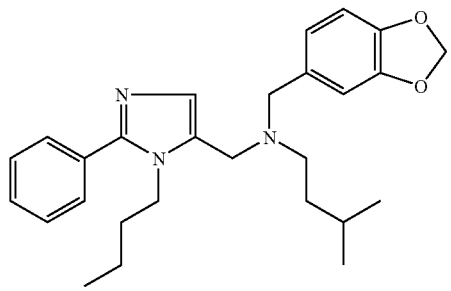

1-(1-Butyl)-2-phenyl-5-(N-[3,4-methylenedioxyphenylmethyl]-N-[1-{3-methyl}butyl]]amino-methylimidazole;

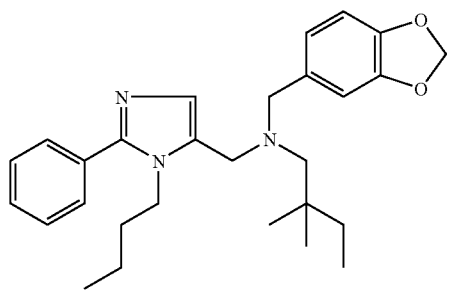

1-(1-Butyl)-2-phenyl-5-(N-[3,4-methylenedioxyphenylmethyl]-N-[1-{2,2-dimethyl}butyl]) aminomethylimidazole;

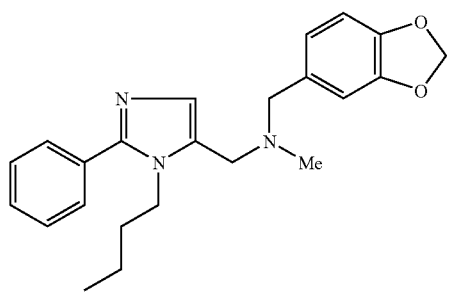

1-(1-Butyl)-2-phenyl-5-(N-[3,4-methylenedioxyphenylmethyl]-N-methyl)aminomethylimidazole;

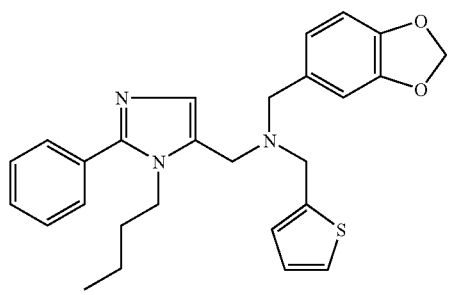

82

1-(1-Butyl)-2-phenyl-5-(N-[3,4-methylenedioxyphenylmethyl]-N-[2-thiophenylmethyl])amino-methylimidazole;

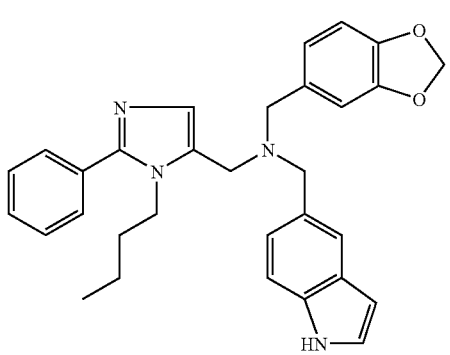

1-(1-Butyl)-2-phenyl-5-(N-[3,4-methylenedioxyphenylmethyl]-N-[indol-5-ylmethyl])amino-methylimidazole;

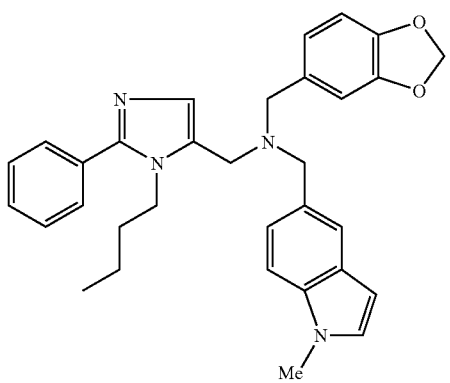

1-(1-Butyl)-2-phenyl-5-(N-[3,4-methylenedioxyphenylmethyl]-N-[{1-methylindol-5-yl}methyl])aminomethylimidazole;

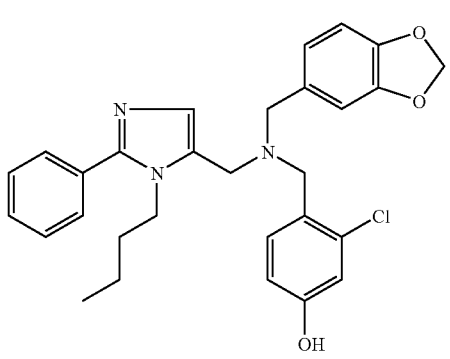

83

1-(1-Butyl)-2-phenyl-5-(N-[3,4-methylenedioxyphenyl]methyl-N-[4-hydroxy-2-chlorophenyl]-methyl)aminomethylimidazole;

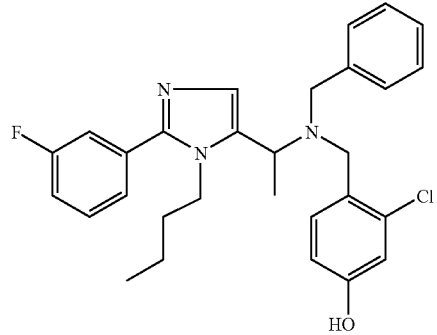

1-(1-Butyl)-2-(3-fluorophenyl)-5-(1-[N-{2-chloro-4-hydroxyphenyl}methyl-N-phenylmethyl]) aminoethylimidazole;

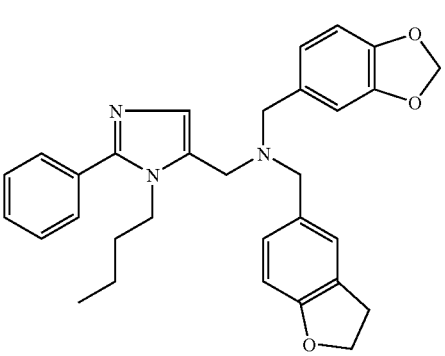

1-(1-Butyl)-2-phenyl-5-(N-[3,4-methylenedioxyphenyl]methyl-N-[2,3-dihydrobenzo[b]furan-5-yl]methyl)aminomethylimidazole;

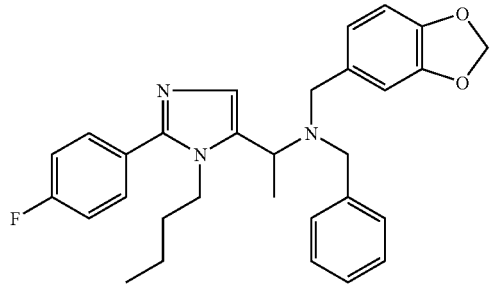

84

1-Butyl-2-(4-fluorophenyl)-5-(1-[N-{3,4-methylenedioxyphenyl}methyl-N-phenylmethyl]-amino)ethylimidazole;

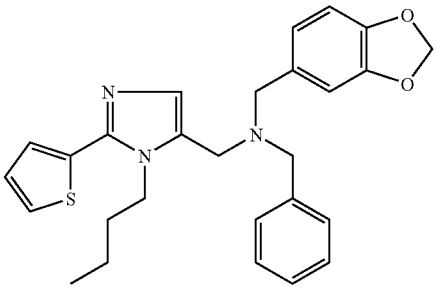

1-(1-Butyl)-2-(2-thienyl)-5-(N-[3,4-methylenedioxyphenyl]methyl-N-phenylmethyl]aminomethylimidazole;

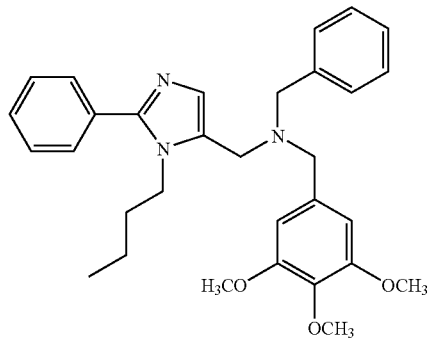

1-(1-Butyl)-2-phenyl-5-(N-[3,4,5-trimethoxyphenylmethyl]-N-phenylmethyl)amino-methylimidazole;

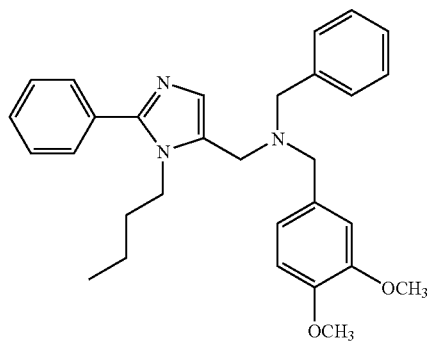

85

1-(1-Butyl)-2-phenyl-5-(N-phenylmethyl-N-[3,4-dimethoxyphenylmethyl])aminomethyl-imidazole;

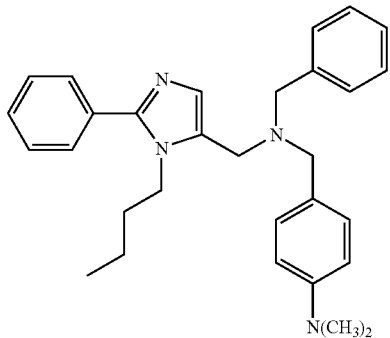

1-(1-Butyl)-2-phenyl-5-(N-[4-dimethylaminophenylmethyl]-N-phenylmethyl)aminomethyl-imidazole;

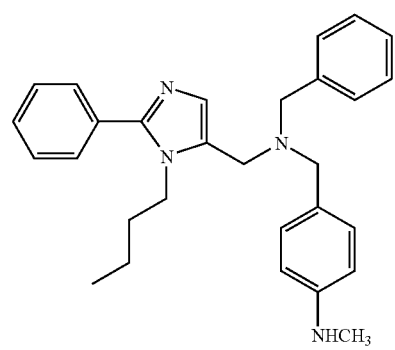

1-(1-Butyl)-2-phenyl-5-(N-[4-methylaminophenylmethyl]-N-phenylmethyl)aminomethyl-imidazole;

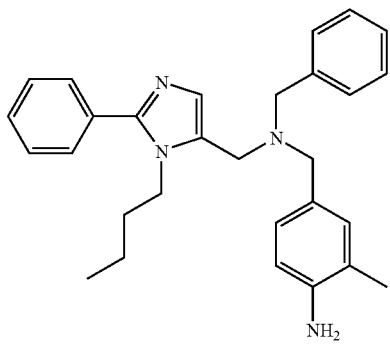

86

1-(1-Butyl)-2-phenyl-5-(N-[3-methyl-4-aminophenylmethyl]-N-phenylmethyl)aminomethyl-imidazole);

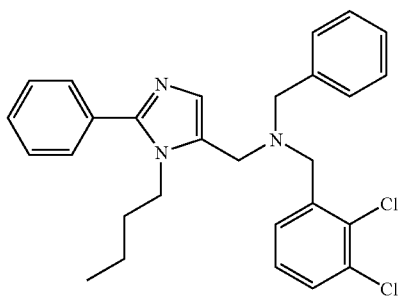

1-(1-Butyl)-2-phenyl-5-(N-[2,3-dichlorophenylmethyl]-N-phenylmethyl)aminomethylimidazole;

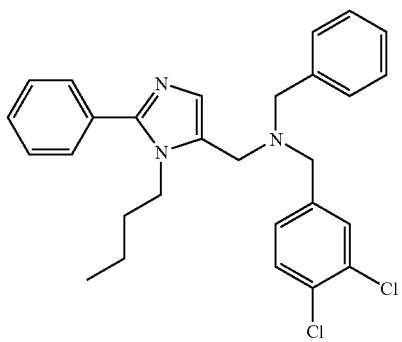

1-(1-Butyl)-2-phenyl-5-(N-[3,4-dichlorophenylmethyl]-N-phenylmethyl)aminomethylimidazole;

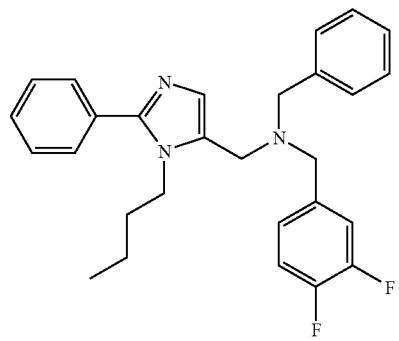

87

1-(1-Butyl)-2-phenyl-5-(N-[3,4-difluorophenylmethyl]-N-phenylmethyl)aminomethylimidazole;

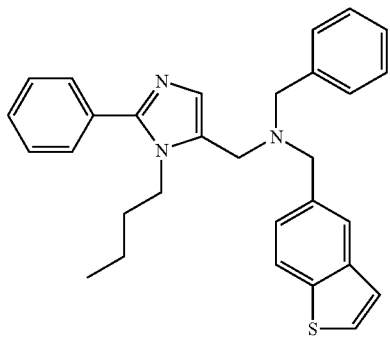

1-(1-Butyl)-2-phenyl-5-(N-(benzo[b]thiophen-5-ylmethyl)-N-phenylmethyl)aminomethyl-imidazole;

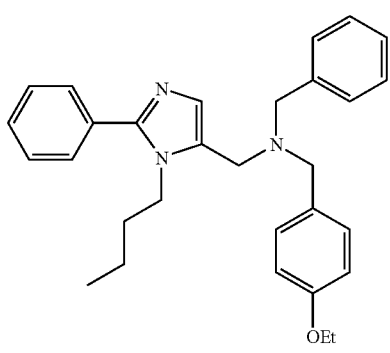

1-(1-Butyl)-2-phenyl-5-(N-[4-ethoxyphenylmethyl]-N-phenylmethyl)aminomethylimidazole;

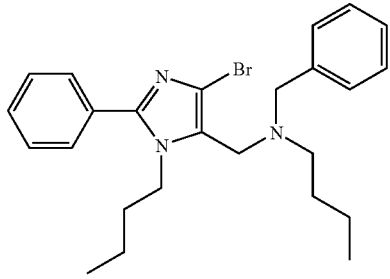

88

1-(1-Butyl)-2-phenyl-4-bromo-5-(N-phenylmethyl-N-[1-butyl])aminomethylimidazole;

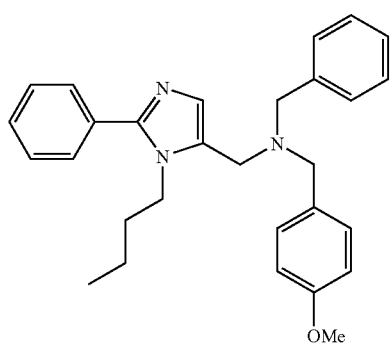

1-(1-Butyl)-2-phenyl-5-(N-[4-methoxyphenylmethyl]-N-phenylmethyl)aminomethylimidazole;

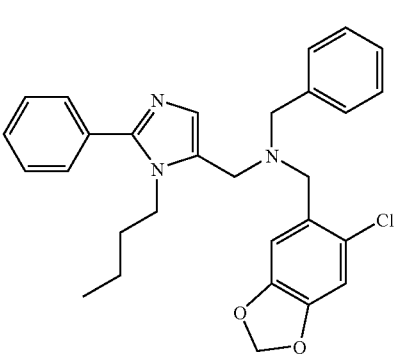

1-(1-Butyl)-2-phenyl-5-(N-[6-chloro-3,4-methylenedioxyphenylmethyl]-N-phenylmethyl)-aminomethylimidazole;

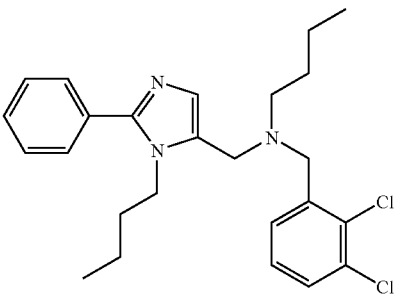

1-(1-Butyl)-2-phenyl-5-(N-[2,3-dichlorophenylmethyl]-N-[1-butyl])aminomethylimidazole;

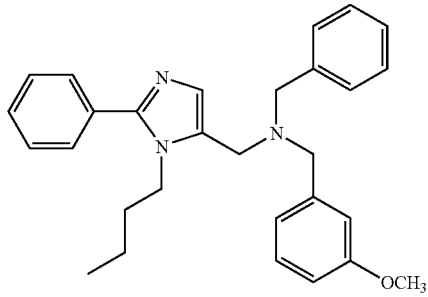

1-(1-Butyl)-2-phenyl-5-(N-[3-methoxyphenylmethyl]-N-phenylmethyl)aminomethylimidazole;

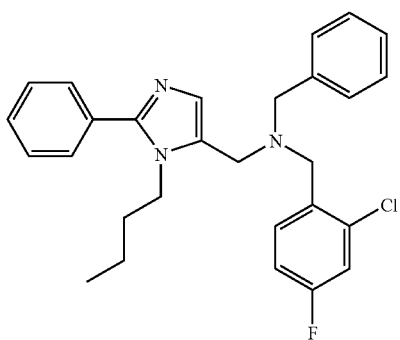

1-(1-Butyl)-2-phenyl-5-(N-[2-chloro-4-fluorophenylmethyl]-N-phenylmethyl)aminomethyl-imidazole;

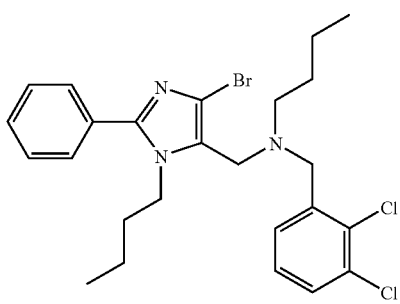

1-(1-Butyl)-2-phenyl-4-bromo-5-(N-[2,3-dichlorophenylmethyl]-N-[1-butyl])aminomethyl-imidazole;

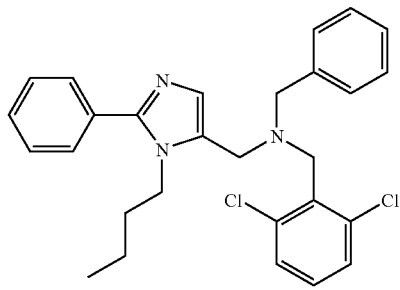

1-(1-Butyl)-2-phenyl-5-(N-[2,6-dichlorophenylmethyl]-N-phenylmethyl)aminomethylimidazole;

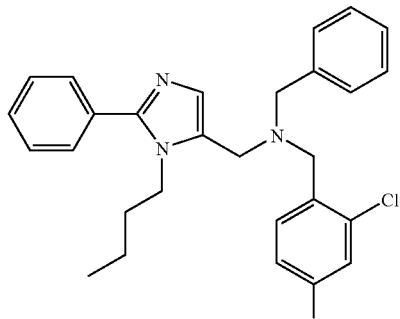

1-(1-Butyl)-2-phenyl-5-(N-[2-chloro-4-hydroxyphenylmethyl]-N-phenylmethyl)aminomethyl-imidazole;

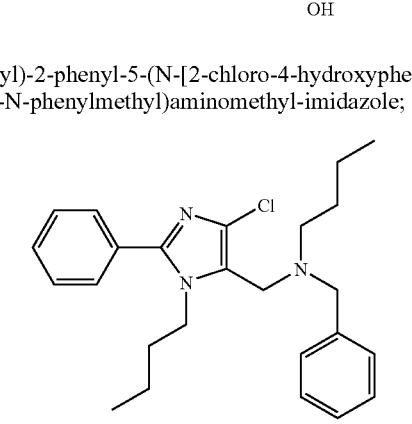

1-(1-Butyl)-2-phenyl-4-chloro-5-(N-phenylmethyl-N-[1-butyl])aminomethylimidazole;

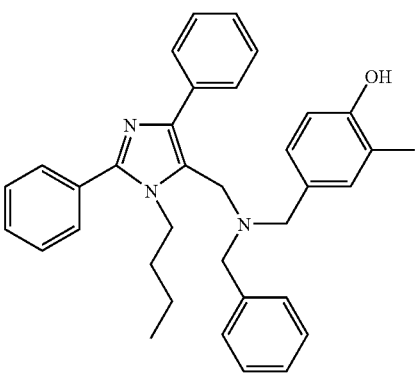

91

4-{[Benzyl-(3-butyl-2,5-diphenyl-3H-imidazol-4-ylmethyl)-amino]-methyl}-2-methyl-phenol

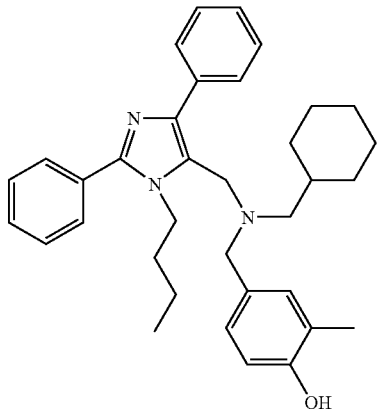

4-{[(3-Butyl-2,5-diphenyl-3H-imidazol-4-ylmethyl)-cyclohexylmethyl-amino]-methyl}-2-methyl-phenol

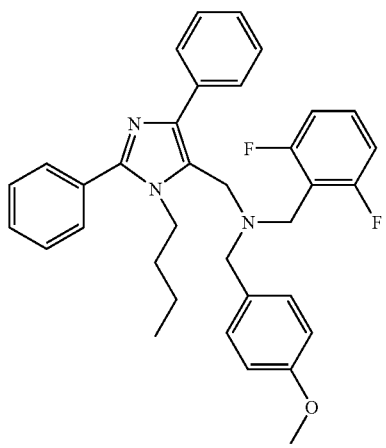

(3-Butyl-2,5-diphenyl-3H-imidazol-4-ylmethyl)-(2,6-difluoro-benzyl)-(4-methoxy-benzyl)-amine

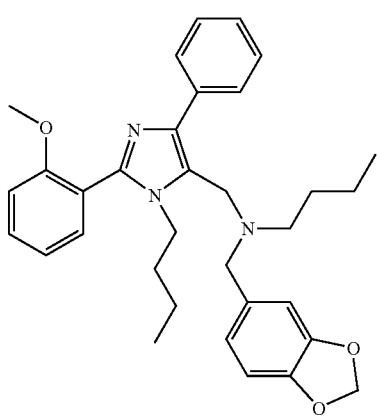

92

Benzo[1,3]dioxol-5-ylmethyl-butyl-[3-butyl-2-(2-methoxyphenyl)-5-phenyl-3H-imidazol-4-yl methyl]-amine

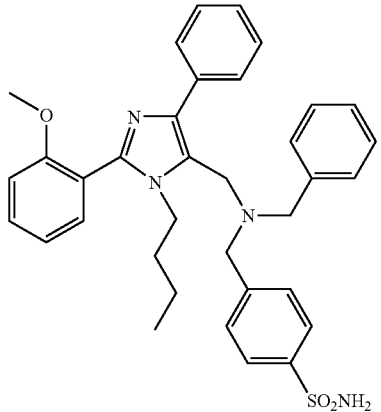

4-({Benzyl-[3-butyl-2-(2-methoxy-phenyl)-5-phenyl-3H-imidazol-4-ylmethyl]-amino}-methyl)-benzenesulfonamide

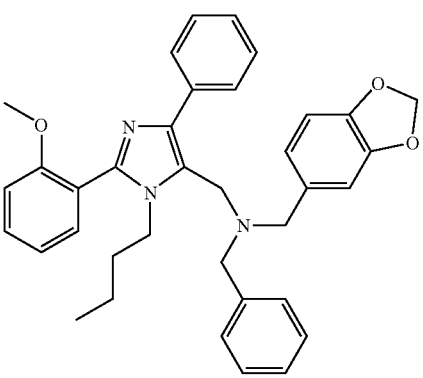

Benzo[1,3]dioxol-5-ylmethyl-benzyl-[3-butyl-2-(2-methoxy-phenyl)-5-phenyl-3H-imidazol-4-yl methyl]-amine

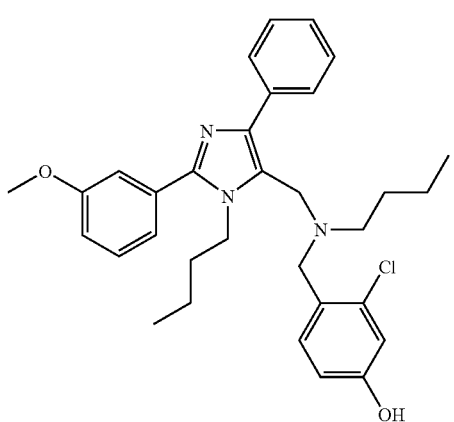

93

4-({Butyl-[3-butyl-2-(3-methoxy-phenyl)-5-phenyl-3H-imidazol-4-ylmethyl]-amino}methyl)-3-chloro-phenol

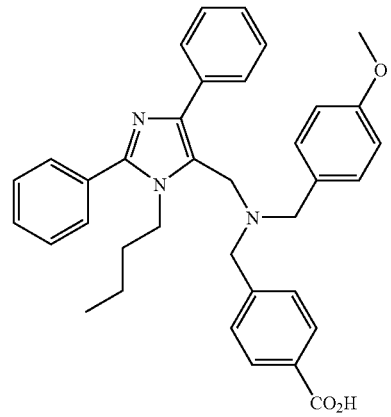

4-{[(3-Butyl-2,5-diphenyl-3H-imidazol-4-ylmethyl)-(4-methoxy-benzyl)-amino]-methyl}-benzoic acid

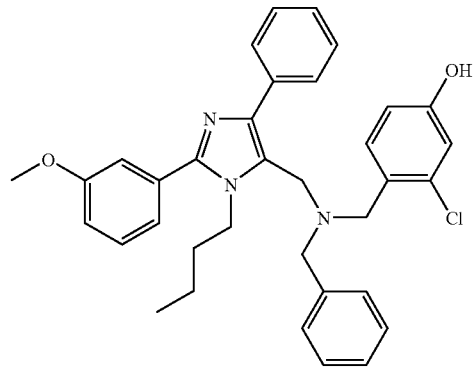

4-({Benzyl-[3-butyl-2-(3-methoxy-phenyl)-5-phenyl-3H-imidazol-4-ylmethyl]-amino}-methyl)-3-chloro-phenol

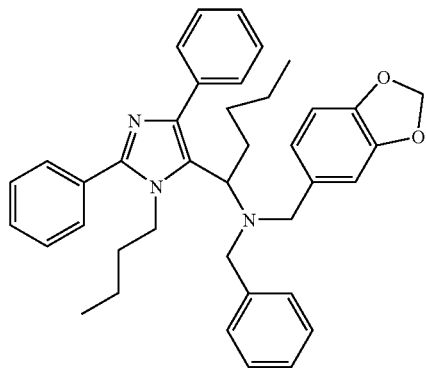

94

Benzo[1,3]dioxol-5-ylmethyl-benzyl-[1-(3-butyl-2,5-diphenyl-3H-imidazol-4-yl)-pentyl]-amine

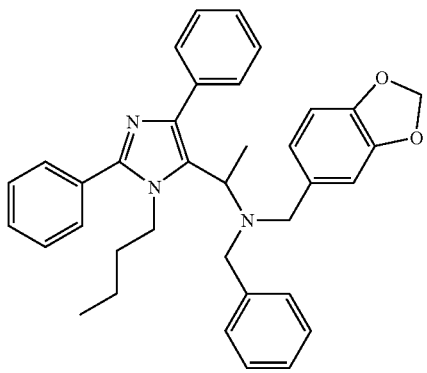

Benzo[1,3]dioxol-5-ylmethyl-benzyl-[1-(3-butyl-2,5-diphenyl-3H-imidazol-4-yl-ethyl]-amine

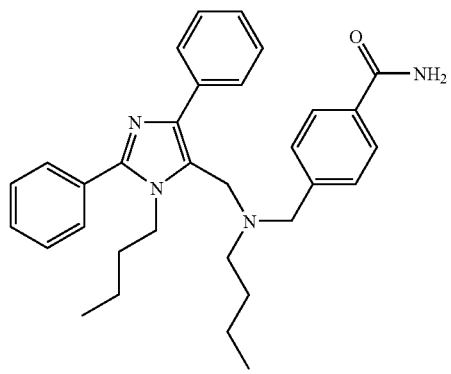

4-{[Butyl-(3-butyl-2,5-diphenyl-3H-imidazol-4-ylmethyl)-amino]-methyl}-benzamide

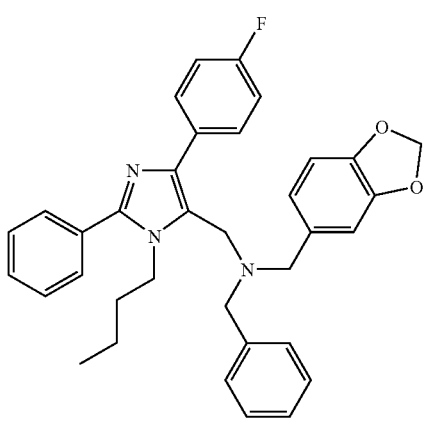

95
Benzo[1,3]dioxol-5-ylmethyl-benzyl-[3-butyl-5-(4-fluoro-phenyl)-2-phenyl-3H-imidazol-4-ylmethyl]amine

96
Benzyl-(3-butyl-2,5-diphenyl-3H-imidazol-4-ylmethyl)-(2,3 dihydro-benzo[1,4]dioxin-6-ylmethyl)-amine

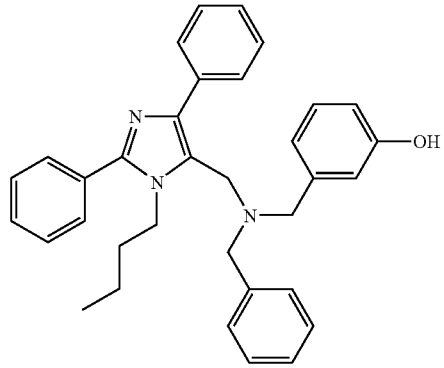

3-{[Benzyl-(3-butyl-2,5-diphenyl-3H-imidazol-4-ylmethyl)-amino]-methyl}-phenol

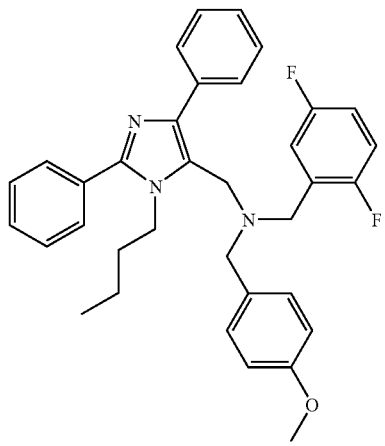

(3-Butyl-2,5-diphenyl-3H-imidazol-4-ylmethyl)-(2,5-difluoro-benzyl)-(4-methoxy-benzyl)-amine

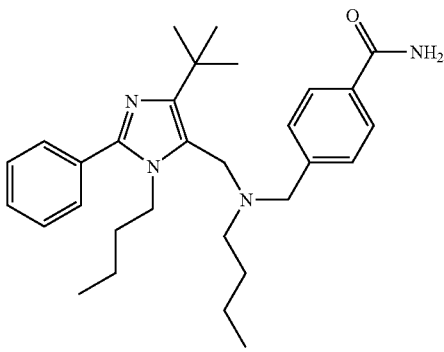

4-{[Butyl-(3-butyl-5-tert-butyl-2-phenyl-3H-imidazol-4-ylmethyl)-amino]-methyl}-benzamide

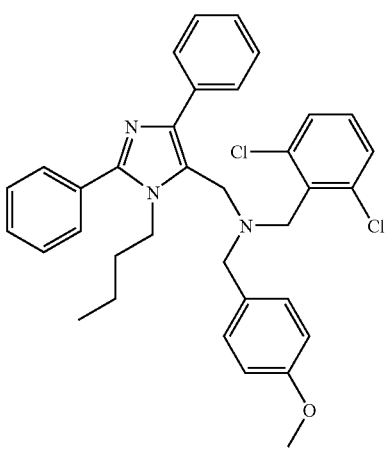

(3-Butyl-2,5-diphenyl-3H-imidazol-4-ylmethyl)-(2,6-dichloro-benzyl)-(4-methoxy-benzyl)-amine

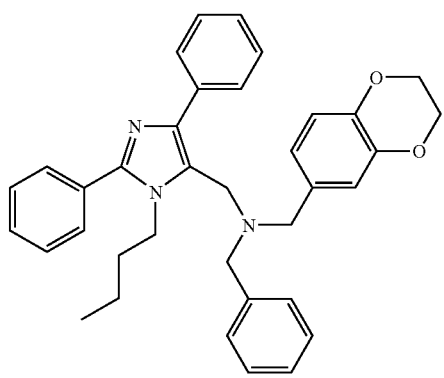

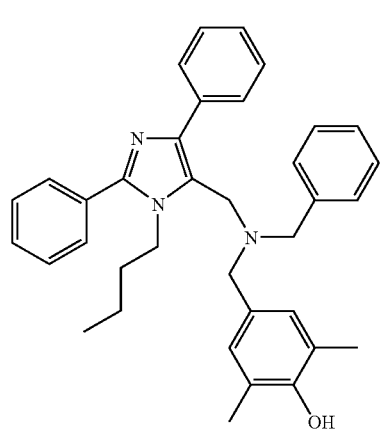

97

4-{[Benzyl-(3-butyl-2,5-diphenyl-3H-imidazol-4-ylmethyl)-amino]-methyl}-2,6-dimethyl-phenol

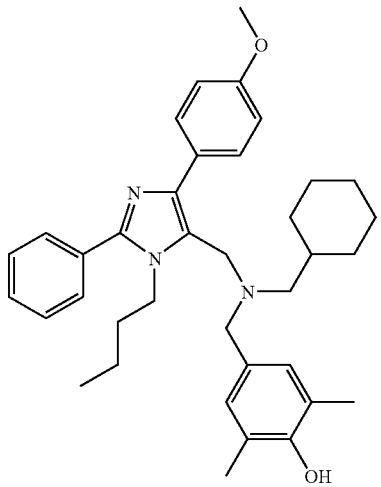

4-({[3-Butyl-5-(4-methoxy-phenyl)-2-phenyl-3H-imidazol-4-ylmethyl]-cyclohexylmethyl-amino}-methyl)-2,6-dimethyl-phenol

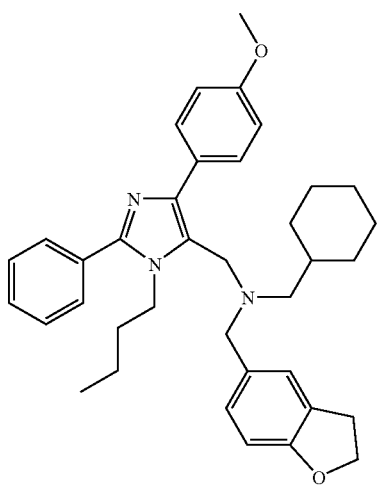

98

[3-Butyl-5-(4-methoxy-phenyl)-2-phenyl-3H-imidazol-4-ylmethyl]-cyclohexylmethyl-(2,3-dihydro-benzo furan-5-ylmethyl)-amine

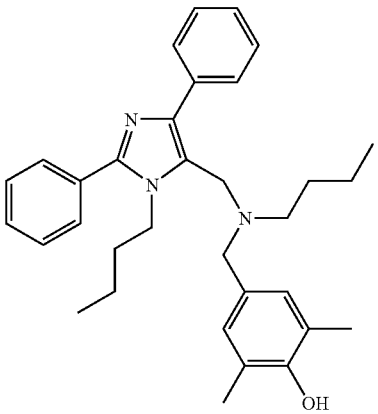

4-{[Butyl-(3-butyl-2,5-diphenyl-3H-imidazol-4-ylmethyl)-amino]-methyl}-2,6-dimethyl-phenol

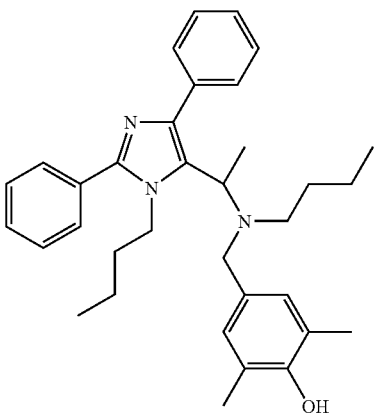

4-({Butyl-[1-(3-butyl-2,5-diphenyl-3H-imidazol-4-yl)-ethyl]-amino}-methyl)-2,6-dimethyl-phenol

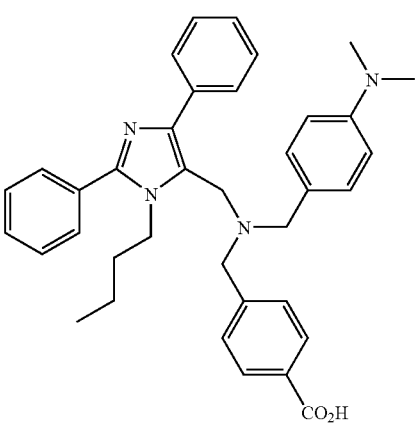

99

4-{[(3-Butyl-2,5-diphenyl-3H-imidazol-4-ylmethyl)-(4-dimethylamino-benzyl)-amino]-methyl}-benzoic acid

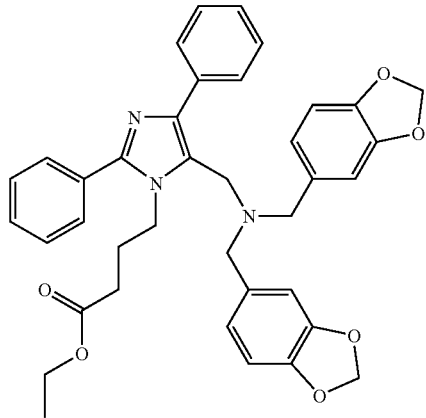

4-{5-[(Bis-benzo[1,3]dioxol-5-ylmethyl-amino)-methyl]-2,4-diphenyl-imidazol-1-yl}-butyric acid ethyl ester

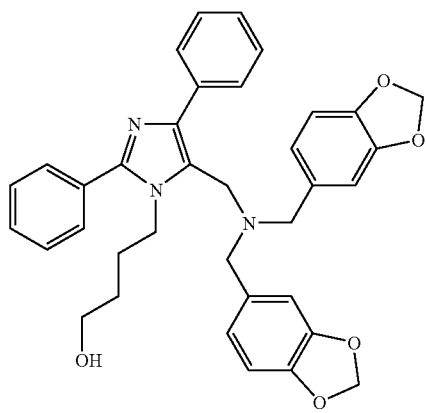

4-{5-[(Bis-benzo[1,3]dioxol-5-ylmethyl-amino)-methyl]-2,4-diphenyl-imidazol-1-yl}-butan-1-ol

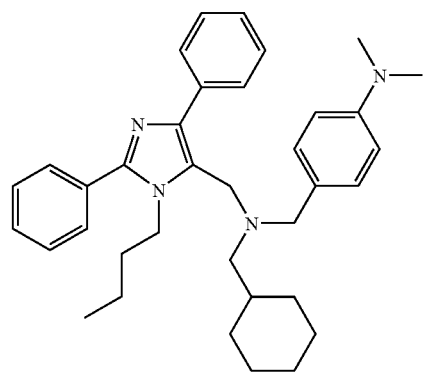

100

(4-{[(3-Butyl-2,5-diphenyl-3H-imidazol-4-ylmethyl)-cyclohexylmethyl-amino]-methyl}-phenyl)-dimethyl-amine

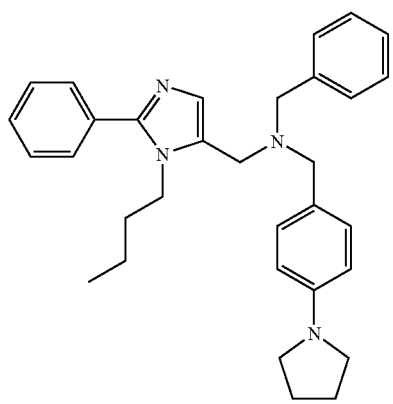

1-(1-Butyl)-2-phenyl-5-(N-[4-{1-pyrrolidinyl}phenylmethyl]-N-phenylmethyl)aminomethyl-imidazole;

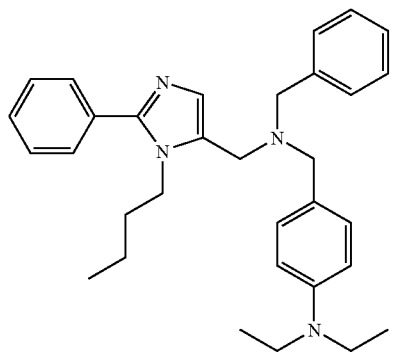

1-(1-Butyl)-2-phenyl-5-(N-[4-diethylaminophenylmethyl]-N-phenylmethyl)aminomethyl-imidazole;

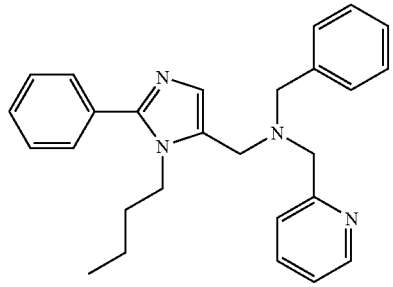

101

1-(1-Butyl)-2-phenyl-5-(N-[pyridin-2-ylmethyl]-N-phenyl-methyl)aminomethylimidazole;

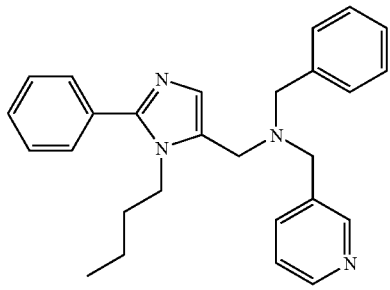

1-(1-Butyl)-2-phenyl-5-(N-[pyridin-3-ylmethyl]-N-phenyl-methyl)aminomethylimidazole;

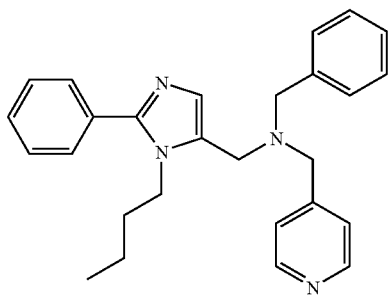

1-(1-Butyl)-2-phenyl-5-(N-[pyridin-4-ylmethyl]-N-phenyl-methyl)aminomethylimidazole;

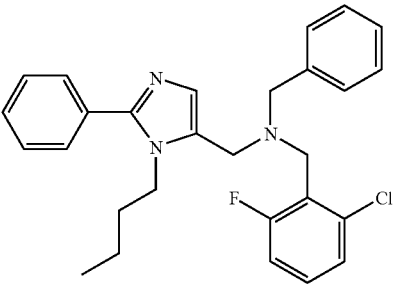

1-(1-Butyl)-2-phenyl-5-(N-[2-fluoro-6-chlorophenylm-ethyl]-N-phenylmethyl)aminomethyl-imidazole);

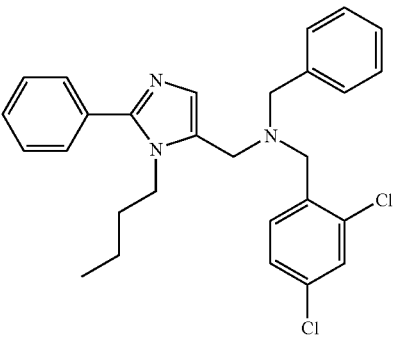

102

1-(1-Butyl)-2-phenyl-5-(N-[2,4-dichlorophenylmethyl]-N-phenylmethyl)aminomethyl-imidazole);

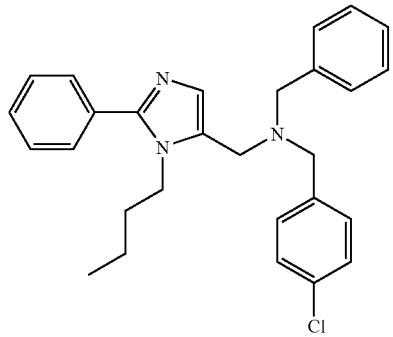

1-(1-Butyl)-2-phenyl-5-(N-[4-chlorophenylmethyl]-N-phenylmethyl)aminomethylimidazole;

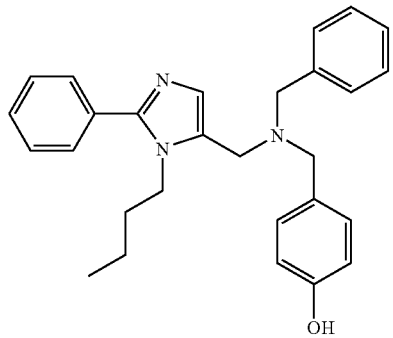

1-(1-Butyl)-2-phenyl-5-(N-[4-hydroxyphenylmethyl]-N-phenylmethyl)aminomethylimidazole;

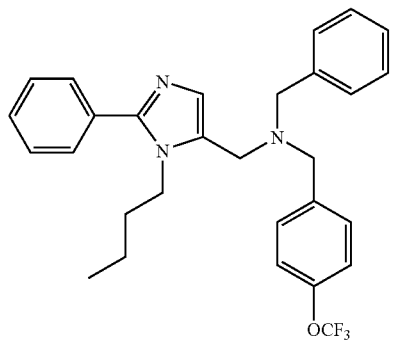

103

1-(1-Butyl)-2-phenyl-5-(N-[4-trifluoromethoxyphenylm-
ethyl]-N-phenylmethyl)aminomethyl-imidazole);

104

1-(1-Butyl)-2-phenyl-5-(N-[4-aminophenylmethyl]-N-phe-
nylmethyl)aminomethylimidazole;

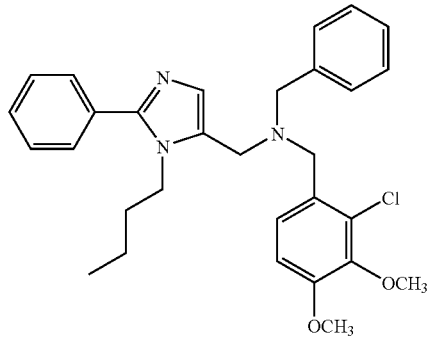

1-(1-Butyl)-2-phenyl-5-(N-[2-chloro-3,4-dimethoxyphenyl-
methyl]-N-phenylmethyl)amino-methylimidazole);

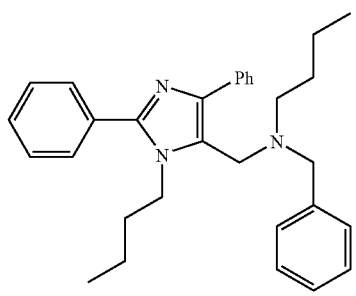

1-(1-Butyl)-2,4-diphenyl-5-(N-phenylmethyl-N-[1-butyl])
aminomethylimidazole;

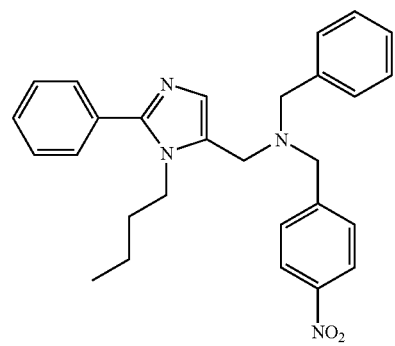

1-(1-Butyl)-2-phenyl-5-(N-[4-nitrophenylmethyl]-N-phe-
nylmethyl)aminomethylimidazole;

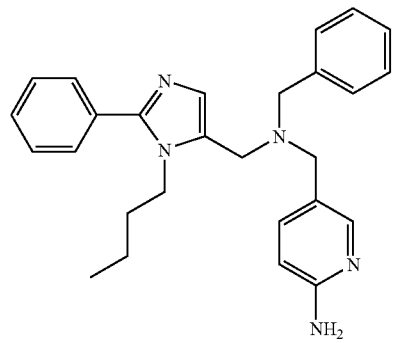

1-(1-Butyl)-2-phenyl-5-(N-[2-aminopyridin-5-ylmethyl]-N-
phenylmethyl)aminomethyl-imidazole

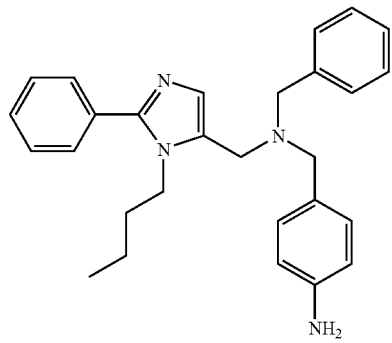

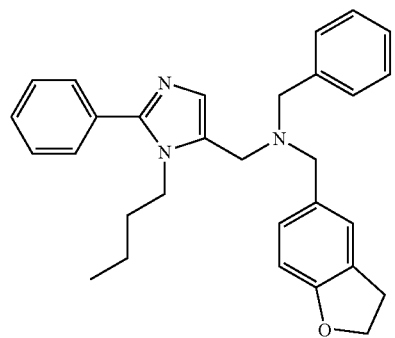

1-(1-Butyl)-2-phenyl-5-(N-[2,3-dihydrobenzo[b]furan-5-yl-methyl]-N-phenylmethyl)amino-methylimidazole;

1-(1-Butyl)-2-(4-fluorophenyl)-5-(N-[2-chloro-4-hydroxyphenylmethyl]-N-phenylmethyl)-aminomethylimidazole;

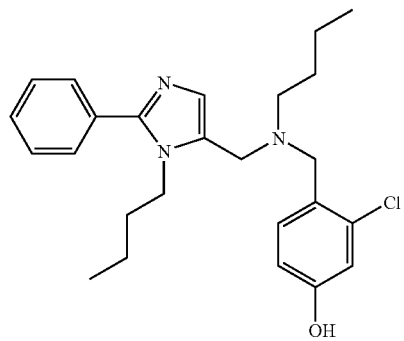

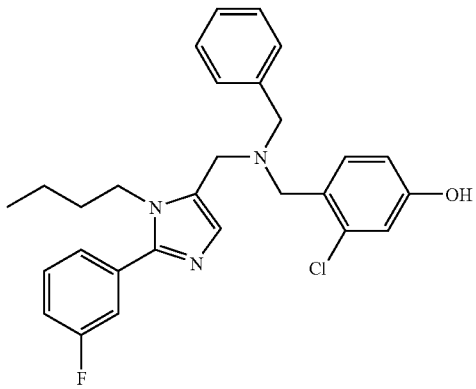

1-(1-Butyl)-2-phenyl-5-(N-[2-chloro-4-hydroxyphenylmethyl]-N-[1-butyl])aminomethyl-imidazole)

1-(1-Butyl)-2-(3-fluorophenyl)-5-(N-[2-chloro-4-hydroxyphenylmethyl]-N-phenylmethyl)-aminomethylimidazole;

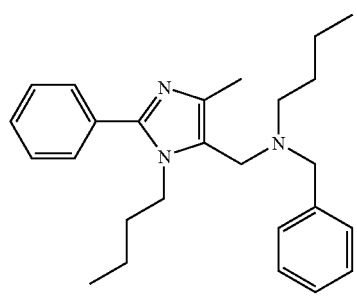

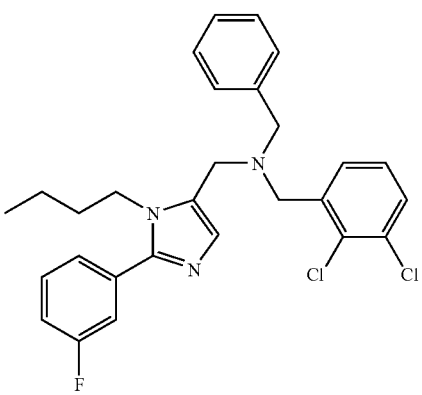

1-(1-Butyl)-2-phenyl-4-methyl-5-(N-phenylmethyl-N-[1-butyl])aminomethylimidazole;

1-(1-Butyl)-2-(3-fluorophenyl)-5-(N-[2,3-dichlorophenyl-methyl]-N-phenylmethyl)aminomethylimidazole;

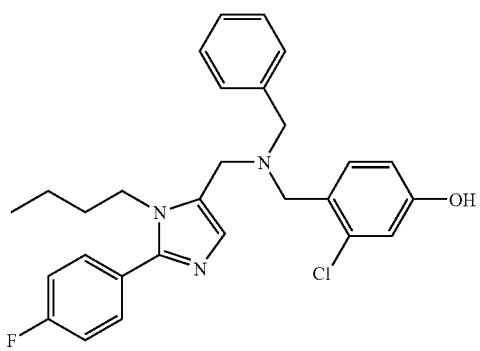

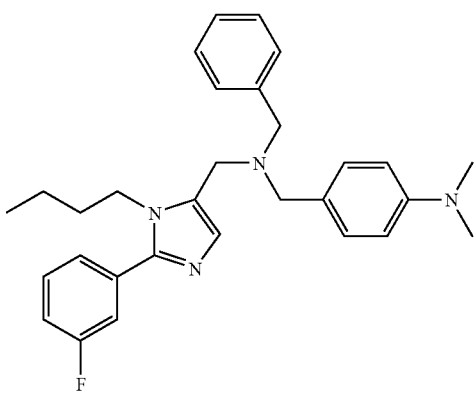

1-(1-Butyl)-2-(3-fluorophenyl)-(N-[4-dimethylaminophenylmethyl]-N-phenylmethyl)amino-methylimidazole;

1-(1-Butyl)-2-phenyl-5-(N-[indol-5-ylmethyl]-N-phenylmethyl)aminomethylimidazole;

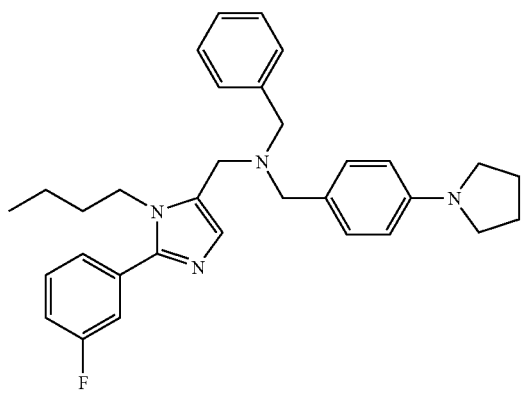

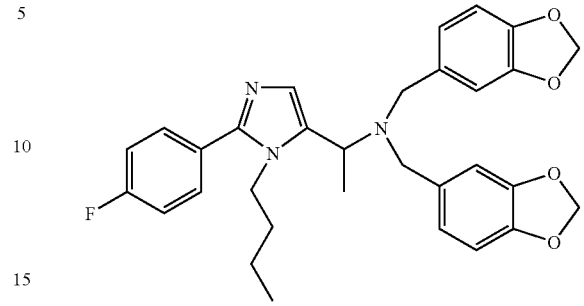

1-(1-Butyl)-2-(4-fluorophenyl)-5-(1-N,N-di[3,4-methylenedioxyphenylmethyl]amino)ethylimidazole;

1-(1-Butyl)-2-(3-fluorophenyl)-5-(N-[4-{1-pyrrolidinyl}phenylmethyl]-N-phenylmethyl)amino-methylimidazole;

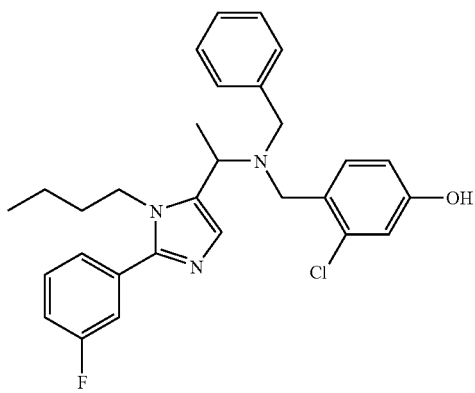

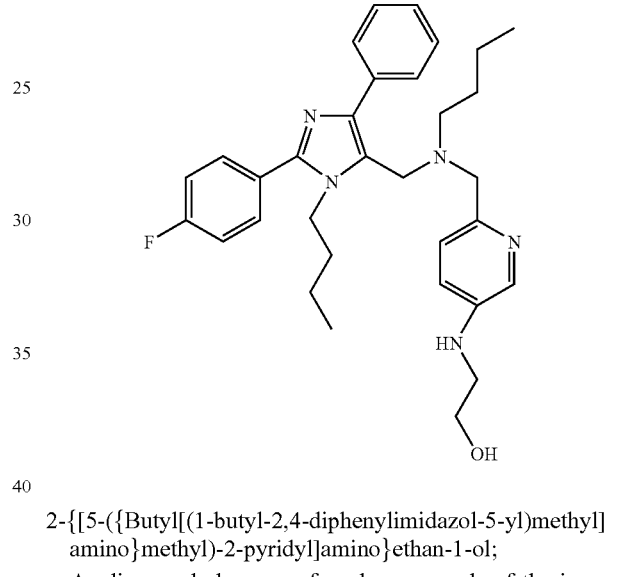

1-(1-Butyl)-2-(3-chlorophenyl)-5-(1-[N-{2-chloro-4-hydroxyphenylmethyl}-N-phenylmethyl]amino)ethylimidazole;

2-{[5-({Butyl[(1-butyl-2,4-diphenylimidazol-5-yl)methyl]amino}methyl)-2-pyridyl]amino}ethan-1-ol;

As discussed above, preferred compounds of the invention exhibit good activity in standard in vitro C5 receptor mediated chemotaxis assay, specifically the assay as specified in Example 12, which follows. References herein to "standard in vitro C5 receptor mediated chemotaxis assay" are intended to refer to that protocol as defined in Example 12 which follows. Preferred compound of the invention exhibit an $EC_{50}$ of about 100 μM or less in such a standard C5a mediated chemotaxis assay, more preferably an $EC_{50}$ of about 10 μM or less in such a standard C5a mediated chemotaxis assay, still more preferably an $EC_{50}$ of about 1 μM in such a standard C5a mediated chemotaxis assay, even more preferably an $EC_{50}$ of about 0.1 μM in such a standard C5a mediated chemotaxis assay.

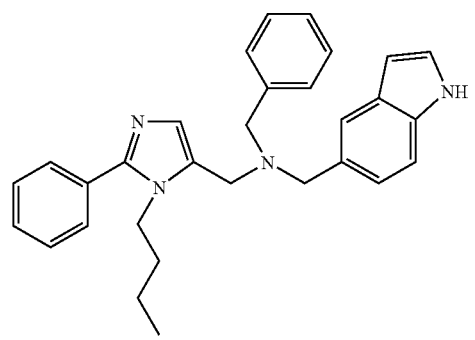

Additional assays suitable for determining the effects of small molecule compounds on C5a receptor binding and receptor modulatory activity, as well as assays suitable for measuring their effects on C5a-induced neutropenia in vivo, can be found in the published literature, for example in U.S. Pat. No. 5,807,824, which is incorporated herein by reference for its disclosure in this regard in Examples 6–9, columns 19–23, as well as for its discussion of complement and inflammation at columns 1–2. Those of skill in the art will recognize that such assays can be readily adapted to the use of cells or animals of different species as deemed appropriate.

In one aspect of the invention, one or more compounds of the invention, preferably in solution in a pharmaceutically acceptable carrier as a pharmaceutical preparation, is used to perfuse a donor organ prior to transplantation of the organ into a recipient patient. Such perfusion is preferably carried out using a solution comprising an concentration of the compound of the invention that is an effective amount sufficient to inhibit C5a mediated effects in vitro or in vivo. Such perfusion preferably reduces the severity or frequency of one or more of the inflammatory sequelae following organ transplantation when compared to that occurring in control (including, without restriction, historical control) transplant recipients who have received transplants of donor organs that have not been so perfused.

Definitions

In certain situations, the compounds of the invention may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. In these situations, the single enantiomers, i.e., optically active forms, can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

The term "substituted", as used herein, means that any one or more hydrogens on the designated atom is replaced with a selection from the indicated group, provided that the designated atom's normal valence is not exceeded, and that the substitution results in a stable compound. When a substituent is keto (i.e., =O), then 2 hydrogens on the atom are replaced. Keto substituents are not present on aromatic moieties. The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

When any variable occurs more than one time in any constituent or formula for a compound, its definition at each occurrence is independent of its definition at every other occurrence. Thus, for example, if a group is shown to be substituted with 0–2 R*, then said group may optionally be substituted with up to two R* groups and R* at each occurrence is selected independently from the definition of R*. Also, combinations of substituents and/or variables are permissible only if such combinations result in stable compounds.

As indicated herein, various substituents of the compounds of the present invention and various formulae set forth herein are "optionally substituted", including, e.g., $Ar_1$, $Ar_2$, R, $R_1$, $R_2$, $R_3$, $R_{3A}$, $R_4$, $R_5$, $R_6$, $R_7$, $R_A$, $R_A'$, $R_B$, and $R_C$. When substituted, those substituents may be substituted at one or more of any of the available positions, typically 1, 2, 3, or 4 positions, by one or more suitable groups such as those disclosed herein.

Suitable groups or "substituted" moities of compounds of the invention include e.g., halogen such as fluoro, chloro, bromo or iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups having those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons, particularly phenyl (e.g. an Ar group being a substituted or unsubstituted biphenyl moiety); arylalkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

As used herein, "alkyl" is intended to include both branched and straight-chain saturated aliphatic hydrocarbon groups, having the specified number of carbon atoms. Examples of alkyl include, but are not limited to, methyl, ethyl, n-propyl, 1-propyl, n-butyl, s-butyl, t-butyl, n-pentyl, and s-pentyl. Preferred alkyl groups are $C_1$–$C_8$ and $C_{1-6}$ alkyl groups. Especially preferred alkyl groups are methyl, ethyl, propyl, butyl, 3-pentyl. The term $C_{1-6}$ alkyl as used herein includes alkyl groups consisting of 1 to 6 carbon atoms, which may contain a cyclopropyl moiety. Suitable examples are methyl or ethyl.

"Cycloalkyl" is intended to include saturated ring groups, having the specified number of carbon atoms, such as cyclopropyl, cyclobutyl, cyclopentyl, or cyclohexyl and bridged or caged saturated ring groups such as norbornane or adamantane and the like.

In the term "($C_{3-6}$ cycloalkyl)$C_{1-4}$ alkyl", as defined above, the point of attachment is on the alkyl group. This term encompasses, but is not limited to, cyclopropylmethyl, cyclohexylmethyl and cyclohexylethyl.

"Alkenyl" is intended to include hydrocarbon chains of either a straight or branched configuration comprising one or more unsaturated carbon—carbon bonds, which may occur in any stable point along the chain, such as ethenyl and propenyl.

"Alkynyl" is intended to include hydrocarbon chains of either a straight or branched configuration comprising one or more triple carbon—carbon bonds that may occur in any stable point along the chain, such as ethynyl and propynyl.

"Haloalkyl" is intended to include both branched and straight-chain saturated aliphatic hydrocarbon groups having the specified number of carbon atoms, substituted with 1 or more halogen (for example —C$_v$(X$^i$)$_{wi}$(H$_{2v+1-\Sigma(wi)}$) where v=1 to 3; X$^i$=F(i=1), Cl(i=2), Br(i=3), I(i=4) and $\Sigma w_i \leq 2v+1$). Examples of haloalkyl include, but are not limited to, trifluoromethyl, trichloromethyl, pentafluoroethyl, and pentachloroethyl.

"Alkoxy" represents an alkyl group as defined above with the indicated number of carbon atoms attached through an oxygen bridge. Examples of alkoxy include, but are not limited to, methoxy, ethoxy, n-propoxy, 1-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

As used herein, the term "carbocyclic aryl" indicates aromatic groups containing only carbon in the aromatic ring. Such aromatic groups may be further substituted with carbon or non-carbon atoms or groups. Typical carbocyclic aryl groups contain 1 to 3 separate of fused rings and from 6 to about 18 ring atoms, without heteroatoms as ring members. Specifically preferred carbocyclic aryl groups include phenyl, napthyl, including 1-naphthyl and 2-naphthyl, and acenaphthyl.

By the term "energetically accessible conformer" is meant any conformer of a compound that falls within about a 15 Kcal/mol window above the lowest energy conformation (as for example that found in a monte carlo or systematic confirmational search) by using MM2, MM3, or MMFF force fields as implemented in molecular modeling software such as MacroModel® v 7.0, Schrödinger, Inc., Portland, Oreg. United States and Jersey City, N.J., United States, http://www.schrodinger.com or the like.

Peptidomimetic compounds are generally compounds with "chemical structures derived from bioactive peptides which imitate natural molecules" (Murray Goodman and Seonggu Ro, "Peptidomimetics for Drug Design" chapter twenty in Burger's Medicinal Chemistry and Drug Discovery, Volume 1: Principles and Practice, Manfred E. Wolff, ed. John Wiley & Sons, Inc., NY, 1995, pp. 801–861.) As used herein and in the claims, the term peptidomimetic additionally comprises peptoid compounds, which are compounds that comprise oligomers of N-substituted natural amino acids, and the term further comprises any compound having more than two amide bonds.

As used herein, the terms "heteroaryl" and "heteroalicyclic" group are intended to indicate a stable 5-to 7-membered monocyclic or bicyclic or 7-to 10-membered bicyclic heterocyclic ring which is saturated, partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The term heteroaryl indicates that the group contains at least 1 aromatic ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized.

It is preferred that when the total number of S and O atoms in the heterocycle exceeds 1, then these heteroatoms are not adjacent to one another. It is preferred that the total number of S and O atoms in the heterocycle is not more than 1, 2, or 3, more typically 1 or 2. It is preferred that the total number of S and O atoms in the aromatic heterocycle is not more than 1.

Examples of heteroaryl groups and other heterocycles include, but are not limited to, acridinyl, azocinyl, benzimidazolyl, benzofuranyl, benzothiofuranyl, benzothiophenyl, benzoxazolyl, benzthiazolyl, benzthiazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred heteroaryl groups include, but are not limited to, pyridinyl, pyrimidinyl, furanyl, and thienyl. Also included are fused ring and spiro compounds containing, for example, the above heterocycles.

The term "halogen" indicates fluorine, chlorine, bromine, or iodine.

The term "pharmaceutically acceptable salts" includes, but is not limited to non-toxic salts with inorganic acids such as hydrochloride, sulfate, phosphate, diphosphate, hydrobromide, and nitrite or salts with an organic acids such as malate, maleate, fumarate, tartrate, succinate, citrate, acetate, lactate, methanesulfonate, p-toluenesulfonate, 2-hydroxyethylsulfonate, salicylate and stearate. Similarly, pharmaceutically acceptable cations include, but are not limited to sodium, potassium, calcium, aluminum, lithium and ammonium. The present invention also encompasses the prodrugs of the compounds disclosed.

Examples of bicyclic oxygen containing groups of the formula:

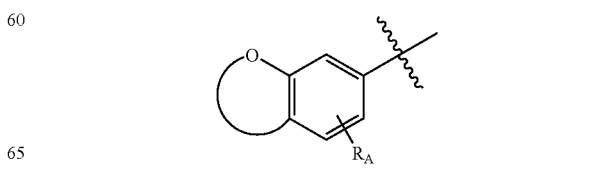

($R_A$ may also be indicated $R_B$) include the following:

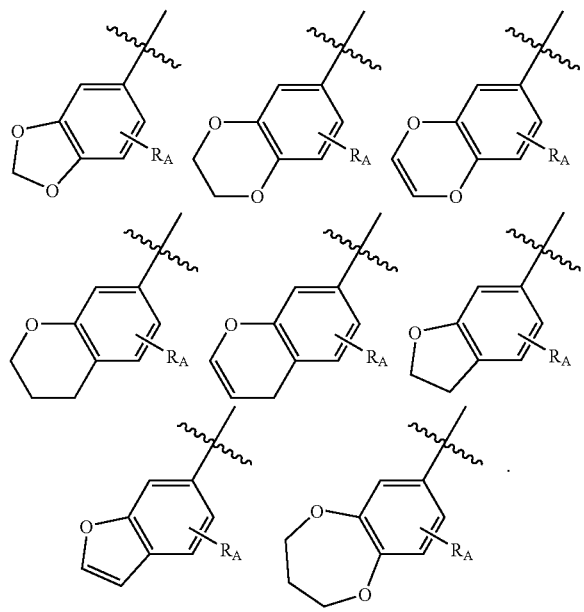

Methods of Treating Patients

The present invention provides methods of treating patients suffering from diseases or disorders involving pathologic activation of C5a receptors. Such diseases and disorders may include the following.

Such disorders that may be autoimmune in nature and are suitable for treatment in accordance with the present invention include e.g. rheumatoid arthritis, systemic lupus erythematosus (and associated glomerulonephritis), psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), and immunovasculitis. Such inflammatory and related conditions include neutropenia, sepsis, septic shock, Alzheimer's disease, stroke, inflammation associated with severe burns, lung injury, myocardial infarction, coronary thrombosis, vascular occlusion, post-surgical vascular reocclusion, artherosclerosis, traumatic central nervous system injury and ischemic heart disease, and ischemia-reperfusion injury, as well as acute (adult) respiratory distress syndrome (ARDS), systemic inflammatory response syndrome (SIRS), multiple organ dysfunction syndrome (MODS), tissue graft rejection, and hyperacute rejection of transplanted organs. Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement) such as extracorporeal post-dialysis syndrome, or in association with contact with other artificial vessel or container surfaces (e.g., ventricular assist devices, artificial heart machines, transfusion tubing, blood storage bags, plasmapheresis, plateletpheresis, and the like).

Treatment methods of the invention include in general administration to a patient a therapeutically effective amount of one or more compounds of the invention. Suitable patients include those subjects suffering from or susceptible to (i.e. propylactic treatment) a disorder or disease identified herein. Typical patients for treatment in accordance with the invention include mammals, particularly primates, especially humans. Other suitable subjects include domesticated companion animals such as a dog, cat, horse, and the like, or a livestock animal such as cattle, pig, sheep and the like.

Pharmaceutical Preparations

The compounds of the invention may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes injections and the like, such as subcutaneous, intradermal, intravascular (e.g., intravenous), intramuscular, intrasternal, spinal, intrathecal, and like injection or infusion techniques, with subcutaneous, intramuscular and intravascular injections or infusions being preferred. In addition, there is provided a pharmaceutical formulation comprising a compound of the invention and a pharmaceutically acceptable carrier. One or more compounds of the invention may be present in association with one or more non-toxic pharmaceutically acceptable carriers and/or diluents and/or adjuvants and if desired other active ingredients. The pharmaceutical compositions containing compounds of the invention may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylceullulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of the invention may also be administered in the form of suppositories e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of the invention may be administered parenterally, preferably in a sterile non-toxic, pyrogen-free medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment or preventions of conditions involving pathogenic C5a activity, particularly those disorders list in the "background of the invention" section (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

Preferred compounds of the invention will have favorable pharmacological properties. Such properties include, but are not limited to bioavailability (e.g., oral bioavailibilty, preferably high enough to permit oral administration of doses of less than 2 grams, preferably of less than or equal to one gram), low toxicity, low serum protein binding and desirable in vitro and in vivo half-lifes. Distribution in the body to sites of complement activity is also desirable, e.g., compounds used to treat CNS disorders will preferably penetrate the blood brain barrier, while low brain levels of compounds used to treat peripheral disorders are typically preferred.

Assays may be used to predict these desirable pharmacological properties. Assays used to predict bioavailability include transport across human intestinal cell monolayers, including Caco-2 cell monolayers. Toxicity to cultured hepatocycles may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage required for the effective administration of a compound. In vivo half-lifes of compounds may be predicted, e.g., from assays of microsomal half-life as described by Kuhnz and Gieschen (Drug Metabolism and Disposition, (1998) volume 26, pages 1120–1127).

Preparation of compounds

Representative methods for preparing the compounds of the invention are shown in the following Schemes. Schemes 1 and 2 show the preparation of arylimidazole compounds. Scheme 1 illustrates the preparation of arylimidazole compounds where $R_1$ is hydrogen or halogen. Scheme 2 represents of the preparation of aryl imidazole compounds where $R_1$ is alkyl. Within Schemes 1 and 2 the variables $Ar_1$, $Ar_2$, $R_1$, $R_2$, $R_3$ and $R_4$~are defined as above for Formula I.

hydrogen) or by treatment with the appropriate organometallic (for cases where $R_4$ is $C_1$–$C_6$ alkyl). The hydroxy group of 14 is converted to either a halogen or sulfonate ester leaving group. Treatment of this intermediate with an appropriate secondary amine in the presence of base provides 2-aryl-4-aminomethylimidazole 15. Alternatively, the aminoalkyl functionality of 15 may be elaborated by sequential amination-acylation-reduction steps. In situations where $R_1$ is a halogen, it may be prepared from 15 ($R_1$=H) by treatment with the molecular halogen, a halosuccinimide or the like.

As shown in Scheme 2, an appropriately substituted 2-aryl-4-substitutedimidazole 20 can be N-alkylated by

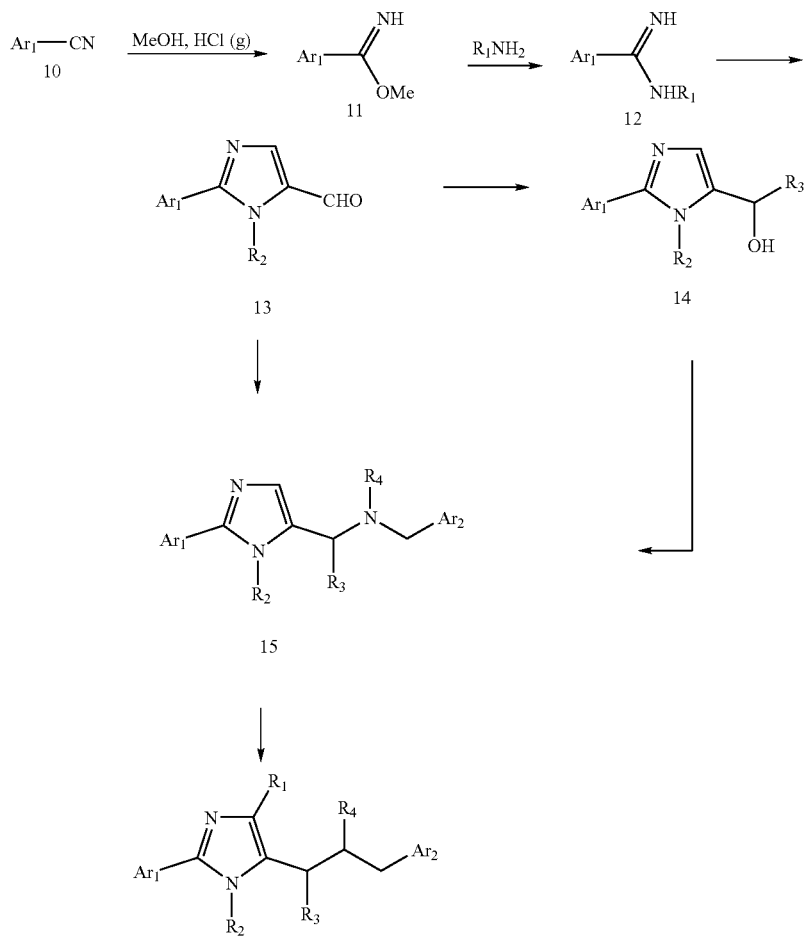

As shown in Scheme 1, an appropriately substituted arylnitrile 10 is converted to the imidate 11 via treatment with hydrogen chloride gas in methanol followed by subsequent treatment with base to release the free base. Amidine 12 is prepared from 11 by treatment with a primary amine. 2-Arylimidazole-4-carboxaldehyde 13 is prepared from 12 by one of several methods described in the chemical literature, for instance, by treatment with 2-bromo-3-isopropoxyacrolein in the presence of base. See, for example, J. Org, Chem., 62: 8449 (Shilcrat et al., 1997).

Aldehyde 13 can then be transformed into hydroxymethylimidazole 14 either by reduction (for cases where $R_4$ is treatment with base such as sodium hydride and an alkyl halide or alkylsulfonate ester to provide the trisubstituted imidazole 21. Hydroxymethylation of 21 under the conditions of the Mannich reaction provides hydroxymethylimidazole 22. In examples where $R_3$ is alkyl, hydroxymethyl derivative 24 is prepared from 22 by oxidation to aldehyde 23 and subsequent treatment with an appropriate organometallic reagent such as an alkyl lithium or Grignard reagent. Conversion of 22 or 24 to the desired 2-aryl-5-aminomethylimidazoles is carried out by conversion of the hydroxymethyl to a halogen or sulfonate ester leaving group followed by treatment with a secondary amine. Alternatively, the aminoalkyl functionality of the 2-aryl-5-aminomethylimidazole product may be elaborated by sequential amination-acylation-reduction steps.

Where $R_1$ is alkyl:

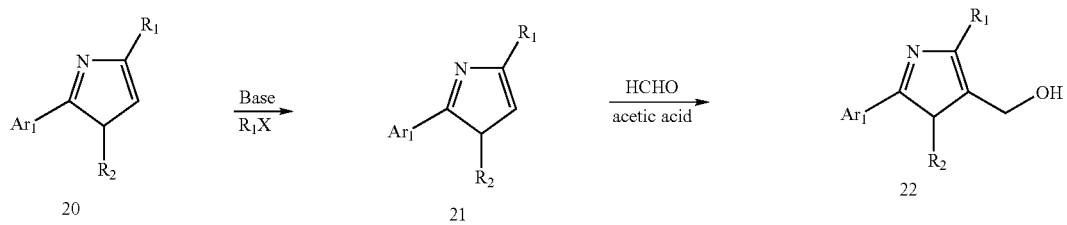

Where $R_3$ is alkyl:

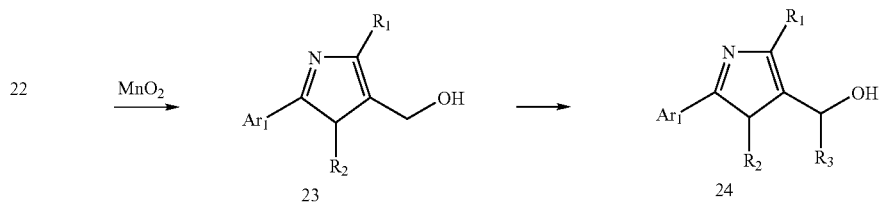

Where $R_3$ is hydrogen:

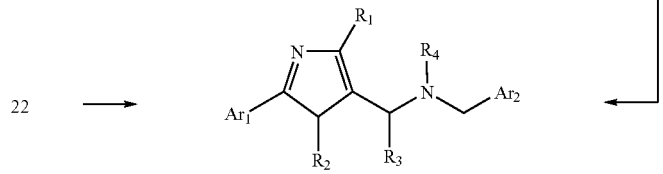

The 2-aryl-4-substitutedimidazole 20 may be prepared by methods described in the chemical literature, for instance, via condensation of an arylamidine with a halomethyl or hydroxymethyl ketone.

Cycloalkylimidazoles

An illustration of the preparation of compounds of the Cycloalkylimidazole compounds of the present invention is given in Scheme 3. Within Scheme 3 the variables n, $Ar_1$, $Ar_2$, $R_2$, $R_3$, $R_{3a}$, $R_4$, RS, $R_6$, $R_{5a}$, $R_{6a}$, $R_7$ and X are defined previously.

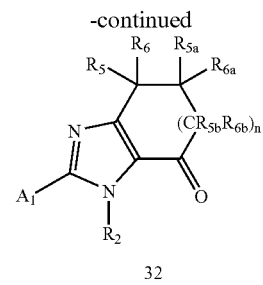

-continued

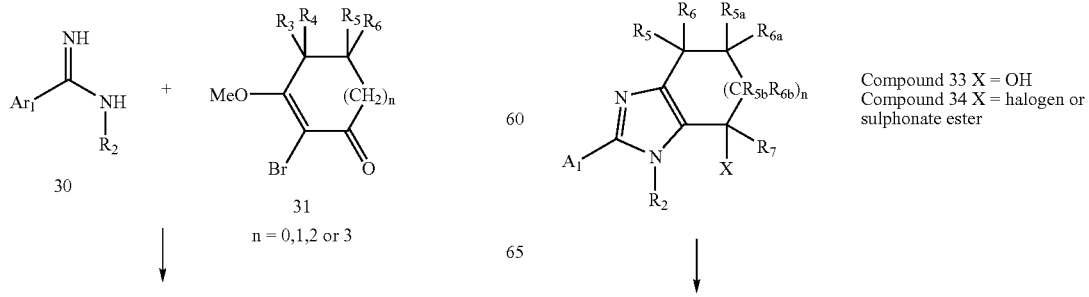

Compound 33 X = OH
Compound 34 X = halogen or sulphonate ester

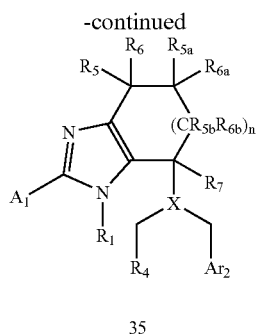

35

As shown in Scheme 3, an appropriately substituted arylamidine 30 is condensed with an appropriately substituted 2-halo-3-alkoxyenone 31 to provide a 2-aryl-4,5-cycloalkylimidazole 32. The ketone functionality of 32 can be either reduced ($R_7$=H) or treated with an appropriate organometallic (for cases where $R_7$ is alkyl) to give the cyclic alcohol 33. Compounds of general formula 34 can be prepared from 33 by one of several methods described in the chemical literature, for instance, by treatment with thionyl chloride or by treatment with an alkyl or arylsulphonyl chloride in the presence of base.

Compounds of formula 34 can then be transformed into compounds of general Formula 35 by direct treatment with the appropriate secondary amine. Alternatively, the X functionality of 34 may be transformed into a tertiary amine in a stepwise manner. In this case, 34 would be treated with a primary amine to provide an intermediate secondary amine. This, in turn, could be alkylated to give cycloalkylimidazole compounds of the invention.

Pyridines

An illustration of the preparation of pyridine compounds of the present invention is given in Scheme 4. Those having skill in the art will recognize that the starting materials may be varied and additional steps employed to produce compounds encompassed by the present invention. Within Scheme 4 the variables $Ar_1$, $Ar_2$, R, $R_1$, $R_2$, $R_3$, and $R_4$ are defined as previously described.

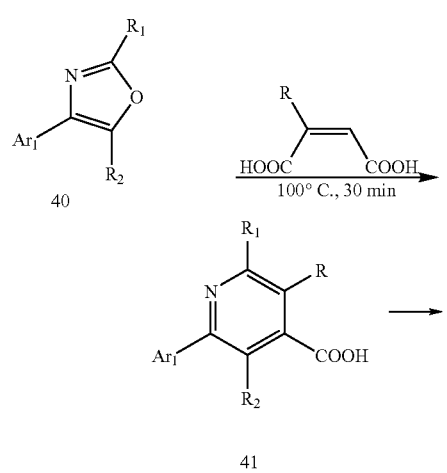

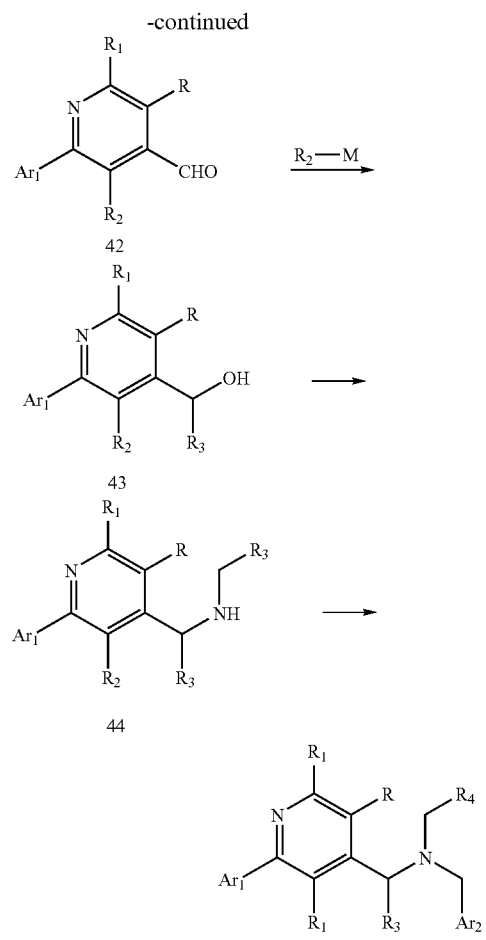

As shown in Scheme 4, an appropriately substituted 4-phenyloxazole 40 is condensed with an appropriately substituted maleic acid to provide a 2-phenylisonicotinic acid 41. The carboxylic acid functionality of 41 can be reduced directly to the primary alcohol (43, $R_3$=H) or converted by methods known to the art to an intermediate aldehyde 42 and subsequently treated with the appropriate organometallic (for cases where $R_3$ is alkyl) to give a secondary alcohol 43. Compounds of general formula 44 can be prepared from 43 by one of several methods described in the chemical literature, for instance, by initial treatment with thionyl chloride or with an alkyl or arylsulphonyl chloride in the presence of base, followed by subsequent condensation with a primary amine. Compounds of formula 44 can then be transformed into compounds of formula 45 by direct treatment with the appropriate alkylating agent or, alternatively, by reductive alkylation. Alternatively, the tertiary amine functionality of formula 45 may be realized directly from compounds of formula 43 by initial treatment with thionyl chloride or with an alkyl or arylsulphonyl chloride in the presence of base, followed by subsequent condensation with a secondary amine.

Pyrazoles

An illustration of the preparation of arylpyrazole compounds of the present invention is given in Scheme 5. Within Scheme 5 the variables $Ar_1$, $Ar_2$, $R_1$, $R_2$, $R_3$, and $R_4$ are defined as previously described.

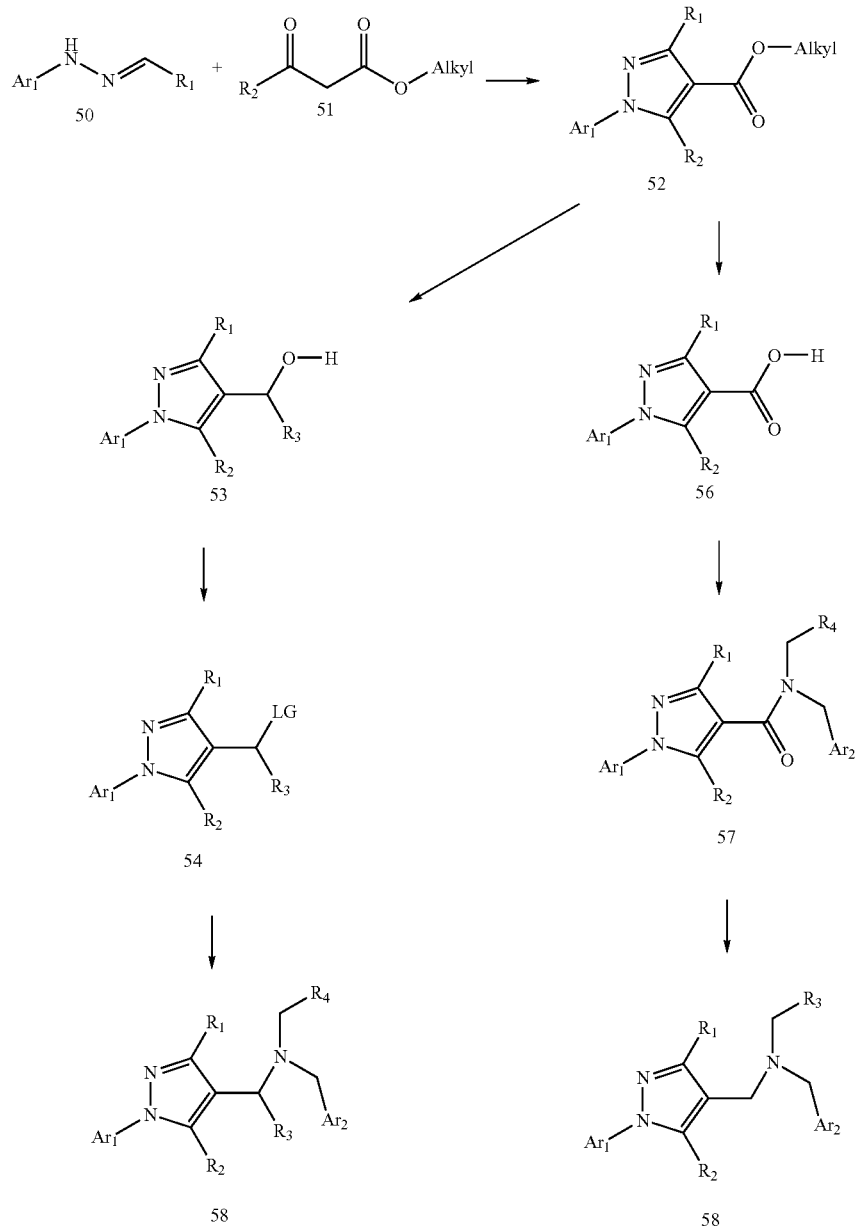

$R_3 = H$

As shown in Scheme 5, an appropriately substituted phenylhydrazine adduct 50 is condensed with an appropriately substituted α-ketoester 51, in the presence of a Lewis acid, preferably $ZnCl_2$, with heating at 50–200° C., preferably at 125° C. to provide a 1-phenylpyrazole ester 52. The carboxylic acid functionality of 52 can be reduced directly to the primary alcohol (53, $R_3$=H) or converted by methods known to the art to an intermediate aldehyde and subsequently treated with the appropriate the appropriate organometallic (for cases where $R_3$ is alkyl) to give a secondary alcohol 53. Compounds of general formula 54, where LG represents a leaving group, can be prepared from 53 by one of several methods described in the chemical literature, for instance, by initial treatment with thionyl chloride or with an alkyl or arylsulphonyl chloride in the presence of base, followed by subsequent condensation with a primary amine. Compounds of formula 54 can then be transformed into compounds of formula 58 by sequential treatment with the appropriate primary amine followed by direct alkylation or reductive alkylation of the intermediate secondary amine. Alternatively, the tertiary amine functionality of formula 58 may be realized directly from compounds of formula 53 by initial treatment with thionyl chloride or with an alkyl or arylsulphonyl chloride in the presence of base, followed by subsequent condensation with a secondary amine.

An alternative route to the preparation of compounds of Formula 58 from the 1-phenylpyrazole ester 52 may be realized by hydrolysis of 52 to a carboxylic acid of general structure 56, followed by amide formation to provide 57 and, finally, reduction of the amide functionality to the tertiary amine of 58 ($R_3$=H).

Scheme 6. Preparation of 2-(1-aryl-1,2,3,4-tetrahydroisoquinolin-2-yl) acetamides and bicyclics of other ring sizes (n=0, 1, 2, 3, etc)

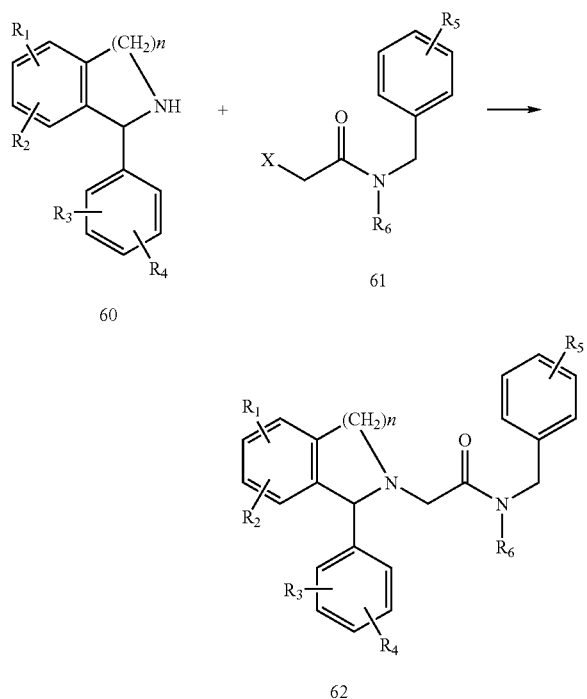

The 2-(1,2,3,4-tetrahydroisoquinolin-2-yl) acetamides of general formula 62 of the present invention may be prepared according to the procedure described graphically in Scheme 6, wherein a compound of general Formula 60, prepared according to literature procedures, (for example: Scully, Frank E., Jr.; Schlager, John J. Synthesis of dihydroisoquinolines and 1-substituted tetrahydroisoquinolines. Heterocycles (1982), 19(4), 653–6 or Shinohara, Tatsumi; Takeda, Akira; Toda, Jun; Terasawa, Noriyo; Sano, Takehiro. A highly efficient synthesis of 1-methyl-, 1-benzyl-, and 1-phenyl-1,2,3,4-tetrahydroisoquinolines by a modified Pummerer reaction. Heterocycles (1997), 46: 555–566.) is combined (in an appropriate solvent in the presence of an organic or inorganic base) with an appropriately substituted acetamide derivative possessing a leaving group X at its 2 position. For example, X may be halogen, alkyl or aryl sulfonate, or polyfluoroalkylsulfonate. Acetamides of general Formula 61 may be prepared via condensation of the appropriate secondary amine with a 2-haloacetylhalide (such as 2-chloroacaetyl chloride) in the presence of base. Alternatively acetamides of general formula 61 can be prepared by condensation of the appropriate secondary amine with either a 2-(alkylsulfonylester)acetic acid or 2-(arylsulfonylester)acetic acid in the presence of an coupling agent such as CDI or the like.

Within Scheme 6, $R_1$, $R_2$, $R_3$, $R_4$ and $R_5$ may be the same or different and are chosen from hydrogen, halogen, $C_1$–$C_6$ alkyl, $C_1$–$C_6$ alkoxy, hydroxy, trifluoromethyl, trifluoromethoxyl, cyano, nitro, hydroxy carbonyl (COOH), aminocarbonyl ($CONH_2$), mono or dialkylaminocarbonyl, sulfonamido, mono or dialkylsulfonamido, amino, mono- or di-alkylamino, aceto, acetoxy or 3,4-methylenedioxy or ethylenedioxy. The term n refers to an integer from 1 to 3. $R_6$ may be $C_1$–$C_9$ straight or branched chain alkyl, benzyl (substituted or unsubstituted), phenylethyl (substituted or unsubstituted), phenylpropyl (substituted or unsubstituted), or may be cycloalkyl fused with an aromatic group such as 1,2,3,4-tetrahydronaphthyl, 1- or 2-indanyl or suberanyl.

Scheme 7. Preparation of Ortho Biarylamides

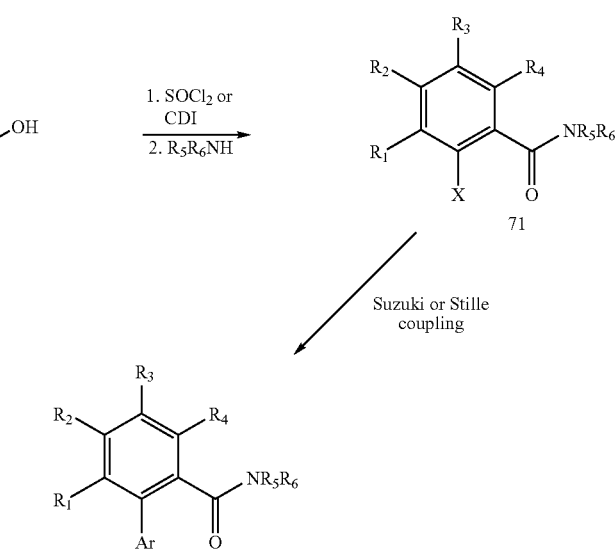

The preparation of the ortho biarylamides of the present invention may be carried out via a series of chemical transformations similar to those displayed graphically in Scheme 7. An individual skilled in the art may find modifications of one or several of the synthetic steps described herein without diverting significantly from the overall synthetic scheme.

Thus, as shown, the synthetic route begins with a benzoic acid of general structure 70 possessing a group X at the ortho position. This X group may be iodine, bromine, chlorine, sulfonate ester or polyfluoroalkylsulfonate ester. The benzoic acid may also be substituted by up to four independently chosen substitutents represented by the variables $R_1$–$R_4$. Examples of suitable substituents include hydrogen, chlorine, fluorine, cyano, $C_1$–$C_6$ straight or branched chain alkyl, $C_1$–$C_6$ straight or branched chain alkoxy, trifluoromethyl, trifluoromethoxy, nitro, amino, mono or dialkyl amino, sulfonamido, mono or dialkylsulfonamido, alkylthio e.g. methylthio, alkylsulfoxide, alkylsulfone, acetyl, acetoxy, alkoxycarbonyl (COOAlkyl) or dialkylaminocarbonyl (CON[alkyl]$_2$). Additionally, two adjacent groups (i.e. $R_1$ and $R_2$, or $R_2$ and $R_3$ or $R_3$ and $R_4$) may be taken together with a chain of from 3 to 5 methylene carbons to form a alkyl ring of from five to seven carbons fused to the benzoic acid moiety. Additionally, two adjacent groups (i.e $R_1$ and $R_2$, or $R_2$ and $R_3$ or $R_3$ and $R_4$) may be taken together with an alkyloxy chain, for example $OCH_2O$ or $OCH_2CH_2O$ to form an oxygen-containing moiety (in this example methylenedioxy or ethylenedioxy, respectively) fused to the benzoic acid.

This benzoic acid is then activated by conversion to an acid chloride with thionyl chloride, oxalyl chloride or the like. Alternatively, it may be activated by treatment with carbonyldiimidazole or a similar agent. The activated benzoic acid is then treated with an appropriate secondary amine in the presence of base to provide a tertiary amide of general structure 71.

Amide 71 is then converted to the biaryl structure 72 through the use of aryl coupling reactions know in the chemical literature. Examples of such reactions are the Stille reaction where an aryl trialkyltin reagent is coupled to an appropriate aryl in the presence of a catalyst such as palladium or nickel; or a Suzuki reaction where a arylboronic acid is coupled to an appropriate aryl in the presence of a nickel or palladium catalyst in the presence of base.

The group "Ar" of General structure 72 may be a phenyl which may be substituted with up to five additional independently chosen substitutents, e.g. hydrogen, halogen, cyano, $C_1$–$C_6$ straight or branched chain alkyl, $C_1$–$C_6$ straight or branched chain alkoxy, trifluoromethyl, trifluoromethoxy, nitro, amino, mono or dialkyl amino, sulfonamido, mono or dialkylsulfonamido, alkylthio e.g. methylthio, alkylsulfoxide, alkylsulfone, acetyl, acetoxy, hydroxycarbonyl (COOH), alkoxycarbonyl (COOAlkyl), aminocarbonyl (CONH$_2$), monoalkylaminocarbonyl, dialkylaminocarbonyl (CON[alkyl]$_2$, methylenedioxy or ethylenedioxy.

The Ar of General Structure 72 may also represent a heteroaryl group such as 1- or 2-thienyl or 1- or 2-furanyl. Such a heteroaryl group which may be additionally substituted by up to three independently chosen substituents, such as hydrogen, halogen, cyano, $C_1$–$C_6$ straight or branched chain alkyl, $C_1$–$C_6$ straight or branched chain alkoxy, trifluoromethyl, trifluoromethoxy, dialkyl amino, sulfonamido, mono or dialkylsulfonamido, alkylthio e.g. methylthio, alkylsulfoxide, alkylsulfone, acetyl, acetoxy, hydroxycarbonyl (COOH), alkoxycarbonyl (COOAlkyl), aminocarbonyl (CONH$_2$), monoalkylcarbonyl, dialkylaminocarbonyl (CON[alkyl]$_2$.

Scheme 8. General Preparation of Azaaryl benzamides

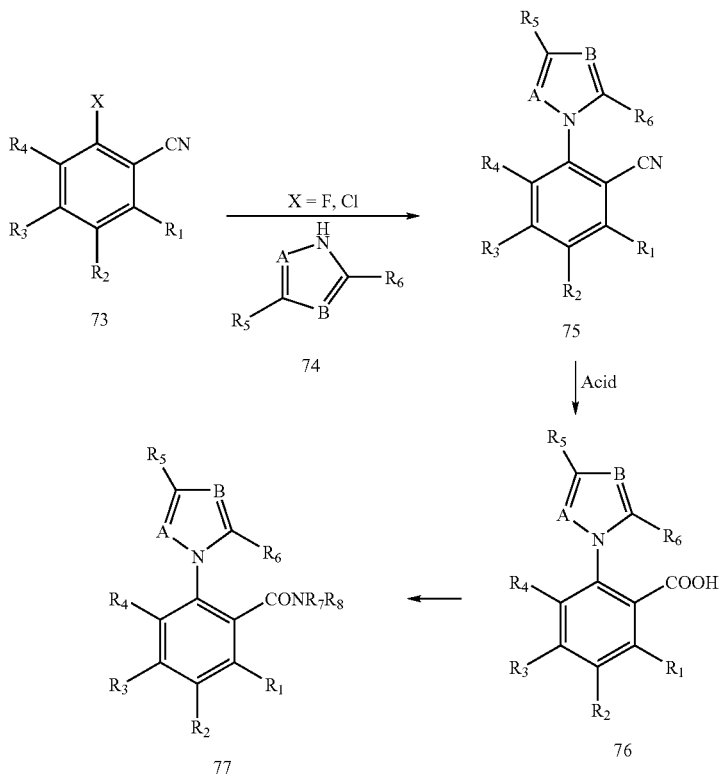

The preparation of 2-imidazolyl, 2-pyrrazolyl and 2-(1,2,4)-triazolyl benzamides begins with an appropriately substituted benzonitrile derivative having a leaving group X at the position ortho to the carboxylic acid functionality. Most commonly this group would be a fluorine or chlorine group. This benzonitrile may be optionally substituted or additionally substituted by up to four substituents ($R_1$–$R_4$) which may be the same or different (examples of such substituents are: hydrogen, halogen, cyano, $C_1$–$C_6$ straight or branched chain alkyl, $C_1$–$C_6$ straight or branched chain alkoxy, trifluoromethyl, trifluoromethoxy, nitro, amino, mono or dialkyl amino, sulfonamido, mono or dialkylsulfonamido, methylthio, alkylsulfoxide, alkylsulfone, acetyl, acetoxy, alkoxycarbonyl (COOAlkyl) or dialkylaminocarbonyl (CON[alkyl]$_2$).

The benzonitrile 73 is mixed with the azaheterocycle 74 (wherein A and B may be either nitrogen or carbon with the caveat that both A and B not be carbon. $R_5$ and $R_6$ may be the same as those groups described for $R_1$–$R_4$.) This condensation may be carried out either in a single phase system in an appropriate solvent and base, or in a two-phase manner using a phase transfer catalyst.

2-Azaheterocyclicbenzonitrile 75 is the hydrolyzed to the corresponding benzoic acid 76 via means common to the chemical literature, for instance mineral acid.

The benzoic acid 76 is then activated via thionyl chloride, CDI or other means known to the chemical literature and condensed with an appropriately substituted secondary amine to provide the desired final products 77.

EXAMPLES

The general methods given in Schemes 1 to 8 above for the preparation of compounds of the present invention are further illustrated by the following examples. Specifically, the methods given in Schemes 1 and 2 for the preparation of aryl imidazoles are illustrated by Examples 1–4, shown below. An example of the method shown in Scheme 3 for the preparation of cycloalkylimidazoles is given in example 5, and example of the method shown in Scheme 4 for the preparation of arylpyridines is given in example 6, and an example of the method shown in Scheme 5 for the preparation of arylpyrazoles is given in example 7. The method shown by Scheme 6 for the preparations of 2-(1-Aryl-1,2,3,4-tetrahydroisoquinolin-2-yl)acetamides is further illustrated in example 8. The methods shown in Schemes 7 and 8 for the preparation of ortho biarylamides and azaarylamides, respectively, are exemplified in Examples 9 and 10. Unless otherwise specified all starting materials and reagents are of standard commercial grade, and are used without further purification, or are readily prepared from such materials by routine methods. Those skilled in the art of organic synthesis will recognize that starting materials and reaction conditions may be varied to achieve the desired end product.

Example 1

Preparation of an arylimidazole compound: 1-(1-butyl)-2-phenyl-5-(N,N-di[3,4-methylenedioxyphenyl methyl])aminomethylimidazole (Compound 106)

N-(n-butyl)-benzamidine (101). To a solution of methyl benzimidate hydrochloride (12 g, 0.07 mole) in dimethylformamide (DMF, 20 mL) is added 7 ml of triethylamine at 0° C. After 2 h the reaction is filtered to remove triethylamine hydrochloride. To the filtrate is added 3.68 g of 1-butylamine and the mixture is heated to 60° C. for 6 h. After cooling the mixture is partitioned between ethyl acetate and water. The organic layer is washed with brine, dried over sodium sulfate and concentrated to provide 13.28 g of the amidine as a yellow oil. $^1$H NMR (400 MHz, CDCl$_3$) δ 7.55 (m, 2H), 7.4 (m, 3H), 3.37 (bm, 2H), 1.62 (m, 2H), 1.42 (m, 2H), 0.95 (t, J=7 Hz, 3H).

1-(1-Butyl)-2-phenylimidazole-5-carboxaldehyde (102). To a solution of 101 (13.28 g) and 2-bromo-3-isopropoxyacrolein (22 g) in chloroform (150 ml) is added potassium carbonate (15.5 g) and water (19 ml). The mixture is stirred at room temperature overnight. The aqueous layer is discarded and the organic layer is washed with water (3×100 mL), dried (Na$_2$SO$_4$) and concentrated. The residue is purified via flash chromatography (5% MeOH/CHCl$_3$) to provide the desired imidazole carboxaldehyde as a pale yellow oil (21.55 g). $^1$H NMR (400 MHz, CDCl$_3$) 5 9.75 (s, 1H), 7.90 (s, 1H), 7.55 (m, 2H), 7.45 (m, 3H), 4.38 (t, J=8 Hz, 2H), 1.75 (m, 2H), 1.22 (m, 2H), 0.91 (t, J=7 Hz, 3H).

Representative preparation of a 1-Alkyl-2-aryl-4-aminomethylimidazole: 1-(1-Butyl)-2-phenyl-5-(N,N-di[3,4-methylendioxyphenylmethyl]) aminomethylimidazole)

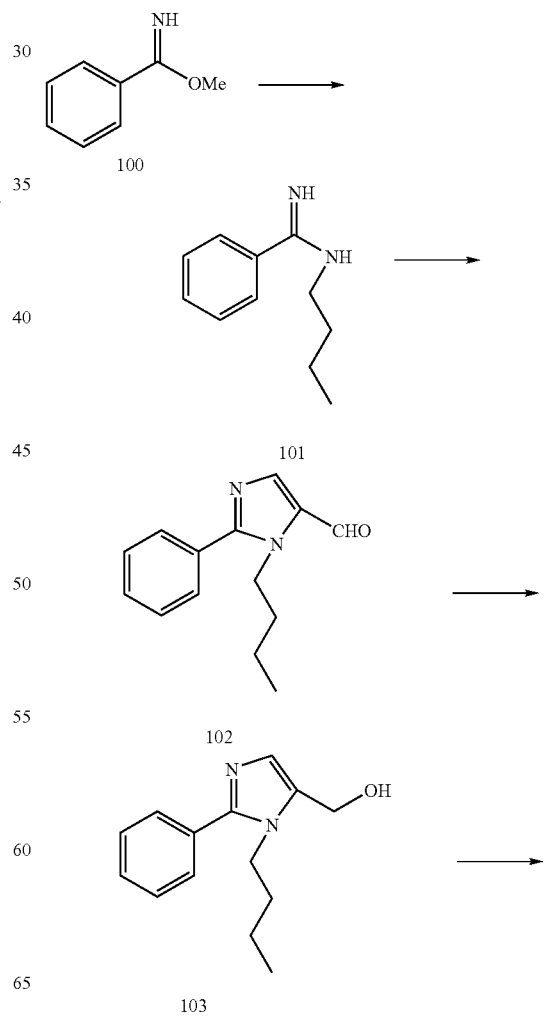

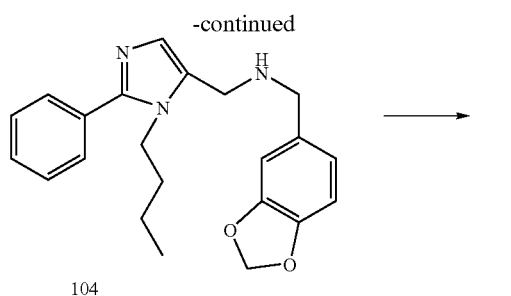

104

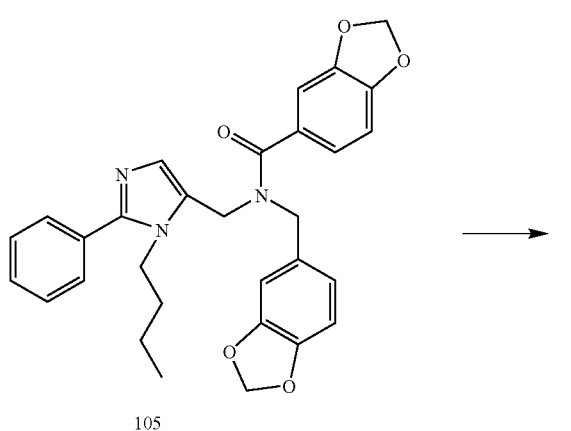

105

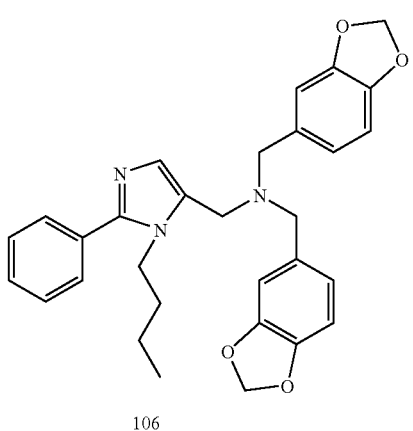

106

1-(1-Butyl)-2-phenyl-5-hydroxymethylimidazole (103). Aldehyde 102 is dissolved in methanol (150 mL). Sodium borohydride (3 g) is added in portions. After the addition was complete, the reaction is diluted with water and concentrated. The residue is dissolved in ethyl acetate, washed with brine, dried ($Na_2SO_4$) and concentrated. The product is purified by flash chromatography on silica gel (5% MeOH/$CHCl_3$) to give 4.17 g of 103 as a cream colored solid. $^1$H-NMR (400 MHz, $CDCl_3$): δ 0.79 (3H, t, d=7.4), 1.18 (2H, m, d=7.4), 1.60 (2H, m, d=7.6), 4.03 (2H, dd, d=7.6), 4.56 (2H, s), 6.84 (1H, s), 7.39–7.50 (3H, m), 7.50–7.53 (2H, m).

1-(1-Butyl)-2-phenyl-5-(N-[3,4-methylenedioxyphenylmethyl])aminomethylimidazole (104). Hydroxymethylimidazole 103 (0.82 g) is dissolved in chloroform (10 ml) and treated with thionyl chloride (1 ml). The solution is heated to 50° C. for 30 min, cooled and evaporated. The residue is washed with benzene and evaporated to give the intermediate chloromethyl hydrochloride as a white powder which is taken up in acetonitrile (30 mL). This is added dropwise to a solution of piperonylamine (5 ml) in acetonitrile (10 mL). The reaction is allowed to stand overnight and then evaporated. The residue is taken up in ethyl acetate and washed with water. The organic layer is dried ($Na_2SO_4$) and concentrated. Purification on silica gel (10% MeOH/$CHCl_3$) provides the product as a pale yellow oil (0.91 g). $^1$H NMR (400 MHz, $CDCl_3$): δ 0.79 (3H, t, d=7.4), 1.18 (2H, m, d=7.4), 1.56 (2H, m, d=7.4), 3.75 (4H, s), 4.04 (2H, dd, d=8), 5.92 (2H, s), 6.76 (2H, m), 6.84 (1H,s), 6.97 (1H, s), 7.38–7.44 (3H, m), 7.53–7.56 (2H, m).

1-(1-Butyl)-2-phenyl-5-(N-[3,4-methylenedioxyphenyl methyl]-N-(3,4-methylenedioxyphenylcarboxy]) aminomethylimidazole (105). Compound 104 (160 mg, 0.44 mmol) is dissolved in chloroform (5 ml, pentene stabilized) and treated sequentially with piperonyloyl chloride (100 mg) and triethylamine (1 ml). The mixture is stirred at room temperature overnight. The solution is concentrated and the residue taken up in ethyl acetate. The organic is washed with water, dried ($Na_2SO_4$) and concentrated. Purification by preparative thin layer chromatography (5% MeOH/$CHCl_3$) provides compound 105 as a pale yellow oil (240 mg). $^1$H-NMR (400 MHz, $CDCl_3$): δ 0.75 (3H, br), 1.16 (2H, br), 1.49 (2H, br), 4.01 (2H, br), 4.54 (2H, br), 4.68 (2H, br), 5.97 (2H, s), 5.99 (2H, s), 6.66 (2H, d, d=7.2), 6.80 (2H, t, d=8), 6.98–7.02 (2H, m), 7.40–7.47 (3H, m), 7.56 (2H, d, d=6.8).

1-(1-Butyl)-2-phenyl-5-(N,N-di[3,4-methylenedioxy phenylmethyl])-aminomethylimidazole (106). Amide 105 (215 mg) in tetrahydrofuran (THF, 3 ml) is added dropwise to a solution of alane (1 M in THF, 2 ml) and the resulting solution is stirred for 2.5 h at room temperature. A solution of sodium hydroxide (15% NaOH, 1 ml) is added and the mixture is extracted with chloroform. The organic extracts are dried ($Na_2SO_4$) and concentrated. Purification by preparative thin layer chromatography (10% MeOH/$CHCl_3$) provided compound 106 as a colorless oil (115 mg). $^1$H-NMR (400 MHz, $CDCl_3$): δ0.70 (3H, t, d=7.6), 0.98 (2H, m, d=7.6), 1.30 (2H, m), 3.44 (4H, s), 3.52 (2H, s), 3.98 (2H, dd, d=8), 5.92 (4H, s), 6.74 (4H, s), 6.69 (2H, s), 7.02 (1H, s), 7.36–7.42 (3H, m), 7.54 (2H, dd, d=1.4, 6.6). The hydrochloride salt (m.p. 187–190° C.) was prepared in isopropanol.

Example 2

Preparation of 1-(1-butyl)-2-phenyl-5-(1-[N-{3,4-methylenedioxyphenylmethyl}-N-phenylmethyl]amino)ethylimidazole (Compound 108)

1-Butyl-2-phenyl-5-(1-hydroxyethyl)imidazole (107). A solution of aldehyde 102 (230 mg) in diethyl ether (30 mL) is placed in a separatory funnel and treated with a solution of Preparation of 1-(1-Butyl)-2-phenyl-5-(1-[N-[{3,4-methylendioxyphenylmethyl]}-N-[phenylmethyl]aminoethylimidazole)

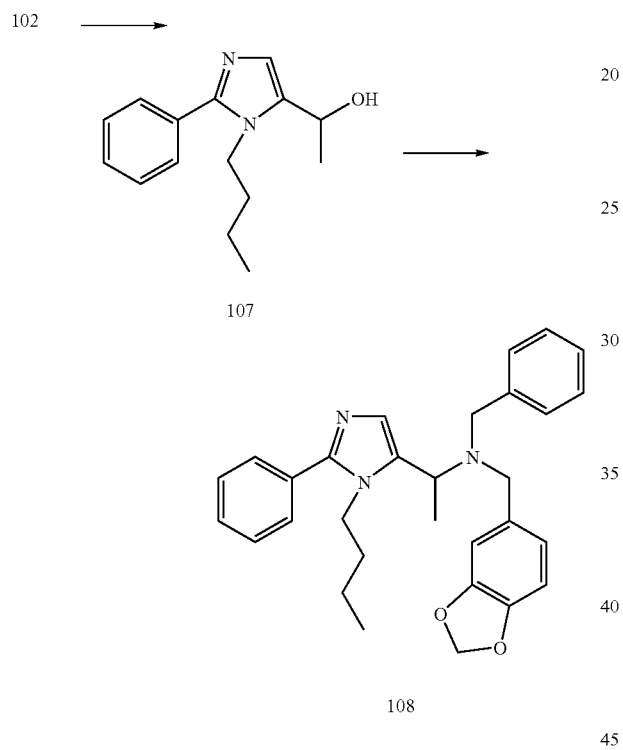

methyl lithium (1.4 M in THF, 1.5 ml). After 10 min, the solution is washed with ammonium chloride solution (1 M, 20 ml), dried (Na₂SO₄) and concentrated. The resulting dark oil is purified by preparative TLC (10% MeOH/CHCl₃) to provide compound 107 as a colorless oil (180 mg). ¹H NMR (400 MHz, CDCl₃) δ7.56 (d, J=2 Hz, 2H), 7.4 (m, 3H), 7.01 (s, 1H), 4.86 (q, J=7 Hz, 1H), 4.18 (m, 1H), 4.0 (m, 1H), 1.63 (d, J=6.6 Hz, 3H), 1.63 (m, 2H), 1.23 (m, 2H), 0.81 (t, J=7 Hz, 3H).

1-Butyl-2-phenyl-5-(N-[3,4-methylenedioxyphenyl]-N-phenylmethyl)aminoethylimidazole (108). A solution of compound 107 (80 mg) in chloroform (10 ml) is treated with thionyl chloride (1 ml) and heated to 50° C. for 30 min. The solution is then concentrated, diluted with chloroform and reconcentrated to provide the intermediate chloromethyl hydrochloride as an oil. This material is taken up in chloroform (5 ml) and treated sequentially with N-benzylpiperonylamine (80 mg) and triethylamine. After stirring overnight, the reaction is washed with saturated potassium carbonate solution, dried (Na₂SO₄) and concentrated. Purification by preparative thin layer chromatography (10% MeOH/CHCl₃) provides compound 108 as a colorless oil (62 mg). ¹H NMR (400 MHz, CDCl₃) δ 7.46–7.43 (m, 1H), 7.2–7.3 (m, 9H), 6.74–6.86 (m, 4H), 5.94 (s, 2H), 4.82 (q, J=6.8 Hz, 1H), 4.33 (m, 2H), 3.78 (s, 2H), 3.53 (s, 2H), 1.83 (d, J=6.8 Hz, 3H), 1.62–1.68 (m, 2H), 1.21 (q, J=7.8 Hz, 2H), 0.82 (t, J=7.8 Hz, 3H).

Example 3

Preparation of 1-Butyl-2-phenyl-4-bromo-5-(N-phenylmethyl-N-[1-butyl])amino-methylimidazole (Compound 110)

Preparation of 1 (1-Butyl)-2-phenyl-4-bromo-5-[N-phenylmethyl-N-[1-butyl]) aminomethylimidazole)

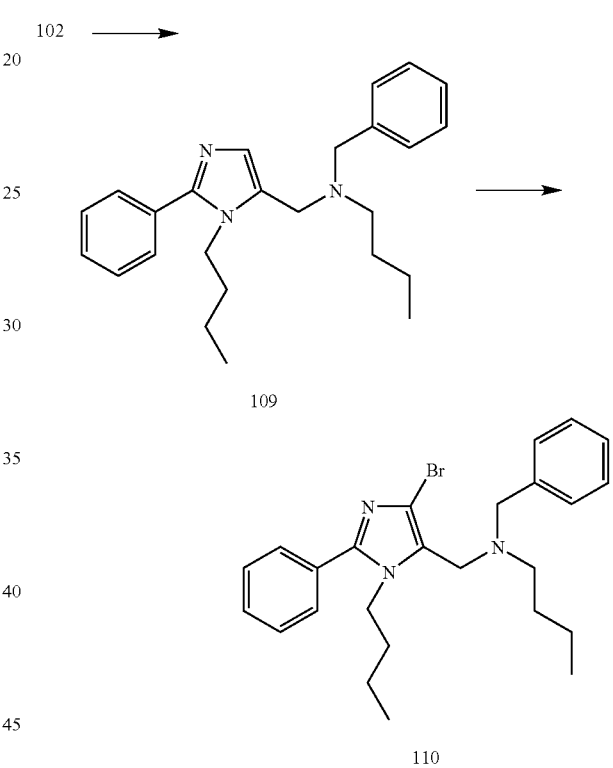

1-Butyl-2-phenyl-5-(N-benzyl-N-butyl)aminomethylimidazole (109). A solution of compound 102 (115 mg) and N-butylbenzylamine (85 mg) in toluene (10 ml) is allowed to stand overnight. Treatment of the reaction with sodium borohydride (100 mg) and ethanol (2 mL) followed by aqueous workup and purification on silica gel (10% MeOH/CHCl₃) provides compound 109 as a colorless oil (35 mg). ¹H NMR (400 MHz, CDCl₃) δ7.2–7.5 (m, 10H), 6.98 (s, 1H), 4.0 (t, J=8 Hz, 2H), 3.55 (s, 2H), 3.52 (s, 2H), 2.42 (t, J=8 Hz, 2H), 1.2–1.55 (m, 6H), 1.05 (m, 2H), 0.84 (t, J=7 Hz, 3H), 0.72 (t, J=7 Hz, 3H).

1-Butyl-2-phenyl-4-bromo-5-(N-phenylmethyl-N-[1-butyl])aminomethylimidazole (110). To a solution of 109 (30 mg) in acetonitrile (4 mL) was added N-bromosuccinimide (16 mg). The resulting mixture was heated to 60° C. and the progress of the reaction followed by TLC. The cooled reaction mixture was diluted with ethyl acetate and washed twice with water. Purification by preparative thin layer chromatography (10% MeOH/CHCl₃) provided compound 110 as a colorless oil (22 mg). $^1$H NMR (400 MHz, CDCl$_3$) δ7.2–7.5 (m, 10H), 3.98 (t, J=8 Hz, 2H), 3.55 (s, 2H), 3.53 (s, 2H), 2.46 (t, J=7 Hz, 2H), 1.52 (m, 2H), 1.3 (m, 4H), 0.98 (q, J=7 Hz, 2H), 0.84 (t, J=7 Hz, 3H), 0.70 (t, J=7 Hz, 3H).

Example 4

Preparation of 1-(1-Butyl)-2-phenyl-4-methyl-5-(N-[3,4-methylenedioxyphenyl-methyl]-N-phenylmethyl)aminomethylimidazole. (Compound 114)

1-Butyl-2-phenyl-4-methylimidazole (112). To a solution of 4-methyl-2-phenylimidazole (111, 15.8 g) in dimethylformamide (100 ml) is added sodium hydride (4.4 g, 60% in mineral oil) in small portions. After the addition is complete, the mixture was stirred for an additional 20 min and treated with 1-iodobutane (18.8 g). The reaction is fitted with a reflux condensor and heated at 100° C. for 12 h. The cooled reaction mixture is partitioned between water (300 ml) and diethyl ether (300 ml). The organic layer is washed with water (3×200 ml), dried (Na$_2$SO$_4$) and concentrated to provide 20.5 g of N-butylimidazoles. Analysis by $^1$H-NMR and GC-MS revealed mixture of 1-butyl-2-phenyl-4-methylimidazole (112) and 1-butyl-2-phenyl-5-methylimidazole in a ratio of 11.5/1. The mixture was carried on to the next step without purification.

1-Butyl-2-phenyl-4-methyl-5-hydroxymethylimidazole (113). A solution of 112 (1 g) in acetic acid (10 mL) and 40% aqueous formaldehyde (2 mL) is refluxed for 14 h. The reaction is then concentrated and dried by repeated reconcentration with toluene. The residue is purified by column chromatography (10% MeOH/CHCl$_3$). The fractions are assayed by GC and those fractions uncontaminated by the isomeric hydroxymethylimidazole combined. Concentration of the combined fractions provides compound 113 (320 mg) as a pale yellow oil. $^1$H NMR (400 MHz, CDCl$_3$) δ 7.4–7.6 (m, 6H), 4.61 (s, 2H, CH$_2$OH), 4.02 (t, J=7 Hz, 2H, NCH$_2$), 2.22 (s, 3H, Me), 1.63 (m, 2H, 1.25 (m, 2H), 0.81 (t, J=7 Hz, 3H).

Preparation of 1-(1-Butyl)-2-phenyl-4-methyl-5-(N-[3,4methylenedioxyphenyl]-N-phenylmethyl) aminomethylimidazole

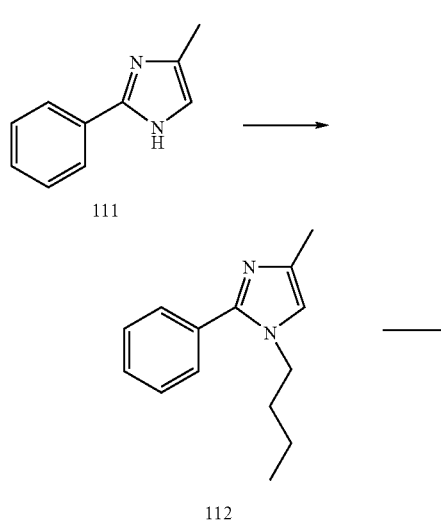

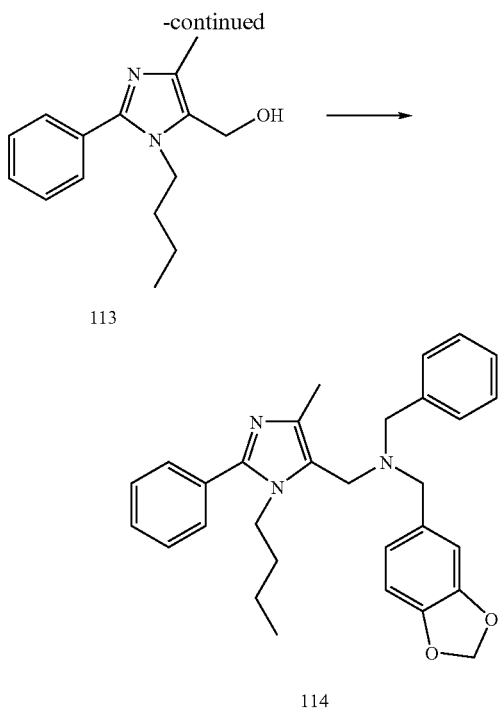

1-Butyl-2-phenyl-4-methyl-5-(N-benzyl-N-butyl)aminomethylimidazole (114). Compound 114 (23 mg) is prepared from 113 (50 mg) in a method similar to that used to obtain compound 108. $^1$H NMR (400 MHz, CDCl$_3$) δ7.5–7.55 (m,2H), 7.38–7.42 (m, 3H), 7.23–7.30 (m, 5H), 3.95 (t, J=7.5 Hz, 2H), 3.55 (s, 2H), 3.53 (s, 2H), 2.40 (t, J=7 Hz, 2H), 2.22 (s, 3H), 1.25–1.40 (m, 6H), 1.05 (m, 2H), 0.82 (t, J=7 Hz, 3H). 0.70 (t, J=7 Hz, 3H); MS (LCMS) m/e 390 (M$^+$+1)

Example 5

Preparation of a cycloalkylimidazole compound: 4-{[butyl(1-butyl-2-phenyl(4,5,6-trihydrocyclopenta[3,2-d]imidazol-6-yl)amino]methyl}-3-chlorophenol N-(n-butyl)-benzamidine (120). To a solution of methyl benzimidate hydrochloride (12 g, 0.07 mole) in dimethylformamide (DMF, 20 mL) is added 7 ml of triethylamine at 0° C. After 2 h the reaction is filtered to remove triethylamine hydrochloride. To the filtrate is added 3.68 g of 1-butylamine and the mixture is heated to 60° C. for 6 h. After cooling the mixture is partitioned between ethyl acetate and water. The organic layer is washed with brine, dried over sodium sulfate and concentrated to provide 13.28 g of the amidine as a yellow oil. $^1$H NMR (CDCl$_3$) 7.55 (m, 2H), 7.4 (m, 3H), 3.37 (bm, 2H), 1.62 (m, 2H), 1.42 (m, 2H), 0.95 (t, J=7 Hz, 3H).

2-Bromo-3-methoxycyclopentenone (131) is prepared via the method of Curran et al JACS, vol 112, page 5601. To a suspension of 1,3-cyclopentanedione (10 g) in chloroform (700 ml) is added a N-bromosuccinimide (18.2 g). The mixture is refluxed for 2 h, cooled and concentrated. Methanol (700 mL) and p-toluenesulfonic acid (1 g) are added and the solution is refluxed overnight. The mixture is concentrated to 100 ml, diluted with methylene chloride (500 mL) and poured into water. The aqueous layer is discarded and the organic layer is washed with water (3×100 mL), dried (Na$_2$SO$_4$) and concentrated. The residue is crystallized from ethyl acetate to give 131 as tan crystals (1.67 g).

1-Butyl-2-phenyl-4,5-dihydrocyclopenty[1,2-d]imidazol-6-one (Compound 132). To a mixture of amidine 130 (3.52 g, 20 mmol) and enone 13 (4.58 g, 24 mmol) in chloroform (40 mL) and water (5 mL) was added solid potassium carbonate (3.32 g, 24 mmol). The resulting mixture is refluxed overnight. After cooling, the mixture is washed with water, dried (Na$_2$SO$_4$) and concentrated. Purification on silica gel eluting with 25% ethyl acetate/hexane gives the desired product 132 (3.0 g) LC-MS (M$^+$+1): 255. $^1$H-NMR (δ, CDCl$_3$): 0.84 (t, J=7.6 Hz, 3H), 1.23 (dt, J=7.0, 7.6 Hz, 2H), 1.81 (m, 2H), 2.95 (m, 4H), 4.13 (t, J=7.6 Hz, 2H) 7.5–7.45 (m, 3H), 7.76–7.6 (m, 2H) ppm. 1-Butyl-2-phenyl-4,5-dihydrocyclopenty[1,2-d]imidazol-6-ol (Compound 133). To a solution of 132 (2.68 g) in methanol (20 mL) is added sodium borohydride (1.5 equiv) and the mixture stirred overnight. The mixture is concentrated, diluted with chloroform and washed with 0.5 N NH$_4$Cl solution. The organic layer is dried (Na$_2$SO$_4$) and concentrated to provide the desired product 133. LC-MS (M+1) 257. Butyl(1-butyl-2-phenyl-4, 5,6-trihydrocyclopentyl[3,2-d]imidazol-6-yl))amine (Compound 135). Compound 133 (2 g) is dissolved in chloroform (20 mL) and thionyl chloride (5 mL) and the resulting solution is stirred at room temperature overnight. The solvent and excess thionyl chloride are evaporated and the crude chloride 134 was dissolved in n-butylamine (10 mL). After 2 h, the excess butylamine was evaporated, the residue dissolved in ethyl acetate and the organic solution washed with 5% NaOH solution and water. The organic layer was dried and concentrated. The organic residue is purified by column chromatography on silaica gel eluting with 10% CH$_3$OH in CHCl$_3$ to provide the desired secondary amine 135 in 82% yield. LC-MS (M+1) 312 $^1$H-NMR (chemical shift, CDCl$_3$): 0.83 (t, J=7.2 Hz, 3H), 0.9 (t, J=7.2 Hz, 3H), 1.23 (q, J=7.2 Hz, 2H), 1.35 (q, J=7.2 Hz, 2H), 1.46 (m, 2H), 1.70 (m, 2H), 2.24 (m, 1H), 2.55–2.66 (m, 4H), 2.73–2.80 (m, 2H), 3.97–4.04 (m, 2H), 4.30 (d, J=5.6 Hz, 1H), 7.37–7.44 (m, 3H), 7.55–7.57 (m, 2H).

4-{[Butyl(1-butyl-2-phenyl(4,5,6-trihydrocyclopenta[3,2-d] imidazol-6-yl))amino]methyl}-3-chlorophenol (Compound 5, Table 1). To a solution of compound 135 (50 mg) in 1,2-dichloroethane (2 mL) and 2-chloro-4-hydroxybenzaldehyde (30 mg) is added sodium triacetoxyborohydride (100 mg). The resulting mixture is allowed to stir overnight. After washing with 0.5 ammonium chloride solution, the organic layer is dried (Na$_2$SO$_4$) and concentrated. Purification using preparative thin layer chromatography eluting with 5% CH$_3$OH/CHCl$_3$ provides the desired product 136 as an oil (21 mg). LC-MS (M+1) 452, (M−1) 450. $^1$H-NMR (chemical shift, CDCl$_3$): 0.74 (t, J=7.2 Hz, 3H), 0.83 (t, J=7.2 Hz, 3H), 1.11 (q, J=7.2 Hz, 2H), 1.21–1.33 (m, 2H), 1.41–1.51 (m, 4H), 2.34–2.44 (m, 3H), 2.51–2.57 (m, 1H), 2.60–2.67 (m, 1H), 2.69–2.75 (m, 1H), 3.38 (d, J=7.6 Hz, 1H), 3.47 (d, J=13.6 Hz, 1H), 3.65 (d, J=13.6 Hz, 1H), 3.78–3.96 (m, 1H), 6.62 (dd, J=8,2 Hz, 1H), 6.78 (d, J=2 Hz, 1H), 7.07 (d, J=8 Hz, 1H), 7.35–7.41 (m, 3H), 7.45–7.48 (m, 2H).

Preparation of 4-{[Butyl(1-butyl-2-phenyl(4,5,6-trihydrocyclopenta [3,2-d]imidazol-6-yl))amino] methyl}-3-chlorophenol

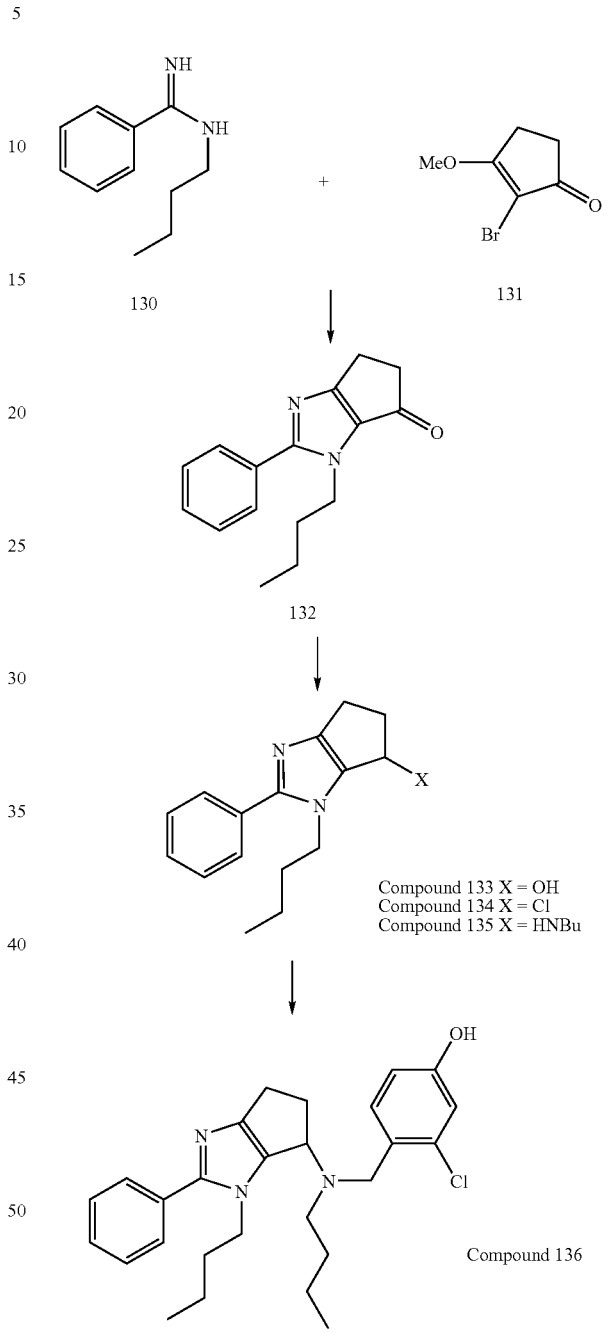

Example 6

Preparation of 2-phenyl-4-(N,N-di{2H-Benzo[3,4-d]-1,3-dioxolan-5-ylmethyl}amino)methyl-3-butylpyridine 4-Phenyl-5-butyloxazole (140). A mixture of α-bromohexanophenone (25.5 g, 0.1 mole), ammonium formate (22 g, 0.35 mole) and formic acid (110 mL) was refluxed with stirring for 3 h. The reaction mixture was poured onto ice and made basic with 10 N NaOH and extracted with ether.

The organic layer was washed with water, dried over sodium sulfate and concentrated. The crude product was purified by flash chromatography on silica gel eluting with 20% ethyl acetate in hexane. To provide the desired compound as an oil (8.3 g, 41%); $^1$H NMR (δ, CDCl$_3$, 400 MHz) 7.55 (m, 2H), 7.40 (s, 1H), 7.34 (dd, J=7,7 Hz, 2H), 7.22 (dd, J=7, 7 Hz, 1H), 2.74 (m, 2H), 1.6 (m, 2H), 1.30 (m, 2H), 0.84 (t, J=7 Hz, 3H) ppm.

2-Phenyl-3-butylisonicotinic acid (141). A mixture of 4-phenyl-5-butyloxazole (12, 5 g, 25 mmol) and maleic acid (3.5 g, 30 mmol) is heated at 100° C. for 30 min. After cooling, the semisolid mass is triturated with ether and the solid collected by filtration. $^1$H NMR (δ, CDCl$_3$, 400 MHz) 11.68 (brs, 1H), 8.72 (d, J=6.0 Hz, 1H), 7.73 (d, J=5.6 Hz, 1H), 7.48–7.51 (m, 2H), 7.42–7.44 (m, 2H), 6.25 (s, 1H), 2.86 (d, J=7.6 Hz, 2H), 1.36 (m, 2H), 1.11 (dt, J=7.6, 7.2 Hz, 2H), 0.68 (t, J=7.6 Hz, 3H). MS (M+1): 256, (M−1) 254.

2-Phenyl-4-hydroxymethyl-3-butylpyridine (142). 4 mL of a 1M solution of lithium aluminum hydride in tetrahydrofuran is added to a solution of 2-phenyl-3-butylisonicotinic acid (13, 510 mg, 2 mmol) in tetrahydrofuran (20 mL). The reaction is stirred overnight and then quenched with 5 mL of 15% aqueous NaOH. The resulting mixture is extracted with ether, dried (Na$_2$SO$_4$) and concentrated to provide the desired hydroxymethylpyridine as an oil (470 mg). LC-MS (M+1): 242; $^1$H NMR ( , CDCL$_3$) 8.35 (1H, d, J=5.2 Hz), 7.30–7.39 (6H, m), 4.59 (2H, s), 2.43 (2H, t, J=8.0 Hz), 1.23 (2H, m), 1.13 (2H, m), 0.70 (3H, t, J=7.2 Hz).

2-Phenyl-4-({2H-benzo[3,4-d]-1,3-dioxolan-5-ylmethyl})aminomethyl-3-butylpyridine (143). Thionyl chloride (200 mg, 1.67 mmol) is added to a solution of 2-phenyl-4-hydroxymethyl-3-butylpyridine (400 mg, 1.66 mmol) in pentene stabilized chloroform (8 mL) and the mixture is heated to 50° C. for 2 h. The resulting mixture is cooled, washed with saturated sodium bicarbonate solution, dried (Na$_2$SO$_4$) and concentrated. The resulting crude chloride is taken up in dimethylformamide (10 mL) and added dropwise to a refluxing solution of piperonylamine (1.0 g, 4 equiv) in dimethylformamide (30 mL) containing 3 g of powdered potassium carbonate. After the addition is complete, the resulting mixture is refluxed for an additional 3 h, cooled and partitioned between water (200 mL) and ether (100 mL). The ethereal layer is washed 2 times with water, dried (Na$_2$SO$_4$) and concentrated. The resulting material is purified by chromatography on silica eluting with 10% CH$_3$OH/CHCl$_3$ to give the desired secondary amine 15. LC-MS (M+1): 375.3; $^1$H-NMR (δ, CDCl$_3$): 0.73 (3H, t, J=7.2 Hz), 1.15 (2H, m J=7.2 Hz), 1.30 (2H, m), 2.58 (2H, t, J=8.0 Hz), 3.79 (2H, s), 3.83 (2H, s), 5.93 (2H, s), 6.75–6.82 (2H, m), 6.89 (1H, d, J=1.2 Hz), 7.36–7.42 (6H, m), 8.45 (1H, d, J=4.8 Hz) ppm.

2-Phenyl-4-(N,N-di{2H-benzo[3,4d]1,3-dioxolan-5-ylmethyl})aminomethyl-3-butylpyridine (144). To a solution of 14 (38 mg) in dichloroethane (5 mL) was added piperonal (30 mg). The resulting mixture was stirred for 3 h after which time sodium triacetoxyborohydride (150 mg) is added in one portion and the resulting mixture is stirred overnight. The reaction mixture was quenched with 10% ammonium hydroxide solution (5 ml). The organic layer is washed with water and extracted with 1N HCl solution. The acidic extract is made basic with 1N NaOH solution and extracted with chloroform. The organic extract is dried (Na$_2$SO$_4$) and concentrated. The resulting oil is purified on preparative thin layer chromatography eluting with 10% CH$_3$OH/CHCl$_3$ to give the desired tertiary amine 144 as an oil (18 mg). LC-MS (M+1): 509.4; $^1$H-NMR (5, CDCl$_3$): 0.71 (3H, t, J=7.2 Hz), 1.10 (2H, m, J=7.2 Hz), 2.60 (2H, t, J=8.0 Hz), 3.48 (4H, s), 3.58 (2H, s), 5.94 (4H, s), 6.75 (1H, d, J=8.0 Hz),6.80 (1H, dd, J=0.8, 8.0 Hz), 6.91 (1H, d, J=0.8 Hz), 7.36–7.43 (5H, m), 7.56 (1H, d, J=5.2 Hz), 8.47 (1H, d, J=5.2 Hz) ppm.

Preparation of 2-Phenyl(N,N-di{2H-benzo[3,4d]-1,3-dioxolan-5-ylmethyl}) aminomethyl-3-butylpyridine

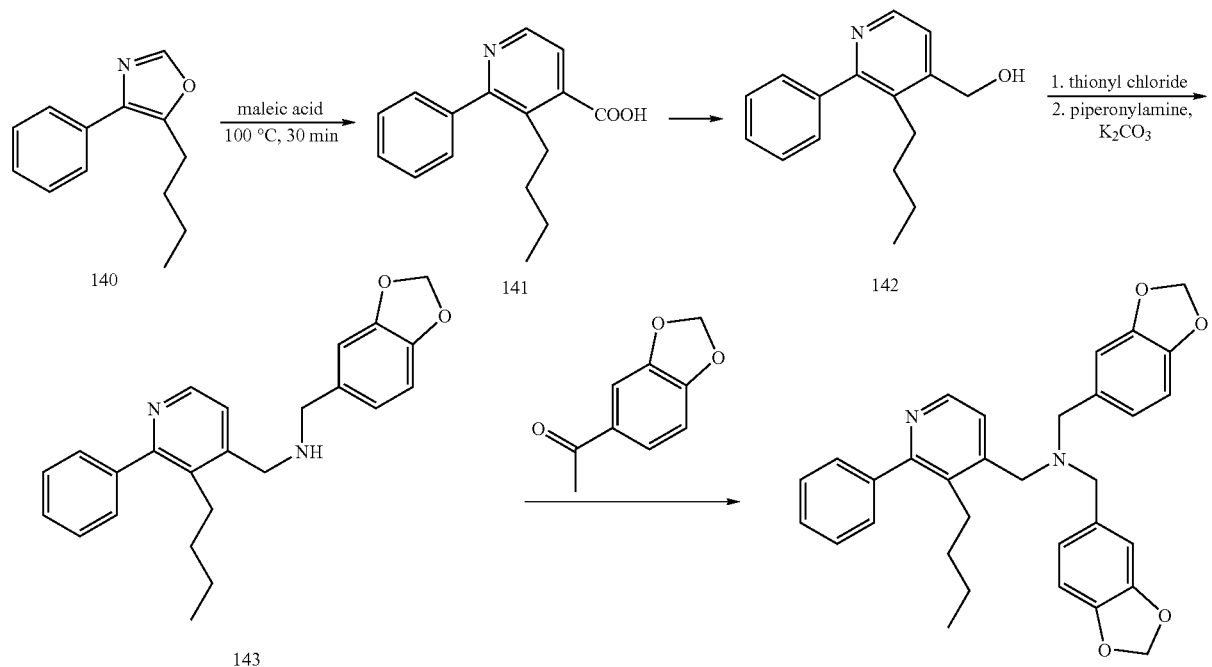

Example 7

Preparation of an Arylpyrazole 1,3-diphenyl-4-(N-{2H-benzo[3,4-d]-1,3-dioxolan-5-ylmethyl}-N-butylamino)methyl-5-propylpyrazole N'-Phenyl-N-phenylhydrazone (150). Benzaldehyde (9.81 g, 9.25 mmol) is added at 0–5° C. to a solution of phenyl hydrazine (10 g, 9.25 mmol) in ethanol (100 mL). A cream colored solid forms and the reaction mixture is allowed to stand for 2h. The solid is collected by filtration, washed with ice-cold ethanol and dried under vacuum to provide the desired compound, compound 150 (14.92 g); LC-MS m/z 197.2, $^1$H NMR ($\delta$, CDCl$_3$, 400 MHz) ppm.

Ethyl 1,3-diphenyl-5-propylpyrazole-4-carboxylate (152). A mixture of 150 (5 g, 25.5 mmol) and ethyl butyrylacetate (20.2 g, 128 mmol) and a catalytic amount of zinc chloride is heated at 125° C. under an air atmosphere for 3h. The reaction vessel is fitted with a short path distillation head and excess ethyl butyrylacetate iss distilled away under vacuum. The resulting material is purified by column chromatography on silica eluting with 10% ethyl acetate in hexanes to provide the desired ester 152 as a yellow oil (6.39 g) which crystallizes upon standing. Recrystallization from diisopropyl ether provides a white solid. $^1$H NMR ($\delta$, CDCl$_3$, 400 MHz) MS (M+1): 335.2

1,3-Diphenyl-4-hydroxymethyl-5-propylpyrazole (153). To a solution of ester 153 (670 mg, 2 mmol) in tetrahydrofuran (20 mL) is added 4 mL of a 1M solution of lithium aluminum hydride in tetrahydrofuran. The reaction is stirred overnight and then quenched with 5 mL of 15% aqueous NaOH. The resulting mixture is extracted with ether, dried (Na$_2$SO$_4$) and concentrated to provide the desired hydroxymethylpyrazole as an oil (505 mg). LC-MS (M+1): 293.3; $^1$H NMR ($\delta$, CDCL$_3$) 7.86 (dd, J=8.4 Hz, 2H), 7.34–7.52 (m, 8H), 4.65 (s, 2H), 2.72 (t, J=8.0 Hz, 2H), 1.52 (m, 2H), 0.87 (t, J=7.6 Hz, 3H).

[(1,3-Diphenyl-5-propylpyrazol-4 µl)methyl]butylamine (154). To a solution of 18 (289 mg) in pentene stabilized chloroform (8 mL) is added thionyl chloride (1 mL) and the mixture heated to 60° C. for 2 h. The resulting mixture is cooled, washed with saturated sodium bicarbonate solution, dried (Na$_2$SO$_4$) and concentrated. The resulting crude chloride is taken up in dimethylformamide (3 mL) and added dropwise to a solution of butylamine (1.0 g) in dimethylformamide (10 mL) containing 2 g of powdered potassium carbonate. After the addition is complete, the resulting mixture is stirred for an additional 3 h and partitioned between water (20 mL) and ether (10 mL). The ethereal layer is washed 2 times with water, dried (Na$_2$SO$_4$) and concentrated. The resulting material is purified by chromatography on silica eluting with 10% CH$_3$OH/CHCl$_3$ to give the desired secondary amine 155 (190 mg). LC-MS (M+1): 348.3; $^1$H-NMR ($\delta$, CDCl$_3$): 7.87 (dd, J=8.0, 1.6 Hz, 2H), 7.32–7.48 (m, 8H), 3.77 (s, 2H), 2.70 (m, 4H), 1.48 (m, 4H), 1.34 (m, 2H), 0.91 (t, J=7.6 Hz, 3H), 0.87 (t, J=7.6 Hz, 3H) ppm.

1,3-Diphenyl-4-(N-{2H-benzo[3,4-d]-1,3-dioxolan-5-ylmethyl}-N-butylamino)methyl-5-propylpyrazole (Compound 155). To a solution of 154 (35 mg) in dichloroethane (5 mL) is added piperonal (30 mg). The resulting mixture is stirred for 3 h after which time sodium triacetoxyborohydride (150 mg) is added in one portion and the resulting mixture is stirred overnight. The reaction mixture is quenched with 10% ammonium hydroxide solution (5 ml). The organic layer is washed with water and extracted with 1N HCl solution. The acidic extract is made basic with 1N NaOH solution and extracted with chloroform. The organic extract is dried (Na$_2$SO$_4$) and concentrated. The resulting oil is purified on preparative thin layer chromatography eluting with 10% CH$_3$OH/CHCl$_3$ to give the desired tertiary amine (Compound 155) as an oil (24 mg). LC-MS (M+1): 482.5; $^1$H-NMR ($\delta$, CDCl$_3$): 7.87 (d, J=7.2 Hz, 2H), 7.47 (d, J=4.4 Hz, 4H), 7.33–7.43 (m, 4H), 6.77 (s, 1H), 6.70 (s, 2H), 5.92 (s, 2H), 3.56 (s, 2H), 3.42 (s, 2H), 2.74 (t, J=8.0 Hz, 2H), 2.37 (t, J=7.2 Hz, 2H), 1.42 (m, 4H), 1.21 (m, 2H), 0.83 (t, J=7.6 Hz, 3H), 0.81 (t, J=7.2 Hz, 3H) ppm.

Preparation of 1,3-Diphenyl-4-(N-{2H-benzo[3,4-d]-1,3-dioxolan-5-ylmethyl}-N-butylamino)methyl-5-propylpyrazole

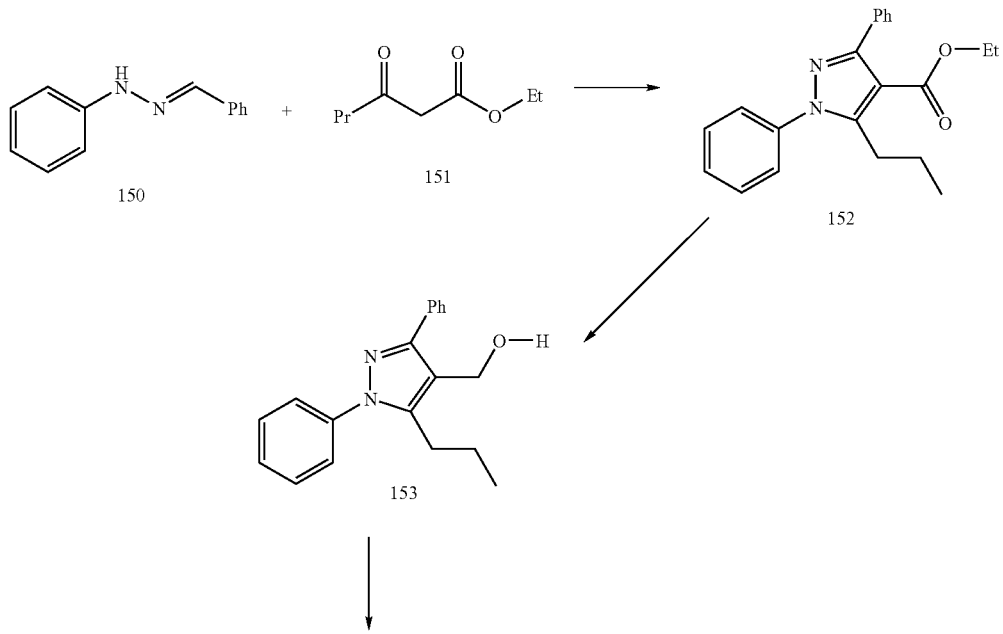

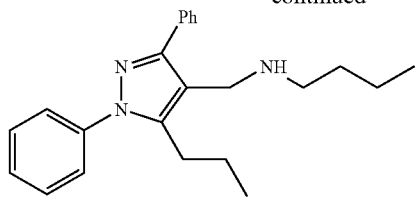

154

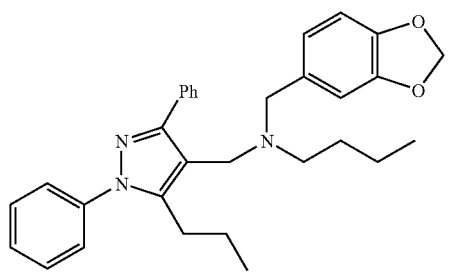

155

Example 8

Synthesis of N-(1-fluorobenzyl)-N-indan-2-yl-2-(6,7-dimethoxy-1-phenyl-1,2,3,4-tetrahydroisoquinolin-1-yl) acetamide (162)

A mixture of 6,7-dimethoxy-1-phenyl-1,2,3,4-tetrahydroisoquinoline hydrochloride (160, 153 mg, 0.5 mmol), N-(1-fluorobenzyl)-N-indan-2-yl-2-bromoacetamide (161, 180 mg, 0.5 mmol) and potassium carbonate (500 mg) in acetonitrile is heated at 80° C. overnight. After cooling, the mixture is filtered and concentrated. The resulting residue is purified by column chromatography eluting with 5% methanol in chloroform to provide the title product (162) as a thick oil (215 mg, 78%). $^1$H NMR (CDCl$_3$) 6.8–7.3 (m, 14H), 6.60(s, 1H), 6.05 (s, 1H),

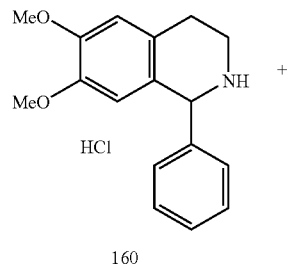

160

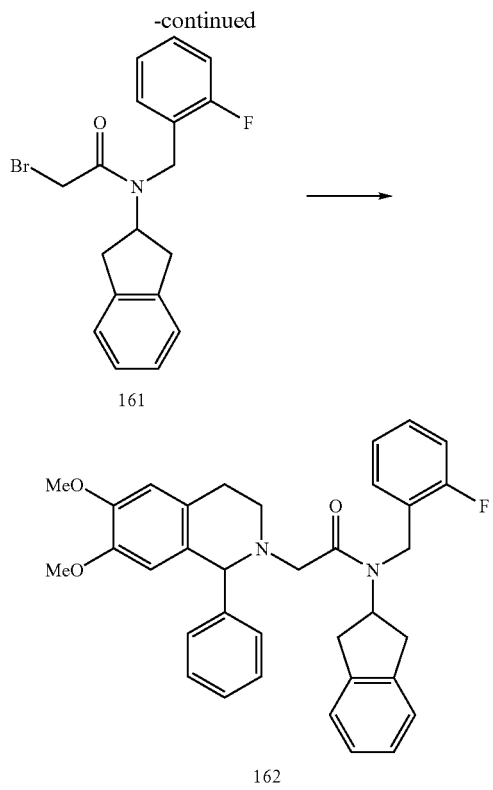

Example 9

Preparation of 4-Trifluoromethyl-biphenyl-2-carboxylic acid benzo[1,3]dioxol-5-ylmethyl-benzyl-amide (174)

1,1'-carbonyldiimidazole (175 mg) is added to a solution of 2-iodobenzoic acid (248 mg, 1 mmol)(170) in tetrahydrofuran (THF, 5 ml). The resulting mixture is stirred overnight at room temperature. A solution of N-3,4-methylenedioxybenzyl-N-benzylamine (241 mg, 1 equiv)(171) in THF (2 mL) is added and the resulting solution is stirred for 1 h, quenched with water and extracted with diethyl ether. The organic extracts are dried (Na$_2$SO$_4$) and concentrated. The residual material is taken up in dimethoxyethane (10 mL) and a catalytic amount (20 mg) of tetrakis(triphenylphosphine)palladium(0) is added. The resulting mixture is stirred under an argon atmosphere for 10 min and solid 4-trifluoromethyllphenylboronic acid (150 mg) is added in one portion. A second phase of 1N aqueous Na$_2$SO$_4$ is added and the mixture is warmed to 80° C. for 6 h under a argon atmosphere. The solution is cooled, diluted with water and ethyl acetate and filtered through a pad of celite. The organic phase is dried over sodium sulfate and concentrated. Purification on silica eluting with 20% ethyl acetate in hexane provided the desired biphenylamide product (174)(410 mg). The proton NMR displays a doubled pattern commonly observed for amides which possess some rotational restriction about the amide nitrogen at room temperature. The ratio of the rotomers is approximately equal. $^1$H NMR (CDCl$_3$) 3.50 and 3.62 (two doublets, J=X Hz, 1H), 3.72 and 3.83 (two doublets, J=X Hz, 1H), 4.10 and 4.18 (two doublets, J=X Hz, 1H), 5.09 and 5.16 (two doublets, J=x Hz, 1H), 5.95 (d, J=X Hz, 2H, OCH$_2$O), 6.30 (m, 1.5H), 6.46 (d, J=1 Hz, 0.5 Hz), 6.60 and 6.66 (two doublets, J=X Hz, 1H), 6.80 (bd, J=X Hz, 1H), 6.86 (m, 1H), 7.16–7.62 (m, 11H).

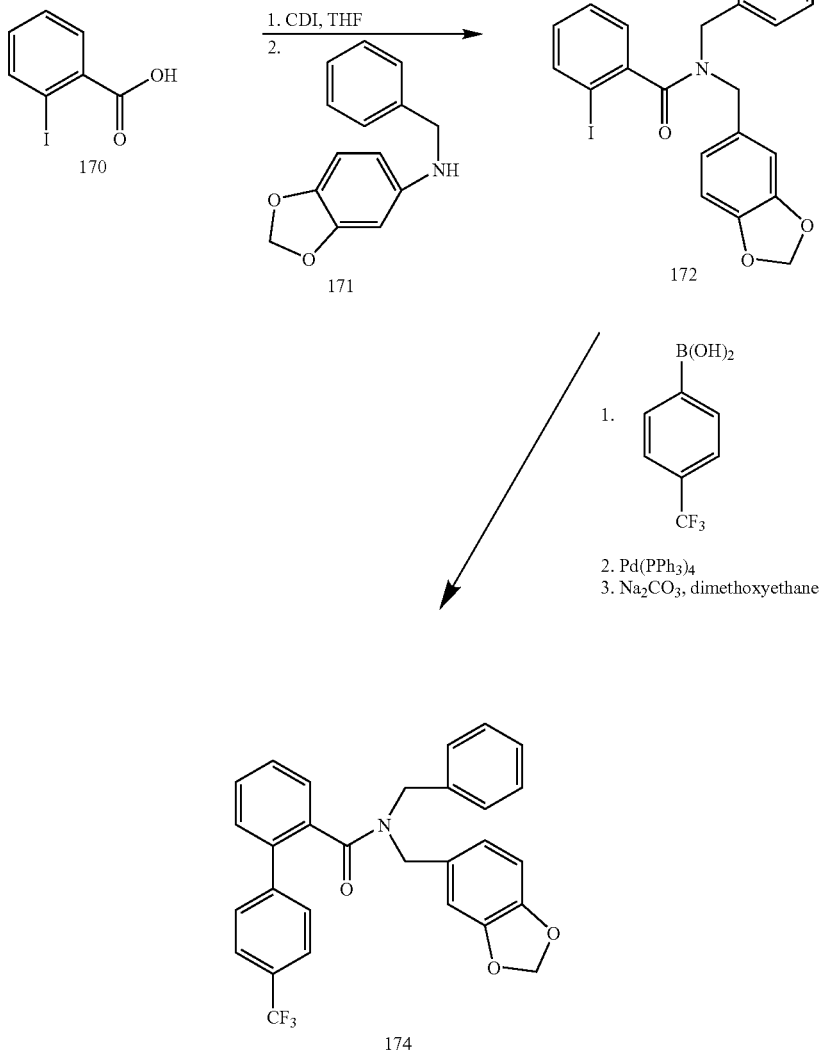

4'-Trifluoromethyl-biphenyl-2-carboxylic acid benzo[1,3]dioxol-5-ylmethyl-benzyl-amide Example 10

Preparation of N-Benzol[1,3]dioxol-5-ylmethyl-N-benzyl-2-pyrazol-1-yl-benzamide

2-Pyrazol-1-yl-benzonitrile, Compound 177. A solution of 20 mmol of 2-fluorobezonitrile and 40 mmol of pyrrazole is mixed together in dimethylformaide with 1 equivalent of potassium hydroxide and a catalytic amount of 18-crown-6. The mixture is stirred at room temperature overnight, quenched with water and ethyl acetate and extracted with ethyl acetate. The organic extract is washed repeatedly with 1 N NaOH solution. The organic layer is then diluted with ether and washed with 1N HCl solution, dried and concentrated. $^1$H NMR (CDCl$_3$) 6.55 (t, J=2 Hz, 1H), 7.42 (M, 1H), 7.65–7.82 m, 4H), 8.15 (d, J=1 Hz, 1H).

2-Pyrazol-1-yl-benzoic acid. Compound 178. A solution of compound 177 in conc HCl is refluxed overnight, cooled and concentrated. The product is precipitated by addition of 1 N NaOH until pH of 5–6, filtered and dried. 1H (CDCl$_3$) 6.52 (t, J=3 Hz, 1H), 7.40 (d, J=8 Hz, 1H), 7.50 (t, J=8 Hz, 1H) 7.62 (t, J=8 hz, 1H), 7.81 (m, 2H), 8.12 (d, J=8 Hz, 1H).

N-Benzo[1,3]dioxol-5-ylmethyl-N-benzyl-2-pyrazol-1-yl-benzamide, Compound 179. 1.1 equiv of carbonyl diimidazole is added to a solution of benzoic acid 178 (200 mg) in tetrahydrofuran (5 mL); the reaction is stirred at room temperature for 3 h. After this time N-piperonyl-N-benzylamine (0.25 g) is added in one portion. After 30 min, the reaction is filtered, diluted with ether and washed with water. The organic layer is dried (Na$_2$SO$_4$) and purified over column chromatography to provide the desired product (390 mg). The proton NMR displays a typically doubled pattern. $^1$H (CDCl$_3$) 3.83 and 4.32 (two doublets, J=16 Hz, 1H), 3.91 (two doublets, J=8 Hz, 1H), 4.18 two doublets (J=6 Hz, 1H), 5.0 and 5.1 (two doublets, J=14 Hz, 1H), 5.93 and 5.98 (s and doublet, J=2 Hz, 2H, OCH$_2$O), 6.35–6.40 (m, 2H), 6.51 (d, J=4 Hz, 0.5H), 6.4 (m, 1.5H), 7.0–7.88 m, 15H). LC-MS 412.3

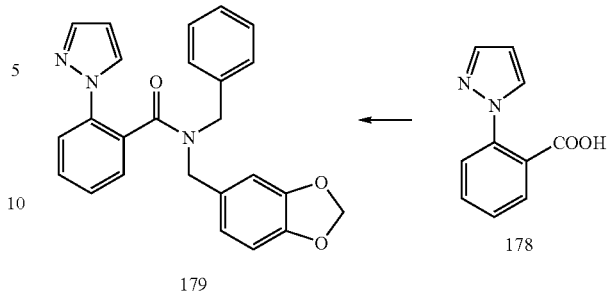

Example 11

Preparation of N-benzoyl-N-(4-methoxybenzyl)-N-(1-propyl-2-methyleno-7-azabenzimidazole 2-aminopropyl-3-nitropyridine

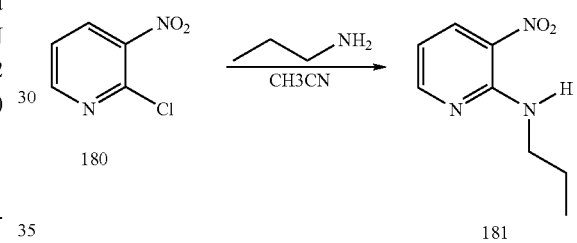

2-chloro-3-nitroaminopyridine (180) (5.5 g, 35 mmol) is dissolved in 150 mL acetonitrile at room temperature. Propylamine (21 g, 350 mmol) is added dropwise and the reaction mixture is stirred for 5 hours at room temperature. The solvent and excess propylamine are removed in vacuo. The residue is dissolved in 150 mL ethyl acetate and washed once with 100 mL saturated NaHCO$_3$ solution and once with 100 mL brine. The organic layer is dried over MgSO4, filtered, and the solvent removed in vacuo to afford 6.3 g of 2-aminopropyl-3-nitropyridine (181).

2-aminopropyl-3-aminopyridine

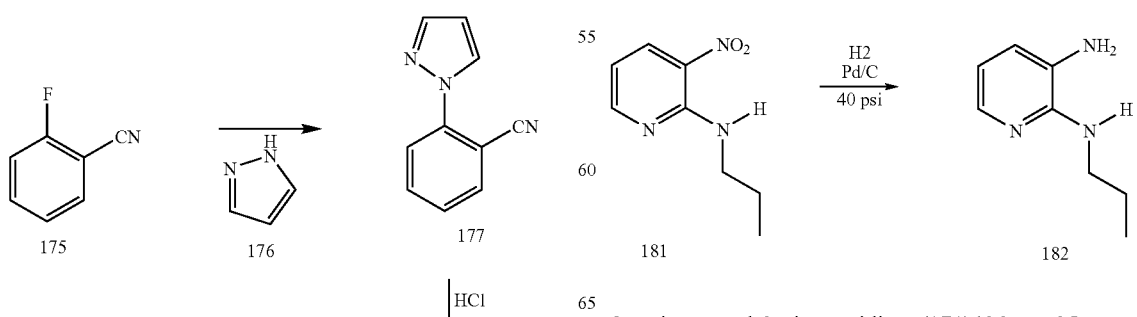

2-aminopropyl-3-nitropyridine (171)(6.3 g, 35 mmol) is dissolved in 100 mL 1/1 ethyl acetate/ethanol in a Parr shaker bottle. Nitrogen is bubbled through the solution for 2 minutes followed by the addition of 10% Pd/C (500 mg). The suspension is hydrogenated on a Parr apparatus under 40 psi of H$_2$ until hydrogen uptake ceased. The suspension is filtered through Celite and the solvent evaporated in vacuo to afford 5.3 g of the 2-aminopropyl-3-aminopyridine (182).

1-propyl-2-chloromethyl-7-azabenzimidazole

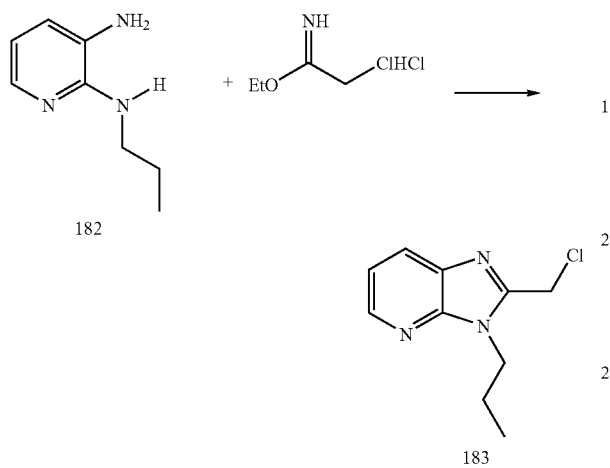

2-aminopropyl-3-aminopyridine (172) (5.3 g, 35 mmol) is dissolved in 100 mL CHCl$_3$ at room temperature. Ethyl chloromethylimidate hydrochloride (14 g, 89 mmol) is added followed by K$_2$CO$_3$ (25 g, 180 mmol). The suspension was stirred vigorously at room temperature for 3 hours. The reaction mixture is filtered through Celite and the solvent removed in vacuo. The residue is passed through a short plug of silica gel eluting with ethyl acetate to afford 3.7 g of 1-propyl-2-chloromethyl-7-azabenzimidazole (183).

1-propyl-2-(4-methoxybenzylamino)methyl-7-aza-benzimidazole

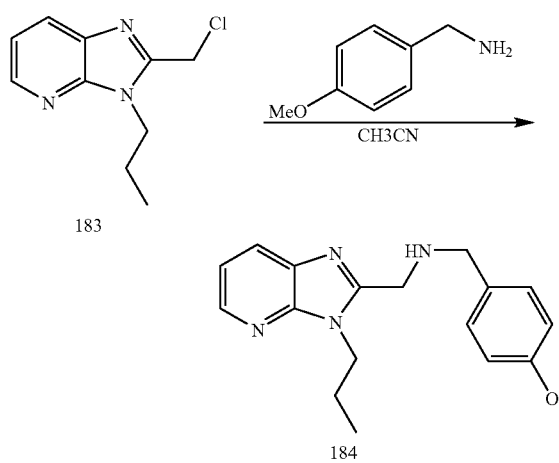

4-Methoxybenzylamine (3.8 g, 27 mmol) is dissolved in 20 mL dry acetonitrile. 1-propyl-2-chloromethyl-7-azabenzimidazole (173)(940 mg, 4.5 mmol) dissolved in 4.5 mL acetonitrile is added dropwise. The mixture is stirred 10 hours at room temperature. The solvent is removed in vacuo and the residue dissolved in 20 mL ethyl acetate. This solution is washed once with 20 mL 1 N NaOH, once with 20 mL water, once with 20 mL 5% HOAc in water, then once with 5 N NaOH. The organic phase was dried over MgSO$_4$, filtered, then concentrated in vacuo. The product mixture is purified by flash chromatography eluting with ethyl acetate followed by 95/5/1 ethyl acetate/methanol/triethylamine to afford 850 mg of the 1-propyl-2-(4-methoxybenzylamino)methyl-7-azabenzimidazole (184).

N-benzoyl-N-(4-methoxybenzyl)-N-(1-propyl-2-methyleno-7-azabenzimidazole

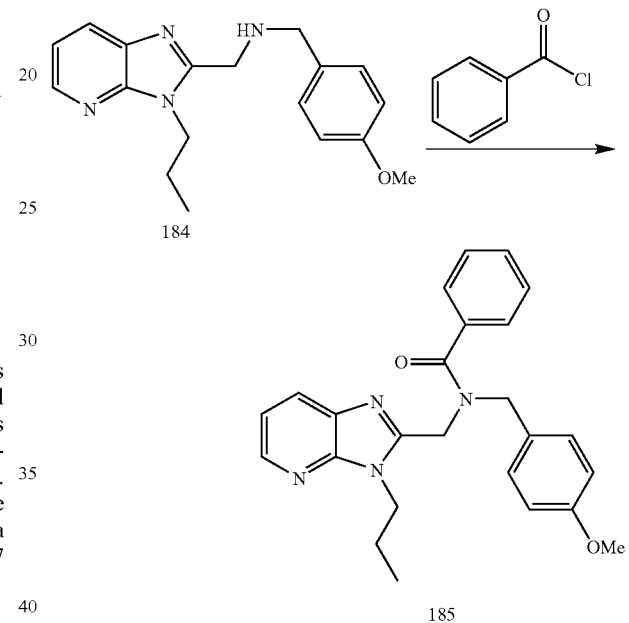

1-propyl-2-(4-methoxybenzylamino)methyl-7-azabenzimidazole (174)(19 mg, 0.06 mmol) is dissolved in 0.6 mL toluene. Saturated sodium bicarbonate solution in water (0.3 mL) is added followed by benzoyl chloride (11 mg, 0.08 mmol). The reaction mixture is stirred at room temperature for 10 hours. It is then diluted with 5 mL ethyl acetate and transferred to a separatory funnel. The aqueous layer is removed and the organic phase washed once with 1N NaOH, once with 5 mL water, then and once with mL brine. The organic phase is dried over MgSO$_4$, filtered and the solvent removed in vacuo. The product is purified by preparatory tlc eluting with 1/1 ethyl acetate/hexanes to afford 20 mg of the desired compound (185). NMR 400 MHz (CDCl$_3$) 8.39 ppm (br d, 1H), 8.15 ppm (br d, 1H), 7.52 ppm (m, 1.5H), 7.40 ppm (s, 1.5H), 7.22 (m, 1H), 7.18 ppm (br d, 1H), 6.83 ppm, (d, J=4 Hz, 2H), 4.93 ppm (br s, 2H), 4.71 ppm (br s, 1H), 4.39 ppm (br s, 1H), 3.79 ppm (s, 3H), 1.89 ppm (br m, 2H), 0.98 pp, (br t, 3H).

Example 12

Assay for C5a Receptor Mediated Chemotaxis

This assay is a standard assay of C5a receptor mediated chemotaxis.

Human promonocytic U937 cells or purified human or non-human neutrophils are treated with dibutyryl cAMP for 48 hours prior to performing the assay. Human neutrophils or those from another mammalian species are used directly after isolation. The cells are pelleted and resuspended in culture media containing 0.1% fetal bovine serum (FBS) and 10 ug/ml calcein AM (a fluorescent dye). This suspension is then incubated at 37° C. for 30 minutes such that the cells take up the fluorescent dye. The suspension is then centrifuged briefly to pellet the cells, which are then resuspended in culture media containing 0.1% FBS at a concentration of approximately $3\times10^6$ cells/mL. Aliquots of this cell suspension are transferred to clean test tubes, which contain vehicle (1% DMSO) or varying concentrations of a compound of interest, and incubated at room temperature for at least 30 minutes. The chemotaxis assay is performed in ChemoTx™ 101–8, 96 well plates (Neuro Probe, Inc. Gaitherburg, Md.). The bottom wells of the plate are filled with medium containing 0–10 nM of C5a, preferably derived from the same species of mammal as are the neutrophils or other cells (e.g., human C5a for the human U937 cells). The top wells of the plate are filled with cell suspensions (compound or vehicle-treated). The plate is then placed in a tissue culture incubator for 60 minutes. The top surface of the plate is washed with PBS to remove excess cell suspension. The number of cells that have migrated into the bottom well is then determined using a fluorescence reader. Chemotaxis index (the ratio of migrated cells to total number of cells loaded) is then calculated for each compound concentration to determine an $IC_{50}$ value.

As a control to ensure that cells retain chemotactic ability in the presence of the compound of interest, the bottom wells of the plate may be filled with varying concentrations chemo-attractants that do not mediate chemotaxis via the C5a receptor, e.g. zymosan-activated serum (ZAS), N-formylmethionyl-leucyl-phenylalanine (FMLP) or leukotriene B4 (LTB4), rather than C5a, under which conditions the compounds of the invention preferably do not inhibit chemotaxis.

Preferred compounds of the invention exhibit $IC_{50}$ values of less than 1 µM in the above assay for C5a mediated chemotaxis.

Example 13

Determination of dopamine $D_4$ receptor binding activity

The following assay is a standard assay for determining the binding affinity of compounds to dopamine $D_4$ receptors.

Pellets of Chinese hamster ovary (CHO) cells containing recombinantly expressing primate dopamine $D_4$ receptors are used for the assays. The dopamine $D_4$ receptor expression vector may be the pCD-PS vector described by Van Tol et al. (Nature (1991) 358: 149–152). The sample is homogenized in 100 volumes (w/vol) of 0.05 M Tris HCl buffer containing 120 mM NaCl, 5 mM $MgCl_2$ and 1 mM EDTA at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05 M Tris $HC_1$ buffer containing 120 mM NaCl.

Incubations for dopaminergic binding are carried out at 25° C. and contain 0.4 ml of tissue sample, 0.1 nM $^3$H-YM 09151-2 (Nemonapride, cis-5-Chloro-2-methoxy-4-(methylamino)-N-(2-methyl-2-(phenylmethyl)-3-pyrrolidinyl)benzamide) and the compound of interest in a total incubation of 1.0 ml. Nonspecific binding is defined as that binding found in the presence of 1 uM spiperone; without further additions, nonspecific binding is less than 20% of total binding.

Example 14

Preparation of radiolabeled probe compounds of the invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably $^3$H), sulfur (preferably $^{35}$S), or iodine (preferably 125I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif. Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 15

Baculoviral Preparations (For C5a Expression)

The human C5a (hC5a) receptor baculoviral expression vector was co-transfected along with BACULOGOLD DNA (BD PharMingen, San Diego, Calif.) into Sf9 cells. The Sf9 cell culture supernatant was harvested three days post-transfection. The recombinant virus-containing supernatant was serially diluted in Hink's TNM-FH insect medium (JRH Biosciences, Kansas City) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques were selected and harvested into 1 ml of insect medium for amplification. Each 1 ml volume of recombinant baculovirus (at passage 0) was used to infect a separate T25 flask containing $2\times10^6$ Sf9 cells in 5 mls of insect medium. After five days of incubation at 27° C., supernatant medium was harvested from each of the T25 infections for use as passage 1 inoculum. Two of seven recombinant baculoviral clones were then chosen for a second round of amplification, using 1 ml of passage 1 stock to infect $1\times10^8$ cells in 100 ml of insect medium divided into 2 T175 flasks. Forty-eight hours post infection, passage 2 medium from each 100 ml prep was harvested and plaque assayed for titer. The cell pellets from the second round of amplification were assayed by affinity binding as described below to verify recombinant receptor expression. A third round of amplification was then initiated using a multiplicity of infection of 0.1 to infect a liter of Sf9 cells. Forty hours post-infection the supernatant medium was harvested to yield passage 3 baculoviral stock.

The remaining cell pellet is assayed for affinity binding using the "Binding Assays" described by DeMartino et al., 1994, J. Biol. Chem. 269 #20, pp. 14446–14450 at page 14447, adapted as follows. Radioligand is 0.005–0.500 nM [$^{125}$I]C5a (human recombinant), New England Nuclear Corp., Boston, Mass.; the hC5a receptor-expressing baculoviral cells are used instead of 293 cells; the assay buffer contains 50 mM Hepes pH. 7.6, 1 mM $CaCl_2$, 5 mM $MgCl_2$, 0.1% BSA, pH 7.4, 0.1 mM bacitracin, and 100 KIU/ml aprotinin; filtration is carried out using GF/C WHATMAN filters (presoaked in 1.0% polyethyeneimine for 2 hours prior to use); and the filters are washed twice with 5 mLs cold binding buffer without BSA, bacitracin, or aprotinin.

Titer of the passage 3 baculoviral stock is determined by plaque assay and a multiplicity of infection, incubation time course, binding assay experiment is carried out to determine conditions for optimal receptor expression.

A multiplicity of infection of 0.1 and a 72-hour incubation were the best infection parameters found for hC5a receptor expression in up to 1-liter Sf9 cell infection cultures.

Example 16

Baculoviral Infections

Log-phase Sf9 cells (INVITROGEN Corp., Carlsbad Calif.), are infected with one or more stocks of recombinant baculovirus followed by culturing in insect medium at 27° C. Infections are carried out either only with virus directing the expression of the hC5a receptor or with this virus in combination with three G-protein subunit-expression virus stocks: 1) rat $Ga_{i2}$ G-protein-encoding virus stock (BIOSIGNAL #V5J008), 2) bovine b1 G-protein-encoding virus stock (BIOSIGNAL #V5H012), and 3) human g2 G-protein-encoding virus stock (BIOSIGNAL #V6B003), which may be obtained from BIOSIGNAL Inc., Montreal.

The infections are conveniently carried out at a multiplicity of infection of 0.1:1.0:0.5:0.5. At 72 hours post-infection, a sample of cell suspension is analyzed for viability by trypan blue dye exclusion, and the remaining Sf9 cells are harvested via centrifugation (3000 rpm/10 minutes/4° C.).

Example 17

Purified Recombinant Insect Cell Membranes

Sf9 cell pellets are resuspended in homogenization buffer (10 mM HEPES, 250 mM sucrose, 0.5 ÿg/ml leupeptin, 2 ÿg/ml Aprotinin, 200 ÿM PMSF, and 2.5 mM EDTA, pH 7.4) and homogenized using a POLYTRON homogenizer (setting 5 for 30 seconds). The homogenate is centrifuged (536×g/10 minutes/4° C.) to pellet the nuclei. The supernatant containing isolated membranes is decanted to a clean centrifuge tube, centrifuged (48,000×g/30 minutes, 4° C.) and the resulting pellet resuspended in 30 ml homogenization buffer. This centrifugation and resuspension step is repeated twice. The final pellet is resuspended in ice cold Dulbecco's PBS containing 5 mM EDTA and stored in frozen aliquots at −80° C. until needed. The protein concentration of the resulting membrane preparation (hereinafter "P2 membranes") is conveniently measured using a Bradford protein assay (Bio-Rad Laboratories, Hercules, Calif.). By this measure, a 1-liter culture of cells typically yields 100–150 mg of total membrane protein.

Example 18

Agonist-Induced GTP Binding

Agonist-stimulated GTP-gamma$^{35}$S binding ("GTP binding") activity can be used to identify agonist and antagonist compounds and to differentiate neutral antagonist compounds from those that possess inverse agonist activity. This activity can also be used to detect partial agonism mediated by antagonist compounds. A compound being analyzed in this assay is referred to herein as a "test compound." Agonist-stimulated GTP binding activity is measured as follows: Four independent baculoviral stocks (one directing the expression of the hC5a receptor and three directing the expression of each of the three subunits of a heterotrimeric G-protein) are used to infect a culture of Sf9 cells as described in Example 16.

Agonist-stimulated GTP binding on purified membranes (prepared as described in Example 17) is assessed using hC5a (Sigma Chemical Co., St. Louis, Mo., USA) as agonist in order to ascertain that the receptor/G-protein-alpha-beta-gamma combination(s) yield a functional response as measured by GTP binding.

P2 membranes are resuspended by Dounce homogenization (tight pestle) in GTP binding assay buffer (50 mM Tris pH 7.0, 120 mM NaCl, 2 mM MgCl2, 2 mM EGTA, 0.1% BSA, 0.1 mM bacitracin, 100KIU/mL aprotinin, 5 µM GDP) and added to reaction tubes at a concentration of 30 ug protein/reaction tube. After adding increasing doses of the agonist hC5a at concentrations ranging from $10^{-12}$ M to $10^{-6}$ M, reactions are initiated by the addition of 100 pM GTP gamma$^{35}$S. In competition experiments, non-radiolabeled test compounds (e.g., compounds of the invention) are added to separate assays at concentrations ranging from $10^{-10}$ M to $10^{-5}$ M along with 10 nM hC5a to yield a final volume of 0.25 mL.

Neutral antagonists are those test compounds that reduce the C5a-stimulated GTP binding activity towards, but not below, baseline (the level of GTP bound by membranes in this assay in the absence of added C5a or other agonist and in the further absence of any test compound).

In contrast, in the absence of added C5a certain preferred compounds of the invention will reduce the GTP binding activity of the receptor-containing membranes below baseline, and are thus characterized as inverse agonists. If a test compound that displays antagonist activity does not reduce the GTP binding activity below baseline in the absence of the C5a agonist, it is characterized as a neutral antagonist.

An antagonist test compound elevates GTP binding activity above baseline in the absence of added hC5a in this GTP binding assay is characterized as having partial agonist activity. Preferred antagonist compounds of the invention do not elevate GTP binding activity under such conditions more than 10% above baseline, preferably not more than 5% above baseline, and most preferably not more than 2% above baseline.

Following a 60-minute incubation at room temperature, the reactions are terminated by vacuum filtration over GF/C filters (pre-soaked in wash buffer, 0.1% BSA) followed by washing with ice-cold wash buffer (50 mM Tris pH 7.0, 120 mM NaCl). The amount of receptor-bound (and thereby membrane-bound) GTP gamma$^{35}$S is determined by measuring the bound radioactivity, preferably by liquid scintillation spectrometry of the washed filters. Non-specific binding is determined using 10 mM GTP gamma $^{35}$S and typically represents less than 5 percent of total binding. Data is expressed as percent above basal (baseline). The results of these GTP binding experiments may be conveniently analyzed using SIGMAPLOT software (SPSS Inc., Chicago, Ill., USA).

Example 19

Calcium Mobilization Assays

A. Response to C5a

U937 cells are grown in differentiation media (1 mM dibutyrl cAMP in RPMI 1640 medium containing 10% fetal bovine serum) for 48 hrs at 37 C then reseeded onto 96-well plates suitable for use in a FLIPR™ Plate Reader (Molecular Devices Corp., Sunnyvale Calif.). Cells are grown an additional 24 hours (to 70–90% confluence) before the assay. The cells are then washed once with Krebs Ringer solution. Fluo-3 calcium sensitive dye (Molecular Probes, Inc. Eugene, Oreg.) is added to 10 ug/mL and incubated with the cells at room temperature for 1 to 2 hours. The 96 well plates are then washed to remove excess dye. Fluorescence responses, measured by excitation at 480 nM and emission at 530 nM, are monitored upon the addition of human C5a to the cells to a final concentration of 0.01–30.0 nM, using the FLIPR™ device (Molecular Devices). Differentiated U937 cells typically exhibit signals of 5,000–50,000 Arbitrary Fluorescent Light Units in response to agonist stimulation.

B. Assays for Determination of ATP Responses

Differentiated U937 cells (prepared and tested as described above under "A. Response to C5a") are stimulated by the addition of ATP (rather than C5a) to a final concentration of 0.01 to 30 uM. This stimulation typically triggers a signal of 1,000 to 12,000 arbitrary fluorescence light units. Certain preferred compounds of the invention produce less than a 10%, preferably less than a 5%, and most preferably less than a 2% alteration of this calcium mobilization signal when this control assay is carried out in the presence or absence of the compounds.

C. Assays for the Identification of Receptor Modulatory Agents: Antagonists and Agonists Those of skill in the art will recognize that the calcium mobilization assay described above may be readily adapted for identifying test compounds as having agonist or antagonist activity, at the human C5a receptor.

For example, in order to identify antagonist compounds, differentiated U937 cells are washed and incubated with Fluo-3 dye as described above. One hour prior to measuring the fluorescence signal, a subset of the cells is incubated with a 1 M concentration of at least one compound to be tested. The fluorescence response upon the subsequent addition of 0.3 nM (final concentration) human recombinant C5a is monitored using the FLIPR™ plate reader. Antagonist compounds elicit at least a 2-fold decrease in the fluorescence response relative to that measured in the presence of human C5a alone. Preferred antagonist compounds elicit at least a 5-fold, preferably at least a 10-fold, and more preferably at least a 20-fold decrease in the fluorescence response relative to that measured in the presence of human C5a alone. Agonist compounds elicit an increase in fluorescence without the addition of C5a, which increase will be at least partially blocked by a known C5a receptor antagonist.

Example 20

Assays to evaluate agonist activity of small molecule C5a receptor antagonists

Preferred compounds of the invention are C5a receptor antagonists that do not possess significant (e.g., greater than 5%) agonist activity in any of the C5a mediated functional assays discussed herein. Specifically, this undesired agonist activity can be evaluated, for example, in the GTP binding assay of Example 18, by measuring small molecule mediated GTP binding in the absence of the natural agonist, C5a. Similarly, in a calcium mobilization assay e.g., that of Example 19, a small molecule compound can be directly assayed for the ability of the compound to stimulate calcium levels in the absence of the natural agonist, C5a. The preferred extent of C5a agonist activity exhibited by compounds of the invention is less than 10%, more preferably less than 5% and most preferably less than 2% of the response elicited by the natural agonist, C5a.

Example 21

Expression of a C5a receptor

A human C5a receptor cDNA was obtained by PCR using 1) a forward primer adding a Kozak ribosome binding site and 2) a reverse primer that added no additional sequence, and 3) an aliquot of a Stratagene Human Fetal Brain cDNA library as template. The sequence of the resulting PCR product is set forth as SEQ ID NO: 1. The PCR product was subcloned into the cloning vector pCR-Script AMP (STR$_A$T-AGENE, La Jolla,Calif.) at the SrfI site. It was then excised using the restriction enzymes EcoRI and NotI and subcloned in the appropriate orientation for expression into the baculoviral expression vector pBacPAK 9 (CLONTECH, Palo Alto, Calif.) that had been digested with EcoRI and NotI.

Example 22

Radioligand Binding Assays

Purified P2 membranes, prepared by the method given above, are resuspended by Dounce homogenization (tight pestle) in binding buffer (50 mM Hepes pH. 7.6, 120 mM NaCl, 1 mM $CaCl_2$, 5 mM $MgCl_2$, o.1% BSA, pH 7.4, 0.1 mM bacitracin, 100 KIU/ml aprotinin).

For saturation binding analysis, membranes (5–50 µg) are added to polypropylene tubes containing 0.005–0.500 nM [$^{125}$I]C5a (human (recombinant), New England Nuclear Corp., Boston, Mass.). Nonspecific binding is determined in the presence of 300 nM hC5a (Sigma Chemical Co., St. Louis, Mo.) and accounted for less than 10% of total binding. For evaluation of guanine nucleotide effects on receptor affinity, GTPγS is added to duplicate tubes at the final concentration of 50 µM.

For competition analysis, membranes (5–50 µg) are added to polypropylene tubes containing 0.030 nM [$^{125}$I]C5a (human). Non-radiolabeled displacers are added to separate assays at concentrations ranging from $10^{-10}$ M to $10^{-5}$ M to yield a final volume of 0.250 mL. Nonspecific binding is determined in the presence of 300 nM hC5a (Sigma Chemical Co., St. Louis, Mo.) and accounted for less than 10% of total binding. Following a 2-hour incubation at room temperature, the reaction is terminated by rapid vacuum filtration. Samples are filtered over presoaked (in 1.0% polyethyleneimine for 2 hours prior to use) GF/C WHATMAN filters and rinsed 2 times with 5 mLs cold binding buffer without BSA, bacitracin, or aprotinin. Remaining bound radioactivity is quantified by gamma counting. $K_i$ and Hill coefficient ("nH") are determined by fitting the Hill equation to the measured values with the aid of SIGMAPLOT software.

As set forth in the tables appended hereto, R groups do not necessarily correlate with those R groups shown in the text of the specification or in the claims.

The following table 1 (214–323) is a list of preferred 1,2,5 substituted imidazoles of the present invention;

The following table 2 (324–429) is a list of preferred 1,2,4,5 substituted imidazoles of the present invention;

The following table 3 (430–431) is a list of preferred pyrazoles of the present invention;

The following table 4 (432–433) is another list of preferred 1,2,4,5 substituted imidazoles of the present invention;

The following table 5 (434–464) is a list of preferred amides of the present invention; and The following table 6 (456–468) is a list of preferred amides of the present invention.

Additional Aspects of Preferred Compounds of the Invention

The most preferred compounds of the invention are suitable for pharmaceutical use in treating human patients. Accordingly, such preferred compounds do not exhibit single or multiple dose acute or long-term toxicity, mutagenicity (e.g., as determined in a bacterial reverse mutation assay such as an Ames test), teratogenicity, tumorogenicity, or the like, and rarely trigger adverse effects (side effects) when administered at therapeutically effective dosages. For example, preferred compounds of the invention will not prolong heart QT intervals (e.g., as determined by electrocardiography, e.g., in guinea pigs, minipigs or dogs). Therapeutically effective doses or concentrations of such compounds do not cause liver enlargement when fed to or injected into laboratory animals (e.g., mice or rats) and do not promote the release of liver enzymes (e.g., ALT, LDH, or AST) from hepatocytes in vitro or in vivo.

Because side effects are often due to undesirable receptor activation or antagonism, preferred compounds of the invention exert their receptor-modulatory effects with high specificity. This means that they only bind to, activate, or inhibit the activity of certain receptors other than C5a receptors with affinity constants of greater than 100 nanomolar, preferably greater than 1 micromolar, more preferably greater than 10 micromolar and most preferably greater than 100 micromolar. Such receptors preferably are selected from neurotransmitter receptors such as alpha- or beta-adrenergic receptors, muscarinic receptors (particularly m1, m2, or m3 receptors), dopamine receptors, and metabotropic glutamate receptors; and also include histamine receptors and cytokine receptors, e.g., interleukin receptors, particularly IL-8 receptors. Such receptors may also include GABAA receptors, bioactive peptide receptors (other than C5a receptors, including NPY or VIP receptors), neurokinin receptors, bradykinin receptors, hormone receptors (e.g., CRF receptors, thyrotropin releasing hormone receptors, or melanocyte-concentrating hormone receptors).

Additionally, preferred compounds of the invention do not inhibit or induce microsomal cytochrome P450 enzyme activities, such as CYP1A2 activity, CYP2A6 activity, $CYP2C_9$ activity, $CYP2C_{19}$ activity, CYP2D6 activity, CYP2E1 activity, or CYP3A4 activity. Preferred compounds of the invention also do not exhibit cytotoxicity in vitro or in vivo, are not clastogenic, e.g., as determined using a mouse erythrocyte precursor cell micronucleus assay, an Ames micronucleus assay, a spiral micronucleus assay, or the like and do not induce sister chromatid exchange, e.g., in Chinese hamster ovary cells.

Highly preferred C5a receptor antagonist compounds of the invention also inhibit the occurrence of C5a-induced oxidative burst (OB) in inflammatory cells, e.g., neutrophil, as can be conveniently determined using an in vitro neutrophil OB assay.

Initial characterization of preferred compounds of the invention can be conveniently carried out using a C5a receptor binding assay or functional assay, such as set forth in the Examples, and may be expedited by applying such assays in a high throughput screening setting.

The foregoing description is illustrative thereof, and it understood that variations and modification can be effected without departing from the scope or spirit of the invention as set forth in the following claims.

TABLE 1
| CMP # | R1 | R2 | R3 | R4 | R5 | Rtn Time | Cmd Mass | H+ Ion Obs |
|---|---|---|---|---|---|---|---|---|
| 200 |  |  | |  |  | 1.95 | 448.2627 | 449.3036 |
| 201 |  |  | |  |  | 1.96 | 462.2784 | 463.3201 |
| 202 |  |  | |  |  | 1.91 | 462.2784 | 463.3241 |
| 203 |  |  | |  |  | 2.09 | 459.2675 | 460.3053 |

TABLE 1-continued

| CMP # | R1 | R2 | R3 | R4 | R5 | Rtn Time | Cmd Mass | H+ Ion Obs |
|---|---|---|---|---|---|---|---|---|
| 204 | phenyl (X1) | X2-(CH2)3-CH3 | | benzyl (X4) | naphthalen-2-ylmethyl (X5) | 2.1 | 459.2675 | 460.2983 |
| 205 | phenyl (X1) | X2-(CH2)4-CH3 | | benzyl (X4) | benzo[1,3]dioxol-5-ylmethyl (X5) | 2.04 | 467.2573 | 468.2888 |
| 206 | phenyl (X1) | X2-(CH2)4-CH3 | | benzyl (X4) | 2,3-dihydrobenzo[1,4]dioxin-6-ylmethyl (X5) | 2.05 | 481.2729 | 482.3052 |
| 207 | phenyl (X1) | X2-(CH2)3-CH3 | | benzyl (X4) | 2,3-dihydrobenzo[1,4]dioxin-6-ylmethyl (X5) | 2 | 467.2573 | 468.2885 |

TABLE 1-continued

| CMP # | R1 | R2 | R3 | R4 | R5 | Rtn Time | Cmd Mass | H+ Ion Obs |
|---|---|---|---|---|---|---|---|---|
| 208 | phenyl (X1) | propyl-CH3 (X2) | | benzyl (X4) | 2,3-dihydrobenzodioxinylmethyl (X5) | 1.96 | 453.2416 | 454.2695 |
| 209 | phenyl (X1) | CH3-propyl-X2 | | butyl (X4) | benzyl (X5) | 1.9 | 375.2675 | 376.2897 |
| 210 | phenyl (X1) | X2-butyl-CH3 | | benzyl (X4) | benzodioxolylmethyl (X5) | 2 | 453.2416 | 454.2688 |

TABLE 1-continued

| CMP # | R1 | R2 | R3 | R4 | R5 | Rtn Time | Cmd Mass | H+ Ion Obs |
|---|---|---|---|---|---|---|---|---|
| 211 | phenyl (X₁) | propyl-CH₃ (X₂) | | benzyl (X₄) | indol-5-ylmethyl (X₅) | 1.9 | 434.247 | 435.2789 |
| 212 | phenyl (X₁) | butyl-CH₃ (X₂) | | benzo[1,3]dioxol-5-ylmethyl (X₄) | indol-5-ylmethyl (X₅) | 1.92 | 492.2525 | 493.2912 |
| 213 | phenyl (X₁) | butyl-CH₃ (X₂) | | benzyl (X₄) | 3,4-dimethoxybenzyl (X₅) | 1.94 | 469.2729 | 470.2986 |

TABLE 1-continued
| CMP # | R1 | R2 | R3 | R4 | R5 | Rtn Time | Cmd Mass | H+ Ion Obs |
|---|---|---|---|---|---|---|---|---|
| 214 | 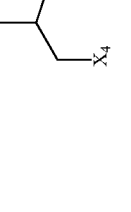 | 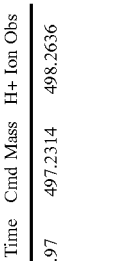 | H | 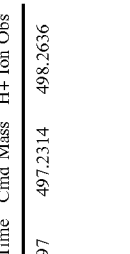 | 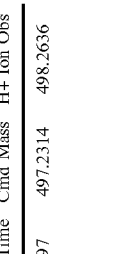 | 1.97 | 497.2314 | 498.2636 |
| 215 | 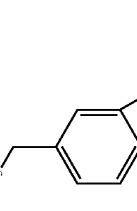 | 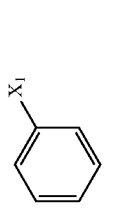 | H | 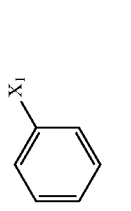 |  | 2.06 | 473.3042 | 474.3346 |
| 216 |  | 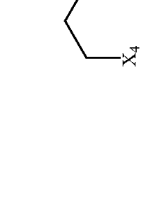 | H | 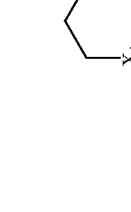 | 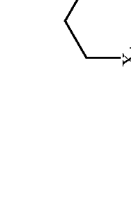 | 2.03 | 445.2729 | 446.302 |

TABLE 1-continued
| CMP # | R1 | R2 | R3 | R4 | R5 | Rtn Time | Cmd Mass | H+ Ion Obs |
|---|---|---|---|---|---|---|---|---|
| 217 |  | 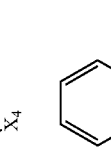 | |  |  | 2.1 | 477.258 | 478.2953 |
| 218 |  |  | |  |  | 2.01 | 485.2479 | 486.2815 |
| 219 | 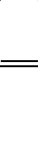 |  | | 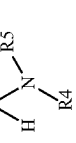 |  | 2.01 | 471.2322 | 472.266 |
| 220 | 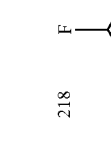 |  | |  |  | 1.8 | 438.2784 | 439.3118 |

TABLE 1-continued

| CMP # | R1 | R2 | R3 | R4 | R5 | Rtn Time | Cmd Mass | H+ Ion Obs |
|---|---|---|---|---|---|---|---|---|
| 221 | phenyl-X₁ | CH₃-(CH₂)₃-X₂ | | benzyl-X₄ | 4-NH₂-3-CH₃-benzyl-X₅ | 1.78 | 438.2784 | 439.313 |
| 222 | phenyl-X₁ | CH₃-(CH₂)₃-X₂ | | benzyl-X₄ | 4-N(CH₃)₂-benzyl-X₅ | 1.86 | 452.294 | 453.3306 |
| 223 | phenyl-X₁ | X₂-(CH₂)₃-CH₃ | | cyclohexylmethyl-X₄ | 3,4-methylenedioxybenzyl-X₅ | 2.08 | 459.2886 | 460.3148 |
| 224 | phenyl-X₁ | X₂-(CH₂)₃-CH₃ | | 2-thienylmethyl-X₄ | 3,4-methylenedioxybenzyl-X₅ | 1.99 | 459.1981 | 460.226 |

TABLE 1-continued

| CMP # | R1 | R2 | R3 | R4 | R5 | Rtn Time | Cmd Mass | H+ Ion Obs |
|---|---|---|---|---|---|---|---|---|
| 225 | phenyl | -(CH2)4CH3 | | -(CH2)4CH3 | benzo[1,3]dioxol-5-ylmethyl | 1.86 | 419.2573 | 420.2867 |
| 226 | phenyl | -(CH2)4CH3 | | -(CH2)2CH3 | benzo[1,3]dioxol-5-ylmethyl | 1.79 | 405.2416 | 406.2684 |
| 227 | phenyl | -(CH2)4CH3 | | 3,4-dichlorobenzyl | benzo[1,3]dioxol-5-ylmethyl | 2.08 | 521.1637 | 522.2009 |

TABLE 1-continued

| CMP # | R1 | R2 | R3 | R4 | R5 | Rtn Time | Cmd Mass | H+ Ion Obs |
|---|---|---|---|---|---|---|---|---|
| 228 | phenyl-X₁ | X₂-(CH₂)₃-CH₃ | | 3,4-dimethoxybenzyl-X₄ | benzo[1,3]dioxol-5-ylmethyl-X₅ | 1.91 | 513.2628 | 514.2951 |
| 229 | phenyl-X₁ | X₂-CH₂CH₂-O-CH₃ | | benzyl-X₄ | naphthalen-1-ylmethyl-X₅ | 2.02 | 461.2467 | 462.2794 |
| 230 | phenyl-X₁ | X₂-CH₂CH₂-O-CH₃ | | benzyl-X₄ | naphthalen-2-ylmethyl-X₅ | 2. | 461.2467 | 462.2892 |
| 231 | phenyl-X₁ | CH₃-(CH₂)₃-X₂ | | benzyl-X₄ | benzo[b]thiophen-5-ylmethyl-X₅ | 2.05 | 465.2239 | 466.267 |

TABLE 1-continued
| CMP # | R1 | R2 | R3 | R4 | R5 | Rtn Time | Cmd Mass | H+ Ion Obs |
|---|---|---|---|---|---|---|---|---|
| 232 |  |  | |  |  | 2.1 | 477.1739 | 478.2021 |
| 233 |  | 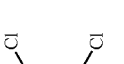 | |  |  | 1.98 | 462.2784 | 463.3135 |
| 234 |  |  | |  | 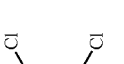 | | | |

TABLE 1-continued

| CMP # | R1 | R2 | R3 | R4 | R5 | Rtn Time | Cmd Mass | H+ Ion Obs |
|---|---|---|---|---|---|---|---|---|
| 235 | phenyl-$X_1$ | $X_2$-(CH$_2$)$_3$-CH$_3$ | | 4-(CH$_2$CH$_3$)-benzyl-$X_4$ | $X_5$-CH$_2$-(benzo[1,3]dioxol-5-yl) | 2.07 | 535.1793 | 536.2415 |
| 236 | phenyl-$X_1$ | $X_2$-(CH$_2$)$_3$-CH$_3$ | | isobutyl-$X_4$ | $X_5$-CH$_2$-(benzo[1,3]dioxol-5-yl) | 2.11 | 495.2886 | 496.3355 |
| 237 | phenyl-$X_1$ | $X_2$-(CH$_2$)$_3$-CH$_3$ | | 4-(OCH$_2$CH$_3$)-benzyl-$X_4$ | $X_5$-CH$_2$-(benzo[1,3]dioxol-5-yl) | | | |

TABLE 1-continued

| CMP # | R1 | R2 | R3 | R4 | R5 | Rtn Time | Cmd Mass | H+ Ion Obs |
|---|---|---|---|---|---|---|---|---|
| 238 | 2-(X₂)methoxyphenyl | X₂-(CH₂)₃-CH₃ | | benzyl-X₄ | 1,3-benzodioxol-5-ylmethyl-X₅ | 2 | 483.2522 | 484.3027 |
| 239 | 2-(X₂)methoxyphenyl | X₂-(CH₂)₃-CH₃ | | benzyl-X₄ | naphthalen-2-ylmethyl-X₅ | 1.87 | 482.3046 | 483.3743 |
| 240 | 2-(X₂)methoxyphenyl | X₂-(CH₂)₃-CH₃ | | 1,3-benzodioxol-5-ylmethyl-X₄ | 1,3-benzodioxol-5-ylmethyl-X₅ | 1.98 | 527.242 | 528.2967 |
| 241 | 2-(X₂)methoxyphenyl | X₂-(CH₂)₃-CH₃ | | benzyl-X₄ | 4-(N,N-dimethylamino)benzyl-X₅ | 1.85 | 482.3046 | 483.3671 |

TABLE 1-continued
| CMP # | R1 | R2 | R3 | R4 | R5 | Rtn Time | Cmd Mass | H+ Ion Obs |
|---|---|---|---|---|---|---|---|---|
| 242 | 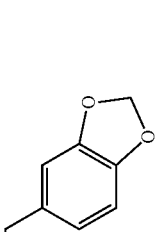 |  | |  | 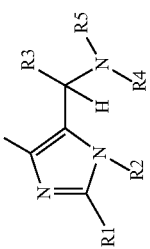 | 2.01 | 483.2522 | 484.3157 |
| 243 | 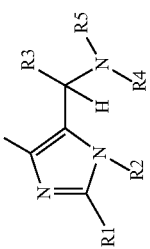 |  | | 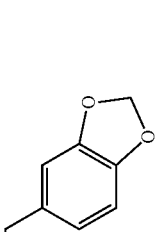 |  | 1.87 | 482.3046 | 483.3743 |
| 244 |  | 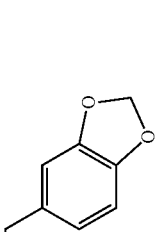 | | 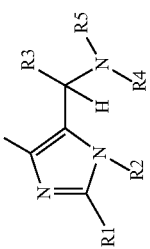 |  | 1.98 | 515.222 | 516.2815 |
| 245 | 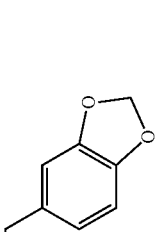 |  | |  |  | 2.01 | 467.2573 | 468.3038 |

TABLE 1-continued

| CMP # | R1 | R2 | R3 | R4 | R5 | Rtn Time | Cmd Mass | H+ Ion Obs |
|---|---|---|---|---|---|---|---|---|
| 246 | 2-methylphenyl | butyl | | benzo[1,3]dioxol-5-ylmethyl | benzo[1,3]dioxol-5-ylmethyl | 2 | 511.2471 | 512.3024 |
| 247 | 3-fluorophenyl | butyl | | benzyl | benzo[1,3]dioxol-5-ylmethyl | 1.99 | 471.2322 | 472.2836 |
| 248 | 3-fluorophenyl | butyl | | benzo[1,3]dioxol-5-ylmethyl | benzo[1,3]dioxol-5-ylmethyl | 1.98 | 515.222 | 516.2795 |
| 249 | 3-methoxyphenyl | butyl | | benzyl | benzo[1,3]dioxol-5-ylmethyl | 2.01 | 483.2522 | 484.3008 |

TABLE 1-continued
| CMP # | R1 | R2 | R3 | R4 | R5 | Rtn Time | Cmd Mass | H+ Ion Obs |
|---|---|---|---|---|---|---|---|---|
| 250 | 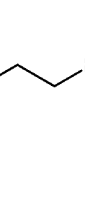 | 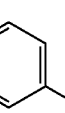 | | 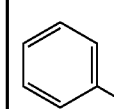 | 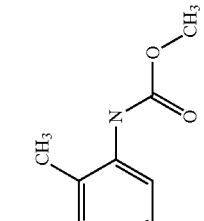 | 2.06 | 503.2573 | 504.3187 |
| 251 | 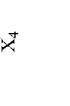 |  | | 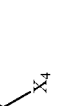 | 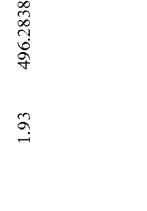 | 2.08 | 477.258 | 478.3242 |
| 252 |  | 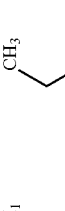 | | 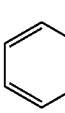 | 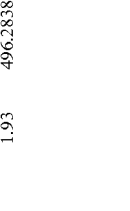 | 1.95 | 496.2838 | 497.3316 |
| 253 |  | 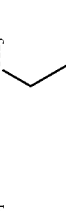 | | 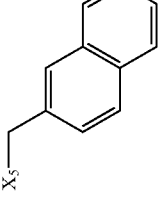 |  | 1.93 | 496.2838 | 497.3374 |

TABLE 1-continued

| CMP # | R1 | R2 | R3 | R4 | R5 | Rtn Time | Cmd Mass | H+ Ion Obs |
|---|---|---|---|---|---|---|---|---|
| 254 | phenyl-X1 | CH3-(CH2)3-X2 | | benzyl-X4 | 4-methoxybenzyl-X5 | 1.99 | 439.2624 | 440.3063 |
| 255 | phenyl-X1 | CH3-(CH2)3-X2 | | benzyl-X4 | 6-chloro-benzo[1,3]dioxol-5-yl-methyl-X5 | 2.05 | 487.2027 | 488.258 |
| 256 | phenyl-X1 | CH3-(CH2)3-X2 | | CH3-(CH2)3-X4 | 2,3-dichlorobenzyl-X5 | 2.1 | 443.1895 | 444.2521 |
| 257 | phenyl-X1 | CH3-(CH2)3-X2 | | benzyl-X4 | 3-methoxybenzyl-X5 | 2 | 439.2624 | 440.3058 |

TABLE 1-continued

| CMP # | R1 | R2 | R3 | R4 | R5 | Rtn Time | Cmd Mass | H+ Ion Obs |
|---|---|---|---|---|---|---|---|---|
| 258 | phenyl-X1 | X2-(CH2)3-CH3 | | 6-quinolinyl-CH2-X4 | 3,4-methylenedioxybenzyl-X5 | 1.78 | 504.2525 | 505.3246 |
| 259 | phenyl-X1 | CH3-(CH2)3-X2 | | benzyl-X4 | 3-chloro-4-hydroxybenzyl-X5 | 1.97 | 459.2077 | 460.287 |
| 260 | phenyl-X1 | CH3-(CH2)3-X2 | | benzyl-X4 | 2,6-dichlorobenzyl-X5 | 2.06 | 477.1739 | 478.2339 |
| 261 | phenyl-X1 | CH3-(CH2)3-X2 | | benzyl-X4 | 2-chloro-4-fluorobenzyl-X5 | 2.06 | 461.2034 | 462.2581 |

TABLE 1-continued
| CMP # | R1 | R2 | R3 | R4 | R5 | Rtn Time | Cmd Mass | H+ Ion Obs |
|---|---|---|---|---|---|---|---|---|
| 262 |  | 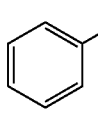 | |  |  | | 480.3253 | 481.4043 |
| 263 | 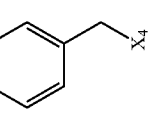 | 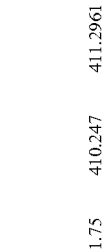 | |  |  | 1.78 | | |
| 264 | 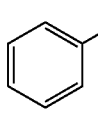 |  | |  |  | 1.75 | 410.247 | 411.2961 |
| 265 | 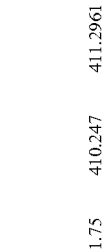 |  | |  |  | 2.01 | 503.2339 | 504.2863 |

TABLE 1-continued
| CMP # | R1 | R2 | R3 | R4 | R5 | Rtn Time | Cmd Mass | H+ Ion Obs |
|---|---|---|---|---|---|---|---|---|
| 266 |  |  | |  |  | 2.07 | 493.2341 | 494.2973 |
| 267 |  |  | |  |  | 1.88 | 425.2467 | 426.2948 |
| 268 |  |  | |  |  | 2.05 | 443.2128 | 444.2672 |
| 269 |  |  | |  |  | 2.04 | 461.2034 | 462.255 |

TABLE 1-continued

| CMP # | R1 | R2 | R3 | R4 | R5 | Rtn Time | Cmd Mass | H+ Ion Obs |
|---|---|---|---|---|---|---|---|---|
| 270 | phenyl-X1 | CH3-...-X2 | | benzyl-X4 | 2,4-dichlorobenzyl-X5 | 2.1 | 477.1739 | 478.2429 |
| 271 | phenyl-X1 | X2-...-CH3 | | 2,3-dichlorobenzyl-X4 | benzo[1,3]dioxol-5-ylmethyl-X5 | 2.06 | 521.1637 | 522.2083 |
| 272 | phenyl-X1 | X2-...-CH3 | | benzo[1,3]dioxol-5-ylmethyl-X4 | indan-2-yl-X5 | 2.02 | 479.2573 | 480.2964 |

TABLE 1-continued
| CMP # | R1 | R2 | R3 | R4 | R5 | Rtn Time | Cmd Mass | H+ Ion Obs |
|---|---|---|---|---|---|---|---|---|
| 273 | 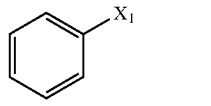 |  | |  |  | 2.03 | 433.2729 | 434.3264 |
| 274 |  |  | |  |  | 1.9 | 433.2729 | 434.3161 |
| 275 |  | | | |  | 1.74 | 424.2627 | 425.298 |
| 276 | | | | |  | 1.98 | 454.2369 | 455.2756 |

TABLE 1-continued
| CMP # | R1 | R2 | R3 | R4 | R5 | Rtn Time | Cmd Mass | H+ Ion Obs |
|---|---|---|---|---|---|---|---|---|
| 277 | 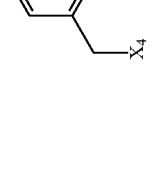 | 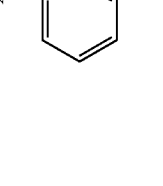 | | 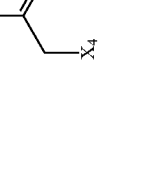 | 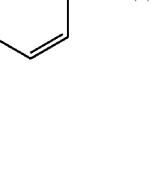 | 2.09 | 495.1644 | 496.227 |
| 278 | 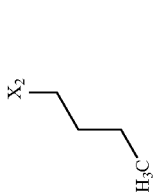 | 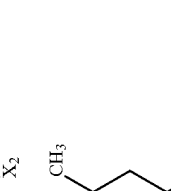 | | 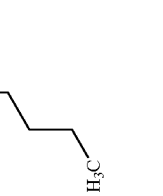 | 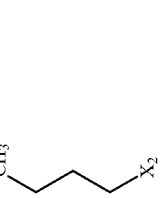 | 1.86 | 470.2846 | 471.3502 |
| 279 | 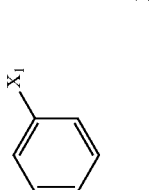 | 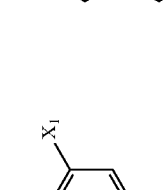 | | 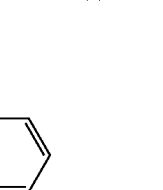 | 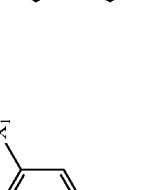 | 2.07 | 496.3002 | 497.375 |
| 280 | 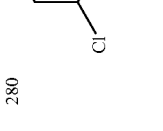 | 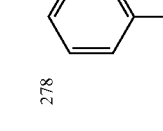 | | 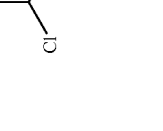 | 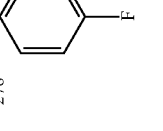 | 2.02 | 487.2027 | 488.2712 |

TABLE 1-continued

| CMP # | R1 | R2 | R3 | R4 | R5 | Rtn Time | Cmd Mass | H+ Ion Obs |
|---|---|---|---|---|---|---|---|---|
| 281 | 4-Cl-C6H4- (X1) | X2-CH2CH2CH2-CH3 | | X4-CH2-C6H5 | X5-CH2-(2,3-dihydrobenzo[1,4]dioxin-6-yl) | 2.02 | 501.2183 | 502.2874 |
| 282 | C6H5- (X1) | X2-CH2CH2CH2-CH3 | X3-CH3 | X4-CH2-C6H5 | X5-CH2-(benzo[1,3]dioxol-5-yl) | | | |
| 283 | C6H5- (X1) | X2-CH2CH2CH2-CH3 | | X4-CH2-C6H5 | X5-CH2-(benzo[1,3]dioxol-5-yl) | 2.01 | 459.2886 | 460.3366 |

TABLE 1-continued
| CMP # | R1 | R2 | R3 | R4 | R5 | Rtn Time | Cmd Mass | H+ Ion Obs |
|---|---|---|---|---|---|---|---|---|
| 284 |  |  | |  | 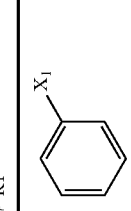 | 2 | 473.3042 | 474.3561 |
| 285 |  | 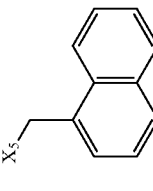 | |  | 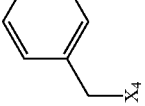 | 2.1 | 465.3144 | 466.3706 |
| 286 |  | 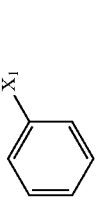 | |  |  | | | |

TABLE 1-continued
| CMP # | R1 | R2 | R3 | R4 | R5 | Rtn Time | Cmd Mass | H+ Ion Obs |
|---|---|---|---|---|---|---|---|---|
| 287 | 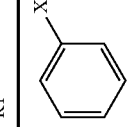 | 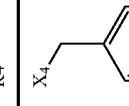 | | 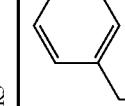 |  | 1.99 | 503.2784 | 504.3394 |
| 288 | 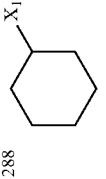 | 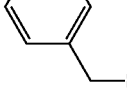 | | 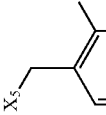 | 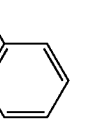 | | | |
| 289 | 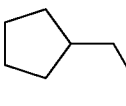 | 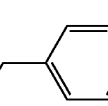 | | | | 1.99 | 459.2886 | 460.3446 |

TABLE 1-continued
| CMP # | R1 | R2 | R3 | R4 | R5 | Rtn Time | Cmd Mass | H+ Ion Obs |
|---|---|---|---|---|---|---|---|---|
| 290 |  |  | |  |  | 2.07 | 447.2886 | 448.3387 |
| 291 |  |  | |  |  | 2.06 | 481.2729 | 482.3294 |
| 292 |  |  | |  |  | 2.08 | 475.3199 | 476.3839 |

TABLE 1-continued
| CMP # | R1 | R2 | R3 | R4 | R5 | Rtn Time | Cmd Mass | H+ Ion Obs |
|---|---|---|---|---|---|---|---|---|
| 293 | 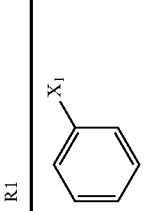 | 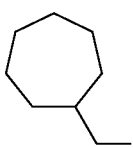 | | 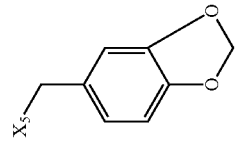 | 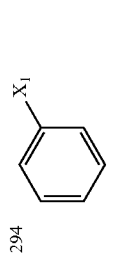 | 2.11 | 473.3042 | 474.361 |
| 294 | 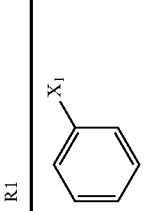 | 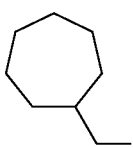 | | 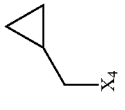 | 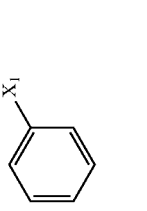 | 1.76 | 417.2416 | 418.2879 |
| 295 | 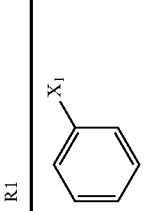 | 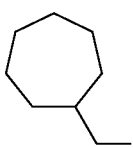 | | 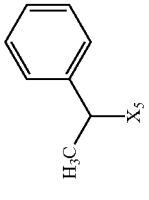 | | 2.05 | 423.2675 | 424.2875 |

TABLE 1-continued
| CMP # | R1 | R2 | R3 | R4 | R5 | Rtn Time | Cmd Mass | H+ Ion Obs |
|---|---|---|---|---|---|---|---|---|
| 296 |  |  | |  |  | 2.06 | 467.2573 | 468.2819 |
| 297 |  | 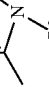 | |  |  | 2.01 | 413.2831 | 414.3154 |
| 298 |  |  | |  |  | 2.05 | 467.2573 | 468.2849 |
| 299 |  |  | |  |  | 2.02 | 451.2624 | 452.2898 |

TABLE 1-continued

| CMP # | R1 | R2 | R3 | R4 | R5 | Rtn Time | Cmd Mass | H+ Ion Obs |
|---|---|---|---|---|---|---|---|---|
| 300 | 4-F-C6H4- | CH3-(CH2)3-X2 | | benzyl-X4 | 3-Cl-4-OH-benzyl-X5 | 2.02 | 477.1983 | 478.2289 |
| 301 | 3-F-C6H4- | CH3-(CH2)3-X2 | | benzyl-X4 | 3-Cl-4-OH-benzyl-X5 | 2.01 | 477.1983 | 478.2308 |
| 302 | C6H5- | X2-(CH2)3-CH3 | | methylenedioxybenzyl-X4 | 2,3-dihydrobenzofuran-5-yl-X5 | 1.95 | 495.2522 | 496.3082 |
| 303 | 4-F-C6H4- | X2-(CH2)3-CH3 | X3-CH3 | methylenedioxybenzyl-X4 | methylenedioxybenzyl-X5 | 1.99 | 529.2377 | 530.2964 |

TABLE 1-continued

| CMP # | R1 | R2 | R3 | R4 | R5 | Rtn Time | Cmd Mass | H+ Ion Obs |
|---|---|---|---|---|---|---|---|---|
| 304 | 4-F-phenyl (X1) | X2-(CH2)3-CH3 | X3-CH3 | benzyl (X4) | 1,3-benzodioxol-5-ylmethyl (X5) | 2.01 | 485.2479 | 486.3004 |
| 305 | 4-F-phenyl (X1) | X2-(CH2)3-CH3 | X3-CH3 | cyclopentylmethyl (X4) | 1,3-benzodioxol-5-ylmethyl (X5) | 2.05 | 277.2791 | 478.3398 |
| 306 | 3-F-phenyl (X1) | CH3-(CH2)3-X2 | H3C-X3 | benzyl (X4) | 4-(pyrrolidin-1-yl)benzyl (X5) | | | |

TABLE 1-continued

| CMP # | R1 | R2 | R3 | R4 | R5 | Rtn Time | Cmd Mass | H+ Ion Obs |
|---|---|---|---|---|---|---|---|---|
| 307 | 3-fluorophenyl-X1 | CH3-CH2-CH2-CH2-X2 | H3C-X3 | benzyl-X4 | 4-hydroxy-3-chlorobenzyl-X5 | 1.99 | 491.214 | 492.2748 |
| 308 | phenyl-X1 | CH3-CH2-CH2-CH2-X2 | | butyl-X4 | 2-chloro-4-hydroxybenzyl-X5 | 1.91 | 425.2234 | 426.2757 |
| 309 | phenyl-X1 | CH3-CH2-CH2-CH2-X2 | | benzyl-X4 | (6-amino-pyridin-3-yl)methyl-X5 | 1.69 | 425.2579 | 426.3054 |
| 310 | 2-thienyl-X1 | X2-CH2-CH2-CH2-CH3 | | benzo[1,3]dioxol-5-ylmethyl-X5 | 4-(pyrrolidin-1-yl)benzyl-X5 | 1.96 | 503.1879 | 504.2485 |

TABLE 1-continued
| CMP # | R1 | R2 | R3 | R4 | R5 | Rtn Time | Cmd Mass | H+ Ion Obs |
|---|---|---|---|---|---|---|---|---|
| 311 |  |  | |  |  | 1.98 | 459.1981 | 460.2525 |
| 312 | 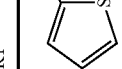 | 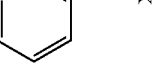 | | 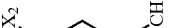 |  | 1.99 | 451.2293 | 452.2899 |
| 313 |  |  |  |  |  | 1.99 | 469.2529 | 470.3111 |
| 314 |  | 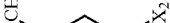 |  |  | 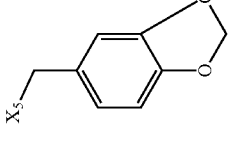 | 2.01 | 483.2686 | 484.3253 |

TABLE 1-continued

| CMP # | R1 | R2 | R3 | R4 | R5 | Rtn Time | Cmd Mass | H+ Ion Obs |
|---|---|---|---|---|---|---|---|---|
| 315 | 3-F-C6H4-X1 | CH3-(CH2)3-X2 | H3C-X3 | benzyl-X4 | 3-F-C6H4-X5 | 1.78 | 512.3315 | 513.4124 |
| 316 | C6H5-X1 | CH3-(CH2)3-X2 | | sec-butyl-X4 | 4-(N(CH3)2)-C6H4-CH2-X5 | 1.81 | 432.3253 | 433.3902 |
| 317 | 3-F-C6H4-X1 | CH3-(CH2)3-X2 | | sec-butyl-X4 | 4-(N(CH3)2)-C6H4-CH2-X5 | 1.83 | 450.3159 | 451.3883 |

TABLE 1-continued

| CMP # | R1 | R2 | R3 | R4 | R5 | Rtn Time | Cmd Mass | H+ Ion Obs |
|---|---|---|---|---|---|---|---|---|
| 318 | phenyl (X1) | X2-(CH2)3-CH3 | | benzo[1,3]dioxol-5-ylmethyl (X4) | 1-methyl-indolin-5-ylmethyl (X5) | 1.97 | 506.2682 | 507.3284 |
| 319 | phenyl (X1) | X2-(CH2)3-CH3 | | 3-chloro-4-(X4-methyl)phenol | benzo[1,3]dioxol-5-ylmethyl (X5) | 1.95 | 503.1976 | 504.2582 |
| 320 | 4-fluorophenyl (X1) | X2-(CH2)3-CH3 | X3-CH3 | 3-chloro-4-(X4-methyl)phenol | benzo[1,3]dioxol-5-ylmethyl (X5) | 1.97 | 535.2038 | 536.2633 |

TABLE 1-continued

| CMP # | R1 | R2 | R3 | R4 | R5 | Rtn Time | Cmd Mass | H+ Ion Obs |
|---|---|---|---|---|---|---|---|---|
| 321 | phenyl (X1) | X2-(CH2)3-CH3 | | 2,3-dihydrobenzofuran-5-ylmethyl (X4) | benzo[1,3]dioxol-5-ylmethyl (X5) | 1.93 | 493.2729 | 494.3287 |
| 322 | 3-fluorophenyl (X1) | CH3-(CH2)3-X2 | | benzyl (X4) | 4-methoxy-2-chlorobenzyl (X5) | 2.06 | 491.214 | 492.2753 |
| 323 | 3-fluorophenyl (X1) | CH3-(CH2)3-X2 | CH3 (X3) | 4-methylpentyl (X4) | 4-hydroxy-2-chlorobenzyl (X5) | 2.02 | 471.2453 | 472.317 |
| 324 | 3-fluorophenyl (X1) | CH3-(CH2)3-X2 | | butyl (X4) | 4-hydroxy-2-chlorobenzyl (X5) | 1.92 | 443.214 | 444.2721 |

TABLE 1-continued

| CMP # | R1 | R2 | R3 | R4 | R5 | Rtn Time | Cmd Mass | H+ Ion Obs |
|---|---|---|---|---|---|---|---|---|
| 325 | 3-F-phenyl (X1) | CH3-(CH2)3-X2 | H3C-X3 | H3C-(CH2)3-X4 | 3-Cl-4-(X5-methyl)phenol | 1.98 | 457.2296 | 458.2892 |
| 326 | 3-F-phenyl (X1) | CH3-(CH2)3-X2 | | CH3-CH(CH3)-CH2-CH2-X4 | 3-Cl-4-(X5-methyl)phenol | 1.97 | 457.2296 | 458.2943 |
| 327 | 3-F-phenyl (X1) | CH3-(CH2)3-X2 | | CH3-CH(CH3)-CH2-CH2-X4 | 2,3-dihydrobenzofuran-5-yl-CH2-X5 | 1.87 | 449.2842 | 450.3473 |
| 328 | 3-F-phenyl (X1) | CH3-(CH2)3-X2 | H3C-X3 | H3C-(CH2)3-X4 | 2,3-dichlorophenyl-CH2-X5 | 2.1 | 475.1957 | 476.2632 |

TABLE 1-continued
| CMP # | R1 | R2 | R3 | R4 | R5 | Rtn Time | Cmd Mass | H+ Ion Obs |
|---|---|---|---|---|---|---|---|---|
| 329 |  |  | |  |  | 2.02 | 423.2675 | 424.3092 |
| 330 |  |  | |  |  | | | |
| 331 |  |  |  |  |  | 1.98 | 491.214 | 492.2755 |
| 332 |  |  |  |  |  | 1.99 | 491.214 | 492.2755 |

TABLE 1-continued

| CMP # | R1 | R2 | R3 | R4 | R5 | Rtn Time | Cmd Mass | H+ Ion Obs |
|---|---|---|---|---|---|---|---|---|
| 333 | phenyl (X1) | 2-indanyl (X2) | | 4-methoxybenzyl (X4) | 4-fluoro-3-methoxybenzyl (X5) | 2.02 | 547.2635 | 548.3262 |
| 334 | phenyl (X1) | 2-indanyl (X2) | | 4-methoxybenzyl (X4) | 2-bromobenzyl (X5) | 2.08 | 577.1729 | 578.25 |
| 335 | phenyl (X1) | n-butyl (X2) | CH3 (X3) | benzo[1,3]dioxol-5-ylmethyl (X4) | benzo[1,3]dioxol-5-ylmethyl (X4) | 1.96 | 511.2471 | 512.298 |

TABLE 1-continued

| CMP # | R1 | R2 | R3 | R4 | R5 | Rtn Time | Cmd Mass | H+ Ion Obs |
|---|---|---|---|---|---|---|---|---|
| 336 | phenyl-X₁ | X₂-butyl | X₃-CH₃ | X₄-methylenebenzodioxole | 3-chloro-4-hydroxybenzyl-X₅ | 1.95 | 517.2132 | 518.2731 |
| 337 | phenyl-X₁ | X₂-butyl | X₃-butyl | X₄-methylenecyclohexyl | 3-chloro-4-hydroxybenzyl-X₅ | 2.15 | 521.3173 | 522.3696 |
| 338 | phenyl-X₁ | X₂-butyl | X₃-butyl | X₄-methylenecyclohexyl | methylenebenzodioxole-X₅ | 2.15 | 515.3512 | 516.4249 |
| 339 | phenyl-X₁ | X₂-butyl | X₃-CH₃ | 4-hydroxybenzyl-X₄ | methylenebenzodioxole-X₄ | 1.88 | 483.2522 | 484.3056 |

TABLE 1-continued

| CMP # | R1 | R2 | R3 | R4 | R5 | Rtn Time | Cmd Mass | H+ Ion Obs |
|---|---|---|---|---|---|---|---|---|
| 340 | phenyl | butyl | butyl | cyclohexylmethyl | 4-hydroxybenzyl | 2.05 | 487.3563 | 488.4303 |
| 341 | phenyl | butyl | butyl | cyclohexylmethyl | 4-carboxybenzyl | 2.08 | 515.3512 | 516.4047 |
| 342 | phenyl | butyl | butyl | cyclohexylmethyl | 4-(hydroxymethyl)benzyl | 2.05 | 501.3719 | 502.4088 |
| 343 | phenyl | butyl | butyl | benzyl | 4-(methoxycarbonyl)benzyl | 1.97 | 467.2573 | 468.2854 |

TABLE 1-continued
| CMP # | R1 | R2 | R3 | R4 | R5 | Rtn Time | Cmd Mass | H+ Ion Obs |
|---|---|---|---|---|---|---|---|---|
| 344 |  | 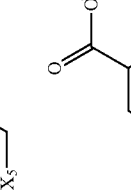 | |  |  | 1.94 | 433.2729 | 434.297 |
| 345 |  |  | |  | 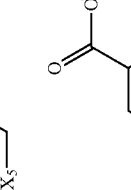 | 2.07 | 473.3042 | 474.3316 |
| 346 | 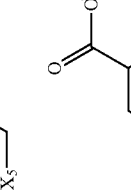 |  | |  |  | 2.01 | 459.2886 | 460.3174 |

TABLE 1-continued

| CMP # | R1 | R2 | R3 | R4 | R5 | Rtn Time | Cmd Mass | H+ Ion Obs |
|---|---|---|---|---|---|---|---|---|
| 347 | phenyl | CH3(CH2)3- | | benzyl | 4-(hydroxymethyl)benzyl | 1.88 | 439.2624 | 440.2939 |
| 348 | phenyl | CH3(CH2)3- | | n-pentyl | 4-(hydroxymethyl)benzyl | 1.7 | 405.278 | 406.3116 |
| 349 | phenyl | CH3(CH2)3- | | cyclohexylmethyl | 4-(hydroxymethyl)benzyl | 1.96 | 445.3093 | 446.3387 |
| 350 | phenyl | CH3(CH2)3- | CH3(CH2)3- | benzyl | 3-(methoxycarbonyl)benzyl | 2.07 | 523.3199 | 524.3464 |

TABLE 1-continued

| CMP # | R1 | R2 | R3 | R4 | R5 | Rtn Time | Cmd Mass | H+ Ion Obs |
|---|---|---|---|---|---|---|---|---|
| 351 | phenyl (X1) | X2-(CH2)3-CH3 | H3C-(CH2)3-X3 | X4-(CH2)3-CH3 | 3-(methoxycarbonyl)benzyl (X5) | 2.04 | 489.3355 | 490.3575 |
| 352 | phenyl (X1) | X2-(CH2)3-CH3 | H3C-(CH2)3-X3 | X4-CH2-cyclohexyl | 3-(methoxycarbonyl)benzyl (X5) | 2.15 | 529.3668 | 530.3951 |
| 353 | phenyl (X1) | X2-(CH2)3-CH3 | H3C-(CH2)3-X3 | X4-CH2-phenyl | 3-carboxybenzyl (X5) | 2.01 | 509.3042 | 510.337 |
| 354 | phenyl (X1) | X2-(CH2)3-CH3 | H3C-(CH2)3-X3 | X4-CH2-cyclohexyl | 3-carboxybenzyl (X5) | 2.08 | 515.3512 | 516.3834 |

TABLE 1-continued
| CMP # | R1 | R2 | R3 | R4 | R5 | Rtn Time | Cmd Mass | H+ Ion Obs |
|---|---|---|---|---|---|---|---|---|
| 355 | 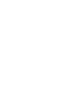 | 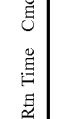 | 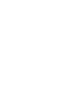 | 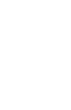 | 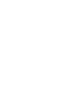 | | | |
| 356 |  |  |  |  |  | | | |
| 357 |  | 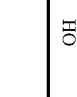 |  |  |  | 2.07 | 501.3719 | 502.3938 |
| 358 |  |  |  |  |  | 2.08 | 539.3148 | 540.3187 |

TABLE 1-continued
| CMP # | R1 | R2 | R3 | R4 | R5 | Rtn Time | Cmd Mass | H+ Ion Obs |
|---|---|---|---|---|---|---|---|---|
| 359 |  phenyl-X1 | X2-butyl | H3C-propyl-X3 | X4-pentyl |  methyl salicylate-CH2-X5 | 2.04 | 505.3304 | 506.3531 |
| 360 | phenyl-X1 | X2-butyl | H3C-propyl-X3 | X4-CH2-cyclohexyl | methyl salicylate-CH2-X5 | 2.16 | 545.3618 | 546.3911 |
| 361 | phenyl-X1 | X2-butyl | | X4-CH2-phenyl | methyl salicylate-CH2-X5 | 2 | 483.2522 | 484.2723 |
| 362 | phenyl-X1 | X2-butyl | | X4-pentyl | methyl salicylate-CH2-X5 | 1.93 | 449.2679 | 450.2899 |

TABLE 1-continued

| CMP # | R1 | R2 | R3 | R4 | R5 | Rtn Time | Cmd Mass | H+ Ion Obs |
|---|---|---|---|---|---|---|---|---|
| 363 | phenyl (X1) | X2-(CH2)3-CH3 | | X4-CH2-cyclohexyl | 2-OH-5-(X5-CH2)-benzoic acid methyl ester | 2.08 | 489.2991 | 490.3192 |
| 364 | phenyl (X1) | X2-(CH2)3-CH3 | H3C-(CH2)3-X3 | X4-CH2-phenyl | 2-OH-5-(X5-CH2)-benzoic acid | 2.06 | 525.2991 | 526.36 |
| 365 | phenyl (X1) | X2-(CH2)3-CH3 | H3C-(CH2)3-X3 | X4-CH2-cyclohexyl | 2-OH-5-(X5-CH2)-benzoic acid | 2.12 | 531.3461 | 532.3955 |
| 366 | phenyl (X1) | X2-(CH2)3-CH3 | | X4-CH2-phenyl | 2-OH-5-(X5-CH2)-benzoic acid | 1.95 | 469.2365 | 470.2861 |

TABLE 1-continued
| CMP # | R1 | R2 | R3 | R4 | R5 | Rtn Time | Cmd Mass | H+ Ion Obs |
|---|---|---|---|---|---|---|---|---|
| 367 |  | X₂-CH₂CH₂CH₂CH₃ | | X₄-CH₂CH₂CH₂CH₃ | 2-OH-5-CH₂X₅-benzoic acid | 1.8 | 435.2622 | 436.2889 |
| 368 |  | X₂-CH₂CH₂CH₂CH₃ | | X₄-CH₂-cyclohexyl | 2-OH-5-CH₂X₅-benzoic acid | 2.03 | 475.2835 | 476.3151 |
| 369 |  | X₂-CH₂CH₂CH₂CH₃ | H₃C-CH₂CH₂CH₂-X₃ | X₄-CH₂-phenyl | 2-OH-5-CH₂X₅-benzyl alcohol | 1.94 | 511.3199 | 512.3583 |
| 370 |  | X₂-CH₂CH₂CH₂CH₃ | H₃C-CH₂CH₂CH₂-X₃ | X₄-CH₂CH₂CH₂CH₃ | 2-OH-5-CH₂X₅-benzyl alcohol | 1.72 | 477.3355 | 478.3816 |

TABLE 1-continued
| CMP # | R1 | R2 | R3 | R4 | R5 | Rtn Time | Cmd Mass | H+ Ion Obs |
|---|---|---|---|---|---|---|---|---|
| 371 |  |  |  |  |  | 1.98 | 517.3668 | 518.4061 |
| 372 |  |  |  |  |  | 2.02 | 553.3304 | 554.3617 |
| 373 |  |  |  |  |  | 1.96 | 519.3461 | 520.382 |
| 374 |  |  |  |  |  | 2.09 | 559.3774 | 560.4091 |

TABLE 1-continued

| CMP # | R1 | R2 | R3 | R4 | R5 | Rtn Time | Cmd Mass | H+ Ion Obs |
|---|---|---|---|---|---|---|---|---|
| 375 | phenyl (X1) | propyl-CH3 (X2) | | benzyl (X4) | methyl 2-methoxy-5-(CH2X5)benzoate | 1.92 | 497.2679 | 498.3003 |
| 376 | phenyl (X1) | propyl-CH3 (X2) | | cyclohexylmethyl (X4) | methyl 2-methoxy-5-(CH2X5)benzoate | 2 | 503.3148 | 504.343 |
| 377 | phenyl (X1) | propyl-CH3 (X2) | butyl-CH3 (X3) | cyclohexylmethyl (X4) | 2-methoxy-5-(CH2X5)benzoic acid | | | |

TABLE 1-continued
| CMP # | R1 | R2 | R3 | R4 | R5 | Rtn Time | Cmd Mass | H+ Ion Obs |
|---|---|---|---|---|---|---|---|---|
| 378 |  |  |  |  |  | 2 | 525.3355 | 526.3682 |
| 379 |  |  |  |  |  | 1.81 | 491.3512 | 492.3873 |
| 380 |  |  |  |  |  | 2.05 | 531.3825 | 532.415 |

TABLE 1-continued

| CMP # | R1 | R2 | R3 | R4 | R5 | Rtn Time | Cmd Mass | H+ Ion Obs |
|---|---|---|---|---|---|---|---|---|
| 381 | phenyl (X1) | X2-propyl-CH3 | | X4-benzyl | 2-methoxy-5-(X5-methyl)benzyl alcohol | | | |
| 382 | phenyl (X1) | X2-propyl-CH3 | | X4-CH2-cyclohexyl | 2-methoxy-5-(X5-methyl)benzyl alcohol | 1.94 | 475.3199 | 476.3517 |
| 383 | phenyl (X1) | X2-butyl-CH3 | | X4-CH2-(4-hydroxyphenyl) | methyl 4-(X4-methyl)benzoate | 1.86 | 483.2522 | 484.2405 |

TABLE 1-continued
| CMP # | R1 | R2 | R3 | R4 | R5 | Rtn Time | Cmd Mass | H+ Ion Obs |
|---|---|---|---|---|---|---|---|---|
| 384 | 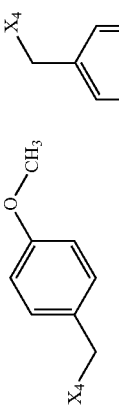 | 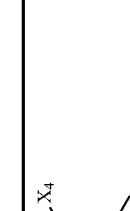 | | 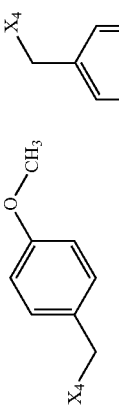 |  | 1.94 | 517.2132 | 518.2035 |
| 385 |  | 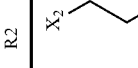 | | 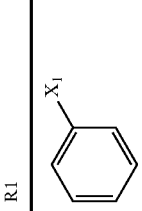 |  | 1.97 | 497.2679 | 498.2453 |

TABLE 1-continued

| CMP # | R1 | R2 | R3 | R4 | R5 | Rtn Time | Cmd Mass | H+ Ion Obs |
|---|---|---|---|---|---|---|---|---|
| 386 | X₁–phenyl | X₂–(CH₂)₃CH₃ | | X₄–CH₂–C₆H₄–C(O)OCH₃ | X₅–CH₂–(benzo[1,3]dioxole) | 1.95 | 511.2471 | 512.2275 |
| 387 | X₁–phenyl | X₂–(CH₂)₃CH₃ | | X₄–CH₂–C₆H₅ | X₅–CH₂–C₆H₃(C(O)OCH₂CH₃)₂ | 2.06 | 553.2941 | 554.2728 |
| 388 | X₁–phenyl | X₂–(CH₂)₃CH₃ | | X₄–(CH₂)₃CH₃ | X₅–CH₂–C₆H₃(C(O)OCH₂CH₃)₂ | 2.05 | 519.3097 | 520.2906 |

TABLE 1-continued
| CMP # | R1 | R2 | R3 | R4 | R5 | Rtn Time | Cmd Mass | H+ Ion Obs |
|---|---|---|---|---|---|---|---|---|
| 389 | 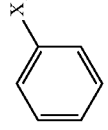 |  | |  |  | 2.13 | 559.341 | 560.3246 |
| 390 |  |  | |  |  | 1.78 | 469.2365 | 470.2381 |
| 391 |  |  | | 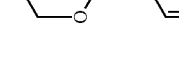 |  | 1.88 | 503.1976 | 504.1985 |

TABLE 1-continued
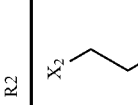
| CMP # | R1 | R2 | R3 | R4 | R5 | Rtn Time | Cmd Mass | H+ Ion Obs |
|---|---|---|---|---|---|---|---|---|
| 392 | 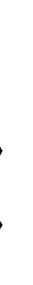 |  | | 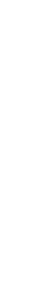 |  | 1.89 | 483.2522 | 484.2435 |
| 393 |  |  | |  | 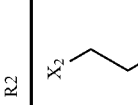 | 1.89 | 497.2314 | 498.227 |
| 394 |  |  | |  |  | 1.71 | 455.2573 | 456.2579 |

TABLE 1-continued
| CMP # | R1 | R2 | R3 | R4 | R5 | Rtn Time | Cmd Mass | H+ Ion Obs |
|---|---|---|---|---|---|---|---|---|
| 395 | 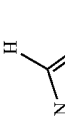 | 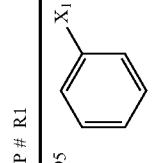 | |  |  | 1.84 | 489.2183 | 490.22 |
| 396 |  | 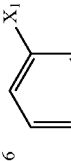 | |  | 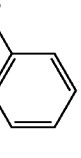 | 1.85 | 469.2729 | 470.2647 |
| 397 |  | 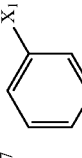 | |  |  | 1.85 | 483.2522 | 484.24 |

TABLE 1-continued
| CMP # | R1 | R2 | R3 | R4 | R5 | Rtn Time | Cmd Mass | H+ Ion Obs |
|---|---|---|---|---|---|---|---|---|
| 398 | 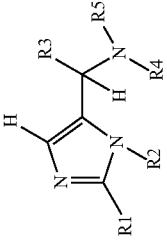 | 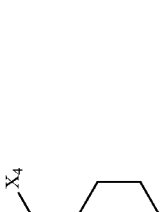 | 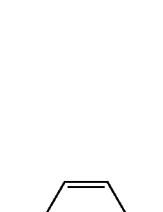 |  | 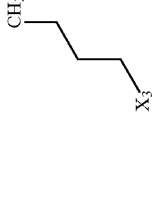 | 1.97 | 531.3825 | 532.3688 |
| 399 | 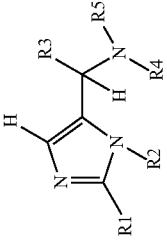 | 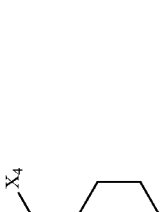 | 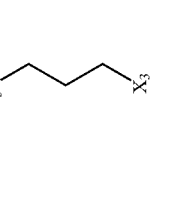 |  | 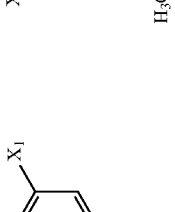 | 2.07 | 509.3042 | 510.2987 |
| 400 | 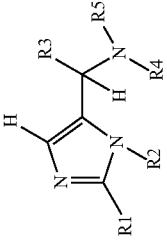 | 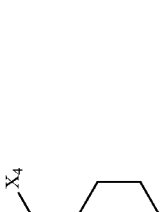 | 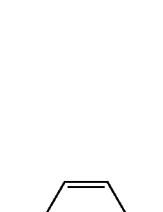 |  |  | 1.99 | 481.3093 | 482.3098 |
| 401 | 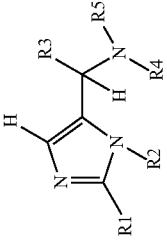 | 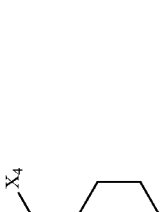 | 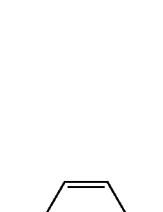 |  |  | 2.05 | 515.2703 | 516.2676 |

TABLE 1-continued

| CMP # | R1 | R2 | R3 | R4 | R5 | Rtn Time | Cmd Mass | H+ Ion Obs |
|---|---|---|---|---|---|---|---|---|
| 402 | phenyl (X1) | butyl (X2) | CH3-propyl (X3) | benzyl (X4) | 3-hydroxyphenyl-ethyl (X5) | 2.01 | 481.3093 | 482.3063 |
| 403 | phenyl (X1) | butyl (X2) | CH3-propyl (X3) | benzyl (X4) | 4-acetoxyphenyl-ethyl (X5) | 2.03 | 523.3199 | 524.3068 |
| 404 | phenyl (X1) | butyl (X2) | CH3-propyl (X3) | benzyl (X4) | 3-acetoxyphenyl-ethyl (X5) | 2.04 | 523.3199 | 524.3074 |
| 405 | phenyl (X1) | butyl (X2) | CH3-propyl (X3) | butyl (X4) | benzo[1,3]dioxol-5-ylmethyl (X5) | 1.96 | 475.3199 | 476.3177 |

TABLE 1-continued
| CMP # | R1 | R2 | R3 | R4 | R5 | Rtn Time | Cmd Mass | H+ Ion Obs |
|---|---|---|---|---|---|---|---|---|
| 410 |  |  |  |  | | 2.01 | 489.3355 | 490.3296 |
| 411 |  |  |  |  |  | 2.08 | 495.325 | 496.3224 |
| 412 |  |  |  |  |  | 1.92 | 461.3406 | 462.3352 |
| 413 |  |  |  |  |  | 2.15 | 501.3719 | 502.3614 |

TABLE 1-continued
| CMP # | R1 | R2 | R3 | R4 | R5 | Rtn Time | Cmd Mass | H+ Ion Obs |
|---|---|---|---|---|---|---|---|---|
| 406 |  |  |  |  |  | 1.79 | 447.325 | 448.3324 |
| 407 |  |  |  |  |  | 2.02 | 481.286 | 482.2877 |
| 408 |  |  |  |  |  | 1.88 | 447.325 | 448.326 |
| 409 |  |  |  |  |  | 1.97 | 489.3355 | 490.3298 |

TABLE 1-continued
| CMP # | R1 | R2 | R3 | R4 | R5 | Rtn Time | Cmd Mass | H+ Ion Obs |
|---|---|---|---|---|---|---|---|---|
| 414 |  |  |  |  |  | 2.1 | 515.3124 | 516.3123 |
| 415 |  |  |  |  |  | 2.08 | 495.325 | 496.3181 |
| 416 |  |  |  |  |  | 2.01 | 461.3400 | 462.3389 |
| 417 |  |  |  |  |  | 2.16 | 501.3719 | 502.3629 |

TABLE 1-continued
| CMP # | R1 | R2 | R3 | R4 | R5 | Rtn Time | Cmd Mass | H+ Ion Obs |
|---|---|---|---|---|---|---|---|---|
| 418 | 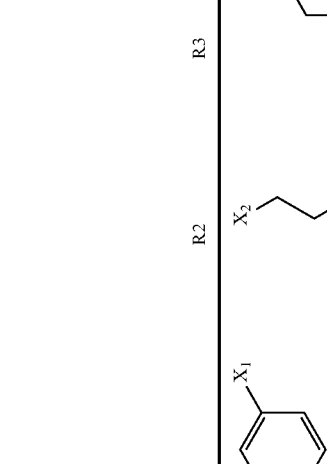 |  |  |  |  | | | |
| 419 | 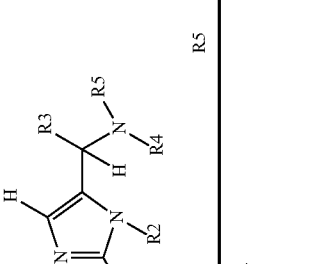 |  |  |  |  | | | |
| 420 | 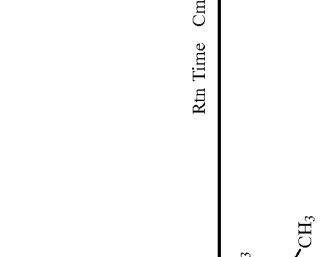 |  |  |  |  | 2.08 | 514.4036 | 515.423 |

TABLE 1-continued
| CMP # | R1 | R2 | R3 | R4 | R5 | Rtn Time | Cmd Mass | H+ Ion Obs |
|---|---|---|---|---|---|---|---|---|
| 421 |  | 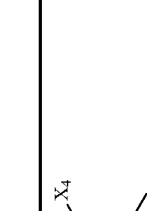 | 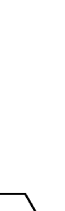 | 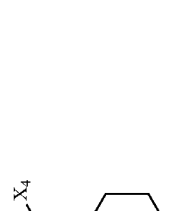 |  | 2.14 | 515.3512 | 516.3379 |
| 422 |  | 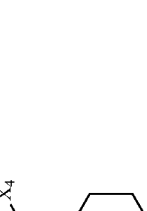 | 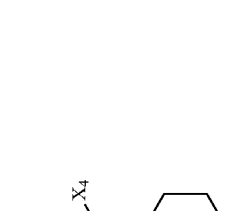 |  |  | 2.14 | 521.3173 | 522.3266 |
| 423 |  |  | 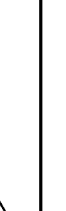 |  |  | | | |

TABLE 1A

R3 is H unless otherwise specified

| CMP # | R1 | R2 | R3 | R4 | R5 | Rtn Time | Cmd Mass | H+ Ion Obs |
|---|---|---|---|---|---|---|---|---|
| 424 | 2-fluorophenyl-X1 | H3C-(CH2)4-X2 | | benzyl-X4 | benzyl-X5 | 2.02 | 427.2424 | 428.2541 |
| 425 | 2-fluorophenyl-X1 | H3C-(CH2)4-X2 | | benzyl-X4 | 3-methylbenzyl-X5 | 2.06 | 441.258 | 442.2744 |
| 426 | 2-fluorophenyl-X1 | H3C-(CH2)4-X2 | | benzyl-X4 | 4-methylbenzyl-X5 | 2.1 | 455.2737 | 456.2899 |
| 427 | 4-fluorophenyl-X1 | H3C-(CH2)4-X2 | | benzyl-X4 | 3,4-dimethylbenzyl-X5 | 2.08 | 455.2737 | 456.2953 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 428 |  | 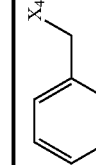 | 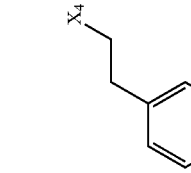 | 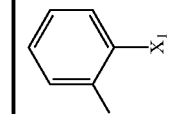 | 2.13 | 469.2893 | 470.3137 |
| 429 | 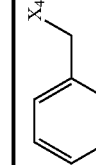 | 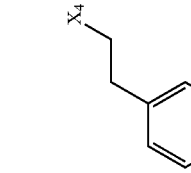 | 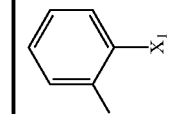 |  | 2.02 | 485.2479 | 486.2833 |
| 430 | 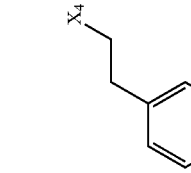 | 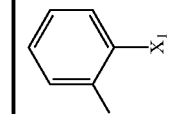 |  | 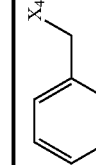 | 2.15 | 481.3093 | 482.332 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 431 | phenyl-X$_1$ | H$_3$C-(CH$_2$)$_3$-X$_2$ | | butyl-X$_4$ | benzo[1,3]dioxol-5-ylmethyl-X$_5$ | 1.98 | 419.2573 | 420.2856 |
| 432 | phenyl-X$_1$ | H$_3$C-(CH$_2$)$_3$-X$_2$ | | isobutyl-X$_4$ | benzo[1,3]dioxol-5-ylmethyl-X$_5$ | 1.91 | 431.2573 | 432.2898 |
| 433 | phenyl-X$_1$ | H$_3$C-(CH$_2$)$_3$-X$_2$ | | cyclobutylmethyl-X$_4$ | benzo[1,3]dioxol-5-ylmethyl-X$_5$ | | | |
| 434 | phenyl-X$_1$ | H$_3$C-(CH$_2$)$_3$-X$_2$ | | pentyl-X$_4$ | benzo[1,3]dioxol-5-ylmethyl-X$_5$ | 1.92 | 433.2729 | 434.3079 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 435 |  |  | |  |  | 1.91 | 433.2729 | 434.3078 |
| 436 |  |  | |  |  | 2.04 | 433.2729 | 434.3079 |
| 437 |  |  | |  |  | 2.04 | 401.2831 | 402.3126 |
| 438 |  |  | |  |  | 2.01 | 445.2729 | 446.3118 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 439 | phenyl-$X_1$ | $H_3C$-(CH$_2$)$_3$-$X_2$ | (CH$_2$)$_5$-$X_4$ | benzo[1,3]dioxol-5-yl-methyl-$X_5$ | 1.99 | 447.2886 | 448.329 |
| 440 | phenyl-$X_1$ | $H_3C$-(CH$_2$)$_3$-$X_2$ | $X_4$-(CH$_2$)$_3$-CH(CH$_3$)- | benzo[1,3]dioxol-5-yl-methyl-$X_5$ | 1.98 | 447.2886 | 448.3293 |
| 441 | phenyl-$X_1$ | $H_3C$-(CH$_2$)$_3$-$X_2$ | $X_4$-(CH$_2$)$_2$-C(CH$_3$)$_2$- | benzo[1,3]dioxol-5-yl-methyl-$X_5$ | 1.95 | 447.2886 | 448.3331 |
| 442 | phenyl-$X_1$ | $H_3C$-(CH$_2$)$_3$-$X_2$ | $X_4$-CH$_2$-CH(CH$_2$CH$_3$)-CH$_2$- | benzo[1,3]dioxol-5-yl-methyl-$X_5$ | 2.06 | 447.2886 | 448.3315 |

TABLE 1A-continued

| CMP # | R1 | R2 | R3 | R4 | R5 | Rtn Time | Cmd Mass | H+ Ion Obs |
|---|---|---|---|---|---|---|---|---|
| 443 | | | | | | 2.09 | 403.2987 | 404.3406 |
| 444 | | | | | | 2.07 | 447.2886 | 448.3385 |
| 445 | | | | | | 1.99 | 459.2886 | 460.3416 |
| 446 | | | | | | 2.07 | 459.2886 | 460.3427 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 447 | 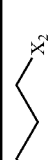 | 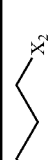 | | 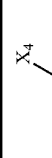 | 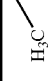 | 2.04 | 461.3042 | 462.362 |
| 448 |  |  | | 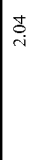 | 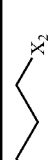 | 2.04 | 473.3042 | 474.3634 |
| 449 |  |  | | 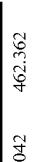 | 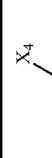 | 2.12 | 473.3042 | 474.3605 |
| 450 |  |  | | 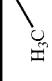 | 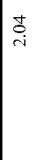 | 2.05 | 473.3042 | 474.3627 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 451 |  |  | 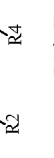 |  | 2.09 | 475.3199 | 476.3831 |
| 452 |  |  | 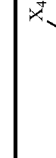 | 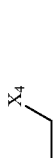 | 2.09 | 529.2729 | 530.334 |
| 453 |  | 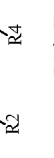 |  | 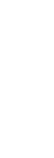 | 2.09 | 545.2678 | 546.3349 |
| 454 |  | 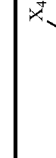 |  |  | 2.02 | 423.2675 | 424.3183 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 455 |  |  | 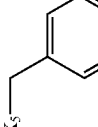 |  | 2.01 | 409.2518 | 410.3021 |
| 456 |  | 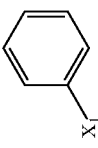 |  |  | 2.07 | 459.2675 | 460.326 |
| 457 |  |  |  |  | 2 | 453.2416 | 454.3023 |
| 458 |  |  |  |  | 2.06 | 437.2831 | 438.3368 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 459 |  |  | |  |  | 2.05 | 423.2675 | 424.318 |
| 460 | 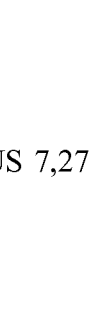 | 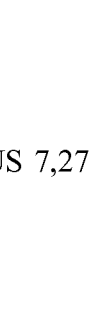 | | 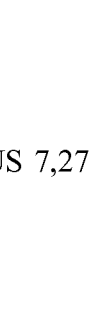 |  | 2.11 | 473.2831 | 474.3436 |
| 461 |  |  | |  |  | 2.04 | 467.2573 | 468.3188 |
| 462 |  |  | |  |  | 2.06 | 437.2831 | 438.3386 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 463 | phenyl-X1 | H3C-(CH2)3-X2 | | benzyl-X4 | 4-methylbenzyl-X5 | 2.11 | 473.2831 | 474.3485 |
| 464 | phenyl-X1 | H3C-(CH2)3-X2 | | 4-methylbenzyl-X4 | naphthalen-1-ylmethyl-X5 | | | |
| 465 | phenyl-X1 | H3C-(CH2)3-X2 | | 4-methylbenzyl-X4 | benzo[1,3]dioxol-5-ylmethyl-X5 | 2.03 | 467.2573 | 468.3192 |
| 466 | phenyl-X1 | H3C-(CH2)3-X2 | | benzyl-X4 | 2-methylbenzyl-X5 | 2.04 | 423.2675 | 424.3211 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 467 | phenyl-X1 | H3C-(CH2)3-X2 | | 2-methylbenzyl-X4 | 1-naphthylmethyl-X5 | 2.1 | 473.2831 | 474.3467 |
| 468 | phenyl-X1 | H3C-(CH2)3-X2 | | 2-methylbenzyl-X4 | benzo[1,3]dioxol-5-ylmethyl-X5 | 2.02 | 467.2573 | 468.3227 |
| 469 | phenyl-X1 | H3C-(CH2)3-X2 | | 3-fluorobenzyl-X4 | benzo[1,3]dioxol-5-ylmethyl-X5 | 1.99 | 471.2322 | 472.3021 |
| 470 | phenyl-X1 | H3C-(CH2)3-X2 | | 2-phenylethyl-X4 | 4-fluorobenzyl-X5 | 2.02 | 441.258 | 442.3175 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 471 | 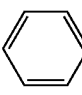 |  |  |  | 1.98 | 471.2322 | 472.3026 |
| 472 |  |  |  |  | 2.03 | 441.258 | 442.3185 |
| 473 | 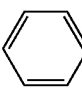 |  |  |  | 2.01 | 427.2424 | 428.3031 |
| 474 |  |  |  |  | 2.07 | 477.258 | 478.3228 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 475 |  |  |  |  | 1.99 | 471.2322 | 472.3008 |
| 476 | 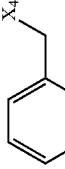 | 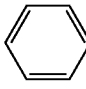 | 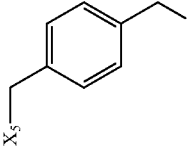 | 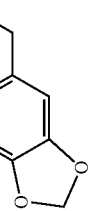 | 2.1 | 451.2987 | 452.3606 |
| 477 | 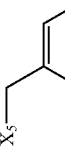 | 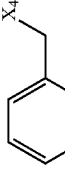 | 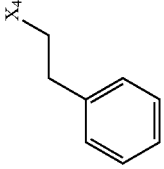 | 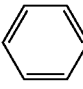 | 2.08 | 437.2831 | 438.351 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 478 | Ph-X1 | H3C-(CH2)3-X2 | | 4-(CH3-CH2)-C6H4-CH2-X4 | 1-naphthyl-CH2-X5 | 2.14 | 487.2987 | 488.3652 |
| 479 | Ph-X1 | H3C-(CH2)3-X2 | | 4-(CH3-CH2)-C6H4-CH2-X4 | benzo[1,3]dioxol-5-yl-CH2-X5 | 2.07 | 481.2729 | 482.3446 |
| 480 | Ph-X1 | H3C-(CH2)3-X2 | | Ph-CH2CH2-X4 | 3,4-dimethylphenyl-CH2-X5 | 2.08 | 451.2987 | 452.3621 |
| 481 | Ph-X1 | H3C-(CH2)3-X2 | | Ph-CH2-X4 | 3,4-dimethylphenyl-CH2-X5 | 2.08 | 437.2831 | 438.346 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 482 |  |  | |  |  | 2.14 | 487.2987 | 488.3646 |
| 483 |  |  | | 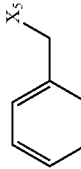 |  | 2.06 | 481.2729 | 482.3413 |
| 484 |  | 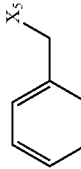 | |  |  | 2.09 | 437.2831 | 438.3447 |
| 485 | 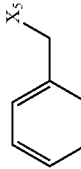 |  | |  |  | 2.07 | 481.2729 | 482.3401 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 486 | phenyl-X1 | H3C-(CH2)3-X2 | | benzyl-CH2-X4 (phenethyl) | 2,3-dimethylphenyl-CH2-X5 | 2.09 | 451.2987 | 452.3614 |
| 487 | phenyl-X1 | H3C-(CH2)3-X2 | | benzyl-X4 | 2,3-dimethylphenyl-CH2-X5 | 2.08 | 437.2831 | 438.3399 |
| 488 | phenyl-X1 | H3C-(CH2)3-X2 | | 2,3-dimethylphenyl-CH2-X4 | benzo[1,3]dioxol-5-yl-CH2-X5 | 2.06 | 481.2729 | 482.3407 |
| 489 | phenyl-X1 | H3C-(CH2)3-X2 | | phenethyl-X4 | 2,5-dimethylphenyl-CH2-X5 | 2.11 | 451.2987 | 452.3647 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 490 |  |  |  |  | 2.09 | 437.2831 | 438.3419 |
| 491 |  |  |  |  | 2.14 | 487.2987 | 488.3654 |
| 492 |  |  |  |  | 2.07 | 481.2729 | 482.3416 |
| 493 |  |  |  |  | 2.1 | 451.2987 | 452.3654 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 494 | phenyl-X1 | H3C-(CH2)4-X2 | benzyl-X4 | 2,4-dimethylphenyl with X5 | 2.09 | 437.2831 | 438.3447 |
| 495 | phenyl-X1 | H3C-(CH2)4-X2 | 2,4-dimethylbenzyl-X4 | naphthalen-1-ylmethyl-X5 | 2.14 | 487.2987 | 488.3656 |
| 496 | phenyl-X1 | H3C-(CH2)4-X2 | 2,4-dimethylbenzyl-X4 | benzo[d][1,3]dioxol-5-ylmethyl-X5 | 2.07 | 481.2729 | 482.3421 |
| 497 | phenyl-X1 | H3C-(CH2)4-X2 | phenethyl-X4 | 3-methoxybenzyl-X5 | 2.02 | 453.278 | 454.3456 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 498 | Ph-X1 | H3C-(CH2)4-X2 | | Bn-X4 | 3-methoxybenzyl-X5 | 2.01 | 439.2624 | 440.3276 |
| 499 | Ph-X1 | H3C-(CH2)4-X2 | | 3-methoxybenzyl-X4 | 1-naphthylmethyl-X5 | 2.06 | 489.278 | 490.3461 |
| 500 | Ph-X1 | H3C-(CH2)4-X2 | | 3-methoxybenzyl-X4 | benzo[1,3]dioxol-5-ylmethyl-X5 | 1.99 | 483.2522 | 484.3252 |
| 501 | Ph-X1 | H3C-(CH2)4-X2 | | phenethyl-X4 | 4-methoxybenzyl-X5 | 2 | 453.278 | 454.3479 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 502 | phenyl-X1 | H3C-(CH2)3-X2 | | benzyl-X4 | 4-methoxybenzyl-X5 | 1.99 | 439.2624 | 440.332 |
| 503 | phenyl-X1 | H3C-(CH2)3-X2 | | 4-methoxybenzyl-X4 | naphthalen-1-ylmethyl-X5 | 2.06 | 489.278 | 490.3477 |
| 504 | phenyl-X1 | H3C-(CH2)3-X2 | | 4-methoxybenzyl-X4 | benzo[1,3]dioxol-5-ylmethyl-X5 | 1.97 | 483.2522 | 484.3253 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 505 |  |  | |  |  | 1.96 | 453.278 | 454.3445 |
| 506 |  |  | |  |  | 1.99 | 439.2624 | 440.3253 |
| 507 |  |  | |  |  | 2.07 | 489.278 | 490.3457 |
| 508 |  |  | |  |  | 1.97 | 483.2522 | 484.3227 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 509 | phenyl-X1 | H3C-(CH2)4-X2 | | phenethyl-X4 | 3-fluoro-4-methylbenzyl-X4 | 2.07 | 455.2737 | 456.3386 |
| 510 | phenyl-X1 | H3C-(CH2)4-X2 | | benzyl-X4 | 3-fluoro-4-methylbenzyl-X4 | 2.06 | 441.258 | 442.3267 |
| 511 | phenyl-X1 | H3C-(CH2)4-X2 | | 3-fluoro-4-methylbenzyl-X4 | naphthalen-1-ylmethyl-X5 | 2.11 | 491.2737 | 492.3441 |
| 512 | phenyl-X1 | H3C-(CH2)4-X2 | | 3-fluoro-4-methylbenzyl-X4 | benzo[d][1,3]dioxol-5-ylmethyl-X5 | 2.04 | 485.2479 | 486.3185 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 513 | phenyl-X1 | H3C-(CH2)3-X2 | | benzyl-X4 | 3-fluoro-2-methylbenzyl-X5 | 2.04 | 441.258 | 442.3253 |
| 514 | phenyl-X1 | H3C-(CH2)3-X2 | | 3-fluoro-2-methylbenzyl-X4 | benzo[1,3]dioxol-5-ylmethyl-X5 | 2.03 | 485.2479 | 486.3174 |
| 515 | phenyl-X1 | H3C-(CH2)3-X2 | | phenethyl-X4 | 4-fluoro-2-methylbenzyl-X5 | 2.05 | 455.2737 | 456.3376 |
| 516 | phenyl-X1 | H3C-(CH2)3-X2 | | benzyl-X4 | 4-fluoro-2-methylbenzyl-X5 | 2.04 | 441.258 | 442.325 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 517 | 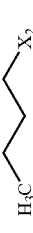 | 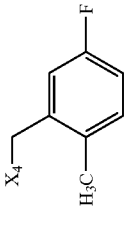 | | 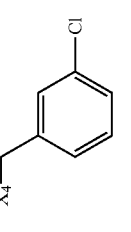 | 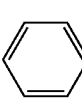 | 2.1 | 491.2737 | 492.3412 |
| 518 | 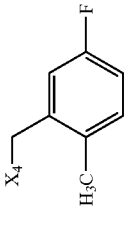 |  | | 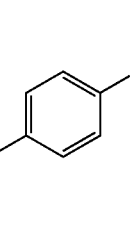 |  | 2.02 | 485.2479 | 486.3193 |
| 519 | 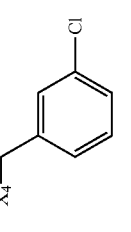 | 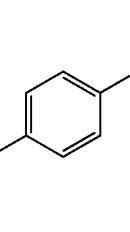 | | 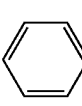 | 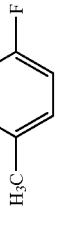 | 2.04 | 487.2027 | 488.2782 |
| 520 |  | 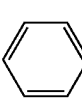 | | 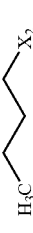 | 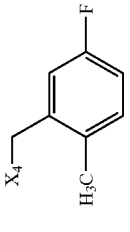 | 2.12 | 493.2285 | 494.3027 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 521 | phenyl-$X_1$ | $H_3C$-(CH$_2$)$_3$-$X_2$ | | 4-chlorobenzyl-$X_4$ | benzo[1,3]dioxol-5-ylmethyl-$X_5$ | 2.04 | 487.2027 | 488.2797 |
| 522 | phenyl-$X_1$ | $H_3C$-(CH$_2$)$_3$-$X_2$ | | phenethyl-$X_4$ | 2-chlorobenzyl-$X_5$ | 2.06 | 457.2285 | 458.2941 |
| 523 | phenyl-$X_1$ | $H_3C$-(CH$_2$)$_3$-$X_2$ | | benzyl-$X_4$ | 2-chlorobenzyl-$X_5$ | 2.04 | 443.2128 | 444.2792 |
| 524 | phenyl-$X_1$ | $H_3C$-(CH$_2$)$_3$-$X_2$ | | 2-chlorobenzyl-$X_4$ | naphthalen-1-ylmethyl-$X_5$ | 2.09 | 493.2285 | 494.3003 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 525 | 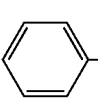 | 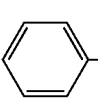 | | 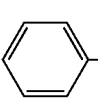 | 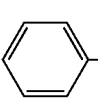 | 2.03 | 487.2027 | 488.278 |
| 526 | 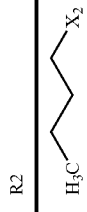 | 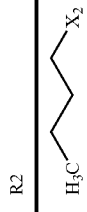 | | 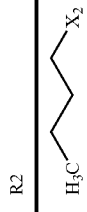 | 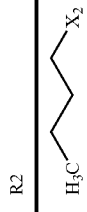 | 2 | 489.2228 | 490.2792 |
| 527 | 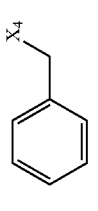 | 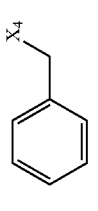 | | 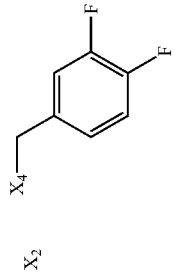 | 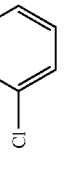 | 2.02 | 445.2329 | 446.2807 |
| 528 | 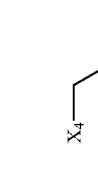 | 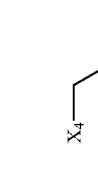 | | 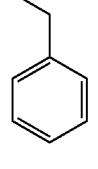 | 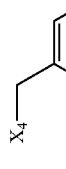 | 2.06 | 495.2486 | 496.2982 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 529 |  |  |  |  | 2 | 489.2228 | 490.2744 |
| 530 |  |  |  |  | 2.01 | 445.2329 | 446.282 |
| 531 |  |  |  |  | 2.07 | 495.2486 | 496.2984 |
| 532 |  |  |  |  | 1.99 | 489.2228 | 490.2794 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 533 | phenyl-X1 | H3C-(CH2)3-X2 | | 2,4-difluorobenzyl-X4 | naphthalen-1-ylmethyl-X5 | 2.08 | 495.2486 | 496.3038 |
| 534 | phenyl-X1 | H3C-(CH2)3-X2 | | 2,4-difluorobenzyl-X4 | benzo[1,3]dioxol-5-ylmethyl-X5 | 2 | 489.2228 | 490.2825 |
| 535 | phenyl-X1 | H3C-(CH2)3-X2 | | phenethyl-X4 | 4-ethylbenzyl-X5 | 2.14 | 465.3144 | 466.3682 |
| 536 | phenyl-X1 | H3C-(CH2)3-X2 | | benzyl-X4 | 4-ethylbenzyl-X5 | 2.13 | 451.2987 | 452.3522 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 537 |  | 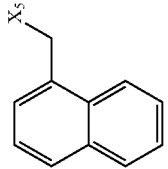 | |  | 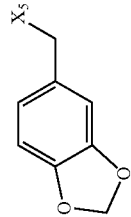 | 2.19 | 501.3144 | 502.3722 |
| 538 |  | 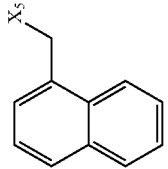 | |  |  | 2.11 | 495.2886 | 496.3486 |
| 539 |  | 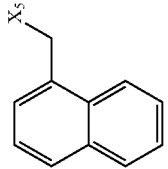 | | 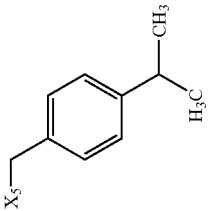 | 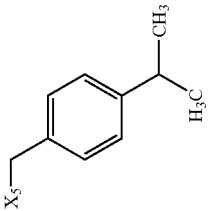 | 2.12 | 451.2987 | 452.3553 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 540 |  |  | |  |  | 2.16 | 501.3144 | 502.3736 |
| 541 |  |  | |  |  | 2.1 | 495.2886 | 496.3533 |
| 542 |  |  | |  |  | 2.05 | 467.2937 | 468.352 |
| 543 |  |  | |  |  | 2.04 | 453.278 | 454.334 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 544 |  |  | |  |  | 2.1 | 503.2937 | 504.355 |
| 545 |  |  | |  |  | 2.02 | 497.2679 | 498.3338 |
| 546 |  |  | |  |  | 2.1 | 503.2937 | 504.3604 |
| 547 |  |  | |  |  | 2.01 | 497.2679 | 498.336 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 548 | phenyl-X1 | H3C-(CH2)3-X2 | | 2-(methoxymethyl)benzyl-X4 | 2-(methoxymethyl)benzyl-X5 | 2.02 | 467.2937 | 468.3528 |
| 549 | phenyl-X1 | H3C-(CH2)3-X2 | | 2-(methoxymethyl)benzyl-X4 | benzo[1,3]dioxol-5-ylmethyl-X5 | 2.01 | 497.2679 | 498.3345 |
| 550 | phenyl-X1 | H3C-(CH2)3-X2 | | phenethyl-X4 | benzo[1,3]dioxol-5-ylmethyl-X5 | 1.99 | 467.2573 | 468.3251 |
| 551 | phenyl-X1 | H3C-(CH2)3-X2 | | benzo[1,3]dioxol-5-ylmethyl-X4 | naphthalen-1-ylmethyl-X5 | 2.05 | 503.2573 | 504.3299 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 552 | phenyl-$X_1$ | $H_3C$-(CH$_2$)$_3$-$X_2$ | | benzodioxole-CH$_2$-$X_4$ | benzodioxole-CH$_2$-$X_5$ | 1.97 | 497.2314 | 498.303 |
| 553 | phenyl-$X_1$ | $H_3C$-(CH$_2$)$_3$-$X_2$ | | PhCH$_2$CH$_2$-$X_4$ | 4-(SCH$_3$)C$_6$H$_4$-CH$_2$-$X_5$ | 2.05 | 469.2552 | 470.3185 |
| 554 | phenyl-$X_1$ | $H_3C$-(CH$_2$)$_3$-$X_2$ | | PhCH$_2$-$X_4$ | 4-(SCH$_3$)C$_6$H$_4$-CH$_2$-$X_5$ | 2.05 | 455.2395 | 456.3164 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 555 | phenyl-X₁ | H₃C-(CH₂)₃-X₂ | | 4-(methylthio)benzyl-X₄ | 1-naphthylmethyl-X₅ | 2.1 | 505.2552 | 506.3273 |
| 556 | phenyl-X₁ | H₃C-(CH₂)₃-X₂ | | 4-(methylthio)benzyl-X₄ | benzo[1,3]dioxol-5-ylmethyl-X₅ | 2.03 | 499.2293 | 500.3005 |
| 557 | phenyl-X₁ | H₃C-(CH₂)₃-X₂ | | phenethyl-X₄ | 3-fluoro-4-methoxybenzyl-X₅ | 1.99 | 471.2686 | 472.3348 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 558 |  | 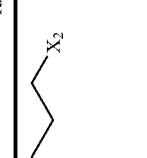 | 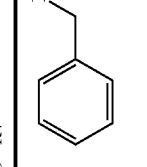 |  | 1.98 | 457.2529 | 458.3177 |
| 559 |  | 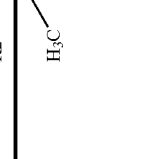 |  |  | 2.05 | 507.2686 | 508.3424 |
| 560 |  |  |  | 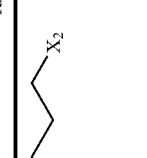 | 1.96 | 501.2428 | 502.3192 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 561 | phenyl-X1 | H3C-(CH2)3-X2 | | benzyl-X4 | 4-chloro-3-methylbenzyl-X5 | 2.1 | 457.2285 | 458.2933 |
| 562 | phenyl-X1 | H3C-(CH2)3-X2 | | 4-chloro-3-methylbenzyl-X4 | naphthalen-1-ylmethyl-X5 | 2.14 | 507.2441 | 508.3201 |
| 563 | phenyl-X1 | H3C-(CH2)3-X2 | | 4-chloro-3-methylbenzyl-X4 | benzo[1,3]dioxol-5-ylmethyl-X5 | 2.08 | 501.2183 | 502.2952 |
| 564 | phenyl-X1 | H3C-(CH2)3-X2 | | 3-chloro-4-fluorobenzyl-X4 | benzo[1,3]dioxol-5-ylmethyl-X5 | 2.04 | 505.1932 | 506.2737 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 565 | phenyl-X1 | H3C-(CH2)3-X2 | benzyl-X4 | 4-butylbenzyl-X5 | 2.17 | 465.3144 | 466.3809 |
| 566 | phenyl-X1 | H3C-(CH2)3-X2 | 4-propylbenzyl-X4 | benzo[1,3]dioxol-5-ylmethyl-X5 | 2.15 | 509.3042 | 510.3789 |
| 567 | phenyl-X1 | H3C-(CH2)3-X2 | phenethyl-X4 | 4-(2-methylpropan-2-yl)benzyl-X5 | 2.15 | 479.33 | 480.3981 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 568 | phenyl-$X_1$ | $H_3C$–(CH$_2$)$_3$–$X_2$ | | benzyl-$X_4$ | 4-(2-methylpropan-2-yl)benzyl-$X_5$ | 2.14 | 465.3144 | 466.3795 |
| 569 | phenyl-$X_1$ | $H_3C$–(CH$_2$)$_3$–$X_2$ | | 4-(2-methylpropan-2-yl)benzyl-$X_4$ | benzo[1,3]dioxol-5-ylmethyl-$X_5$ | 2.13 | 509.3042 | 510.383 |
| 570 | phenyl-$X_1$ | $H_3C$–(CH$_2$)$_3$–$X_2$ | | 4-propoxybenzyl-$X_4$ | benzo[1,3]dioxol-5-ylmethyl-$X_5$ | 2.06 | 511.2835 | 512.3632 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 571 | Ph-X1 | H3C-(CH2)3-X2 | X4-CH2-Ph | X5-CH2-C6H4-O-CH(CH3)2 | 2.06 | 467.2937 | 468.3609 |
| 572 | Ph-X1 | H3C-(CH2)3-X2 | X4-CH2-C6H4-O-CH(CH3)2 | X5-CH2-naphthyl | 2.12 | 517.3093 | 518.3871 |
| 573 | Ph-X1 | H3C-(CH2)3-X2 | X4-CH2-C6H4-O-CH(CH3)2 | X5-CH2-(benzo[1,3]dioxole) | 2.04 | 511.2835 | 512.3613 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 574 | 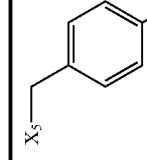 | 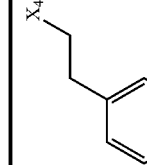 | 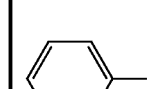 |  | 2.1 | 483.2708 | 484.3423 |
| 575 | 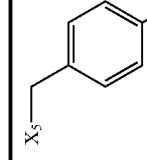 | 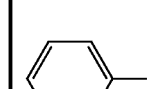 |  | 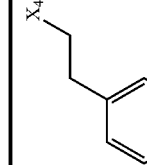 | 2.08 | 469.2552 | 470.3222 |
| 576 | 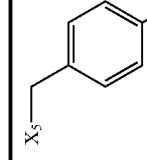 |  |  | 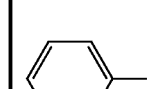 | 2.13 | 519.2708 | 520.3477 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 577 | phenyl-X1 | H3C-(CH2)3-X2 | 4-(ethylthio)benzyl-X4 | benzo[1,3]dioxol-5-ylmethyl-X5 | 2.06 | 513.245 | 514.3214 |
| 578 | phenyl-X1 | H3C-(CH2)3-X2 | benzyl-X4 | 2,3,5-trifluorobenzyl-X5 | 2.02 | 481.2141 | 482.2788 |
| 579 | phenyl-X1 | H3C-(CH2)3-X2 | benzo[1,3]dioxol-5-ylmethyl-X4 | 2,3,5-trifluorobenzyl-X5 | 2 | 525.2039 | 526.2794 |
| 580 | phenyl-X1 | H3C-(CH2)3-X2 | 2,3-difluorobenzyl-X4 | naphthalen-1-ylmethyl-X5 | 2.08 | 513.2392 | 514.3017 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 581 | phenyl-X1 | H3C-X2 (butyl) | | benzodioxole-X4 | 2,3,5,6-tetrafluorobenzyl-X4 | 2 | 507.2133 | 508.2841 |
| 582 | phenyl-X1 | H3C-X2 (butyl) | | 2,3-difluorobenzyl-X4 | naphthyl-X5 | 2.06 | 513.2392 | 514.3171 |
| 583 | phenyl-X1 | H3C-X2 (butyl) | | benzodioxole-X4 | 2,3-difluorobenzyl-X4 | 1.98 | 507.2133 | 508.2843 |
| 584 | phenyl-X1 | H3C-X2 (butyl) | | benzyl-X4 | 2-chloro-6-fluorobenzyl-X5 | 2.03 | 461.2034 | 462.2718 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 585 | phenyl-X1 | H3C-X2 (butyl) | | 2-Cl-6-F-benzyl-X4 | 1-naphthylmethyl-X5 | 2.08 | 611.2101 | 612.2986 |
| 586 | phenyl-X1 | H3C-X2 (butyl) | | benzo[1,3]dioxol-5-ylmethyl-X4 | 2-Cl-6-F-benzyl-X5 | 2.01 | 505.1932 | 506.2769 |
| 587 | phenyl-X1 | H3C-X2 (butyl) | | 2,6-dichlorobenzyl-X4 | 1-naphthylmethyl-X5 | 2.17 | 561.1505 | 562.2524 |
| 588 | phenyl-X1 | H3C-X2 (butyl) | | 2-(2,4-dimethoxyphenyl)ethyl-X4 | benzo[1,3]dioxol-5-ylmethyl-X5 | 1.99 | 527.2784 | 528.3599 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 589 | phenyl-X1 | H3C-(CH2)3-X2 | | 2,6-difluorophenethyl-X4 | benzyl-X5 | 2.02 | 459.2486 | 460.326 |
| 590 | phenyl-X1 | H3C-(CH2)3-X2 | | 2,6-difluorophenethyl-X4 | (benzo[1,3]dioxol-5-yl)methyl-X5 | 2.01 | 503.2384 | 504.3166 |
| 591 | phenyl-X1 | H3C-(CH2)3-X2 | | 4-(methylthio)phenethyl-X4 | benzyl-X5 | 2.06 | 469.2552 | 470.3206 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 592 | 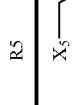 | 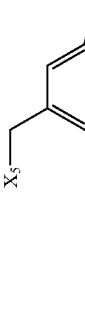 |  | 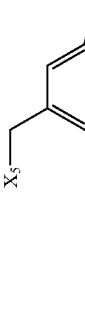 | 2.03 | 513.245 | 514.321 |
| 593 |  | 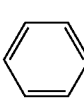 | 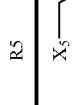 |  | 2 | 467.2573 | 468.3217 |
| 594 | 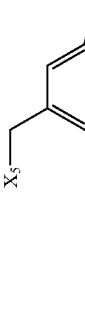 |  |  | 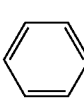 | 1.97 | 511.2471 | 512.3246 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 595 | phenyl-$X_1$ | $H_3C$-(CH$_2$)$_3$-$X_2$ | | benzo[1,3]dioxol-5-ylmethyl-$X_4$ | 4-chloro-3-(methylthio)benzyl-$X_5$ | 2.07 | 533.1904 | 534.271 |
| 596 | phenyl-$X_1$ | $H_3C$-(CH$_2$)$_3$-$X_2$ | | benzyl-$X_4$ | 4-bromo-3-methylbenzyl-$X_5$ | 2.09 | 501.1779 | 502.2356 |
| 597 | phenyl-$X_1$ | $H_3C$-(CH$_2$)$_3$-$X_2$ | | 4-bromo-3-methylbenzyl-$X_4$ | benzo[1,3]dioxol-5-ylmethyl-$X_5$ | 2.08 | 545.1678 | 546.2542 |
| 598 | phenyl-$X_1$ | $H_3C$-(CH$_2$)$_3$-$X_2$ | | 4-chloro-4,5-dimethoxybenzyl-$X_4$ | naphth-1-ylmethyl-$X_5$ | 2.04 | 553.2496 | 554.1792 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 599 | phenyl-X1 | H3C-(CH2)3-X2 | | 2-Br-3-CH3-benzyl-X4 | benzo[1,3]dioxol-5-ylmethyl-X5 | 2.07 | 545.1678 | 546.1213 |
| 600 | phenyl-X1 | H3C-(CH2)3-X2 | | 4-Cl-3-CF3-benzyl-X4 | benzo[1,3]dioxol-5-ylmethyl-X5 | 2.05 | 555.1901 | 556.1432 |
| 601 | phenyl-X1 | H3C-(CH2)3-X2 | | 2-Br-4,5-dimethoxy-benzyl-X4 | naphth-1-ylmethyl-X5 | 2.05 | 597.1991 | 598.16 |
| 602 | phenyl-X1 | H3C-(CH2)3-X2 | | benzyl-X4 | 2-(methylthio)benzyl-X5 | 2.04 | 455.2395 | 456.2075 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 603 | 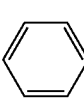 |  |  | 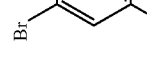 | 2.01 | 499.2293 | 500.2002 |
| 604 | 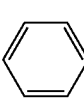 |  | 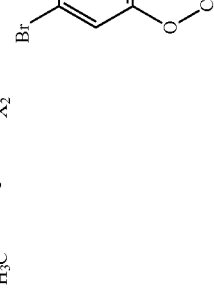 |  | 1.99 | 605.1889 | 606.17 |
| 605 | 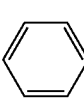 |  | 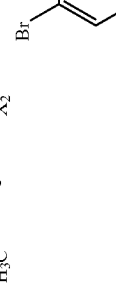 |  | 2.06 | 575.1783 | 576.16 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 606 | phenyl-X1 | H3C-(CH2)3-X2 | | X4-CH2CH2-(4-benzyloxyphenyl) | X5-CH2-(benzo[1,3]dioxol-5-yl) | 2.09 | 573.2991 | 574.2837 |
| 607 | phenyl-X1 | H3C-(CH2)3-X2 | | X4-CH2CH2-(2,3-dimethoxyphenyl) | X5-CH2-(benzo[1,3]dioxol-5-yl) | 1.97 | 527.2784 | 528.259 |
| 608 | phenyl-X1 | H3C-(CH2)3-X2 | | X4-CH2CH2-(2,3-difluorophenyl) | X5-CH2-(benzo[1,3]dioxol-5-yl) | 2 | 503.2384 | 504.2233 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 609 | 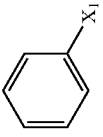 |  |  | 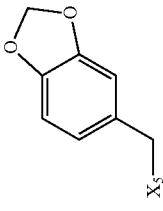 | 2.1 | 559.2835 | 560.2635 |
| 610 | 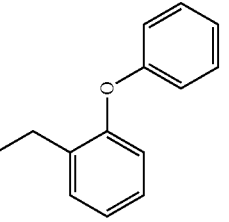 | 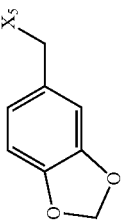 | 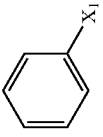 | 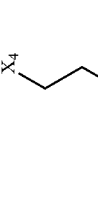 | 2.1 | 593.1539 | 594.1388 |
| 611 | 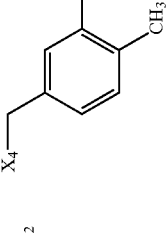 | 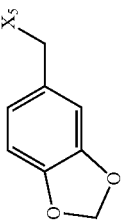 | 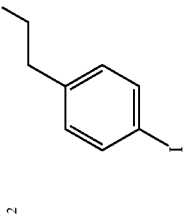 | 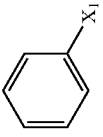 | 2.07 | 593.1539 | 594.146 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 612 | phenyl-X1 | H3C-(CH2)3-X2 | | phenethyl-X4 | benzo[1,3]dioxol-5-ylmethyl-X5 | 1.99 | 467.2573 | 468.2505 |
| 613 | phenyl-X1 | H3C-(CH2)3-X2 | | 5-methylthiophen-2-ylmethyl-X4 | benzo[1,3]dioxol-5-ylmethyl-X5 | 2.02 | 473.2137 | 474.2052 |
| 614 | phenyl-X1 | H3C-(CH2)3-X2 | | 4-methylphenethyl-X4 | benzo[1,3]dioxol-5-ylmethyl-X5 | 2.03 | 481.2729 | 482.2651 |
| 615 | phenyl-X1 | H3C-(CH2)3-X2 | | 2-methylphenethyl-X4 | benzo[1,3]dioxol-5-ylmethyl-X5 | 2.03 | 481.2729 | 482.2703 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 616 | phenyl-X1 | H3C-...-X2 (butyl) | | H3C-CH(Ph)-CH2-X4 | benzyl-X5 | 2.05 | 437.2831 | 438.2783 |
| 617 | phenyl-X1 | CH3-...-X2 | | X4-CH2-CH(CH3)-Ph | benzo[1,3]dioxol-5-ylmethyl-X5 | 2.03 | 481.2729 | 482.2692 |
| 618 | phenyl-X1 | H3C-...-X2 | | X4-CH2-CH2-O-Ph | benzo[1,3]dioxol-5-ylmethyl-X5 | 1.98 | 483.2522 | 484.2532 |
| 619 | phenyl-X1 | H3C-...-X2 | | X4-CH2-CH2-(2-F-Ph) | benzo[1,3]dioxol-5-ylmethyl-X5 | 2 | 485.2479 | 486.2474 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 620 | phenyl-$X_1$ | $H_3C$-(CH$_2$)$_3$-$X_2$ | $X_4$-CH$_2$-phenyl | $H_3C$-CH($X_5$-CH$_2$)-phenyl | 2.08 | 451.2987 | 452.2939 |
| 621 | phenyl-$X_1$ | CH$_3$-CH(-(CH$_2$)$_2$-$X_2$) | $X_4$-CH$_2$-CH(CH$_3$)-CH$_2$-phenyl | benzo[1,3]dioxol-5-yl-CH$_2$-$X_5$ | 2.07 | 495.2886 | 496.2867 |
| 622 | phenyl-$X_1$ | $H_3C$-(CH$_2$)$_3$-$X_2$ | $X_4$-CH$_2$-CH(CH$_3$)-(2-CH$_3$-phenyl) | $X_5$-CH$_2$-phenyl | 2.08 | 451.2987 | 452.2961 |
| 623 | phenyl-$X_1$ | CH$_3$-CH(-(CH$_2$)$_2$-$X_2$) | $X_4$-CH$_2$-CH(CH$_3$)-(2-CH$_3$-phenyl) | benzo[1,3]dioxol-5-yl-CH$_2$-$X_5$ | | | |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 624 |  |  | |  |  | | | |
| 625 |  |  | |  |  | 1.99 | 497.2679 | 498.2035 |
| 626 |  |  | |  |  | 2.02 | 497.2479 | 498.1985 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 627 |  |  | |  |  | 2.02 | 511.2835 | 512.236 |
| 628 |  |  | |  |  | 2.04 | 511.2835 | 512.2421 |
| 629 |  |  | |  |  | 2.03 | 497.2679 | 498.2339 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 630 | phenyl-X1 | H3C-(CH2)3-X2 | 3-methoxyphenoxyethyl-X4 | benzo[1,3]dioxol-5-ylmethyl-X5 | 1.98 | 513.2628 | 514.2338 |
| 631 | phenyl-X1 | H3C-(CH2)3-X2 | (Z)-3-(2,5-dimethoxyphenyl)allyl-X4 | naphthalen-1-ylmethyl-X5 | 2.11 | 545.3042 | 546.2813 |
| 632 | phenyl-X1 | H3C-(CH2)3-X2 | (Z)-3-(2,5-dimethoxyphenyl)allyl-X4 | benzo[1,3]dioxol-5-ylmethyl-X5 | 1.99 | 539.2784 | 540.2627 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 633 |  |  |  |  | 2.01 | 509.3042 | 510.2987 |
| 634 |  |  |  |  | 2.11 | 545.3042 | 546.2994 |
| 635 |  |  |  |  | 2.01 | 539.2784 | 540.2756 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 636 | phenyl-X1 | H3C-(CH2)3-X2 | | 3-(trifluoromethyl)phenyl-CH=CH-CH2-X4 | benzo[1,3]dioxol-5-yl-CH2-X5 | 2.06 | 547.2447 | 548.2516 |
| 637 | phenyl-X1 | H3C-(CH2)3-X2 | | 2,6-dichlorophenyl-CH=CH-CH2-X4 | benzo[1,3]dioxol-5-yl-CH2-X5 | | | |
| 638 | 3,5-dimethoxyphenyl-CH=CH-CH2-X4 (with X1) | benzo[1,3]dioxol-5-yl-CH2-X2 | | 3-bromophenyl-CH=CH-CH2-X4 | phenyl-CH2-CH2-X5 | 2.09 | 527.1936 | 528.22 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 639 | 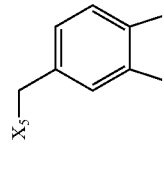 |  | |  |  | 1.99 | 441.2239 | 442.2316 |
| 640 |  |  | |  |  | | | |
| 641 |  | 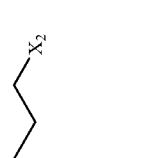 | |  |  | 2.09 | 491.2395 | 492.2484 |
| 642 |  | 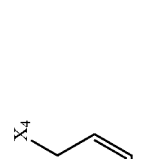 | |  |  | 1.97 | 485.2137 | 486.2251 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 643 | phenyl-X1 | H3C-(CH2)3-X2 | | furan-CH=CH-CH2-X4 | naphthyl-CH2-X5 | 2.07 | 475.2624 | 476.2701 |
| 644 | phenyl-X1 | H3C-(CH2)3-X2 | | furan-CH=CH-CH2-X4 | benzo[1,3]dioxol-CH2-X5 | 1.95 | 469.2365 | 470.2487 |
| 645 | phenyl-X1 | H3C-(CH2)3-X2 | | 4-(1-methylethyl)phenyl-CH=CH-CH2-X4 | benzo[1,3]dioxol-CH2-X5 | 2.11 | 521.3042 | 522.3236 |

TABLE 1A-continued

| CMP # | R1 | R2 | R3 R4 | R5 | Rtn Time | Cmd Mass | H+ Ion Obs |
|---|---|---|---|---|---|---|---|
| 646 | phenyl-X1 | H3C-(CH2)3-X2 | phenethyl-X4 | phenyl-cyclopropyl-CH2-X5 | 2.01 | 463.2987 | 464.304 |
| 647 | phenyl-X1 | H3C-(CH2)3-X2 | benzyl-X4 | phenyl-cyclopropyl-CH2-X5 | 2.02 | 449.2831 | 450.2887 |
| 648 | phenyl-X1 | H3C-(CH2)3-X2 | benzo[d][1,3]dioxol-5-ylmethyl-X4 | phenyl-cyclopropyl-CH2-X5 | 1.99 | 493.2729 | 494.2809 |
| 649 | phenyl-X1 | H3C-(CH2)3-X2 | (E)-2-fluoro-3-phenylallyl-X4 | benzyl-X5 | 2.06 | 453.258 | 454.2635 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 650 |  |  |  |  | 2.11 | 503.2737 | 504.279 |
| 651 |  |  |  |  | 2.05 | 497.2479 | 498.2578 |
| 652 |  |  |  |  | 2.05 | 457.2285 | 458.2423 |
| 653 |  |  |  |  | 2.03 | 501.2183 | 502.2353 |

TABLE 1A-continued
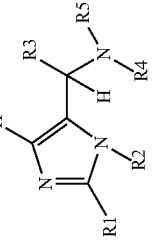
R3 is H unless otherwise specified
| CMP # | R1 | R2 | R3 | R4 | R5 | Rtn Time | Cmd Mass | H+ Ion Obs |
|---|---|---|---|---|---|---|---|---|
| 654 | | | | | | 2.13 | 465.3144 | 466.33 |
| 655 | | | | | | 2.1 | 509.3042 | 510.315 |
| 656 | | | | | | 2.04 | 467.2937 | 468.3029 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 657 |  |  | 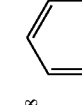 | 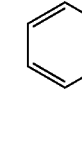 | 2.02 | 511.2835 | 512.2963 |
| 658 | 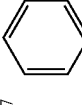 | 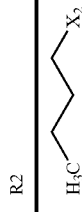 |  |  | 2.06 | 467.2937 | 468.3049 |
| 659 | 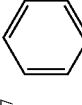 | 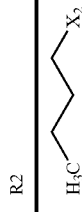 | 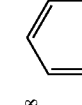 | 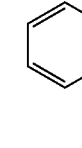 | 2.04 | 511.2835 | 512.2961 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 660 | Ph-X1 | H3C-(CH2)3-X2 | | X4-CH2-Ph | H3C-CH2-CH(Ar(4-OMe))-CH2-X5 | 2.07 | 481.3093 | 482.3199 |
| 661 | Ph-X1 | X2-(CH2)3-CH3 | | X4-CH2-CH(Ar(4-OMe))-CH2-CH3 | benzo[1,3]dioxol-5-yl-CH2-X5 | 2.05 | 525.2991 | 526.3086 |
| 662 | Ph-X1 | H3C-(CH2)3-X2 | | X4-CH2-CH2-(2,5-dimethoxyphenyl) | X5-CH2-Ph | 2.01 | 483.2886 | 484.3015 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 663 | 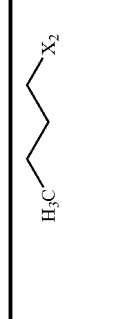 |  |  | 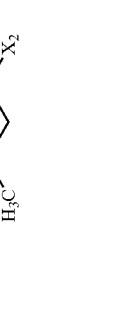 | 1.98 | 527.2784 | 528.3032 |
| 664 | 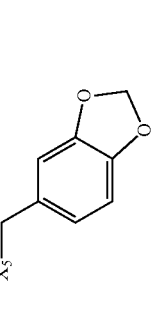 | 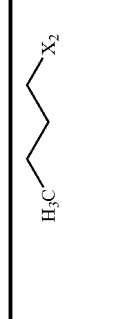 |  |  | 2.03 | 535.2447 | 536.2623 |
| 665 | 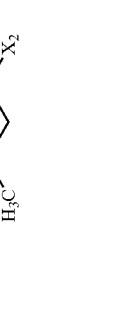 | 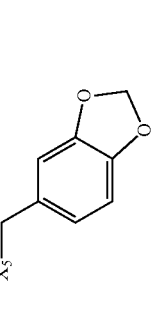 | 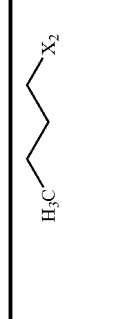 |  | 2.16 | 535.3199 | 536.342 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 666 | 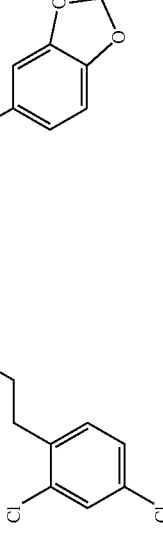 | 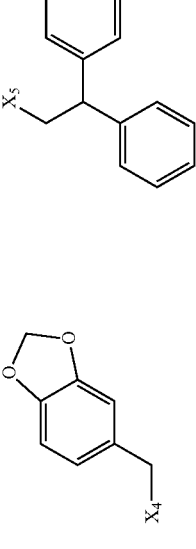 | |  | 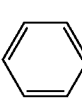 | | | |
| 667 | 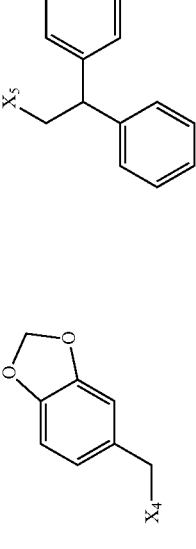 |  | |  | 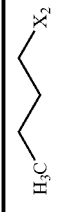 | 2.07 | 543.2886 | 544.3081 |
| 668 | 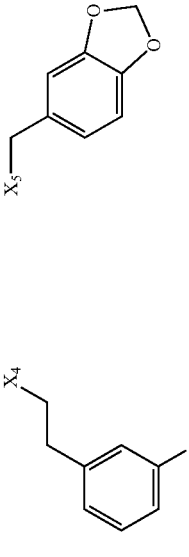 |  | | 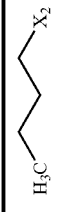 | 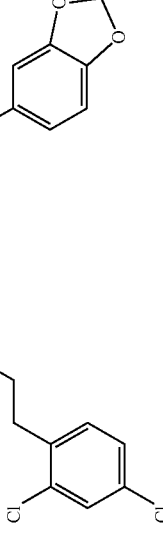 | | | |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 669 |  |  | |  |  | | | |
| 670 |  | 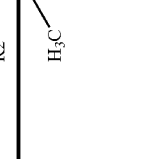 | |  | 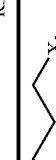 | | | |
| 671 |  |  | |  | 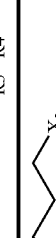 | 2.19 | 549.3355 | 550.3612 |

TABLE 1A-continued

| CMP # | R1 | R2 | R3 | R4 | R5 | Rtn Time | Cmd Mass | H+ Ion Obs |
|---|---|---|---|---|---|---|---|---|
| 672 | phenyl-X1 | CH3-(CH2)3-X2 | | benzo[1,3]dioxol-5-ylmethyl-X4 | 2,3-dimethoxybenzyl-X5 | 1.95 | 513.2628 | 514.2707 |
| 673 | phenyl-X1 | CH3-(CH2)3-X2 | | benzo[1,3]dioxol-5-ylmethyl-X4 | 2,3-dimethoxybenzyl-X5 | 1.96 | 513.2628 | 514.2808 |
| 674 | phenyl-X1 | CH3-(CH2)3-X2 | | benzo[1,3]dioxol-5-ylmethyl-X4 | 2,5-dimethoxybenzyl-X5 | | | |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 675 | phenyl-X1 | CH3-(CH2)3-X2 | | benzodioxole-CH2-X4 | 2-OCH3, 5-OCH3 benzyl-X5 | | | |
| 676 | phenyl-X1 | CH3-(CH2)3-X2 | | benzodioxole-CH2-X4 | 4-Cl, 2-OCH3 benzyl-X5 | 2.03 | 517.2132 | 518.2341 |
| 677 | phenyl-X1 | CH3-(CH2)3-X2 | | benzodioxole-CH2-X4 | 4-Cl, 2-OCH3 benzyl-X5 | | | |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 678 | phenyl-X1 | CH3-CH(CH3)-...-X2 | benzyl-X4 | 2-Br-4-CH3-benzyl-X5 | 2.09 | 501.1779 | 502.2102 |
| 679 | phenyl-X1 | CH3-CH(CH3)-...-X2 | benzyl-X4 | 2-Br-4-CH3-benzyl-X5 | | | |
| 680 | phenyl-X1 | CH3-CH(CH3)-...-X2 | phenethyl-X4 | 2-Br-4-CH3-benzyl-X5 | 2.11 | 515.1936 | 516.229 |
| 681 | phenyl-X1 | CH3-CH(CH3)-...-X2 | phenethyl-X4 | 2-Br-4-CH3-benzyl-X5 | | | |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 682 | 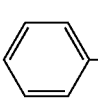 | 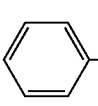 | | 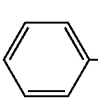 | 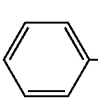 | 2.15 | 551.1936 | 552.23 |
| 683 |  |  | |  |  | | | |
| 684 |  |  | |  |  | 2.08 | 545.1678 | 546.202 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 685 |  | 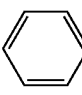 | |  | 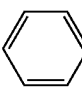 | | | |
| 686 |  | 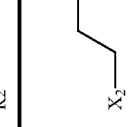 | |  | 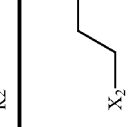 | | | |
| 687 |  |  | |  |  | | | |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 688 | 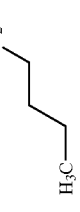 |  | | 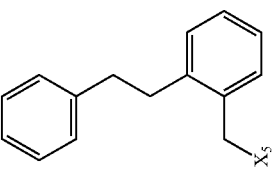 | 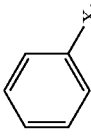 | 2.13 | 557.3042 | 558.3334 |
| 689 |  | 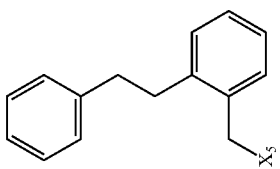 | | 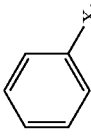 | 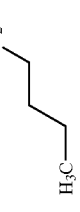 | | | |
| 690 | 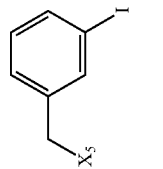 | 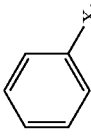 | | 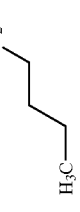 |  | 2.07 | 535.1484 | 536.1722 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 691 | phenyl-X1 | (CH3)CH-CH2CH2-X2 | | benzyl-X4 | 3-iodobenzyl-X5 | | | |
| 692 | phenyl-X1 | (CH3)CH-CH2CH2-X2 | | 3-iodobenzyl-X4 | (benzo[1,3]dioxol-5-yl)methyl-X5 | 2.06 | 579.1383 | 580.1661 |
| 693 | phenyl-X1 | (CH3)CH-CH2CH2-X2 | | 3-iodobenzyl-X4 | (benzo[1,3]dioxol-5-yl)methyl-X5 | | | |
| 694 | phenyl-X1 | (CH3)CH-CH2CH2-X2 | | benzyl-X4 | 4-iodobenzyl-X5 | 2.07 | 535.1484 | 536.1789 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 695 | phenyl-X1 | (CH3)CH-(CH2)3-X2 | | X4-benzyl | 4-iodobenzyl-X5 | | | |
| 696 | phenyl-X1 | (CH3)CH-(CH2)3-X2 | | 4-iodobenzyl-X4 | X5-CH2-benzo[1,3]dioxole | 2.05 | 579.1383 | 580.1685 |
| 697 | phenyl-X1 | (CH3)CH-(CH2)3-X2 | | 4-iodobenzyl-X4 | X5-CH2-benzo[1,3]dioxole | | | |

TABLE 1A-continued
| CMP # | R1 | R2 | R3 R4 | R5 | Rtn Time | Cmd Mass | H+ Ion Obs |
|---|---|---|---|---|---|---|---|
| 698 |  |  |  |  | 2.04 | 579.1383 | 580.1639 |
| 699 |  |  |  |  | | | |
| 700 |  |  |  |  | | | |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 701 | phenyl-X1 | X2-(CH2)3-CH3 | | 5-bromo-2-fluorophenyl-CH=CH-CH2-X4 | benzo[1,3]dioxol-5-yl-CH2-X5 | | | |
| 702 | phenyl-X1 | X2-(CH2)3-CH3 | | 4-bromo-2-fluorophenyl-CH=CH-CH2-X4 | benzo[1,3]dioxol-5-yl-CH2-X5 | | | |
| 703 | phenyl-X1 | X2-(CH2)3-CH3 | | 4-bromo-2-fluorophenyl-CH=CH-CH2-X4 | benzo[1,3]dioxol-5-yl-CH2-X5 | | | |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 704 | 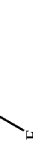 | 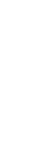 CH₃ | | 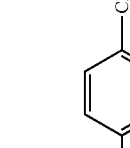 | 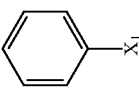 | 2.08 | 531.2089 | 532.2461 |
| 705 | 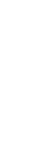 |  CH₃ | | 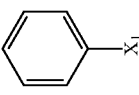 |  | 2.07 | 531.2089 | 532.2447 |
| 706 | 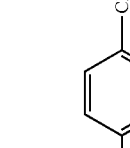 | 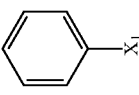 | | 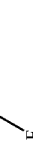 | 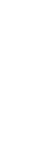 | | | |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 707 | 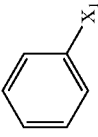 | 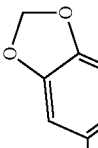 | | 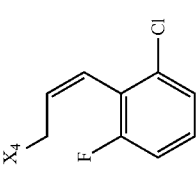 | 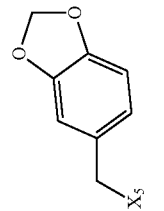 | | | |
| 708 | 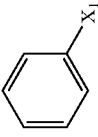 | 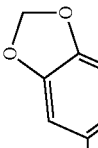 | | 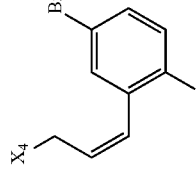 | 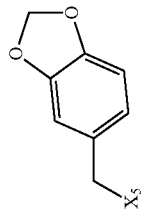 | 2.12 | 601.194 | 602.24 |
| 709 | 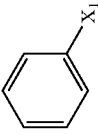 | 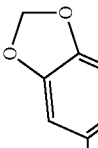 | | 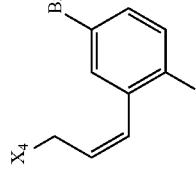 | 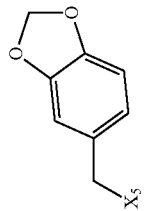 | | | |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 710 | 4-F-phenyl-X1 | H3C-(CH2)3-X2 | | H3C-(CH2)2-CH2-X4 | benzo[1,3]dioxol-5-ylmethyl-X5 | 1.84 | 437.2479 | 438.2715 |
| 711 | 4-F-phenyl-X1 | H3C-(CH2)3-X2 | | (H3C)2CH-CH2-X4 | benzo[1,3]dioxol-5-ylmethyl-X5 | 1.97 | 437.2479 | 438.2693 |
| 712 | 4-F-phenyl-X1 | H3C-(CH2)3-X2 | | cyclobutyl-CH2-X4 | benzo[1,3]dioxol-5-ylmethyl-X5 | 1.9 | 449.2479 | 450.2746 |
| 713 | 4-F-phenyl-X1 | H3C-(CH2)3-X2 | | H3C-(CH2)3-CH2-X4 | benzo[1,3]dioxol-5-ylmethyl-X5 | 1.91 | 451.2635 | 452.2936 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 714 | 4-F-C6H4-X1 | H3C-(CH2)3-X2 | CH3-CH(OH)-CH2-CH2-X4 (H3C-CH-CH2-CH2-X4 with OH) | piperonyl (X5-CH2-benzo[1,3]dioxole) | 1.91 | 451.2635 | 452.2922 |
| 715 | 4-F-C6H4-X1 | H3C-(CH2)3-X2 | (CH3)2C(CH3)-CH2-X4 (neopentyl) | piperonyl | 2.02 | 451.2635 | 452.2937 |
| 716 | 4-F-C6H4-X1 | H3C-(CH2)3-X2 | cyclopentyl-CH2-X4 | piperonyl | 2 | 463.2635 | 464.2918 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 717 | 4-F-C6H4-X1 | H3C-(CH2)3-X2 | | X4-(CH2)5-CH3 | piperonyl-X5 | 1.98 | 465.2791 | 466.3056 |
| 718 | 4-F-C6H4-X1 | CH3-(CH2)3-X2 | | X4-(CH2)3-CH(CH3)- | piperonyl-X5 | 1.97 | 465.2791 | 466.3057 |
| 719 | 4-F-C6H4-X1 | H3C-(CH2)3-X2 | | X4-(CH2)2-C(CH3)2- | piperonyl-X5 | 1.94 | 465.2791 | 466.3067 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 720 | 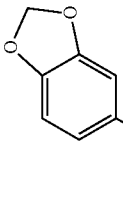 | 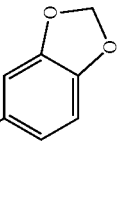 | |  |  | 2.05 | 465.2791 | 466.31 |
| 721 |  |  | |  |  | 2.06 | 465.2791 | 466.309 |
| 722 | | | | | | 1.99 | 477.2791 | 478.3101 |
| 723 | | | | | | 2.06 | 477.2791 | 478.3092 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 724 | 4-F-C6H4-X1 | H3C-(CH2)3-X2 | | H3C-(CH2)5-X4 | piperonyl-X5 | 2.03 | 479.2948 | 480.3289 |
| 725 | 4-F-C6H4-X1 | H3C-(CH2)3-X2 | | cyclohexyl-CH2CH2-X4 | piperonyl-X5 | 2.03 | 491.2948 | 492.327 |
| 726 | 4-F-C6H4-X1 | H3C-(CH2)3-X2 | | cycloheptyl-CH2-X4 | piperonyl-CH2-X5 | 2.1 | 491.2948 | 492.3293 |

TABLE 1A-continued

| CMP # | R1 | R2 | R3 | R4 | R5 | Rtn Time | Cmd Mass | H+ Ion Obs |
|---|---|---|---|---|---|---|---|---|
| 727 | 4-F-C6H4 | H3C-(CH2)3-X2 | | 3-cyclopentylpropyl-X4 | piperonyl-X5 | 2.04 | 491.2948 | 492.3288 |
| 728 | 4-F-C6H4 | H3C-(CH2)3-X2 | | n-octyl-X4 | piperonyl-X5 | 2.08 | 493.3105 | 494.3472 |
| 729 | 3-F-C6H4 | CH3-(CH2)3-X2 | | 2-methyl-2-(methyl)propyl-X4 | piperonyl-X5 | 2.06 | 465.2791 | 466.3023 |
| 730 | 3-F-C6H4 | H3C-(CH2)3-X2 | | 2,2-bis(methyl)propyl-X4 | piperonyl-X5 | 2.08 | 465.2791 | 466.3028 |

R3 is H unless otherwise specified

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 731 | 3-F-phenyl-X1 | H3C-(CH2)3-X2 | | 2-cyclopentylethyl-X4 | benzo[1,3]dioxol-5-ylmethyl-X5 | 1.99 | 477.2791 | 478.3062 |
| 732 | 3-F-phenyl-X1 | H3C-(CH2)3-X2 | | cyclohexylmethyl-X4 | benzo[1,3]dioxol-5-ylmethyl-X5 | 2.07 | 477.2791 | 478.3031 |
| 733 | 3-F-phenyl-X1 | H3C-(CH2)3-X2 | | H3C-(CH2)6-X4 | benzo[1,3]dioxol-5-ylmethyl-X5 | 2.04 | 479.2948 | 480.323 |
| 734 | 4-F-phenyl-X1 | H3C-(CH2)3-X2 | | benzyl-X4 | benzo[1,3]dioxol-5-ylmethyl-X5 | 1.99 | 471.2322 | 472.2518 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 735 | 4-F-C6H4-X1 | H3C-(CH2)3-X2 | 3-CH3-C6H4-CH2-X4 | benzo[1,3]dioxol-5-yl-CH2-X5 | 2.03 | 485.2479 | 486.2677 |
| 736 | 4-F-C6H4-X1 | H3C-(CH2)3-X2 | 4-CH3-C6H4-CH2-X4 | benzo[1,3]dioxol-5-yl-CH2-X5 | 2.05 | 485.2479 | 486.2654 |
| 737 | 4-F-C6H4-X1 | H3C-(CH2)3-X2 | cyclohexyl-CH2-X4 | 4-CH3-C6H4-CH2-X5 | 2.12 | 447.305 | 448.3199 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 738 | 4-F-C6H4-X1 | H3C-(CH2)4-X2 | | 2-F-benzyl-X4 | benzo[1,3]dioxole-CH2-X5 | 1.99 | 489.2228 | 490.2399 |
| 739 | 4-F-C6H4-X1 | H3C-(CH2)4-X2 | | CH3-CH(CH3)-CH2-CH2-X4 | 3,4-dimethylbenzyl | | | |
| 740 | 4-F-C6H4-X1 | H3C-(CH2)4-X2 | | 3,4-dimethylbenzyl-X5 | benzo[1,3]dioxole-CH2-X5 | 2.05 | 499.2635 | 500.2832 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 741 | 4-F-C6H4-X1 | H3C-(CH2)3-X2 | | cyclohexyl-CH2- | 3,4-dimethylphenyl-CH2-X5 | 2.14 | 461.3206 | 462.3372 |
| 742 | 4-F-C6H4-X1 | H3C-(CH2)3-X2 | | 2,3-dimethylphenyl-CH2-X2 | benzo[1,3]dioxol-5-yl-CH2 | 2.04 | 499.2635 | 500.2898 |
| 743 | 4-F-C6H4-X1 | H3C-(CH2)3-X2 | | CH3CH(OH)CH2CH2-X4 | benzo[1,3]dioxol-5-yl-CH2-X5 | 1.9 | 451.2635 | 452.2902 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 744 | 4-F-phenyl-X1 | H3C-(CH2)3-X2 | | benzo[1,3]dioxol-5-yl-CH2-X4 | benzo[1,3]dioxol-5-yl-CH2-X5 | 1.96 | 515.222 | 516.245 |
| 745 | 4-F-phenyl-X1 | H3C-(CH2)3-X2 | | cyclohexyl-CH2-X4 | benzo[1,3]dioxol-5-yl-CH2-X5 | 2.06 | 477.2791 | 478.3002 |
| 746 | 4-F-phenyl-X1 | H3C-(CH2)3-X2 | | 4-(CH3S)-phenyl-CH2-X4 | benzo[1,3]dioxol-5-yl-CH2-X5 | 2.03 | 517.2199 | 518.246 |
| 747 | 3-F-phenyl-X1 | H3C-(CH2)3-X2 | | cyclohexyl-CH2-X4 | benzyl-X5 | 2.08 | 433.2893 | 434.3055 |

TABLE 1A-continued

| CMP # | R1 | R2 | R3 | R4 | R5 | Rtn Time | Cmd Mass | H+ Ion Obs |
|---|---|---|---|---|---|---|---|---|
| | | | R3 is H unless otherwise specified | | | | | |
| 748 | 3-F-phenyl-X1 | H3C-(CH2)3-X2 | | CH3-CH(CH3)-CH2-CH2-X4 | 4-CH3-benzyl-X5 | 1.96 | 421.2893 | 422.306 |
| 749 | 3-F-phenyl-X1 | H3C-(CH2)3-X2 | | cyclohexyl-CH2-X4 | 4-CH3-benzyl-X5 | 2.11 | 447.305 | 448.3214 |
| 750 | 3-F-phenyl-X1 | H3C-(CH2)3-X2 | | CH3-CH(CH3)-CH2-CH2-X4 | 3,4-di-CH3-benzyl-X5 | 1.99 | 435.305 | 436.3263 |
| 751 | 3-F-phenyl-X1 | H3C-(CH2)3-X2 | | cyclohexyl-CH2-X4 | 4-OCH3-benzyl-X5 | 2.05 | 463.2999 | 464.3266 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 752 | 3-F-C6H4-X1 | H3C-(CH2)3-X2 | | H3C-CH(OH-like)-CH2-CH2-X4 (4-methyl-2-ol chain) | 4-(2-X5-ethyl)phenyl with CH3 | 2.05 | 449.3206 | 450.3442 |
| 753 | 3-F-C6H4-X1 | H3C-(CH2)3-X2 | | H3C-CH(...)-CH2-CH2-X4 | 4-(1-methyl-X5-methyl)phenyl (α-methylbenzyl) | 2.04 | 449.3206 | 450.3435 |
| 754 | 3-F-C6H4-X1 | H3C-(CH2)3-X2 | | cyclohexyl-CH2-X4 | 4-(1-methyl-X5-methyl)phenyl (α-methylbenzyl) | 2.18 | 475.3363 | 476.3594 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 755 | 3-F-C6H4-X1 | H3C-(CH2)3-X2 | X4-CH2CH(CH3)CH2CH3 (with H3C) | X5-CH2-(benzo[1,3]dioxol-5-yl) | 1.91 | 451.2635 | 452.2869 |
| 756 | 3-F-C6H4-X1 | H3C-(CH2)3-X2 | X4-CH2-(benzo[1,3]dioxol-5-yl) | X5-CH2-(benzo[1,3]dioxol-5-yl) | 1.97 | 515.222 | 516.2496 |
| 757 | 3-F-C6H4-X1 | H3C-(CH2)3-X2 | X4-CH2-cyclohexyl | X5-CH2-(benzo[1,3]dioxol-5-yl) | 2.08 | 477.2791 | 478.3031 |
| 758 | 3-F-C6H4-X1 | H3C-(CH2)3-X2 | X4-CH2CH(CH3)CH2CH3 (with H3C) | X5-CH2-(4-SCH3-C6H4) | 1.99 | 453.2614 | 454.2874 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 759 | 3-F-phenyl-X1 | H3C-(CH2)3-X2 | | 4-(SCH3)-benzyl-X4 | benzo[1,3]dioxol-5-ylmethyl-X5 | 2.02 | 517.2199 | 518.2543 |
| 760 | 3-F-phenyl-X1 | H3C-(CH2)3-X2 | | CH3CH(OH)CH2CH2-X4 | 4-pentyl-benzyl-X5 | 2.1 | 463.3363 | 464.3699 |
| 761 | 3-F-phenyl-X1 | H3C-(CH2)3-X2 | | CH3CH(OH)CH2CH2-X4 | 4-(SCH2CH3)-benzyl-X5 | 2.03 | 467.277 | 468.306 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 762 | 4-F-phenyl-X1 | H3C-(CH2)3-X2 | 3,5-dimethoxybenzyl-X4 | benzodioxole-CH2-X5 | 1.98 | 531.2534 | 532.2854 |
| 763 | 4-F-phenyl-X1 | H3C-(CH2)3-X2 | benzodioxole-CH2-X4 | 2,5-dimethoxybenzyl-X5 | 1.97 | 531.2534 | 532.2903 |
| 764 | 4-F-phenyl-X1 | H3C-(CH2)3-X2 | benzodioxole-CH2-X4 | 2,5-dimethoxybenzyl-X5 | 1.93 | 531.2534 | 532.285 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 765 | 4-F-C6H4- (X1) | H3C-(CH2)3-X2 | | benzo[1,3]dioxol-5-yl-CH2-X4 | 2,5-diCl-C6H3-CH2-X5 | 2.06 | 539.1542 | 540.1926 |
| 766 | 4-F-C6H4- (X1) | H3C-(CH2)3-X2 | | 3-Br-C6H4-CH2-X4 | benzo[1,3]dioxol-5-yl-CH2-X5 | 2.04 | 549.1427 | 550.1876 |
| 767 | 4-F-C6H4- (X1) | H3C-(CH2)3-X2 | | 4-Br-C6H4-CH2-X4 | benzo[1,3]dioxol-5-yl-CH2-X5 | 2.04 | 549.1427 | 550.1861 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 768 | 4-F-phenyl (X1) | H3C-(CH2)3-X2 | 2-Br-benzyl (X4) | benzo[1,3]dioxol-5-ylmethyl (X5) | 2.03 | 549.1427 | 550.1867 |
| 769 | 4-F-phenyl (X1) | H3C-(CH2)3-X2 | benzo[1,3]dioxol-5-ylmethyl (X4) | 2-phenethyl-phenyl | 2.13 | 575.2948 | 576.329 |
| 770 | phenyl (X1) | phenethyl (X2) | (CH3)2CH-CH2-X4 | 2-F-benzyl (X5) | | | |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 771 |  | 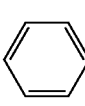 | 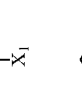 | 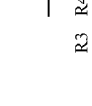 | | | |
| 772 |  |  | 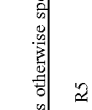 | 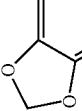 | | | |
| 773 |  |  |  |  | 2.02 | 465.3144 | 466.3379 |
| 774 | | | | | 2.01 | 463.3144 | 466.3359 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 775 | phenyl-X1 | phenethyl-X2 | | X4-CH(CH3)-CH2-CH3 | 2,3-dimethylphenyl-X5 | 2.06 | 465.3144 | 466.3358 |
| 776 | 4-F-phenyl-X1 | n-butyl-X2 | | benzo[1,3]dioxol-5-yl-CH2-X4 | 2,4,6-trifluorophenyl-X5 | 1.99 | 525.2039 | 526.2423 |
| 777 | 4-F-phenyl-X1 | n-butyl-X2 | | benzo[1,3]dioxol-5-yl-CH2-X4 | 2,3,6-trifluorophenyl-X5 | 1.99 | 525.2039 | 526.2429 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 778 | 4-F-C6H4-X1 | H3C-(CH2)3-X2 | | 3,4-dimethoxyphenethyl-X4 | benzo[1,3]dioxol-5-ylmethyl-X5 | 1.93 | 545.269 | 546.3107 |
| 779 | 4-F-C6H4-X1 | H3C-(CH2)3-X2 | | benzo[1,3]dioxol-5-ylethyl-X4 | benzo[1,3]dioxol-5-ylmethyl-X5 | | | 536.3018 |
| 780 | 4-F-C6H4-X1 | H3C-(CH2)3-X2 | | 2-naphthylethyl-X4 | benzo[1,3]dioxol-5-ylmethyl-X5 | 2.07 | 535.2835 | 536.3018 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 781 | 4-F-phenyl-X1 | H3C-(CH2)3-X2 | 3-methylbenzothiophen-2-yl-CH2CH2-X4 | benzo[1,3]dioxol-5-yl-CH2-X5 | 2.09 | 555.2356 | 556.2706 |
| 782 | 3-F-phenyl-X1 | H3C-(CH2)3-X2 | benzo[1,3]dioxol-5-yl-CH2-X4 | 2,4-dimethoxyphenyl-CH2-X5 | 1.97 | 531.2534 | 532.2892 |
| 783 | 3-F-phenyl-X1 | H3C-(CH2)3-X2 | benzo[1,3]dioxol-5-yl-CH2-X4 | 2,4-dimethoxyphenyl-CH2-X5 | 1.94 | 531.2534 | 532.2867 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 784 | 3-F-phenyl | n-butyl-X2 | | CH3-CH(OH)-CH2-CH2-X4 | 3-Cl-4-OMe-benzyl-X5 | 2 | 471.2453 | 472.2802 |
| 785 | 3-F-phenyl | n-butyl-X2 | | cyclohexylmethyl-X4 | 2,3,4-triOMe-benzyl-X5 | 2 | 523.321 | 524.354 |
| 786 | 4-F-phenyl | n-butyl-X2 | | 4-methylphenethyl-X4 | 3,4-methylenedioxybenzyl-X5 | 2.03 | 499.2635 | 500.2993 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 787 | 4-F-C6H4-X1 | H3C-(CH2)3-X2 | | 3-methoxyphenethyl-X4 | benzo[1,3]dioxol-5-ylmethyl-X5 | 1.98 | 515.2584 | 516.2964 |
| 788 | 4-F-C6H4-X1 | H3C-(CH2)3-X2 | | 4-methoxyphenethyl-X4 | benzo[1,3]dioxol-5-ylmethyl-X5 | 1.98 | 515.2584 | 516.2967 |
| 789 | 4-F-C6H4-X1 | H3C-(CH2)3-X2 | | 4-chlorophenethyl-X4 | benzo[1,3]dioxol-5-ylmethyl-X5 | 2.03 | 519.2089 | 520.2536 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 790 | 3-F-phenyl-$X_1$ | $H_3C$-(CH$_2$)$_3$-$X_2$ | 3-OCH$_3$-phenethyl-$X_4$ | piperonyl-$X_5$ | 1.99 | 515.2584 | 516.2904 |
| 791 | 3-F-phenyl-$X_1$ | $H_3C$-(CH$_2$)$_3$-$X_2$ | 4-OCH$_3$-phenethyl-$X_4$ | piperonyl-$X_5$ | 1.98 | 515.2584 | 516.3315 |
| 792 | 4-F-phenyl-$X_1$ | $H_3C$-(CH$_2$)$_3$-$X_2$ | 4-I-phenethyl-$X_4$ | piperonyl-$X_5$ | 2.06 | 611.1445 | 612.2336 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 793 | 4-F-C6H4-X1 | H3C-(CH2)3-X2 | | 4-Br-C6H4-CH2CH2-X4 | benzo[1,3]dioxol-5-yl-CH2-X5 | 2.05 | 563.1584 | 564.26 |
| 794 | 4-F-C6H4-X1 | H3C-(CH2)3-X2 | | 4-SCH3-C6H4-CH2CH2-X4 | benzo[1,3]dioxol-5-yl-CH2-X5 | 2.03 | 531.2356 | 532.3217 |
| 795 | 3-F-C6H4-X1 | H3C-(CH2)3-X2 | | 4-I-C6H4-CH2CH2-X4 | benzo[1,3]dioxol-5-yl-CH2-X5 | 2.06 | 611.1445 | 612.2438 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 796 | 3-F-phenyl-X1 | H3C-(CH2)-X2 | 4-(SCH3)-phenyl-CH2CH2-X4 | benzo[1,3]dioxol-5-yl-CH2-X5 | 2.02 | 531.2356 | 532.3212 |
| 797 | phenyl-X1 | phenyl-CH2CH2-X2 | 4-(SCH3)-phenyl-CH2CH2-X4 | benzo[1,3]dioxol-5-yl-CH2-X5 | 2.03 | 561.245 | 562.3386 |
| 798 | 3-F-phenyl-X1 | H3C-(CH2)-X2 | (CH3)2CH-CH(CH3)-X4 | 4-(N(CH3))-phenyl-CH2-X5 | 1.74 | 436.3002 | 437.386 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 799 | 3-F-phenyl-X1 | H3C-(CH2)3-X2 | | cyclohexyl-CH2-X4 | 4-(N(CH3))-phenyl-CH2-X5 | 1.88 | 462.3159 | 463.4108 |
| 800 | 3-F-phenyl-X1 | H3C-(CH2)3-X2 | | cyclohexyl-CH2-X4 | 2-CH3-3-NH2-phenyl-CH2-X5 | 1.87 | 462.3159 | 463.4136 |
| 801 | 4-F-phenyl-X1 | H3C-(CH2)3-X2 | | 2-F-phenyl-CH2-X4 | 3,4-methylenedioxyphenyl-CH2-X5 | 1.97 | 507.2133 | 508.3045 |
| 802 | 4-F-phenyl-X1 | H3C-(CH2)3-X2 | | 3,4-methylenedioxyphenyl-CH2-X4 | 2-(SCH3)-phenyl-CH2-X5 | 2.01 | 517.2199 | 518.3113 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 803 | 4-F-C6H4-X1 | H3C-(CH2)3-X2 | | benzo[1,3]dioxol-5-yl-CH2-X4 | 2-(OCF3)-C6H4-CH2-X6 | 2.02 | 555.2145 | 556.3143 |
| 804 | 4-F-C6H4-X1 | H3C-(CH2)3-X2 | | benzo[1,3]dioxol-5-yl-CH2-X4 | 2,5-bis(OCH2CF3)-C6H3-CH2-X3 | 2.02 | 667.2281 | 668.3466 |
| 805 | 4-F-C6H4-X1 | H3C-(CH2)3-X2 | | 2-Br-3-CH3-C6H3-CH2-X4 | benzo[1,3]dioxol-5-yl-CH2-X5 | 2.06 | 563.1584 | 564.27 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 806 | 4-F-phenyl-X1 | H3C-(CH2)3-X2 | | benzo[1,3]dioxol-5-yl-CH2-X4 | 4-Cl-3-(SCH3)-benzyl-X5 | 2.06 | 551.181 | 552.2875 |
| 807 | 4-F-phenyl-X1 | H3C-(CH2)3-X2 | | benzo[1,3]dioxol-5-yl-CH2-X4 | naphthalen-1-yl-CH2-X5 | 2.03 | 521.2479 | 522.3456 |
| 808 | 4-F-phenyl-X1 | H3C-(CH2)3-X2 | | benzo[1,3]dioxol-5-yl-CH2-X4 | 9H-fluoren-4-yl-CH2-X5 | 2.09 | 559.2635 | 560.3663 |
| 809 | 3-F-phenyl-X1 | H3C-(CH2)3-X2 | | benzyl-X4 | 2-(SCH3)-benzyl-X5 | 2.03 | 473.2301 | 474.313 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 810 | 3-F-phenyl-X1 | H3C-(CH2)3-X2 | | benzodioxole-CH2-X4 | 2-(SCH3)-phenyl-CH2-X5 | 2.02 | 517.2199 | 518.3132 |
| 811 | 3-F-phenyl-X1 | H3C-(CH2)3-X2 | | (CH3)2CH-CH2-CH2-X4 | 2-Cl-3,4-dimethoxy-phenyl-CH2-X5 | 2.01 | 501.2558 | 502.358 |
| 812 | 3-F-phenyl-X1 | H3C-(CH2)3-X2 | | cyclohexyl-CH2-X4 | 5-Cl-2,4-dimethoxy-phenyl-CH2-X5 | 2.09 | 527.2715 | 528.3815 |
| 813 | 4-F-phenyl-X1 | H3C-(CH2)3-X2 | | benzodioxole-CH2-X4 | naphthalen-2-yl-CH2-X5 | 2.05 | 521.2479 | 522.3471 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 814 | 4-F-C6H4-X1 | H3C-(CH2)3-X2 | | (CH3)2CH-CH2-CH2-X4 | 3-I-4-CH3-C6H3-CH2-X5 | | | |
| 815 | 4-F-C6H4-X1 | H3C-(CH2)3-X2 | | (CH3)2CH-CH2-CH2-X4 | 3-Cl-4-CH3-C6H3-CH2-X5 | 2.09 | 455.2504 | 456.3523 |
| 816 | 4-F-C6H4-X1 | H3C-(CH2)3-X2 | | 3-Cl-4-CH3-C6H3-CH2-X4 | 3,4-methylenedioxybenzyl-X5 | 2.07 | 519.2089 | 520.3145 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 817 | 4-F-phenyl-X1 | H3C-(CH2)3-X2 | | CH(CH3)CH2CH2-X4 | 2,3-dihydrobenzofuran-5-yl-CH2-X5 | 1.85 | 449.2842 | 450.3776 |
| 818 | 4-F-phenyl-X1 | H3C-(CH2)3-X2 | | benzo[1,3]dioxol-5-yl-CH2-X4 | 2,3-dihydrobenzofuran-5-yl-CH2-X5 | 1.95 | 513.2428 | 514.3442 |
| 819 | 4-F-phenyl-X1 | H3C-(CH2)3-X2 | | cyclohexyl-CH2-X4 | 2,3-dihydrobenzofuran-5-yl-CH2-X5 | 2.04 | 475.2999 | 476.4023 |

TABLE 1A-continued

| CMP # | R1 | R2 | R3 | R4 | R5 | Rtn Time | Cmd Mass | H+ Ion Obs |
|---|---|---|---|---|---|---|---|---|
| | | | R3 is H unless otherwise specified | | | | | |
| 820 | 4-F-phenyl-X1 | H3C-(CH2)3-X2 | | 4-(OCHF2)-benzyl-X4 | benzo[1,3]dioxol-5-ylmethyl-X5 | 1.98 | 537.2239 | 538.3297 |
| 821 | 3-F-phenyl-X1 | H3C-(CH2)3-X2 | | CH3CH(OH)CH2CH2-X4 | naphthalen-2-ylmethyl-X5 | | | |
| 822 | 3-F-phenyl-X1 | H3C-(CH2)3-X2 | | CH3CH(OH)CH2CH2-X4 | 3-I-4-CH3-benzyl-X5 | 2.04 | 457.2893 | 458.3844 |
| 823 | 3-F-phenyl-X1 | H3C-(CH2)3-X2 | | cyclohexylmethyl-X4 | 3-I-4-CH3-benzyl-X5 | | | |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 824 | 3-F-phenyl-X1 | H3C-(CH2)3-X2 | benzo[1,3]dioxole-5-yl-CH2-X4 | 2,3-dihydrobenzofuran-5-yl-CH2-X5 | 1.96 | 513.2428 | 514.345 |
| 825 | 3-F-phenyl-X1 | H3C-(CH2)3-X2 | cyclohexyl-CH2-X4 | 2,3-dihydrobenzofuran-5-yl-CH2-X5 | 2.04 | 475.2999 | 476.3996 |
| 826 | 3-F-phenyl-X1 | H3C-(CH2)3-X2 | (CH3)2CH-CH2-X4 | 4-(OCHF2)-phenyl-CH2-X5 | 1.97 | 473.2654 | 474.3578 |
| 827 | 3-F-phenyl-X1 | H3C-(CH2)3-X2 | cyclohexyl-CH2-X4 | 4-(OCHF2)-phenyl-CH2-X5 | 2.08 | 499.281 | 500.3929 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 828 | phenyl-X₁ | phenethyl-X₂ | | | 3-iodo-4-methylbenzyl-X₅ | | | |
| 829 | 4-F-phenyl-X₁ | butyl-X₂ | | 4-methyl-butyl-X₄ (with CH₃) | benzo[1,3]dioxol-5-ylmethyl-X₅ | 2.08 | 577.274 | 578.3961 |
| 830 | 4-F-phenyl-X₁ | butyl-X₂ | | 2-(2-F-phenyl)ethyl-X₄ | benzo[1,3]dioxol-5-ylmethyl-X₅ | 2 | 503.2384 | 504.3399 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 831 | 4-F-phenyl-X1 | H3C-(CH2)3-X2 | | 2-methoxyphenyl-CH2CH2-X4 | benzo[1,3]dioxol-5-yl-CH2-X5 | 1.99 | 515.2584 | 516.3593 |
| 832 | 4-F-phenyl-X1 | X2-(CH2)3-CH3 | | 2-ethoxyphenyl-CH2CH2-X4 | benzo[1,3]dioxol-5-yl-CH2-X5 | 2.03 | 529.274 | 530.3805 |
| 833 | 4-F-phenyl-X1 | H3C-(CH2)3-X2 | | 2-bromophenyl-CH2CH2-X4 | benzo[1,3]dioxol-5-yl-CH2-X5 | 2.03 | 563.1584 | 564.2842 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 834 | 4-F-C6H4-X1 | H3C-(CH2)3-X2 | | 2,5-dimethoxyphenethyl-X4 | benzo[1,3]dioxol-5-ylmethyl-X5 | 1.98 | 545.269 | 546.3808 |
| 835 | 4-F-C6H4-X1 | H3C-(CH2)3-X2 | | 2,3-dimethoxyphenethyl-X4 | benzo[1,3]dioxol-5-ylmethyl-X5 | 1.97 | 545.269 | 546.374 |
| 836 | 4-F-C6H4-X1 | H3C-(CH2)3-X2 | | 2,4-dimethoxyphenethyl-X4 | benzo[1,3]dioxol-5-ylmethyl-X5 | 1.98 | 545.269 | 546.3859 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 837 | 3-F-C6H4-X1 | H3C-(CH2)3-X2 | | 3,4-dimethoxyphenethyl-X4 | benzo[1,3]dioxol-5-ylmethyl-X5 | 1.92 | 545.269 | 546.3798 |
| 838 | 3-F-C6H4-X1 | H3C-(CH2)3-X2 | | 3-methoxy-4-ethoxyphenethyl-X4 | benzo[1,3]dioxol-5-ylmethyl-X5 | 1.96 | 559.2846 | 560.3983 |
| 839 | 3-F-C6H4-X1 | H3C-(CH2)3-X2 | | 2-naphthylethyl-X4 | benzo[1,3]dioxol-5-ylmethyl-X5 | 2.05 | 535.2635 | 536.3757 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 840 | 4-F-C6H4-X1 | H3C-(CH2)3-X2 | | benzo[1,3]dioxol-5-yl-CH2-X4 | 2-(4-methylphenoxy)-6-methyl-pyridin-3-yl-CH2-X5 | 2.04 | 592.285 | 593.4103 |
| 841 | 4-F-C6H4-X1 | H3C-(CH2)3-X2 | | benzo[1,3]dioxol-5-yl-CH2-X4 | 2-phenoxy-pyridin-3-yl-CH2-X5 | | | |
| 842 | 4-F-C6H4-X1 | H3C-(CH2)3-X2 | | benzo[1,3]dioxol-5-yl-CH2-X4 | 2-(allylthio)-pyridin-3-yl-CH2-X5 | 2.01 | 544.2308 | 545.3511 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 843 |  |  | |  |  | 1.88 | 547.2026 | 548.3105 |
| 844 |  |  | |  |  | 1.9 | 549.2228 | 550.3254 |
| 845 |  |  | |  |  | 1.97 | 525.2592 | 526.3528 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 846 | 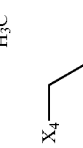 |  | |  | 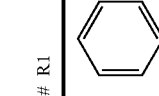 | 1.94 | 577.2132 | 578.3243 |
| 847 | 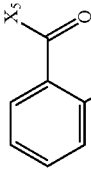 |  | |  |  | 2.01 | 553.2496 | 554.3531 |
| 848 |  | 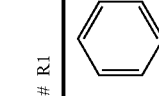 | |  |  | 1.92 | 581.229 | 582.3329 |

TABLE 1A-continued
R3 is H unless otherwise specified
| CMP # | R1 | R2 | R3 R4 | R5 | Rtn Time | Cmd Mass | H+ Ion Obs |
|---|---|---|---|---|---|---|---|
| 849 |  |  |  | 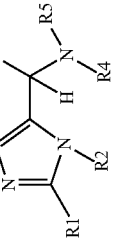 | 1.95 | 551.1531 | 552.2697 |
| 850 |  | 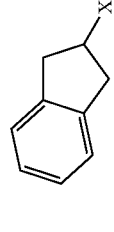 | 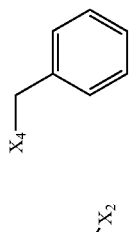 |  | 1.95 | 581.1637 | 582.2848 |
| 851 |  | 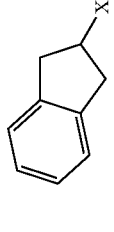 | 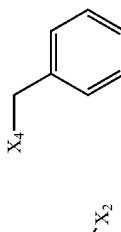 |  | 2.03 | 557.2001 | 558.311 |
| 852 | 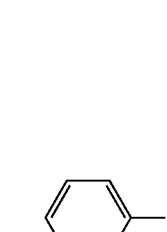 |  | 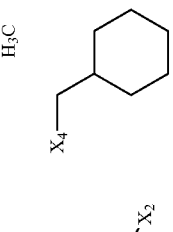 |  | 1.9 | 591.1522 | 592.27 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 853 | | | | | | 2.02 | 617.3042 | 618.4236 |
| 854 | | | | | | 1.92 | 639.1383 | 640.2621 |
| 855 | | | | | | 1.95 | 607.2238 | 608.3556 |

TABLE 1A-continued
R3 is H unless otherwise specified
| CMP # | R1 | R2 | R3 | R4 | R5 | Rtn Time | Cmd Mass | H+ Ion Obs |
|---|---|---|---|---|---|---|---|---|
| 856 | 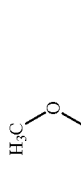 |  | | 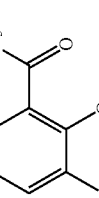 |  | 1.92 | 621.1627 | 622.29 |
| 857 |  | 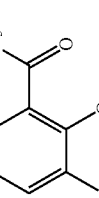 | |  | 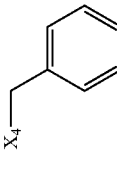 | 1.96 | 651.1733 | 652.31 |
| 858 | 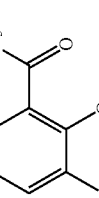 |  | | 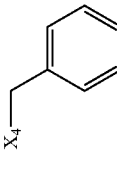 | 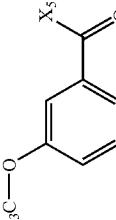 | 1.93 | 657.1288 | 658.2678 |

TABLE 1A-continued

R3 is H unless otherwise specified

| CMP # | R1 | R2 | R3 R4 | R5 | Rtn Time | Cmd Mass | H+ Ion Obs |
|---|---|---|---|---|---|---|---|
| 859 | phenyl-X1 | 2-indanyl-X2 | 4-methoxybenzyl-X4 | 2-bromo-5-methylbenzoyl-X5 | 1.95 | 605.1678 | 606.29 |
| 860 | phenyl-X1 | 2-indanyl-X2 | cyclohexylmethyl-X4 | 2-bromo-5-methylbenzoyl-X5 | 2.02 | 581.2042 | 582.32 |
| 861 | phenyl-X1 | 2-indanyl-X2 | 4-methoxybenzyl-X4 | 2-chloro-5-(methylthio)benzoyl-X5 | 1.96 | 593.1904 | 594.3127 |

TABLE 1A-continued

R3 is H unless otherwise specified

| CMP # | R1 | R2 | R3 | R4 | R5 | Rtn Time | Cmd Mass | H+ Ion Obs |
|---|---|---|---|---|---|---|---|---|
| 862 | phenyl-X$_1$ | indanyl-X$_2$ | | 4-methoxybenzyl-X$_4$ | 2-Cl-5-CF$_3$-benzoyl-X$_5$ | 1.97 | 615.1901 | 616.3185 |
| 863 | phenyl-X$_1$ | indanyl-X$_2$ | | cyclohexylmethyl-X$_4$ | 2-Cl-5-CF$_3$-benzoyl-X$_5$ | 2.04 | 591.2264 | 592.3466 |
| 864 | phenyl-X$_1$ | indanyl-X$_2$ | | 4-methoxybenzyl-X$_4$ | 2-(pyrrol-1-yl)benzoyl-X$_5$ | 1.93 | 578.2682 | 579.3848 |

TABLE 2

| CMP # | R1 | R2 | R3 | R4 | R5 | R6 | Rtn. Time | Cmd. Mass | H+ Ion Obs |
|---|---|---|---|---|---|---|---|---|---|
| 900 | X₁–phenyl | CH₃–(CH₂)₃–X₂ | X₃–Br | | X₅–CH₂–phenyl | X₆–(CH₂)₃–CH₃ | 1.99 | 453.1779 | 456.2343 |
| 901 | X₁–phenyl | CH₃–(CH₂)₃–X₂ | X₃–Br | | X₅–CH₂–(2,3-diCl-phenyl) | X₆–(CH₂)₃–CH₃ | | | |
| 902 | X₁–phenyl | CH₃–(CH₂)₃–X₂ | X₃–Cl | | X₅–CH₂–phenyl | X₆–(CH₂)₃–CH₃ | 1.96 | 409.2285 | 410.2904 |
| 903 | X₁–phenyl | X₂–(CH₂)₃–CH₃ | X₃–phenyl | | X₅–CH₂–phenyl | CH₃–(CH₂)₃–X₆ | 1.98 | 451.2987 | 452.3564 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 904 | phenyl-X₁ | CH₃-(CH₂)₃-X₂ | X₃—CH₃ | | benzyl-X₅ | X₆-(CH₂)₃-CH₃ | 1.91 | 389.2831 | 390.327 |
| 905 | phenyl-X₁ | CH₃-(CH₂)₃-X₂ | phenyl-X₃ | | 3-Cl-4-(X₅-CH₂)-phenol | X₆-CH(CH₃)-CH₂-CH₃ | 2.06 | 515.2703 | 516.3389 |
| 906 | phenyl-X₁ | CH₃-(CH₂)₃-X₂ | phenyl-X₃ | | 3-Cl-4-(X₅-CH₂)-phenol | X₆-(CH₂)₃-CH₃ | 2.02 | 501.2547 | 502.3203 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 907 | phenyl-X₁ | CH₃-(CH₂)₃-X₂ | phenyl-X₃ | | 3-chloro-4-HO-benzyl-X₅ | benzyl-X₆ | 2.05 | 535.239 | 536.3062 |
| 908 | phenyl-X₁ | CH₃-(CH₂)₃-X₂ | phenyl-X₃ | | 1,3-benzodioxol-5-ylmethyl-X₅ | CH₃-(CH₂)₃-X₆ | 1.95 | 495.2886 | 496.338 |
| 909 | phenyl-X₁ | CH₃-(CH₂)₃-X₂ | phenyl-X₃ | 2,3-dihydro-1,4-benzodioxin-6-ylmethyl-X₂ | | CH₃-(CH₂)₃-X₆ | 1.95 | 509.3042 | 510.349 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 910 | 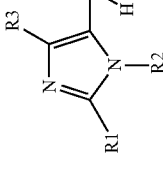 | 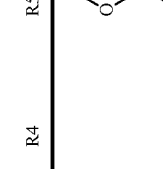 | 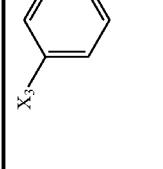 | | 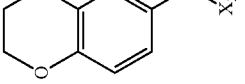 | 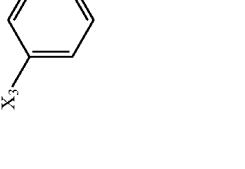 | 2.06 | 543.2886 | 544.3537 |
| 911 | 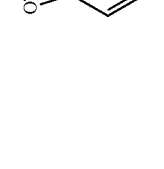 | 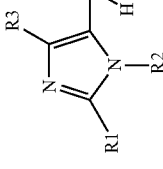 | 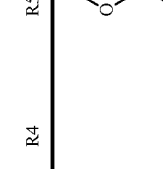 | | 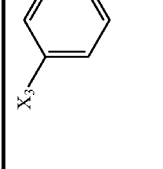 | 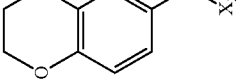 | 2.06 | 529.2729 | 530.3288 |
| 912 | 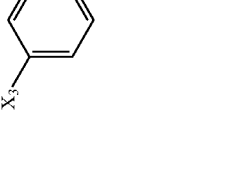 | 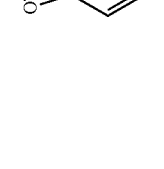 | 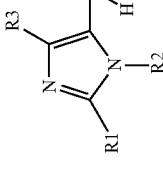 | | 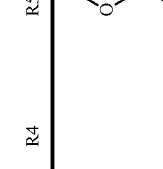 | 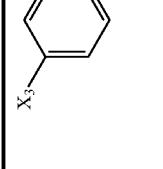 | 2.06 | 527.2936 | 528.3539 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 913 | X1-phenyl | CH3-(CH2)3-X2 | X3-phenyl | | 2,3-dihydrobenzofuran-5-CH2-X5 | X6-(CH2)3-CH3 | 1.91 | 493.3093 | 494.3662 |
| 914 | X1-phenyl | CH3-(CH2)3-X2 | X3-phenyl | | 4-HO-C6H4-CH2-X5 | X6-CH2-phenyl | 1.98 | 501.278 | 502.3292 |
| 915 | X1-phenyl | X2-(CH2)3-CH3 | X3-C(CH3)3 | | 2-Cl-4-HO-C6H3-CH2-X5 | X6-(CH2)3-CH3 | 2.04 | 481.286 | 482.3375 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 916 | phenyl-X₁ | X₂-(CH₂)₃-CH₃ | H₃C-C(CH₃)(CH₃)-X₃ | | benzo[1,3]dioxol-5-ylmethyl-X₅ | benzyl | 2.06 | 509.3042 | 510.3504 |
| 917 | phenyl-X₁ | X₂-(CH₂)₃-CH₃ | H₃C-C(CH₃)(CH₃)-X₃ | | benzo[1,3]dioxol-5-ylmethyl-X₅ | benzo[1,3]dioxol-5-ylmethyl | 2.04 | 533.2941 | 544.3566 |
| 918 | phenyl-X₁ | X₂-(CH₂)₃-CH₃ | H₃C-C(CH₃)(CH₃)-X₃ | | benzo[1,3]dioxol-5-ylmethyl-X₅ | 3-chloro-4-hydroxybenzyl | 2.01 | 599.2602 | 560.3214 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 919 | X1-phenyl | X2-(CH2)3-CH3 | C(CH3)3-X3 | | 3,4-methylenedioxybenzyl-X5 | 3-chloro-4-hydroxybenzyl-X6 | 1.98 | 599.2602 | 560.3226 |
| 920 | X1-phenyl | X2-(CH2)3-CH3 | phenyl-X3 | | 4-methoxybenzyl-X5 | benzyl-X6 | 2.07 | 515.2936 | 516.3561 |
| 921 | X1-phenyl | X2-(CH2)3-CH3 | phenyl-X3 | | 4-hydroxybenzyl-X5 | X6-(CH2)3-CH3 | 1.8 | 467.2937 | 466.3449 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 922 | X₁-phenyl | CH₃-(CH₂)₃-X₂ | X₃-phenyl | | 6-chloropyridin-3-yl-CH₂-X₅ | X₆-(CH₂)₃-CH₃ | 1.97 | 486.255 | 487.3133 |
| 923 | X₁-phenyl | CH₃-(CH₂)₃-X₂ | X₃-phenyl | | 6-chloropyridin-3-yl-CH₂-X₅ | X₆-CH₂-phenyl | 1.96 | 520.2394 | 521.3087 |
| 924 | X₁-phenyl | CH₃-(CH₂)₃-X₂ | X₃-phenyl | | 6-(pyrrolidin-1-yl)pyridin-3-yl-CH₂-X₅ | X₆-(CH₂)₃-CH₃ | 1.77 | 521.3519 | 522.4169 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 925 |  |  | 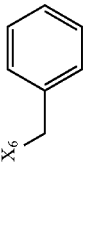 | | 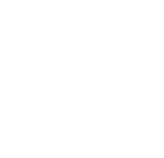 |  | 1.79 | 555.3362 | 566.421 |
| 926 |  |  |  | |  |  | 2.06 | 565.2496 | 566.3239 |
| 927 |  |  |  | |  |  | 1.76 | 545.3155 | 546.3849 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 928 | X1-phenyl | CH3-(CH2)3-X2 | X3-C6H4-OCH3 (para) | | X5-CH2-(3-Cl,4-OH-phenyl) | X6-(CH2)3-CH3 | 2.02 | 531.2563 | 532.3318 |
| 929 | X1-phenyl | CH3-(CH2)3-X2 | X3-C6H4-OCH3 (para) | | X5-CH2-(4-OH-phenyl) | X6-(CH2)3-CH3 | 1.79 | 497.3042 | 498.3625 |
| 930 | X1-phenyl | CH3-(CH2)3-X2 | X3-C6H4-OCH3 (para) | | X5-CH2-(3,4-methylenedioxyphenyl) | X6-(CH2)3-CH3 | 1.95 | 525.2991 | 526.3686 |

TABLE 2-continued
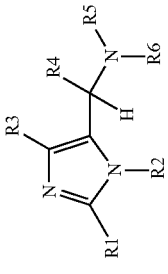
| CMP # | R1 | R2 | R3 | R4 | R5 | R6 | Rtn. Time | Cmd. Mass | H+ Ion Obs |
|---|---|---|---|---|---|---|---|---|---|
| 931 | 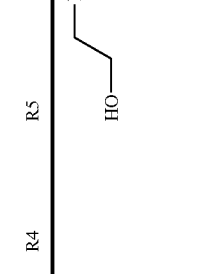 | 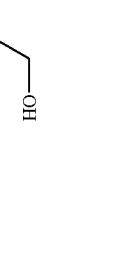 |  | | 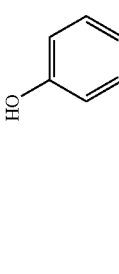 | 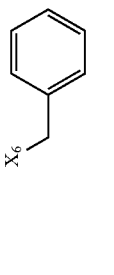 | 1.74 | 511.3311 | 512.3882 |
| 932 | 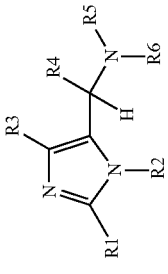 | 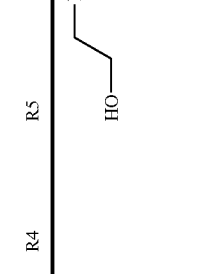 | 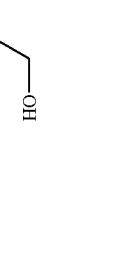 | | 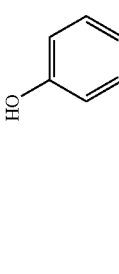 | 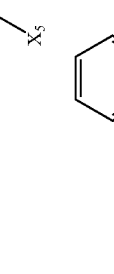 | 2 | 531.2886 | 532.3475 |
| 933 | 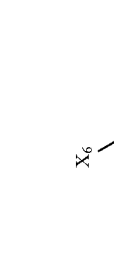 | 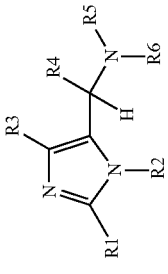 | 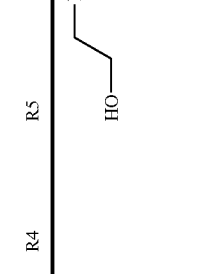 | | 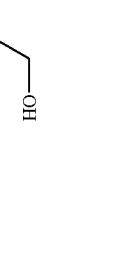 | 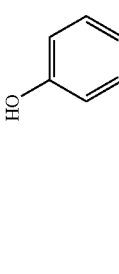 | 2 | 469.2893 | 470.3573 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 934 | X₁–C₆H₅ | CH₃–(CH₂)₃–X₂ | X₃–(4-F-C₆H₄) | | X₅–CH₂–(2-Cl-4-OH-C₆H₃) | X₆–(CH₂)₃–CH₃ | 2.03 | 519.2452 | 520.3179 |
| 935 | X₁–C₆H₅ | CH₃–(CH₂)₃–X₂ | X₃–(4-F-C₆H₄) | | X₅–CH₂–(2-Cl-4-OH-C₆H₃) | X₆–CH₂–C₆H₅ | 2.05 | 553.2296 | 554.3043 |
| 936 | X₁–C₆H₅ | CH₃–(CH₂)₃–X₂ | X₃–(4-F-C₆H₄) | | X₅–CH₂–(3,4-methylenedioxyphenyl) | X₆–(CH₂)₃–CH₃ | 1.97 | 513.2792 | 514.3508 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 937 | X₁-phenyl | CH₃-(CH₂)₃-X₂ | X₃-(4-F-phenyl) | | X₅-CH₂-(benzo[1,3]dioxol-5-yl) | X₆-CH₂-phenyl | 2.06 | 547.2635 | 548.3326 |
| 938 | X₁-phenyl | CH₃-(CH₂)₃-X₂ | X₃-phenyl | | X₅-CH₂-(2,4-dihydroxyphenyl) | X₆-(CH₂)₃-CH₃ | 1.71 | 483.2886 | 484.3469 |
| 939 | X₁-phenyl | CH₃-(CH₂)₃-X₂ | X₃-phenyl | | X₅-CH₂-phenyl | X₆-CH₂-CH₃ | 1.86 | 423.2675 | 424.3207 |

TABLE 2-continued

| CMP # | R1 | R2 | R3 | R4 R5 | R6 | Rtn. Time | Cmd. Mass | H+ Ion Obs |
|---|---|---|---|---|---|---|---|---|
| 940 | phenyl-X1 | X2-(CH2)3-CH3 | phenyl-X3 | X5-CH2-thiazole | (CH2)3-CH3 with X6 | 1.94 | 458.2504 | 459.2958 |
| 941 | phenyl-X1 | X2-(CH2)3-CH3 | phenyl-X3 | X5-CH2-thiazole | X6-CH2-phenyl | 1.93 | 492.2378 | 493.2848 |
| 942 | phenyl-X1 | CH3-(CH2)3-X2 | phenyl-X3 | H2N-pyridine-CH2-X5 | X6-(CH2)2-CH3 | 1.74 | 437.3049 | 466.3629 |
| 943 | phenyl-CH2-X5 | X2-(CH2)2-CH3 | phenyl-X3 | X5-CH2-phenyl | X6-(CH2)3-CH3 | 1.92 | 437.2831 | 438.2847 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 944 | Ph-X1 | CH3-(CH2)3-X2 | Ph-X3 | | H3C-CH2-N(H)-pyridyl-CH2-X5 | -(CH2)3-CH3 (X6) | 1.77 | 495.3362 | 496.4057 |
| 945 | Ph-X1 | CH3-(CH2)3-X2 | Ph-X3 | | H3C-N(H)-pyridyl-CH2-X5 | -(CH2)3-CH3 (X6) | 1.74 | 481.3206 | 482.3854 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 946 | phenyl (X1) | CH3-(CH2)3-X2 | phenyl (X3) | | methoxyethyl-N-(pyridinyl-CH2-X5) | butyl-CH3 (X6) | 1.76 | 525.3467 | 526.4145 |
| 947 | phenyl (X1) | X2-(CH2)3-CH3 | phenyl (X3) | | benzyl (X5) | CH2C(O)OCH2CH3 (X6) | 1.98 | 481.2729 | 482.3188 |
| 948 | phenyl (X1) | X2-(CH2)3-CH3 | phenyl (X3) | | 2-hydroxybenzyl (X5) | benzyl (X6) | 2.01 | 501.278 | 502.3374 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 949 | phenyl (X1) | X2-CH2CH2CH2-CH3 | phenyl (X3) | | 3-hydroxybenzyl (X5) | benzyl (X6) | 1.99 | 501.278 | 502.3323 |
| 950 | phenyl (X1) | X2-CH2CH2CH2-CH3 | phenyl (X3) | | 2-hydroxybenzyl (X5) | X6-CH2CH2CH2-CH3 | 1.88 | 467.2937 | 468.3544 |
| 951 | phenyl (X1) | X2-CH2CH2CH2-CH3 | phenyl (X3) | | 3-hydroxybenzyl (X5) | X6-CH2CH2CH2-CH3 | 1.88 | 467.2937 | 468.352 |
| 952 | phenyl (X1) | X2-CH2CH2CH2-CH3 | phenyl (X3) | | 4-(methoxycarbonyl)benzyl (X5) | benzyl (X6) | 2.04 | 543.2886 | 544.3618 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 953 | X1-phenyl | X2-(CH2)3CH3 | X3-phenyl | | X5-CH2-(4-methoxycarbonyl-phenyl) | X6-(CH2)3CH3 | 2.03 | 509.3042 | 510.364 |
| 954 | X1-phenyl | X2-(CH2)3CH3 | X3-phenyl | | X5-CH2-(quinolin-3-yl) | X6-CH2-phenyl | 1.93 | 536.294 | 537.3635 |
| 955 | X1-phenyl | X2-(CH2)3CH3 | X3-phenyl | | X5-CH2-(quinolin-3-yl) | X6-(CH2)3CH3 | 1.94 | 502.3097 | 503.3694 |
| 956 | X1-phenyl | X2-(CH2)3CH3 | X3-phenyl | | X5-CH2-(quinolin-3-yl) | X6-CH2-cyclohexyl | 2.05 | 542.3409 | 543.4108 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 957 | X₁-phenyl | X₂-(CH₂)₃-CH₃ | X₃-phenyl | | X₅-CH₂-C₆H₄-O-CH₃ (4-methoxy) | X₆-(CH₂)₃-CH₃ | 1.92 | 481.3093 | 482.3674 |
| 958 | X₁-phenyl | X₂-(CH₂)₃-CH₃ | X₃-phenyl | | X₅-CH₂-C₆H₄-COOH (4-carboxy) | X₆-CH₂-phenyl | 1.99 | 529.2729 | 530.3309 |
| 959 | X₁-phenyl | X₂-(CH₂)₃-CH₃ | X₃-phenyl | | X₅-CH₂-C₆H₄-COOH (4-carboxy) | X₆-(CH₂)₃-CH₃ | 1.97 | 495.2886 | 496.3324 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 960 |  |  |  | | 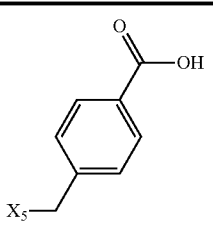 | 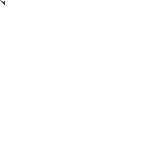 | 2.08 | 535.3199 | 536.3663 |
| 961 | 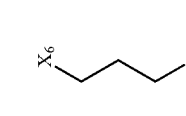 |  |  | | 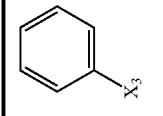 | 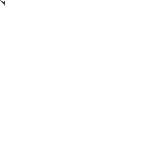 | 1.93 | 502.3097 | 503.3532 |
| 962 |  |  |  | |  | 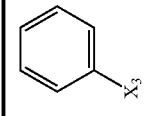 | 2.06 | 542.3409 | 543.387 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 963 | X₁–C₆H₅ | CH₃(CH₂)₃–X₂ | X₃–C₆H₅ | | H₃C-O-CH₂CH₂-NH-(pyridyl)-CH₂-X₅ | X₆-CH₂-C₆H₅ | 1.77 | 559.3311 | 560.4 |
| 964 | X₁–C₆H₅ | CH₃(CH₂)₃–X₂ | X₃–C₆H₅ | | H₃C-O-CH₂CH₂-NH-(pyridyl)-CH₂-X₅ | X₆-CH₂-C₆H₅ | 1.77 | 529.3206 | 530.373 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 965 | phenyl (X1) | X2-propyl-CH3 | phenyl (X3) | | 4-Br-benzyl (X5) | cyclohexylmethyl (X6) | | | |
| 966 | phenyl (X1) | X2-propyl-CH3 | phenyl (X3) | | 4-(N,N-dimethylamino)benzyl (X5) | benzyl (X6) | 1.94 | 528.3253 | 529.3721 |
| 967 | phenyl (X1) | X2-propyl-CH3 | phenyl (X3) | | 4-(N,N-dimethylamino)benzyl (X5) | X6-propyl-CH3 | 1.88 | 494.3409 | 495.3921 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 968 | phenyl-X₁ | X₂-(CH₂)₃-CH₃ | phenyl-X₃ | | 4-(dimethylamino)benzyl-X₅ | cyclohexylmethyl-X₆ | 2.05 | 534.3723 | 535.461 |
| 969 | phenyl-X₁ | X₂-(CH₂)₃-CH₃ | phenyl-X₃ | | benzimidazol-5-ylmethyl-X₅ | X₆-(CH₂)₃-CH₃ | 1.77 | 491.3049 | 492.3542 |
| 970 | phenyl-X₁ | X₂-(CH₂)₃-CH₃ | phenyl-X₃ | | 4-(thiazol-5-yl)benzyl-X₅ | benzyl-X₆ | 2.03 | 568.2661 | 569.3215 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 971 | phenyl-X1 | X2-(CH2)3-CH3 | phenyl-X3 | | 5-(thiazol-5-yl)phenyl-CH2-X5 | X6-(CH2)3-CH3 | 1.98 | 534.2817 | 535.3365 |
| 972 | phenyl-X1 | X2-(CH2)3-CH3 | phenyl-X3 | | 5-(thiazol-5-yl)phenyl-CH2-X5 | X6-CH2-cyclohexyl | 2.14 | 574.313 | 575.38 |
| 973 | phenyl-X1 | X2-(CH2)3-CH3 | phenyl-X3 | | 4-(N-methylcarbamoyl)phenyl-CH2-X5 | X6-(CH2)3-CH3 | 1.94 | 542.3049 | 543.3302 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 974 | X₁-phenyl | X₂-(CH₂)₃CH₃ | X₃-phenyl | | 4-(N,N-dimethylcarbamoyl)benzyl-X₅ | X₆-(CH₂)₃CH₃ | 1.89 | 507.3202 | 509.3457 |
| 975 | X₁-phenyl | X₂-(CH₂)₃CH₃ | X₃-phenyl | | 4-(N,N-dimethylcarbamoyl)benzyl-X₅ | X₆-(CH₂)₃CH₃ | 1.91 | 522.3359 | 523.3574 |
| 976 | X₁-phenyl | X₂-(CH₂)₃CH₃ | X₃-phenyl | | 4-(N,N-dimethylcarbamoyl)benzyl-X₅ | X₆-CH₂-cyclohexyl | 2.03 | 562.3672 | 563.3868 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 977 | X₁-phenyl | X₂-CH₂CH₂CH₂CH₃ | X₃-phenyl | | X₅-(4-hydroxymethyl)benzyl | X₆-benzyl | 1.96 | 515.2936 | 516.3203 |
| 978 | X₁-phenyl | X₂-CH₂CH₂CH₂CH₃ | X₃-phenyl | | X₅-(4-hydroxymethyl)benzyl | X₆-CH₂CH₂CH₂CH₃ | 1.86 | 481.3093 | 482.3423 |
| 979 | X₁-phenyl | X₂-CH₂CH₂CH₂CH₃ | X₃-phenyl | | X₅-(4-hydroxymethyl)benzyl | X₆-cyclohexylmethyl | 2.05 | 521.3406 | 522.3415 |
| 980 | X₁-phenyl | X₂-CH₂CH₂CH₂CH₃ | X₃-phenyl | | X₅-(2-methoxy)benzyl | X₆-benzyl | 2.06 | 515.2936 | 516.3033 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 981 | X1-phenyl | X2-(CH2)3CH3 | X3-phenyl | | X5-CH2-(2-methoxyphenyl) | X6-(CH2)3CH3 | 1.89 | 481.3093 | 482.3204 |
| 982 | X1-phenyl | X2-(CH2)3CH3 | X3-phenyl | | X5-CH2-(2-methoxyphenyl) | X6-CH2-cyclohexyl | 2.12 | 521.3406 | 522.3559 |
| 983 | X1-phenyl | X2-(CH2)3CH3 | X3-phenyl | | X5-CH2-(3-methoxyphenyl) | X6-CH2-phenyl | 2.06 | 515.2936 | 516.3141 |
| 984 | X1-phenyl | X2-(CH2)3CH3 | X3-phenyl | | X5-CH2-(3-methoxyphenyl) | X6-(CH2)3CH3 | 1.99 | 481.3093 | 482.3264 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 985 | 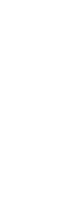 | 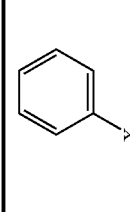 |  | | 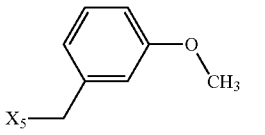 |  | 2.15 | 521.3406 | 522.3597 |
| 986 | 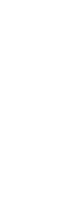 | 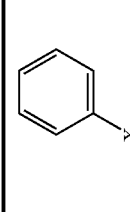 |  | | 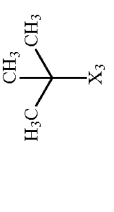 |  | 2.03 | 489.3355 | 490.3545 |
| 987 | 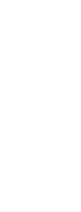 |  | 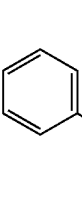 | | 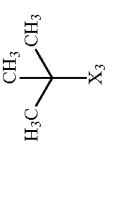 |  | 1.93 | 461.3406 | 462.3651 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 988 | phenyl (X1) | propyl-CH3 (X2) | phenyl (X3) | | 4-(acetoxy)benzyl (X5) | cyclohexylmethyl (X6) | 2.1 | 549.3355 | 550.3556 |
| 989 | phenyl (X1) | propyl-CH3 (X2) | phenyl (X3) | | 4-(carboxymethoxy)benzyl (X5) | benzyl (X6) | 1.99 | 559.2835 | 560.3169 |
| 990 | phenyl (X1) | propyl-CH3 (X2) | phenyl (X3) | | 4-(carboxymethoxy)benzyl (X5) | cyclohexylmethyl (X6) | 2.06 | 565.3304 | 566.3608 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 991 | 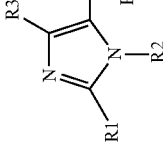 |  | 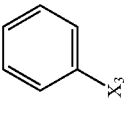 |  |  |  | 1.98 | 545.3042 | 546.332 |
| 992 | 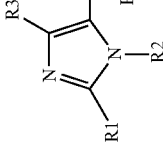 |  |  | |  |  | 1.82 | 511.3199 | 512.3492 |
| 993 |  | 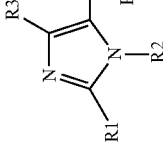 |  | |  |  | 2.05 | 551.3512 | 552.3806 |

TABLE 2-continued

| CMP # | R1 | R2 | R3 | R4 R5 | R6 | Rtn. Time | Cmd. Mass | H+ Ion Obs |
|---|---|---|---|---|---|---|---|---|
| 994 | phenyl (X1) | X2-(CH2)3-CH3 | C(CH3)3-X3 | 4-(N-methylcarbamoyl)benzyl (X5) | -(CH2)3-CH3 (X6) | 1.91 | 488.3515 | 489.3748 |
| 995 | phenyl (X1) | X2-(CH2)3-CH3 | phenyl (X3) | 4-hydroxy-3-nitrobenzyl (X5) | benzyl (X6) | 2.02 | 546.2631 | 547.2886 |
| 996 | phenyl (X1) | X2-(CH2)3-CH3 | phenyl (X3) | 4-hydroxy-3-nitrobenzyl (X5) | -(CH2)3-CH3 (X6) | 2 | 512.2787 | 513.3031 |
| 997 | phenyl (X1) | X2-(CH2)3-CH3 | phenyl (X3) | 4-hydroxy-3-nitrobenzyl (X5) | cyclohexylmethyl (X6) | 2.11 | 522.3101 | 553.335 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 998 | 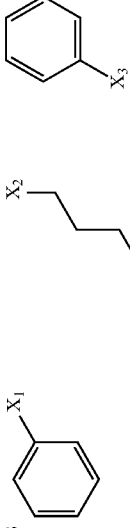 | 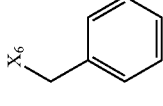 | 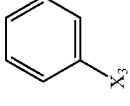 | | 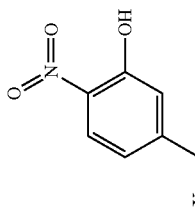 |  | 2.02 | 546.2631 | 547.2888 |
| 999 | 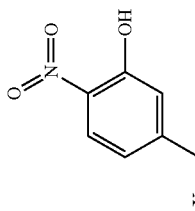 | 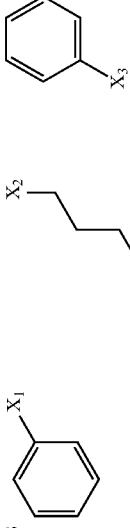 | 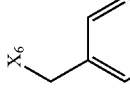 | | 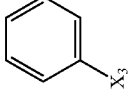 | 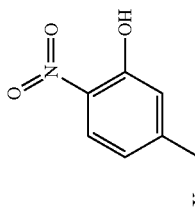 | 2.03 | 512.2787 | 513.3018 |
| 1000 |  | 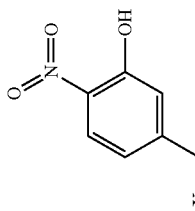 | 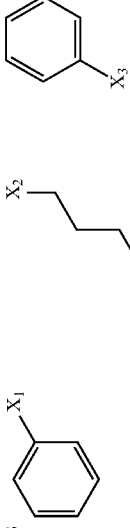 | | 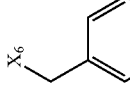 | 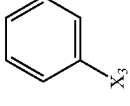 | 2.11 | 552.3101 | 553.3454 |

TABLE 2-continued
| CMP # | R1 | R2 | R3 | R4 R5 R6 | Rtn. Time | Cmd. Mass | H+ Ion Obs |
|---|---|---|---|---|---|---|---|
| 1001 | 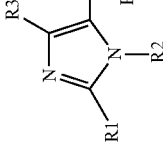 | 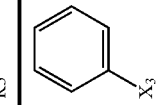 | 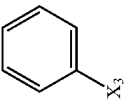 | 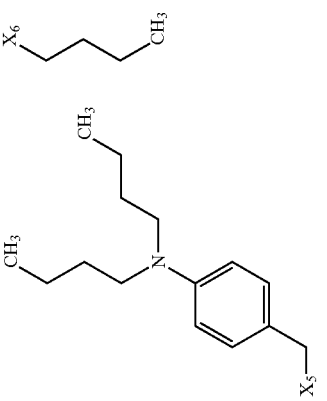 | 2.06 | 578.4349 | 579.501 |
| 1002 | 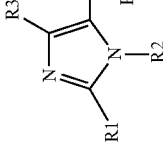 | 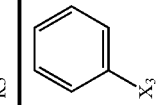 | 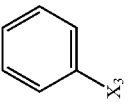 | 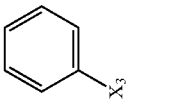 | 2.14 | 318.4661 | 619.54 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1003 | phenyl-X1 | H3C-CH2CH2CH2-X2 | phenyl-X3 | | | X6-CH(CH3)CH2CH3 with N(CH3)CH2CH2CH2-O-phenyl-X5 | 1.71 | 552.3828 | 553.43 |
| 1004 | phenyl-X1 | H3C-CH2CH2CH2-X2 | phenyl-X3 | | | X6-CH(cyclohexyl) with N(CH3)CH2CH2CH2-O-phenyl-X5 | 1.92 | 592.4141 | 593.47 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1005 | phenyl (X1) | X2-(CH2)3-CH3 | (CH3)3C-X3 | | 4-(X5-CH2)-benzamide | X6-(CH2)3-CH3 | 1.9 | 474.3359 | 475.3617 |
| 1006 | phenyl (X1) | X2-(CH2)3-CH3 | phenyl (X3) | | 4-(X5-CH2)-phenyl O-C(O)-CH2-NH2 | X6-CH2-phenyl | 1.81 | 558.2995 | 559.3615 |
| 1007 | phenyl (X1) | X2-(CH2)3-CH3 | (CH3)3C-X3 | | 4-(X5-CH2)-benzyl-NH2 | X6-(CH2)3-CH3 | 1.78 | 460.3566 | 461.4005 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1008 | X1-phenyl | X2-(CH2)3CH3 | X3-phenyl | | X5-2-(methyl benzoate)methyl | X6-benzyl | 2.03 | 543.2886 | 544.3141 |
| 1009 | X1-phenyl | X2-(CH2)3CH3 | X3-phenyl | | X5-2-(methyl benzoate)methyl | X6-(CH2)3CH3 | 1.95 | 509.3042 | 510.3276 |
| 1010 | X1-phenyl | X2-(CH2)3CH3 | X3-phenyl | | X5-2-(methyl benzoate)methyl | X6-cyclohexylmethyl | 2.08 | 549.3355 | 550.3668 |
| 1011 | X1-phenyl | X2-(CH2)3CH3 | X3-phenyl | | X5-2-(hydroxymethyl)benzyl | X6-benzyl | 1.96 | 515.2936 | 516.3184 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1012 |  |  | 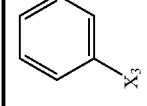 | | 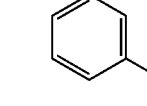 | 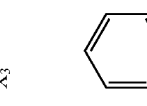 | 1.84 | 481.3093 | 482.3309 |
| 1013 | 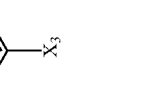 |  |  | | 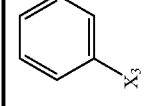 | 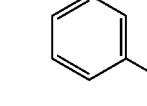 | 1.98 | 521.3406 | 522.3765 |
| 1014 | 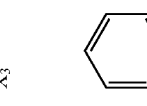 | 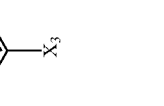 |  | |  | 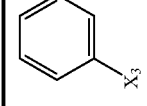 | 1.88 | 564.2559 | 565.3013 |
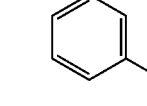

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1015 | X₁–Ph | X₂–(CH₂)₃–CH₃ | X₃–Ph | | X₅–C₆H₄–SO₂NH₂ | X₆–(CH₂)₃–CH₃ | 1.87 | 530.2715 | 531.3078 |
| 1016 | X₁–Ph | X₂–(CH₂)₃–CH₃ | X₃–C₆H₄–OCH₃ (2-OMe) | | X₅–C₆H₄–OCH₃ | X₆–(CH₂)₃–CH₃ | 1.88 | 511.3199 | 512.3484 |
| 1017 | X₁–Ph | X₂–(CH₂)₃–CH₃ | X₃–C₆H₄–OCH₃ (2-OMe) | | X₅–C₆H₄–OCHF₂ | X₆–(CH₂)₃–CH₃ | 1.98 | 547.301 | 548.3231 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1018 | X₁-phenyl | X₂-(CH₂)₃-CH₃ | X₃-phenyl | | X₅-CH₂-phenyl | X₆-(CH₂)₅-C(O)-O-CH₃ | 1.96 | 523.3199 | 524.3481 |
| 1019 | X₁-phenyl | X₂-(CH₂)₃-CH₃ | X₃-phenyl | | X₅-(CH₂)₅-C(O)-O-CH₃ | X₆-(CH₂)₃-CH₃ | 1.82 | 489.3355 | 490.3575 |
| 1020 | X₁-phenyl | X₂-(CH₂)₃-CH₃ | X₃-phenyl | | X₅-CH₂-phenyl | X₆-(CH₂)₅-C(O)-OH | 1.9 | 509.3042 | 510.3383 |
| 1021 | X₁-phenyl | X₂-(CH₂)₃-CH₃ | X₃-phenyl | | X₅-CH₂-phenyl | X₆-(CH₂)₆-OH | 1.88 | 495.325 | 496.3488 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1022 | 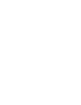 |  |  | |  |  | 1.77 | 461.3406 | 462.3634 |
| 1023 |  |  |  | |  |  | 2.03 | 573.2628 | 574.2927 |
| 1024 |  |  | 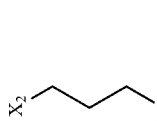 | | | | 2.03 | 587.2784 | 588.3088 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1025 | phenyl-X1 | X2-(CH2)3-CH3 | phenyl-X3 | | 1,3-benzodioxol-5-ylmethyl-X5 | 4-(carboxy)benzyl-X6 | 1.96 | 573.2628 | 574.3035 |
| 1026 | phenyl-X1 | X2-(CH2)3-CH3 | phenyl-X3 | | 4-(N-methyl-N-methanesulfonyl-methanesulfonamido)benzyl-X5 | X6-(CH2)3-CH3 | | | |
| 1027 | phenyl-X1 | X2-(CH2)3-CH3 | phenyl-X3 | | 4-(N-methyl-N-methanesulfonyl-methanesulfonamido)benzyl-X5 | X6-(CH2)3-CH3 | 1.85 | 544.2872 | 545.3313 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1028 | X1-phenyl | X2-CH2CH2CH2CH3 | X3-phenyl | | X5-(3-benzyl methyl benzoate) | X6-benzyl | 2.03 | 543.2886 | 544.3122 |
| 1029 | X1-phenyl | X2-CH2CH2CH2CH3 | X3-phenyl | | X5-(3-benzyl methyl benzoate) | X6-CH2CH2CH2CH3 | 2.03 | 509.3042 | 510.3173 |
| 1030 | X1-phenyl | X2-CH2CH2CH2CH3 | X3-phenyl | | X5-(3-benzyl methyl benzoate) | X6-CH2-cyclohexyl | 2.12 | 549.3355 | 550.3542 |
| 1031 | X1-phenyl | X2-CH2CH2CH2CH3 | X3-phenyl | | X5-(3-benzyl benzoic acid) | X6-benzyl | 1.98 | 529.2729 | 530.2999 |

TABLE 2-continued

| CMP # | R1 | R2 | R3 | R4 R5 | R6 | Rtn. Time | Cmd. Mass | H+ Ion Obs |
|---|---|---|---|---|---|---|---|---|
| 1032 | phenyl-X₁ | X₂-butyl-CH₃ | phenyl-X₃ | 3-(X₅-CH₂)-benzoic acid | X₆-CH₂-cyclohexyl | 2.08 | 535.3199 | 536.3453 |
| 1033 | phenyl-X₁ | X₂-butyl-CH₃ | phenyl-X₃ | 3-(X₅-CH₂)-benzyl alcohol | X₆-CH₂-phenyl | 1.97 | 515.2936 | 516.3203 |
| 1034 | phenyl-X₁ | X₂-butyl-CH₃ | phenyl-X₃ | 3-(X₅-CH₂)-benzyl alcohol | X₆-propyl-CH₃ | 1.87 | 481.3093 | 482.3294 |
| 1035 | phenyl-X₁ | X₂-butyl-CH₃ | phenyl-X₃ | methyl 2-hydroxy-5-(X₅-CH₂)benzoate | X₆-CH₂-phenyl | 2.06 | 559.2835 | 560.311 |

TABLE 2-continued
| CMP # | R1 | R2 | R3 | R4 R5 | R6 | Rtn. Time | Cmd. Mass | H+ Ion Obs |
|---|---|---|---|---|---|---|---|---|
| 1036 | 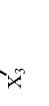 X1-phenyl |  X2-butyl | 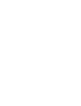 X3-phenyl |  methyl 2-hydroxy-5-(X5-methyl)benzoate |  X6-pentyl | 2.03 | 525.2991 | 526.3195 |
| 1037 | 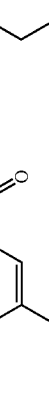 X1-phenyl |  X2-butyl | 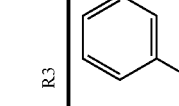 X3-phenyl |  methyl 2-hydroxy-5-(X5-methyl)benzoate |  X6-methylcyclohexyl | 2.17 | 565.3304 | 566.35 |
| 1038 |  X1-phenyl |  X2-butyl |  X3-phenyl |  2-hydroxy-5-(X5-methyl)benzoic acid |  X6-benzyl | | | |
| 1039 |  X1-phenyl | 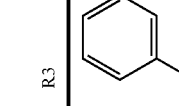 X2-butyl | 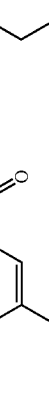 X3-phenyl |  2-hydroxy-5-(X5-methyl)benzoic acid | 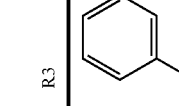 X6-methylcyclohexyl | 2.12 | 551.3148 | 552.3455 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1040 | X₁-phenyl | X₂-CH₂CH₂CH₂-CH₃ | X₃-phenyl | | X₅-CH₂-(4-OH, 3-CH₂OH phenyl) | X₆-CH₂-phenyl | 1.93 | 531.2886 | 532.3281 |
| 1041 | X₁-phenyl | X₂-CH₂CH₂CH₂-CH₃ | X₃-phenyl | | X₅-CH₂-(4-OH, 3-CH₂OH phenyl) | X₆-CH₂CH₂CH₂-CH₃ | 1.74 | 497.3042 | 498.3471 |
| 1042 | X₁-phenyl | X₂-CH₂CH₂CH₂-CH₃ | X₃-phenyl | | X₅-CH₂-(4-OH, 3-CH₂OH phenyl) | X₆-CH₂-cyclohexyl | 1.99 | 537.3355 | 538.3746 |
| 1043 | X₁-phenyl | X₂-CH₂CH₂CH₂-CH₃ | X₃-phenyl | | X₅-CH₂-(3,4-methylenedioxyphenyl) | X₆-CH₂-(4-C(O)NH₂-phenyl) | 1.91 | 572.2787 | 573.3109 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1044 |  |  |  | |  |  | 1.88 | 494.3046 | 495.3434 |
| 1045 | 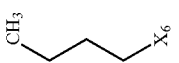 |  |  | |  |  | 1.91 | 572.2821 | 573.3249 |
| 1046 |  | 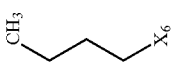 |  |  |  |  | | | |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1047 | phenyl (X1) | X2-(CH2)3-CH3 | phenyl (X3) | | benzodioxole-CH2-X5 | benzyl (X6) | | | |
| 1048 | phenyl (X1) | CH3-(CH2)3-X2 | 4-(OCH2CH2Cl)phenyl-X3 | X4-CH3 | 4-(OCHF2)phenyl-CH2-X5 | X6-(CH2)3-CH3 | 2.04 | 595.2777 | 596.3219 |
| 1049 | phenyl (X1) | CH3-(CH2)3-X2 | 4-(OCH2CH2N(CH3)2)phenyl-X3 | | 3-Cl-4-(CH2-X5)-phenol | X6-(CH2)3-CH3 | 1.85 | 588.3231 | 589.3849 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1050 | X1-phenyl | CH3-(CH2)3-X2 | X3-(4-phenoxy)-CH2CH2-N(CH3)2 | | X5-CH2-(3-hydroxyphenyl) | X6-CH2CH2-CH3 | 1.72 | 554.3621 | 555.4208 |
| 1051 | X1-phenyl | CH3-(CH2)3-X2 | X3-(4-phenoxy)-CH3 | | X5-CH2-(4-(OCHF2)phenyl) | X6-CH2CH2-CH3 | 2 | 547.301 | 548.3278 |
| 1052 | X1-phenyl | CH3-(CH2)3-X2 | X3-(4-phenoxy)-CH2CH2-N(CH3)2 | | X5-CH2-(benzo[1,3]dioxol-5-yl) | X6-CH2CH2CH2-CH3 | 1.78 | 582.357 | 583.4136 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1053 | 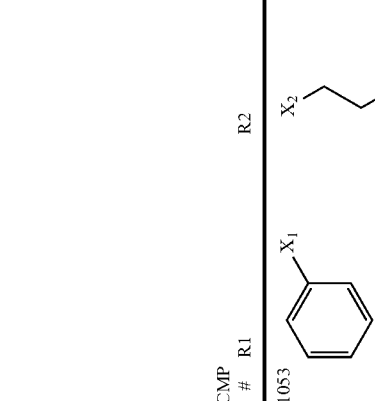 | 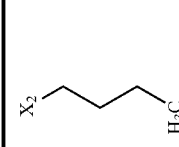 | 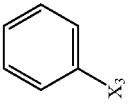 | 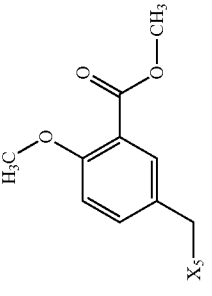 | 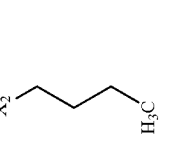 | 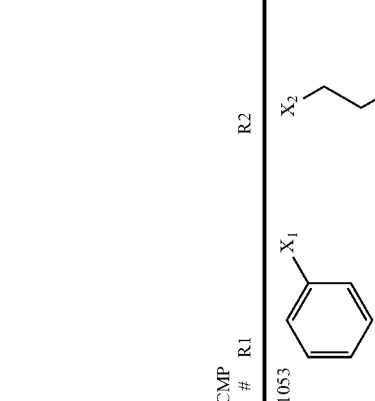 | 1.99 | 573.2991 | 574.3322 |
| 1054 | 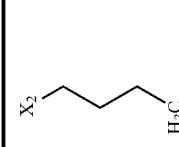 | 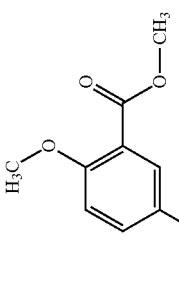 | 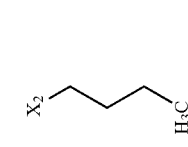 | | 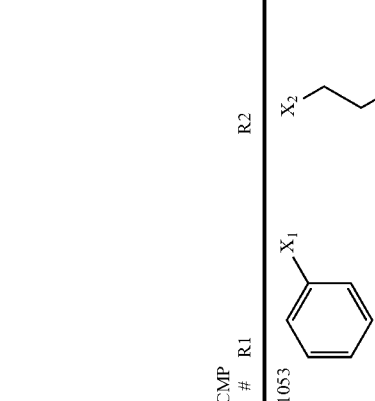 | 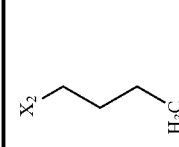 | 1.95 | 539.3148 | 540.3422 |
| 1055 | 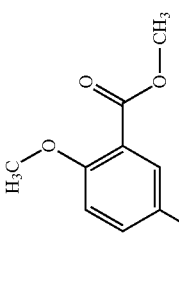 | 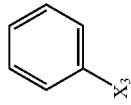 | | | | | 2.1 | 579.3461 | 580.3743 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1056 | phenyl (X1) | butyl (X2) | phenyl (X3) | | 2-methoxy-5-(X5-methyl)benzyl alcohol | benzyl (X6) | 1.97 | 545.3042 | 546.3319 |
| 1057 | phenyl (X1) | butyl (X2) | phenyl (X3) | | 2-methoxy-5-(X5-methyl)benzyl alcohol | n-butyl (X6) | 1.81 | 511.3199 | 512.3505 |
| 1058 | phenyl (X1) | butyl (X2) | phenyl (X3) | | 2-methoxy-5-(X5-methyl)benzyl alcohol | cyclohexylmethyl (X6) | 2.04 | 551.3512 | 552.3825 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1059 | 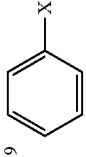 | 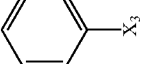 | 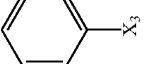 | | 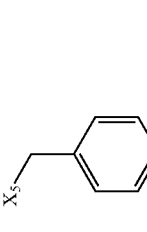 | 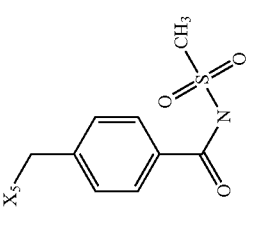 | 1.93 | 606.2665 | 607.3164 |
| 1060 | 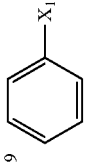 | 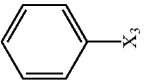 | 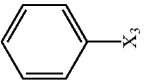 | | 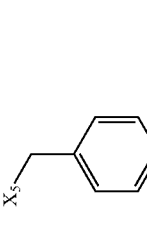 | 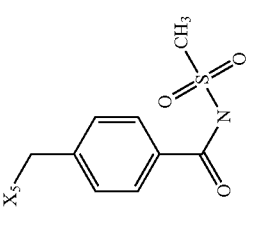 | 1.91 | 528.2889 | 529.3276 |
| 1061 | 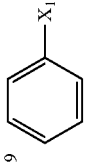 | 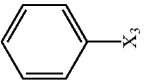 | 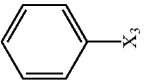 | | 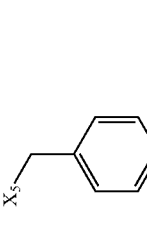 | 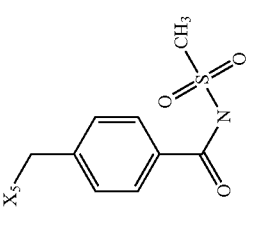 | | | |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1062 | 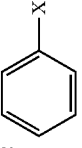 | 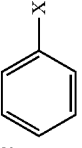 |  | | 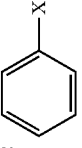 |  | 1.98 | 527.2971 | 508.3281 |
| 1063 | 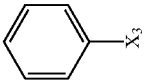 |  |  | |  |  | 2.09 | 561.2814 | 562.3166 |
| 1064 |  |  |  | |  |  | 1.87 | 608.2457 | 609.2976 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1065 | phenyl-X₁ | H₃C-CH₂CH₂CH₂-X₂ | phenyl-X₃ | | X₅-CH₂-C₆H₄-SO₂NH₂ | 4-methoxybenzyl-X₆ | | | |
| 1066 | phenyl-X₁ | H₃C-CH₂CH₂CH₂-X₂ | phenyl-X₃ | | X₅-CH₂-C₆H₄-SO₂NHC(O)CH₃ | n-butyl-X₆ | 1.9 | 572.2821 | 573.3206 |

TABLE 2-continued

| CMP # | R1 | R2 | R3 | R4 R5 | R6 | Rtn. Time | Cmd. Mass | H+ Ion Obs |
|---|---|---|---|---|---|---|---|---|
| 1067 | phenyl-X1 | H3C-CH2-CH2-CH2-X2 | phenyl-X3 | 4-sulfamoylbenzyl-X5 | 4-hydroxybenzyl-X6 | 1.79 | 580.2508 | 581.3011 |
| 1068 | phenyl-X1 | H3C-CH2-CH2-CH2-X2 | phenyl-X3 | benzo[1,3]dioxol-5-ylmethyl-X5 | 4-(N-acetylsulfamoyl)benzyl-X6 | 1.9 | 650.2563 | 651.3043 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1069 | phenyl (X1) | H3C-CH2CH2CH2-X2 | phenyl (X3) | | 4-(X5-CH2)-C6H4-SO2-NH-C(O)CH3 | benzyl (X6) | 1.92 | 606.2665 | 607.2383 |
| 1070 | phenyl (X1) | H3C-CH2CH2CH2-X2 | phenyl (X3) | | benzo[1,3]dioxol-5-ylmethyl (X5) | 4-(X6-CH2)-C6H4-C(O)-NH-SO2-CH3 | 1.9 | 650.2563 | 651.2313 |

TABLE 2-continued
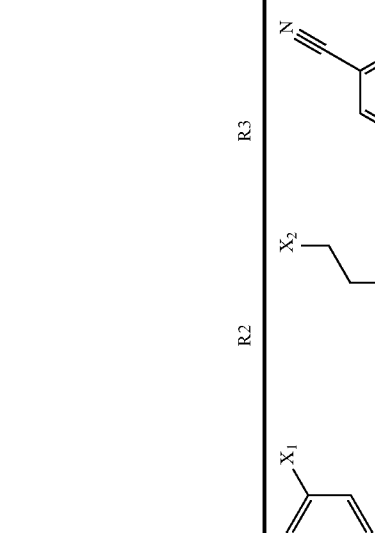
| CMP # | R1 | R2 | R3 | R4 | R5 | R6 | Rtn. Time | Cmd. Mass | H+ Ion Obs |
|---|---|---|---|---|---|---|---|---|---|
| 1071 | 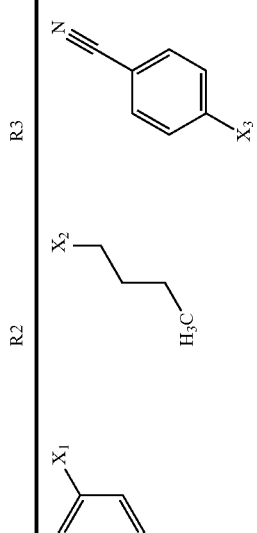 |  |  | |  |  | 1.96 | 520.2838 | 521.3221 |
| 1072 |  |  |  | |  |  | 1.88 | 602.2927 | 603.3342 |
| 1073 |  |  |  | |  |  | 1.93 | 631.3192 | 632.3643 |
| 1074 |  |  |  | |  | 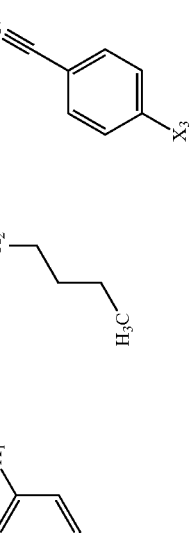 | 1.78 | 552.3464 | 553.3979 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1075 |  |  |  | |  |  | 1.9 | 582.3206 | 583.3616 |
| 1076 |  |  |  | |  |  | 1.95 | 534.2995 | 535.3354 |
| 1077 |  |  |  | |  |  | 1.99 | 571.3311 | 572.3079 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1078 |  |  | 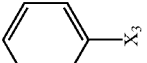 | |  |  | 1.75 | 574.2978 | 575.2848 |
| 1079 |  |  | 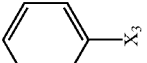 | |  |  | 1.97 | 614.329 | 615.3132 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1080 | 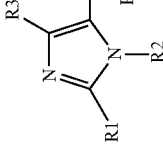 |  | 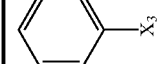 |  |  |  | 1.97 | 587.2784 | 588.2736 |
| 1081 | 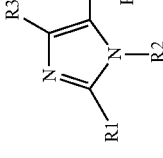 |  | 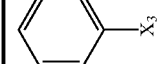 | |  |  | 1.78 | 608.2457 | 609.2491 |
| 1082 | 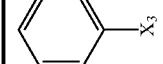 |  | | | | | 2.03 | 531.2653 | 532.2452 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1083 | 3-CH3O-phenyl-X1 | H3C-(CH2)3-X2 | phenyl-X3 | | benzo[1,3]dioxol-5-ylmethyl-X5 | X6-(CH2)3-CH3 | 1.97 | 525.2991 | 526.2742 |
| 1084 | 3-CH3O-phenyl-X1 | H3C-(CH2)3-X2 | phenyl-X3 | | 4-carboxybenzyl-X5 | X6-(CH2)3-CH3 | 1.98 | 525.2991 | 529.2836 |
| 1085 | phenyl-X1 | H3C-(CH2)3-X2 | phenyl-X3 | | 2-methoxy-4-[(methanesulfonyl-methylamino)methyl]benzyl-X5 | CH3-(CH2)3-X6 | 1.82 | 588.3134 | 589.3152 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1086 | 3-methoxyphenyl (X1) | butyl (X2) | phenyl (X3) | | 4-(methyl)benzyl (X5) | butyl (X6) | 1.93 | 511.3199 | 512.2905 |
| 1087 | 3-methoxyphenyl (X1) | butyl (X2) | phenyl (X3) | | 2-chloro-4-hydroxybenzyl (X5) | benzyl (X6) | 2.06 | 565.2496 | 566.2386 |
| 1088 | 3-methoxyphenyl (X1) | butyl (X2) | phenyl (X3) | | benzo[1,3]dioxol-5-ylmethyl (X5) | benzyl (X6) | 2.07 | 559.2835 | 560.2629 |

TABLE 2-continued
| CMP # | R1 | R2 | R3 | R4 R5 | R6 | Rtn. Time | Cmd. Mass | H+ Ion Obs |
|---|---|---|---|---|---|---|---|---|
| 1089 |  | 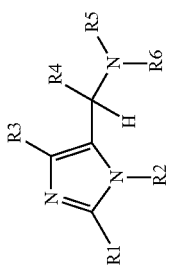 | 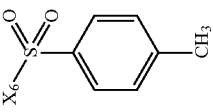 | 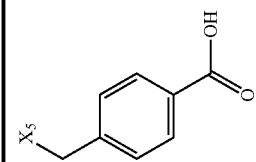 | 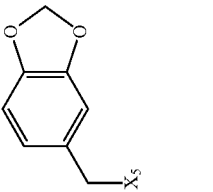 | 1.99 | 559.2835 | 560.2698 |
| 1090 | 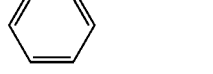 | 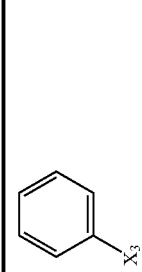 | 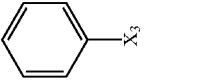 | 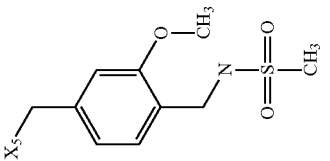 |  | 2.02 | 628.3447 | 629.3398 |
| 1091 | 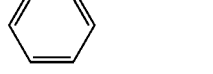 | 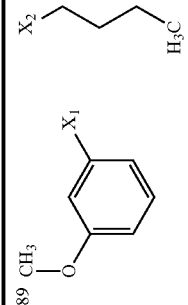 |  | 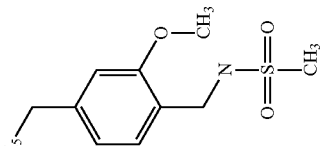 | 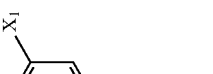 | 2 | 593.2348 | 594.2117 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1092 | X₁-phenyl | H₃C-CH₂-CH₂-CH₂-X₂ | X₃-phenyl | | X₅-CH₂-C₆H₄-C(O)OCH₃ | X₆-CH₂-C₆H₄-OH (4-OH) | 1.95 | 559.2835 | 560.2643 |
| 1093 | X₁-phenyl | H₃C-CH₂-CH₂-CH₂-X₂ | X₃-phenyl | | X₅-CH₂-C₆H₄-C(O)OCH₃ | X₆-CH₂-C₆H₃(Cl)-OH | 2.02 | 593.2445 | 594.2274 |

TABLE 2-continued

| CMP # | R1 | R2 | R3 | R4 R5 | R6 | Rtn. Time | Cmd. Mass | H+ Ion Obs |
|---|---|---|---|---|---|---|---|---|
| 1094 | phenyl (X₁) | H₃C-CH₂-CH₂-CH₂-X₂ | phenyl (X₃) | 4-(methoxycarbonyl)benzyl (X₅) | 4-methoxybenzyl (X₆) | 2.03 | 573.2991 | 574.271 |
| 1095 | phenyl (X₁) | H₃C-CH₂-CH₂-CH₂-X₂ | phenyl (X₃) | 4-sulfamoylbenzyl (X₅) | 4-carbamoylbenzyl (X₆) | 1.71 | 607.2617 | 608.2644 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1096 | phenyl (X1) | H3C-CH2CH2CH2-X2 | phenyl (X3) | | 3,5-bis(ethoxycarbonyl)benzyl (X5) | benzyl (X6) | 2.11 | 629.3254 | 630.3112 |
| 1097 | phenyl (X1) | H3C-CH2CH2CH2-X2 | phenyl (X3) | | 3,5-bis(ethoxycarbonyl)benzyl (X5) | n-butyl (CH3(CH2)3-, X6) | 2.11 | 595.341 | 596.3187 |
| 1098 | phenyl (X1) | H3C-CH2CH2CH2-X2 | phenyl (X3) | | 4-carboxybenzyl (X5) | 4-hydroxybenzyl (X6) | 1.89 | 545.2678 | 546.2605 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1099 | X1-phenyl | H3C-(CH2)3-X2 | X3-phenyl | | 3-Cl-4-OH-benzyl (X5) | 4-(CO2H)-benzyl (X6) | 1.96 | 579.2289 | 580.2228 |
| 1100 | X1-phenyl | H3C-(CH2)3-X2 | X3-phenyl | | 4-(CO2H)-benzyl (X5) | 4-OCH3-benzyl (X4) | 1.97 | 559.2835 | 560.2682 |
| 1101 | X1-phenyl | H3C-(CH2)3-X2 | X3-phenyl | | 3,5-(CO2H)2-benzyl (X5) | benzyl (X6) | 1.94 | 573.2628 | 574.2623 |

TABLE 2-continued
| CMP # | R1 | R2 | R3 | R4 R5 | R6 | Rtn. Time | Cmd. Mass | H+ Ion Obs |
|---|---|---|---|---|---|---|---|---|
| 1102 |  | 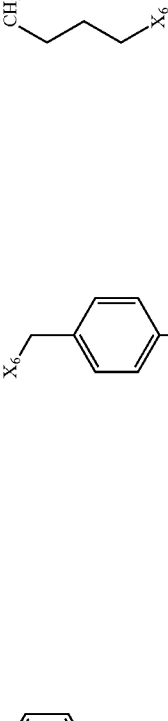 | 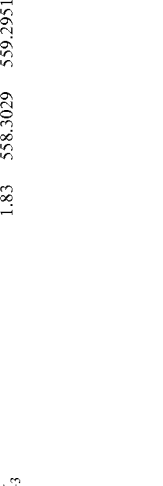 |  | 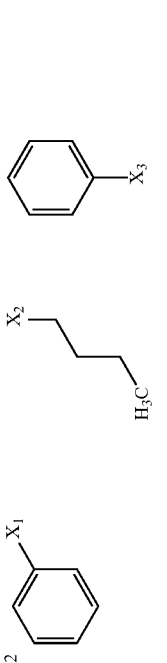 | 1.83 | 558.3029 | 559.2951 |
| 1103 |  | 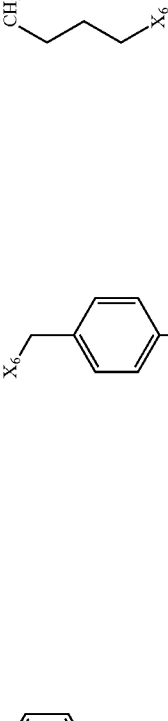 | 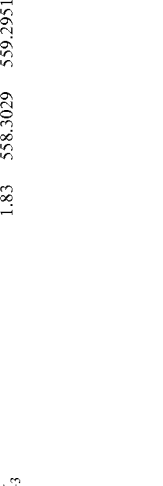 | 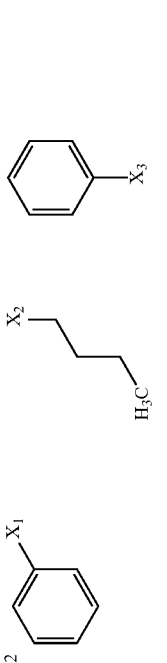 |  | 1.87 | 531.2886 | 532.2817 |
| 1104 |  | 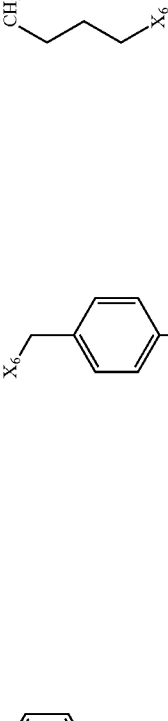 | 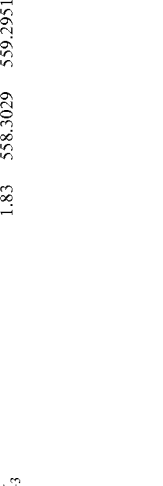 | 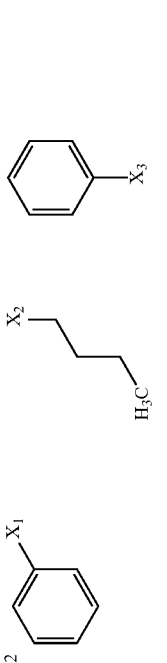 |  | 1.93 | 565.2496 | 566.248 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1105 | phenyl (X1) | H3C-CH2CH2CH2-X2 | phenyl (X3) | | 1,4-bis(hydroxymethyl)benzyl (X5) | 4-methoxybenzyl (X6) | 1.95 | 565.3042 | 546.2853 |
| 1106 | phenyl (X1) | H3C-CH2CH2CH2-X2 | phenyl (X3) | | 3,5-bis(hydroxymethyl)benzyl (X5) | benzyl (X6) | 1.89 | 545.3042 | 546.2955 |
| 1107 | phenyl (X1) | H3C-CH2CH2CH2-X2 | phenyl (X3) | | 3,5-bis(hydroxymethyl)benzyl (X5) | cyclohexylmethyl (X6) | 1.98 | 551.3512 | 552.3348 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1108 | benzyl (X1-phenyl) | X2-CH2CH2CH3 | X3-phenyl | | X5-benzo[1,3]dioxole | X6-4-sulfamoylbenzyl | 1.83 | 594.2301 | 595.2273 |
| 1109 | H3CO-phenyl-X1 | X2-(CH2)3-CH3 | X3-phenyl | | X5-CH2-(3-Cl-4-OH-phenyl) | X6-(CH2)3-CH3 | 2.01 | 531.2653 | 532.2531 |
| 1110 | H3CO-phenyl-X1 | X2-(CH2)3-CH3 | X3-phenyl | | X5-CH2-(4-OH-phenyl) | X6-(CH2)3-CH3 | 1.8 | 497.3042 | 498.2937 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1111 | H3C-O-C6H4-X1 | X2-CH2CH2CH2-CH3 | C6H5-X3 | | benzodioxole-CH2-X5 | X6-CH2CH2CH2-CH3 | 1.96 | 525.2991 | 526.2787 |
| 1112 | H3C-O-C6H4-X1 | X2-CH2CH2CH2-CH3 | C6H5-X3 | | 3-Cl-4-OH-C6H3-CH2-X5 | X6-CH2-C6H5 | 2.04 | 565.2496 | 566.2412 |
| 1113 | H3C-O-C6H4-X1 | X2-CH2CH2CH2-CH3 | C6H5-X3 | | benzodioxole-CH2-X5 | X6-CH2-C6H5 | 2.06 | 559.2835 | 560.2628 |
| 1114 | H3C-O-C6H4-X1 | X2-CH2CH2CH2-CH3 | C6H5-X3 | | 4-SO2NH2-C6H4-CH2-X5 | X6-CH2-C6H5 | 1.89 | 594.2665 | 295.256 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1115 | phenyl-X₁ | X₂-(CH₂)₃-CH₃ | 4-methoxyphenyl-X₃ | | X₅-CH₂-C₆H₄-COOH | X₆-(CH₂)₃-CH₃ | 1.97 | 252.2991 | 526.292 |
| 1116 | phenyl-X₁ | X₂-(CH₂)₃-CH₃ | 4-methoxyphenyl-X₃ | | X₅-CH₂-C₆H₄-SO₂NH₂ | X₆-(CH₂)₃-CH₃ | 1.87 | 260.2821 | 561.2739 |
| 1117 | 2-methoxyphenyl-X₁ | X₂-(CH₂)₃-CH₃ | phenyl-X₃ | | X₅-CH₂-C₆H₄-SO₂NH₂ | X₆-(CH₂)₃-CH₃ | 1.86 | 560.2821 | 561.2766 |

TABLE 2-continued

| CMP # | R1 | R2 | R3 | R4 R5 | R6 | Rtn. Time | Cmd. Mass | H+ Ion Obs |
|---|---|---|---|---|---|---|---|---|
| 1118 | 3-methoxyphenyl | X2-(CH2)3-CH3 | phenyl (X3) | X5-benzyl-sulfonamide | X6-(CH2)3-CH3 | 1.88 | 560.2821 | 561.2753 |
| 1119 | 3-methoxyphenyl | X2-(CH2)3-CH3 | phenyl (X3) | X5-benzamide | X6-(CH2)3-CH3 | 1.89 | 524.3151 | 525.3075 |
| 1120 | phenyl | X2-(CH2)3-C(O)O-CH3 | phenyl (X3) | X5-methylenedioxyphenyl | X6-methyl 4-benzoate | 2 | 645.2839 | 646.274 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1121 | phenyl (X1) | ethyl 4-X2-butanoate | phenyl (X3) | | methyl 4-(X6-methyl)benzoate | 3-chloro-4-hydroxyphenyl-X6-methyl | 1.99 | 651.25 | 652.2567 |
| 1122 | phenyl (X1) | ethyl 4-X2-butanoate | phenyl (X3) | | methyl 4-(X6-methyl)benzoate | 4-methoxyphenyl-X6-methyl | 2.01 | 631.3049 | 632.2967 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1123 |  |  | 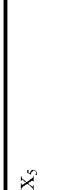 | |  |  | 1.89 | 644.3362 | 645.35 |
| 1124 | 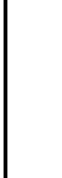 |  |  | |  |  | 2.01 | 631.2682 | 632.2625 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1125 | phenyl (X1) | ethyl 4-X2-butanoate | phenyl (X3) | | benzo[1,3]dioxol-5-ylmethyl (X5) | 3-chloro-4-hydroxybenzyl (X6) | 2 | 637.2344 | 638.2382 |
| 1126 | phenyl (X1) | ethyl 4-X2-butanoate | phenyl (X3) | | benzo[1,3]dioxol-5-ylmethyl (X5) | 4-methoxybenzyl (X6) | 2.01 | 617.289 | 618.2725 |
| 1127 | phenyl (X1) | ethyl 4-X2-butanoate | phenyl (X3) | | benzo[1,3]dioxol-5-ylmethyl (X5) | 4-(N,N-dimethylamino)benzyl (X6) | 1.9 | 630.3206 | 631.3359 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1128 | phenyl (X1) | H3C-CH2CH2CH2-X2 | phenyl (X3) | | 4-(trifluoromethoxy)benzyl (X5) | methyl 4-(X6-methyl)benzoate | 2.07 | 627.2709 | 628.2573 |
| 1129 | phenyl (X1) | H3C-CH2CH2CH2-X2 | phenyl (X3) | | 3-methoxybenzyl (X5) | methyl 4-(X6-methyl)benzoate | 2.02 | 573.2991 | 574.2791 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1130 | 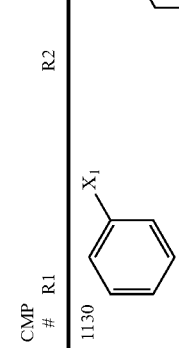 | 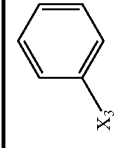 |  | |  |  | 1.92 | 586.3307 | 587.3427 |
| 1131 | 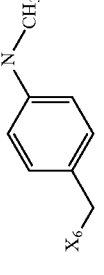 | 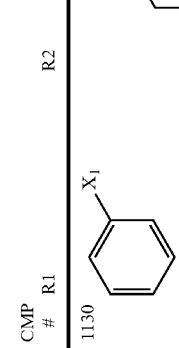 |  | |  |  | | | |
| 1132 | 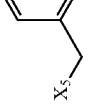 | 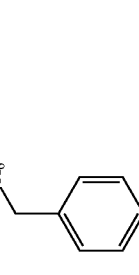 |  | |  |  | 1.87 | 561.2991 | 562.3006 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1133 | X₁–phenyl | X₂–(CH₂)₄–OH | X₃–phenyl | | X₅–(4-N,N-dimethylamino)benzyl | X₆–(4-hydroxymethyl)benzyl | | | |
| 1134 | X₁–phenyl | X₂–(CH₂)₄–OH | X₃–phenyl | | X₅–(benzo[1,3]dioxol-5-yl)methyl | X₆–(benzo[1,3]dioxol-5-yl)methyl | | | |
| 1135 | X₁–phenyl | X₂–(CH₂)₄–OH | X₃–phenyl | | X₅–(benzo[1,3]dioxol-5-yl)methyl | X₆–(2,4-dihydroxy)benzyl | | | |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1136 | X₁–Ph | X₂–(CH₂)₄–OH | X₃–Ph | | X₅–CH₂–(benzo[1,3]dioxole) | X₆–C₆H₄–OCH₃ | | | |
| 1137 | X₁–Ph | X₂–(CH₂)₄–OH | X₃–Ph | | X₅–CH₂–(benzo[1,3]dioxole) | X₆–C₆H₄–N(CH₃)₂ | | | |
| 1138 | X₁–Ph | X₂–(CH₂)₃–CH₃ | X₃–Ph | | X₅–CH₂–C₆H₄–OCF₃ | X₆–CH₂–C₆H₄–CH₂OH | | | |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1139 | phenyl (X1) | butyl (X2) | phenyl (X3) | | 3-methoxyphenyl (X5) | 4-(hydroxymethyl)phenyl (X6) | 1.81 | 558.3359 | 559.3449 |
| 1140 | phenyl (X1) | butyl (X2) | phenyl (X3) | | 4-(N,N-dimethylamino)phenyl (X5) | 4-(hydroxymethyl)phenyl (X6) | | | |
| 1141 | phenyl (X1) | 3-carboxypropyl (X2) | phenyl (X3) | benzo[1,3]dioxol-5-yl (X4) | benzo[1,3]dioxol-5-ylmethyl (X5) | | 1.96 | 603.2369 | 604.2373 |

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1142 | 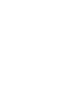 |  | 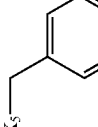 | |  |  | 1.95 | 609.2031 | 610.2124 |
| 1143 | 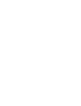 |  |  | |  |  | 2.02 | 613.2552 | 614.2456 |
| 1144 |  |  |  | | 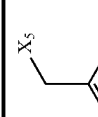 | 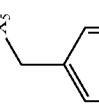 | 1.96 | 559.2835 | 560.2794 |
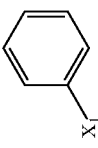

TABLE 2-continued
| CMP # | R1 | R2 | R3 | R4 | R5 | R6 | Rtn. Time | Cmd. Mass | H+ Ion Obs |
|---|---|---|---|---|---|---|---|---|---|
| 1145 |  | 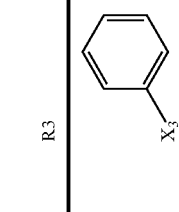 | 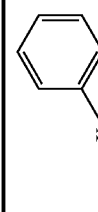 | | 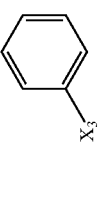 | 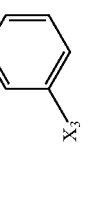 | 1.86 | 572.3151 | 573.3293 |
| 1146 | 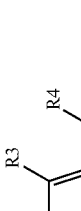 | 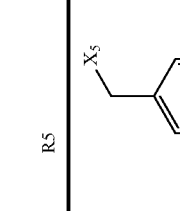 | 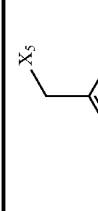 | | 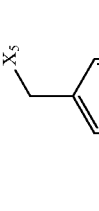 | 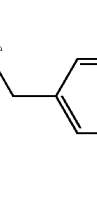 | 1.98 | 603.2733 | 604.278 |
| 1147 |  |  |  | | 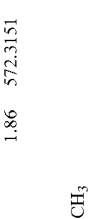 |  | 2.05 | 575.3148 | 576.3073 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1148 | X1-Ph | H3C-CH2CH2CH2-X2 | Ph-X3 | | X5-CH2-(3-OCH3-5-CO2CH3-C6H3) | X6-CH2CH2CH2-CH3 | 2.04 | 539.3148 | 540.3035 |
| 1149 | X1-Ph | H3C-CH2CH2CH2-X2 | Ph-X3 | | X5-CH2-(3-OCH3-5-CO2CH3-C6H3) | X6-CH2-(4-CO2CH3-C6H4) | 2.01 | 631.3046 | 632.2966 |
| 1150 | X1-Ph | H3C-CH2CH2CH2-X2 | Ph-X3 | X4-CH3 | X5-CH2-(4-CONH2-C6H4) | X6-CH2CH2CH2-CH3 | 1.91 | 508.3202 | 509.323 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1151 | X1-phenyl | X2-(CH2)3-CH3 | X3-phenyl | | 3,5-dimethyl-4-hydroxybenzyl-X5 | X6-CH2-cyclohexyl | 2.1 | 535.3563 | 536.3535 |
| 1152 | X1-phenyl | X2-(CH2)3-CH3 | X3-phenyl | | 3-methyl-4-hydroxybenzyl-X5 | X6-CH2-cyclohexyl | 2.07 | 521.3406 | 522.3412 |
| 1153 | X1-phenyl | X2-(CH2)3-CH3 | X3-phenyl | | 3-methoxy-5-(hydroxymethyl)benzyl-X5 | X6-(CH2)3-CH3 | 1.88 | 511.3199 | 512.3171 |
| 1154 | X1-phenyl | X2-(CH2)3-CH3 | X3-phenyl | | 3,5-bis(methoxy... hydroxymethyl)benzyl-X5 | X5-CH2-(4-hydroxymethyl)phenyl | 1.85 | 575.3148 | 576.3098 |

TABLE 2-continued

| CMP # | R1 | R2 | R3 | R4 | R5 | R6 | Rtn. Time | Cmd. Mass | H+ Ion Obs |
|---|---|---|---|---|---|---|---|---|---|
| 1155 | X1-phenyl | H3C-CH2CH2CH2-X2 | X3-phenyl | X4-CH3 | X5-CH2-(3,5-dimethyl-4-hydroxyphenyl) | X5-CH2CH2CH2-CH3 | 1.91 | 509.3406 | 510.3491 |
| 1156 | X1-phenyl | H3C-CH2CH2CH2-X2 | X3-phenyl | | X5-CH2-(3,5-dimethyl-4-hydroxyphenyl) | X6-CH2CH2CH2-CH3 | 1.86 | 495.325 | 496.3272 |

TABLE 2A

| CMP # | R1 | R2 | R3 | R4 | R5 | R6 | Rtn. Time | Cmp. Mass | H+ Ion Obs |
|---|---|---|---|---|---|---|---|---|---|
| | | | | R4 is H unless otherwise specified | | | | | |
| 1157 | X₁-phenyl | H₃C-(CH₂)₃-X₂ | X₃-phenyl | | X₅-CH₂-phenyl | X₆-(CH₂)₃-CH₃ | 1.98 | 451.2987 | 452.3944 |
| 1158 | X₁-phenyl | H₃C-(CH₂)₄-X₂ | X₃-phenyl | | X₅-CH₂-phenyl | X₆-CH₂-phenyl | 2.07 | 485.2831 | 486.3753 |
| 1159 | X₁-phenyl | H₃C-(CH₂)₄-X₂ | X₃-phenyl | | X₅-CH₂-(4-methoxyphenyl) | X₆-CH₂-phenyl | 2.05 | 515.2936 | 516.3962 |
| 1160 | X₁-phenyl | H₃C-(CH₂)₄-X₂ | X₃-phenyl | | X₅-CH₂-phenyl | X₆-CH₂-cyclohexyl | 2.15 | 491.33 | 492.4342 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1161 | 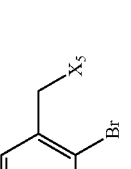 | 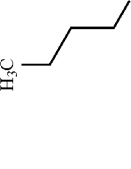 | 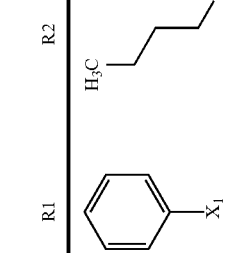 | | 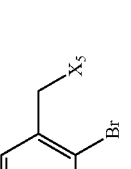 | 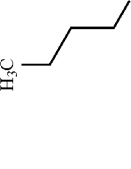 | 2.11 | 529.2093 | 530.32 |
| 1162 | 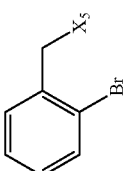 | 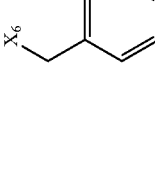 | 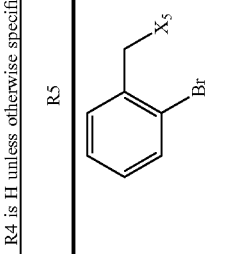 | | 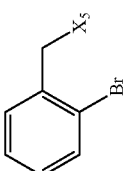 | 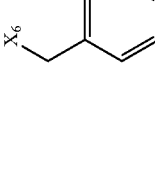 | 2.11 | 563.1936 | 564.31 |
| 1163 | 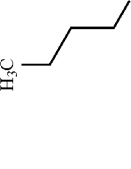 | 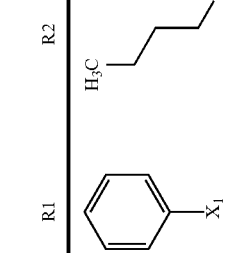 | 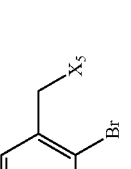 | | 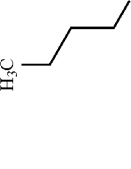 | 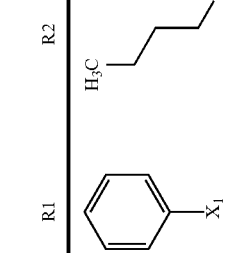 | 2.11 | 593.2042 | 594.33 |
| 1164 | 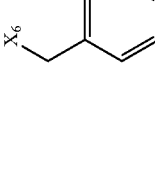 | 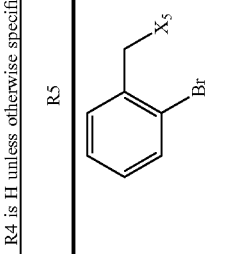 | 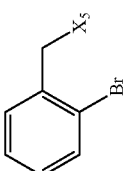 | | 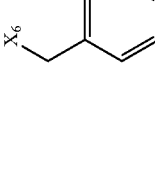 | 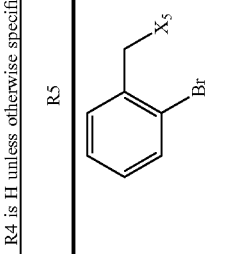 | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1165 | X1-phenyl | H3C-CH2CH2CH2-X2 | X3-phenyl | | 2-F-benzyl-X5 | X2-CH2CH2CH2-CH3 | 2.05 | 469.2893 | 470.3595 |
| 1166 | X1-phenyl | H3C-CH2CH2CH2-X2 | X3-phenyl | | 2-F-benzyl-X5 | X6-benzyl | 2.06 | 503.2737 | 504.3713 |
| 1167 | X1-phenyl | H3C-CH2CH2CH2-X2 | X3-phenyl | | 4-OCH3-benzyl-X5 | 2-F-benzyl-X6 | 2.05 | 533.2442 | 534.3885 |
| 1168 | X1-phenyl | H3C-CH2CH2CH2-X2 | X3-phenyl | | 2-F-benzyl-X5 | X6-CH2-cyclohexyl | 2.15 | 504.3206 | 510.9258 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1169 | phenyl-X₁ | H₃C-(CH₂)₃-X₂ | phenyl-X₃ | | 2-Cl-benzyl-X₅ | X₆-(CH₂)₃-CH₃ | 2.10 | 485.2578 | 486.3618 |
| 1170 | phenyl-X₁ | H₃C-(CH₂)₃-X₂ | phenyl-X₃ | | 2-Cl-benzyl-X₅ | X₆-benzyl | 2.09 | 579.2441 | 520.3508 |
| 1171 | phenyl-X₁ | H₃C-(CH₂)₃-X₂ | phenyl-X₃ | | 4-OCH₃-benzyl-X₆ | 2-Cl-benzyl-X₆ | 2.10 | 549.2547 | 550.3768 |
| 1172 | phenyl-X₁ | H₃C-(CH₂)₃-X₂ | phenyl-X₃ | | 2-Cl-benzyl-X₅ | cyclohexylmethyl-X₆ | 2.18 | 525.2911 | 526.4115 |

TABLE 2A-continued
| CMP # | R1 | R2 | R3 | R4 | R5 | R6 | Rtn. Time | Cmp. Mass | H+ Ion Obs |
|---|---|---|---|---|---|---|---|---|---|
| | | | | R4 is H unless otherwise specified | | | | | |
| 1173 | 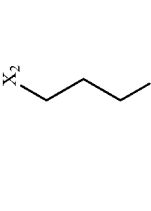 | 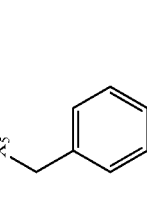 | 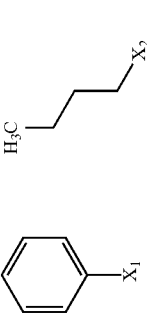 | | 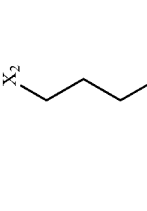 | 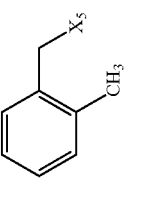 | 2.06 | 465.3144 | 466.4148 |
| 1174 | 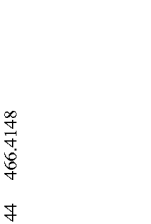 | 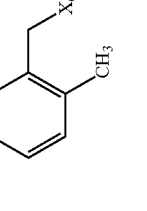 | 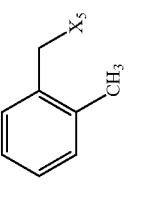 | | 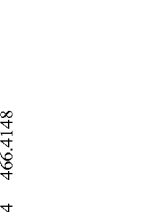 | 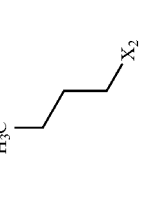 | 2.10 | 499.2987 | 500.4062 |
| 1175 | 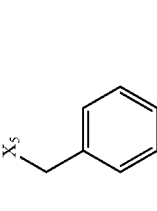 | 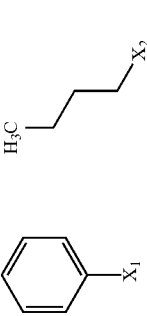 | 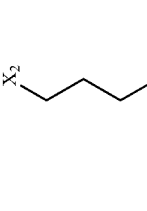 | | 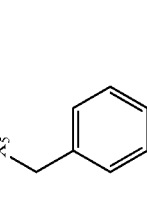 | 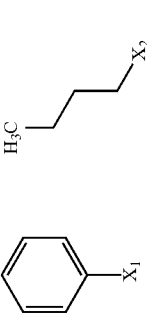 | 2.10 | 529.3093 | 530.4219 |
| 1176 | 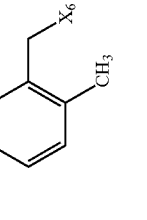 | 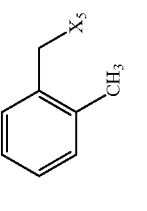 | 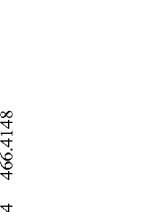 | | 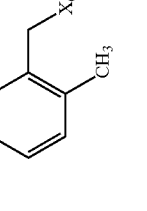 | 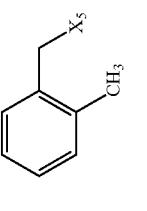 | | | |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1177 | 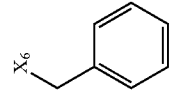 | 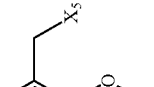 | 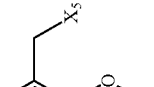 | | 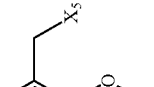 | 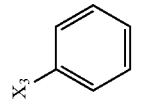 | 1.86 | 481.3093 | 482.4177 |
| 1178 | 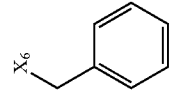 | 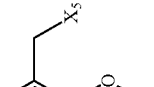 | 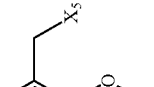 | | 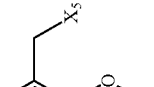 | 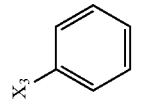 | 2.07 | 515.2036 | 516.4023 |
| 1179 | 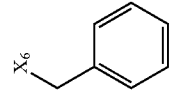 | 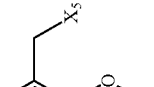 | 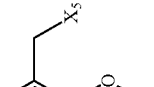 | | 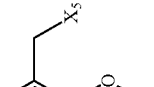 | 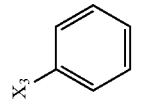 | 2.06 | 545.3042 | 546.4252 |
| 1180 | 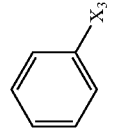 | 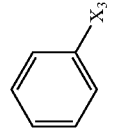 | 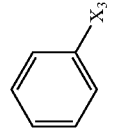 | | 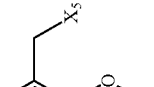 | 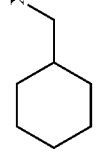 | 2.12 | 621.3408 | 622.4584 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1181 | Ph-X1 | H3C-(CH2)3-X2 | Ph-X3 | | 2-CF3-benzyl-X5 | H3C-(CH2)3-X6 | 2.11 | 619.2881 | 520.4012 |
| 1182 | Ph-X1 | H3C-(CH2)3-X2 | Ph-X3 | | 2-CF3-benzyl-X5 | benzyl-X6 | 2.09 | 553.2705 | 554.3881 |
| 1183 | Ph-X1 | H3C-(CH2)3-X2 | Ph-X3 | | 2-CF3-benzyl-X5 | 4-methoxybenzyl-X6 | 2.1 | 583.2811 | 584.4048 |
| 1184 | Ph-X1 | H3C-(CH2)3-X2 | Ph-X3 | | 2-CF3-benzyl-X5 | cyclohexylmethyl-X6 | 2.17 | 559.3174 | 560.4424 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1185 |  | 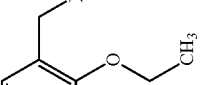 | 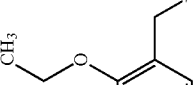 | | 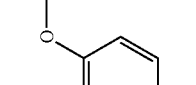 |  | 1.95 | 495.325 | 496.4399 |
| 1186 | 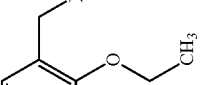 | 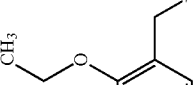 | 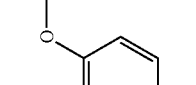 | |  | 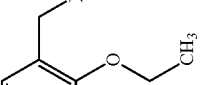 | 2.11 | 529.3093 | 530.4105 |
| 1187 | 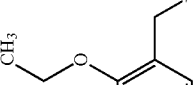 | 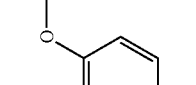 |  | | 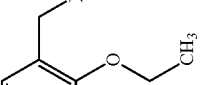 | 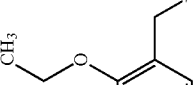 | 2.09 | 559.3199 | 560.4452 |
| 1188 | 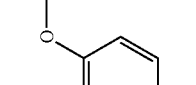 | | | | | | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1189 | phenyl-X₁ | H₃C-(CH₂)₃-X₂ | X₃-phenyl | | 2,4-dichlorobenzyl-X₅ | X₆-(CH₂)₃-CH₃ | 2.15 | 519.2208 | 520.3397 |
| 1190 | phenyl-X₁ | H₃C-(CH₂)₃-X₂ | X₃-phenyl | | 2,4-dichlorobenzyl-X₅ | X₆-CH₂-phenyl | 2.15 | 553.2051 | 554.3284 |
| 1191 | phenyl-X₁ | H₃C-(CH₂)₃-X₂ | X₃-phenyl | | 2,4-dichlorobenzyl-X₅ | X₆-CH₂-cyclohexyl | 2.26 | 559.2521 | 560.3608 |
| 1192 | phenyl-X₁ | H₃C-(CH₂)₃-X₂ | X₃-phenyl | | 2,4-dimethoxybenzyl-X₅ | X₆-(CH₂)₃-CH₃ | 1.85 | 511.3199 | 512.4327 |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| 1193 | phenyl-X1 | H3C-(CH2)3-X2 | phenyl-X3 | | 2,4-dimethoxybenzyl-X5 | benzyl-X6 | 2.05 | 545.3042 | 546.4219 |
| 1194 | phenyl-X1 | X2-(CH2)3-CH3 | phenyl-X3 | | 2,4-dimethoxybenzyl-X5 | 4-methoxybenzyl-X6 | 2.04 | 575.3148 | 576.4352 |
| 1195 | phenyl-X1 | X2-(CH2)3-CH3 | phenyl-X3 | | 2,4-dimethoxybenzyl-X5 | cyclohexylmethyl-X6 | 2.09 | 551.3512 | 552.4758 |
| 1196 | phenyl-X1 | H3C-(CH2)3-X2 | phenyl-X3 | | 2,5-dimethoxybenzyl-X5 | X6-(CH2)3-CH3 | 1.91 | 511.3199 | 512.4281 |

R4 is H unless otherwise specified

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1197 | phenyl-X₁ | H₃C-(CH₂)₃-X₂ | phenyl-X₃ | | 2,5-dimethoxybenzyl-X₅ | benzyl-X₆ | 2.05 | 545.3042 | 546.4178 |
| 1198 | phenyl-X₁ | X₂-(CH₂)₃-CH₃ | phenyl-X₃ | | 2,5-dimethoxy-methylbenzyl-X₅ | 4-methoxybenzyl-X₆ | 2.05 | 575.3148 | 576.4329 |
| 1199 | phenyl-X₁ | X₂-(CH₂)₃-CH₃ | phenyl-X₃ | | 2,5-dimethoxy-methylbenzyl-X₅ | cyclohexylmethyl-X₆ | 2.12 | 551.3512 | 552.4684 |
| 1200 | phenyl-X₁ | H₃C-(CH₂)₃-X₂ | phenyl-X₃ | | 4-bromobenzyl-X₅ | X₆-(CH₂)₃-CH₃ | 2.09 | 529.2093 | 530.33 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1201 | X₁-phenyl | H₃C-(CH₂)₃-X₂ | X₃-phenyl | | X₅-CH₂-C₆H₄-Br | X₆-CH₂-phenyl | 2.11 | 563.1936 | 564.32 |
| 1202 | X₁-phenyl | H₃C-(CH₂)₃-X₂ | X₃-phenyl | | X₅-CH₂-C₆H₄-OCH₃ | X₆-CH₂-C₆H₄-Br | 2.11 | 593.2042 | 594.34 |
| 1203 | X₁-phenyl | H₃C-(CH₂)₃-X₂ | X₃-phenyl | | X₅-CH₂-C₆H₄-Br | X₆-CH₂-cyclohexyl | | | |
| 1204 | X₁-phenyl | H₃C-(CH₂)₃-X₂ | X₃-phenyl | | X₅-CH₂-C₆H₄-F | X₆-(CH₂)₃-CH₃ | 2 | 469.2893 | 470.3277 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1205 | X₁-phenyl | H₃C-(CH₂)₃-X₂ | X₃-phenyl | | X₅-CH₂-(4-F-phenyl) | X₆-CH₂-phenyl | 2.05 | 503.2737 | 504.3181 |
| 1206 | X₁-phenyl | H₃C-(CH₂)₃-X₂ | X₃-phenyl | | X₅-CH₂-(4-F-phenyl) | X₆-CH₂-cyclohexyl | 2.14 | 509.3206 | 510.3687 |
| 1207 | X₁-phenyl | H₃C-(CH₂)₃-X₂ | X₃-phenyl | | (4-Cl-phenyl)-CH₂-X₅ | X₆-(CH₂)₃-CH₃ | 2.06 | 485.2598 | 486.3074 |
| 1208 | X₁-phenyl | H₃C-(CH₂)₃-X₂ | X₃-phenyl | | X₅-CH₂-(4-Cl-phenyl) | X₆-CH₂-phenyl | 2.1 | 519.2441 | 520.2955 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1209 | X₁-Ph | H₃C-(CH₂)₃-X₂ | X₃-Ph | | 4-MeO-C₆H₄-CH₂-X₅ | 4-Cl-C₆H₄-CH₂-X₆ | 2.09 | 549.2547 | 550.3127 |
| 1210 | X₁-Ph | H₃C-(CH₂)₃-X₂ | X₃-Ph | | 4-Cl-C₆H₄-CH₂-X₅ | cyclohexyl-CH₂-X₆ | 2.19 | 525.2911 | 526.3676 |
| 1211 | X₁-Ph | H₃C-(CH₂)₃-X₂ | X₃-Ph | | 4-Me-C₆H₄-CH₂-X₅ | X₆-(CH₂)₃-CH₃ | 1.99 | 465.3144 | 466.3385 |
| 1212 | X₁-Ph | H₃C-(CH₂)₃-X₂ | X₃-Ph | | 4-HO-C₆H₄-CH₂-X₅ | X₆-CH₂-Ph | 2.1 | 499.2987 | 500.3643 |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| | | | | R4 is H unless otherwise specified | | | | | |
| 1213 | phenyl-X1 | H3C-(CH2)3-X2 | phenyl-X3 | | 4-methoxybenzyl-X5 | 4-methylbenzyl-X6 | 2.19 | 505.3457 | 506.4082 |
| 1214 | phenyl-X1 | H3C-(CH2)3-X2 | phenyl-X3 | | 4-methylbenzyl | cyclohexylmethyl-X6 | | | |
| 1215 | phenyl-X1 | H3C-(CH2)3-X2 | phenyl-X3 | | 1,4-bis(methylene)benzene-X5 | X6-(CH2)3-CH3 | 2.04 | 479.33 | 480.3875 |
| 1216 | phenyl-X1 | H3C-(CH2)3-X2 | phenyl-X3 | | 1,4-bis(methylene)benzene-X5/CH3 | benzyl-X6 | 2.13 | 513.3144 | 514.3647 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1217 | X₁-phenyl | H₃C-(CH₂)₃-X₂ | X₃-phenyl | | X₅-CH₂-C₆H₄-CH₂-CH₃ | X₆-CH₂-(4-methoxyphenyl) | 2.13 | 543.325 | 544.3829 |
| 1218 | X₁-phenyl | H₃C-(CH₂)₃-X₂ | X₃-phenyl | | X₅-CH₂-C₆H₄-CH₂-CH₃ | X₆-CH₂-cyclohexyl | 2.22 | 519.3813 | 520.4385 |
| 1219 | X₁-phenyl | H₃C-(CH₂)₃-X₂ | X₃-phenyl | | H₃C-(CH₂)₃-X₂ | X₆-(CH₂)₃-CH₃ | 1.91 | 481.3093 | 482.3635 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1220 | phenyl-X₁ | H₃C-(CH₂)₃-X₂ | phenyl-X₃ | | 4-methoxybenzyl-X₅ | benzyl-X₆ | 2.06 | 515.2936 | 516.3668 |
| 1221 | phenyl-X₁ | H₃C-(CH₂)₃-X₂ | phenyl-X₃ | | 2,5-dimethoxybenzyl-X₅ | 4-methoxybenzyl-X₆ | 2.05 | 545.3042 | 546.3696 |
| 1222 | phenyl-X₁ | H₃C-(CH₂)₃-X₂ | phenyl-X₃ | | 4-methoxybenzyl-X₅ | cyclohexylmethyl-X₆ | 2.13 | 521.3406 | 522.4055 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1223 | X₁-phenyl | H₃C-(CH₂)₃-X₂ | X₃-phenyl | | X₅-CH₂-(4-OCH₂CH₃-phenyl) | X₆-(CH₂)₃-CH₃ | 1.97 | 495.325 | 496.3876 |
| 1224 | X₁-phenyl | H₃C-(CH₂)₃-X₂ | X₃-phenyl | | 4-(OCH₂CH₃)-benzyl-X₅ | X₆-CH₂-phenyl | 2.09 | 529.3093 | 530.3716 |
| 1225 | X₁-phenyl | H₃C-(CH₂)₃-X₂ | X₃-phenyl | | 4-(OCH₂CH₃)-benzyl-X₅ | X₆-CH₂-(4-OCH₃-phenyl) | 2.08 | 559.3199 | 560.3892 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1226 | X₁-phenyl | H₃C-(CH₂)₃-X₂ | X₃-phenyl | | X₅-CH₂-(4-phenyl)-O-CH₂-CH₃ | X₆-CH₂-cyclohexyl | 2.17 | 535.3563 | 536.4433 |
| 1227 | X₁-phenyl | H₃C-(CH₂)₃-X₂ | X₃-phenyl | | X₅-CH₂-(4-phenyl)-O-(CH₂)₃-CH₃ | X₆-(CH₂)₃-CH₃ | 2.06 | 523.3563 | 524.4395 |
| 1228 | X₁-phenyl | H₃C-(CH₂)₃-X₂ | X₃-phenyl | | X₅-CH₂-(4-phenyl)-O-(CH₂)₃-CH₃ | X₆-CH₂-phenyl | 2.17 | 557.3406 | 558.4227 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1229 |  |  |  | |  |  | 2.16 | 587.3512 | 588.4426 |
| 1230 |  |  |  | |  |  | 2.26 | 563.3876 | 564.4906 |
| 1231 |  |  |  | |  |  | 2.08 | 519.2861 | 520.3691 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1232 | phenyl-X₁ | H₃C-(CH₂)₃-X₂ | phenyl-X₃ | | 4-(trifluoromethyl)benzyl-X₅ | benzyl-X₆ | 2.09 | 553.2705 | 554.355 |
| 1233 | phenyl-X₁ | H₃C-(CH₂)₃-X₂ | phenyl-X₃ | | 4-(trifluoromethyl)benzyl-X₅ | 4-methoxybenzyl-X₆ | 2.08 | 583.2811 | 584.3691 |
| 1234 | phenyl-X₁ | H₃C-(CH₂)₃-X₂ | phenyl-X₃ | | 4-(trifluoromethyl)benzyl-X₅ | cyclohexylmethyl-X₆ | 2.17 | 559.3174 | 560.4126 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1235 | X₁-phenyl | H₃C-(CH₂)₃-X₂ | X₃-phenyl | | 4-(1-methylethyl)benzyl-X₅ | X₆-(CH₂)₃-CH₃ | 2.07 | 493.3457 | 494.4268 |
| 1236 | X₁-phenyl | H₃C-(CH₂)₃-X₂ | X₃-phenyl | | 4-(1-methylethyl)benzyl-X₅ | X₆-CH₂-phenyl | 2.17 | 527.3301 | 528.4103 |
| 1237 | X₁-phenyl | H₃C-(CH₂)₃-X₂ | X₃-phenyl | | 4-(1-methylethyl)benzyl-X₅ | X₆-CH₂-(4-methoxyphenyl) | 2.15 | 557.3406 | 558.4276 |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| | | | | R4 is H unless otherwise specified | | | | | |
| 1238 | X₁-phenyl | H₃C-(CH₂)₃-X₂ | X₃-phenyl | | 4-(X₅-CH₂)-C₆H₄-CH(CH₃)- | X₆-CH₂-cyclohexyl | | | |
| 1239 | X₁-phenyl | H₃C-(CH₂)₃-X₂ | X₃-phenyl | | 4-(X₅-CH₂)-biphenyl | X₆-(CH₂)₃-CH₃ | 2.11 | 527.3301 | 528.4191 |
| 1240 | X₁-phenyl | H₃C-(CH₂)₃-X₂ | X₃-phenyl | | 4-(X₅-CH₂)-biphenyl | X₆-CH₂-phenyl | 2.16 | 561.3144 | 562.409 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1241 | 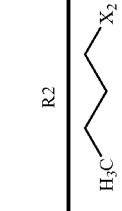 | 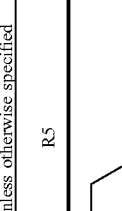 | 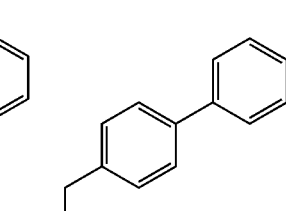 | | 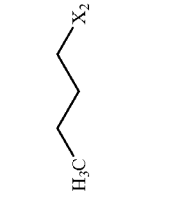 | 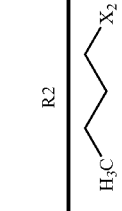 | 2.15 | 591.325 | 592.4272 |
| 1242 | 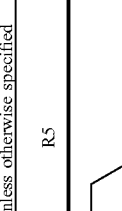 | 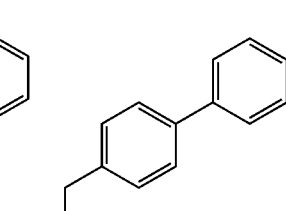 | 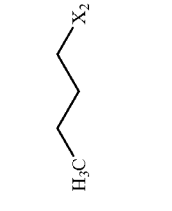 | | 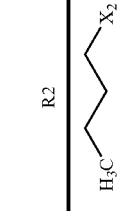 | 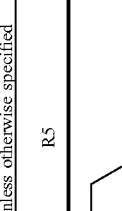 | 2.26 | 567.3613 | 568.463 |
| 1243 | 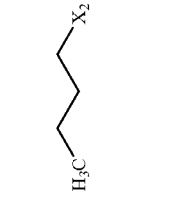 |  | 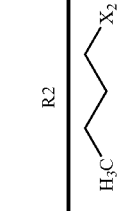 | | 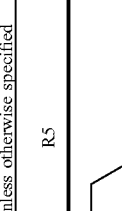 | 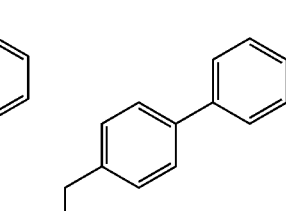 | 1.94 | 495.2886 | 496.3611 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1244 | X₁-phenyl | H₃C-(CH₂)₃-X₂ | X₃-phenyl | | X₅-CH₂-benzo[1,3]dioxole | X₆-CH₂-phenyl | 2.05 | 529.2729 | 530.3501 |
| 1245 | X₁-phenyl | H₃C-(CH₂)₃-X₂ | X₃-phenyl | | X₅-CH₂-benzo[1,3]dioxole | X₆-CH₂-(4-methoxyphenyl) | 2.04 | 559.2835 | 560.3697 |
| 1246 | X₁-phenyl | H₃C-(CH₂)₃-X₂ | X₃-phenyl | | X₅-CH₂-benzo[1,3]dioxole | X₆-CH₂-cyclohexyl | 2.13 | 535.3199 | 536.4042 |
| 1247 | X₁-phenyl | H₃C-(CH₂)₃-X₂ | X₃-phenyl | | X₅-CH₂-(2,3-dihydrobenzo[1,4]dioxine) | X₆-(CH₂)₃-CH₃ | 1.94 | 509.3042 | 510.3796 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1248 | X1-phenyl | H3C-(CH2)3-X2 | X3-phenyl | | X5-CH2-(2,3-dihydro-1,4-benzodioxin-6-yl) | X6-CH2-phenyl | 2.05 | 543.2886 | 544.3738 |
| 1249 | X1-phenyl | H3C-(CH2)3-X2 | X3-phenyl | | X5-CH2-(2,3-dihydro-1,4-benzodioxin-6-yl) | X6-CH2-(4-methoxyphenyl) | 2.04 | 573.2991 | 574.3901 |
| 1250 | X1-phenyl | H3C-(CH2)3-X2 | X3-phenyl | | X3-CH2-(2,3-dihydro-1,4-benzodioxin-6-yl) | X6-CH2-cyclohexyl | 2.13 | 549.3355 | 550.4245 |
| 1251 | X1-phenyl | H3C-(CH2)3-X2 | X3-phenyl | | X5-CH2-(4-phenoxyphenyl) | X6-(CH2)3-CH3 | 2.1 | 543.325 | 544.4181 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1252 | phenyl-X1 | H3C-(CH2)3-X2 | phenyl-X3 | | 4-phenoxybenzyl-X5 | cyclohexylmethyl-X6 | 2.24 | 583.3563 | 584.4531 |
| 1253 | phenyl-X1 | H3C-(CH2)3-X2 | phenyl-X3 | | 2,4,6-trimethoxybenzyl-X5 | butyl-X6 | 1.82 | 541.3304 | 542.4101 |
| 1254 | phenyl-X1 | X2-(CH2)3-CH3 | phenyl-X3 | | 2,4,6-trimethoxybenzyl-X5 | benzyl-X6 | 2.02 | 575.3148 | 576.4094 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1255 | phenyl-X1 | X2-(CH2)3-CH3 | phenyl-X3 | | 2,6-dimethoxy-4-methoxy benzyl-X5 | 4-methoxybenzyl-X6 | 1.97 | 605.3254 | 606.4261 |
| 1256 | phenyl-X1 | X2-(CH2)3-CH3 | phenyl-X3 | | 2,6-dimethoxy-4-methoxy benzyl-X5 | cyclohexylmethyl-X6 | 2 | 581.3618 | 582.4799 |
| 1257 | phenyl-X1 | H3C-(CH2)3-X2 | phenyl-X3 | | 3-benzyloxybenzyl-X5 | cyclohexylmethyl-X6 | 2.25 | 597.3719 | 598.4869 |
| 1258 | phenyl-X1 | H3C-(CH2)3-X2 | phenyl-X3 | | 4-benzyloxybenzyl-X5 | X6-(CH2)3-CH3 | 2.04 | 557.3406 | 558.4506 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1259 | phenyl-X₁ | H₃C-(CH₂)₃-X₂ | phenyl-X₃ | | 4-(benzyloxy)benzyl-X₅ | 4-methoxybenzyl-X₆ | 2.15 | 621.3355 | 622.458 |
| 1260 | phenyl-X₁ | H₃C-(CH₂)₃-X₂ | phenyl-X₃ | | 4-(benzyloxy)benzyl-X₅ | cyclohexylmethyl-X₆ | 2.24 | 597.3719 | 598.4882 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1261 | X1-phenyl | H3C-(CH2)3-X2 | X3-phenyl | | 3-(X5-CH2)-4-methoxy-2-benzyloxyphenyl | X6-(CH2)3-CH3 | 2.02 | 587.3512 | 588.4437 |
| 1262 | X1-phenyl | H3C-(CH2)3-X2 | X3-phenyl | | 3-benzyloxy-4-methoxy-(X5-CH2)phenyl | X6-CH2-phenyl | 2.09 | 621.3355 | 622.4498 |
| 1263 | X1-phenyl | H3C-(CH2)3-X2 | X3-phenyl | | 3-benzyloxy-4-methoxy-(X5-CH2)phenyl | X6-CH2-cyclohexyl | 2.16 | 627.3825 | 628.4863 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1264 | Ph-X1 | H3C-(CH2)3-X2 | Ph-X3 | | 2-OMe, 1-OBn phenyl-CH2-X5 | cyclohexyl-CH2-X6 | 2.18 | 627.3825 | 628.485 |
| 1265 | Ph-X1 | H3C-(CH2)3-X2 | Ph-X3 | | 3,4-di(OMe) phenyl-CH2-X5 (with CH2X5 branch) | n-butyl-X6 | | | |
| 1266 | Ph-X1 | H3C-(CH2)3-X2 | Ph-X3 | | 3,4-di(OEt) phenyl-CH2-X5 | benzyl-X6 | | | |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| 1267 | phenyl-X1 | H3C-(CH2)3-X2 | phenyl-X3 | | 3,4-dimethoxyethoxy benzyl-X5 | 4-methoxybenzyl-X6 | | | |
| 1268 | phenyl-X1 | H3C-(CH2)3-X2 | phenyl-X3 | | 3,4-dimethoxyethoxy benzyl-X5 | cyclohexylmethyl-X6 | | | |
| 1269 | phenyl-X1 | H3C-(CH2)3-X2 | phenyl-X3 | | 2,3-dimethoxybenzyl-X5 | butyl-X6 | 1.91 | 511.3199 | 512.4009 |
| 1270 | phenyl-X1 | H3C-(CH2)3-X2 | phenyl-X3 | | 2,3-dimethoxybenzyl-X5 | benzyl-X6 | 2.04 | 545.3042 | 546.3881 |

R4 is H unless otherwise specified

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1271 | X1-phenyl | X2-(CH2)3-CH3 | X3-phenyl | | X5-CH2-(2,3-dimethoxyphenyl) | X6-CH2-(4-methoxyphenyl) | 2.03 | 575.3148 | 576.4091 |
| 1272 | X1-phenyl | X2-(CH2)3-CH3 | X3-phenyl | | X5-CH2-(2,3-dimethoxyphenyl) | X6-CH2-cyclohexyl | 2.12 | 551.3512 | 552.4484 |
| 1273 | X1-phenyl | H3C-(CH2)3-X2 | X3-phenyl | | X5-CH2-(3,4-dimethoxyphenyl) | X6-(CH2)3-CH3 | 1.85 | 511.3199 | 512.394 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1274 | phenyl-X1 | H3C-(CH2)3-X2 | phenyl-X3 | | 3,4-dimethoxybenzyl-X5 | benzyl-X6 | 1.99 | 545.3042 | 546.3782 |
| 1275 | phenyl-X1 | H3C-(CH2)3-X2 | phenyl-X3 | | 3,4-dimethoxybenzyl-X5 | 4-methoxybenzyl-X6 | 1.97 | 575.3148 | 576.4008 |
| 1276 | phenyl-X1 | H3C-(CH2)3-X2 | phenyl-X3 | | 3,4-dimethoxybenzyl-X5 | cyclohexylmethyl-X6 | 2.07 | 551.3512 | 552.4422 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1277 | phenyl-X₁ | H₃C—(CH₂)₃—X₂ | phenyl-X₃ | | 2-nitrobenzyl-X₅ | 4-methoxybenzyl-X₆ | 2.02 | 560.2787 | 561.3565 |
| 1278 | phenyl-X₁ | H₃C—(CH₂)₃—X₂ | phenyl-X₃ | | 3-methoxy-2-nitrobenzyl-X₅ | H₃C—(CH₂)₃—X₆ | 2 | 526.2944 | 527.3669 |
| 1279 | phenyl-X₁ | X₂—(CH₂)₃—CH₃ | phenyl-X₃ | | 3-methoxy-2-nitrobenzyl-X₅ | cyclohexylmethyl-X₆ | 2.08 | 556.3257 | 567.418 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1280 | phenyl-X1 | H3C-(CH2)3-X2 | phenyl-X3 | | 2-chloro-6-nitrobenzyl-X5 | H3C-(CH2)3-X6 | 2.05 | 530.2449 | 531.3361 |
| 1281 | phenyl-X1 | H3C-(CH2)3-X2 | phenyl-X3 | | 2-chloro-6-nitrobenzyl-X5 | 4-methoxybenzyl-X6 | 2.05 | 594.2397 | 595.334 |
| 1282 | phenyl-X1 | H3C-(CH2)3-X2 | phenyl-X3 | | 2-chloro-6-nitrobenzyl-X5 | cyclohexylmethyl-X6 | 2.12 | 570.2762 | 571.3751 |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| 1283 | phenyl-X1 | H3C-(CH2)3-X2 | phenyl-X3 | | 4-Cl-2-nitro-benzyl-X5 | 4-methoxy-benzyl-X6 | 2.07 | 594.2397 | 595.3354 |
| 1284 | phenyl-X1 | H3C-(CH2)3-X2 | phenyl-X3 | | 2,4-dimethyl-benzyl-X5 | X6-(CH2)3-CH3 | 2.08 | 479.33 | 480.4123 |
| 1285 | phenyl-X1 | H3C-(CH2)3-X2 | phenyl-X3 | | 2,4-dimethyl-benzyl-X5 | benzyl-X6 | 2.14 | 513.3144 | 514.3954 |
| 1286 | phenyl-X1 | X2-(CH2)3-CH3 | phenyl-X3 | | 2,4-dimethyl-benzyl-X5 | 4-methoxy-benzyl-X6 | 2.13 | 543.325 | 544.4046 |

R4 is H unless otherwise specified

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| | | | | R4 is H unless otherwise specified | | | | | |
| 1287 | phenyl-X1 | X2-(CH2)3-CH3 | X3-phenyl | | 2,4-dimethylbenzyl-X5 | cyclohexylmethyl-X6 | | | |
| 1288 | phenyl-X1 | H3C-(CH2)3-X2 | X3-phenyl | | 2,5-difluorobenzyl-X5 | X6-(CH2)3-CH3 | 2.05 | 487.2799 | 488.3539 |
| 1289 | phenyl-X1 | H3C-(CH2)3-X2 | X3-phenyl | | 2,5-difluorobenzyl-X5 | X6-benzyl | 2.06 | 521.2643 | 522.3414 |
| 1290 | phenyl-X1 | H3C-(CH2)3-X2 | X3-phenyl | | 2,5-difluorobenzyl-X5 | X6-(4-methoxybenzyl) | 2.05 | 551.2748 | 552.3583 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1291 | X1-phenyl | H3C-CH2CH2CH2-X2 | X3-phenyl | | 2,5-difluorobenzyl-X5 | X6-CH2-cyclohexyl | | | |
| 1292 | X1-phenyl | H3C-CH2CH2CH2-X2 | X3-phenyl | | 2,3-dichlorobenzyl-X5 | X6-CH2CH2CH2CH3 | 2.14 | 527.3112 | 528.4017 |
| 1293 | X1-phenyl | H3C-CH2CH2CH2-X2 | X3-phenyl | | 2,3-dichlorobenzyl-X5 | X6-CH2-(4-methoxyphenyl) | 2.14 | 519.2208 | 520.312 |
| 1294 | X1-phenyl | H3C-CH2CH2CH2-X2 | X3-phenyl | | 2,3-dichlorobenzyl-X5 | X6-CH2-cyclohexyl | 2.13 | 583.2157 | 584.3151 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1295 | phenyl-X1 | H3C-(CH2)3-X2 | phenyl-X3 | | 3,5-bis(trifluoromethyl)benzyl-X5 | X6-(CH2)3-CH3 | | | |
| 1296 | phenyl-X1 | H3C-(CH2)3-X2 | phenyl-X3 | | 3,5-bis(trifluoromethyl)benzyl-X5 | 4-methoxybenzyl-X6 | 2.14 | 651.2684 | 652.3798 |
| 1297 | phenyl-X1 | H3C-(CH2)3-X2 | phenyl-X3 | | 3,5-bis(trifluoromethyl)benzyl-X5 | cyclohexylmethyl-X6 | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1298 | X₁-phenyl | H₃C-(CH₂)₃-X₂ | X₃-phenyl | | 3,4-difluorobenzyl-X₅ | X₆-(CH₂)₃-CH₃ | 2.06 | 487.2799 | 488.3528 |
| 1299 | X₁-phenyl | H₃C-(CH₂)₄-X₂ | X₃-phenyl | | 3,4-difluorobenzyl-X₅ | X₆-benzyl | 2.05 | 521.2643 | 522.3441 |
| 1300 | X₁-phenyl | H₃C-(CH₂)₄-X₂ | X₃-phenyl | | 3,4-difluorobenzyl-X₅ | X₆-CH₂-(4-methoxyphenyl) | 2.06 | 551.2748 | 552.3575 |
| 1301 | X₁-phenyl | H₃C-(CH₂)₄-X₂ | X₃-phenyl | | 3,4-difluorobenzyl-X₅ | X₆-CH₂-cyclohexyl | 2.14 | 527.3112 | 528.3984 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1302 | Ph-X₁ | H₃C-(CH₂)₃-X₂ | Ph-X₃ | | 3,4-diCl-benzyl-X₅ | n-butyl-X₆ | 2.14 | 519.2208 | 520.3089 |
| 1303 | Ph-X₁ | H₃C-(CH₂)₃-X₂ | Ph-X₃ | | 3,4-diCl-benzyl-X₅ | 4-methoxybenzyl-X₆ | 2.13 | 583.2157 | 584.3103 |
| 1304 | Ph-X₁ | H₃C-(CH₂)₃-X₂ | Ph-X₃ | | 3,4-diCl-benzyl-X₅ | cyclohexylmethyl-X₆ | | | |
| 1305 | Ph-X₁ | H₃C-(CH₂)₃-X₂ | Ph-X₃ | | 2,6-diCl-benzyl-X₅ | n-butyl-X₆ | 2.14 | 519.2208 | 520.3032 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1306 | X$_1$-phenyl | H$_3$C-CH$_2$CH$_2$CH$_2$-X$_2$ | X$_3$-phenyl | | 2,6-dichlorophenyl-CH$_2$-X$_5$ | X$_6$-CH$_2$-phenyl | 2.13 | 553.2051 | 554.2903 |
| 1307 | X$_1$-phenyl | H$_3$C-CH$_2$CH$_2$CH$_2$-X$_2$ | X$_3$-phenyl | | 2,6-dichlorophenyl-CH$_2$-X$_5$ | X$_6$-CH$_2$-(4-methoxyphenyl) | 2.13 | 583.2157 | 584.3069 |
| 1308 | X$_1$-phenyl | H$_3$C-CH$_2$CH$_2$CH$_2$-X$_2$ | X$_3$-phenyl | | 2,6-dichlorophenyl-CH$_2$-X$_5$ | X$_6$-CH$_2$-cyclohexyl | | | |
| 1309 | X$_1$-phenyl | H$_3$C-CH$_2$CH$_2$CH$_2$-X$_2$ | X$_3$-phenyl | | 2-fluoro-6-chlorophenyl-CH$_2$-X$_5$ | X$_6$-CH$_2$CH$_2$CH$_2$CH$_3$ | 2.11 | 503.2504 | 504.3281 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1310 | Ph-X1 | H3C-CH2CH2CH2-X2 | Ph-X3 | | 2-Cl-6-F-benzyl-X5 | benzyl-X6 | 2.09 | 537.2347 | 538.3116 |
| 1311 | Ph-X1 | H3C-CH2CH2CH2-X2 | Ph-X3 | | 2-Cl-6-F-benzyl-X5 | 4-methoxybenzyl-X6 | 2.09 | 567.2452 | 568.3282 |
| 1312 | Ph-X1 | H3C-CH2CH2CH2-X2 | Ph-X3 | | 2-Cl-6-F-benzyl-X5 | cyclohexylmethyl-X6 | 2.18 | 543.2817 | 544.3722 |
| 1313 | Ph-X1 | H3C-CH2CH2CH2-X2 | Ph-X3 | | 2,3-difluorobenzyl-X5 | n-butyl-X6 | 2.08 | 487.2799 | 488.381 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1314 | phenyl-X1 | H3C-CH2CH2CH2-X2 | phenyl-X3 | | 2,3-difluorobenzyl-X5 | benzyl-X6 | 2.05 | 521.2643 | 522.3368 |
| 1315 | phenyl-X1 | H3C-CH2CH2CH2-X2 | phenyl-X3 | | 2,3-difluorobenzyl-X5 | 4-methoxybenzyl-X6 | 2.06 | 551.2748 | 552.3557 |
| 1316 | phenyl-X1 | H3C-CH2CH2CH2-X2 | phenyl-X3 | | 2,3-difluorobenzyl-X5 | cyclohexylmethyl-X6 | 2.16 | 527.3112 | 528.3931 |
| 1317 | phenyl-X1 | H3C-CH2CH2CH2-X2 | phenyl-X3 | | 2,6-difluorobenzyl-X5 | n-butyl-X6 | 2.07 | 487.2799 | 288.3499 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1318 | X₁-phenyl | H₃C-CH₂CH₂CH₂-X₂ | X₃-phenyl | | 2,6-difluorobenzyl-X₅ | X₆-CH₂-phenyl | 2.05 | 521.2643 | 522.3353 |
| 1319 | X₁-phenyl | H₃C-CH₂CH₂CH₂-X₂ | X₃-phenyl | | 2,6-difluorobenzyl-X₅ | X₆-CH₂-(4-methoxyphenyl) | 2.06 | 551.2748 | 552.3566 |
| 1320 | X₁-phenyl | H₃C-CH₂CH₂CH₂-X₂ | X₃-phenyl | | 2,6-difluorobenzyl-X₅ | X₆-CH₂-cyclohexyl | 2.14 | 527.3112 | 528.3936 |
| 1321 | X₁-phenyl | H₃C-CH₂CH₂CH₂-X₂ | X₃-phenyl | | 2,4-difluorobenzyl-X₅ | X₆-CH₂CH₂CH₂-CH₃ | 2.08 | 487.2799 | 488.3528 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1322 | X1-phenyl | H3C-CH2CH2CH2-X2 | X3-phenyl | | 2,4-difluorobenzyl-X5 | benzyl-X6 | 2.08 | 521.2643 | 522.3411 |
| 1323 | X1-phenyl | H3C-CH2CH2CH2-X2 | X3-phenyl | | 2,4-difluorobenzyl-X5 | 4-methoxybenzyl-X6 | 2.06 | 551.2748 | 552.3599 |
| 1324 | X1-phenyl | H3C-CH2CH2CH2-X2 | X3-phenyl | | 2,4-difluorobenzyl-X5 | cyclohexylmethyl-X6 | 2.17 | 527.3112 | 528.3907 |
| 1325 | X1-phenyl | H3C-CH2CH2CH2-X2 | X3-phenyl | | 3-(trifluoromethoxy)benzyl-X5 | n-pentyl-X6 | 2.13 | 535.2811 | 336.38 |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| | | | | R4 is H unless otherwise specified | | | | | |
| 1326 | phenyl-X1 | H3C-(CH2)3-X2 | phenyl-X3 | | 3-(OCF3)-benzyl-X5 | benzyl-X6 | 2.12 | 569.2654 | 570.3573 |
| 1327 | phenyl-X1 | H3C-(CH2)3-X2 | phenyl-X3 | | 3-(OCF3)-benzyl-X5 | 4-methoxybenzyl-X6 | 2.11 | 599.2759 | 600.3768 |
| 1328 | phenyl-X1 | H3C-(CH2)3-X2 | phenyl-X3 | | 3-(OCF3)-benzyl-X5 | cyclohexylmethyl-X6 | 2.19 | 575.3124 | 576.4055 |
| 1329 | phenyl-X1 | H3C-(CH2)3-X2 | phenyl-X3 | | 4-(OCHF2)-benzyl-X5 | n-pentyl-X6 | 2.01 | 517.2905 | 518.3644 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1330 | phenyl-X₁ | H₃C-(CH₂)₃-X₂ | phenyl-X₃ | | 4-(OCHF₂)benzyl-X₅ | benzyl-X₆ | 2.05 | 551.2748 | 552.3568 |
| 1331 | phenyl-X₁ | H₃C-(CH₂)₃-X₂ | phenyl-X₃ | | 4-(OCHF₂)benzyl-X₅ | 4-methoxybenzyl-X₆ | 2.04 | 581.2854 | 582.3729 |
| 1332 | phenyl-X₁ | H₃C-(CH₂)₃-X₂ | phenyl-X₃ | | 4-(OCHF₂)benzyl-X₅ | cyclohexylmethyl-X₆ | 2.12 | 557.3218 | 558.4104 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1333 | phenyl-X1 | H3C-(CH2)3-X2 | phenyl-X3 | | 4-(OCF3)benzyl-X5 | X6-(CH2)3-CH3 | 2.1 | 535.2811 | 536.3671 |
| 1334 | phenyl-X1 | H3C-(CH2)3-X2 | phenyl-X3 | | 4-(OCF3)benzyl-X5 | benzyl-X6 | 2.11 | 569.2654 | 570.3599 |
| 1335 | phenyl-X1 | H3C-(CH2)3-X2 | phenyl-X3 | | 4-(OCF3)benzyl-X5 | 4-methoxybenzyl-X6 | 2.11 | 599.2759 | 600.3785 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1336 | phenyl-X₁ | H₃C-(CH₂)₃-X₂ | phenyl-X₃ | | 4-(trifluoromethoxy)benzyl-X₅ | cyclohexylmethyl-X₆ | 2.18 | 575.3124 | 576.4045 |
| 1337 | phenyl-X₁ | H₃C-(CH₂)₃-X₂ | phenyl-X₃ | | 3,5-difluorobenzyl-X₅ | X₆-(CH₂)₃-CH₃ | 2.08 | 487.2799 | 488.3532 |
| 1338 | phenyl-X₁ | H₃C-(CH₂)₃-X₂ | phenyl-X₃ | | 3,5-difluorobenzyl-X₅ | benzyl-X₆ | 2.08 | 521.2643 | 522.3442 |
| 1339 | phenyl-X₁ | H₃C-(CH₂)₃-X₂ | phenyl-X₃ | | 4-methoxybenzyl-X₅ | 3,5-difluorobenzyl-X₆ | 2.07 | 551.2748 | 552.3596 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1340 | X1-phenyl | H3C-(CH2)3-X2 | X3-phenyl | | 3,5-difluoro benzyl-X5 | cyclohexylmethyl-X6 | 2.16 | 527.3112 | 528.3984 |
| 1341 | X1-phenyl | H3C-(CH2)3-X2 | X3-phenyl | | 3,4-dichloro-6-fluoro benzyl-X5 | X6-(CH2)3-CH3 | 2.1 | 503.2504 | 504.3321 |
| 1342 | X1-phenyl | H3C-(CH2)3-X2 | X3-phenyl | | 3-chloro-4-fluoro benzyl-X5 | benzyl-X6 | 2.1 | 537.2347 | 538.3232 |
| 1343 | X1-phenyl | H3C-(CH2)3-X2 | X3-phenyl | | 3-chloro-4-fluoro benzyl-X5 | 4-methoxybenzyl-X6 | 2.1 | 567.2452 | 568.3386 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1344 | 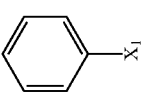 | 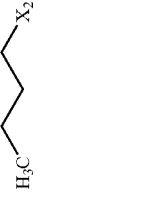 | 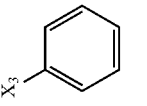 | | 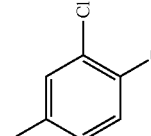 |  | | | |
| 1345 |  | 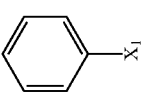 | 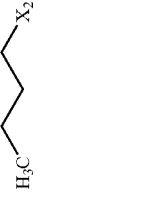 | | 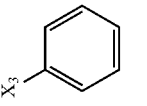 | 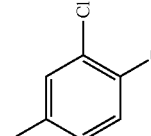 | 2.09 | 537.2767 | 538.3624 |
| 1346 |  |  | 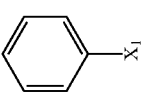 | | 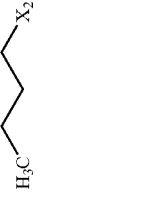 | 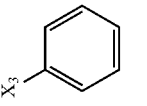 | 2.09 | 571.261 | 572.3517 |
| 1347 | 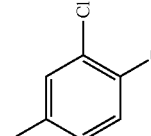 |  |  | | 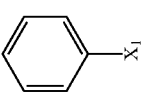 | 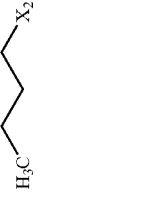 | 2.08 | 601.2716 | 602.369 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1348 | phenyl-X1 | H3C-(CH2)3-X2 | phenyl-X3 | | 4-F, 3-CF3 benzyl-X5 | cyclohexylmethyl-X6 | 2.16 | 577.308 | 578.4044 |
| 1349 | phenyl-X1 | H3C-(CH2)3-X2 | phenyl-X3 | | 3-Br, 4-F benzyl-X5 | n-butyl-X6 | 2.1 | 547.1998 | 548.2905 |
| 1350 | phenyl-X1 | H3C-(CH2)3-X2 | phenyl-X3 | | 3-Br, 4-F benzyl-X5 | benzyl-X6 | 2.11 | 581.1842 | 582.29 |
| 1351 | phenyl-X1 | H3C-(CH2)3-X2 | phenyl-X3 | | 3-Br, 4-F benzyl-X5 | 4-methoxybenzyl-X6 | 2.1 | 611.1948 | 612.3 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1352 |  | 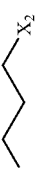 |  | |  |  | 2.19 | 587.2311 | 598.34 |
| 1353 | 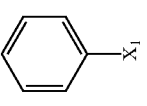 | 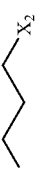 |  | |  |  | 2.05 | 559.2198 | 560.31 |
| 1354 | 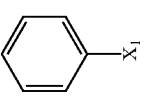 | 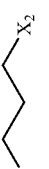 |  | |  |  | | | |
| 1355 | 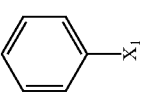 | 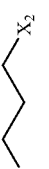 |  | |  |  | 2.08 | 623.2147 | 624.31 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1356 | phenyl-X₁ | H₃C-(CH₂)₃-X₂ | phenyl-X₃ | | 3-Br-4-methoxybenzyl-X₅ | cyclohexylmethyl-X₆ | | | |
| 1357 | phenyl-X₁ | H₃C-(CH₂)₃-X₂ | phenyl-X₃ | | 4-(2-methoxyethoxy)benzyl-X₅ | X₆-(CH₂)₃-CH₃ | 2.02 | 509.3406 | 510.4212 |
| 1358 | phenyl-X₁ | H₃C-(CH₂)₃-X₂ | phenyl-X₃ | | 4-(2-methoxyethoxy)benzyl-X₅ | benzyl-X₆ | 2.14 | 543.325 | 544.3982 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1359 | X1-phenyl | H3C-(CH2)3-X2 | X3-phenyl | | X5-CH2-C6H4-O-CH2CH2-CH3 | 4-methoxybenzyl-X6 | 2.13 | 573.3355 | 574.4336 |
| 1360 | X1-phenyl | H3C-(CH2)3-X2 | X3-phenyl | | X5-CH2-C6H4-O-CH2CH2-CH3 | cyclohexylmethyl-X6 | | | |
| 1361 | X1-phenyl | H3C-(CH2)3-X2 | X3-phenyl | | X5-CH2-C6H4-C(CH3)2-CH3 | X6-(CH2)3-CH3 | 2.11 | 507.3614 | 508.4463 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1362 | phenyl-X1 | H3C-(CH2)3-X2 | phenyl-X3 | | 4-(C(CH3)2)-benzyl-X5 | benzyl-X6 | 2.19 | 541.3457 | 542.4313 |
| 1363 | phenyl-X1 | H3C-(CH2)3-X2 | phenyl-X3 | | 4-(C(CH3)2)-benzyl-X5 | 4-methoxybenzyl-X6 | 2.18 | 571.3563 | 572.447 |
| 1364 | phenyl-X1 | H3C-(CH2)3-X2 | phenyl-X3 | | 4-(C(CH3)2)-benzyl-X5 | cyclohexylmethyl-X6 | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1365 | X₁-phenyl | H₃C-(CH₂)₃-X₂ | X₃-phenyl | | 4-methoxy-3-fluorobenzyl-X₅ | X₆-(CH₂)₃-CH₃ | 1.98 | 499.2999 | 500.366 |
| 1366 | X₁-phenyl | H₃C-(CH₂)₃-X₂ | X₃-phenyl | | 3-fluoro-4-methoxybenzyl-X₅ | benzyl-X₆ | 2.05 | 533.2842 | 534.366 |
| 1367 | X₁-phenyl | H₃C-(CH₂)₃-X₂ | X₃-phenyl | | 3-fluoro-4-methoxybenzyl-X₅ | 4-methoxybenzyl-X₆ | 2.04 | 563.2948 | 564.3766 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1368 | 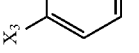 | 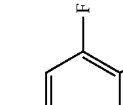 |  | | 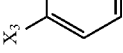 | 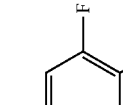 | | | |
| 1369 |  | 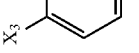 | 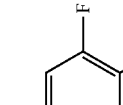 | |  | 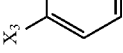 | 1.87 | 423.2675 | 424.3263 |
| 1370 | 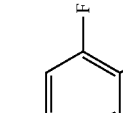 |  | 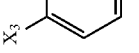 | | 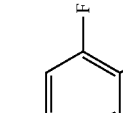 |  | 1.93 | 437.2831 | 438.3482 |
| 1371 | 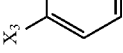 | 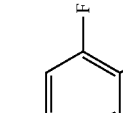 |  | | 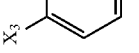 | 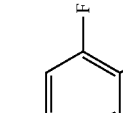 | 1.97 | 451.2987 | 452.3679 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1372 | 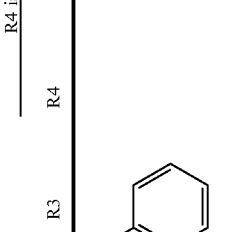 | 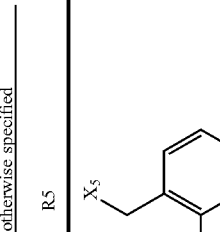 | 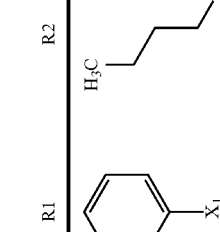 | | 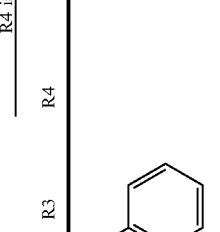 | 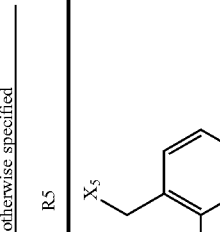 | 2.03 | 501.1779 | 502.2567 |
| 1373 | 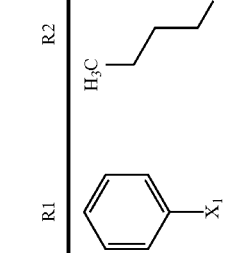 | 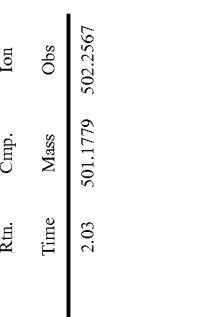 | 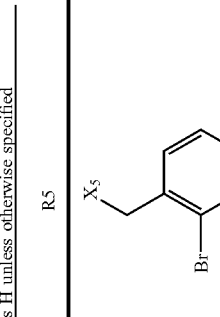 | | 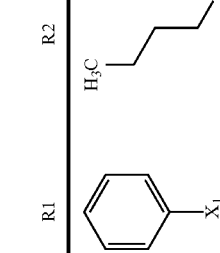 | 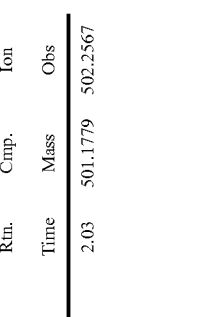 | 2.08 | 515.1936 | 516.27 |
| 1374 | 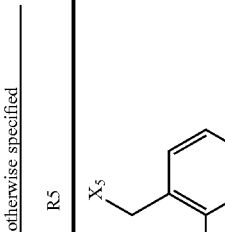 | 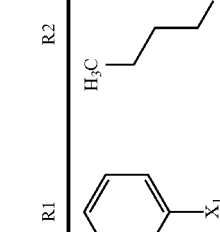 | 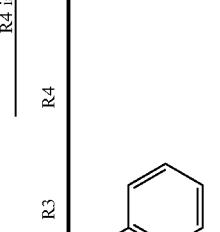 | | 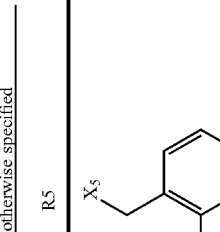 | 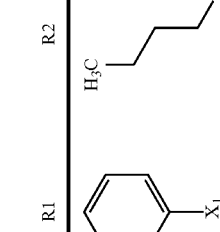 | 2.12 | 529.2093 | 530.29 |
| 1375 | 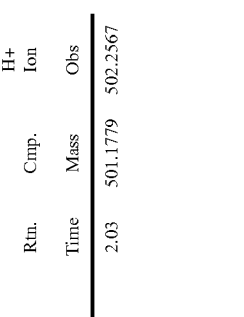 | 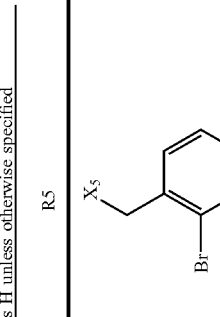 | 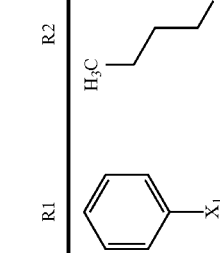 | | 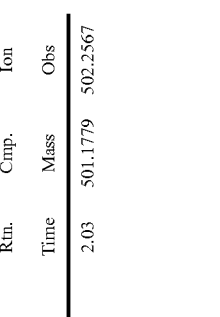 | 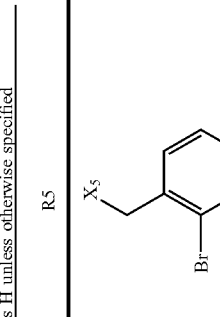 | 1.96 | 441.528 | 442.3157 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1376 | phenyl-X1 | H3C-CH2CH2CH2-X2 | X3-phenyl | | 2-fluorobenzyl-X5 | X6-CH2CH2-CH3 | 2.01 | 455.2737 | 456.3356 |
| 1377 | phenyl-X1 | H3C-CH2CH2CH2-X2 | X3-phenyl | | 2-fluorobenzyl-X5 | X6-CH2CH2CH2-CH3 | 2.05 | 469.2893 | 470.3576 |
| 1378 | phenyl-X1 | H3C-CH2CH2CH2-X2 | X3-phenyl | | X5-CH2-(2-chlorophenyl) | H3C-CH2-X6 | 2.02 | 457.2285 | 458.3003 |
| 1379 | phenyl-X1 | H3C-CH2CH2CH2-X2 | X3-phenyl | | 2-chlorobenzyl-X5 | X6-CH2CH2-CH3 | 2.07 | 471.2441 | 472.3165 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1380 | X₁-phenyl | H₃C-CH₂CH₂CH₂-X₂ | X₃-phenyl | | 2-Cl-benzyl (X₅) | X₆-CH₂CH₂CH₂-CH₃ | 2.11 | 485.2598 | 486.3203 |
| 1381 | X₁-phenyl | H₃C-CH₂CH₂CH₂-X₂ | X₃-phenyl | | 2-CH₃-benzyl (X₅) | H₃C-CH₂-X₆ | 1.97 | 437.2831 | 438.3451 |
| 1382 | X₁-phenyl | H₃C-CH₂CH₂CH₂-X₂ | X₃-phenyl | | 2-CH₃-benzyl (X₅) | X₆-CH₂-CH₃ | 2.02 | 451.2987 | 452.3678 |
| 1383 | X₁-phenyl | H₃C-CH₂CH₂CH₂-X₂ | X₃-phenyl | | 2-OCH₃-benzyl (X₅) | X₆-CH₂-CH₃ | 1.85 | 467.2937 | 468.3646 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1384 | Ph-X1 | H3C-...-X2 | Ph-X3 | | 2-methoxybenzyl-X5 | X6-(CH2)3-CH3 | 1.88 | 481.3093 | 482.3853 |
| 1385 | Ph-X1 | H3C-...-X2 | Ph-X3 | | 2-(trifluoromethyl)benzyl-X5 | H3C-CH2-X6 | 2.04 | 491.2548 | 492.3256 |
| 1386 | Ph-X1 | H3C-...-X2 | Ph-X3 | | 2-(trifluoromethyl)benzyl-X5 | H3C-(CH2)2-X6 | 2.07 | 505.2705 | 506.3494 |
| 1387 | Ph-X1 | H3C-...-X2 | Ph-X3 | | 2-(trifluoromethyl)benzyl-X5 | H3C-(CH2)3-X6 | 2.11 | 519.2861 | 520.37 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1388 | phenyl-X1 | H3C-(CH2)3-X2 | phenyl-X3 | | 2-(methoxymethoxy)benzyl-X5 | H3C-CH2-X6 | 1.84 | 467.2937 | 468.3647 |
| 1389 | phenyl-X1 | H3C-(CH2)3-X2 | phenyl-X3 | | 2-(ethoxy)benzyl-X5 | X6-(CH2)2-CH3 | 1.91 | 481.3093 | 482.3842 |
| 1390 | phenyl-X1 | H3C-(CH2)3-X2 | phenyl-X3 | | 2-(ethoxy)benzyl-X5 | X6-(CH2)3-CH3 | 1.96 | 495.325 | 496.4054 |
| 1391 | phenyl-X1 | H3C-(CH2)3-X2 | phenyl-X3 | | 2,4-dichlorobenzyl-X5 | X6-CH2-CH2-CH3 | 2.13 | 505.2051 | 506.2906 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1392 | X1-phenyl | H3C-CH2CH2CH2-X2 | X3-phenyl | | 2,4-dichlorobenzyl-X5 | X6-CH2CH2CH2CH3 | 2.16 | 519.2208 | 520.3135 |
| 1393 | X1-phenyl | H3C-CH2CH2CH2-X2 | X3-phenyl | | 2,4-dimethoxybenzyl-X5 | X6-CH2CH(CH3)2 | 1.81 | 497.3042 | 498.3747 |
| 1394 | X1-phenyl | H3C-CH2CH2CH2-X2 | X3-phenyl | | 2,4-dimethoxybenzyl-X5 | X6-CH2CH2CH2CH3 | 1.86 | 511.3199 | 512.4008 |
| 1395 | X1-phenyl | H3C-CH2CH2CH2-X2 | X3-phenyl | | 2,5-dimethoxybenzyl-X5 | X6-CH2CH3 | 1.8 | 483.2886 | 484.2823 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1396 | Ph-X1 | H3C-...-X2 | Ph-X3 | | 2,5-dimethoxybenzyl-X5 | X6-CH2CH2CH3 | 1.86 | 497.3042 | 498.2973 |
| 1397 | Ph-X1 | H3C-...-X2 | Ph-X3 | | 2,5-dimethoxybenzyl-X5 | X6-(CH2)3CH3 | 1.91 | 511.3199 | 512.3188 |
| 1398 | Ph-X1 | H3C-...-X2 | Ph-X3 | | 3-bromobenzyl-X5 | X6-CH2CH3 | 2.01 | 501.1779 | 502.1894 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1399 | X1-phenyl | H3C-(CH2)3-X2 | X3-phenyl | | 3-Br-benzyl-X5 | X6-CH2CH2-CH3 (with H3C branch) | 2.06 | 515.1936 | 516.206 |
| 1400 | X1-phenyl | H3C-(CH2)3-X2 | X3-phenyl | | 3-Br-benzyl-X5 | X6-(CH2)3-CH3 | 2.08 | 529.2093 | 530.222 |
| 1401 | X1-phenyl | H3C-(CH2)3-X2 | X3-phenyl | | 3-F-benzyl-X5 | X6-CH2-CH3 | 1.94 | 441.258 | 442.2664 |
| 1402 | X1-phenyl | H3C-(CH2)3-X2 | X3-phenyl | | 3-F-benzyl-X5 | X6-CH2CH2-CH3 | 2 | 455.2737 | 456.28 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1403 | phenyl-X1 | H3C-(CH2)3-X2 | phenyl-X3 | | 3-F-benzyl-X5 | X6-(CH2)3-CH3 | 2.03 | 469.2893 | 470.2926 |
| 1404 | phenyl-X1 | H3C-(CH2)3-X2 | phenyl-X3 | | 3-CH3-benzyl-X5 | X6-CH2-CH3 | 1.9 | 437.2831 | 438.2925 |
| 1405 | phenyl-X1 | H3C-(CH2)3-X2 | phenyl-X3 | | 3-CH3-benzyl-X5 | X6-CH2-CH3 (H3C) | 1.96 | 451.2987 | 452.3093 |
| 1406 | phenyl-X1 | H3C-(CH2)3-X2 | phenyl-X3 | | 3-CH3-benzyl-X5 | X6-(CH2)3-CH3 | 2 | 465.3144 | 466.3223 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1407 | X1-phenyl | H3C-CH2CH2CH2-X2 | X3-phenyl | | 3-(CF3)-benzyl-X5 | X6-CH2CH2CH3 | 2 | 491.2548 | 492.2683 |
| 1408 | X1-phenyl | H3C-CH2CH2CH2-X2 | X3-phenyl | | 3-(CF3)-benzyl-X5 | X6-CH2CH2CH2CH3 | 2.05 | 505.2705 | 506.2844 |
| 1409 | X1-phenyl | H3C-CH2CH2CH2-X2 | X3-phenyl | | 3-(CF3)-benzyl-X5 | X6-CH2CH2CH2CH2CH3 | 2.08 | 519.2861 | 520.2956 |
| 1410 | X1-phenyl | H3C-CH2CH2CH2-X2 | X3-phenyl | | 3-(OCH3)-benzyl-X5 | X6-CH2CH2CH3 | | | |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1411 |  |  |  | |  |  | 1.95 | 467.2937 | 467.1446 |
| 1412 |  |  |  | |  |  | 1.98 | 481.3093 | 482.2171 |
| 1413 |  |  |  | |  |  | 2 | 457.2285 | 458.1478 |
| 1414 |  |  |  | |  |  | 2.04 | 471.2441 | 472.1711 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1415 | X₁-phenyl | H₃C-(CH₂)₃-X₂ | X₃-phenyl | | X₅-CH₂-(3-Cl-phenyl) | X₆-(CH₂)₃-CH₃ | 2.09 | 485.2598 | 486.1973 |
| 1416 | X₁-phenyl | H₃C-(CH₂)₃-X₂ | X₃-phenyl | | X₅-CH₂-(3-phenoxyphenyl) | X₆-CH₂-CH₃ | 2.05 | 515.2936 | 516.2304 |
| 1417 | X₁-phenyl | H₃C-(CH₂)₃-X₂ | X₃-phenyl | | X₅-CH₂-(3-phenoxyphenyl) | X₆-(CH₂)₂-CH₃ | 2.09 | 529.3093 | 530.2516 |
| 1418 | X₁-phenyl | H₃C-(CH₂)₃-X₂ | X₃-phenyl | | X₅-CH₂-(3-phenoxyphenyl) | X₆-(CH₂)₃-CH₃ | 2.12 | 543.325 | 544.2772 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1419 | 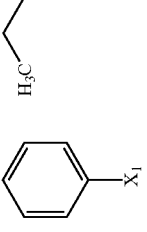 |  |  | | 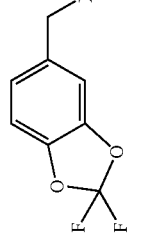 | 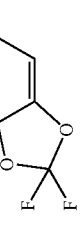 | 2 | 503.2384 | 504.2027 |
| 1420 | 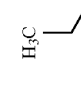 | 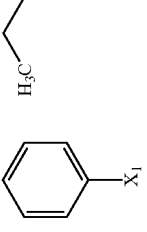 |  | | 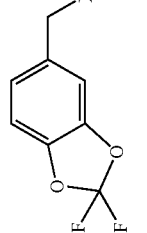 | 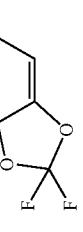 | 2.06 | 517.2541 | 518.2202 |
| 1421 | 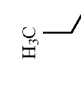 | 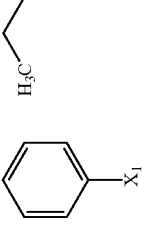 |  | | 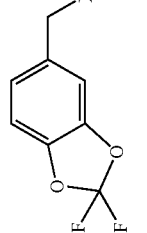 | 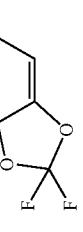 | 2.08 | 531.2697 | 532.2498 |
| 1422 | 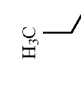 | 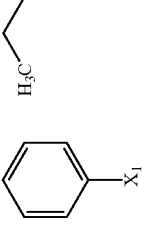 |  | | 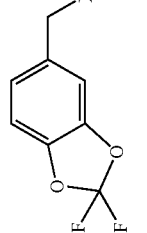 | 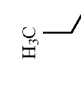 | 1.96 | 487.1623 | 488.1573 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1423 | X₁-phenyl | H₃C-(CH₂)₃-X₂ | X₃-phenyl | | X₅-(4-Br-benzyl) | X₆-CH₂-CH₃ | 1.98 | 501.1779 | 502.1747 |
| 1424 | X₁-phenyl | H₃C-(CH₂)₂-X₂ | X₃-phenyl | | X₅-(4-Br-benzyl) | X₆-CH₂CH₂-CH₃ | 2.04 | 515.1936 | 516.1976 |
| 1425 | X₁-phenyl | H₃C-(CH₂)₂-X₂ | X₃-phenyl | | X₅-(4-Br-benzyl) | X₆-(CH₂)₃-CH₃ | 2.09 | 529.2093 | 530.21 |
| 1426 | X₁-phenyl | H₃C-(CH₂)₃-X₂ | X₃-phenyl | | X₅-(4-F-benzyl) | X₆-CH₂-CH₃ | 1.89 | 441.258 | 442.2531 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1427 | X1-phenyl | H3C-propyl-X2 | X3-phenyl | | 4-F-benzyl-X5 | X6-propyl-CH3 | 1.95 | 455.2737 | 456.2708 |
| 1428 | X1-phenyl | H3C-propyl-X2 | X3-phenyl | | 4-F-benzyl-X5 | X6-butyl-CH3 | 2 | 469.2893 | 470.2896 |
| 1429 | X1-phenyl | H3C-butyl-X2 | X3-phenyl | | 4-Cl-benzyl-X5 | X6-ethyl-CH3 | 1.96 | 457.2285 | 458.2379 |
| 1430 | X1-phenyl | H3C-propyl-X2 | X3-phenyl | | 4-Cl-benzyl-X5 | X6-propyl-CH3 | 2.03 | 471.2441 | 472.2611 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1431 | phenyl-$X_1$ | $H_3C$-(CH$_2$)$_3$-$X_2$ | phenyl-$X_3$ | | 4-Cl-benzyl-$X_5$ | $X_6$-(CH$_2$)$_3$-CH$_3$ | 2.06 | 485.2598 | 486.2763 |
| 1432 | phenyl-$X_1$ | $H_3C$-(CH$_2$)$_3$-$X_2$ | phenyl-$X_3$ | | 4-CH$_3$-benzyl-$X_5$ | $X_6$-CH$_2$-CH$_3$ | 1.89 | 437.2831 | 438.2931 |
| 1433 | phenyl-$X_1$ | $H_3C$-(CH$_2$)$_3$-$X_2$ | phenyl-$X_3$ | | 4-CH$_3$-benzyl-$X_5$ | $X_6$-(CH$_2$)$_2$-CH$_3$ | 1.94 | 451.2987 | 452.3127 |
| 1434 | phenyl-$X_1$ | $H_3C$-(CH$_2$)$_3$-$X_2$ | phenyl-$X_3$ | | 4-CH$_3$-benzyl-$X_5$ | $X_6$-(CH$_2$)$_3$-CH$_3$ | 1.98 | 465.3144 | 466.3366 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1435 | X1-phenyl | H3C-(CH2)3-X2 | X3-phenyl | | 1,4-bis(CH2) phenyl with CH3 and X5 | X6-C3 | 1.9 | 437.2831 | 438.2971 |
| 1436 | X1-phenyl | H3C-(CH2)3-X2 | X3-phenyl | | 1,4-bis(CH2) phenyl with H3C and X5 | X6-CH2CH3 | 1.93 | 451.2987 | 452.3194 |
| 1437 | X1-phenyl | H3C-(CH2)3-X2 | X3-phenyl | | 1,4-bis(CH2) phenyl with H3C and X5 | X6-CH2CH2CH3 | 1.99 | 485.3144 | 466.3413 |
| 1438 | X1-phenyl | X1-phenyl | X3-phenyl | | 1,4-bis(CH2) phenyl with H3C and X5 | X6-(CH2)3CH3 | 2.03 | 479.33 | 480.3666 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1439 | X₁-phenyl | H₃C-CH₂CH₂CH₂-X₂ | X₃-phenyl | | 4-(H₃CO)-C₆H₄-CH₂-X₅ | X₆-CH₂CH₂-CH₃ | 1.81 | 453.278 | 454.3067 |
| 1440 | X₁-phenyl | H₃C-CH₂CH₂CH₂-X₂ | X₃-phenyl | | 4-(H₃CO)-C₆H₄-CH₂-X₅ | X₆-CH₂CH₂CH₂-CH₃ | 1.88 | 467.2937 | 468.3209 |
| 1441 | X₁-phenyl | H₃C-CH₂CH₂CH₂-X₂ | X₃-phenyl | | 4-(H₃CO)-C₆H₄-CH₂-X₅ | X₆-CH₂CH₂CH₂CH₂-CH₃ | 1.91 | 481.3093 | 482.3407 |
| 1442 | X₁-phenyl | H₃C-CH₂CH₂CH₂-X₂ | X₃-phenyl | | 4-(H₃COCH₂O)-C₆H₄-CH₂-X₅ | X₆-CH₂CH₂-CH₃ | 1.87 | 467.2937 | 468.3278 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1443 | 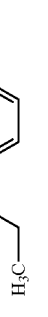 | 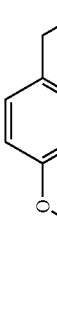 |  | | 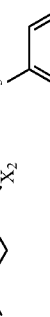 |  | 1.93 | 481.3093 | 482.3481 |
| 1444 | | | | | | | 1.95 | 495.325 | 496.3688 |
| 1445 | | | | | | X6—CH3 | 1.95 | 481.3093 | 482.356 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1446 | X1-phenyl | H3C-(CH2)3-X2 | X3-phenyl | | 4-(H3C(CH2)3O)-benzyl-X5 | X6-CH2CH2CH3 | 1.97 | 495.325 | 496.3746 |
| 1447 | X1-phenyl | H3C(CH2)2-X2 | X3-phenyl | | 4-(H3C(CH2)3O)-benzyl-X5 | X6-CH2CH2CH3 | 2.03 | 509.3406 | 510.4019 |
| 1448 | X1-phenyl | H3C(CH2)2-X2 | X3-phenyl | | 4-(H3C(CH2)3O)-benzyl-X5 | X6-(CH2)3CH3 | 2.05 | 523.3563 | 514.4143 |
| 1449 | X1-phenyl | H3C(CH2)2-X2 | X3-phenyl | | 4-(CF3)-benzyl-X5 | X6-CH2CH2CH3 | 2.05 | 505.2705 | 506.3199 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1450 | X₁-phenyl | H₃C-(CH₂)₃-X₂ | X₃-phenyl | | 4-(CF₃)-C₆H₄-CH₂-X₅ | X₆-(CH₂)₃-CH₃ | 2.08 | 519.2861 | 520.3441 |
| 1451 | X₁-phenyl | H₃C-(CH₂)₃-X₂ | X₃-phenyl | | 4-(X₅-CH₂)-C₆H₄-CH(CH₃)- | X₆-CH₃ | 1.95 | 451.2987 | 452.3453 |
| 1452 | X₁-phenyl | H₃C-(CH₂)₃-X₂ | X₃-phenyl | | 4-(CH(CH₃)₂)-C₆H₄-CH₂-X₅ | X₆-CH₂-CH₃ | 1.97 | 465.3144 | 466.3662 |
| 1453 | X₁-phenyl | H₃C-(CH₂)₃-X₂ | X₃-phenyl | | 4-(CH(CH₃)₂)-C₆H₄-CH₂-X₅ | X₆-CH₂-CH₂-CH₃ | 2.03 | 479.33 | 480.3838 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1454 | $X_1$-phenyl | $H_3C$-(CH2)3-$X_2$ | $X_3$-phenyl | | 4-(1-methylethyl)benzyl-$X_5$ | $X_6$-(CH2)3-CH3 | 2.07 | 493.3457 | 494.4073 |
| 1455 | $X_1$-phenyl | $H_3C$-(CH2)3-$X_2$ | $X_3$-phenyl | | 4-phenylbenzyl-$X_5$ | $X_6$-CH(CH3)-CH3 | 2.07 | 513.3144 | 514.367 |
| 1456 | $X_1$-phenyl | $H_3C$-(CH2)3-$X_2$ | $X_3$-phenyl | | benzo[1,3]dioxol-5-ylmethyl-$X_5$ | $X_6$-CH3 | 1.8 | 453.2416 | 454.2823 |
| 1457 | $X_1$-phenyl | $H_3C$-(CH2)3-$X_2$ | $X_3$-phenyl | | benzo[1,3]dioxol-5-ylmethyl-$X_5$ | $X_6$-CH2-CH3 | 1.83 | 467.2573 | 468.2991 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1458 |  | 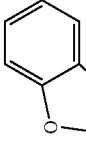 | 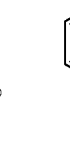 | | 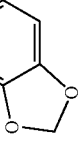 | 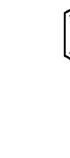 | 1.9 | 481.2729 | 482.3186 |
| 1459 | 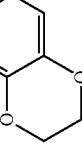 |  |  | |  |  | 1.94 | 495.2886 | 496.3361 |
| 1460 |  |  |  | |  | 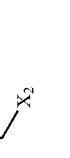 | 1.82 | 481.2729 | 482.3166 |
| 1461 |  | 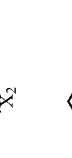 |  | |  | 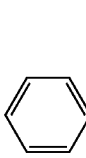 | 1.89 | 495.2886 | 496.3342 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1462 | X1-phenyl | H3C-(CH2)3-X2 | X3-phenyl | | 2,3-dihydrobenzo[1,4]dioxin-CH2-X5 | X6-(CH2)3-CH3 | 1.93 | 509.3042 | 510.3551 |
| 1463 | X1-phenyl | H3C-(CH2)3-X2 | X3-phenyl | | 4-phenoxybenzyl-X5 | X6-CH2-CH3 | 2 | 515.2936 | 516.3452 |
| 1464 | X1-phenyl | H3C-(CH2)3-X2 | X3-phenyl | | 4-phenoxybenzyl-X5 | X6-(CH2)2-CH3 | 2.07 | 529.3093 | 530.368 |
| 1465 | X1-phenyl | H3C-(CH2)3-X2 | X3-phenyl | | 4-phenoxybenzyl-X5 | X6-(CH2)3-CH3 | 2.08 | 543.325 | 544.3928 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1466 | 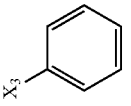 |  | 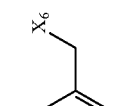 | | 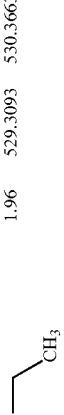 | 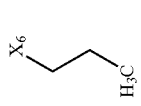 | 1.96 | 529.3093 | 530.3663 |
| 1467 | 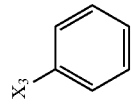 | 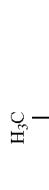 | 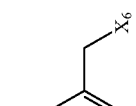 | |  | 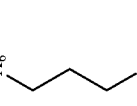 | 2.02 | 543.325 | 544.387 |
| 1468 | 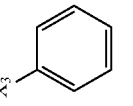 | 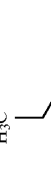 | 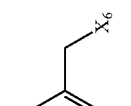 | |  | 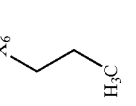 | 2.05 | 557.3406 | 558.4091 |
| 1469 | 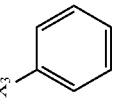 | 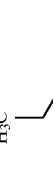 | 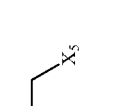 | |  |  | 1.97 | 573.3355 | 574.3986 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1470 | X1-Ph | H3C-CH2CH2CH2-X2 | X3-Ph | | 3-benzyloxy-4-methoxy-benzyl-X5 | X6-CH2CH2CH2CH3 | 2.01 | 687.3612 | 688.4052 |
| 1471 | X1-Ph | H3C-CH2CH2CH2-X2 | X3-Ph | | 4-benzyloxy-3-methoxy-benzyl-X5 | X6-CH2CH2CH2CH3 | 2 | 587.3512 | 588.4127 |
| 1472 | X1-Ph | H3C-CH2CH2CH2-X2 | X3-Ph | | 3,4-bis(methoxymethoxy)-benzyl-X5 | X6-CH2CH2CH3 | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1473 | phenyl-X₁ | H₃C-CH₂CH₂CH₂-X₂ | phenyl-X₃ | | 3,4-dimethoxybenzyl-X₅ | X₆-CH₂CH₂CH₂-CH₃ | | | |
| 1474 | phenyl-X₁ | H₃C-CH₂CH₂CH₂-X₂ | phenyl-X₃ | | 2,3-dimethoxybenzyl-X₅ | X₆-CH₂CH₂-CH₃ | 1.87 | 497.3042 | 498.347 |
| 1475 | phenyl-X₁ | H₃C-CH₂CH₂CH₂-X₂ | phenyl-X₃ | | 2,3-dimethoxybenzyl-X₅ | X₆-CH₂CH₂CH₂-CH₃ | 1.91 | 511.3199 | 512.3705 |
| 1476 | phenyl-X₁ | H₃C-CH₂CH₂CH₂-X₂ | phenyl-X₃ | | 3,4-dimethoxybenzyl-X₅ | X₆-CH₂CH₂CH₂-CH₃ | 1.85 | 511.3199 | 512.367 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1477 | X1-phenyl | X2-CH2CH2-CH3 | X3-phenyl | | benzyl (X5) | X6-CH2CH2CH2-CH3 | 1.93 | 437.2831 | 438.3286 |
| 1478 | X1-phenyl | X2-CH2CH2CH2CH2-CH3 | X3-phenyl | | benzyl (X5) | X6-CH2CH2CH2-CH3 | 2.01 | 465.3144 | 466.3688 |
| 1479 | X1-phenyl | X2-CH2CH2-CH3 | X3-phenyl | | 2-Br-benzyl (X5) | X6-CH2CH2CH2-CH3 | 2.09 | 515.1936 | 516.2552 |
| 1480 | X1-phenyl | X2-CH2CH2CH2CH2-CH3 | X3-phenyl | | 2-Br-benzyl (X5) | X6-CH2CH2CH2-CH3 | 2.14 | 543.2249 | 544.29 |
| 1481 | X1-phenyl | X2-CH2CH2-CH3 | X3-phenyl | | 2-F-benzyl (X5) | X6-CH2CH2CH2-CH3 | 2 | 455.2737 | 456.3135 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1482 | X1-Ph | X2-(CH2)4-CH3 | X3-Ph |  | 2-F-benzyl (X5) | X6-(CH2)3-CH3 | 2.08 | 483.305 | 484.3603 |
| 1483 | X1-Ph | X2-CH2-CH3 | X3-Ph |  | 2-Cl-benzyl (X5) | 2-CH3-benzyl (X6) | 2.04 | 457.2285 | 458.2748 |
| 1484 | X1-Ph | X2-(CH2)2-CH3 | X3-Ph |  | 2-Cl-benzyl (X5) | X6-(CH2)3-CH3 | 2.06 | 471.2441 | 472.2965 |
| 1485 | X1-Ph | X2-(CH2)4-CH3 | X3-Ph |  | 2-Cl-benzyl (X5) | X6-(CH2)3-CH3 | 2.13 | 499.2754 | 500.3322 |
| 1486 | X1-Ph | X2-(CH2)4-CH3 | X3-Ph |  | 2-CH3-benzyl (X5) | X6-(CH2)3-CH3 | 2.1 | 479.33 | 480.3871 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1487 | phenyl-X1 | X2–CH2CH2–CH3 | phenyl-X3 | | 2-methoxyphenyl-CH2-X3 (O-CH3) | H3C–CH2CH2CH2–X6 | 1.84 | 467.2937 | 468.3388 |
| 1488 | phenyl-X1 | X2–(CH2)4–CH3 | phenyl-X3 | | 2-methoxyphenyl-CH2-X5 | X6–CH2CH2CH2–CH3 | 1.93 | 495.325 | 496.3778 |
| 1489 | phenyl-X1 | X2–CH2CH2–CH3 | phenyl-X3 | | 2-(trifluoromethyl)phenyl-CH2-X5 | X6–CH2CH2CH2–CH3 | 2.07 | 505.2705 | 506.284 |
| 1490 | phenyl-X1 | X2–CH2CH2–CH3 | phenyl-X3 | | 2-(methoxymethoxy)phenyl-CH2-X5 | H3C–CH2CH2CH2–X6 | 1.91 | 481.3093 | 482.3268 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1491 | X1-phenyl | X2-(CH2)4-CH3 | X3-phenyl | | X5-CH2-(2-(2-methoxyethoxy)phenyl) | X6-(CH2)3-CH3 | 2 | 509.3406 | 510.3873 |
| 1492 | X1-phenyl | X2-CH2-CH(CH3)- | X3-phenyl | | X5-CH2-(2,4-dimethoxyphenyl with X5-CH2) | X6-(CH2)3-CH3 | 1.81 | 497.3042 | 498.338 |
| 1493 | X1-phenyl | X2-(CH2)4-CH3 | X3-phenyl | | X5-CH2-(2,4-dimethoxyphenyl with X5-CH2) | X6-(CH2)3-CH3 | 1.89 | 525.3355 | 526.3815 |

TABLE 2A-continued
| CMP # | R1 | R2 | R3 | R4 | R5 | R6 | Rtn. Time | Cmp. Mass | H+ Ion Obs |
|---|---|---|---|---|---|---|---|---|---|
| 1494 | 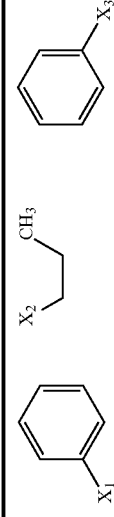 | 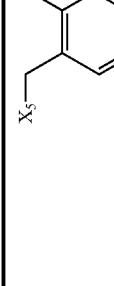 |  | | 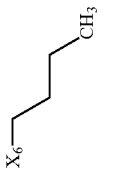 | 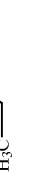 | 1.86 | 497.3042 | 498.333 |
| 1495 | 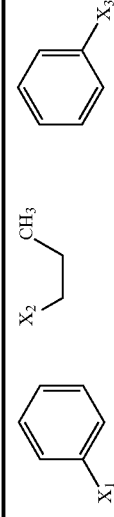 | 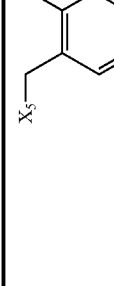 |  | | 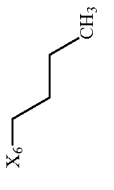 | 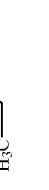 | 1.94 | 525.3355 | 526.3823 |
| 1496 | 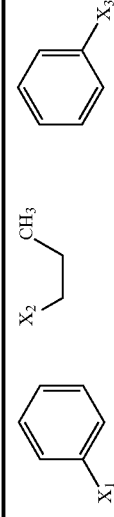 | 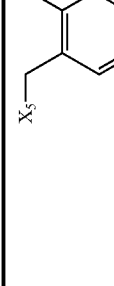 |  | |  | 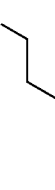 | 2 | 455.2737 | 456.3067 |
| 1497 | 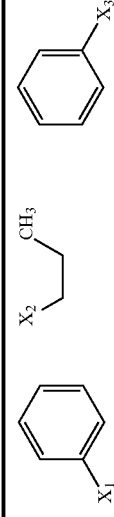 | 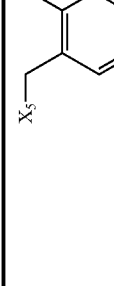 |  | | 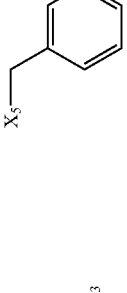 | 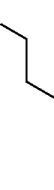 | 1.95 | 451.2987 | 452.3412 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1498 | X1-phenyl | X2-(CH2)4CH3 | X3-phenyl | | X5-benzyl, 3-CH3 | X6-(CH2)3CH3 | 2.05 | 479.33 | 480.3812 |
| 1499 | X1-phenyl | X2-(CH2)2CH3 | X3-phenyl | | X5-benzyl, 3-OCH3 | X6-(CH2)3CH3 | 1.95 | 467.2937 | 468.3324 |
| 1500 | X1-phenyl | X2-(CH2)4CH3 | X3-phenyl | | X5-benzyl, 3-OCH3 | X6-(CH2)3CH3 | 2.02 | 495.325 | 496.3728 |
| 1501 | X1-phenyl | X2-(CH2)2CH3 | X3-phenyl | | X5-benzyl, 3-Cl | X6-(CH2)3CH3 | 2.06 | 471.2441 | 472.2934 |
| 1502 | X1-phenyl | X2-(CH2)2CH3 | X3-phenyl | | X5-benzyl, 4-Br | X6-(CH2)3CH3 | 2.05 | 516.19936 | 516.24 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1503 | X1-phenyl | X2-(CH2)4CH3 | X3-phenyl | | X5-CH2-(4-Br-phenyl) | X6-(CH2)3-CH3 | 2.12 | 543.2249 | 544.28 |
| 1504 | X1-phenyl | X2-(CH2)2CH3 | X3-phenyl | | X5-CH2-(4-F-phenyl) | X6-(CH2)3-CH3 | 1.95 | 455.2737 | 456.315 |
| 1505 | X1-phenyl | X2-(CH2)4CH3 | X3-phenyl | | X5-CH2-(4-Cl-phenyl) | X6-(CH2)3-CH3 | 2.04 | 283.305 | 484.3472 |
| 1506 | X1-phenyl | X2-(CH2)2CH3 | X3-phenyl | | X5-CH2-(4-Cl-phenyl) | X6-(CH2)3-CH3 | 2.04 | 471.2441 | 472.2987 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1507 | X1-phenyl | X2-(CH2)4CH3 | X3-phenyl | | X5-CH2-(4-Cl-phenyl) | X6-(CH2)3CH3 | 2.1 | 499.2754 | 500.3232 |
| 1508 | X1-phenyl | X2-CH2CH3 | X3-phenyl | | X5-CH2-(4-CH3-phenyl) | X6-(CH2)3CH3 | 1.93 | 437.2831 | 438.3264 |
| 1509 | X1-phenyl | X2-(CH2)2CH3 | X3-phenyl | | X5-CH2-(4-CH3-phenyl) | X6-(CH2)3CH3 | 1.94 | 451.2987 | 452.3422 |
| 1510 | X1-phenyl | X2-(CH2)4CH3 | X3-phenyl | | X5-CH2-(4-CH3-phenyl) | X6-(CH2)3CH3 | 2.03 | 479.33 | 480.3817 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1511 |  |  | 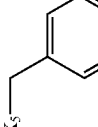 | |  |  | 1.94 | 437.2831 | 438.3318 |
| 1512 | 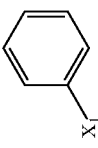 |  |  | |  |  | 1.98 | 451.2987 | 452.3448 |
| 1513 |  |  |  | | 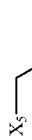 |  | 2 | 465.3144 | 466.3637 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1514 | phenyl-X1 | X2-(CH2)4-CH3 | phenyl-X3 | | X5-CH2-C6H4-CH2-CH3 (para) | H3C-(CH2)3-X6 | | | |
| 1515 | phenyl-X1 | X2-(CH2)2-CH3 | phenyl-X3 | | X5-CH2-C6H4-CH2-CH3 (para) | H3C-(CH2)3-X6 | 1.87 | 467.2937 | 468.338 |
| 1516 | phenyl-X1 | X2-(CH2)4-CH3 | phenyl-X3 | | X5-CH2-C6H4-O-CH3 (para) | H3C-(CH2)3-X6 | 1.96 | 495.325 | 496.3754 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1517 | X1-Ph | X2-CH2CH3 | X3-Ph | | X5-CH2-C6H4-OCH2CH3 | X6-(CH2)3-CH3 | 1.9 | 467.2937 | 468.3403 |
| 1518 | X1-Ph | X2-(CH2)2CH3 | X3-Ph | | X5-CH2-C6H4-OCH2CH3 | X6-(CH2)3-CH3 | 1.92 | 481.3093 | 482.358 |
| 1519 | X1-Ph | X2-(CH2)4CH3 | X3-Ph | | X5-CH2-C6H4-OCH2CH3 | X6-(CH2)3-CH3 | 2 | 509.3406 | 510.3971 |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| 1520 | C6H5-X1 | X2-(CH2)3-CH3 | C6H5-X3 | | X5-CH2-C6H4-O-(CH2)3-CH3 | X6-(CH2)3-CH3 | 2.03 | 509.3406 | 510.3994 |
| 1521 | C6H5-X1 | X2-(CH2)4-CH3 | C6H5-X3 | | X5-CH2-C6H4-O-(CH2)3-CH3 | X6-(CH2)3-CH3 | | | |
| 1522 | C6H5-X1 | X2-(CH2)4-CH3 | C6H5-X3 | | X5-CH2-C6H4-CF3 | X6-(CH2)3-CH3 | 2.12 | 533.3018 | 534.3584 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1523 |  |  |  | |  |  | 2.01 | 465.3144 | 466.3678 |
| 1524 |  |  |  | |  |  | 2.04 | 479.33 | 480.3809 |
| 1525 |  |  | | | | | | | |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1526 | 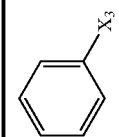 | 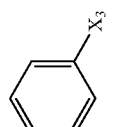 |  | | 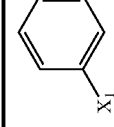 | 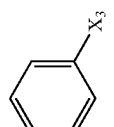 | 1.88 | 467.2573 | 468.2988 |
| 1527 |  | 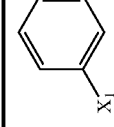 |  | | 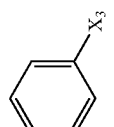 | 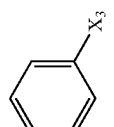 | 1.91 | 481.2720 | 482.3167 |
| 1528 |  |  |  | | 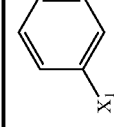 | 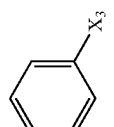 | 1.99 | 509.3042 | 510.3497 |
| 1529 |  | 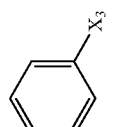 |  | | 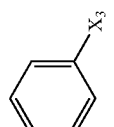 | 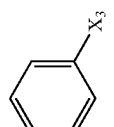 | 1.88 | 481.2729 | 482.3152 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1530 | $X_1$-phenyl | $X_2$-(CH$_2$)$_2$-CH$_3$ | $X_3$-phenyl | | $X_5$-CH$_2$-(2,3-dihydro-1,4-benzodioxin-6-yl) | $X_6$-(CH$_2$)$_3$-CH$_3$ | 1.89 | 495.2666 | 496.3308 |
| 1531 | $X_1$-phenyl | $X_2$-(CH$_2$)$_4$-CH$_3$ | $X_3$-phenyl | | $X_5$-CH$_2$-(2,3-dihydro-1,4-benzodioxin-6-yl) | $X_6$-(CH$_2$)$_3$-CH$_3$ | 1.97 | 523.3199 | 524.3652 |
| 1532 | $X_1$-phenyl | $X_2$-(CH$_2$)$_4$-CH$_3$ | $X_3$-phenyl | | $X_5$-CH$_2$-(4-phenoxyphenyl) | $X_6$-(CH$_2$)$_3$-CH$_3$ | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1533 | X1–C6H5 | X2–(CH2)4–CH3 | X5–C6H5 | | 4-benzyloxybenzyl (X5) | H3C–(CH2)3–X6 | | | |
| 1534 | X1–C6H5 | X2–(CH2)4–CH3 | X3–C6H5 | | 3-benzyloxy-4-methoxybenzyl (X5) | H3C–(CH2)3–X6 | 2.04 | 601.3668 | 602.4158 |
| 1535 | X1–C6H5 | X2–(CH2)4–CH3 | X3–C6H5 | | 3,4-dimethoxybenzyl (X5) | H3C–(CH2)3–X6 | 1.9 | 525.3355 | 526.3354 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1536 | 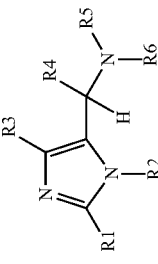 | H₃C–CH₂–CH₂–CH₂–X₂ | 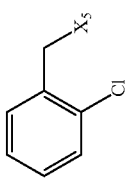 | | 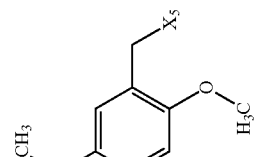 (2-Cl-benzyl-X₅) | X₆–CH₂–CH₂–CH₂–CH₃ | 2.1 | 485.2598 | 486.306 |
| 1537 | 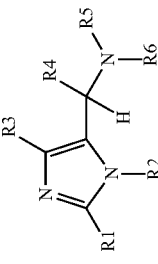 | H₃C–CH₂–CH₂–CH₂–X₂ | 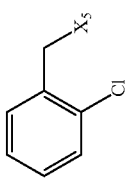 | | 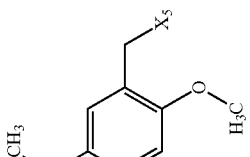 (2,5-dimethoxybenzyl-X₅) | X₆–CH₂–CH₃ | 1.8 | 483.2886 | 484.3271 |
| 1538 | 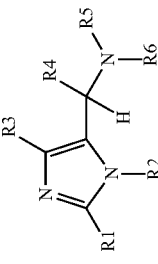 | H₃C–CH₂–CH₂–CH₂–X₂ | 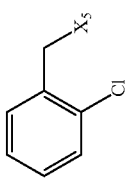 | | 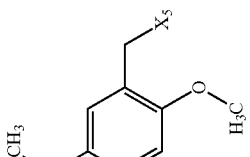 (2,5-dimethoxybenzyl-X₅) | X₆–CH₂–CH(CH₃)₂ | 1.86 | 497.3042 | 498.3447 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1539 | phenyl-X1 | H3C-(CH2)3-X2 | phenyl-X3 | | 2,5-dimethoxybenzyl-X5 | X6-(CH2)3-CH3 | 1.91 | 511.3199 | 512.3699 |
| 1540 | phenyl-X1 | H3C-(CH2)3-X2 | phenyl-X3 | | 3-bromobenzyl-X5 | X6-CH2-CH3 | 2.02 | 501.1779 | 502.23 |
| 1541 | phenyl-X1 | H3C-(CH2)3-X2 | phenyl-X3 | | 3-bromobenzyl-X5 | X6-(CH2)2-CH3 | 2.07 | 515.1936 | 516.24 |
| 1542 | phenyl-X1 | H3C-(CH2)3-X2 | phenyl-X3 | | 3-bromobenzyl-X5 | X6-(CH2)3-CH3 | 2.11 | 529.2093 | 530.27 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1543 | X1-phenyl | H3C-(CH2)3-X2 | X3-phenyl | | 3-F-benzyl-X5 | X4-CH2CH2-CH3 | 1.94 | 441.258 | 442.2997 |
| 1544 | X1-phenyl | H3C-(CH2)2-X2 | X3-phenyl | | 3-F-benzyl-X5 | X6-CH2CH2CH2-CH3 | 1.99 | 455.2737 | 456.321 |
| 1545 | X1-phenyl | H3C-(CH2)2-X2 | X3-phenyl | | 3-F-benzyl-X5 | X6-(CH2)3-CH3 | 2.04 | 469.2893 | 470.3382 |
| 1546 | X1-phenyl | H3C-(CH2)2-X2 | X3-phenyl | | 3-CH3-benzyl-X5 | X6-CH2CH2-CH3 | 1.97 | 461.2987 | 462.3466 |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| | | | | R4 is H unless otherwise specified | | | | | |
| 1547 | X1-phenyl | H3C-CH2CH2CH2-X3 | X3-phenyl | | 3-methylbenzyl-X5 | X6-CH2CH2CH2CH3 | 2 | 465.3144 | 466.3688 |
| 1548 | X1-phenyl | H3C-CH2CH2CH2-X2 | X3-phenyl | | 3-(trifluoromethyl)benzyl-X5 | X6-CH2CH3 | 2.01 | 491.2548 | 492.3076 |
| 1549 | X1-phenyl | H3C-CH2CH2CH2-X2 | X3-phenyl | | 3-(trifluoromethyl)benzyl-X5 | X6-CH2CH2CH3 | 2.06 | 505.2705 | 506.3239 |
| 1550 | X1-phenyl | H3C-CH2CH2CH2-X2 | X3-phenyl | | 3-(trifluoromethyl)benzyl-X5 | X6-CH2CH2CH2CH3 | 2.09 | 610.2881 | 620.3437 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1551 | X₁-phenyl | H₃C-CH₂CH₂CH₂-X₂ | X₃-phenyl | | 3-methoxybenzyl-X₅ | X₆-CH₂CH₃ | 1.88 | 453.278 | 454.32 |
| 1552 | X₁-phenyl | H₃C-CH₂CH₂CH₂-X₂ | X₃-phenyl | | 3-methoxybenzyl-X₅ | X₆-CH₂CH₂CH₃ | 1.95 | 487.2937 | 466.3404 |
| 1553 | X₁-phenyl | H₃C-CH₂CH₂CH₂-X₂ | X₃-phenyl | | 3-methoxybenzyl-X₅ | X₆-CH₂CH₂CH₂CH₃ | 1.98 | 481.3093 | 482.3591 |
| 1554 | X₁-phenyl | H₃C-CH₂CH₂CH₂-X₂ | X₃-phenyl | | 3-chlorobenzyl-X₅ | X₆-CH₂CH₃ | 1.99 | 457.2285 | 458.2789 |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| | | | | R4 is H unless otherwise specified | | | | | |
| 1555 | phenyl-X₁ | H₃C-CH₂CH₂CH₂-X₂ | phenyl-X₃ | | 3-Cl-benzyl-X₅ | X₆-CH₂CH₂-CH₃ (with H₃C branch) | 2.05 | 471.2441 | 472.2944 |
| 1556 | phenyl-X₁ | H₃C-CH₂CH₂CH₂-X₂ | phenyl-X₃ | | 3-Cl-benzyl-X₅ | X₆-CH₂CH₂CH₂-CH₃ | 2.09 | 485.2598 | 486.3078 |
| 1557 | phenyl-X₁ | H₃C-CH₂CH₂CH₂-X₂ | phenyl-X₃ | | 3-phenoxy-benzyl-X₅ | X₆-CH₂CH₂-CH₃ (with H₃C branch) | 2.11 | 529.3093 | 530.3656 |
| 1558 | phenyl-X₁ | H₃C-CH₂CH₂CH₂-X₂ | phenyl-X₃ | | 4-Br-benzyl-X₅ | X₆-CH₂CH₂-CH₃ (with H₃C branch) | 2.05 | 515.1936 | 516.25 |

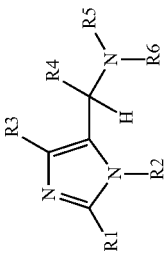

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1559 | X1-phenyl | H3C-(CH2)3-X2 | X3-phenyl | | 4-Br-benzyl-X5 | X6-(CH2)3-CH3 | 2.09 | 529.2093 | 630.2776 |
| 1560 | X1-phenyl | H3C-(CH2)3-X2 | X3-phenyl | | 4-F-benzyl-X5 | X6-CH2-CH(CH3) (H3C branch) | 1.97 | 455.2737 | 456.3232 |
| 1561 | X1-phenyl | H3C-(CH2)3-X2 | X3-phenyl | | 4-F-benzyl-X5 | X6-(CH2)3-CH3 | 2 | 469.2893 | 470.3403 |
| 1562 | X1-phenyl | H3C-(CH2)3-X2 | X3-phenyl | | 4-Cl-benzyl-X5 | X6-CH2-CH3 | 1.98 | 457.2285 | 458.2803 |

TABLE 2A-continued
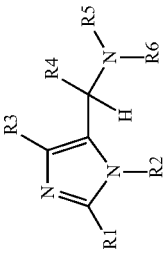
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1563 | phenyl-X1 | H3C-CH2CH2CH2-X2 | phenyl-X3 | | 4-Cl-benzyl-X5 | X6-CH2CH2-CH3 | 2.03 | 471.2441 | 472.2929 |
| 1564 | phenyl-X1 | H3C-CH2CH2CH2-X2 | phenyl-X3 | | 4-Cl-benzyl-X5 | X6-CH2CH2CH2-CH3 | 2.07 | 485.2598 | 486.3048 |
| 1565 | phenyl-X1 | H3C-CH2CH2CH2-X2 | phenyl-X3 | | 4-CH3-benzyl-X5 | X6-CH2CH2-CH3 | 1.95 | 451.2987 | 452.3497 |
| 1566 | phenyl-X1 | H3C-CH2CH2CH2-X2 | phenyl-X3 | | 4-CH3-benzyl-X5 | X6-CH2CH2CH2-CH3 | 1.99 | 465.3144 | 466.3694 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1567 | X₁-phenyl | H₃C-(CH₂)₃-X₂ | X₃-phenyl | | 2,5-(H₃C, X₅CH₂)-phenyl | X₆-CH₂CH₃ | 1.94 | 451.2987 | 452.3482 |
| 1568 | X₁-phenyl | H₃C-(CH₂)₃-X₂ | X₃-phenyl | | 2,5-(H₃C, X₅CH₂)-phenyl | X₆-CH₂CH₂CH₃ | 2 | 465.3144 | 466.3705 |
| 1569 | X₁-phenyl | H₃C-(CH₂)₃-X₂ | X₃-phenyl | | 2,5-(H₃C, X₅CH₂)-phenyl | X₆-(CH₂)₃CH₃ | 2.04 | 479.33 | 480.3848 |
| 1570 | X₁-phenyl | H₃C-(CH₂)₃-X₂ | X₃-phenyl | | 4-(H₃CO)-, X₅CH₂-phenyl | X₆-CH₂CH₃ | 1.81 | 453.278 | 454.3195 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1571 | X₁-C₆H₅ | H₃C-CH₂CH₂CH₂-X₂ | X₃-C₆H₅ | | 4-MeO-C₆H₄-CH₂-X₅ | X₆-CH₂CH₂-CH₃ (with H₃C branch) | 1.88 | 467.2937 | 468.3429 |
| 1572 | X₁-C₆H₅ | H₃C-CH₂CH₂CH₂-X₂ | X₃-C₆H₅ | | 4-MeO-C₆H₄-CH₂-X₅ | X₆-CH₂CH₂CH₂-CH₃ | 1.92 | 481.3093 | 482.358 |
| 1573 | X₁-C₆H₅ | H₃C-CH(CH₃)CH₂CH₂-X₂ | X₃-C₆H₅ | | 4-EtO-C₆H₄-CH₂-X₅ | X₆-CH₂-CH₃ | 1.87 | 467.2937 | 468.3413 |
| 1574 | X₁-C₆H₅ | H₃C-CH₂CH₂CH₂-X₂ | X₃-C₆H₅ | | 4-EtO-C₆H₄-CH₂-X₅ | X₆-CH₂CH₂CH₂-CH₃ | 1.92 | 481.3093 | 182.3646 |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| 1575 | X1-phenyl | H3C-CH2CH2CH2-X2 | X3-phenyl | | 4-(methoxymethoxy)benzyl-X5 | X6-CH2CH2CH2CH3 | 1.96 | 495.326 | 496.383 |
| 1576 | X1-phenyl | H3C-CH2CH2CH2-X2 | X3-phenyl | | 4-(butoxy)benzyl-X5 | X6-CH2CH2CH3 | 2.03 | 509.3406 | 510.391 |
| 1577 | X1-phenyl | H3C-CH2CH2CH2-X2 | X3-phenyl | | 4-(butoxy)benzyl-X5 | X6-CH2CH2CH2CH3 | | | |
| 1578 | X1-phenyl | H3C-CH2CH2CH2-X2 | X3-phenyl | | 4-(trifluoromethyl)benzyl-X5 | X6-CH2CH2CH3 | 2.05 | 505.2705 | 506.3306 |

R4 is H unless otherwise specified

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1579 | X1-Ph | H3C-CH2CH2CH2-X2 | X3-Ph | | 4-(CF3)-C6H4-CH(X5) | X6-CH2CH2CH2-CH3 | 2.09 | 519.2861 | 520.3426 |
| 1580 | X1-Ph | H3C-CH2CH2CH2CH2-X2 | X3-Ph | | 4-CH(CH3)2-C6H4-CH2-X5 | X6-CH2-CH3 | 1.98 | 465.3144 | 466.3676 |
| 1581 | X1-Ph | H3C-CH2CH2CH2-X2 | X3-Ph | | 4-CH(CH3)2-C6H4-CH2-X5 | X6-CH2CH2-CH3 | | | |
| 1582 | X1-Ph | H3C-CH2CH2CH2-X2 | X3-Ph | | 4-CH(CH3)2-C6H4-CH2-X5 | X6-CH2CH2CH2-CH3 | | | |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1583 | 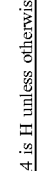 |  | 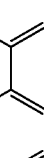 | |  | 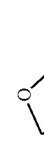 | 2.07 | 513.3144 | 514.3667 |
| 1584 | 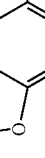 |  |  | | 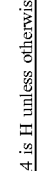 |  | 2.07 | 526.258 | 527.32 |
| 1585 | 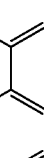 |  | 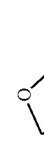 | | 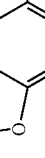 |  | 2.06 | 554.2893 | 555.3538 |
| 1586 |  | 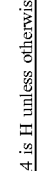 |  | | 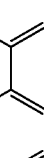 |  | 2.03 | 451.2987 | 452.3538 |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| 1587 | X₁-phenyl | X₂-CH₂CH₂CH₃ | X₃-phenyl | | X₅-CH₂-(2,4-dimethylphenyl) | X₆-(CH₂)₃CH₃ | 2.05 | 465.3144 | 466.3634 |
| 1588 | X₁-phenyl | X₂-(CH₂)₄CH₃ | X₃-phenyl | | X₅-CH₂-(2,4-dimethylphenyl) | X₆-(CH₂)₃CH₃ | 2.12 | 493.3457 | 494.4006 |
| 1589 | X₁-phenyl | X₂-CH₂CH₂CH₃ | X₃-phenyl | | X₅-CH₂-(2,5-difluorophenyl) | X₆-(CH₂)₃CH₃ | 2.03 | 473.2643 | 474.2992 |
| 1590 | X₁-phenyl | X₂-(CH₂)₄CH₃ | X₃-phenyl | | X₅-CH₂-(2,5-difluorophenyl) | X₆-(CH₂)₃CH₃ | 2.1 | 501.2956 | 502.3373 |
| 1591 | X₁-phenyl | X₂-CH₂CH₃ | X₃-phenyl | | X₅-CH₂-(2,6-dichlorophenyl) | X₆-(CH₂)₃CH₃ | 2.1 | 491.1895 | 192.2394 |

R4 is H unless otherwise specified

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1592 | Ph-X1 | X2-CH2CH2CH3 | Ph-X3 | | 2,6-diCl-benzyl | X6-(CH2)3-CH3 | 2.11 | 505.2051 | 506.2584 |
| 1593 | Ph-X1 | X2-(CH2)4-CH3 | Ph-X3 | | 2,6-diCl-benzyl | X6-(CH2)3-CH3 | 2.18 | 533.2365 | 534.3019 |
| 1594 | Ph-X1 | X2-CH2-CH3 | Ph-X3 | | 2-Cl-6-F-benzyl | X6-(CH2)3-CH3 | 2.06 | 475.2191 | 476.2581 |
| 1595 | Ph-X1 | X2-CH2CH2CH3 | Ph-X3 | | 2-Cl-6-F-benzyl | X6-(CH2)3-CH3 | 2.08 | 489.2347 | 490.2856 |
| 1596 | Ph-X1 | X2-(CH2)4-CH3 | Ph-X3 | | 2-Cl-6-F-benzyl | X6-(CH2)3-CH3 | 2.14 | 517.266 | 518.3196 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1597 | X1-phenyl | X2-CH2CH2CH3 | X3-phenyl | | 2,3-difluorobenzyl-X5 | X6-CH2CH2CH2CH3 | 2.04 | 473.2643 | 474.3057 |
| 1598 | X1-phenyl | X2-CH2CH2CH2CH2CH3 | X3-phenyl | | 2,3-difluorobenzyl-X5 | X6-CH2CH2CH2CH3 | 2.1 | 501.2956 | 502.3344 |
| 1599 | X1-phenyl | X2-CH3 | X3-phenyl | | 2,6-difluorobenzyl-X5 | H3C-CH2CH2CH2-X6 | 2 | 445.2329 | 446.2716 |
| 1600 | X1-phenyl | X2-CH2CH3 | X3-phenyl | | 2,6-difluorobenzyl-X5 | H3C-CH2CH2CH2-X6 | 2.02 | 459.2486 | 460.2865 |
| 1601 | X1-phenyl | X2-CH2CH2CH3 | X3-phenyl | | 2,6-difluorobenzyl-X5 | H3C-CH2CH2CH2-X6 | 2.05 | 473.2643 | 474.3071 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1602 | X1-phenyl | X2-(CH2)4CH3 | X3-phenyl | | 2,6-difluorobenzyl (X5) | X6-(CH2)3CH3 | 2.1 | 501.2956 | 502.3315 |
| 1603 | X1-phenyl | X2-CH2CH3 | X3-phenyl | | 2,4-difluorobenzyl (X5) | X6-(CH2)3CH3 | 1.98 | 445.2329 | 446.2758 |
| 1604 | X1-phenyl | X2-(CH2)3CH3 | X3-phenyl | | 2,4-difluorobenzyl (X5) | X6-(CH2)3CH3 | 2.03 | 473.2643 | 474.3029 |
| 1605 | X1-phenyl | X2-(CH2)4CH3 | X3-phenyl | | 2,4-difluorobenzyl (X5) | X6-(CH2)3CH3 | 2.1 | 501.2956 | 502.3305 |
| 1606 | X1-phenyl | X2-(CH2)3CH3 | X3-phenyl | | 4-fluoro-3-methoxybenzyl (X5) | X6-(CH2)3CH3 | 2.03 | 485.2842 | 486.3231 |

TABLE 2A-continued
| CMP # | R1 | R2 | R3 | R4 | R5 | R6 | Rtn. Time | Cmp. Mass | H+ Ion Obs |
|---|---|---|---|---|---|---|---|---|---|
| | | | | R4 is H unless otherwise specified | | | | | |
| 1607 | 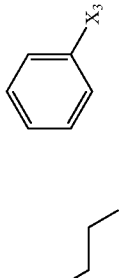 | 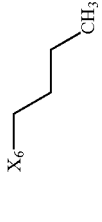 |  | | 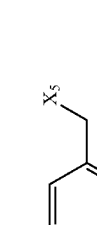 |  | 2.09 | 513.3156 | 514.3523 |
| 1608 | 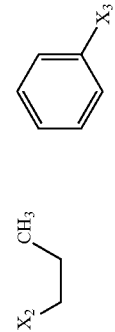 | 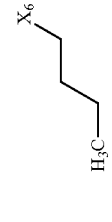 |  | |  | 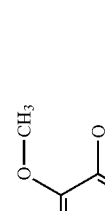 | 1.85 | 527.3148 | 528.3573 |
| 1609 | 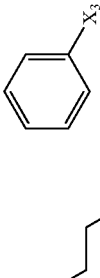 | 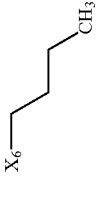 |  | | 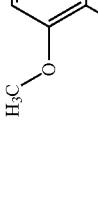 | 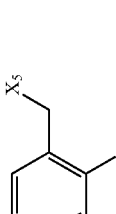 | 1.93 | 555.3461 | 556.3929 |
| 1610 | 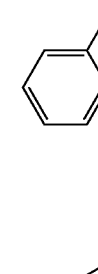 | 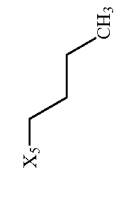 |  | | 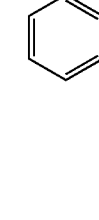 | 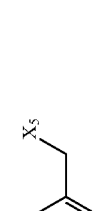 | 2.06 | 509.3042 | 510.3471 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1611 | X1-phenyl | X2-CH2CH2-CH3 | X3-phenyl | | X5-CH2-(3-methyl-4-methoxyphenyl) | X6-(CH2)3-CH3 | 1.9 | 467.2937 | 467.3423 |
| 1612 | X1-phenyl | X2-CH2CH2-CH3 | X3-phenyl | | X5-CH2-(3-methyl-4-methoxyphenyl) | X6-(CH2)3-CH3 | 1.92 | 481.3093 | 482.3568 |
| 1613 | X1-phenyl | X2-(CH2)4-CH3 | X3-phenyl | | X5-CH2-(3-methyl-4-methoxyphenyl) | X6-(CH2)3-CH3 | 2 | 509.3406 | 510.4003 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1614 |  | 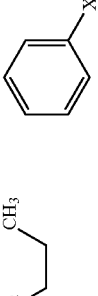 | 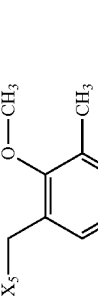 | |  |  | 1.89 | 511.3199 | 512.3646 |
| 1615 | 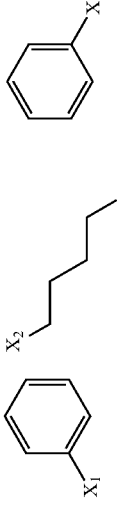 |  |  | | 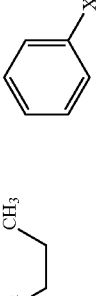 | 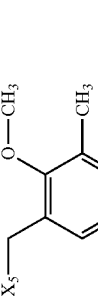 | 1.96 | 539.3512 | 540.4082 |
| 1616 |  | 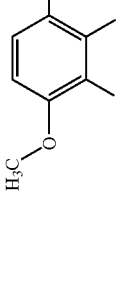 |  | |  | 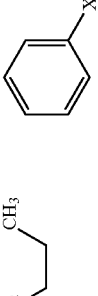 | 2.05 | 491.2548 | 492.3016 |
| 1617 | 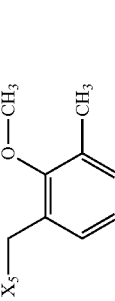 |  | 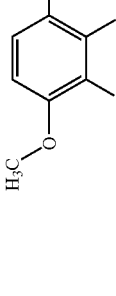 | |  |  | 2.07 | 523.261 | 524.3156 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1618 | X1-phenyl | X2-CH2CH2-CH3 | X3-phenyl | | 2,5-dimethyl-4-methoxy (X5) benzyl | H3C-(CH2)3-X6 | 1.99 | 481.3093 | 482.3597 |
| 1619 | X1-phenyl | X2-CH2CH2-CH3 | X3-phenyl | | X5-CH2-(2,5-dimethyl-4-methoxy)phenyl | X6-(CH2)3-CH3 | 2 | 495.325 | 496.3752 |
| 1620 | X1-phenyl | X2-(CH2)3-CH3 | X3-phenyl | | X5-CH2-(2,5-dimethyl-4-methoxy)phenyl | X6-(CH2)3-CH3 | 2.07 | 523.3563 | 524.4204 |
| 1621 | X1-phenyl | X2-CH2CH2-CH3 | X3-phenyl | | X5-CH2-(2-chloro-3,4-dimethoxy)phenyl | X6-(CH2)3-CH3 | 2.02 | 531.2653 | 532.3195 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1622 | X1-phenyl | X2-(CH2)4CH3 | X3-phenyl | | X5-CH2-(3-Cl,4-OCH3,6-CH3O)phenyl | X6-(CH2)3CH3 | 2.09 | 559.2966 | 560.3568 |
| 1623 | X1-phenyl | X2-(CH2)2CH3 | X3-phenyl | | X5-CH2-(2-Cl,4-F)phenyl | X6-(CH2)3CH3 | 2.09 | 489.2347 | 490.2897 |
| 1624 | X1-phenyl | X2-(CH2)4CH3 | X3-phenyl | | X5-CH2-(2-Cl,4-F)phenyl | X6-(CH2)3CH3 | 2.14 | 517.266 | 518.3209 |
| 1625 | X1-phenyl | X2-(CH2)4CH3 | X3-phenyl | | (2,6-diOCH3)phenyl-CH2-X5 | X6-(CH2)3CH3 | 1.87 | 525.3355 | 526.3839 |
| 1626 | X1-phenyl | X2-(CH2)4CH3 | X3-phenyl | | X5-CH2-(2-OH,3-OCH3)phenyl | X6-(CH2)3CH3 | 1.86 | 511.3199 | 512.3685 |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| 1627 | X₁-phenyl | X₂-(CH₂)₃CH₃ | X₃-phenyl | | X₅-CH₂-(2-OH, 3-OCH₂CH₃ phenyl) | X₆-(CH₂)₃CH₃ | 1.83 | 497.3042 | 498.3462 |
| 1628 | X₁-phenyl | X₂-(CH₂)₄CH₃ | X₃-phenyl | | X₅-CH₂-(2-OH, 3-OCH₂CH₃ phenyl) | X₆-(CH₂)₃CH₃ | 1.91 | 525.3355 | 526.3853 |
| 1629 | X₁-phenyl | X₂-(CH₂)₄CH₃ | X₃-phenyl | | X₅-CH₂-(2-OH, 4-OCH₃ phenyl) | X₆-(CH₂)₃CH₃ | 1.85 | 511.3199 | 512.3719 |
| 1630 | X₁-phenyl | X₂-(CH₂)₃CH₃ | X₃-phenyl | | X₅-CH₂-(4-Br, 2-OH, 6-OCH₃ phenyl) | X₆-(CH₂)₃CH₃ | 1.96 | 561.1991 | 562.2613 |

R4 is H unless otherwise specified

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| 1631 | phenyl-X1 | X2-(CH2)4-CH3 | phenyl-X3 | | 2-OH, 3-OMe, 5-Br, 6-CH2X5 phenyl | X6-(CH2)3-CH3 | 2.03 | 589.2304 | 590.29 |
| 1632 | phenyl-X1 | X2-(CH2)2-CH3 | phenyl-X3 | | 2-OH, 3-CH3, 6-CH2X5 phenyl | X6-(CH2)3-CH3 | 1.88 | 467.2937 | 468.3345 |
| 1633 | phenyl-X1 | X2-(CH2)4-CH3 | phenyl-X3 | | 2-OH, 3-CH3, 6-CH2X5 phenyl | X6-(CH2)3-CH3 | 1.97 | 495.325 | 496.3788 |
| 1634 | phenyl-X1 | X2-CH2-CH3 | phenyl-X3 | | 2-OH, 4-CH3, 6-CH2X5 phenyl | X6-(CH2)3-CH3 | 1.77 | 453.278 | 454.3158 |

R4 is H unless otherwise specified

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1635 | X₁-Ph | X₂-CH₂CH₂CH₃ | X₃-Ph | | X₅-CH₂-(4-methyl-2-OH-phenyl) | X₆-CH₂CH₂CH₂CH₃ | 1.81 | 467.2937 | 468.3368 |
| 1636 | X₁-Ph | X₂-CH₂CH₂CH₃ | X₃-Ph | | X₅-CH₂-(3-OCH₃-4-OH-phenyl) | X₆-CH₂CH₂CH₂CH₃ | 1.81 | 497.3042 | 498.3435 |
| 1637 | X₁-Ph | X₂-CH₂CH₂CH₂CH₃ | X₃-Ph | | X₅-CH₂-(3-OCH₃-4-OH-phenyl) | X₆-CH₂CH₂CH₂CH₃ | 1.89 | 525.3355 | 526.3845 |
| 1638 | X₁-Ph | X₂-CH₃ | X₃-Ph | | X₅-CH₂-(3,5-dimethyl-4-OH-phenyl) | X₆-CH₂CH₂CH₂CH₃ | 1.77 | 453.278 | 454.3218 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1639 | 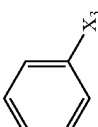 | 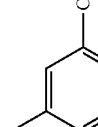 | 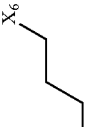 | | 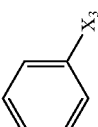 |  | 1.8 | 467.2937 | 468.3422 |
| 1640 | 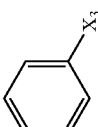 | 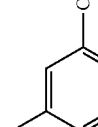 | 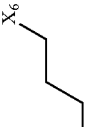 | | 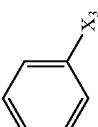 |  | 1.82 | 481.3093 | 482.3608 |
| 1641 | 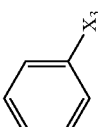 | 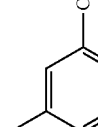 | 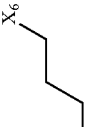 | | 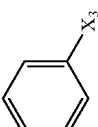 |  | | | |
| 1642 | 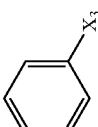 | 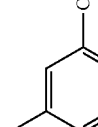 | 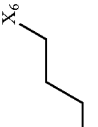 | | 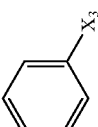 |  | 1.73 | 439.2624 | 440.3095 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1643 | X₁-phenyl | X₂-CH₂-CH₃ | X₃-phenyl | | 4-(X₅-CH₂)-2-methylphenol | X₆-(CH₂)₃-CH₃ | 1.77 | 453.278 | 454.3231 |
| 1644 | X₁-phenyl | X₂-(CH₂)₂-CH₃ | X₃-phenyl | | 4-(X₅-CH₂)-2-methylphenol | X₆-(CH₂)₃-CH₃ | 1.81 | 467.2937 | 468.3407 |
| 1645 | X₁-phenyl | X₂-(CH₂)₄-CH₃ | X₃-phenyl | | 4-(X₅-CH₂)-2-methylphenol | X₆-(CH₂)₃-CH₃ | 1.88 | 495.325 | 496.385 |
| 1646 | X₁-phenyl | H₃C-(CH₂)₃-X₂ | X₃-(4-Cl-phenyl) | | 2-Br-benzyl-X₅ | X₆-(CH₂)₃-CH₃ | 2.11 | 563.1703 | 564.29 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1647 | X1-Ph | H3C-CH2CH2CH2-X2 | X3-Ph-Cl | | X5-CH2-(2-F-Ph) | X6-CH2CH2CH2-CH3 | | | |
| 1648 | X1-Ph | H3C-CH2CH2CH2-X2 | X3-Ph-OCH3 | | X5-CH2-(2-F-Ph) | X6-CH2CH2CH2-CH3 | 2.06 | 499.2999 | 500.3384 |
| 1649 | X1-Ph | H3C-CH2CH2CH2-X2 | X3-Ph-Cl | | X5-CH2-(2-Cl-Ph) | X6-CH2CH2CH2-CH3 | | | |
| 1650 | X1-Ph | H3C-CH2CH2CH2-X2 | X3-Ph-Cl | | X5-CH2-(2,4-diCl-Ph) | X6-CH2CH2CH2-CH3 | 2.16 | 553.1818 | 554.31 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1651 |  |  | 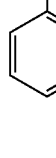 | | 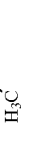 | 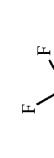 | | | |
| 1652 | 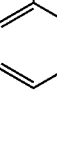 | 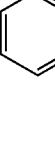 |  | |  |  | 2.01 | 495.325 | 496.3744 |
| 1653 |  | 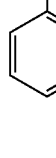 | 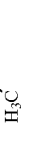 | | 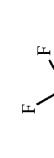 | 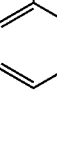 | | | |
| 1654 | 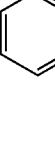 |  |  | |  |  | 2 | 499.2999 | 500.344 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1655 | $X_1$-phenyl | H$_3$C-(CH$_2$)$_3$-$X_2$ | $X_3$-(4-Cl-phenyl) | | $X_5$-CH$_2$-(3-OMe-phenyl) | $X_6$-(CH$_2$)$_3$-CH$_3$ | 2 | 511.3199 | 512.3674 |
| 1656 | $X_1$-phenyl | H$_3$C-(CH$_2$)$_3$-$X_2$ | $X_3$-(4-OMe-phenyl) | | $X_5$-CH$_2$-(3-OMe-phenyl) | $X_6$-(CH$_2$)$_3$-CH$_3$ | | | |
| 1657 | $X_1$-phenyl | H$_3$C-(CH$_2$)$_3$-$X_2$ | $X_3$-(4-Cl-phenyl) | | $X_5$-CH$_2$-(3-Cl-phenyl) | $X_6$-(CH$_2$)$_3$-CH$_3$ | | | |
| 1658 | $X_1$-phenyl | H$_3$C-(CH$_2$)$_3$-$X_2$ | $X_3$-(4-Cl-phenyl) | | $X_5$-CH$_2$-(3-phenoxy-phenyl) | $X_6$-(CH$_2$)$_3$-CH$_3$ | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1659 | X1-phenyl | H3C-CH2CH2CH2-X2 | X3-(4-Cl-phenyl) | | X5-CH2-(4-Cl-phenyl) | X6-CH2CH2CH2-CH3 | | | |
| 1660 | X1-phenyl | H3C-CH2CH2CH2-X2 | X3-(4-Cl-phenyl) | | X5-CH2-(4-CH3-phenyl) | X6-CH2CH2CH2-CH3 | | | |
| 1661 | X1-phenyl | H3C-CH2CH2CH2-X2 | X3-(4-OCH3-phenyl) | | X5-CH2-(4-CH3-phenyl) | X6-CH2CH2CH2-CH3 | 1.99 | 495.325 | 496.3893 |
| 1662 | X1-phenyl | H3C-CH2CH2CH2-X2 | X3-(4-Cl-phenyl) | | X5-CH2-(4-CH2CH3-phenyl) | X6-CH2CH2CH2-CH3 | | | |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1663 | 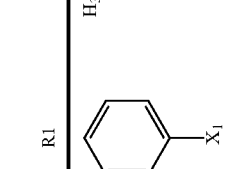 | 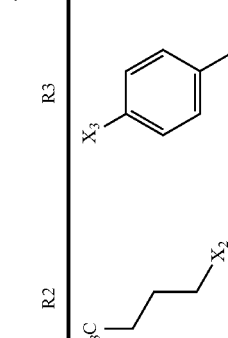 | 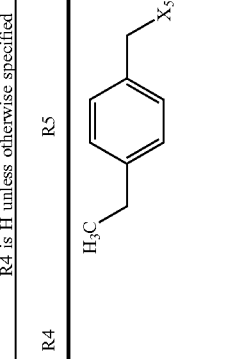 | | 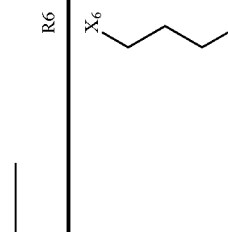 | 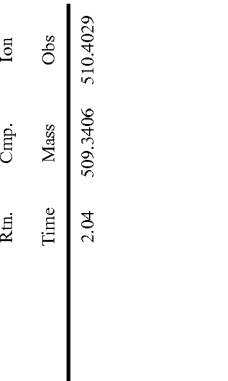 | 2.04 | 509.3406 | 510.4029 |
| 1664 | 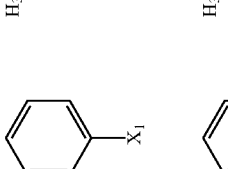 | 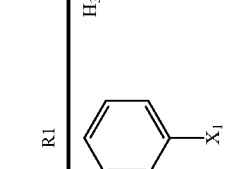 | 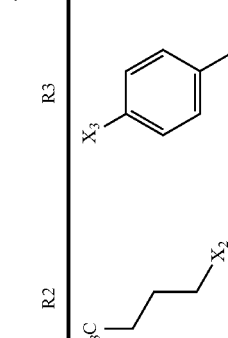 | | 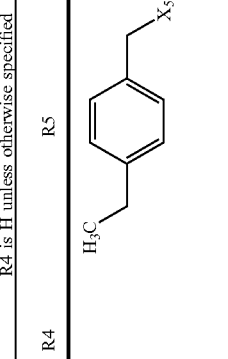 | 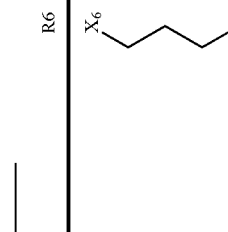 | | | |
| 1665 | 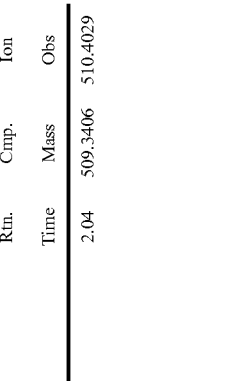 | 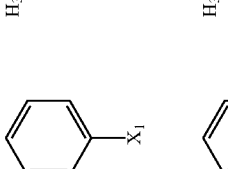 | 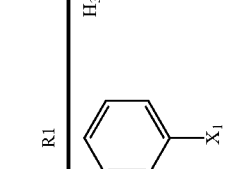 | | 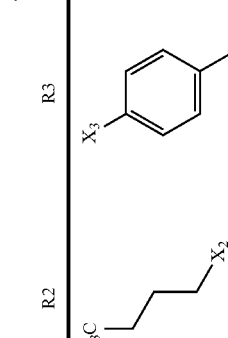 | 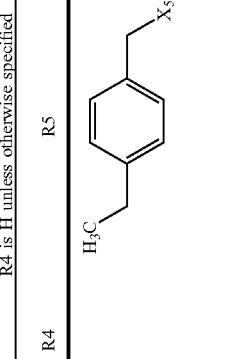 | 1.92 | 511.3199 | 512.3715 |
| 1666 | 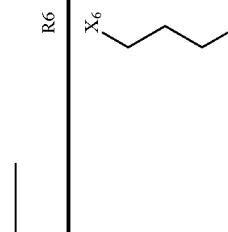 | 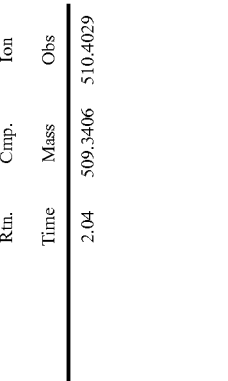 | 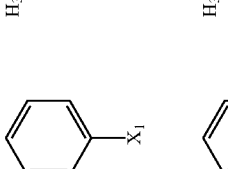 | | 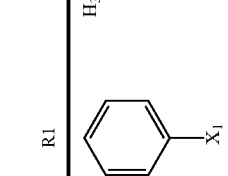 | 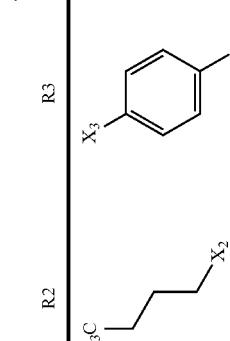 | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1667 | phenyl-X1 | H3C-(CH2)3-X2 | 4-methoxyphenyl-X3 | | 4-(2-methoxyethoxy)benzyl-X5 | X6-(CH2)3-CH3 | 1.96 | 525.3355 | 526.388 |
| 1668 | phenyl-X1 | H3C-(CH2)3-X2 | 4-chlorophenyl-X3 | | 4-(3-methoxypropoxy)benzyl-X5 | X6-(CH2)3-CH3 | | | |
| 1669 | phenyl-X1 | H3C-(CH2)3-X2 | 4-methoxyphenyl-X3 | | 4-(3-methoxypropoxy)benzyl-X5 | X6-(CH2)3-CH3 | 2.06 | 553.3668 | 554.4324 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1670 | X₁-phenyl | H₃C-(CH₂)₃-X₂ | X₃-(4-Cl-phenyl) | | 4-(CF₃)-benzyl-X₅ | X₆-(CH₂)₃-CH₃ | | | |
| 1671 | X₁-phenyl | H₃C-(CH₂)₃-X₂ | X₃-(4-Cl-phenyl) | | 4-(CH(CH₃)₂... 1-methylethyl)benzyl-X₅ | X₆-(CH₂)₃-CH₃ | | | |
| 1672 | X₁-phenyl | H₃C-(CH₂)₃-X₂ | X₃-(4-OCH₃-phenyl) | | 4-(1-methylethyl)benzyl-X₅ | X₆-(CH₂)₃-CH₃ | 2.08 | 523.3563 | 524.4255 |
| 1673 | X₁-phenyl | H₃C-(CH₂)₃-X₂ | X₃-(4-Cl-phenyl) | | 4-phenylbenzyl-X₅ | X₆-(CH₂)₃-CH₃ | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1674 | X₁-phenyl | H₃C-CH₂CH₂CH₂-X₂ | 4-F-phenyl-X₃ | | benzodioxole-CH₂-X₅ | X₆-CH₂CH₂CH₂-CH₃ | 1.98 | 513.2792 | 514.3397 |
| 1675 | X₁-phenyl | H₃C-CH₂CH₂CH₂-X₂ | 4-Cl-phenyl-X₃ | | benzodioxole-CH₂-X₅ | X₆-CH₂CH₂CH₂-CH₃ | | | |
| 1676 | X₁-phenyl | H₃C-CH₂CH₂CH₂-X₂ | 4-OCH₃-phenyl-X₃ | | benzodioxole-CH₂-X₅ | X₆-CH₂CH₂CH₂-CH₃ | 1.95 | 525.2991 | 526.3698 |
| 1677 | X₁-phenyl | H₃C-CH₂CH₂CH₂-X₂ | 2-OCH₃-phenyl-X₃ | | benzodioxole-CH₂-X₅ | X₆-CH₂CH₂CH₂-CH₃ | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1678 | phenyl-X1 | H3C-(CH2)3-X2 | 4-F-phenyl-X3 | | 2,3-dihydro-1,4-benzodioxin-6-yl-CH2-X5 | X6-(CH2)3-CH3 | 1.97 | 527.2948 | 528.3601 |
| 1679 | phenyl-X1 | H3C-(CH2)3-X2 | 4-Cl-phenyl-X3 | | 2,3-dihydro-1,4-benzodioxin-6-yl-CH2-X5 | X6-(CH2)3-CH3 | | | |
| 1680 | phenyl-X1 | H3C-(CH2)3-X2 | 4-OCH3-phenyl-X3 | | 2,3-dihydro-1,4-benzodioxin-6-yl-CH2-X5 | X6-(CH2)3-CH3 | 1.95 | 539.3148 | 540.3774 |
| 1681 | phenyl-X1 | H3C-(CH2)3-X2 | 2-OCH3-phenyl-X3 | | 2,3-dihydro-1,4-benzodioxin-6-yl-CH2-X5 | X6-(CH2)3-CH3 | | | |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| 1682 | phenyl-X1 | H3C-(CH2)3-X2 | 4-Cl-C6H4-X3 | | 4-(benzyloxy)benzyl-X5 | X6-(CH2)3-CH3 | | | |
| 1683 | phenyl-X1 | H3C-(CH2)3-X2 | 4-Cl-C6H4-X3 | | 3-(benzyloxy)-4-methoxybenzyl-X6 | X6-(CH2)3-CH3 | | | |
| 1684 | phenyl-X1 | H3C-(CH2)3-X2 | 4-MeO-C6H4-X3 | | 3,4-bis(ethoxy)benzyl-X6 | X6-(CH2)3-CH3 | | | |

R4 is H unless otherwise specified

TABLE 2A-continued
| CMP # | R1 | R2 | R3 | R4 | R5 | R6 | Rtn. Time | Cmp. Mass | H+ Ion Obs |
|---|---|---|---|---|---|---|---|---|---|
| | | | | R4 is H unless otherwise specified | | | | | |
| 1685 | 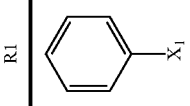 | 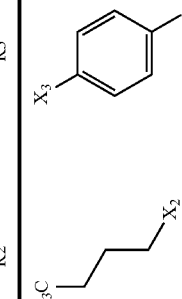 | 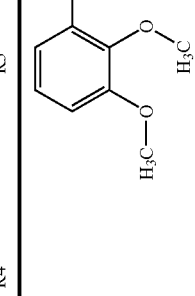 | |  | 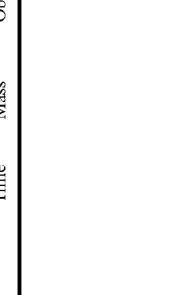 | | | |
| 1686 | 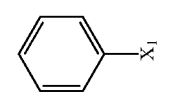 | 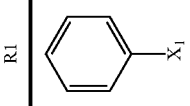 | 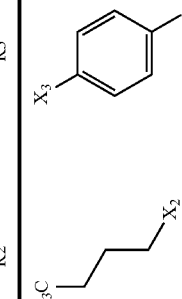 | | 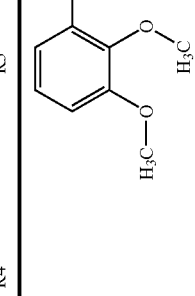 | 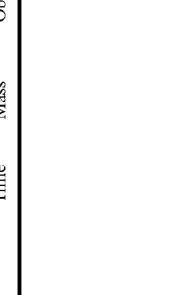 | 1.91 | 541.3304 | 542.3954 |
| 1687 |  | 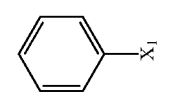 | 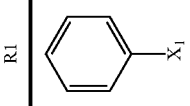 | | 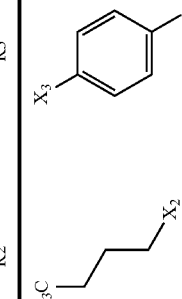 | 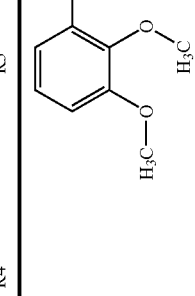 | 1.89 | 529.3105 | 530.3705 |
| 1688 | 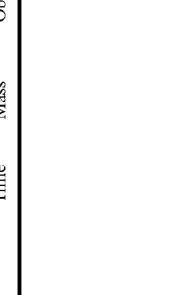 |  | 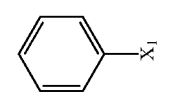 | | 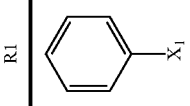 | 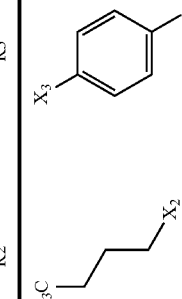 | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1689 | X1-phenyl | H3C-(CH2)3-X2 | X3-(4-Cl-phenyl) | | X5-CH2-(3-NO2-phenyl) | X6-(CH2)3-CH3 | | | |
| 1690 | X1-phenyl | H3C-(CH2)3-X2 | X3-(4-Cl-phenyl) | | X5-CH2-(2-NO2-3-OCH3-phenyl) | H3C-(CH2)3-X6 | | | |
| 1691 | X1-phenyl | H3C-(CH2)3-X2 | X3-(4-OCH3-phenyl) | | X5-CH2-(2-NO2-3-OCH3-phenyl) | H3C-(CH2)3-X6 | 2.03 | 556.3049 | 557.3685 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1692 | 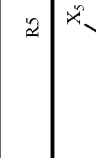 | 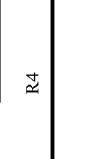 | 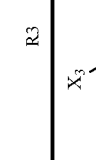 | | 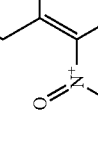 |  | | | |
| 1693 | 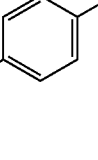 | 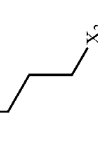 | 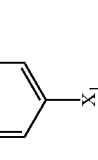 | |  | 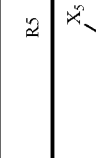 | | | |
| 1694 | 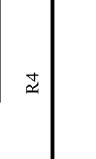 | 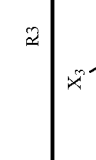 | 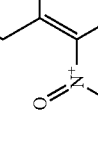 | |  | 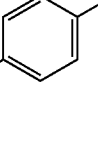 | | | |
| 1695 | 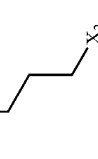 | 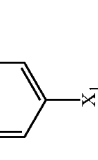 |  | | 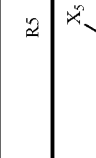 | 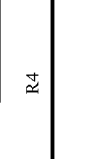 | 2.15 | 553.1818 | 554.32 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1696 |  | 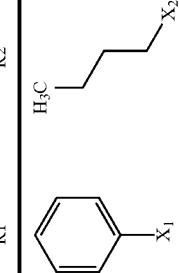 | 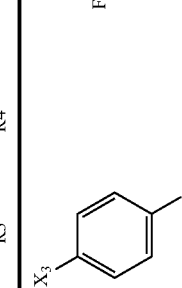 | | 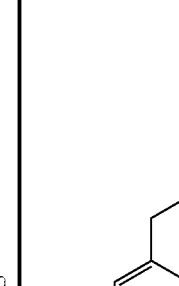 |  | | | |
| 1697 |  | 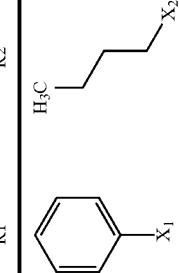 | 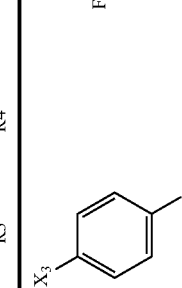 | | 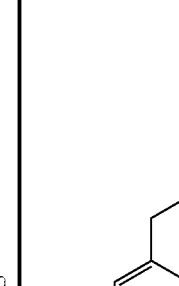 |  | 2.15 | 553.1818 | 554.31 |
| 1698 |  | 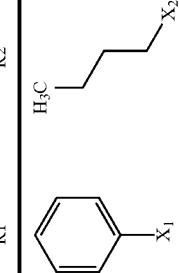 | 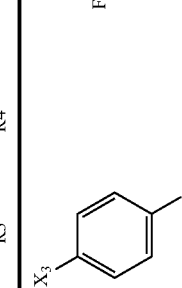 | | 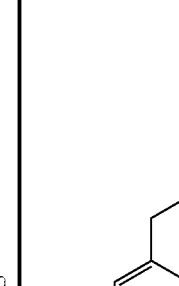 |  | | | |
| 1699 |  | 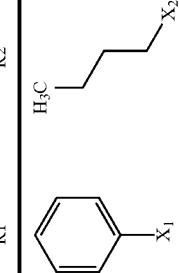 | 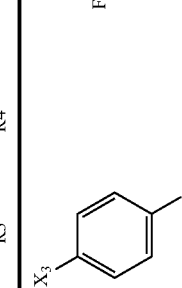 | | 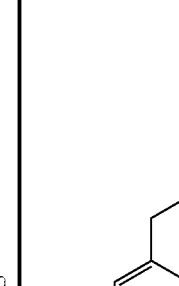 |  | 2.09 | 505.2705 | 506.3293 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1700 | phenyl-X₁ | H₃C-CH₂CH₂CH₂-X₂ | 4-Cl-phenyl-X₃ | | 2,4-difluorobenzyl-X₅ | X₆-CH₂CH₂CH₂-CH₃ | | | |
| 1701 | phenyl-X₁ | H₃C-CH₂CH₂CH₂-X₂ | 4-Cl-phenyl-X₃ | | 2,4-difluorobenzyl-X₅ | X₆-CH₂CH₂CH₂-CH₃ | | | |
| 1702 | phenyl-X₁ | H₃C-CH₂CH₂CH₂-X₂ | 4-Cl-phenyl-X₃ | | 4-Cl-2-OH-benzyl-X₅ | X₆-CH₂CH₂CH₂-CH₃ | | | |
| 1703 | phenyl-X₁ | H₃C-CH₂CH₂CH₂-X₂ | 4-Cl-phenyl-X₃ | | 5-Br-2-OH-3-OMe-benzyl-X₅ | X₆-CH₂CH₂CH₂-CH₃ | 1.97 | 609.1758 | 608.2943 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1704 | | | | | | | 1.95 | 499.2999 | 500.3528 |
| 1705 | | | | | | | | | |
| 1706 | | | | | | | | | |
| 1707 | | | | | | | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1708 | Ph-X1 | H3C-(CH2)3-X2 | 4-F-C6H4-X3 | | 3-(OCH2CH3)-4-OH-C6H3-CH2-X5 | X6-(CH2)3-CH3 | 1.87 | 529.3105 | 530.3679 |
| 1709 | Ph-X1 | H3C-(CH2)3-X2 | 2-OCH3-C6H4-X3 | | 3-(OCH2CH3)-4-OH-C6H3-CH2-X5 | X6-(CH2)3-CH3 | | | |
| 1710 | Ph-X1 | H3C-(CH2)3-X2 | 4-F-C6H4-X3 | | 3,5-(CH3)2-4-OH-C6H2-CH2-X5 | X6-(CH2)3-CH3 | 1.89 | 513.3156 | 514.3675 |
| 1711 | Ph-X1 | H3C-(CH2)3-X2 | 4-Cl-C6H4-X3 | | 3,5-(CH3)2-4-OH-C6H2-CH2-X5 | X6-(CH2)3-CH3 | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1712 | phenyl-X₁ | H₃C-(CH₂)₃-X₂ | 4-methoxyphenyl-X₃ | | 3,5-dimethyl-4-hydroxybenzyl-X₅ | X₆-(CH₂)₃-CH₃ | 1.86 | 525.3355 | 526.3887 |
| 1713 | phenyl-X₁ | H₃C-(CH₂)₃-X₂ | 2-methoxyphenyl-X₃ | | 3,5-dimethyl-4-hydroxybenzyl-X₅ | X₆-(CH₂)₃-CH₃ | | | |
| 1714 | phenyl-X₁ | H₃C-(CH₂)₃-X₂ | 4-fluorophenyl-X₃ | | 3-methyl-4-hydroxybenzyl-X₅ | X₄-(CH₂)₃-CH₃ | | | |
| 1715 | phenyl-X₁ | H₃C-(CH₂)₃-X₂ | 4-chlorophenyl-X₃ | | 3-methyl-4-hydroxybenzyl-X₅ | X₆-(CH₂)₃-CH₃ | 1.88 | 499.2999 | 500.3582 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1716 | phenyl-X1 | H3C-(CH2)3-X2 | 4-methoxyphenyl-X3 | | 4-hydroxy-3-methylbenzyl-X5 | X6-(CH2)3-CH3 | 1.83 | 511.3199 | 512.3775 |
| 1717 | phenyl-X1 | H3C-(CH2)3-X2 | 2-methoxyphenyl-X3 | | 4-hydroxy-3-methylbenzyl-X5 | X6-(CH2)3-CH3 | | | |
| 1718 | phenyl-X1 | H3C-(CH2)3-X2 | 4-chlorophenyl-X3 | | 9-ethylcarbazol-3-ylmethyl-X5 | X6-(CH2)3-CH3 | | | |
| 1719 | phenyl-X1 | H3C-(CH2)3-X2 | 4-fluorophenyl-X3 | | 3-hydroxybenzyl-X5 | X6-(CH2)3-CH3 | 1.91 | 485.2842 | 486.3395 |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1720 | phenyl-X1 | H3C-(CH2)3-X2 | 4-Cl-phenyl-X3 | | 3-HO-benzyl-X5 | X6-(CH2)3-CH3 | | | |
| 1721 | phenyl-X1 | H3C-(CH2)3-X2 | 4-CH3O-phenyl-X3 | | 3-HO-benzyl-X5 | X6-(CH2)3-CH3 | 1.89 | 497.3042 | 498.3563 |
| 1722 | phenyl-X1 | H3C-(CH2)3-X2 | 2-CH3O-phenyl-X3 | | 3-HO-benzyl-X5 | X6-(CH2)3-CH3 | | | |
| 1723 | phenyl-X1 | H3C-(CH2)3-X2 | 4-F-phenyl-X3 | | 3-HO-4-CH3O-benzyl-X5 | X6-(CH2)3-CH3 | 1.86 | 515.2948 | 516.3523 |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| 1724 | phenyl-X1 | H3C-butyl-X2 | 2-methoxyphenyl-X3 | | 3-hydroxy-4-methoxybenzyl-X5 | X6-butyl-CH3 | | | |
| 1725 | phenyl-X1 | H3C-butyl-X2 | 4-fluorophenyl-X3 | | 4-hydroxybenzyl-X5 | X6-butyl-CH3 | 1.83 | 486.2842 | 486.3419 |
| 1726 | phenyl-X1 | H3C-butyl-X2 | 4-methoxyphenyl-X3 | | 4-hydroxybenzyl-X5 | X6-butyl-CH3 | | | |
| 1727 | phenyl-X1 | H3C-butyl-X2 | 2-methoxyphenyl-X3 | | 4-hydroxybenzyl-X5 | X6-butyl-CH3 | 1.8 | 497.3042 | 498.3629 |

R4 is H unless otherwise specified

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1728 | phenyl-X1 | H3C-(CH2)3-X2 | 4-F-phenyl-X3 | 4-OH-3-OCH3-benzyl | | X6-(CH2)3-CH3 | 1.83 | 515.2948 | 516.3555 |
| 1729 | phenyl-X1 | H3C-(CH2)3-X2 | 2-OCH3-phenyl-X3 | 4-OH-3-OCH3-benzyl | | X6-(CH2)3-CH3 | | | |
| 1730 | phenyl-X1 | H3C-(CH2)3-X2 | 4-F-phenyl-X3 | | 4-OH-2-Cl-benzyl-X5 | X6-(CH2)3-CH3 | 2.04 | 519.2452 | 520.3127 |
| 1731 | phenyl-X1 | H3C-(CH2)3-X2 | 4-Cl-phenyl-X3 | | 4-OH-2-Cl-benzyl-X5 | X6-(CH2)3-CH3 | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1732 | X1-phenyl | H3C-CH2CH2CH2-X2 | 2-OCH3-phenyl-X3 | | 2-Cl-4-OH-benzyl-X5 | X6-CH2CH2CH2-CH3 | | | |
| 1733 | X1-phenyl | H3C-CH2CH2CH2-X2 | 4-OCH3-phenyl-X3 | | 2,3-dimethoxy-benzyl-X5 | X6-CH2CH2CH2-CH3 | 1.88 | 571.341 | 572.4042 |
| 1734 | X1-phenyl | H3C-CH2CH2CH2-X2 | 4-Cl-phenyl-X3 | | benzo[1,3]dioxol-4-ylmethyl-X5 | H3C-CH2CH2CH2-X6 | | | |
| 1735 | X1-phenyl | H3C-CH2CH2CH2-X2 | 4-Cl-phenyl-X3 | | 3-methyl-4-methoxy-benzyl-X5 | X6-CH2CH2CH2-CH3 | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1736 | Ph-X1 | H3C-(CH2)3-X2 | 4-MeO-C6H4-X3 | | 4-MeO-3-Me-C6H3-CH2-X5 | X6-(CH2)3-CH3 | 1.96 | 525.3355 | 526.3864 |
| 1737 | Ph-X1 | H3C-(CH2)3-X2 | 4-F-C6H4-X3 | | 2,4-diMeO-3-Me-C6H2-CH2-X5 | X6-(CH2)3-CH3 | 1.96 | 543.3261 | 544.3817 |
| 1738 | Ph-X1 | H3C-(CH2)3-X2 | 4-Cl-C6H4-X3 | | 2,4-diMeO-3-Me-C6H2-CH2-X5 | X6-(CH2)3-CH3 | | | |

TABLE 2A-continued
| CMP # | R1 | R2 | R3 | R4 | R5 | R6 | Rtn. Time | Cmp. Mass | H+ Ion Obs |
|---|---|---|---|---|---|---|---|---|---|
| 1739 | 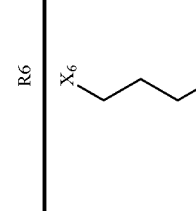 |  | 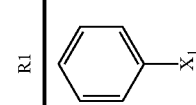 | |  | 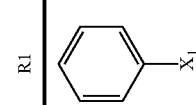 | 1.92 | 555.3461 | 556.3982 |
| 1740 |  |  | 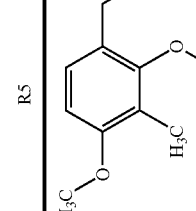 | |  | 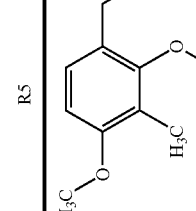 | | | |
| 1741 |  | 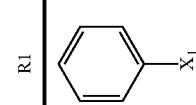 | 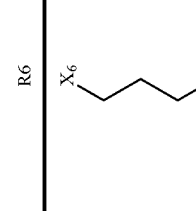 | | 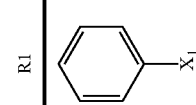 | 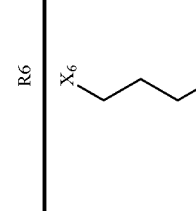 | | | |
| 1742 |  | 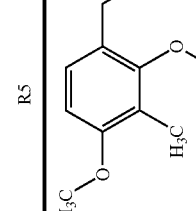 |  | | 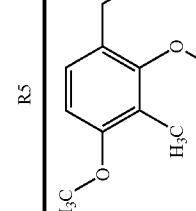 |  | | | |
R4 is H unless otherwise specified TABLE 2A-continued R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1743 | | | | | | | | | |
| 1744 | | | | | | | | | |
| 1745 | | | | | | | 2.02 | 535.2811 | 536.3478 |
| 1746 | | | | | | | | | |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1747 | 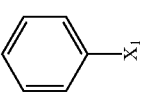 | 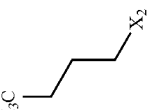 | 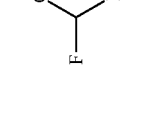 | |  | 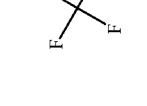 | | | |
| 1748 |  | 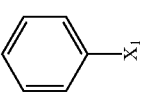 | 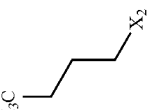 | | 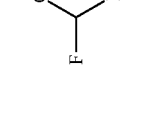 |  | | | |
| 1749 | 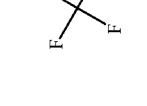 |  | 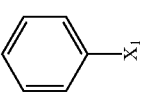 | | 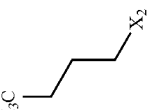 | 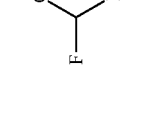 | | | |
| 1750 |  | 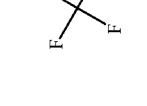 |  | | 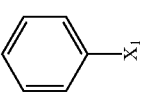 | 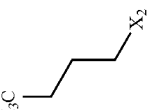 | | | |

TABLE 2A-continued

R4 is H unless otherwise specified

| CMP # | R1 | R2 | R3 | R4 | R5 | R6 | Rtn. Time | Cmp. Mass | H+ Ion Obs |
|---|---|---|---|---|---|---|---|---|---|
| 1751 | Ph-X1 | H3C-propyl-X2 | 4-Cl-C6H4-X3 | | 3-Br-4-F-benzyl-X5 | X6-butyl-CH3 | | | |
| 1752 | Ph-X1 | H3C-propyl-X2 | 4-Cl-C6H4-X3 | | 3-Br-4-OMe-benzyl-X5 | X6-butyl-CH3 | 2.07 | 589.2304 | 590.3111 |
| 1753 | Ph-X1 | H3C-propyl-X2 | 4-OMe-C6H4-X3 | | 3-Br-4-OMe-benzyl-X5 | X6-butyl-CH3 | | | |
| 1754 | Ph-X1 | H3C-propyl-X2 | 4-F-C6H4-X3 | | 4-(OCH2CH3)-benzyl-X5 | X6-butyl-CH3 | 2.04 | 527.3312 | 528.3896 |

TABLE 2A-continued
R4 is H unless otherwise specified
| CMP # | R1 | R2 | R3 | R4 | R5 | R6 | Rtn. Time | Cmp. Mass | H+ Ion Obs |
|---|---|---|---|---|---|---|---|---|---|
| 1755 | 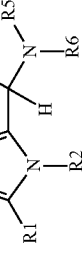 | 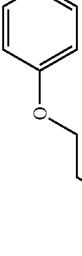 | 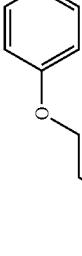 | | 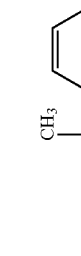 |  | | | |
| 1756 |  |  | 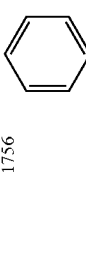 | |  |  | 2.02 | 539.3512 | 540.4099 |
| 1757 | 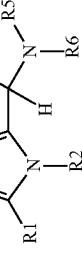 | 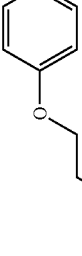 | 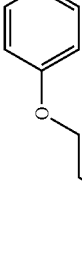 | | 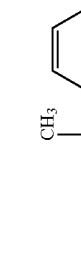 |  | | | |

TABLE 2A-continued

| CMP # | R1 | R2 | R3 | R4 | R5 | R6 | Rtn. Time | Cmp. Mass | H+ Ion Obs |
|---|---|---|---|---|---|---|---|---|---|
| 1758 | phenyl-X7 | H3C-(CH2)3-X2 | 4-methoxyphenyl-X3 | | 4-(2-propyl)phenyl-CH2-X5 | X6-(CH2)3-CH3 | 2.1 | 537.3719 | 538.4346 |
| 1759 | phenyl-X1 | H3C-(CH2)3-X2 | 4-chlorophenyl-X3 | | 3-fluoro-4-methoxyphenyl-CH2-X5 | X6-(CH2)3-CH3 | | | |

TABLE 3

| CMP # | R1 | R2 | R3 | R4 | R5 | Rtn. Time | Cmp. Mass | H + Ion Obs |
|---|---|---|---|---|---|---|---|---|
| 1800 | phenyl-X₁ | X₂-CH₃ | phenyl-X₁ | X₄-CH₂-(benzodioxole) | X₅-CH₂-(benzodioxole) | 1.9 | 531.2158 | 532.2805 |
| 1801 | phenyl-X₁ | X₂-CH₃ | phenyl-X₁ | X₄-CH₂-(benzodioxole) | X₅-CH₂-(benzodioxole) | | | |
| 1802 | phenyl-X₁ | X₂-CH₂-CH₃ | phenyl-X₁ | X₄-CH₂-(benzodioxole) | X₅-CH₂-(2-Cl-4-OH-phenyl) | 1.98 | 565.2132 | 566.2751 |
| 1803 | phenyl-X₁ | X₂-CH₂-CH₃ | phenyl-X₃ | X₄-CH₂-(benzodioxole) | X₅-CH₂-phenyl | 1.99 | 515.2573 | 516.3182 |
| 1804 | phenyl-X₁ | X₂-CH₂-CH₃ | phenyl-X₃ | X₄-CH₂-(benzodioxole) | X₅-CH₂-(benzodioxole) | 1.96 | 559.2471 | 560.3251 |
| 1805 | phenyl-X₁ | X₂-CH₂-CH₃ | phenyl-X₃ | X₄-CH₂-(benzodioxole) | X₅-CH₂CH₂CH₂CH₃ | 1.87 | 481.2729 | 482.34 |

TABLE 3-continued

| CMP # | R1 | R2 | R3 | R4 | R5 | Rtn. Time | Cmp. Mass | H + Ion Obs |
|---|---|---|---|---|---|---|---|---|
| 1806 | phenyl-$X_1$ | $X_2$-CH($CH_3$)- | phenyl-$X_3$, $X_4$- | 2-chloro-4-hydroxybenzyl | benzyl-$X_5$ | 2.01 | 521.2234 | 522.2883 |
| 1807 | phenyl-$X_1$ | $X_2$-CH($CH_3$)- | phenyl-$X_3$, $X_4$- | 2-chloro-4-hydroxybenzyl | n-butyl-$X_5$ | 1.91 | 487.239 | 488.3032 |
| 1808 | phenyl-$X_1$ | $X_2$-CH($CH_3$)- | phenyl-$X_3$, $X_1$- | n-butyl-X | benzyl | 2.07 | 515.2573 | 516.2889 |

TABLE 4

| CMP # | R1 | R2 | R3 and R4 | R5 | R6 | Rtn. Time | Cmp. Mass | H + Ion Obs |
|---|---|---|---|---|---|---|---|---|
| 1809 | phenyl-$X_1$ | $X_1$-(CH$_2$)$_3$-CH$_3$ | $X_3$-(CH$_2$)$_2$-$X_4$ | benzo[1,3]dioxol-4-ylmethyl-$X_6$ | benzyl-$X_6$ | 2.04 | 493.2729 | 494.3307 |
| 1810 | phenyl-$X_1$ | $X_1$-(CH$_2$)$_3$-CH$_3$ | $X_3$-(CH$_2$)$_2$-$X_4$ | 2-chloro-4-hydroxybenzyl-$X_6$ | benzyl-$X_6$ | 2.02 | 499.239 | 500.3034 |

TABLE 4-continued

| CMP # | R1 | R2 | R3 and R4 | R5 | R6 | Rtn. Time | Cmp. Mass | H+ Ion Obs |
|---|---|---|---|---|---|---|---|---|
| 1811 | phenyl-X1 | X2-CH(butyl)-CH3 | X3-CH2-CH2-X4 | benzo[1,3]dioxol-5-ylmethyl-X6 | benzyl-X6 | | | |
| 1812 | phenyl-X1 | X2-CH(butyl)-CH3 | X3-CH2-CH2-X4 | benzo[1,3]dioxol-5-ylmethyl-X6 | X6-CH2-CH2-CH2-CH3 | | | |
| 1813 | phenyl-X1 | X2-CH(butyl)-CH3 | X3-CH2-CH2-X4 | 3-chloro-4-(X6-methyl)phenol | X6-CH2-CH2-CH2-CH3 | | | |
| 1814 | phenyl-X1 | X2-CH(butyl)-CH3 | X3-CH2-CH2-X4 | 3-chloro-4-(X6-methyl)phenol | benzyl-X6 | 2.01 | 485.2234 | 486.3 |
| 1815 | phenyl-X1 | X1-butyl | X3-CH2-CH2-X4 | 4-(X6-methyl)phenol | benzyl-X4 | | | |
| 1816 | phenyl-X1 | X1-butyl | X3-CH2-CH2-X4 | 4-(X6-methyl)phenol | X6-CH2-CH2-CH2-CH3 | | | |
| 1817 | phenyl-X1 | X1-butyl | X3-CH2-C(CH3)2-CH2-X4 | benzo[1,3]dioxol-5-ylmethyl-X3 | benzyl-X6 | 2.05 | 521.3042 | 522.3529 |

TABLE 4-continued

| CMP # | R1 | R2 | R3 and R4 | R5 | R6 | Rtn. Time | Cmp. Mass | H + Ion Obs |
|---|---|---|---|---|---|---|---|---|
| 1818 | phenyl-X₁ | X₁-butyl-CH₃ | CH₃,CH₃ quaternary with X₃,X₄ | X₃-CH₂-(2-CN,5-OH-phenyl) | X₃-pentyl-CH₃ | 2.08 | 493.286 | 494.3401 |
| 1819 | phenyl-X₁ | X₁-butyl-CH₃ | CH₃,CH₃ quaternary with X₃,X₄ | X₃-CH₂-(3-OH-phenyl) | X₃-pentyl-CH₃ | 2.02 | 459.325 | 460.3719 |
| 1820 | phenyl-X₁ | X₁-butyl-CH₃ | CH₃,CH₃ quaternary with X₃,X₄ | X₄-CH₂-(4-OH-phenyl) | X₃-pentyl-CH₃ | 2.01 | 469.325 | 460.3708 |
| 1821 | phenyl-X₁ | X₁-butyl-CH₃ | CH₃,CH₃ quaternary with X₃,X₄ | X₄-CH₂-(2-CN,5-OH-phenyl) | X₃-benzyl | 2.05 | 527.2703 | 628.3184 |
| 1822 | phenyl-X₁ | X₁-butyl-CH₃ | CH₃,CH₃ quaternary with X₃,X₄ | X₃-CH₂-(4-CO₂CH₃-phenyl) | X₃-butyl-CH₃ | 2.04 | 501.3355 | 502.3303 |
| 1823 | phenyl-X₁ | X₁-butyl-CH₃ | CH₃,CH₃ quaternary with X₃,X₄ | X₃-(4-CO₂H-phenyl) | X₃-butyl-CH₃ | 1.99 | 487.3199 | 488.3148 |

TABLE 5
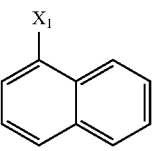
| CMP # | R1 | R2 | R3 | Rtn. Time | Cmp. Mass | H + Ion Obs |
|---|---|---|---|---|---|---|
| 1832 | 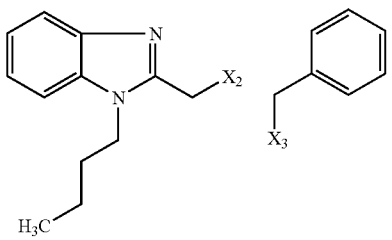 | 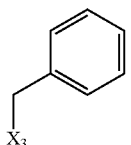 | 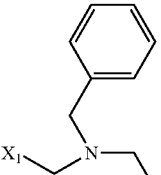 | 2 | 447.231 | 448.2516 |
| 1833 | 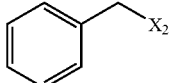 | 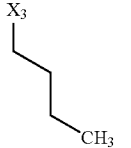 | 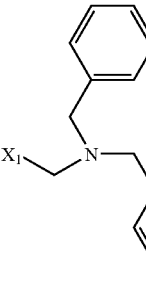 | 1.91 | 444.2413 | 445.2811 |
| 1834 | 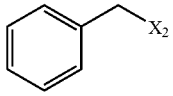 | 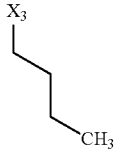 | 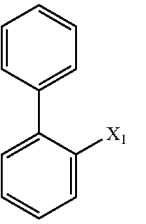 | | | |
| 1835 | 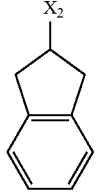 | 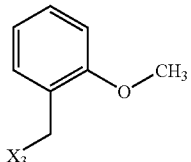 | 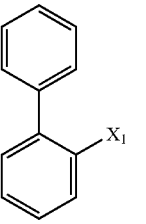 | 2.36 | 433.2042 | 434.2552 |
| 1836 | 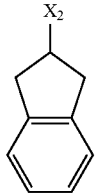 | 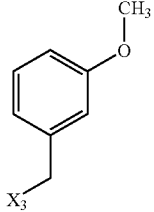 | | 2.33 | 433.2042 | 434.2509 |

TABLE 5-continued
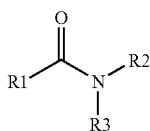
| CMP # | R1 | R2 | R3 | Rtn. Time | Cmp. Mass | H + Ion Obs |
|---|---|---|---|---|---|---|
| 1837 | biphenyl-X₁ | indane-X₂ | 4-methoxybenzyl-X₃ | 2.33 | 433.2042 | 434.2613 |
| 1838 | biphenyl-X₁ | indane-X₂ | 3-hydroxybenzyl-X₃ | 2.22 | 419.1885 | 420.2401 |
| 1839 | biphenyl-X₁ | indane-X₂ | 3-(ethoxycarbonylmethoxy)benzyl-X₃ | 2.3 | 505.2253 | 506.2785 |
| 1840 | biphenyl-X₁ | 3-methoxybenzyl-X₂ | phenethyl-X₃ | 2.31 | 421.2042 | 422.2463 |
| 1841 | biphenyl-X₁ | indane-X₂ | 4-hydroxybenzyl-X₃ | 2.2 | 419.1885 | 420.2424 |

TABLE 5-continued
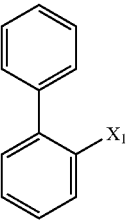
| CMP # | R1 | R2 | R3 | Rtn. Time | Cmp. Mass | H + Ion Obs |
|---|---|---|---|---|---|---|
| 1842 |  | 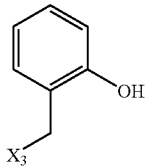 | 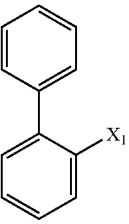 | 2.27 | 419.1885 | 420.2401 |
| 1843 | 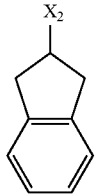 | 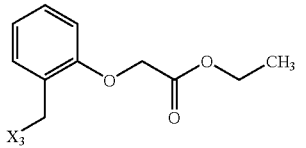 | 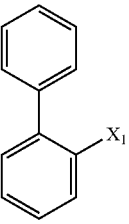 | 2.32 | 505.2253 | 506.2746 |
| 1844 |  | 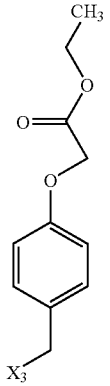 | 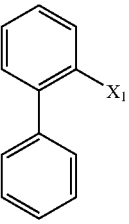 | 2.3 | 505.2253 | 506.2814 |
| 1845 | 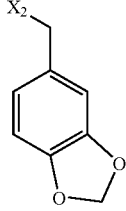 | 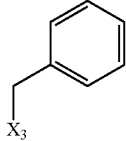 | 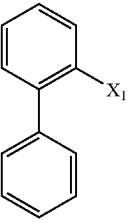 | 2.27 | 421.1678 | 422.2155 |
| 1846 | 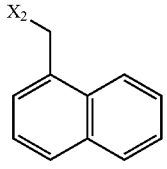 | 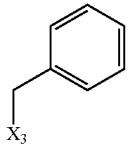 | | 2.4 | 427.1936 | 428.2449 |

TABLE 5-continued

| CMP # | R1 | R2 | R3 | Rtn. Time | Cmp. Mass | H + Ion Obs |
|---|---|---|---|---|---|---|
| 1847 | 2-biphenyl-X₁ | X₂-CH₂-benzo[1,3]dioxole | X₃-CH₂-cyclopentyl | 2.33 | 413.1991 | 414.2406 |
| 1848 | 2-biphenyl-X₁ | X₂-CH₂-benzo[1,3]dioxole | X₃-CH₂-benzo[1,3]dioxole | 2.25 | 465.1576 | 466.216 |
| 1849 | 2-biphenyl-X₁ | X₂-CH₂-C₆H₄-N(CH₃)₂ | X₃-CH₂-phenyl | 2.12 | 420.2202 | 421.262 |
| 1850 | 2-(4'-CF₃-biphenyl)-X₁ | X₂-CH₂-benzo[1,3]dioxole | X₃-CH₂-phenyl | 2.33 | 489.1552 | 490.2146 |
| 1851 | 2-(4'-CF₃-biphenyl)-X₁ | X₂-CH₂-naphthyl | X₃-CH₂-cyclohexadienyl | 2.46 | 495.181 | 496.2438 |

TABLE 5-continued
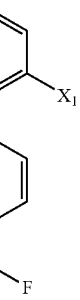
| CMP # | R1 | R2 | R3 | Rtn. Time | Cmp. Mass | H + Ion Obs |
|---|---|---|---|---|---|---|
| 1852 | 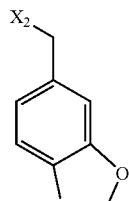 | 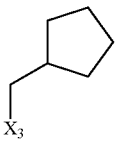 | 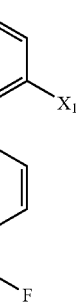 | 2.37 | 481.1865 | 482.2455 |
| 1853 | 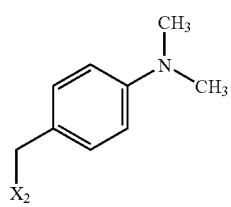 | 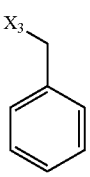 | 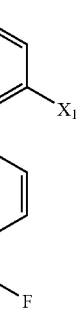 | 2.17 | 488.2076 | 489.2776 |
| 1854 |  | 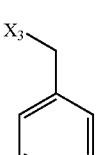 | 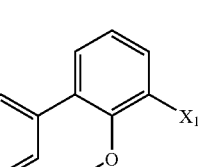 | 2.4 | 471.181 | 472.2344 |
| 1855 | 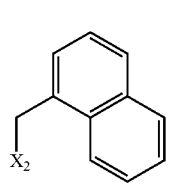 | 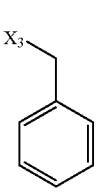 | 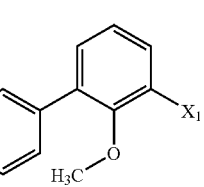 | 2.49 | 457.2042 | 458.2641 |
| 1856 | 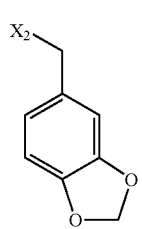 | 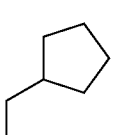 | | 2.4 | 443.2097 | 444.2538 |

TABLE 5-continued

| CMP # | R1 | R2 | R3 | Rtn. Time | Cmp. Mass | H + Ion Obs |
|---|---|---|---|---|---|---|
| 1857 | 2-ethyl-3-phenyl-phenyl-X1, H3C | X2-indanyl | benzyl-X3 | 2.42 | 433.2042 | 434.2522 |
| 1858 | 1-(3-methylphenyl)-tetrahydroisoquinolin-2-yl-CH2-X1 | X2-indanyl | 2-fluorobenzyl-X3 | | | |
| 1859 | 1-(4-methylphenyl)-tetrahydroisoquinolin-2-yl-CH2-X1 | X2-indanyl | 2-fluorobenzyl-X3 | | | |
| 1860 | 1-(3-chlorophenyl)-tetrahydroisoquinolin-2-yl-CH2-X1 | X2-indanyl | 2-fluorobenzyl-X3 | | | |
| 1861 | biphenyl-X1 | 3-propyl-imidazo[4,5-b]pyridin-2-yl-CH2-X2 | 3-methoxybenzyl-X2 | 2.17 | 490.2369 | 491.2785 |
| 1862 | 2-(pyrrol-1-yl)phenyl-X1 | 3-propyl-imidazo[4,5-b]pyridin-2-yl-CH2-X2 | 3-methoxybenzyl-X2 | 2.1 | 479.2321 | 480.2817 |

TABLE 5-continued

| CMP # | R1 | R2 | R3 | Rtn. Time | Cmp. Mass | H + Ion Obs |
|---|---|---|---|---|---|---|
| 1863 | | | | | | |
| 1864 | | | | | | |
| 1865 | | | | | | |
| 1866 | | | | 2.15 | 485.2027 | 486.248 |
| 1867 | | | | 2.29 | 472.1762 | 473.2223 |

TABLE 5-continued
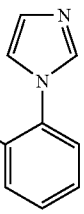
| CMP # | R1 | R2 | R3 | Rtn. Time | Cmp. Mass | H + Ion Obs |
|---|---|---|---|---|---|---|
| 1868 | 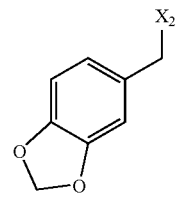 | 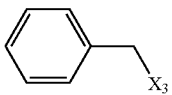 | 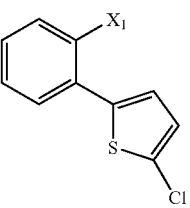 | 1.78 | 411.1583 | 412.1952 |
| 1869 | 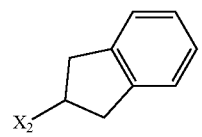 | 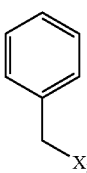 | 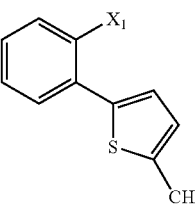 | 2.44 | 443.1111 | 444.1614 |
| 1870 | 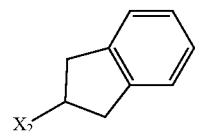 | 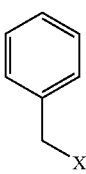 | 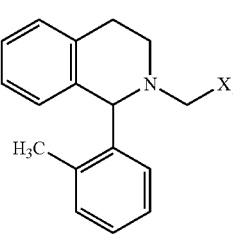 | 2.4 | 423.1657 | 424.1971 |
| 1871 | 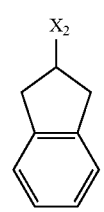 | 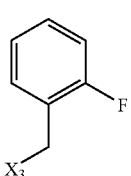 | 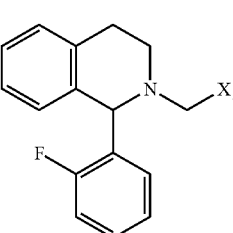 | 2.11 | 504.2577 | 505.2372 |
| 1872 | 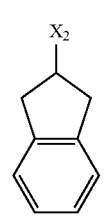 | 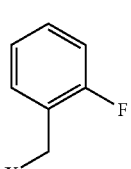 | 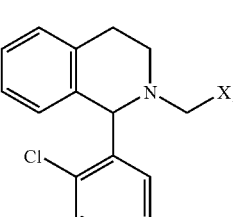 | 2.08 | 508.2326 | 509.2144 |
| 1873 | 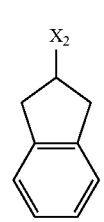 | 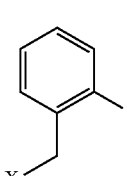 |  | 2.21 | 524.2031 | 525.1942 |

TABLE 5-continued

| CMP # | R1 | R2 | R3 | Rtn. Time | Cmp. Mass | H + Ion Obs |
|---|---|---|---|---|---|---|
| 1874 | 1-(2-trifluoromethylphenyl)-1,2,3,4-tetrahydroisoquinolin-2-yl-CH2-X1 | indan-2-yl-X2 | 2-fluorophenyl-X3 | 2.4 | 558.2294 | 559.21 |
| 1875 | 1-phenyl-1,2,3,4-tetrahydroisoquinolin-2-yl-CH2-X1 | indan-2-yl-X2 | 2-fluorophenyl-X3 | 2.01 | 490.242 | 491.2217 |
| 1876 | 1-(4-chlorophenyl)-1,2,3,4-tetrahydroisoquinolin-2-yl-CH2-X1 | indan-2-yl-X2 | 2-fluorophenyl-X3 | 2.11 | 524.2031 | 525.1987 |
| 1877 | 1-(4-fluorophenyl)-1,2,3,4-tetrahydroisoquinolin-2-yl-CH2-X1 | indan-2-yl-X2 | 2-fluorophenyl-X3 | 2.04 | 508.2326 | 509.2227 |
| 1878 | biphenyl-X1 | indan-2-yl-X2 | 3-methylphenyl-X3 | 2.43 | 417.2093 | 418.29 |
| 1879 | biphenyl-X1 | indan-2-yl-X2 | 2-methylphenyl-X3 | 2.42 | 417.2093 | 418.2941 |

TABLE 5-continued

| CMP # | R1 | R2 | R3 | Rtn. Time | Cmp. Mass | H + Ion Obs |
|---|---|---|---|---|---|---|
| 1880 | 2-biphenyl-X₁ | indan-2-yl-X₂ | 4-methylbenzyl-X₃ | 2.4 | 417.2093 | 418.2959 |
| 1881 | 2-biphenyl-X₁ | indan-2-yl-X₂ | 2-fluorobenzyl-X₃ | 2.35 | 421.1842 | 422.275 |
| 1882 | 1-(2-methylphenyl)-2-methylpropyl-X₁ | indan-2-yl-X₂ | 4-methylbenzyl-X₃ | 2.53 | 411.2562 | 412.3455 |
| 1883 | cyclopentyl(2-methylphenyl)methyl-X₁ | indan-2-yl-X₂ | 4-methylbenzyl-X₃ | 2.57 | 423.2562 | 424.3539 |
| 1884 | 2-biphenyl-X₁ | indan-2-yl-X₂ | 4-chlorobenzyl-X₃ | 2.42 | 437.1546 | 438.1642 |
| 1885 | 2-biphenyl-X₁ | tetralin-2-yl-X₂ | benzyl-X₃ | 2.37 | 417.2093 | 418.2095 |
| 1886 | 2-biphenyl-X₁ | indan-2-yl-X₂ | phenethyl-X₃ | 2.41 | 417.2093 | 418.2095 |

TABLE 5-continued

| CMP # | R1 | R2 | R3 | Rtn. Time | Cmp. Mass | H + Ion Obs |
|---|---|---|---|---|---|---|
| 1887 | biphenyl-X1 | indane-X2 | phenylpropyl-X3 | 2.42 | 431.2249 | 432.2221 |
| 1888 | methylnaphthyl-X1 | indane-X2 | 2-methylbenzyl-X3 | 2.48 | 517.0903 | 518.1107 |
| 1889 | fluorenyl-X1 | indane-X2 | 3-methylbenzyl-X3 | 2.46 | 429.2093 | 430.2187 |
| 1890 | fluorenyl-X1 | indane-X2 | 2-methylbenzyl-X3 | 2.48 | 429.2093 | 430.2192 |
| 1891 | fluorenyl-X1 | indane-X2 | 2-fluorobenzyl-X3 | 2.41 | 433.1842 | 434.2012 |
| 1892 | 8-bromonaphthyl-X1 | indane-X2 | 2-methylbenzyl-X3 | 2.46 | 469.1041 | 470.13 |
| 1893 | 8-bromonaphthyl-X1 | 6-chloro-1-cyclopentylbenzimidazolylmethyl-X2 | cyclopentyl-X3 | 2.21 | 549.1182 | 550.13 |
| 1894 | 2-(methylthio)phenyl-X1 | indane-X2 | 2-cyclohexylethyl-X3 | 2.49 | 393.2126 | 394.2145 |

TABLE 5-continued

| CMP # | R1 | R2 | R3 | Rtn. Time | Cmp. Mass | H + Ion Obs |
|---|---|---|---|---|---|---|
| 1895 | | | | 2.39 | 407.246 | 408.2388 |
| 1896 | | | | 2.75 | 477.1837 | 478.2005 |
| 1897 | | | | | | |
| 1898 | | | | 2.6 | 525.1529 | 526.1517 |
| 1899 | | | | 2.47 | 409.2406 | 410.246 |
| 1900 | | | | 2.58 | 437.2719 | 438.2745 |
| 1901 | | | | 2.38 | 433.2042 | 434.2162 |
| 1902 | | | | 2.44 | 413.2355 | 414.2371 |

TABLE 5-continued $$R1-\underset{\underset{R3}{|}}{\overset{\overset{O}{\|}}{C}}-N-R2$$

| CMP # | R1 | R2 | R3 | Rtn. Time | Cmp. Mass | H + Ion Obs |
|---|---|---|---|---|---|---|
| 1903 | H₃C–(propoxy)–phenyl-X₁ | indan-X₂ | 2-methylphenyl-CH₂-X₃ | 2.42 | 413.2355 | 414.239 |
| 1904 | H₃C–(propoxy)–phenyl-X₁ | tetralin-X₂ | benzyl-X₃ | 2.39 | 413.2355 | 414.2406 |
| 1905 | 2,3-dimethoxyphenyl-X₁ | indan-X₂ | 2-methylphenyl-CH₂-X₃ | 2.27 | 401.1991 | 402.2075 |
| 1906 | 2,3-dimethoxyphenyl-X₁ | indan-X₂ | 4-methylphenyl-CH₂-X₃ | 2.28 | 401.1991 | 402.2055 |
| 1907 | fluorenyl-X₁ | indan-X₂ | 4-chlorophenyl-CH₂-X₃ | 2.3 | 421.1445 | 422.163 |
| 1908 | 2-(trifluoromethoxy)phenyl-X₁ | indan-X₂ | benzyl-X₃ | 2.28 | 411.1446 | 412.1578 |
| 1909 | 3,5-dimethoxyphenyl-X₁ | 1-(2-cyclohexylethyl)-1,2,3,4-tetrahydroisoquinolin-X₂ |  | 2.47 | 407.246 | 408.2634 |

TABLE 5-continued
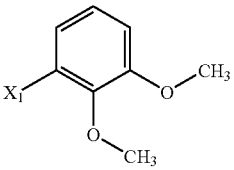
| CMP # | R1 | R2 | R3 | Rtn. Time | Cmp. Mass | H + Ion Obs |
|---|---|---|---|---|---|---|
| 1910 | 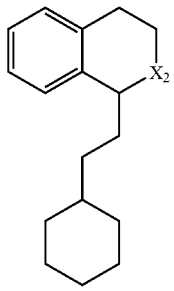 | 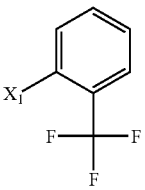 | | 2.45 | 407.246 | 408.2503 |
| 1911 | 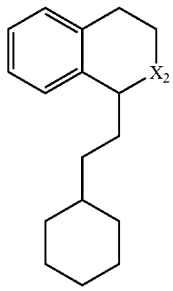 | 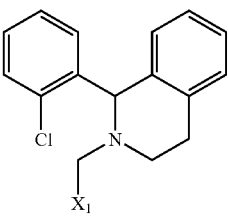 | | 2.46 | 415.2123 | 416.2284 |
| 1912 | 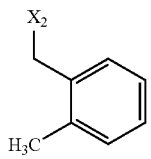 | 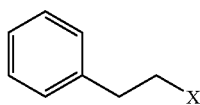 | 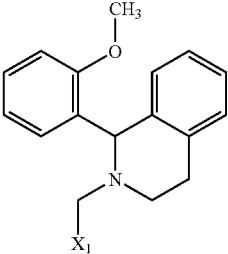 | 2.16 | 508.2281 | 509.2342 |
| 1913 | 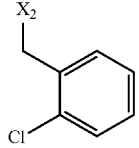 | 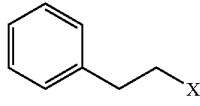 | 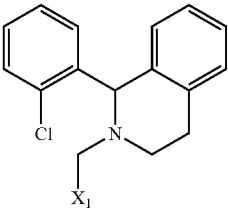 | 1.99 | 524.2231 | 525.2272 |
| 1914 | 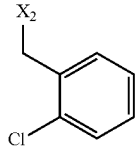 | 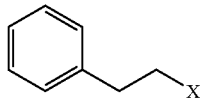 |  | 2.19 | 528.1735 | 529.1874 |

TABLE 5-continued

| CMP # | R1 | R2 | R3 | Rtn. Time | Cmp. Mass | H + Ion Obs |
|---|---|---|---|---|---|---|
| 1915 | | | | 2.38 | 562.1999 | 563.214 |
| 1916 | | | | | | |
| 1917 | | | | | | |
| 1918 | | | | 2.13 | 494.2482 | 495.2661 |
| 1919 | | | | | | |

TABLE 5-continued

| CMP # | R1 | R2 | R3 | Rtn. Time | Cmp. Mass | H + Ion Obs |
|---|---|---|---|---|---|---|
| 1920 | phenyl-pyrrole-X₁ | H₃C-CH-(imidazo[4,5-b]pyridine)-CH₂-X₂ | X₃-benzyl | 2.13 | 449.2216 | 450.2522 |
| 1921 | phenyl-pyrrole-X₁ | CH₃-CH-(imidazo[4,5-b]pyridine)-CH₂-X₂ | X₃-(2-fluorobenzyl) | 2.11 | 467.2121 | 468.2447 |
| 1922 | phenyl-pyrrole-X₁ | H₃C-CH-(imidazo[4,5-b]pyridine)-CH₂-X₂ | X₃-(4-fluorobenzyl) | 2.14 | 467.2121 | 468.2424 |
| 1923 | phenyl-pyrrole-X₁ | H₃C-CH-(imidazo[4,5-b]pyridine)-CH₂-X₂ | X₃-(4-methoxybenzyl) | 2.11 | 479.2321 | 480.2583 |
| 1924 | phenyl-pyrrole-X₁ | X₂-CH(phenyl)-CH₂-CH₂-cyclohexyl | CH₃-X₃ | 2.52 | 400.2515 | 401.2748 |
| 1925 | phenyl-pyrrole-X₁ | X₂-isochroman-CH₂-CH₂-cyclohexyl |  | 2.52 | 412.2515 | 413.2805 |

TABLE 5-continued
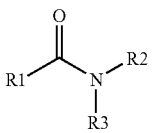
| CMP # | R1 | R2 | R3 | Rtn. Time | Cmp. Mass | H + Ion Obs |
|---|---|---|---|---|---|---|
| 1926 | 2-(1H-pyrrol-1-yl)phenyl-$X_1$ | $X_3$-benzyl | $X_3$-pentyl-$CH_3$ | 2.28 | 346.2045 | 347.2321 |
| 1927 | 2-(1H-pyrrol-1-yl)phenyl-$X_1$ | $X_3$-(2-fluorobenzyl) | benzyl-$X_3$ | 2.25 | 366.1732 | 367.2062 |
| 1928 | 2-(1H-pyrrol-1-yl)phenyl-$X_1$ | $X_3$-(4-methoxybenzyl)-$X_3$-CH$_3$ | $H_3C$-pentyl-$X_3$ | 2.11 | 531.3097 | 532.3127 |
| 1929 | 1-propyl-1H-imidazo[4,5-b]pyridin-2-yl-CH$_2$-$X_2$ | | $H_3C$-butyl-$X_3$ | 1.96 | 503.2243 | 504.2599 |
| 1930 | $X_2$-(1-phenyl-3-cyclohexylpropyl) | $X_3$-(4-methoxybenzyl) | $H_3C$-pentyl-$X_3$ | 2 | 517.2399 | 518.2693 |

TABLE 5-continued

| CMP # | R1 | R2 | R3 | Rtn. Time | Cmp. Mass | H + Ion Obs |
|---|---|---|---|---|---|---|
| 1931 | 3,4-dihydroisochromen-1-yl with 2-cyclohexylethyl substituent (X2) | 4-methoxybenzyl (X3) | hexyl (X3) | 1.96 | 519.2534 | 520.2534 |
| 1932 | 4-chloro-3-methylphenyl (X1) | (2,6-dimethoxybenzyl)-2-(X2-methyl)benzimidazole | butyl (X3) | 2.02 | 505.2132 | 506.2226 |
| 1933 | 4-propoxyphenyl (X1) | 4-methoxybenzyl (X3) | hexyl (X3) | 2.05 | 529.2941 | 530.2949 |
| 1934 | 4-isopropoxyphenyl (X1) | 4-methoxybenzyl (X3) | hexyl (X3) | 2.03 | 529.2941 | 530.2936 |
| 1935 | 3,4-dimethoxyphenyl (X1) | 4-methoxybenzyl (X3) | hexyl (X3) | 1.92 | 531.2733 | 532.2859 |
| 1936 | 3,4-dimethoxyphenyl (X1) | 4-methoxybenzyl (X3) | 3-methylbutyl (X3) | 1.91 | 531.2733 | 532.2828 |

TABLE 5-continued

| CMP # | R1 | R2 | R3 | Rtn. Time | Cmp. Mass | H + Ion Obs |
|---|---|---|---|---|---|---|
| 1937 | fluorene-X1 | imidazopyridine-CH2-(2-Cl-benzyl) | pentyl-X3 | 2.27 | 520.203 | 521.2229 |
| 1938 | fluorene-X1 | imidazopyridine-CH2-(2-Cl-benzyl) | isobutyl-X3 | 2.25 | 520.203 | 521.2301 |
| 1939 | fluorene-X1 | imidazopyridine-CH2-(2-Cl-benzyl) | hexyl-X3 | 2.32 | 534.2186 | 535.2426 |
| 1940 | 2-Cl-3,4-dimethoxyphenyl-X1 | imidazopyridine-CH2-(2-Cl-benzyl) | hexyl-X3 | 2.19 | 540.1695 | 541.1906 |
| 1941 | 5-Br-acenaphthyl-X1 | imidazopyridine-CH2-(2-Cl-benzyl) | pentyl-X3 | 2.23 | 560.0978 | 561.14 |

TABLE 5-continued
| CMP # | R1 | R2 | R3 | Rtn. Time | Cmp. Mass | H + Ion Obs |
|---|---|---|---|---|---|---|
| 1942 | 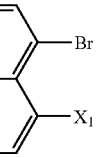 | 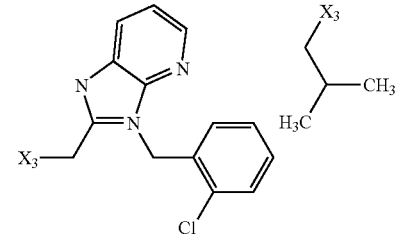 | 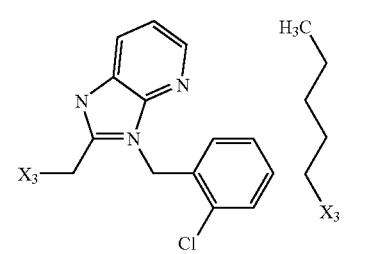 | 2.23 | 560.0978 | 561.14 |
| 1943 | 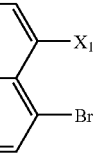 | 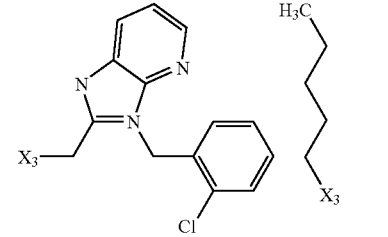 | 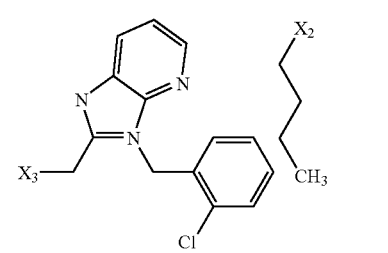 | 2.28 | 574.1135 | 575.16 |
| 1944 | 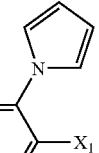 | 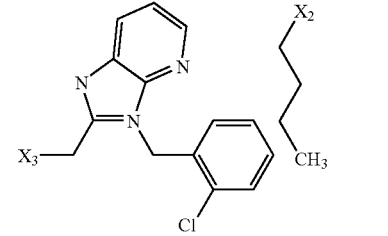 | 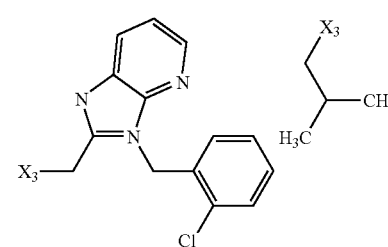 | | | |
| 1945 | 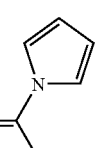 | 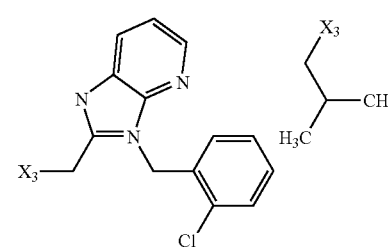 | 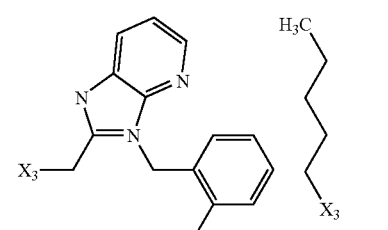 | 2.19 | 497.1982 | 498.2381 |
| 1946 | 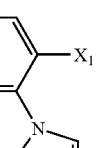 | 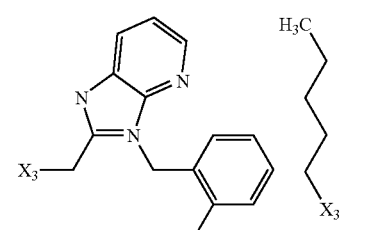 |  | 2.26 | 511.2139 | 512.2437 |

TABLE 5-continued

| CMP # | R1 | R2 | R3 | Rtn. Time | Cmp. Mass | H + Ion Obs |
|---|---|---|---|---|---|---|
| 1947 | pyrrol-1-yl phenyl-X₁ | imidazo[4,5-b]pyridine with 2-chlorobenzyl, X₃-CH₂- | 3-methylbutyl-X₃ | 2.25 | 511.2139 | 512.2531 |
| 1948 | fluorenyl-X₁ | imidazo[4,5-b]pyridine Cl-substituted, 3-chlorobenzyl, X₂-CH₂- | butyl-CH₃ | 2.3 | 520.203 | 521.2333 |
| 1949 | pyrrol-1-yl phenyl-X₁ | imidazo[4,5-b]pyridine Cl-subst, 3-chlorobenzyl, X₂-CH₂- | butyl-CH₃ | 2.25 | 497.1982 | 498.2341 |
| 1950 | pyrrol-1-yl phenyl-X₁ | imidazo[4,5-b]pyridine Cl-subst, 3-chlorobenzyl, X₂-CH₂- | isobutyl-CH₃ | 2.25 | 497.1982 | 498.2305 |
| 1951 | pyrrol-1-yl phenyl-X₁ | imidazo[4,5-b]pyridine Cl-subst, 3-chlorobenzyl, X₂-CH₂- | pentyl-X₃ | 2.3 | 511.2139 | 512.2459 |
| 1952 | pyrrol-1-yl phenyl-X₁ | imidazo[4,5-b]pyridine Cl-subst, 3-chlorobenzyl, X₂-CH₂- | 3-methylbutyl-X₃ | 2.3 | 511.2139 | 512.2452 |

TABLE 5-continued

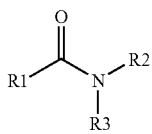

| CMP # | R1 | R2 | R3 | Rtn. Time | Cmp. Mass | H + Ion Obs |
|---|---|---|---|---|---|---|
| 1953 | 1-(3-methylphenyl)-1,2,3,4-tetrahydroisoquinolin-2-yl-CH2-X1 | indan-2-yl-X2 | 2-fluorobenzyl-X3 | 2.07 | 504.2577 | 505.2828 |
| 1954 | 1-(3-methylphenyl)-1,2,3,4-tetrahydroisoquinolin-2-yl-CH2-X1 | indan-2-yl-X2 | 2-fluorobenzyl-X3 | 2.07 | 504.2577 | 505.2755 |
| 1955 | 1-(4-fluorophenyl)-1,2,3,4-tetrahydroisoquinolin-2-yl-CH2-X1 | indan-2-yl-X2 | 2-fluorobenzyl-X3 | 2.05 | 508.2326 | 509.2624 |
| 1956 | 1-(4-methoxyphenyl)-1,2,3,4-tetrahydroisoquinolin-2-yl-CH2-X1 | indan-2-yl-X2 | 2-fluorobenzyl-X3 | 2.03 | 520.2526 | 521.2831 |
| 1957 | 1-(3-chlorophenyl)-1,2,3,4-tetrahydroisoquinolin-2-yl-CH2-X1 | indan-2-yl-X2 | 2-fluorobenzyl-X3 | | | |
| 1958 | 1-(3-methylphenyl)-1,2,3,4-tetrahydroisoquinolin-2-yl-CH2-X1 | indan-2-yl-X2 | benzyl-X3 | 2.05 | 486.2671 | 487.2196 |

TABLE 5-continued

| CMP # | R1 | R2 | R3 | Rtn. Time | Cmp. Mass | H + Ion Obs |
|---|---|---|---|---|---|---|
| 1959 | | | | 2.06 | 486.2671 | 487.2379 |
| 1960 | | | | 2.02 | 502.262 | 503.2366 |
| 1961 | | | | 2.55 | 507.098 | 508.09 |
| 1962 | | | | 2.49 | 449.1329 | 450.125 |
| 1963 | | | | 2.49 | 449.1329 | 450.1363 |

TABLE 5-continued
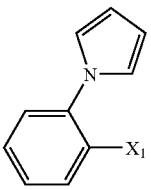
| CMP # | R1 | R2 | R3 | Rtn. Time | Cmp. Mass | H + Ion Obs |
|---|---|---|---|---|---|---|
| 1964 | 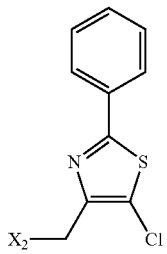 | 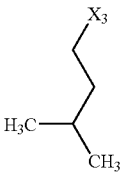 | 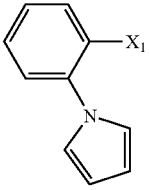 | 2.55 | 463.1485 | 464.155 |
| 1965 | 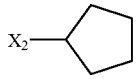 | 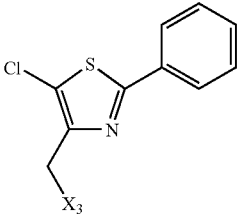 | 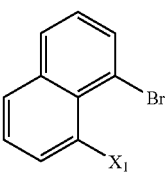 | 2.5 | 461.1329 | 462.152 |
| 1966 | 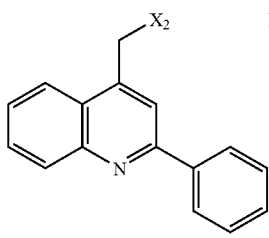 | 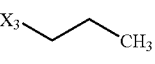 | 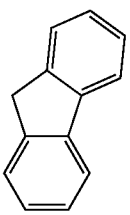 | 2.13 | 508.115 | 509.1421 |
| 1967 | 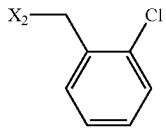 | 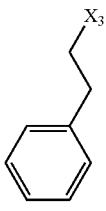 | 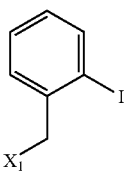 | 2.39 | 437.1546 | 438.191 |
| 1968 | 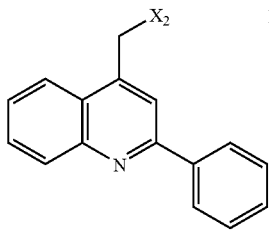 | 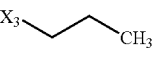 | X₃ CH₃ | 2.1 | 520.1011 | 521.1198 |

TABLE 5-continued

| CMP # | R1 | R2 | R3 | Rtn. Time | Cmp. Mass | H + Ion Obs |
|---|---|---|---|---|---|---|
| 1969 | 2-phenoxybenzyl (X₁) | (4-(2-phenylquinolinyl))methyl (X₂) | n-propyl (X₃) | 2.16 | 486.2307 | 487.2447 |
| 1970 | 2-methoxybenzyl (X₁) | (4-(2-phenylquinolinyl))methyl (X₂) | n-propyl (X₃) | 2.01 | 424.2151 | 425.2368 |
| 1971 | 2-bromobenzyl (X₁) | (4-(2-phenylquinolinyl))methyl (X₂) | n-propyl (X₃) | 2.08 | 472.115 | 473.1456 |
| 1972 | fluoren-4-yl (X₁) | benzyl (X₂) | 2-(2-chlorophenyl)ethyl (X₃) | 2.38 | 437.1546 | 438.1952 |
| 1973 | fluoren-4-yl (X₁) | benzyl (X₂) | 3-phenylbutyl (X₃) | 2.37 | 431.2249 | 432.2486 |
| 1974 | fluoren-4-yl (X₁) | benzyl (X₂) | 2-(4-chlorophenyl)ethyl (X₃) | 2.38 | 437.1546 | 438.1897 |

TABLE 5-continued

| CMP # | R1 | R2 | R3 | Rtn. Time | Cmp. Mass | H + Ion Obs |
|---|---|---|---|---|---|---|
| 1975 | 2-biphenyl-X₁ | 2-indanyl-X₂ | benzyl-X₃ | 2.33 | 403.1936 | 404.224 |
| 1976 | 4-fluorenyl-X₁ | 2-indanyl-X₂ | benzyl-X₃ | 2.36 | 415.1936 | 416.2279 |
| 1977 | 4-fluorenyl-X₁ | benzyl-X₂ | 4-fluorophenethyl-X₃ | 2.3 | 421.1842 | 422.218 |
| 1978 | 4-fluorenyl-X₁ | benzyl-X₂ | 4-methoxyphenethyl-X₃ | 2.29 | 433.2042 | 434.2361 |
| 1979 | 4-fluorenyl-X₁ | benzyl-X₂ | 1-(4-methoxyphenyl)propan-2-yl-X₃ | 2.32 | 447.2198 | 448.251 |

TABLE 5-continued

| CMP # | R1 | R2 | R3 | Rtn. Time | Cmp. Mass | H + Ion Obs |
|---|---|---|---|---|---|---|
| 1980 | 2-Cl-C6H4-X1 | 2-phenyl-1-(indan-2-yl)-5-(X2-methyl)imidazole | 4-methoxybenzyl-X3 | 1.88 | 547.2026 | 548.3105 |
| 1981 | 2,5-diF-C6H3-X1 | 2-phenyl-1-(indan-2-yl)-5-(X2-methyl)imidazole | 4-methoxybenzyl-X3 | 1.9 | 549.2228 | 550.3254 |
| 1982 | 2,5-diF-C6H3-X1 | 2-phenyl-1-(indan-2-yl)-5-(X2-methyl)imidazole | cyclohexylmethyl-X3 | 1.97 | 525.2592 | 526.3528 |
| 1983 | 5-Cl-2-OMe-C6H3-X1 | 2-phenyl-1-(indan-2-yl)-5-(X2-methyl)imidazole | cyclohexylmethyl-X3 | 1.94 | 577.2132 | 578.3243 |

TABLE 5-continued

| CMP # | R1 | R2 | R3 | Rtn. Time | Cmp. Mass | H + Ion Obs |
|---|---|---|---|---|---|---|
| 1984 | 5-Cl, 2-OCH3 phenyl-X1 | 1-(indan-2-yl)-2-phenyl-5-(CH2-X2)-imidazole | cyclohexylmethyl-X3 | 2.01 | 553.2496 | 554.3531 |
| 1985 | 2-CF3 phenyl-X1 | 1-(indan-2-yl)-2-phenyl-5-(CH2-X2)-imidazole | 4-methoxybenzyl-X3 | 1.92 | 581.229 | 582.3329 |
| 1986 | 2,5-diCl phenyl-X1 | 1-(indan-2-yl)-2-phenyl-5-(CH2-X2)-imidazole | benzyl-X3 | 1.95 | 551.1531 | 552.2697 |
| 1987 | 2,5-diCl phenyl-X1 | 1-(indan-2-yl)-2-phenyl-5-(CH2-X2)-imidazole | 4-methoxybenzyl-X3 | 1.95 | 581.1637 | 582.2848 |

US 7,271,270 B2
1095                                                                 1096
TABLE 5-continued
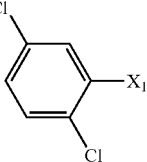
| CMP # | R1 | R2 | R3 | Rtn. Time | Cmp. Mass | H + Ion Obs |
|---|---|---|---|---|---|---|
| 1988 | 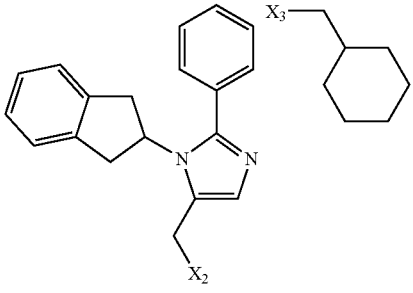 |  | 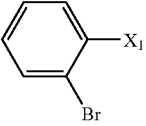 | 2.03 | 557.2001 | 558.311 |
| 1989 | 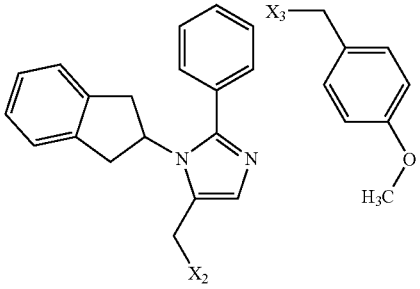 |  | 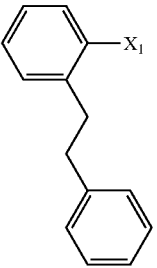 | 1.9 | 591.1522 | 592.27 |
| 1990 | 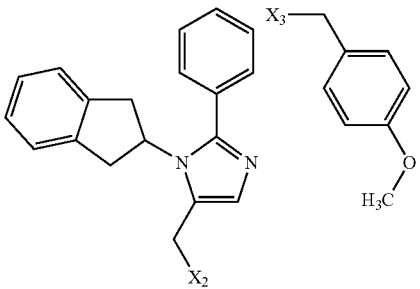 |  | 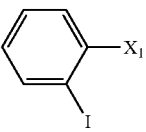 | 2.02 | 617.3042 | 618.4236 |
| 1991 | 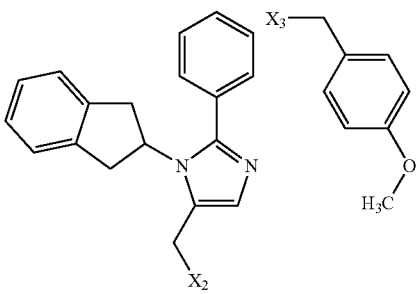 | |  | 1.92 | 639.1383 | 640.2621 |

TABLE 5-continued
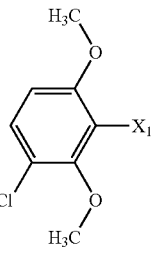
| CMP # | R1 | R2 | R3 | Rtn. Time | Cmp. Mass | H + Ion Obs |
|---|---|---|---|---|---|---|
| 1992 | 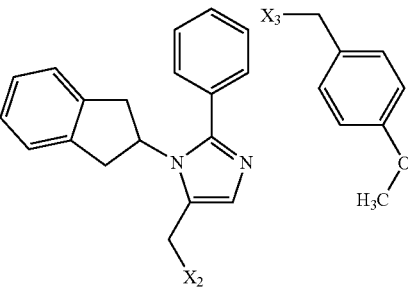 | | 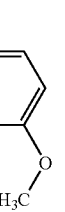 | 1.95 | 607.2238 | 608.3556 |
| 1993 | 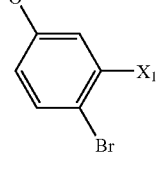 | | 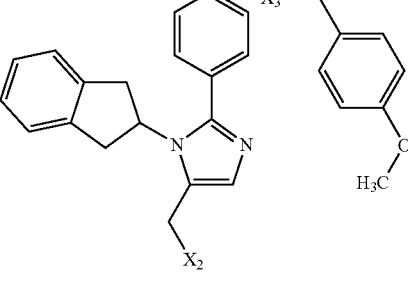 | 1.92 | 621.1627 | 622.29 |
| 1994 | 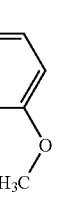 | | 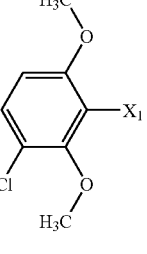 | 1.96 | 651.1733 | 652.31 |
| 1995 | 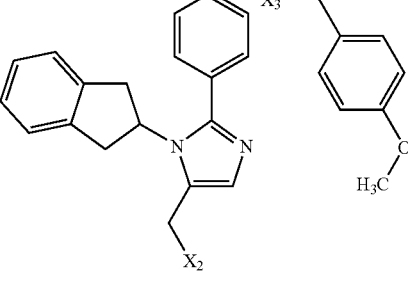 | | 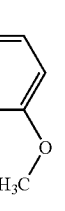 | 1.93 | 657.1288 | 658.2678 |

TABLE 5-continued
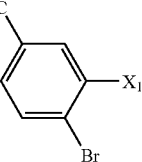
| CMP # | R1 | R2 | R3 | Rtn. Time | Cmp. Mass | H + Ion Obs |
|---|---|---|---|---|---|---|
| 1996 | 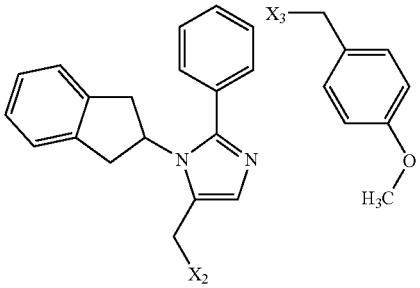 |  | 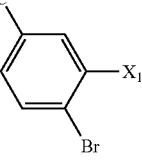 | 1.95 | 605.1678 | 606.29 |
| 1997 | 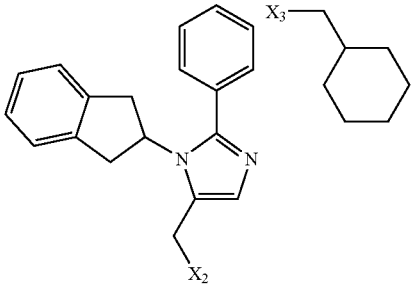 |  | 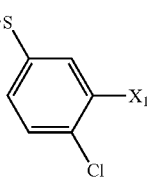 | 2.02 | 581.2042 | 582.32 |
| 1998 | 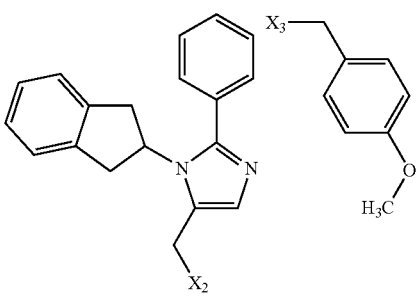 |  | 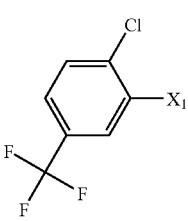 | 1.96 | 593.1904 | 594.3127 |
| 1999 | 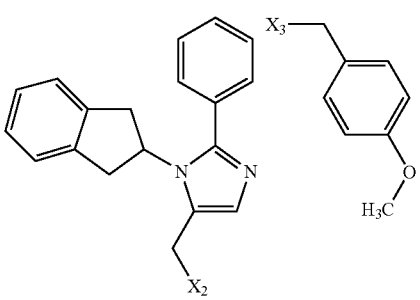 |  | | 1.97 | 615.1901 | 616.3185 |

TABLE 5-continued
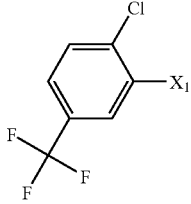
| CMP # | R1 | R2 | R3 | Rtn. Time | Cmp. Mass | H + Ion Obs |
|---|---|---|---|---|---|---|
| 2000 | 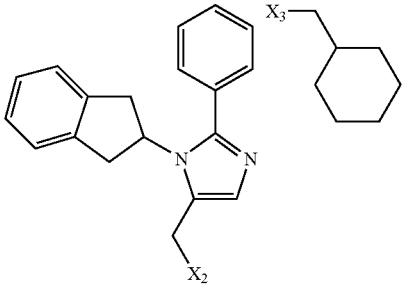 | 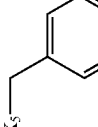 | 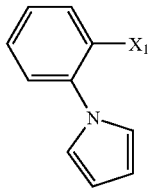 | 2.04 | 591.2264 | 592.3466 |
| 2001 | 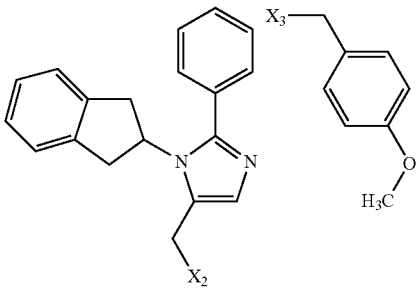 | 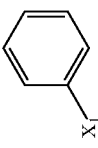 | 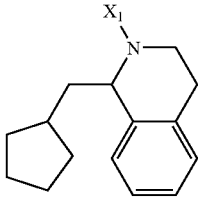 | 1.93 | 578.2682 | 579.3848 |
| 2002 | 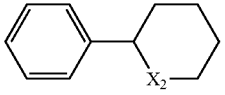 | | 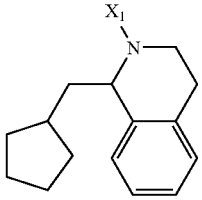 | | | |
| 2003 | 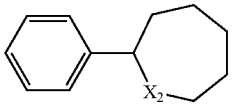 | | 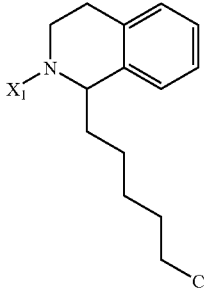 | | | |
| 2004 | 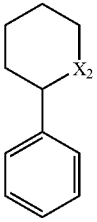 | | | | | |

TABLE 5-continued

| CMP # | R1 | R2 | R3 | Rtn. Time | Cmp. Mass | H + Ion Obs |
|---|---|---|---|---|---|---|
| 2005 | | | | | | |
| 2006 | | | | 2.47 | 475.2511 | 476.2856 |
| 2007 | | | | 2.36 | 403.1936 | 404.2317 |
| 2008 | | | | 2.42 | 427.1936 | 428.2387 |
| 2009 | | | | 2.43 | 437.1546 | 438.2044 |
| 2010 | | | | 2.39 | 433.15 | 434.1996 |

TABLE 5-continued
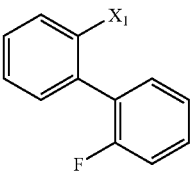
| CMP # | R1 | R2 | R3 | Rtn. Time | Cmp. Mass | H + Ion Obs |
|---|---|---|---|---|---|---|
| 2011 | 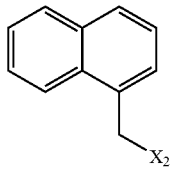 | 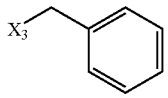 | 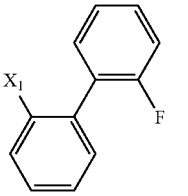 | 2.39 | 445.1842 | 446.226 |
| 2012 | 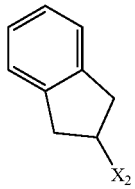 | 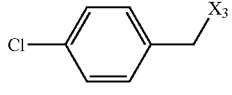 | 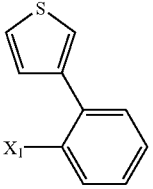 | 2.41 | 455.1452 | 456.196 |
| 2013 | 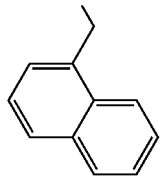 | 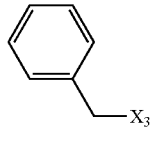 | 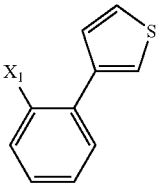 | 2.41 | 433.15 | 434.1984 |
| 2014 | 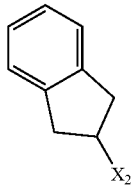 | 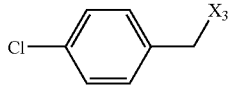 | 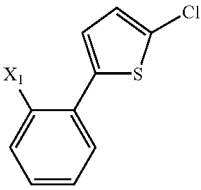 | 2.42 | 443.1111 | 444.1632 |
| 2015 | 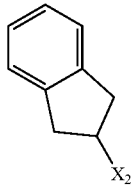 | 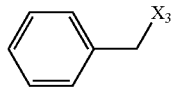 | 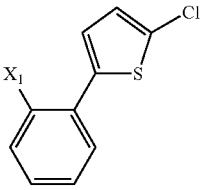 | 2.47 | 443.1111 | 444.1649 |
| 2016 | 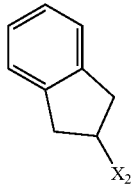 | 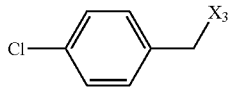 | | 2.53 | 477.0721 | 478.137 |

TABLE 5-continued

| CMP # | R1 | R2 | R3 | Rtn. Time | Cmp. Mass | H + Ion Obs |
|---|---|---|---|---|---|---|
| 2017 | 2-(5-methylthiophen-2-yl)phenyl-X₁ | 2-indanyl-X₂ | benzyl-X₃ | 2.41 | 423.1657 | 424.2055 |

TABLE 6

| CMP # | R1 or R1 and R2 | R3 | R4 | R5 | R6 | Rtn. time | Cmp Mass | H+ Ion Obs |
|---|---|---|---|---|---|---|---|---|
| 1824 | phenyl-X₁,X₂,X₃ | X₄ | butyl-CH₃ | 1,3-benzodioxol-5-ylmethyl-X₅ | | 1.91 | 424.2151 | 425.2364 |
| 1825 | phenyl-X₁,X₂,X₃ | X₄ | butyl-CH₃ | 1,3-benzodioxol-5-ylmethyl-X₅ | 1,3-benzodioxol-5-ylmethyl-X₆ | 2.17 | 558.2518 | 559.2742 |
| 1826 | phenyl-X₁,X₂,X₃ | X₄ | butyl-CH₃ | 1,3-benzodioxol-5-ylmethyl-X₅ | benzyl-X₆ | 2.2 | 514.262 | 515.286 |
| 1827 | phenyl-X₃ | X₄ | butyl-CH₃ | 1,3-benzodioxol-5-ylmethyl-X₅ | 1,3-benzodioxol-5-ylmethyl-X₆ | 2.09 | 508.2362 | 509.2629 |

TABLE 6-continued

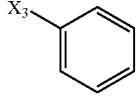

| CMP # | R1 or R1 and R2 | R3 | R4 | R5 | R6 | Rtn. time | Cmp Mass | H+ Ion Obs |
|---|---|---|---|---|---|---|---|---|
| 1828 | 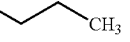 | | 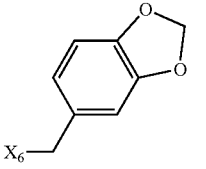 | 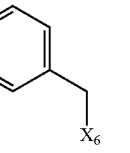 | 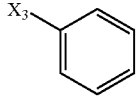 | 2.1 | 464.2464 | 465.2729 |
| 1829 | 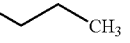 | | 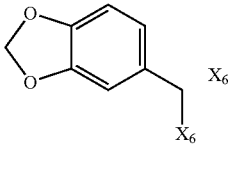 | 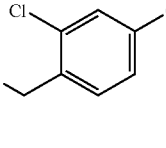 | 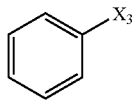 | 2.04 | 514.2023 | 515.2661 |
| 1830 | 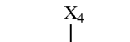 | | 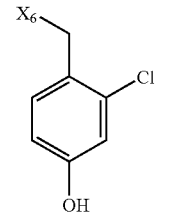 | 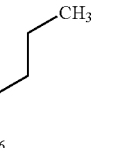 | 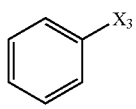 | 1.98 | 436.2281 | 437.2896 |
| 1831 | 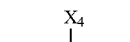 | | 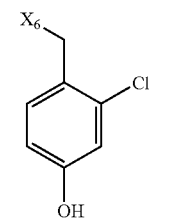 | 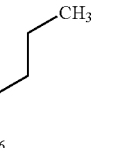 | 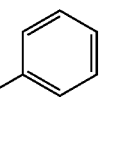 | 2.06 | 470.2126 | 471.2746 |

What is claimed is:

1. A compound of the formula:

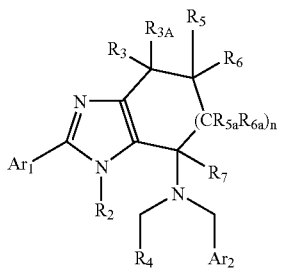

or a pharmaceutically acceptable salt, prodrug or hydrate thereof, wherein:

n is an integer from 0 to 3;

$R_2$ is chosen from optionally substituted $C_1$–$C_8$ alkyl, optionally substituted $C_3$–$C_8$ cycloalkyl, optionally substituted $C_3$–$C_8$ cycloalkyl($C_1$–$C_8$)alkyl optionally substituted $C_2$–$C_8$ alkenyl, optionally substituted $C_2$–$C_8$ alkynyl, haloalkyl, and aminoalkyl, each of which is unsubstituted or substituted with one or more substituents selected from oxo, hydroxy, alkoxy, amide, ester, cyano, acetoxy and nitro;

$R_4$ is hydrogen or alkyl, alkenyl, alkynyl, cycloalkyl, (cycloalkyl)alkyl or haloalkyl, each of which is substituted or unsubstituted; or $R_4$ is optionally substituted carbocyclic aryl, optionally substituted arylalkyl, or an optionally substituted heteroaromatic or heteroalicyclic group having from 1 to 3 rings, 3 to 8 members in each ring and from 1 to 3 heteroatoms;

$R_3$ and $R_{3A}$ are the same or different and represent hydrogen or alkyl; or $R_3$ and $R_{3A}$, taken together with the carbon atom to which they are attached, form a cycloalkyl ring;

$R_5$ and $R_6$ are the same or different and represent hydrogen, halogen, hydroxy, alkyl, or alkoxy; or $R_5$ and $R_6$, taken together with the carbon atom to which they are attached form a cycloalkyl ring;

$R_{5a}$ and $R_{6a}$ are independently selected at each occurrence from hydrogen, halogen, hydroxy, alkyl, and alkoxy;

$R_7$ represents hydrogen or alkyl;

$Ar_1$ is optionally substituted carbocyclic aryl, optionally substituted arylalkyl, or an optionally substituted heteroaryl or heteroalicyclic group having from 1 to 3 rings, 3 to 8 members in each ring and from 1 to 3 heteroatoms; and $Ar_2$ is optionally substituted carbocyclic aryl, optionally substituted arylalkyl, or an optionally substituted heteroaryl or heteroalicyclic group having from 1 to 3 rings, 3 to 8 members in each ring and from 1 to 3 heteroatoms.

2. A compound or salt, prodrug or hydrate thereof according to claim 1, wherein:

$R_4$ is hydrogen or alkyl, alkenyl, alkynyl, cycloalkyl, (cycloalkyl)alkyl, haloalkyl, each of which is unsubstituted or substituted with one or more substituents independently selected from halogen, nitro, cyano, trifluoromethyl, trifluoromethoxy, haloalkyl, hydroxy, acetoxy, alkyl, alkenyl, alkynyl, alkoxy, amino and mono- or dialkylamino, $R_4$ is phenyl, ethylenedioxyphenyl, methylenedioxyphenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which is optionally substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, mono- or dialkylamino, aminoalkoxy, carboxylic acid, esters of carboxylic acids, aminocarbonyl, mono or dialkylaminocarbonyl, N-alkylsulfonylaminocarbonyl, 1-azetidinyl, 1-pyrrolidinyl, 1-piperidyl and —$X_4R_B$, wherein $X_4$ and $R_B$ are as defined below; or $R_4$ is a bicyclic oxygen-containing group of the formula:

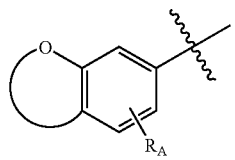

wherein $R_A$ represents from 0 to 3 groups independently selected from halogen, intro, cyano, trifluoromethyl, trifluoromethoxy, haloalkyl, hydroxy, acetoxy, alkyl, alkenyl, alkynyl, alkoxy, amino, and mono- or dialkylamino;

$Ar_1$ is chosen from i) ethylenedioxyphenyl, methylenedioxyphenyl, phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, and quinoxalinyl, each of which is optionally substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, mono- or di-alkylamino, aminoalkoxy, carboxylic acid, esters of carboxylic acids, aminocarbonyl, mono- or di-alkylaminocarbonyl, N-alkylsulfonylaminocarbonyl, 1-azetidinyl, 1-pyrrolidinyl, 1-piperidyl and —$X_4R_B$, wherein $X_4$ and $R_B$ are as defined below; and ii) bicyclic oxygen-containing groups of the formula:

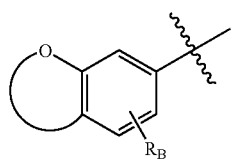

wherein $R_B$ represents from 0 to 3 groups independently selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino;

$Ar_2$ is chosen from i) phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, and quinoxalinyl, each of which optionally substituted with up to four groups independently selected from halogen, nitro, cyano, trifluoromethyl, trifluoromethoxy, haloalkyl, hydroxy, acetoxy, alkyl, alkenyl, alkynyl, alkoxy, amino, mono- or dialkylamino, aminoalkoxy, carboxylic acid, esters of carboxylic acids, aminocarbonyl, mono or dialkylaminocarbonyl, N-alkylsulfonylaminocarbonyl, 1-azetidinyl, 1-pyrrolidinyl, 1-piperidyl and —$X_4R_B$, wherein $X_4$ and $R_B$ are as defined below; and ii) bicyclic oxygen-containing groups of the formula:

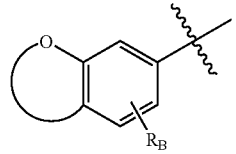

wherein $R_B$ represents from 0 to 3 groups independently selected from halogen, nitro, cyano, trifluoromethyl, trifluoromethoxy, haloalkyl, hydroxy, acetoxy, alkyl, alkenyl, alkynyl, alkoxy, amino, and mono- or dialkylamino, $X_4$ is independently selected at each occurrence from —$CH_2$—, —$CHR_C$—, —O—, —$S(O)_m$—, —NH—, —$NR_C$—, —C(=O)NH—, —C(=O)$NR_C$—, —$S(O)_m$NH—, —$S(O)_mNR_C$—, —NHC(O)—, —$NR_C$C(=O)—, —NHS(O)$_m$—, —C(O)NHS(O)$_m$-, and —$NR_CS(O)_m$ wherein m is 0, 1, or 2; and $R_B$ and $R_C$ are independently selected at each occurrence from:

hydrogen and straight, branched, or cyclic alkyl groups, which optionally contain one or more double or triple bonds, each of which is unsubstituted or substituted with one or more substituent(s) independently selected from: oxo, hydroxy, —O(alkyl), —NH(alkyl), —N(alkyl)(alkyl), —NHC(O)(alkyl), —N(alkyl)C(O)(alkyl), —NHS(O)$_x$(alkyl), —S(O)$_x$(alkyl), —S(O)$_x$NH(alkyl), and —S(O)$_x$N($C_1$–$C_6$ alkyl)($C_1$–$C_6$ alkyl), (wherein x is 0, 1, or 2.

3. A compound or salt, prodrug or hydrate thereof according to claim 1, wherein:

$R_3$ and $R_{3A}$ are the same or different and represent hydrogen or $C_1$–$C_6$ alkyl; or $R_3$ and $R_{3A}$, taken together with the carbon atom to which they are attached, form a $C_{3-8}$ cycloalkyl ring;

$R_5$ and $R_6$ are the same or different and represent hydrogen, halogen, hydroxy, $C_1$–$C_6$ alkyl, or $C_1$–$C_6$ alkoxy; or $R_5$ and $R_6$, taken together with the carbon atom to which they are attached form a $C_{3-8}$ cycloalkyl ring;

$R_{5a}$ and $R_{6b}$ are independently selected at each occurrence from hydrogen, halogen, hydroxy, $C_1$–$C_6$ alkyl, and $C_1$–$C_6$ alkoxy;

$R_4$ is hydrogen or $C_{1-8}$ alkyl, $C_{2-8}$ alkenyl, $C_{2-8}$ alkynyl, $C_{3-8}$ cycloalkyl, ($C_{3-8}$ cycloalkyl)$C_{1-4}$alkyl, or haloalkyl, each or which is unsubstituted or substituted with one or more substituents independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino and mono- or di($C_1$–$C_6$)alkylamino, or $R_4$ is phenyl, ethylenedioxyphenyl, methylenedioxyphenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which is optionally substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, and —$X_4R_B$, wherein $X_4$ and $R_B$ are as defined below; or $R_4$ is a bicyclic oxygen-containing group of the formula:

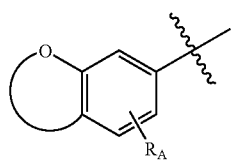

wherein $R_A$ represents from 0 to 3 groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$)alkylamino;

$Ar_1$ is chosen from i) ethylenedioxyphenyl, methylenedioxyphenyl, phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, and quinoxalinyl, each of which is optionally substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_{1-6}$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, and —$X_4R_B$, wherein $X_4$ and $R_B$ are as defined below; and ii) bicyclic oxygen-containing groups of the formula:

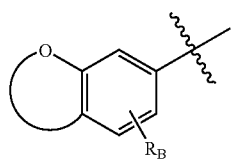

wherein $R_B$ represents from 0 to 3 groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$)alkylamino;

$Ar_2$ is chosen from i) phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, and quinoxalinyl, each of which optionally substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, and —$X_4R_B$, wherein $X_4$ and $R_B$ are as defined below; and ii) bicyclic oxygen-containing groups of the formula:

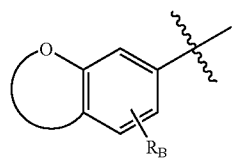

wherein $R_B$ represents from 0 to 3 groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$)alkylamino;

$X_4$ is independently selected at each occurrence from —$CH_2$—, —$CHR_C$—, —O—, —S(O)$_m$—, —NH—, —$NR_C$—, —C(=O)NH—, —C(O)$NR_C$—, —S(O)$_m$NH—, —S(O)$_m NR_C$—, —NHC(=O)—, —$NR_C$C(=O)—, —NHS(O)$_m$—, —C(=O)NHS(O)$_m$—, and —$NR_C$S(O)$_m$ wherein x is 0, 1, or 2; and $R_B$ and $R_C$, which are the same or different, are independently selected at each occurrence from hydrogen and straight, branched, or cyclic alkyl groups, which optionally contain one or more double or triple bonds, each of which is unsubstituted or substituted with one or more substituent(s) independently selected from: oxo, hydroxy, —O($C_1$–$C_6$ alkyl), —NH($C_1$–$C_6$ alkyl), —N($C_1$–$C_6$ alkyl)($C_1$–$C_6$ alkyl), —NHC(O)($C_1$–$C_6$ alkyl), —N($C_1$–$C_6$ alkyl)C(O)($C_{1-6}$ alkyl), —NHS(O)$_x$($C_1$–$C_6$ alkyl), —S(O)$_x$($C_1$–$C_6$ alkyl), —S(O)$_x$NH ($C_1$–$C_6$ alkyl), and —S(O)$_x$N($C_1$–$C_6$ alkyl)($C_1$–$C_6$ alkyl), (wherein x is 0, 1, or 2.

4. A compound or salt, prodrug or hydrate thereof according to claim 1, wherein $R_4$ is hydrogen or $C_1$–$C_8$ alkyl, $C_2$–$C_8$ alkenyl, $C_2$–$C_8$ alkynyl, $C_3$–$C_8$cycloalkyl, ($C_3$–$C_8$cycloalkyl) $C_1$–$C_4$alkyl, haloalkyl, each of which is unsubstituted or substituted with one or more substituents independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino and mono- or di($C_1$–$C_6$)alkylamino, or $R_4$ is phenyl, ethylenedioxyphenyl, methylenedioxyphenyl, naphthyl, thienyl, pyridyl, pyrimidyl, dihydrobenzofuranyl, furanyl, benzodioxanyl, or indolyl, each of which is optionally substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, and —$X_4R_B$, wherein $X_4$ and $R_B$ are as defined below; or $R_4$ is a bicyclic oxygen-containing group of the formula:

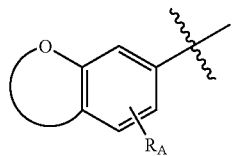

wherein $R_A$ represents from 0 to 3 groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino;

$Ar_1$ is phenyl, ethylenedioxyphenyl, methylenedioxyphenyl, thienyl, pyridyl, pyrimidyl, dihydrobenzofuranyl, furanyl, benzodioxanyl, or indolyl, each of which is unsubstituted or substituted with up to four substituents independently selected from:

halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, and —$X_4R_B$, wherein $X_4$ and $R_B$ are as defined below;

$Ar_2$ is phenyl, naphthyl, thienyl, pyridyl, pyrimidyl, dihydrobenzofuranyl, furanyl, benzodioxanyl, or indolyl, each of which is optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, and —$X_4R_B$, wherein $X_4$ and $R_B$ are as defined below; or $Ar_2$ is a bicyclic oxygen-containing group of the formula:

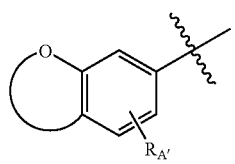

wherein $R_{A'}$ represents from 0 to 3 groups independently selected from halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, and mono- or di($C_1$–$C_6$)alkylamino;

$X_4$ is independently selected at each occurrence from the group consisting of —$CH_2$—, —$CHR_C$—, —O—, —$S(O)_m$—, —NH—, —$NR_C$—, —C(=O)NH—, —C(O)$NR_C$—, —$S(O)_m$NH—, —$S(O)_m NR_C$—, —NHC(=O)—, —$NR_C$C(=O)—, —$NHS(O)_m$—, —C(=O)$NHS(O)_m$—, and —$NR_C S(O)_m$— wherein m is 0, 1, or 2; and $R_B$ and $R_C$, which are the same or different, are independently selected at each occurrence from:

hydrogen and straight, branched, or cyclic alkyl groups, which optionally contain one or more double or triple bonds, each of which is unsubstituted or substituted with one or more substituent(s) independently selected from: oxo, hydroxy, —O($C_1$–$C_6$ alkyl), —NH($C_1$–$C_6$ alkyl), —N($C_1$–$C_6$ alkyl)($C_1$–$C_6$ alkyl), —NHC(O)($C_1$–$C_6$ alkyl), —N($C_1$–$C_6$ alkyl)C(O)($C_1$–$C_6$ alkyl), —$NHS(O)_x$($C_1$–$C_6$ alkyl), —$S(O)_x$($C_1$–$C_6$ alkyl), —$S(O)_x$NH($C_1$–$C_6$ alkyl), and —$S(O)_x$($C_1$–$C_6$ alkyl)($C_1$–$C_6$ alkyl), wherein x is 0, 1, or 2.

5. A compound or salt, prodrug or hydrate thereof according to claim 4 wherein:

$R_3$ and $R_4$ are the same or different and represent hydrogen or methyl;

$R_5$ and $R_6$ are the same or different arid represent hydrogen or methyl; and $R_{5a}$ and $R_{6a}$ are independently selected at each occurrence from hydrogen and methyl.

6. A compound or salt, prodrug or hydrate thereof according to claim 4 wherein:

$R_3$ and $R_4$ are hydrogen;

$R_5$ and $R_6$ are the same or different and represent hydrogen or methyl; and $R_{5a}$ and $R_{6a}$ are independently selected at each occurrence from hydrogen and methyl.

7. A compound according to claim 4 of the formula:

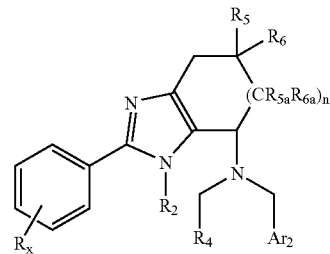

or a pharmaceutically acceptable salt, prodrug or hydrate thereof, wherein:

$R_5$ and $R_6$ are the same or different and represent hydrogen or methyl;

$R_{5a}$ and $R_{6a}$ are independently chosen at each occurrence from hydrogen and methyl; and $R_X$ represents up to four substituents independently chosen from hydrogen, halogen, nitro, cyano, trifluoromethyl, trifluoromethoxy, haloalkyl, hydroxy, acetoxy, $C_1$–$C_6$ alkyl, $C_2$–$C_6$ alkenyl, $C_2$–$C_6$ alkynyl, $C_1$–$C_6$ alkoxy, amino, mono- or di($C_1$–$C_6$)alkylamino, and amino($C_1$–$C_6$)alkoxy.

8. A compound according to claim 6, of the formula:

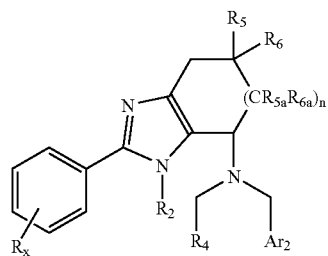

or a pharmaceutically acceptable salt, prodrug or hydrate thereof, wherein:
- $R_2$ is $C_3$–$C_8$ straight or branched chain alkyl, $C_2$–$C_8$ alkenyl, or $C_2$–$C_8$ alkynyl;
- $R_5$ and $R_6$ are the same or different and represent hydrogen or methyl;
- $R_{5a}$ and $R_{6a}$ are independently chosen at each occurrence from hydrogen and methyl, and
- $R_X$ represents up to four substituents independently chosen from hydrogen, halogen, nitro, cyano, trifluoromethyl, trifluoromethoxy, haloalkyl, hydroxy, acetoxy, $C_1$–$C_6$ alkyl, $C_2$–$C_8$ alkenyl, $C_2$–$C_8$ alkynyl, $C_1$–$C_6$ alkoxy, amino, mono- or di($C_1$–$C_6$)alkylamino, and amino($C_1$–$C_6$)alkoxy.

9. A compound according to claim 7, or a pharmaceutically acceptable salt, prodrug or hydrate thereof, wherein:
- $R_2$ is $C_3$–$C_8$ straight or branched chain alkyl, $C_2$–$C_8$ alkenyl, or $C_2$–$C_8$ alkynyl; and
- $R_4$ is $C_1$–$C_8$ straight or branched chain alkyl, $C_2$–$C_8$ alkenyl, or $C_2$–$C_8$ alkynyl.

10. A compound according to claim 7, or a pharmaceutically acceptable salt, prodrug or hydrate thereof, wherein:
- $R_2$ is $C_3$–$C_8$ straight or branched chain alkyl, $C_2$–$C_8$ alkenyl, or $C_2$–$C_8$ alkynyl;
- $R_4$ is phenyl, which is unsubstituted or substituted with:
  $C_1$–$C_6$ alkyl, $C_2$–$C_6$ alkenyl, $C_2$–$C_6$ alkynyl, $C_3$–$C_8$ cycloalkyl, ($C_3$–$C_8$ cycloalkyl)$C_1$–$C_4$ alkyl, haloalkyl, $C_1$–$C_6$ alkoxy, halogen, hydroxy, amino, or mono- or di($C_1$–$C_6$)alkylamino; or
- $R_4$ is a bicyclic oxygen containing group of the formula:

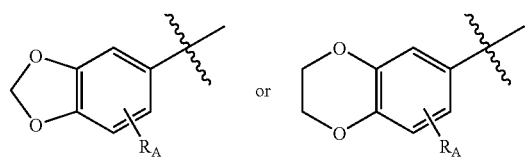

wherein $R_A$ is hydrogen, $C_1$–$C_6$ alkyl, $C_2$–$C_6$ alkenyl, $C_2$–$C_6$ alkynyl, $C_3$–$C_8$ cycloalkyl, ($C_3$–$C_8$cycloalkyl)$C_1$–$C_4$ alkyl, haloalkyl, alkoxy, halogen, hydroxy, amino, or mono- or di($C_1$–$C_6$)alkylamino;

$Ar_2$ is phenyl which is unsubstituted or substituted with up to four groups independently selected from: halogen, $C_1$–$C_7$ alkyl, $C_1$–$C_7$ alkoxy, cyano, amino, mono- or di($C_1$–$C_6$)alkylamino, carboxylic acid, esters of carboxylic acids, aminocarbonyl, mono or dialkylaminocarbonyl, N-alkylsulfonylaminocarbonyl, 1-azetidinyl, 1-pyrrolidinyl, 1-piperidyl, 1-morpholino, nitro, hydroxy, acetoxy, trifluoromethyl, trifluoromethoxy and —$X_4 R_B$, wherein $X_4$ and $R_B$ are as defined for claim 4; or $Ar_2$ is a bicyclic oxygen-containing group of the formula:

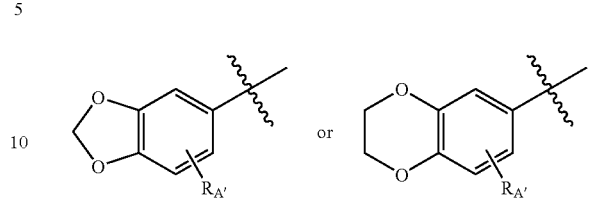

wherein $R_A{'}$ is as defined in claim 4.

11. A compound according to claim 7, or a pharmaceutically acceptable salt, prodrug or hydrate thereof, wherein:
- $R_2$ is $C_3$–$C_8$ straight or branched chain alkyl, $C_2$–$C_8$ alkenyl, or $C_2$–$C_8$ alkynyl;
- $R_4$ is $C_1$–$C_8$ straight or branched chain alkyl, $C_2$–$C_8$ alkenyl, or $C_2$–$C_8$ alkynyl;
- $Ar_2$ is a bicyclic oxygen containing group of the formula:

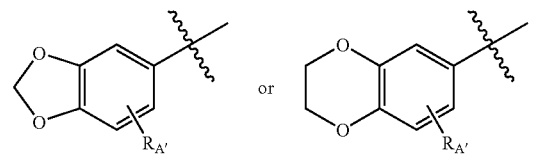

wherein $R_A{'}$ is as defined for claim 4.

12. A process for preparing a compound of the formula:

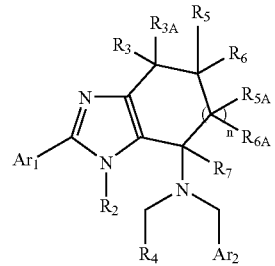

wherein:
- n is an integer from 0 to 3; and
- $R_2$ is hydrogen or alkyl, alkenyl, alkynyl, cycloalkyl, (cycloalkyl)alkyl, or haloalkyl, each of which is substituted or unsubstituted;
- $R_4$ is hydrogen or
  alkyl, alkenyl, alkynyl, cycloalkyl, (cycloalkyl)alkyl; haloalkyl, each or which is substituted or unsubstituted; or
- $R_4$ is optionally substituted carbocyclic aryl, optionally substituted arylalkyl, or an optionally substituted heteroaromatic or heteroalicyclic group having from 1 to 3 rings, 3 to 8 members in each ring and from 1 to 3 heteroatoms;
- $R_3$ and $R_{3A}$ are the same or different and represent hydrogen or alkyl; or
- $R_3$ and $R_{3A}$, taken together with the carbon atom to which they are attached, form a cycloalkyl ring;
- $R_5$ and $R_6$ are the same or different and represent hydrogen, halogen, hydroxy, alkyl, or alkoxy; or $R_5$ and $R_6$, taken together with the carbon atom to which they are attached form a cycloalkyl ring;

$R_{5a}$ and $R_{6a}$ are independently selected at each occurrence from hydrogen, halogen, hydroxy, alkyl, and alkoxy;

$R_7$ represents hydrogen or alkyl;

$Ar_1$ is optionally substituted carbocyclic aryl, optionally substituted arylalkyl, or an optionally substituted heteroaryl or heteroalicyclic group having from 1 to 3 rings, 3 to 8 members in each ring and from 1 to 3 heteroatoms;

$Ar_2$ is optionally substituted carbocyclic aryl, optionally substituted arylalkyl, or an optionally substituted heteroaryl or heteroalicyclic group having from 1 to 3 rings, 3 to 8 members in each ring and from 1 to 3 heteroatoms;

the process comprising:

reacting a compound of the formula:

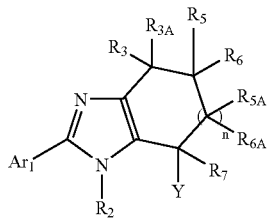

wherein Y is halogen or sulfonate ester, in a suitable solvent in the presence of a suitable base, with a secondary amine of the formula:

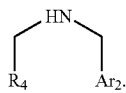

13. A process according to claim 12, wherein n and Y are as defined in claim 12;

$R_3$ and $R_{3A}$ are the same or different and represent hydrogen or $C_1$–$C_6$ alkyl; or $R_3$ and $R_{3A}$, taken together with the carbon atom to which they are attached, form a $C_{3-8}$ cycloalkyl ring;

$R_5$ and $R_6$ are the same or different and represent hydrogen, halogen, hydroxy, $C_1$–$C_6$ alkyl, or $C_1$–$C_6$ alkoxy; or $R_5$ and $R_6$, taken together with the carbon atom to which they are attached form a $C_{3-8}$ cycloalkyl ring;

$R_{5a}$ and $R_{6a}$ are independently selected at each occurrence from hydrogen, halogen, hydroxy, $C_1$–$C_6$ alkyl, and $C_1$–$C_6$ alkoxy;

$R_2$ is hydrogen or $C_{1-8}$ alkyl, $C_{2-8}$ alkenyl, $C_{2-8}$ alkynyl, $C_{3-8}$ cycloalkyl, $(C_{3-8}$ cycloalkyl) $C_{1-3}$ alkyl, or $C_1$–$C_6$ haloalkyl, each of which is unsubstituted or substituted by one or more substituents independently chosen from halogen, nitro, cyano, trifluormethyl, trifluoromethoxy, $C_{1-3}$ haloalkyl, hydroxy, acetoxy, alkoxy, amino, and mono- or di($C_1$–$C_6$)alkylamino;

$R_4$ is hydrogen or $C_{1-8}$ alkyl, $C_{2-8}$ alkenyl, $C_{2-8}$ alkynyl, $C_{3-8}$cycloalkyl, $(C_{3-8}$ cycloalkyl)$C_{1-4}$alkyl, or haloalkyl, each of which is unsubstituted or substituted with one or more substituents independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino and mono- or di($C_1$–$C_6$)alkylamino, or $R_4$ is phenyl, ethylenedioxyphenyl, methylenedioxyphenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, or quinoxalinyl, each of which is optionally substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$) alkylaminocarbonyl, N—($C_1$–$C_6$)alkylsulfonylaminocarbonyl, 1-azetidinyl, 1-pyrrolidinyl, 1-piperidyl, —$X_4R_B$, wherein $X_4$ and $R_B$ are as defined below; or $R_4$ is a bicyclic oxygen-containing group of the formula:

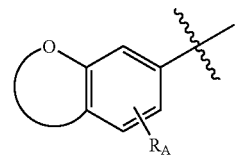

wherein $R_A$ represents from 0 to 3 groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$)alkylamino;

$Ar_1$ is chosen from i) ethylenedioxyphenyl, methylenedioxyphenyl, phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, and quinoxalinyl, each of which is optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$, alkoxy, amino, mono- or di($C_1$–$C_6$)alkylamino, amino($C_1$–$C_6$)alkoxy, carboxylic acid, caters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, and —$X_4R_B$, wherein $X_4$ and $R_B$ are as defined below; and ii) bicyclic oxygen-containing groups of the formula:

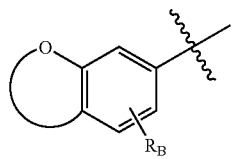

wherein $R_B$ represents from 0 to 3 groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$)alkylamino;

$Ar_2$ is chosen from i) phenyl, phenylalkyl, chromanyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, indanyl, isoindolyl, benzofuranyl, isobenzofuranyl, benzo[b]thiophenyl, benzodioxanyl, benzodioxinyl, benzodioxolyl, benz[d]isoxazolyl, quinolinyl, isoquinolinyl, cinnolinyl, quinazolinyl, and quinoxalinyl, each of which is optionally substituted or substituted with up to four groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, mono- or di($C_1$–$C_6$)alkylamino, amino($C_1$–$C_6$)alkoxy, carboxylic acid, esters of carboxylic acids, aminocarbonyl, mono or di($C_1$–$C_6$)alkylaminocarbonyl, N—($C_1$–$C_6$)alkylsulfonylaminocarbonyl, 1-azetidinyl, 1-pyrrolidinyl, 1-piperidyl, and —$X_4R_B$, wherein $X_4$ and $R_B$ are as defined below; and ii) bicyclic oxygen-containing groups of the formula:

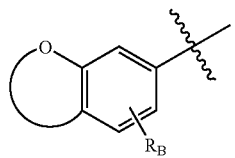

wherein $R_B$ represents from 0 to 3 groups independently selected from halogen, nitro, cyano, trifluoromethyl, trifluoromethoxy, haloalkyl, hydroxy, acetoxy, $C_1$–$C_6$ alkyl, $C_{2-6}$ alkenyl, $C_{2-6}$ alkynyl, $C_1$–$C_6$ alkoxy, amino, and mono- or di($C_1$–$C_6$)alkylamino;

$X_4$ is independently selected at each occurrence from the group consisting of —$CH_2$—, —$CHR_C$—, —O—, —$S(O)_m$—, —NH—, —$NR_C$—, —C(=O)NH—, —C(O)$NR_C$—, —$S(O)_m$NH—, —$S(O)_mNR_C$—, —NHC(=O)—, —$NR_CC$(=O)—, —$NHS(O)_m$—, —C(O)$NHS(O)_m$—, and —$NR_CS(O)_m$— wherein m is 0, 1, or 2; and $R_B$ and $R_C$ are independently selected at each occurrence from the group consisting of: hydrogen, straight, branched, or cyclic alkyl groups, which optionally contain one or more double or triple bonds, each of which is unsubstituted or substituted with one or more substituent(s) selected from:

oxo, hydroxy, —O($C_1$–$C_6$ alkyl), —NH($C_1$–$C_6$ alkyl), —N($C_1$–$C_6$ alkyl)($C_1$–$C_6$ alkyl), —NHC(O)($C_1$–$C_6$ alkyl), —N($C_1$–$C_6$ alkyl)C(O)($C_{1-6}$ alkyl), —NHS(O)$_x$($C_1$–$C_6$ alkyl), —alkyl), wherein x is 0, 1, or 2.

14. A compound according to claim 1, wherein $R_3$, $R_{3A}$, and $R_7$ are hydrogen;

$Ar_1$ is phenyl, ethylenedioxyphenyl, or methylenedioxyphenyl;

$Ar_2$ is phenyl, ethylenedioxyphenyl, or methylenedioxyphenyl, each of which is optionally substituted with up to four substitutents independently selected from $C_1$–$C_6$alkyl, $C_1$–$C_6$alkoxy, halogen, hydroxy, carboxylate, and $C_1$–$C_6$alkoxycarbonyl;

$R_2$ is $C_3$–$C_8$alkyl;

$R_4$ is $C_3$–$C_8$alkyl, phenyl, ethylenedioxyphenyl, or methylenedioxyphenyl, each of which is optionally substituted with up to four substitutents selected from $C_1$–$C_6$alkyl, $C_1$–$C_6$alkoxy, halogen, hydroxy, carboxylate, and $C_1$–$C_6$alkoxycarbonyl;

$R_5$, $R_{5a}$, $R_6$ and $R_{6a}$ are independently selected from hydrogen and $C_1$–$C_6$alkyl; and n is 0 or 1.

15. A compound of the formula:

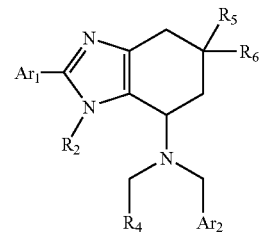

or a pharmaceutically acceptable salt, prodrug or hydrate thereof, wherein $Ar_1$ is phenyl, ethylenedioxyphenyl, or methylenedioxyphenyl;

$Ar_2$ is phenyl, ethylenedioxyphenyl, or methylenedioxyphenyl, each of which is optionally substituted with up to four substitutents selected from $C_1$–$C_6$alkyl, $C_1$–$C_6$alkoxy, halogen, hydroxy, carboxylate, and $C_1$–$C_6$alkoxycarbonyl;

$R_2$ is $C_3$–$C_8$alkyl;

$R_4$ is $C_3$–$C_8$alkyl or phenyl which is optionally substituted with up to four substitutents selected from $C_1$–$C_6$alkyl, $C_1$–$C_6$alkoxy, halogen, hydroxy, carboxylate, and $C_1$–$C_6$alkoxycarbonyl; and $R_5$ and $R_6$ are independently selected from hydrogen and $C_1$–$C_6$alkyl.

16. A compound of the formula:

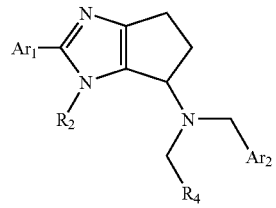

wherein $Ar_1$ is phenyl, ethylenedioxyphenyl, or methylenedioxyphenyl;

Ar₂ is phenyl, ethylenedioxyphenyl, or methylenedioxyphenyl, each of which is optionally substituted with up to four substituents selected from $C_1$–$C_6$alkyl, $C_1$–$C_6$alkoxy, halogen, hydroxy, carboxylate, and $C_1$–$C_6$alkoxycarbonyl;

$R_2$ is $C_3$–$C_8$alkyl; and $R_4$ is $C_3$–$C_8$alkyl or phenyl which is optionally substituted with up to four substitutents selected from $C_1$–$C_6$alkyl, $C_1$–$C_6$alkoxy, halogen, hydroxy, carboxylate, $C_1$–$C_6$alkoxycarbonyl.

17. A compound of claim 1 selected from:

Benzo[1,3]dioxol-5-ylmethyl-benzyl-(3-butyl-2-phenyl-4,5,6,7-tetrahydro-3H-benzoimidazol-4-yl)-amine;

4-{[Benzyl-(3-butyl-2-phenyl-4,5,6,7-tetrahydro-3H-benzoimidazol-4-yl)-amino]-methyl}-3-chloro-phenol;

Benzo[1,3]dioxol-5-ylmethyl-benzyl-(3-butyl-2-phenyl-3,4,5,6-tetrahydro-cyclopentaimidazol-4-yl)-amine;

Benzo[1,3]dioxol-5-ylmethyl-butyl-(3-butyl-2-phenyl-3,4,5,6-tetrahydro-cyclopentaimidazol-4-yl)-amine;

4-{[Butyl-(3-butyl-2-phenyl-3,4,5,6-tetrahydro-cyclopentaimidazol-4-yl)-amino]-methyl}-3-chloro-phenol;

4-{[Benzyl-(3-butyl-2-phenyl-3,4,5,6-tetrahydro-cyclopentaimidazol-4-yl)-amino]-methyl}-3-chloro-phenol;

4-{[Benzyl-(3-butyl-2-phenyl-3,4,5,6-tetrahydro-cyclopentaimidazol-4-yl)-amino]-methyl}-phenol;

4-{[Butyl-(3-butyl-2-phenyl-3,4,5,6-tetrahydro-cyclopentaimidazol-4-yl)-amino]-methyl}-phenol;

Benzo[1,3]-dioxol-5-ylmethyl-benzyl-(3-butyl-6,6-dimethyl-2-phenyl-4,5,6,7-tetrahydro-3H-benzoimidazol-4-yl)-amine;

4-{[Butyl-(3-butyl-6,6-dimethyl-2-phenyl-4,5,6,7-tetrahydro-3H-benzoimidazol-4-yl)-amino]-methyl}-3-chloro-phenol;

3-{[Butyl-(3-butyl-6,6-dimethyl-2-phenyl-4,5,6,7-tetrahydro-3H-benzoimidazol-4-yl)-amino]-methyl}-phenol;

4-{[Butyl-(3-butyl-6,6-dimethyl-2-phenyl-4,5,6,7-tetrahydro-3H-benzoimidazol-4-yl)-amino]-methyl}-phenol;

4-{[Butyl-(3-butyl-6,6-dimethyl-2-phenyl-4,5,6,7-tetrahydro-3H-benzoimidazol-4-yl)-amino]-methyl}-3-chloro-phenol;

4-{[Butyl-(3-butyl-6,6-dimethyl-2-phenyl-4,5,6,7-tetrahydro-3H-benzoimidazol-4-yl)-amino]-methyl}-benzoic acid methyl ester; and 4-{[Butyl-(3-butyl-6,6-dimethyl-2-phenyl-4,5,6,7-tetrahydro-3H-benzoimidazol -4-yl)-amino]-methyl}-benzoic acid.

18. A pharmaceutical composition comprising a compound of claim 1 or a salt, prodrug or hydrate thereof and a pharmaceutically acceptable carrier therefor.

* * * * *

SEQUENCE LISTING

<160> NUMBER OF SEQ ID NOS: 1

<210> SEQ ID NO 1
<211> LENGTH: 1078
<212> TYPE: DNA
<213> ORGANISM: Homo sapiens

<400> SEQUENCE: 1

```
cccaggagac cccaccatga actccttcaa ttataccacc cctgattatg ggcactatga      60
tgacaaggat accctggacc tcaacacccc tgtggataaa acttctaaca cgctgcgtgt     120
tccagacatc ctggccttgg tcatctttgc agtcgtcttc ctggtgggag tgctgggcaa     180
tgccctggtg gtctgggtga cggcattcga ggccaagcgg accatcaatg ccatctggtt     240
cctcaacttg gcggtagccg acttcctctc ctgcctggcg ctgccccatct tgttcacgtc     300 cattgtacag catcaccact ggcccttttgg cggggccgcc tgcagcatcc tgccctccct     360
```

-continued

```
catcctgctc aacatgtacg ccagcatcct gctcctggcc accatcagcg ccgaccgctt    420
tctgctggtg tttaaaccca tctggtgcca gaacttccga ggggccggct tggcctggat    480
cgcctgtgcc gtggcttggg gtttagccct gctgctgacc atacctcct tcctgtaccg     540 ggtggtccgg gaggagtact ttccaccaaa ggtgttgtgt ggcgtggact acagccacga    600
caaacggcgg gagcgagccg tggccatcgt ccggctggtc ctgggcttcc tgtggcctct    660
actcacgctc acgatttgtt acactttcat cctgctccgg acgtggagcc gcagggccac    720
gcggtccacc aagacactca aggtggtggt ggcagtggtg gccagtttct ttatcttctg    780
gttgccctac caggtgacgg ggataatgat gtccttcctg gagccatcgt cacccacctt    840
cctgctgctg aataagctgg actccctgtg tgtctccttt gcctacatca actgctgcat    900 caacccatc atctacgtgg tggccggcca gggcttccag ggccgactgc ggaaatccct     960
ccccagcctc ctccggaacg tgttgactga agagtccgtg gttagggaga gcaagtcatt    1020
cacgcgctcc acagtggaca ctatggccca gaagacccag gcagtgtagg cgacagcc     1078
```